(12) United States Patent
Hjörleifsdottir et al.

(10) Patent No.: US 6,492,161 B1
(45) Date of Patent: Dec. 10, 2002

(54) BACTERIOPHAGE RM 378 OF A THERMOPHILIC HOST ORGANISM

(75) Inventors: Sigridur Hjörleifsdottir; Gudmundur O. Hreggvidsson; Olafur H. Fridjonsson, all of Reykjavik; Arnthor Aevarsson, Hveragerdi; Jakob K. Kristjansson, Reykjavik, all of (IS)

(73) Assignee: Prokaria ltd., Reykjavik (IS)

( * ) Notice: Subject to any disclaimer, the term of this patent is extended or adjusted under 35 U.S.C. 154(b) by 0 days.

(21) Appl. No.: 09/585,858

(22) Filed: Jun. 1, 2000

Related U.S. Application Data
(60) Provisional application No. 60/137,120, filed on Jun. 2, 1999.

(51) Int. Cl.$^7$ .............. C12N 7/00; C12N 15/00; G01N 33/00; C07H 21/02
(52) U.S. Cl. ............... 435/235.1; 435/320.1; 436/94; 536/23.1
(58) Field of Search .............. 435/235.1, 320.1; 486/94; 536/23.1

(56) References Cited

U.S. PATENT DOCUMENTS
5,436,149 A  7/1995  Barnes ................ 435/194

FOREIGN PATENT DOCUMENTS
WO  WO94 26766  11/1994

OTHER PUBLICATIONS

Wang, J. et al., "Crystal Structure of a Pol α Family Replication DNA Polymerase from Bacteriophage RB69," *Cell*, 89(7): 1087–1099 (1997).

Hopfner Karl–Peter et al., "Crystal Structure of a Thermostable Type B DNA Polymerase From Thermococcus Gorgonarius," *Proc. Nat. Acad. of Sci.*, 96(7): 3600–3605 (1999).

"Exonuclease III (*E. coli*)," *New England Biolabs Catalog*, 94 (XP002164084) 1998–1999.

"DNA Polymerase I, Klenow (Exonuclease–Free)," *Mol. Bio. Reagents*, 88 (XP000606205), (1990).

Pisani, F.M., et al., "Amino Acid Residues Involved in Determining the Processivity of the 3'–d' Exonuclease Activity in a Family B DNA Polymerase from the Thermoacidophilic Archaeon Sulfolobus Solfataricus," *Biochem.* 37(42): 15005–15012 (1998).

"DNA polymerase and formulations comprising it—allowing the amplification of sequences up to 35 kilobases and reducing the mutagenicity generated by the PCR process." WPI Acc No. 1995–006692/199501 (Abstract).

Alfredsson, G.A., et al., "*Rhodothermus marinus*, gen. nov., sp. nov., a Thermophilic Halophilic Bacterium from Submarine Hot Springs in Iceland", *J. Gen. Microbiol.*, 134 (Pt. 2):299–306 (1988).

Nunes, O.C., et al., "Isolation and Characterization of Rhodothermus Strains from S. Miguel, Azores", *Syst. Appl. Microbiol.*, 15(1):92–97 (1992).

Moreira, L., et al., "Genomic Typing and Fatty Acid Composition of *Rhodothermus marinus*", *Syst. Appl. Microbiol.*, 19(1):83–90 (1996).

Andresson, O.S. and Fridjonsson, O.H., "The Sequence of the Single 16S rRNA Gene of the Thermophilic Eubacterium *Rhodothermus marinus* Reveals a Distant Relationship to the Group Containing Flexibacter, Bacteroides, and Cytophaga Species", *J. Bacteriol.*, 176(19):6165–6169 (1994).

*Primary Examiner*—James Housel
*Assistant Examiner*—Shanon Foley
(74) *Attorney, Agent, or Firm*—Hamilton, Brook, Smith & Reynolds, P.C.

(57) ABSTRACT

A novel bacteriophage RM 378 of *Rhodothermus marinus*, the nucleic acids of its genome, nucleic acids comprising nucleotide sequences of open reading frames (ORFs) of its genome, and polypeptides encoded by the nucleic acids, are described.

4 Claims, 83 Drawing Sheets

```
TTCGCTAAAATAAGGGCGGTCTTGGTCGGGGAGAGCTTGGAATCGTTATG
CTTCCTTCGGGGTGGGGTAAGTCATGGTTCCTTGTTTCACTTGGTCTTCA
TGCCTTTCGAACGGGTAAGCGCGTGATTTATTTCACTCTGGAGCTTGACC
AAAAATATGTGATGAAGCGGTTTTTAAAGATGTTTGCACCTTATTGCAAA
GGACGCGCTTCTTCCTATCGCGACGTTTATCAAATAATGAAAGAGCTTAT
GTTTTCTCAGGATAATCTTTTGAAGATTGTTTTCTGTAATGCGATGGAAG
ATATTGAGCACTATATTGCGCTGTATAACCCCGACGTTGTGCTGATTGAC
TATGCCGATCTTATTTATGATGTGGAAACCGACAAAGAGAAAATTATCT
GCTTTTGCAAAAAATTTATAGGAAACTTCGTCTCATTGCAAAGGTATATA
ATACAGCAGTATGGAGCGCCTCTCAGCTTAATCGCGGTTCCCTTTCAAAG
CAAGCCGACGTCGATTTCATTGAGAAATACATTGCCGATTCATTTGCAAA
AGTTTTTGAAATCGACTTCGGGATGGCGTTTATTCCGGATAGCGAGAACT
CAACCCCCGATATTCACGTCGGATTCGGTAAAATCTTCAAAAACCGTATG
GGTGCGGTAAGAAAGCTGGAATATACAATTAACTTTGAAAACTATACGGT
AGACGTTGCTGTTAAATGACACAAGTTAAGACAAAAGGGCTTAAAGACAT
CAGAATAGGTAGAAAGGAGGGTAAGTTCACACATGTAAATACAACAAAGA
AAGGAAAGAATAAGAAATATTTCAGGGCGGAACATGAACGCCTGTTTCTC
AACCTTATTCGAGCACTTCAGGTTGGGGATTATGCCGAAATCAATTCTCT
TTTTCCTCTTGTCGAAAAGCAACTCCGATGGATGGTACGAAAGATAGTGA
ACCGACTCAATCTCACTTCACTTGTTTCATATTATGACCACGGCGAATGG
GAGCATGATATTGTAAGTTATGTGTTCTCCAAACTCGATAACTATTCTCC
CGAAAAGGGAAGGGTGTTCAGTTATATCAGTGTTATCATAGTCAATTATG
CTATCAATTTGAACAATAAAATTTATTATAACCGGGTGGGGTATCATTCA
GATTTCTATGCAGATAATCCTACCACCGAAGACTACAAGGGTCTGGATGA
AAAGGAAGAGTTGAGTTATGAAATAGACGATCAGATTAATCTGAAGATTG
ATTTTGAGCATTTCTGCAATCTGTTTTAAATGCTTCCGAAGAAACTTTA
CTCAAGCATTTTCAGGAAGACGAAGTTTTTATTGTTAAAAATATTGCGCT
TTCTCTGAAATATGATCCGGATATTATCACGACGCCTTTTCTGGGGGTTG
TACATCGGATGATCTGTGAGTTTTGTGGGGTGGAATTTTCCCGCTATAAG
TTTTCCAAAGTGTTCAAGAAAATGGTTCAACTATACCACGAAGTTTTTAA
CGGGGGGTAAAGGTTATTTAAATAAAAAATATGTTTTCGGCTTCTGATTA
TAAAGGAAACGTAACTTTTAGTTTTCACTTCCCTTCGCTTCTCACCAATG
CCGGATCGCACCCAAATAAGGCATATGTGTATTACGACTATATGGGTAGT
GATCTGGTGTTCACTTTTTCTCGAATAAGATTCAGCCTGTCGGCACCCGG
CACCTACGATGCTTATTTTGACGCTCATATTCAGGATGTTGACACCATTA
CCTTCGATTCAAACGGATACCGTGAGCTTTATTTCATTTTCAGCGTTTCC
TGGGAAGGATCCAACACTTCGGGCACCATTTCGGGTGCCAATCTTATCAG
CGTATCTTCCTTTGTTACTGGATACCCCGAAAACAGTTTTCTTGCCTATA
CGCTTTCCGTTTACTCTGCTTCCGCCACAACCTATCTTAACCTTAATGAT
GCTTACAGAATTTACGTAGGGAACATTTTCGGCACCCCGCAATGGGAAGT
TGGTTTTACCGGTAGTTTCACGGTTTCTGCTACGCCTTCAATTTCTCACA
ACCGTTTCAGGATTTTACTTCTTTCTAACTTTGATAGTGCACTTAATTAC
TATATTACTACGTTCAGCGCACCAGCATTCGCCTCACATTCATTTCAGGT
TATCAGGAAAATATATGAAGTTGAGCCACTTTCTGCTTACACAGTACCGT
CTATCGTGTTTTTCTACACGGTTTCAGCTACTAACAGCTTCGGGTGGAGC
TATTCCAATATAGAAATGGGGTCTCTTTACAGAATATCAACTATGTCCAT
TCTAAGTTATCCTTACCCCTACACGGCACCGGCTATAACGTATATCACTT
TTTCTGGCGGAATTGTTTCGGATGAAGAATTTATTGTAAAGGTGCCCATA
ACCCTTTCTTATATTAACAACATAATACCGTATTTCATCGGCAACCCCAC
TACCACTTCAAACATTGACGATGTGAATGCTACTGAAGATAAAATTATCC
CTACTTCGATAAGTAACTTTAAAACAACCCTTTCATTTCAGGTTTTTGCT
TTTCCGAACACACTCCCTGTTAAAACGGAACAAGTATCAATTCCCGTTAC
CTTCAGTCCGGAAACGGGCAACATTTCTATTCCTGTTTCCATCTCATTTC
CTGCGTTTGTAAGAACTGCTGCGGCTACAATGGATAATCCGGGCAATTTT
TCCACTTCTGTCGGAAATGGTATCGTGGTTAGCGATCTTGTGTGTCAGAA
TACAGGGAATATACCTATTACATTTAGTGGTGTCAGTCTTGCAATAGACG
ATGGTAACTGGTATGTGGACACCCCCTCCGTGGGATATGGTTTTAACCCG
AACAGCGGGTTTTGGTTCGATGTTCACTTTATGCCTTATGGGGATGTAAA
CTACAGTCAATCCATTTATTTTACGTTTTCGTTCAATTATCCAACAAATT
ATGGAAATATATTGTCAGGTAGTTTTGTTGAATCCATTTCTTTCCATGCG
```

FIG. 1A

```
GTTGCTACAGGAACCGCCCCTTCCGGTCAGGTGGGTATTACGGTGTCCAA
CTGGAATGTGGACAACCCTAACACCGTTATGGTTGGTAAATATGTTACCG
GTTCCTTCAGCATCACGGCAAGTGCTACAAACAATCAGATCGCTCAGGTT
ACCCTGACTTCATCAACCCCAATCTGTATTTCACGACGGTTTCAGGTGT
TGGTATTAACAATCTTCATGCTACGGCGGTAAATTCTCTGGCGCTACAGG
TTGCTCCGGAGCTTCTCTTTCTGTTTATACCCAGTGGTATATGAATATG
GTTTATACGGCTTCGGCTCCTGATGTAACCATATCGGTAACGTCTTCTAA
TGCTACGGAAATGAACGGCGTGCCGGGATTGACGGAAGTTAAGCGATCGC
ATTCGCTGACGAACCCTGCTCGATATGCAAATTTGAATATAGGAATTTTT
TCACTCAGTGCTTATGGTCCCTTCTATCAATCAACCGCCTCTATTTTGCC
GTTCCCTTATTCTTTTAGTCTTGGGGGCATCAACGTCGTTAGAAATGTTG
GTTTGGCTTGGCTTGATTTTTATCCAACGAACAGCACTCATTCTGAAATG
TATGTTAAATTGACCATGTCTCTGACAGGATCGGCTTTAAATGTTCATAG
CGTAGTAACTTCATCGTATTTTTCTGATCCTTCTAATTTCGAGTGGGAAG
TCAACACTTTGCAGCATACTCTGTTCAGCCCCCCTTATGGATATTTCTT
CATATTAGAATAAGACCGACTCCAAGTGATATTAACATAATACCGACTTC
AAGTGCATATGGATATGGTACGTTTGTTGTAAGTTGGAGCATGAGTCTTA
TTTCCCATATAAATGGGGTAAGCGTGGCTTCTCTTGGACAGGGGTATTCA
AATGCTTTGAGTTTGTGGTTTGATCATACTGTTTTCTATGAAGCACCATA
GTAATTTCTTATCTATACGACACATACTTGATAAAATTGCCGCTTTCTCC
CATTTCAAAATATTTTCTGAGCGTAGAAGGAGTAAAATCCGTGGCGTCTC
CAAGCTTTCGAGTGGGGGTGATCAGTGTTGCGTTGATTTTGACATAGTGG
CTTTTGATCATTTTGTTGTGGGGAAAAGCAGGTTGTAAAGCGCCATCTG
GTTTACGTCGTTCAAAAGATGTTCATGCCAGAGAATATCGTAAGTGCGGG
TAAGCAGCGCAAGAAGATTGGTGTAGTAGTTCCGTTCTTCCTTAATGGTG
TAAAGCGGCGTGCAGGAAATGATGATCGCTTGAATTTCCTCACCCGGCTT
TAATTCTTTAAGTTTAATAAGGTTTTCAATGGTAAACCCAAGCGGAATCA
CTTCTCTTACCCCACCGTCTACATAGGTGTTGTCTCCGATTTTAACCGGA
GGAAAGACCAGCGGAATGCTACAAGAAGCAAGAATGGATTTGAGAAGAAG
TTCCTCTTTTTGCTCTTCCGGGATTTCCTGATCTTCAAAAAGGTAGTTAC
CGTCTTTTACAACGATTCCGGTGGATTTGCCGTTTTGCAAATTCACAGAA
CAATTGATATAGATTTTATTGAAATTCAGAAGCGGGAGCACGTTTTCTC
AAGGTATTTCCCAAGAGGGGAAAAATCATACAGATAATTTCGTTTGAGAA
TAAGTGTTTTGAGAAGGGCAAACCACTCAGGCTGCTGTTTGTAAACCTGT
TTCGGGGAAAGAGAAAGCCACATTTGCTTCGATGAGATCGGTACCTTTCGG
GGTAAGCGCCGCGCGGGAAGCACACCACACGCCGTTGATACTTCCCACCG
AAGTTCCGGCTACAGCAAGAATTTCGTTGTCTTTAAGCGCTCCTTCCCTC
ACCAGACAGGAAATGACGCCCGCCTGAAAAGCACCTTTGGCTCCTCCCCC
CGACAGGATCAGCAGTTTTTTCATTTTTAATTAAATAATGCTCATTTTCC
CGATGGAAGCATGGAAATCCACTTCAATTTGGCAAATCCGTCTTCCGTTT
TCCCGTTGATCATATATGCGTAGGCTCCAAAGACGTGAGCTATCTTGCAA
TACTCCTCTTCGTTGTCAATAAAGATTGTATAGTGGTTGGGTGGAATGAT
TCCATAGATGAGTTCGTTTACTTTCCCGATTTTTTTGCCCCCGACAATGC
GGTTGGGAAGTGGAAGATTATGTTTTTTCAAATACGACTCGATGTTTTCC
CGGTGGTTTGCGCTCAGGATGTAAAGGCGGTGATAGTTCGGATTTCTTTT
TACCAGATCGTAAAGATAGGTGTACAGGTTATGAAATTTCGTAATCGTTC
CGTCGAAGTCTATACACACCGCCACCTTGATTGGTTTGACAAGAATCCGG
GAGAGCAATATATGAGCGGATTTGTGCATAGTCATAGACACCTGATCCGG
TGAAAGATCGATAATGCGGGAAATTTGTAAATGCGGCGGAGACGGTTGG
TAAGGTAGCGGATGTATCTATCCATTCCCATGTACTTCTCGATAATATCA
AGGTATTCCGGATTTTCCTTACAAACACCTCTTTCATCAGGTGTTTAAT
ATGAATGGTTTCCCGTCGGGTGAGAAGAAGTTTGTTAAACCTCTCACCC
GCAACTCTTCGAGAATCTCCGGAGATAAATCTTCGAACTGGAGATAAAGC
GTTTCGTCAATGGTCTGCATATTCATAGTTTACTCAGGTATTTTTTGAA
CATTGTATTAATGGTGTCGATTTTCTTGATGTAATCGACGAATTTGACAC
CAAGTTTTCCTGTAACATTTCCGATAAGAATATTGGAAGCGTTCAATGCC
AGTGCGGGAGTCAGATTTGAAAGTCTTGCAATTTCAAACAGCGTCGGGAG
AATATGGTTTTTATTTTCGATTTCTTCCATCAAAATGGCGTCTACGGCGT
TGTATTCCACCAACTTTTTATCCGGGTAGACAGGAATCTCATGATAGAAT
CTTACGTCGAAATCCACCTTACCTTCTCCTATTTCCTCTCGCGCAATATA
GTCGAGCCGGTAGGACTCCAACTCTTTGTATGCCACAAAGGAGCGATAAA
```

FIG. 1B

```
GCCGCATGTAATCAAAAAACACAAATTCTACAGGGGTACGGGGATTGAAA
TAGAATGGTAGGTTTCGATCGGAAATTTTCCGCACCAGCTTCCAGTCCGG
AAGCAACTTATCACTAATGACATTCACCTCATGGATATGACTACGAATGA
GCAGGTAGGGATAATCGAACTGATAACCGTTCCATGCGAGCATGAAAGTA
AATTTTGGTTTCAGCACATTCCAGAAATACTCGAGCAATCTTTTTTCCGA
AAGGAATGTTCTGTAATGAATTTCAAATGTGTTATCCCCTACGCTGGTGG
TAAATTTGTTAAAGTTATCGATATGAGCCTCCGGTTGGTGATAAGGAGA
AGCACTACCACCACCGGTTTTCCATACGGTTTGATGGAAATGGAATAAAC
TGGGTCTCTCCACGGGTCGGGAAAGCTTTTTTTCGGGGAAATCGTCTCAA
TATCGATAAAGACGCACTGAGACAAAGCTTCCGGCGTGATGTGGCTTTTT
TGTTCTCTGATGTAATAGGATATAGCCTCAGCCTCAATCTTCCCTCGATT
CTGCTGAGCGATGCGCTTCAAATGTGGGGTACGGGTGATTGAAATAAGT
GTTTTTTCCCCTCGATTAGCTCCACTCCGTAAATTTTCATCGATCGGGGG
TATACGCTTGCGCTTAGCGTGATCTTCATAATTCTCCTTCAGGTCTTCTT
CGAGGAAATCGTTTAACGATTGAAGCAACTGATAATAAGCTTCGCGGGTT
TCGAGCATGTCGAATACTTGCCTGTGAAAAAACAGAAAATCTCTTATCTT
GCGCGTGGCTCCGATCAGAAGACGGTGTTTCCGCTGGAGGATGTTATACC
TTATGATATAAGTAATCAGCACCCCACTTACGGTTGCCGCAATAGCAACC
CCCAACCAGAAATATACTTCCTGCATGGTTTCTTTTTTTCTTCAAAAAAA
CCTTTCCGTGAAAAAATAGTTTCAACTGGTAACTGCAAACAAACATAAGG
AGAGAGTCATGCTCGACTTTTATCGCTGCTTTGTCAAAATCTTTCAGAAT
AGCTACTTCGCCAACCCAACAAAATACCGGTTTGGCGAAAAGGTCAGAGA
AGCAGTGTTCAACTGGGGAGCACGCGTGGCACACCACGACATCAATTCGC
GAGAAACCGAAATCGTTGCAGATCCGGAGATGGATGATTATTTCAGAAGA
TCATTTTTCTCCGAAAACCCCTATATGCTTGTTAAAATTACCCATCCCGA
TGAATCGATGATAAATACGGTAATATGGCAAAGCAAGCGATATGAAAACT
TTTCCCGCGTCTATCAACTCATTCGCACAATTGCACAGATGAGAGAAGAA
GAAGTCGATAACTACATGAATCAGATCATGCCGTTTATTGCGTTGAATCT
CAATACGATCAATCGCTATATGAACAAAACAAATCTTCTCTTTCAAACCC
CTTATGATGAGTTATACGGTTTCACTCTGCTTTTCAAGTCGGTAATTCGC
ATTGCCGAAGAAGAAAACGAACTGGAGTATCTTGCGAATAAAGATGTCAT
TGATAGTTATAATAAGAAGATTGAGGAATTTTTCAATACCGATGAAAATA
TCGCTACATTTGGATATGTTCTAAAAGATATGCTGTCTCACTGCATTATT
GCCATCGGTATGATCCTGCTGGAAGCGAAGGATAAAACACACATGAAGTT
TTATGAGGAACTTGGTGAGTTTATGGCGGAAATAGGTAAGGTATACTTAA
AAGTGATAGAGGAAGGTGAGAAAGATATGAATGCGCTGACGCATTTATAC
CTCTGGTGTATGATTGCCGGTTGTATCATTAACATGTTGAACGTCAGGAT
TCCGGATGAATTGCGGTTGGCTGCTATCATGGTTGAAGAAACGCTTGCCT
CGCACCAACTGCAACCCTTTATTTCGTTAAACTGAAGAGGGGTATGATAC
AGAAAACAACCCCGTATAAAAACTACAAAAAGTACATGGATCAGCGGGGA
GAAGTGCTGAGACCGCACCCCCGCAAGAAGGTATATATCCCATTTCTTAT
TGCGGAATGTGGAACTTATCTATGGAACGACATAAGAAACATGATGTTTG
CGCTTCCGGGGTGGAAAGATGTGGTGAAAAAATACGGTGTGGGGAAAAA
TCCACCCCGGAGCCTTTCTATGATTTCCTTTCGCTTTTTATCAAGAATAC
TACGCTTTACAGTGATTATAGAACCAAACAAACGCTTTTTCAATCGCGAA
TAGAGCGCATAAAAATGGAAGAGGAAGTCTGGAATCTTTCCAATGCACTG
ATCAATCTGTTCTTTTATCTGAAAGAGCATTATCCCTATTATTTCTCAAA
AGAGTTTGTCTTTTACTTTGACATTAATTTCTATTTCAGGAAGCTCACAT
TTTATGATATTCTTGCCGGGGAAGATTTGCGGAATAAAATCAACGACACA
TTTCAGAAAATGCTCTCTAAAGGTTACACGGTACACCTTTCAAAAATGAA
ACCTCAGAGTAGAGAAGATTATCTATGTTTGCGTTATGCCGAATATATGG
AAGCTATTATGGCTCGAGATGAGTTCAAGCAGGAAATGGATATGAAAGGG
AGTGGGAATCTTTTTTATCTTATTGATGGTTTTAAATGGGGTTGATAAA
TAGAAAAGATGAAGTAGAATTTGTTGTACTGGTAAGGTAAAAACTATATA
AATAAAAGGGGTTAGTTTATGGCGAGCTGGACTTACGATACCACTTCGCG
TATTCTGTCAATTACCGTTAGTGTGGTGGATCTCGACAATAACGATGTAC
TGGTTTACACCGGTAGCAATTATCCTACATGGTTGAGTCCGCCGACCACT
TCGTACGTTTCCGGTTCGTTGTCTCCAAAGCAGTTTGATGTGTATATCAG
CGGTAGCACGCTCAACGTTCAGACAGGGTCTTATCAGGTTGATTTGCTTG
CCATTGAACAGGGTGTGTCGTTCCCGCTCACCTCTTCGGCAAGCTTCACG
ATTACGGTTACGGCGGTTTAACAAATTTTAGGCAAGAAGTCTCCATCCTC
```

FIG. 1C

```
TACAGGGTGGAGATGAATTGCCTATTGACAAAATTCAGTGGTGTATTACA
ATAAAAGCAAGATGTTTAGAGCATACAAATACAGGATATATCCTAACAAA
AAACAAAAAGAACCCTTAGAGAAAACTTTTGGTTGTGTGGGGTTCTACTG
GAACAGGGCATTAGAAATCAAACTCAAAGCTTTAGGAAATAAAGAGAAAA
TACCACAGGTCTTGCCCGCCTTAAGGGTGGTAGGGTCGGAACGACCCGAA
CTTATGCCTGTGGAGGAGCGGGTAGCTCCGATGAAGCAGGAAGCTCCATC
TTCTACAAGATGGAGTAGTTCACTTCACAGAAACTTTATTTCTGTTTTAT
CGTTTTTTCCGTAAAAAAAAGAAATTATGGTTGTAAAACTACCGCTGCA
TGATTTTTACCCTGAAGGTTCACCTTTCAAAACCGAAAACTTTACGGTAA
AAGACCCCACCATTGAAGACGAAGACCGCCTTTTCAACCCGGATCGCATC
AAGGGGGGATATGCTCTGGATGATTTTGTGAGAGGACTCCTTCCCGAAGA
GGCTCAGCGCCAGTACGGAAACATGTTCCTCATTGACAGGAATTTCATTC
TGTATGCCGTCAGGGTGGCAATGTTCGGAGACACCATTGAATTTCGGGAA
AACATCGAATGTTCTCATTGCGGCGCTTCGCTTCGGGAGGCTACCATAGA
CAGCGAGGTTTTTATTCCCGAAAATCGTAAGTTTGAGTTAAAAGAAGGGG
GTTATTTTATCCGTTTTAAGTTGCTTACCGTTTCAGATCAGAATGTTATG
AGAAAAGATCCACTCATGAAAAGCAACTTTCTGACGCGCACGCTTTATTA
CGTAATCGATACGATTGAAAAGAAGAGAGCGACATTACCGACAAATATG
CGCTTATCCGTTCTATTCCTATTTCACTTGGCACCAAGATCAGAGAGTTT
CTGAATACACAATATCCTCGATTTGATATTTTCATCAAATGCGGTTCGTG
CGAAAGCACCATCCCCTTTGAGATGAACGAATCCTTTTTTTGGAATAAGT
TATGATTCAGAAGAAGAGCTTGAAAAAATCGTGGTAGAACGGTATGAAGC
CCGAAGGAAATTGCTTCTCTTTCTGAAAGAACTGGATACCTATTCCAGTT
TAAAAACGAAAATTTCTATATCAGAACTCCGGGTAATTGCCTATATGTAT
ACCCAGCAACTGGAAGAGCAGGAAAGAGAGTTCAAGCGTTTTCGGGGACC
GCACTGAAGTCAAGCGTGGCGTAGTCAAATTGAAGGGTAAGCTGCACGTT
CACAAGACCCGAAGCATCGGAGAAGTCGAGCGAGTCGCCGTTGATGTCGG
CAACCCAGGCTCCGTGGAAAGTCCATTGTTCAATTACGGCACCCTGAGGA
TCAAGAAGCAGAAGCTGGATATTTTCTTGTAAACATCCTGATAGCCGTC
GCGCCCGGTGGTAGGATCGTGGTGTGCAAGTACCCACTGGTAAACCGCCA
TCATCCCCGATTCCTCGATTGGATCATAAAGCGTCAGGTTGATTGGGTTC
CAGCTAATTTTTCCCTTATATTTGAAGTAGGTGTTAATGTGGTGCACTTC
GCCGACGGCAAAGCTGAAATTAGGACGCGCCGAAGCGTAGACCATGTAGG
CGGGAATCCCGTCGATCTGCATGAGGAAAAGGCGTTTCTGCTTGGGTTCA
AAACGCCGGAAAAGCATGTTTTCAACAACGCGTGCCATATCGTTCCTTTT
TCTTTAAATATGTATAAATCGTTTTTCAAAAAAATGACAGGGAAAAATAT
TTAAAGTTGACAATTAACAACAAAACCGGAAAAAATATGTATAGGGTAAA
CGTAAAAGAAGTAGACCTTTCGATTACCCCTGAAGTCGGGACACCGGTCC
AAACGGCGCTTGTAGGTGCGTTCGATCTACCGATTCCCAGCGAACTTCCG
GTATCGGTAACCCCCGATGAATTCCGCCGCGTCGGATCAACCGAACTCAG
TCTCATTGCAGATTCGCTGGTGGGTGGTCAGGAGGTTACGGTGATCAGAC
CGCGAGGAGAAACGCAATCGCTGAATGCGGCATTTGTTGTGGTGGGTGGT
TATAATGTAACCCTTGGTGCCTTCAACGTTTTCTATCTGATGTTTCTGGG
GTATGATCCTCAGAAAGGATATACTGATGTGTCTTATGTAGATGTGCAAT
TGGCTGGTACCCCAACGGATACCATTCTGTTCAGCTACTCGCTGGACGGT
TCTTCGACAACGCATTCACTTACCATAAATCTAAACGCCCCAGTGTTAC
GCTACCTTCTAATATCGTACCGCTCTTTTTCTACTATGAACCTTATACGG
GTTCGATTACGCTCCAGAGTTCCGTTAACTATAGTGGATTAACACTGAAT
TATACGGTCAGCAAAGCGACCACTCCTTGGGTGTATTTTGCTGAATATGG
CACGCCAACATCTTCTCTTACGCTTTATAAAGGATTTTATCTGGAAGGAA
TTGACCTGAACAGCTTTAACAAACAATTTGTTGTATCTATCGAAAATATT
ACGGTAAATAGAGAAAAGGTCAGGTGCTTTATCCTTCGTTTGATGTGGT
GGTACACTTCCGGGATATTAGGGGGGTCAGTGCCAATACCGAATATATTC
GCTTCCGTCAGGTCAATCTCAACCCTGAATCTCCGAATTATATCGAGCGC
GTAATTGGCAACATGACCTTTGAGTTTGACGGTGAGCGCATTGTTACAGG
CGGTGAATACCCCAATCAGGTACCCTTCCTCCGCGTGGTGGTCTCTCAGG
ATATTAAGCAAAACGTCGCCGGGGTTGAAAAGTGGGTTCCGGTTGGATTT
GAAGGTATTTATTCTGTAGGCGACTTCACTGTTATTGTTAACGAATTGAC
CAATGTGTCAATCCCGGTTACGGATTCGGCTATTATTCCGCCCATGCGGT
TTACCCGCATTGAACAGATTACGCTGTCGGGCGGTGCTTCGTTCAGCGTG
```

FIG. 1D

```
ATCAGCAATCAACCGTATGGTTTCAATATTCAGGATTCTCGTCATAGCTA
CTGGCTCTCACCTTTCAAAGATGATGAACTGATAATCGGAACCGAACTGG
TACTTCCGGCTCTGGATGTTTCAACGGAATTCGGAGTTTCAAGTTGGGAA
GAAGCACTTCCTGAATTCAGCTTCCTGATGCCGTTCCAGGGCGGTTCAGA
CGGATACATTCGCGTTGATGAAATGAGCCGGATACAATCGGGCGCGTGA
AGATCACTCCGGCATTGCTTGCCAACTATGAAAGGTTGCTTCCGCTTCTG
ACGGAAGATCAATTCGATCTGGTGCTCACGCCCTATCTGACGTTTGCTGA
TCATGCCGGAACGGTGAATGCTTTCATCAATCGCGCCGAAAACAGGTTCC
TATATCTGTTTGACATTGCCGGAGATGATGATACCGAAATCTGGCTATT
TCGCTTGCTGGATATATCAACTCCAGCTTCGCAACTACGTTCTTTCCGTG
GGTGCGTCGTCTGACCAATAAGGGAATGCGTACGGTTCCGGCTTCTCTTG
CAGCCTACCGGAGCATTCGCACCACCGATCCGGAGACGGGTCTGGCTCCG
GTGGGAGCGCGGCGCGGCGTGGTAACGGGCGAGCCGGTGCGTCAGGTGGA
TTGGGAAGACCTGTACAACAACCGAATCAACCCGATCGTTCGCGTCGGAA
ACGATGTGCTTCTCTTCGGTCAGAAGACGATGCTCAATGTCAATTCGGCG
CTCAATCGAATCAACGTGCGTCGACTCCTGATTGTTATGCGCAATCGGAT
TTCTCAGATTCTTTCCAGCTACCTGTTTGAGAACAACACCAGTGAAAACC
GGCTTCGTGCCGAAGCGCTGGTGCGCCAGTATTTGGAATCACTCCGTCTC
CGGGGCGCTGTAACCGACTATGAGGTGGCGATCGATTCGGTTACCACACC
GACGGATATCGACAACAACACGCTCCGCGCACGGGTTACGGTGCAGCCCG
CCCGCTCGATCGAATACATCGATATTACCTTTGTTATCACGCCGACAGGC
GTAGAAATCACCTGAGAAATAAACCTTTCAAAATATAAACCCGCCTATCA
AAAGGGGCGGGTTTTTTATTTAAAATAAAATGAAGTTTAACAACTGGGT
TGAGTATACCGACGACGTACCTCCGACTTGAGTATTACCTTGAGTACGAAA
TTCGCCGGTGGAGATATCAGTATTGTGATCCGTTCCCCACTTTTGAAGAT
TTCAAAGAGGCGGTCAAAAAAGCCCCTCGAATTATCGTAACGCCGGAACT
TGATAAAATTATAAGAAATCGTTCTCGAACCCGCACGTTTGACGAACTGC
TTGCATTGATTAAAACTTACCGGGGATATCCGAAATTTCGCAATGAAAAG
ACGCTTCAGGCTATATATGACGGGTTTAAAAACAATAAACCCATGAAAAT
GCCGATCGTGTTGGAGCTTCCCGACGGAACATTACGGGTTATGTCTGGAA
ATACCCGTATGGATGTGGCATTCCAGCTCGGGATAAACCCCAAAGTTATT
CTGGTGAAGGTTCCTGATAGGTGCCATTAATCCACACTTTCCATATCACC
ATACTGATCTACAATGTAAATCTTGTTGCAGAATTCTTTAAATTTATTCA
GCGGAACCACTTTGGGGTTGGTGATAGCCCATTCGTTTACGATAAATGCG
TGGAGACGCGATCCCATTTCTTTCAAATCCCTCTGGATTTGTTCAACTTC
ATCATCCCATTCCCCATCACTTATCTTATGGATTCCTCCACTTGGTACGG
GTTTGCCAAGATAGTGAAAAATGAAAGGGTGGGAGGAGTCGTTTTTAAGC
CGCTGCAGGATTTTCTGACCTGCTTTCGAGGAAACGCTGAACATTTTCTT
TTAAATAAGATTCATAATCTTCAATTAGCGGAAAGTGTTCAAGCTGTTTG
AGCAGGGTGTTAACTTCATAGGCAAAACGAAAGCGGGAGTTCTGGTAGAA
GTCTCCGATTGTTACCGGAATTCTGAAATCAGGAATGTTTTTGATTTCAT
TGTCTTCAATATTGAAGACGAAATAGCAGTGAATGAGCGGGTTTTGAAGC
TCTTGCTTGATAACATAACGATCGAACATTTTGATATATTTCCAGATCAC
TTCCCGGTTGTTCAAATAGATTTCTTTTGCCCGATTCGGGAGAAACTTTG
TTATGAAGAAATCGTCAAGCAGCTCTTCGATCTCACTTAGTGCACTGGTC
TGCTTGTTAATAAAGCTTTTAATTACTCCGTTGAAATCCCCAAGCACACA
TTCGGAGCTATCGTGCATGAGCACACAATAGCCGAAAAGCGCATCGCTAC
ACACTTCGCGAGCCACGTCGTAAACAATCAGACTATGTTCGAGCACGGAA
TAAAAATATTTTCCTCCGTTTCCCTGATAGCGGCAAATGTTGGAGAGCCT
TGCAGCAACATCTTCAATGGTAATACGGTGAAGGCTCGGGTGCAATTCGA
GTTTCATGGTGTTATGACTGTTTGGTTCACACGACACAATCCTTAAAGAG
GATAAGGTTAAAAGAGGTTCCCTTCCTTCAATTAAAATTCAAAAATGTCA
ATATCAATGTCAAGATCAGTGTCGTCTTCGGTTTTACGTTTTCGAAGAAC
ATAATCGACGTAATCTATATGGACCACAAAGTAGGAGGTATCGTAAATCT
GAACCAAAATCGCATTGACAAACCGTTCAACATACTTTTTGGAGGAAAAG
AAAGCATTTATCAAAATATCTAACATCATCTTATAATACCTATCGTCTGT
GTTCATTACATTTTTAACAAGTACATCTTTAATTTCATCTAATATAGATT
TGTTTTGAGGTATAGTTTTTATTGCTTGATCTGTGATAGCTTTCAATAAT
TCATCGTCATTAAGTATTGTTATTACAGTTTTCCATAAATTTGTAATCAT
ATTGCTGTTATTTGAAGAGAAAAAGTTGCGTGGGTCACTTAAATGCAAAA
```

FIG. 1E

```
CTACACTTGGTATAAATAAACGGTAAGTATTACTTACATTATCTTTTAAT
CCATTATCTTTTAATCCCAGAAGAGATTTATAGGTATCGATAATTATAGA
AATTTTGTCAACATCCATTATAATATCTTTGTATTTAAGTATATTTTCTC
TGGTGGCGTCATTAAAATCTCTTGTCGGGGTACCAAACAGCGTTTTAATA
ATCTCATCTTTCAGTTTAGGTATAATCTCATTTAAAATTTCCTCTCTTTT
TGATTCGTATTGTTTTACTTTGTTTTCTATAACTAAAGACGCGAGAAATG
TAGAAAAAAGGTCAAATACTGTTTTTTTGGTCTTTTCATTATTAGGTCTC
ACCAGATCTTGATATTTATAATCTATAAAAAATTTCAAATTGTTTTCTAT
TTTTTTTCTGTTTATGTTAATAAATTTATCTCTGAGCGTTTTATATACGA
CTTCGTTTTGAAGATGGAAATCTCCCACAAGATCTATGGCTGACGAACTT
TCTGGTGGTATGAATTGAAGTTTGACGTTCTTCACAAGGGGAGAATCCTC
TTCATAGTTGGCTTCTGCAATTCTAAACGTTTCGGAGCTAATTATATCTG
AAATAACTTCCAGTTGGGACTCTCTGATAAAGAAGGAAATAAAATCTTTT
ATTTTATCTTTCAATTGATTCCAGAGATCGTAACCGGGTACGTATTCCTG
AAAATCTGTATTCAACCATATATTAAGTACTTTTCCCACACTTTCTATTC
CCTCCTTTATTTCCTTACTATTAACAGATAAACCAATGACTTTGTTAATA
ACATTTTGTGCAATAGTTTTAACTATACCCTCAATGACTTTTTCATCCAA
ACTCTGAGAGGGTTGAAGAATATAGATGTTAGATACAAGGTTCTGGAGTA
ATAGTAGGGCTTCGGGGGAAACATTTTTCATGAATTTATCTAAAGTGGAG
TAAAGCTCTTCGAGTTCTTTCTTTGCTTTATCACTGAGACCGATTATTTC
CGCTATTTTAAAGTTAATCTCTTTAATAATGGGCAAAGGTAGCGAAAGTG
TTTCGAGATTTTGATTGAACTGGTTTTTATACTCTCTGATATCGGTTGAT
TTGTAAGTAATGACATGGGCAATGACGCCGCTGGTTTCAATTGTTCCGGT
AAATGTGGATACTTTTATTTTATGGTAAAAGTCATTTCTCGGGTGTATAA
AGAGAATAAAAACATAATCATGTTTATAATTATCCCAATAGCTATCGTTT
TGAGCAATACAGACGGTGGTACTTTTGTTGGTGTTGGTTTCGGTTAACAT
TTCTTTGATTCCTTGATAGGATATTTCAGGTAAAAGTCGAACAAGTACGG
CATCGCTATCTTCCATTTCCGGTTTATTATGATAGACAAGTTCTATGTCC
CCGTTCTTGATATATTTCTGACGGCTTCCATGGTGTTGTTCCAGCGATC
CAGGTAGCGAACCGTATAAGAGGGGAGGTATGTATCGATGATCTGCTCGA
GATCGATAAAGCTTTTAATAAACTTGAACTTCATAGAATGAAGTTCGTCT
TTTCTTCCCTCCTGACTCAATTTTTTATTGATAACAAAAAGAGCCGCCAG
TTTATCTACATTGCTGAGCATGTTATGATAATAAAAACGATTCTCCACCG
GAATATGACTTTCATCCGATCGATTTGTATACATTGCTACAATACCCTGT
AGAATAAAAACCTGAGCCTGCTCCGGAAGAGGTGTGTTGTAGGTGGTTTT
TGCCGATTGCATAATTCGATCGACAAGTTCTTTTTTGACCTTATCTTTTA
CAAAACTGAAAACATACTTTTAAGCTCTTGCTCTGTAGCCGTTTCCGGA
TCAATTTCTATATTGAGTGTGGGGTCTTCGTTTATTTTTTGTGCCAGCTT
ACGTGCAAAATTAATATCGAATTGCATATTTGTAGACTTTTATTTTAAAT
AACTTTTCGTTTTCGGGTATAAAAAGGTCTGGTTTTGCTGGTGGATTCCT
CCACCTGAATGTTCAGCGAGAAGTTCGGATCACGCGGAAATTCCTGATAG
TTTTCCATATGCATTAAAATTTTCAGGTGATAGTTTATTTCCGCCACAAA
TACCAGTTCATCAGACGACGGGTTGATCATACGATCGGAAATTCCTTCTA
CGACAATATCCCATACCGCCGCATTGTCTTTGGTAAGGATAAGATCGGGT
CTTACGTTTGAGAGAATCTGAGTGATCTCGCTTTCTTTTGTAAGATAATA
AAAAGCACGATAGTTGACTTTATAGGGAACCGGCACCCTGTACTGAATGG
TGGATTGGTGTTGATTTTCCGTAAAGGTAAGAAAAGCAGGAAAATTCTGT
ATAACTTCGATTCCTTCTCGCATGACAACAACGAAGGGATACTCCACTTT
GAACATATCCGTTACCATCGATTTCCTTTGCGCCTGAGATTTGTCGAAAA
TAATGCGCGGTTTGGTGCCAAGAGCCTTTTGATAGATTTCTTTTGCAAAA
ACTACGGCAAAGTAATCGGCTGTAATAATTTCGTTCATTCTTCTTCAGGG
AATGGAAGTTCTTCTTCACCACCACCCGTTTCTTCTTCGAATTCTTCGAA
GGCTCCGCCAAGATTAAGTTCGCCGCCCAGTTCTTCTCCGCCTTCCGTTC
CGAAATCGAATTCCGTTCTTCCTCTTGGCGATTCGATCGGGGAGCCGCGC
TCGCCAAGGAAGTCGGCGGGGGTTGTTTCCTCACCGAATCCGCCCGTGTC
GAAAAGACCGCCGCCACCGGCTGCTTCCGCCACTTCCTCCTGGGCTTGA
GATCGTAGGGAATCTGAAGAATGTTACTATAAATCCAGTCTTCACGAACC
CAGCCTTTGAGGCGTTCGGCAATACCGATTCGCTGCTCAATCACGGCAAA
GCGCTCACCTTCCACAATCGAATTCGAGCGGTTCATTACCAGGCGGAAAT
CCTGATCGGCAAACTCTTTGTTCATGCGCACCATGCGTTCGAGTTCTTCC
```

FIG. 1F

```
ACAAAGAACCCCTGAATGCGTTTGATCGTGTTGTTGAATTTGATATCCTG
AGTAGCCAGTGTGTTTTTAGCATTCACGTCTCCTTCATAACCAATGAACG
CCTTTGGTACCTTGAGTGCGGAGATGAGTCGGTTGAGCATGTATTCCACA
TCTTCAGCAAGATCTACTTTGGAACCCTGAAGAATATCGATTTCCACCGC
ACGACGATCTCCGCGCCGGGGAATGAAGTAATCTTTGAGAATGCTTTCGA
TAGAAAAGTAGTTATCGATTCCAGAAATTGATTCTGATTATTTCTTACC
CAATAGTCTCGCTTATACTGCATGGCAATATTGGTCAGATATTCGTTGAT
CTTGTCGGGCGGCACGTTTCCGACATCTACGTAAAACACCCGTCTATCGA
CACTACGAACCACACGGTAAAGCATGAGCGCATCTTCCATGAGTCGAAGC
TGGTTCCATATCGCTCGAGCACTTTCAAGGTAGCTTCTACCATAGGGAA
GAAGTTGGTGTCGATTTTGTGAGAAAAGTGAATGACATCTTCCTCAGGAA
TATCTTCGTTAAAGTATCCGCTTACAACGTTACGGTAAACGTCGGTAATA
ACATAATACCAGGTATCCGTTTCGGGGTTATATCGCTTTGAGAAAATGTA
AGGAGAGACCACCTGAAATTTTTCGATCGTGCCATCCGAACCTTTTTCAA
GAATATGAAGAAACATATCTCCGTATTTGATCATGTTGCGAATGATAGGA
TAGGCGTTCTTTTCAATATTTATAACATAATCCAGATAGGAGAGTATTGC
TTTTGCAAGCTCAATGTCTTTTGTTACCACATCCACAATATTACCGTTTT
CGTTGGGAATCGTGCATTCATCTGCAATGATATCCAGCACCGTGGAAATA
AGCGGATCGGTATAATCCATGCGATCGTACATATCGTAGAGGAAAAACCG
GTTGAATTCTATTCCTCCGTAGAACCTGCTCGCATACCCCGCTGTCGCAA
ACGGGTGGTACATGTTAATCGGAATCATGGAAGAGCCACCCGCACCGTGC
GGCGCTCCCATACCATACATCGGAGAAAGGAAATTGGTGAAGTTGACAGC
TTCGTTCAGTTTTTTATATTTTTCCAGAGACGGCATATTCTCCACTTTTT
TGTTAAATAACATTAACCTAATAATGTACCAAATAACGAAATGGTTTCGT
TTATTTAAAAGAAAATGACCTATCGGGAAGCCAGAGCACTTTTCAACAAG
ATCAAAACACTCCCTGATTATAGAAACCGCGTTGTCATTCGGATGTCTGA
AATCAGAGAAAGACCCACCTTCAACCCTCGAGGACAATATAATACCACAC
CCCCCGGCACTTATGCCTATCCACTTGGCTTCGTACTGGACATCGGGGGT
GGGGGCGAGGATTTTGTCGATTTTATTGCGGGTATTATGCTTTTGCCCTA
CGCTTCACATGCCGAATGGGTACATATCTTTTACATAAAAGACATGGGTT
GTTTTCTGAATCTTGGGGATAAAGAGGATACAGAGGAATTCCTGAGAAAG
TATGCAGAGAAAAATCCTTTTATAAATACTTTAATAGAGCACATTCGCAT
TTATCAGCCGATAAATGATAATACGCTCTTTCCCATTCTAAACCGCTATC
TTGTCGGAATGCCTTATGAAAACATATCAAGCGAAGAGTTTCACCAGAGT
TTCAACAGGGTTCTGGAAAAGCTGAAAGAAGGATACATAGACATTTTCAA
AGGTGTTTACCAGCATATCACCCCAGATGACGCACCTGCTGTTGCTTTCG
TGAACGAATTCAGAGATTTTATTTCCAATCTGGGGATTATCACACTGGA
AAAAATATACTGGAAGTGGCAATAGCCCGAATTGTGTTCGCCGTTTTCAG
ACGTCATGAACTTATAGAAATGATCGAAGCAATGATCGGTAATGCACCGG
GAGAAATTACCTCCTCACGCTTTATCAACTATCTTCCGGTTTCTGATTCC
AGAAGTCTGAGTGCATTTACCCGATGGTTTGCCATTACACATCGCCTGTT
TTACTATGCTTTCAATAAAGGGGTAATCAGAGAGCAATATCTTGAAGAAT
CGGCTACGCTGTTTGTGGATATGATTTTCACCATTGCCTTTTCAAAGGAA
AAAATAAGAGCTGCTATGGATACAATGTTCAGAATGTTAATAGATCAAAT
CAAAGATAAAGGTATACCCAAATCCTATCGGGTTTACAGCGAACTTGGTT
ATTGCGGAATATACGATCCGGGAACCGGCGGTGTGCATGAAGCCGAACCT
GCTCAGGTGGTCTGGTGGGATCCCTCCGTGGTGGAATACTACGGGGCGAT
TCCCAACATAGGGATGCGAGAACGTAAAATTCAGAACCTGAAGGATTATA
TAACCGCCCTTGACGTGGTCAGATTTTTTGTCAAGGTGTTTATATACAAT
AAACATTTACTTACACAAGAACCCGTTTGTTTAATCAATCGGCTGAGGA
TATTGCTTGGCATTTTAAAAGAATATTTTATAAGAAAGAATTCATTTACC
TTTTTGAAAAGGTTTGCGGATGATTAGTAGATTTATCAAAACAGGAAAT
GTAAATCAGTTGATGTCTCTTATTCATGATGTACTCATGTTGCACCTTAG
AACAGATCTCCTCGCGAGGGTATCTGCAGTTTATAGATCATACTCTCTTG
AAGATTATTATAACGAAGAACTCAAACATATGAAGAGGGTGGTAGGTGAT
ATTGCCGATAACATGGTTGCACTTCTTACAAATTACGCCGTGGATATTCT
GACCGGTAAAGAGCAGGTTAAGGATATAGACAGCGCATTTCCCATTATC
TCGATCATCTCAGAGAAAACTTCAAGAATTGTTAGATAAGTCTGCTTTA
GAGTTGCGCGGAAAAGCAGGTACAAAAACACTATTGCAAAGATCTTTAGC
AGTAGAGTCGGGGATAGAGTCTATTCTTTCAGGAATTATCTTCATGAGAA
```

FIG. 1G

```
AGTTTCTGGAAGCTTATGATTCGGATAGAGAGAAGATTGAGGAAGCGTTC
AGGGTGGTAAAAGAAAGACTAAGGGATTAAATACTGGTAATTGGGATTGT
GTGGAATGGGTATTTTTGAAAAGAAGGTGAATCTGAAAGAGGGGTGGATC
CACCTTACAACATTTCCGTAGAAAGAGGCAAAAAGGGGAGAATGCTATGA
AGATCAAAAAGGTAATTATAGCGCTGCTGTTTCTACTCACAGCCTTCCAG
CTTGGGGGATTATGGCATTGTATCTTTTTCCGCGATAAGCGCCTGTAGC
TCAACCGGAAAGAGCACCAGCCTTCTAAGCTGGTGGTTGTGGGTTCGAGT
CCCACCGGGCGCTCAGGTGTAATCAGAAACAAAAAAGGGAGGGAGTCAT
GACAGTCATATGGGCAATCTTTTTTATAGTCATGGTGTTGATGGAAATTC
GAACCTTTCGGGTAAAGAGGTATCTGGAAGATCACTCCACCCGACAAGGT
TCTTATGCAACCGAATGGTATTACCGGGTGGTGAATGAAAGGAGGAACG
TAAAAAACCGGGTTCGCAATGGGATTTGTAAGAAAAAAGAGCGCCTTAT
TATCAAGCGTGATTTCGACGCGCTTAAATTTGAAGACGCGTTCGATCTTG
AGATCGTGTTTCACGTCAACCCCGAAGTTGAAATTATTGATCGGGGAGAA
GACGTGGTTGTCGTATATGCCCCGCTTGGCATTTTGGGAAGCGGGGAAAC
AGTTGAAGAGGCAATGAATAGTTTGCTTCTTCAGGCTGTAAAGGAATATA
AAGAGAGCACTTATGAAGGAGAGCGAGAGATACTTCGTTCCTTTATAAAG
TTGTACACGTCGTTTCTCCCGCCCGACTGGAAAGTCGGGTTTGAGTAAT
AGGGCATTCGTCTGCTCTCATGAGTAACCGATAACCAAACAAACGGAGGT
AGCCATGAAAGAGGTCAGCGTCACCCATGTCGTCGTTTGCCCCTTCTGTG
GCAAGACGGGCGAAGTCACCATTACGGCGGATGGGAGTGGTCCCCGCCTC
GTGGAAATGGAGCGCATTTGCCCCCACGTAGATACTGAATACGACGAAAG
AAAGCGGGGATTTACGTACATTTCAGTGACGGCGAAAGGGGGACTACG
TCTTCCTATACGCCCCCTTGCGCTGTACGTCCGGGAGGGCGATCCCCAT
CTGATCGCCCGTGCGCTCCGCCGGCGGGGCTTTAAGGTACGGGTCGACGG
GCGCCACATCATCTTCAAGACACCCGTCTACCCGTATCCGGTGGACTTGG
CGCTTAGGCAGTATATGCTTAACGCCGGGCGCACGGTCTCATACAAACAC
GTGCATCTGTGAAGATTATGTGAGGGGTTGCGCGGCGCTTGGCATTTTC
GTATATTAGAACTGTCACCAACCAAACAAACCAAGGAGGTAGCCACGAAA
GCGATTGACGTTCTCAAGACATTCCCAGCCCCGGACAGCTTCGAGGGCGT
CTATTACTGTCCGGAGCATCCAGAGGTTGAAATCAAAGAAACCGTCCGTT
GGACGGAGGTTCCAAACCCCAACCCCGACGCCCGCAACCCGGTCGCAGTA
CACCGGGTTGTGGACCGCTGGTGCCCGGTCTGCGGGAGACCGGCTGTTCT
GGGAGCTCGATCCGCATGACGGGTGTTTCGGCGATATTCGCAATCTTCGC
AACGCCGAAGCAAAGCTTGCCCGCCACATTTTAAAGTAATTTCCGTTTAT
ATTTACTTATATTTACATAGGGGTTTAGAACAAACCGGAAGATATTATGA
AGTGGTTTAAACGACTTACGACGCTGGAGATTTCCCTTCTTATTCCTCTC
TTTATTTCCTTGAGCGTTTACTTCTCCACTCAGGGAGTCGCCAAATTTGT
GGCGCTTCCTGTGTGGGTGGTGGCACTGGTAATAGCGGCTATTGACGTGG
CAAAGTTCGTAAGTGTGGGTCTCCTTGTTACCACAAGGGGATGGCTGCTC
AAAACAATTCTGATTCCGGTCATCCTGTGCGCCGTCTTTGCCACTTCTTT
CAGTTTTTATGCGGCACTTGTTTATTCACACGCGGAGTCGGTGTCTTCAG
AGAAAGTTGAAAACATCACAGAAGCTACCATAACTCGTGAAACCGTTCAG
CGTCAGATCGCGCGTTATGAGCAGCTTCTTGAGGAGGTTGACCGTTCTAT
TGAAAATATGAACAACACAACCACAGAGAGCATCTGGCAAGAACGTCTCC
GCAAGCGAGAGTTGGAGTCGCTGGTGAATCGAAAGGAGGAGTACCTTGCC
GCTATTGACTCTCTTGAAGCCGTTCTTGTAAGCAGCACGGTGGAATCGAA
TCAGCGTCAAAATCTATTTTCCTCAACTATATTACTCCCAACTTCTATT
TCGTGCTTCTTACGATCATTTTCGATCCGCTTGCCGTTCTTCTTTACGCG
CTGTTTGTGCGCATGCTGAAGCAAATGCGCGTGAGGAAGATGAAAAAGA
AGTGAAAGAGGAAAAAACGGGAGTGGAGGTTGTGAAACCTAATGAACCCG
AAGAGCAGGATTTCGTTTCCAAGCAAGAGGAAGCGGAGCAGCTGCTGATG
GATAAAGTTTTTCAAACCAAACGCTTTGCATTTGATCCAACCCGAATGCA
ACCCCAGAAGGTGGTTATACGGGAAAAAGGAGGAGGTGATATGTACATT
GTAAAAAAGTCAGGATATTGAGTGAGACGGCAACGGTAATCGTCGAATA
TTCAGATTACAGGGCAAATGTATGGGTTGGGAAGGGAATCTCCTGTAGAG
CCTTTCTCAAAAGCAAAGAGGTTAGAACAGGGGTAATCCCTTACCTGACC
ATTTACAAAAGATACCCCAGAAATGGAAAGCTACTGGAAGATTTCTTAAA
ATCGATGGAACAACAATATGTACAACATACGCGTCAACACATATAGTGTA
GGGCTGCATTCGCACCAAGTTCCGATTCTCAAAGCAGCCAACGATCCTTC
```

FIG. 1H

```
CATTGTTGATCACAACATGTATCTGTACATTACCGCCCGCCACCCCTTTT
TGCGGCTCAAGATAGATTTCACGTTTAACGGCAACAAAAGGGTGGCGTCA
TCGGCAATTATTTCCATGCACAACAGGGGGAAAGATCTGATTAAAGAATA
TAAGCTGTTCGATCTTGATATATACAAACCGACAACTGCTTCGTATAAAC
CCTCAGATAAGACCAAGACTGTAAAGTTGATTTATAACTTTTAAATGATA
ATAGACGTTGGGTGATTATGTATTGTCTTCGATATAAAATAGCAGATATA
CGTTGTGCCGCCCTTAACGTACATGCGTCGAAAGTGGCACCCCCTCCTA
TGTAGACATAGTGATTAAGGGGGTTTTTAAGATAAAAAAGGGGCGCTCA
GTATCGCGGTTCATCCTGATACACCTGTGGGAGACATAAGGTTTGATTGT
CTCATGAAGGTTTATGGAAGCGGAGATGTGTTTGAAATACACTGTTTTAA
AATCATTTTTCATTTGAATGATATTAAAAAGAGGTGTTATCGGAATCTTT
TAAAGTTGGTTATAAGTTAGTGTAAATATGTGGGTTCTAAAACGGCAAGA
GCAGGAAATAGGGATAAAGAGTCAGGATACGCCGATTCTGGCTCCTATTA
ATGCTGAGGTGGAAATACACATAGAAAGTATATAGGCGGATTTCCGAAG
ACAAAAGGCTTGTATGCAGAAGTGATCTATGCGTCAAAATATAACAAACC
GGTTGTTTTGCGCAAACCTTAAATGCGAACTACGAAATGTACTTATGTT
CTATTGGTATTTATAAAACGTCGGAAGACAGAATAACATTATAAACATC
TTAAAACTTTATGTAAACCTGTAACACCATGTACGTTTTAAAAATTAAAA
AATACAGCTTTCATACCGGATTTTACAAAATTCCGGCAAATGGTATGGTA
CGGGATCCTGAGAATGGGTATATTGATCTTTGTCTCAAAACGGAACTCCC
GTTATGTGCTTTCTTTGTAAACTATGAGGAAGAAGATGAACCGCGCGTTT
TTGTTATAAAGAGGCTGGAAAAGATCCTCAGGAAACTATCGTAGAATTT
ATTGTAAGTAAAAACTTTCCCATTAATAGGAATTTCAACATAATCAAACT
GATATTTGCGCCATGATGGTTGTTGCCGGTAGAAATTACAAGCTGGAATC
CAGCGAAATGCTGATTCCCAACGTGGTGGTTACATCCAAAAACCGAATCT
ATAACGTTTCGATATGGGTTATAGACATCGGATATTTCTATGCGGGAAAT
GAACGGGGGTATCTTGGATTAAGATGTGGGGTTGAAAAAACGTTTACTGG
CTTTAAAATTAATGTCTATAAAACCACAAATCGCGGGAAGTGATATGTAT
ATGATAAGATTGAAATGCCACGATTATCCCAATACGGTCAACAGCAAAAA
AATGGTTAATTACAAAATAACTCTGAAATCAGAACACCCATCAAACACAC
TTACCATTCTGATAAACTGGGTTTCAACCAATATCGAAAGATATGGCAAC
CATATTATGTTTCAGCGTCCCGGTTATTACCTGAGCGCTACGTTTTGTT
TAAAAAACATCTTTATTTCAAAGGCGGTTACCATCTACAAAGCTTTCGAC
TGTAAAAAATGTAAACCGATATGTATCTCATAAGACATAGTCTCAAAAAT
AGGGTTGCCTATCCAGAGGATCCTTACTACAAACCACCGGTTTCCACCGG
CGGGAAATGGGTTACGCATCTGGGAAAGCTTTGTAAAATAGAATTTCACG
CACTGGTTTTGCAGAAGGAAATGTGGGAAGAGATAAGAAGTAGGAACAAA
TCACTATTCAACGATCGGATTCGCAAAGTACTTTTGTACGATACTGAAGA
AAACCTATTTGCCATATATAAGATAATCTGATGTTTCTGCTTAAGACAAC
ACCGCGCAATCACAATCCGCGTCAGGTATGGTTGAAACTACCTGACCAGA
GACGGGTGTTTTTTGAGGTTTCCTACAGATTCGTAGAAATTTCACATGCG
ACTGGAAACCGTGTTAACAGAATTCTATTACAACTCCTGTCGGAATATCA
TTTTACATTTGTAAAAAAGGCGGACTATGCTGCTGGTCAAAAACAGCCAC
ATCGATCCCAATGATGGTGAAATGCGGCTAAAATACAGCCGCGTTATGGA
TGTTAAAATTTATCTTGGGCGTTTGGGAAATACCCAAACCCCCGAAGGG
TGTCTTATAGTCTGGCACCCTTTGATGAACTGTTTGAGTTTGCAAGCTGG
ATGTCACTTTTGATGATAGAAAAGCACATAAACCGGAAAAGTAATATGT
ACGTGTTTAAAGTAAGTTATTTTATGAACGGCGAGCCGATAGGCATACGT
ACCCTTTCAAGGTGGGTGCAGGTTGAAATTGCCTACTGGGGTAAAGAAGG
TACACGTTATAAAAGAGTTACCGGTGGGAGATTTGAGGAAATGATTACT
GGTACGAAATAGAGATAAAAAAATAGAATGTGTCATTATGTATCTTATGA
GAATGAATAAAGTGTACCAATAACACCCATTTCCGGGAGGGGAGTACA
CTGAGCGGGCATAGCGAGATTAGAATAGGAGCCGCGTGTTTTCGCGCCAT
GCACTGGACTTATATAATAAGTGTACACATACCGAACAATCAGTTTAGTG
TTTGTTTAATGGAAAAAAGAGAATTAATAAACGTATTTTTAGACAAGCAT
ATAAAATGTACGTATTAAGTACAGGTGTTGATGATCCACTATTTATGACC
GGAACTTCTACACCGGGTGTGATCACTCCCAAAGAGGGTTTTTATACAAC
```

FIG. 1I

```
CCAGAAGTTTATTCGTGTGTGGTTTTTTGTACGCTACTACAGTGTTCCCC
CAAAATCCCACAACGTTGTACATTTTACCAGCGCCAACCATTATAAACTT
ATAAAAAAATTCTATTATGTATACTATTAAATTAAACAAAGGGGTTAAAA
ACAACGAATGTTTTGTGGTTGTCGGAAACGAAATTCTCTCCAATGACCCC
ATTGTAAACTATAATATATTTAGCAAACAGGATGATCTGTTCGCATTTAC
AATTCAATACTGGCATAGCTTAAGAACACTGGGACCAGAAGGCACACCAC
TTGATCTGGAACTGACGTCTAATGCGATAAATCTTGGAAGGATTTATAAC
GAAGAAGATGAACCCTTCCCGGATTTCATTTTTGAAAAACTGATATATAA
AGACTTTCAAGAAAGCTCTAAATTTGGGTGGTGATGTATATAACAATCAG
AAAACAAATCGAATCGGTAGTATACGTAGAACCTGAATTGCTATATCATA
TGTTCGTAGAAATGCTGGGATACGATGTGGTAGTTTATACGCTATATGCC
GCCCAATGTACCAAATATCCCGATAATAAAACGGGGGTGGTTAAGATGTT
TAGTAAAAGAAGGTGTTTTATGTGCTGAAGGTGATAAAAGTGAGCAGGA
AACCTTCTTTCTGGAAACGTCTTTTAGAATGGGTAAAAGCTATTATCAGG
GGGTGATATGTATTACCTCAAGTTGCCGGTAGCAAAGCACTCACCCTTTG
ATTGTATCTGGGTGTTGTTTATGATACATTACTTTCCTGTAAGTGTTTCT
TTAAACACCCCGAACGCTGTATATTTAACATCAAAAATTTTAAACTTAT
TAAGAGAATTTATCAAAGGTTATAATGTGGAACAATCAACTTTGGGGTGA
TCACAATGATTGTACTTAAAACACCGATACTCAGAGTTACTTCGTGGTTA
GATATTAGAACCGTTTTGTACGTTGAGGGGATTGGATTTGTTACCAGAAT
CCCCTGGATGTGGGATATTATCTTTGAAATTGTTTACGTTTATAATAAAA
TTGAGCGTAATGCTTGTTATTATACCAATTACATCAATTTCACTTTGAAT
CTTGATTCAGTAGGCGGTAAAGCGTTTGCTGTGTTGAAAGGGGTCGCACC
AGAACAGGTTTTTTCCATTATTATGGTGGTTAGAAGATAGAAAGGTGTCA
TGTTCGTATTGAAAATGCGTGTTGTCGAAAAGATTAGAGATCATTATGTA
CCTTCCGACTATAGATCTTTTATACGTCTTGGTAACTATACTTGGTTCTA
TCTTTTTTATCATGACACCCATGACATACCGTTGACACCGGCGCATAATA
CCTTCCCACAAACGTTTGCCGCCATGCAGACGCTCACGGTCAAATGCAAG
CTGGTCCTCTCTAAGGAGCAGCGAGAAGCACTTGACACCACCATGCGAGC
GTTTGCCGCCGCGTGCAACGATGCAATCGCCGTCGGTCGAAGACTGAATA
CCGCGTCGAACATTCGCATCCACCGCGTCTGCTACAGCGACCTCAGAGCA
AGGCATGGTCTTACAGCCAACCTTGCCGTCCGTGCCATTGCCCGAGCAGC
AGGCATTCTCAAAGTCAAGAAGCGCCAGTGCAGTACAGTACGCCCGACAA
GCATCGACTACGACGCCCGCATCTTCTCCTTCCGAGAAGCCAACAAGCGC
CGTGGTCTGGAAGACGCGGCAAGGAGACTACTACATCGGTATCCACATTA
ACGTAGAGACGCCCCCACCTGAAGATGAGCACGGGTGGATTGGCGTCGAC
CTTGGAATCGCGAGCATTGCCACGCTGAGCGACGGCACGGTGTTCAGCGG
CGACCAGATAGAGCGGGTCCGTGCTCGGTATGAAAGAACCCGCCGCTCCC
TCCAGCGAAAAGGCACGAGGGGCGCAAAGCGCGTCCTGAAACGGCTCTCG
GGAAGGGAGCGGCGCTTCCAGCAGGCGATCAACCACACCATCAGTCGCCG
TATCGTAGACCGGGCTATCGCCGAGGGTAAGGGTGTCCGGCTCGAAGACC
TCAGCGGCATTCGCAAAAGTGTGCGCGTTCGAAAATCGCAGCGCAGAAGA
ATCCACCGCTGGGCGTTCTATGATTTGCGCATTAAAATCGCGTACAAGTG
CGCCCTTGCCGGGGTGCCCTTCGAGCTGATTGATCCCCGATATACGTCTC
AGCGCTGTCCGGTCTGCGGGCATACCGAGAGGGCAAACCGCAAGAGCCAG
AGCAAGTTTGTCTGCCGCTCGTGCGGATTGGAAGCGAACGCCGATGTGGT
TGGCGCAATTAACATTGCACTCGGGGCGTTGTCAACCGTCCCGAAGTAG
CGCCCGATGATGTCGAAGCGGTGTTGCATGGTCAGCGCCGAACTGAGACG
GAGGGCAGCTACAAGCCCACGACTGAAGTCGTGGGTAGTTGATGAATATC
CATAGCCATTTATTTAATCAAAAATGCTTCTCGAAAGCCGAAAAGGAGAA
TTCCTACAACAGGAAATTCTTCGGTTGTATAAAACCTATGGGGATCGTCT
TCTGGTAAGATTTTCCAGCGCCGAACGCGAAACCTTCAATCCCGACGCCG
ACTATTTCACAACGCCTATCGGTACTTACGCCTATCCTGTCGGTGCTATC
TTCCACATTTCGGAAGACGATGTGGTGATCGATCCCGACATGTACGGGGT
TTCCGAAAGAAATATATTTATTTTTTTGTGGCAAGTAAAGATGCTTCTT
GGCTTAACATATCCTCTCAACATCCGGCGTTTGAAATTCCCCTTGTTTTG
TACAACCAGTTCAGAAATTATGCCGATCTCTATGACGTTTCACTGGATGA
TGTTTTCCGGAATCGAAACAGTATGGAAAGCTATCTTACCTACTGGTGCT
TTGCCATTGCATCCCGTGTTTTCTCCGATCTTACAGAGACACTCAAGCAG
AACTTGATGGAATTGCTTCGAAAGATCTTCCCCGTATGCGGGGATATTA
TCAGGAGCTTTCAAATATTTGCAGGGAATTTGACGTCGATGTTTCAAGAT
```

FIG. 1J

```
TCTATCATGCACGTAACAATCCCGAAGAATGGCTCAATTTGCTGATTGCA
GAACTTCTTGACCGGCTCAACAGCGGCTTCAGACACATGAAATCAGCCGG
GGATGTAAAGCATAAGTATTTCATGTATCCTCTGATCGTTTTTATAACAT
TGCTTCACAACAGGTATGCACCTTATCCGAATTCCATTGAAGCGGCTTAT
AATATAGGAGCCAAAAAAGACCCTGTTGTTCTGACGGGTTTCCTTCGAAA
GGTGGGATATGATGGAATCTGGATCATGGCACCGGAGCCATTCACTCCA
ATGAACCCGCTCAGGTGGTCTGGTGGAAACCCACTGCTGCAAGGCTGGTG
AACAAAATGGATAACCCTCTTTATGTTTCGCCTTCCTCCATAGGATTCGG
TTATCTTGCGTTTGCCGATGAAGGGGTTGCACCCTCCAATGAAAACAGA
AAAAATATTTATGGAATCTGATTTTAAGTGGTAAAATGGATGAGTTTATT
GAAATCATGGATATGATCATGTACCGTAAGTATCTTGCAGCGCTTTTCAA
CGCGTTTTTGAATGAAAGACGGGTGGCTCTCAAACACGCTATCGGATTCA
AGGCATTCAAGGAATATCTCAAGCAAAATGCAGAGGAAATCAGAAACTTT
TTCAGAGTGAGCAGCAATGCGCCGGTGCAGCTTGTATGGGACCGGTTCAG
AAAAGCATTCAGAATTTCTGAATTACTTCGAAACTACGAAGAATTGATTG
ACCGGCACCCTTATGAGGTGGATGATTTTGCCCACAAGCTTCTTGGTAAT
TTTAACTTTTTGAAAGAACTGATTAAGCCCACCAGACTATAAAACGCAAA
ATAATTAAAAAAATGAAAGTTAATTAAAATAAAAGGAGGTCAAAATGAAG
AGGTTGACAAAAGAACAGTTTATTAACAATTTTCACGAGCCCAACTCGCT
GCATTTGTTCCCATCTATAGAGGATTTCATTAACCCTCGACAAGGAGATA
TTACTCAATCCTACTGTTATGTATTACCTGTTCAGGATTTAAAAATCGAC
AACAAAATGGGCATACCGGTAAATTTTGATTTATCACAGGCTTTAAATAA
GATGATAGGTTCTAAAGGTGAGTTGAACAAAAATTTGATCAAACAAAAAA
ACTCGGCACTTAAGGAATTAAAAAATATATTACAGAAGTTTCACAAAATT
TTACAATCATTAAAATCTAATTTTAATGAAGGGATAGCACTGGTTTTTCA
TTCCTTTTTTTTATGAAAAAGTGCACTCCTTTGATCATGCTCGCGCATC
GTATGATTATGTAAAAAGCAACCCCAAAAGTGTTTTAGAGCCACTCAATG
AAGCATTAAAATACGATGAAGAAATCGTCGAGGAAGCTATTAGAGAAACA
GTATCAGATTATCTGGAAAGTGGAGACTGGTATGATATGATTGAAAATGC
AGTCGAAAAGTATTTGAGGGGTTAATTAAAAGAAAACCATGCTTGATCAG
CTTCTTTCTCTTTCCGGGCTTTACTTTGATCAACAGCTTTTTGCGGGTTC
ACCGGGAGAGTTGTTTTTGCGGTTGGTGGCGGAAGCACTCGATGAAGCGG
AGTTCAATGTAAGGAGTCTGCAGAACCGAAGCTATCCGCTGACTGTAGAG
AATACTGATGATCTGCTGAGACTGGCACACCTGAACGGTGTAAGTATTAC
CCCCTACGTTCAGGGAATTGTCAAAGCAGAACTTCTTGTTACTTTCCCCA
TTTCGGTTACCACATCTGTTCCTGACTTGACAACACATGCACCGGAAATT
CTCTACATGGATATTCTTGCCGATACGGATTATTTCTATCTGGATTATAC
CGATTTCCGCCAGACCGATACCCGTATCATTACCACCAGCACCAATCTTA
TCTACTCAAGAGACGTAGTCTTTCGTCATGGTAGGGTTGAGCGGAGAAGC
TATCCGGTAAGTCAGACGATCCCCTTCATGATGTTAGAACTTGAGGAAGA
TGTGGTGGATGTTAAGAACGTTTTCGTGGAATACCCTGATGGAAGGCTGG
TCAAGTTTTACCGCTCACGTAATCTTCATGAAAATCTGGTGGTTGAAAAT
GCGGTAATTTACAACACCCGCCACATTTACGACGTGGTGTTTTCCTCGGG
GAGAGTGCATTTGCTTTTCGGTAGAAAGATTTCTCTGGAAGACCCGATTT
CACATACCGGCTATACTTTTCCCGCCGGAAGCACCATATATGTCGACACG
GTTGCAATCGATCCGACTACCCTGAACAGCTTCATTCCGGAACTTGAAGC
AGATATCAAAACCGTTAAGATCAACAACCGTATTGGGCAACCCCTCAGA
TTCAGGTGCTCACCGAAGGTGGATACACTTCCCGTCTTAAAGACATCGAA
TATCTCAAACGGGAACTGCTTGTCGCTCTTCAGAAAGACGAACTGGAAAG
AGAAATCGCAAAATATTTCGATAAATACAGATTCGTTCGAGAAGATGATA
TTGTCTATGTGGAAGGAGCCATATACCGCAACGGTAGATTCACCTTCCAC
GAAGCCGATCGATTCTATATGCAGAAAGTGGTTTCCACCTACAACCGCAA
CATGATCGTCAGGAAAATTCCGATCACCCCCTCAAGATCATCATTCGCG
CTTCCAACATTCTGAACCCCGGAGAACTGATCACTTTCGTAAAAGATTAT
ATCAGAAAACTTCCGATCGGTGGAACGTGGATCACAAATGAACTTGTGGG
GTTAATAAAAGAAAATTCAATGTCGTATGTGTGCTGGAAATTTATTTTG
GAGAAACTTATGCCCGAAAGGTTTCGGAAGATATTATCATCTACGACGGC
GTACTCGACGTTGAAAGTGTAGAAGTCAAACCCGTACTGGTTTGATGGGG
CGCTATGCAAAAACCAAGGGAAGGAAATTTCAGAACTTTGTAAAATCGCT
GCTTGAATCCACCTTCAAAAATTGGAGCTTCAAGACAGCAATCATGGGCG
AATCAGGTTCAGATGTCAAGATATTTCCGGAGCAGATTTTTTCGGTTGAA
```

FIG. 1K

```
GTAAAACACCACAAAAACGGATTGATCAGAAAGGATGATATGCCTTCTGA
AACCGTACTCAAGCAAGCACGCGAGCTTATCCGTAAGGAAAACAGTCATT
TCTGTTTGATCGTTTTGAAGGAGAATTACAAAACCCCACAATATTTTGTG
CTTTATCGAAACGGAAAGCTGAGAAAGCTGGAAGATATATCGGAGCTTAA
GGAAATTGTAAAAAGATATAAATGATAGTTACTTTGAGAGAAAGACCGTA
TTGGAGATATATTTACCTGTTGAAAATTCCATAGCGGCGCTTAAGCAAAA
ACTGGCAAGGTTAGCCGCTGCAAACGAAACCGCAGGTGGAACGCCTGGAC
CCCCCATTTTGCTGAACTCCTGAGCAAACTTGCGCATCATCTTCGTCATG
AAAGAATTGAAAGATTTTCCAAGAAGCGCATTTTCGGTAGCGCTACTGGT
ATTGCCTATATAAACCCTGTCTCCATGTAGATACATCCGTTCGGTGGAAA
TCCTCACCTTTCTCTCCGCACCCATTAGCAATTCTTCCTGCATGGCAAGG
TGCAATTTTTTGCAGCCACAAGGATTCGCTCACGTTGCAGCAGGTGCAG
TGAATCCGATCTTATTTTAACAACGTAACCGCCACTTTCTTCATCCACCG
ACTCATTCTTGAAAGATATTTTATATGATTTCAGATTTACCTGATCGCCG
TCTATTTTACCATAGATTCCATACGGGGATTTATCTTCGTCGACAGAAGT
GGTTAAATCGTCAGAGACTTCATCACTGTACTTTCCAAGAAACAGATTTC
CCTCTTCGTCAAACCATAGCGCCTGCATTCCCTTTCCGTTGAGAAAATAT
TCACCCGGAAACGATCTTATCCGTGCCCGTTTCAATTGATTAATCGTAAC
ACCACTTTCATTGTCGTTGGTGGTTTGAAGGTAGTTTGACATGTTGACGG
GGAAGGGGAAATACCAGAGCCTTCCATTGATTTCCACATAAGCAAGGAGA
TCACCCACCTCAGGATAAAATCCTATGTGCACGAAAATGGATAGGCTAC
ACCAATCACTTCTTCAGAAATGTCTTTGATTCTGACCGCCATGTATCTTT
CGGGAGTATCGACATCATCTACTTCCAGTACCAATCCGAATTTTACCGGA
GATGAAAAGAAAGATATTTTGCTGCTTTTGTTAGAAAAGAATTCCTGAGT
GTTGAACCCCATTTTTTATTTTATTTTGTTAGTTAAACATATAAACTAT
ATAGTTTTCTTTTAAATAAAACACCAAATGATTTTTAACACTTCATACTA
TTGAAGATTTTTCAGAATACGATCCACGACCTGTTTCCATTTTCGGTTAT
CCTTATATTCACCAACAATCTCCTGCTATCTCGAATACCGCTTCTCCA
AAATACCACAAATGTTTTTCCAGTTCTACGTGCACATGATATTCGTTCCT
TTCAATATAGTCTTCAATTAATCGTTTGATAAAATGATGTAAAACGTATT
CACCTTCGAATCTTTCTTTAACATAAAACACCACAATTTCTGCTCCCAGA
GATACCGCATCTGTACCTCTTTGACTGATAGGTTCATCATAACGCATTCC
AACCACAATACTCATAAGAACTTCTGAGGGTAATGGATGACCTTCATGAG
AGTGGAAAAGATAGTGGTTAGTTATTTTAGTCAGCAGCTTTTTTACCGTC
TCTCTATCCAGAAAGTGTGTGTAGTTATTGATTCTATCTTCAATATAGTC
AACGAATTCCAATTGCAGTTTGGTGAATATAAATTCTTCTTGGGCGTATA
GTTTATCATATACAAAATCTACAAGATCATCATTTTGTTCATTGTACTGA
TCAATAATGGAAGTAACAATTTTTTCTATCTTATTCTCTATAAATTTATC
TACGTTCAATGCGTGTTTTAAACCTTCCTTTATAATCTCTAAAATTTCGG
GGTCTGATAAATAATCTTCCCACAAATCATCTTTAAGCATATCTTTATAA
ACAATGAAGGCAATCGCATCTTTTACCGGTTCGGGAATGTGTGGAATAAG
GTCTTCAGGTTCATTTATGCGTATTGCTCTTTCGATCAACAAACGAATAT
AAAAATCTATAGATTCGGGGGTTTGAATATTAAAGTCAAGTATCCTATCA
AGGTCTGTTCTGTCATCAATGCCATATTTTAGCAACAGTCTCTGCTTATA
AGATGGAATAGACGGCACCTGTTCCACAATAAATTCATAAAGAGGAGAAC
CCTCTTTAAGATTGATTACAAAAAGGTCTCTCAAATAATTAGCAGCCGTC
ATCTTTACTCGAGCATTGACAAACGCCATTTTTATAACGTGGGGTTCATT
ATAGTTTTGAACAACATTAAAAAGTGAATGGAAATGTTCAGTTGATTCGG
CTACTATTAGTTTCCCATTTCTGGTTCCCACTATCATAAAAGAATAAAAC
AGGGATGTGAAATATTCCTTGCCGGTTATGCTGTATGGAAAATTAGACTT
TCGTAGTCCACAAAAACAAGGGCTACGCCCTGTCAACAATTGATTTCA
ACTTGTTTAATATTTGCGAACCTTTGGTTTTTATCTCATTTTGTTTATGA
ATAATGAAGTTTCTAAGTTGCAAAAATTGATCTTGGGTGACCCTTGATGA
ATGCTTATAGATATAATTGAATGTTTCTAATAAGTGGTGATTCAAGGGAA
TGCCTTCTTGGGGATGAAAACTAAGTTTTTCTACGGGTAAAACATAACAC
CTTAAAAACAGCGAATCCCCACTATCGTTTGGTAAAACATACATGAACCA
GTTAATTGAAGAAAAAAGCTTAACGCCTCTTTGCTGTGGAAGTTATCCG
CAAATTGTTCTCTTGTCAGTATCAGCATATAACCTAAGCAAAGTTTATTA
TACAAGGTAAATTTGGATTAAATAATAACCAGACTTCTCAGATGTAATTA
TTCGTCTTTTCCAACCACATCAGAATAAAACGTTTCTATTTCGTTAAGAT
CTTTGTTGATCAGAGTTTCAATTTGTTTTTTTCAGCCCCATGACACACCC
```

FIG. 1L

```
TCCATTTTTTGGCATACTAAACAAGGCAAAACCCAGACAGTTCCATAGCC
GCCGACTTATTTAAAGAAAATAAATGAAAATGCTTCAAGTACTGAAAG
ACACCTATTTAAACAGCGCTTCCCCGCATAACAACTATGGAGCCGACGAA
ATTCTCCGGCTCAATGCCACTTCCAGCATTGCATTGCAGTTTGAAAACCC
GATTGGAACGGGTTATGAGATTCGCCTGTTTGTTGCCGACGCGTGGATTC
CCCATGTAGAATATCTGGGTGGGGAAGCTATCACCGGCTGCTCCTCACC
GTTTCGCTCTACAGCTTTTCTATGGATGAAGGATATGGAACCGAAGTAGA
ACCGCTTATAAGCCAGAGTTTCAACTATGCGTCGCTGTCAACGCTTCCTT
TACCACTGGAAGTTCGCACGGTAAGCGCATTTATTCATCTGGCACCGCTC
AAGCGGCGTATGGTAAGCATTCCACTTACAAACTTTTTCAACGCCGGAAA
CTTTGTTCTTATCGAATCGGCTGAGGAAATGGCGGTCAACTTTTTCAGCA
GACAGACGCGCACGGCTTTCATTCCCTATACTATTCCGACAGTATCCTTG
CAGCCCCCGGCGCTTTCAGACTTCGTATACGATACCCGCATAGACGACTA
CGGAGTATATCTGCAGGCTTGGGAGCGGAAGATTCCCATTGCGGTAAGGG
GTTATCTCATGCAGACGCTGTCATACATAGACCTCTCAACCGTATGGTTT
GAAGTATACGTGTTCGACATGATCACCGGTGAGGAACACTATTATACATC
GCTGCTTCCCACTCCCGTTGGGAATAACTGGTACTATATTGACATGAGCC
GTGTCAATATGAAAAGAACCCAGTATGTGAGACTCAAACCGGTTGGAAGC
ACCAACGACATTTTCCTTTCCTTCCACAACCGCTATCTGAGACTATGAAC
ACCCAACAGATTATAAAACAGGAGCTTGAAAAATGTAAAAACGATCCGAT
TTATTTCATTCGTAAATATGTGAAAATCCAGCACCCGATCAAGCGCGTCA
TACCGTTCGATCTATACCCGATTCAGGAGAAACTCATTAACTTTTATCAT
ACACACCGATATGTAATCACGGAAAAACCCCGCCAGATGGGTGTAACGTG
GTGTGCAGTGGCGTATGCACTTCATCAGATGATCTTCAACTCCAACTACA
AGGTACTGATTGCAGCCAACAAGGAAGCCACGGCAAAAAACGTGCTGGAA
CGTATCAAGTTTGCTTATGAGCAGCTTCCCAGATTTCTTCAGATTAAAAA
ACGTACATGGAATAAAACCTATATCGAATTTTCCAACTATTCTTCCGCAA
GAGCCGTCTCTTCCAAAAGTGATTCTGGACGTTCGGAAAGTATTACGCTT
CTGATTGTGGAAGAAGCCGCGTTCATTTCCAACATGGAGGAACTCTGGGC
TTCGGTGCAGCAGACGCTTGCCACCGGTGGTAAATGTATCGTCAACTCCA
CCTACAACGGGGTTGGAAACTGGTACGAACGCACAATCCGAGCCGCCAAG
GAAGGAAAAGCGAATTCAAGTATTTTGGTATCAAATGGAGTGATCATCC
TGAGCAGATGAAAAATGGTTTGAGGAGCAAAAAGATTGCTTCCCCCAC
GTGTGTTTGCTCAGGAGATTCTCTGCATTCCTCAGGGTTCGGGAGAAAAC
GTCATTCCGTTCCATTTGATCAGAGAAGAAGAATTTATCGATCCGTTTGT
GGTAAAATACGGTGGAGATTACTGGGAGTGGTACCGCAAACCCGGTTATT
ACTTTATCAGCGTAGACCCTGCTTCGGGTAGAGGGGAAGATCGATCCGCC
GTAGGTGTGCAGGTGCTGTGGGTAGACCCTCAGACGCTCACCATTGAACA
GGTGGCGGAATTCGCCTCCGATAAAACCTCGCTTCCCGTCATGCGTCAGG
TGATCAAGCAGATTTATGACGAATTCAAACCACAACTCATTTTCATCGAG
ACAAACGGTATCGGCATGGGCTCTATCAGTTCATGGAAGCTTACACGCC
CAGTATTGTAGGATACTATACCACACAGCGGAAAAAGGTGCACGGATCGG
ACCTTCTGGCAAAACTCTACGAAGACGGTAGATTGATTCTGAGATCGAAA
AGACTCTTGGAGCAGCTTCAGCGCACAACATGGGTTAAAAACAAAGTGGA
AACAGCAGGAAGAAATGACCTTTACATGGCGCTTATCAACGGTCTCATGG
CTATCGCTACTCACGAAATCATGGAAGCCAACCCTGAATGGGAAAAGATT
AACGTAACCTTCAACAGTTATCTTGGGAATAAGGTAACCCCCAGCACGCT
CGACATCAACCAAGAGTTTGGAGGAGAATTTACCTATATCGCCACACCGA
AGGTAAATCCTGATCTGAACAAAAATCTATTAATTCAAAAAAAATCCGAA
GATTTCATCTGGTATATCTGAAAACGGCTTTCCACACAATCCCAATTACC
AGTATTTAATATCCCTCTCTGATATACTCCCCCGTTATTTAAAAGAAAAT
GCCACTGAGTAGAGACATCATAAATCGAATCAAAGAGAAACAGGATACTC
TCAGAGAGAATATTACCTACAGCGCAAAGCTTCTCAAGAAGATTACAGAA
ACCAACCTTCAGAAATTCTTTTCAGAGACGCTTACATGGGGATAAGGGA
AGCCAAAAACCTTGTACTGGCACAACTTCCTCCTGAATACAGAACTCAAA
ATCTAAACAACCCCACACTTACTCTTCACTGGTTTACCTTCAATTTCAAT
CCCTTTGTTTACAAACGCGAAGTTAAAAGCAAACTTTATGATTCTCCGAC
TCCCAAGGTTTATCCTCTTAAAAGCCATGATTATGGGTATAGAACGGAGC
TTTTGAGTGGGTCTCCGGTTCCTGCTCCCAACCTTCGCTATATTGTCAGA
TACAATCCTGAAACCGATCGTCTTGAAGCTCGCACGGTGGATATTACCAC
CGAAGAAGGAATCAGATATGTGTGGGGTGCGTCGGGTAATATTCCTCAGG
```

FIG. 1M

```
ATACGCTCGAGTTTACATCGCTACGTGGTCTTGGTAAAGACGATATGATC
GATCTGGCTCAGAGCGGCGTTCCCTATGAGAACTCGCTGGTGCAGCTTTT
CCGAAACAGAGCTTCCATTGGGTTTCAGTATGATGAAGACCTTCGCAAAC
CCATTCAGGTGGATCGTATCAATATGGAAGGATTTACTCAGAACGAATCG
GAGATTATCAATGATTATGTTACGTTCTATTTCAAGAGCGTAGTGAGCGG
CTGGATATGTCAGTTCAGAGCTTTTATCAACAGTTTTGGTGAATCCACCA
ACGCTTCATACAACACTCAGGATTATATCTTCAACATCATCAAAATGTAT
TCGTATATCAATGTAGAGACCACCTATAACATTTCGTTCACCCTGTTTCC
TATGAGTAAGCAGGAGCTTTCAAAAATATGGGGTAAGCTCTCATTTCTCA
AGCACACCTGTTTCCGGCAAAGCGGGTAACACCCGGCGGCAACTTTGTA
CCTCCGGTACTTGAAGTAACGCTTGGCAACGTCTGGAGAAAAAGGAAGGT
GCTTCTTACTTCTCTCAATATCTCATTCGGGGAAGATACCGTATGGGAAC
TGGATCCAGGTATGCAACTTCCCCAGTGGATCAAAGTGGATCTGAATTTG
ATTTTGCTGTACGAACAGAATATTACCACGGAAGACTGGCTTCAAAACCG
CGTTAAAATGTTCGATTATACGACAAACAAGCCGCCTTCTACGCTTGCCG
CCTCCGACTCCATGATCGATCCCGCAACAGGCGTGGCACTTGACATTTCG
ACGTTCAAATACCCGGAACCCGAAAGTTTTAACCTGAAACTTGCAAAACT
CGATATACTTAAAAACCTTGGATAAATTATGAAAGTATATTCTTTTTCGG
GAACGCGACGCGCTCAGAACATAGCCGTACAGGAATATGGAGATTACTCC
TACTGGCAAGATATGCTGCTTGCAAACGGTATTTACTCCGGATCGATCAT
TCCCCCGTATGTTCCGTCGCTTTCCATTTACACCCCGGAGGAACTCGAGA
ACCGTCTGGTAGATAAATACCATATTCCCGATCTGAAATATTTTTAACCT
ATGCTGATAAGAAGCCTGCACCCTTCCGTTGTAAAGTATATCAGACAATT
TGCTTCGACATCGACGGTTCAGAAGATTTCCGCAAGGCTTGTGTTCATGG
TGCGCGTGAGAGACGCCGCACCTTTCAGAGCGTACAACATTGTCTTAAAC
AACATAAATTTCTATACCATTGAAAACGAAATCACTCCTGATCTCCAGTC
GTACTACGATTATCTTCCGGCTCCAGCTATTCTTTCGGTGGACGTCGATC
CGGCTCCTGACGGGATATACGGTATGATGGCGCGTGCCACCGTCAATGTG
CGTTGCTTTCTCTCAAACAACTTCGGGAACTGGAGTGGAGCCTGTTTCC
GGGAATTACGGCGCTCATTGAAGTAGTGCGCACAAACAATGAAATTCCCG
TGGATTTTATTTCTGATCGCTATGTGCGAAATCCTTCGCTTCTGAAAGAC
ATTCTTTTTAGCCCGCAATCGGTAATCAAACTCCATGAGAGAGATGAAGG
CAATAGGATATTTTTCCCCGGAATACTTAAAAGAACAAATGTTTCGTATA
ACAACAATACCTTTGACATTACCTTTGAGTTTAGTAATTTTAGTATAGCT
TCCGTATTTTTTTCTCGAAACTACGATATTAAGGATGTAGAGACGGCTCG
AAAAACGCTGGCTGGTTTCTACAATGAGCGCTGGAGTACGCTTTCCAGCC
AGAAGAAAGTCAGATCGGGTCAGGATCTGAACCTTGACAGAACCTATCAG
ATGTTCGGTGGGGGGAATAAAGCATTTCCCGCCGAAAAGGGTATTGAAGT
GGGCGTGGGTACTCATTTCGATACAGGCGACAAAACTTTCGCCCCTTCGC
TTCCTTCCAACACCTTCGAGTCGCTGGAATATATTCGTTTTGAAGATTTC
CTGAAGGAAATTCTGATTCCCTATATTCGGGACACCTACCCGGAAGATGT
TCCTCCGGAAATGGCAATTCTACCGATCGACATAGACAACTCCTATATGT
TCATTCATAAACACTTGAGAACCAACAACGTAGATATCATTTTCCCAACC
GAATACATGGTGTTCGATTCTACGAATATGACGCCGGATTACATTATGGG
ATTTTCAGATTATGAGGATCATGCAGAGTGGTTCGAGAAGAATTTCGGGA
AACCTTACACCCGTCACCCGATTGGATCAGTTGGTAAAGTGGGGAAAGTG
ATGTTGGCTCGAAAGTATCTTTCCGAACTGATCGGAGAATTCGAACGCGG
CGACGACAAGCCGTTCAGTTTCATTATTGATAGAATCATTCAGGATATAA
TAAAATCCACCTATGGCTTTTCTCAGCTTTTCCTGATGAAGGTGGGAGAG
CAATACGTCATTTATGATAATAGACTTCTGGATGTAGAGACGCCTGTTCA
GCAGGTGGAAAACAAATCCCGTCTTGAACCGGAAGAAATCAAGATATGGG
AACTTCACGACATCAGCTATACGCTGGATATTCCTGAATATCTTGCGATG
GCGGTAATGATGAAGCGTCTTTCAGACTCGCTGAATACCTACGTCAACGA
TCCAGTGGATTTCCTTATTCCCGGTTCCGTTGAGGATGTGGTGCTGAAGA
CGCTTACCGGAGAGCGTGTGAAAGGAACCGCGCTGGAAGATACCACGGAA
AGTTCGGATGTGGTTGTTACCAAGGTGAACCTGAGCGCTGAAGTAATCCG
TGCACTCATGAACAATCCCAATTTCAGAGCGCTCATGAATGTAATCAAAG
AAAATGAATCGGGGGGCAACTACGAAGCCATTGAAATAGAACATATTATA
GCAAACACGGAAGTTATGATAACGCTTTTGCGCTGGCGCGGCTGGCGAA
CACCCGCTTTGCGCGGGGTAAAGTGTGGTATCGGGTAAGAGGCGATCAGA
AAGAGGAAATTACCGGAGAGCTTGTAAGAAAGGTCGAACAGGCTTCCAGC
```

FIG. 1N

```
TTCAGCGATCTGGTTACGCACCCGTTCGTCGATGTGCCGAAATCTCAGGT
GTCGCTTCCGGTTTCTCCCGGAAGATATACCACCGCCTGTGGCGCTTACC
AGTTTACGGAAACAACATGGCGGTGGATCGAGAGAGAGTACGCCGATCTG
TGGCGGGAGCTTAGTAAGAAAGCGGATGTGGCGGTGGATTCCGCCGGAAA
TGAAATGGTGGTTACCGGTCTTCCACCCGCTACGGTATATGAATATCAGG
CGGTTGTCGACACTACCGTTCAGTCTCGAATTGTGGTTCCTCCCACCCCC
GTCAATCAGGATTACATGGTGGCAATTTATCTCACGATCATTCTCAACAA
CGCAAACCTTACCGAAGAAGAGTGGAATCTGTTTTTGAACGAAGGATTCG
GGTTTAAGCGTGAGGAAATAGTTAAAGAAAAACTTACCACCCATTTTGCT
TCCCTCAGAAAAGTCAATCTCAATGCTTCAATCAGAAGAGACGCGTTTGA
GCGCAAAGGAAATGTCAGTACATTTTTGAGTATAAAACATAAGGATCTGA
GCGAAACAAAAGTGTTAAATCTATTACATTTGATGTAACGAAGGTTGAC
GATAGATATGTAGCCTACATTCCCATGCACCTGTCAACCTATTACAAAGT
GCTTCTTTATATGGGCACGCTCCCGGAAAGACAGCGGGGGAAGGGTGCTC
AGTATCTGACCGGTATTACACTCAACATAACGGTTCCGGGTAATTCGCTC
TGGAGGATTTTTGACACGTTCAAAATAGAAGGTATTCCCGAAATCTATTA
TGAAAACGGCTATTTCATTGTAACGAAAATCTCCCACAACATATCAGGCG
GAACATGGACCACCGGGGTTACGGCAAAATACTTTTACACGGGCAAAACG
TAAAAAAAAACTATGAGCAAGTACTTTCTAAAACCAACTTCTTACGCTTC
CGACGTTTATCTTGCACCACACGTTCCCGAACTGGAATACGTTCCAAAGG
AACTGATAAAGGGTTTGACATGCTCCTCAACTGGATCAGTGCACTGGAA
ACAAATCATCTGTTTTACAGCGCAATCAACTATCTGGCTAAAGATTACCA
TGTAAAGAAACACCGCGAATATGTGATCCATTTCATTTATCCTAAATTCA
ATCTTTCGGAAAAGGATTATCCAGAAAAAGATGAAGATTCCCTTATTATG
CTTCCCGATCACCCTTTTGCTCGGCACCGCAAAGAGGAAATCTTAAAACC
ATTTAAGGGTAGATATCTTGCGTTTACCGCTTCCGGAAGATATCAGTTTA
TTCGATCCACATGGAAACATCTTGTAATGAATTATCACACTCAGAAAATT
ACCGCCTTTTCTTCGCTAAATCAGGATTATCTTGCGCTGTGTCTTGTAAG
GGAAGCCTTAATGCGCGTTAAGGCAACGGGAATAAACGGTATATGAACC
TCTGGGAGTATTTTATAGACTACGGATATATTCATTTCGATGAATTCATG
CACCATAAACAGGTAGTATATGCCCTTTCAATGGTATGGGAAGCTTTCCA
GAAATTTCCTGAGGGGCTTCAGAGTGATGAATTTATTAAAGAATATGAAA
AGCTCTATCGCTGACGAGTTTCTGTTACATACCCCGTCGATTTGATCTGC
ATAATCGCTTCTCTTCTGGTAGAGTCGTACAGGATAGAAGTCTCATGATC
CATGTAACCCAACTCTCCGGCTTTTTCATGAAGGATACCGCTCAGCGTCT
GCGCCAGGTTCGAGTTGGGAAGAATACCCGGCGTGATTTCGATAAGATAT
TTTCCTCCCTGTTTCGATCCGTTGAGTTTGCCGCCCCAAGACCAAATTC
CCGCAAAACAGATTTCAACCTTTCGACGTTAATTTCTTTGCTTTGAGCCG
TAACGTATATCGAGATCGTATTCCGCTCTTTTTCCTGCTGGTATTTGTGG
TTGAACACCACTTCGATCTTTTCAGGGGTTTCAAAAGCAGTTTGCAGTCT
GGAGACAAAACGCTCAAGTACCGGAATGCGGAGCGCGGCTTTTACAAGTT
GACGCGTTCCCTTCTTCTGGATAATTTTGTGAGAGCGCTGAATGATGAAT
GAAAGATGCTGAAGCACTTCCACAGTGAATTCGGCAATGCTTTCGTCTAC
TTCGGCAAGCTGATCGTCGGGTAAATTGTCGGCTTCTTCCAGCGATTGAT
AAAGTGCGTTAATGTATTGCCTTACTTCATCAGGGATATAGAAATGCATG
ACCGGCTCAACTCTGAAAGGTAGCGTGCCGTAAAAAAGTACGGCATGACC
GTTTTCTCTGTTAATTTCGATCATGGTGGTACCGATATTCTGTAAATAAT
TACCTTCAATCGGCACCCTTCTTTTGGACGCCCGCTCCAGAGGAATCTCC
ATCTCCTCCTGTTCGATTTCTTCCTCTTCTTCCTCCTCTTCTTCCTGAGC
TAAAACAAGCATGTCATCTTCTTCCTCGACATAAGCAGGCTCACCGG
TGGTCTTGAAGAATTGGAGCGTAATGATTGCCACCTCTTGCGGCTGAGGA
AGTCTGATCACACCACCTTCTCCCCACCCCGGCGGCGGCTCAAAACCCAT
GCGAATCAGCGCTTGCATTTCCTCCGGGGTTGGAGCCGGAAGTTCCATAC
CCCCTTCGGTAATCTGACAGATAATTGAAAGCTCCGGGGGATTGATGCGC
CTTACGTAAACGATGCGATCGTAAGGGCTGTACGCACCGACGTATTCGTG
CTCCTGCAAAGTGGAAAAATAGGAAAGAAATGTCTGTATTCCCTTTAGCG
GATTCATTTTCTTTTAAATATATGCTTCTTCAGGAACAAGCGAAATGGTG
GGAGGAGACGTGATTCGGGAAAAATCTTTAAATTCATAATCATTCCCACG
ATACAGTAGATATGGAGAGATTCCCCCTACAGGCAAAGGTGGTGTGGGTT
TTCTTGGGGGAGTACCACCGCCGCCGGGTTCATCTTCATCGTCATCCATA
TCTTTGTTTCTTTTTCCACCAAACAGATTTTGGCGGTATTTTGCCTCGAA
```

FIG. 1O

```
AATAATTTCAATAATGTAGTAAAGAACAACGCACATGACGATACAGGCGA
GCAGAAAAACGCTGACGACAAATATGTACTGGATCAGGTACTCCATGTTA
CAAACCGTTCAAAACAACTTTTACATACGGGTTTATAATGGCTTACCTCC
GGCACAATTAAATAAGGGTCTTCCAGAGGGTTCAGGTAACCCATTCCCCT
CAAATCCACACTTCCATTCACAAATCGTATGTTGTATTGCGTTGGATTAC
CGCACTCACAACGACTGGAAATGTTTATTTTAATGGGATTGTATTTTTCT
TCGATCTGTTTCCATACCGGAAATTCTTCCAAGATAGTCGGTTCTGAG
ACCGCTGAGCACCACTTCTATTTTCCACGAAAAAATAAATTCGATCTCTT
CAGGTGTTGCAAACTGGAATTCATCAACGGCTATGAGCGAACACCTACCG
GTTTTAAGCTGGAGATATTCGGCTTCATAAAATGTGGGGTTTTGAATGAA
GTCGGTAAGATTGTAAACGCAAGAATGGGTAAATCCGCTTCGAGATTTCA
AGGTAGGGGAATAGCCGTAAATGCTTCCGGGTTTAAAGACAAGATAATCG
TCAAAGTTTTCTAAAAGTTTTATAAGAAAATGAGTTTTACCCGATGCCAT
CGCCCCGTTGATGACGGTAACGGAGCGGGTTGAGCGTTCCTTCAGAAATT
TTATAACAGCCTTATCCAGTTCGATATTGTGCAGGGTGGTATCTCCGGAA
AGCGTCTCAGGGAAATCGTACTTCATAGTTGATTTATTTTTAAGCCGAAG
TCTCTGACCACAAGGGGTTTGTCATCGGTTCTACCCCAGTTGTCGATCAG
GGTAAAATCCTCACCCAGCAGATTGAATTGCCGAATCAGCCTTACGGTTT
CCCGGATTACAGGATTTTTAAGAACGGTGAAGTAAAAAGTGTGCCTATCT
TCTACGCTTACGTTGTCAAGCGTGAGTCTATTAATGGCATTTCCAAATAT
ATCGGCAAAACGCCTATCATAAGCAGAAACCACCTCGAAACCCTCGAACG
TTGCGTCTTCCCGTAAGTAGCGTTTCCGGATAAACCCTTCAATCAGAACA
CTATAAACATCAAAGTCAATATCAGCGACACTTTCAAAATAGGCTTCATT
GACAGGTGCGACAAATTCGGTGATTAGAACCCCACCTTCTTTGAAAACCT
GAGCGTAGTCGACGGCGATTTCACTTCCTGACCTACGCACCACCTCATAT
TCGGTAATGTTCTGTTTGATTCCATTGTCATTATGAGCAATTTTCAAAAC
CAGTTCGGTGTCGGGTATTCTGAATACTTCTCTCCCTCTTCCCCTTTTGA
CGGGTTCAAGGTATTTCTTTTGAGCCAGAAGGTAAGCCGCGCGAAGCGGG
TTTTCACTTCGCTGAAAGTAAGTCAGAATATCCCGGAGCGTGTCTGTTTC
TTTTAAGGTTATCATAGGCTAATCCAGTGTTATATCATACATGATTTGTG
CGGCAACCACTTCTTTAAAATATTCAACGAAATCTCTGTCGTCTCTAACG
TCCTTTAAATACTTTTCTATTTCCGGTTTTACATATTCAAAAAACTCATC
CATAATAACTTGTTTGATAAATAATGTAAAATGATCCCCCTCTTCATCCA
TATTGAGTTTGTTAATGATAACACCATAAGCAATTCGTATAAAGGTTTGT
ACATCTATTACGTGGCGAAGGTCTTTCTGAATAAGGATATTTCTATCTT
ATGCTTTATTGGAAAATATCCGGAAAGAAACCGAATCGCTTCCTCAAGAT
TTTTGCTGACAAAAGCTATAATATCGCTCTGCAGTTTTCGCAAAATATAA
TGATAATGTGCATCTTCGATTTTATAATAAGCCGCATCTCTGAGATAATC
GTATATCTGATCCGCGATATTAAGATGATCTATTGCTTCCTTTATGGCTT
TTGCTTTGAAATTTCTGTCAAAGAAAATTGGGTGTTGCCTTCTTTCCTCT
TCTTCAAATTTACGTACAACATATTGTGCGATCGGATTTAAATGATCTTG
CCCGTAATGATAAGCCGCGAATCTTATGACATTTGACCAGAAATATTCGA
TTTGGGGAGGAAAAGCACATTTATTAGACTGGTTCCACCGTATTCTTCA
TAAAGAAAAGAGCGAACACACCAGCGGATAATGTCTTCGTTATTTTTATA
ATCCGACAGAATCAAATAAACCTGATTGGTGGGATCGAAGCCGCCAAGTA
CATCTCGAGTCAATTTTGAGATTGTCTCTTTCAGTTCAAAAGAAGGGGTG
GTTTCTTTTAGCAGGAATATCATTCCGTCCCGCGGGTATTTTACCTTC
GTGGATGTAAAAATAGTAGTACATTTCACGGGTTACAATGATATTCCAGA
GAGGAGTAGCCACCCATTGATAAACTTCGTCATCATACCGCGCCCCTATA
AGTATAGAACCCATAAACAGAAAATCTATATCTCGATACTTTTCATTGAG
CGTGCTTACCTCAATAATCACAAAAAATGGTCTGTCATGGACTTTCAATT
TTCTTTCCAATAACACCAATGTTTTTCCTGTTTTTATCAACGCTTTCCGT
GTTTCTTCAAGTAGTTCACCCGCCCATTGGTGCTGTCTTAATTTTTCTTC
AATGAAATTTTTGTAAATCTGTTGGTACATAACATTTGACAGGCTTGTTC
TGGTAAGATCCTCTGAAGTCAATATGAAATAGTTGGTGTTGTAATAATAT
GGGGTGTTTGGGGGCAAATTGGTTTTAATAAACTGTTGACTTAACCCGTT
GAACAACGGTTTATTAAGAACAAAGGTATCGGTGTTTATCGTTTCCATTG
GTTTTTATTTAAATAAAAAGAACGTATGAGAGAACCTTTTCTGTTTCGAG
ATCCGACAATCGAAAGCTTTGGAAGCTTTTTATTGGAATACCTTGACATT
CAGGAAGTTCGTGTTAAAACCGAATTTTTCGGCGGTAAACTGCAAAAACT
CAAAGATGGTTATCATTTTCCGGATGTAAAACTTAAACCCGGTAAAGATG
```

FIG. 1P

```
TCGAAAAGTTCCGAACTCTGTGCAACGCATTCGGGTTTGATGTGGAAATA
TCCGAAAACGGGATAACGTTCACAAAAAGACAGGAATATTGTTTTATCGA
GGAGGCTCTGAAAAAGGCGACAGAGAAATATCAGATTTTCGTTCTTGCAC
CAATAGAAGTTGATCTTGTTTTTACATGTTGCAACCAGATATTTGTCGAA
TATGAAATATGAGCACTGTTAAAATACCTTTAGCCGTTAACATATACGAC
CCCAAGGGCGACGAATGGGAATTTATCTACAGCAACTATGCGGTAGAAGT
TGTAGGAAGTGAATATCTGGTTCCGGTTGTAACACTGAAAACCGGATCGG
TTAACTATTTCAGATTCAATGTGCTTCTAACCTACTCTCAGACCGGGTCT
TTCCCCCTTTATCTGAATTTTCTGAACAAAAACACCAATCAGATCAATGT
AGTTTACCGAAATATCAGTTACAGTTATATCAGTTCCAGCAATGTGAACT
GGTATCCCACAAGTATATCCGGTCTTCTTGGTTGGTGGCAAGCATATCAT
CCGTCACGTGTTAAAGATTACATCATAGACCGCACTGAAAACCAGAGCCA
TCTGGTAAAAATTGAAAGGTATACCTATAATGATCAGTGGCTTAACCCTA
CAACAACATTCGTTTCTCATGAGAGTAATAGGATAAAAATGATGCTTCCA
ATGAATGATTTGATTGATAATCACGGGAATAACTGGGTGTCAGAACCCCG
AAATTCTTATGTAGGATATGTTTCACAATCTCAGAAATTCCTGTCGAAGG
AATACACTTTTTTCTATGTTTTTTCGGTAGTTGAAAAAAACCCCTATGTA
ACAGTAAGTGGGGAGCCGCTGATACCGGGTGCTGCATATCCCGCCCTTTC
AACAAGCTATTACTCTATTATTCCCAAGGGTGGCGAATATCTGGCTGGTT
TACATATATTTCGTTCTAAAACTTATAGTTCTGTAAACGATAAAATGAAT
ACGGCTTCTCTTATGATTCTTTTTACCACCTATCCCGTTATAAGTAGTTC
TACGTTTGCTCCGGAATATAAGGGGGATAATGAAAACGCTTTTTCCAATA
CACAATATCGCATACACCCCGCTATAGCGGCTATCGGAGAGAAAGATTTA
AAGTCTCATTATGTTCCGGGAATAAGAATAGTCTATCATACAGAATCTAC
AATGAACCCGGGAGTTCAGCTTTATGAGCTTTATCTTGGTTATAAGAATA
CCACTTCACTTTATGAACTGGAAGTAACTTCTTCAGATATAGCACGTTTT
GATGTACCTACCATTGTAGGGTACCGCATTAAACAAAGTGGTAGCGTTAT
TTCTTATTCTGTTACTTTGAACAATGAACCGCCGGTATGGTATGTAATTA
CGGCAAGCATTCCTTCCATCGATCTTTCTGATCCGATTTTTACCGATCAT
AGAAACGAAGCCGGCATTATTATAGGGTCGCTGTACGGGTATCTATATGA
TTATCAGCTTGGAGATGTCGGAAATCTTTCGGCTATTTATCGGTGGGGAT
CCAAGGGTATTTACTTTTATGAAGCACTGTTATATACCCGCTCGCTTGAC
GATGCAGAATACCAGCAAGTGAACGAACACCTTGTTAAGAAATACCGATT
CGGGCTGTAATGGGAAGAATAAATACGACATATTTTATTTATCTGTATTT
CCCGCGTATAGATATAAGCGGTCTTGATAATATACATATTGAAATAGAAA
TATTGGGTGGCTTTAGTTTTACACCCGTTTCTTATACCTACAATACATCT
GGCTCTTTTATTACAACAGAAACCCCGTTGTCAGGGTGATGGAAAATCG
CACACCGGATATATACCTTCATGTTGTGAGTTTAAGTGCTTTATATAGTA
ATTTCGACCCCTCTCTTCATTCTTGGCATATCTGGCTTGATTTCACAAGG
CTTACGGCTTCTAAAACCGACGGTCAACCTGTTTATACATCGGATATACA
ATCCATTCAGAGTGATATATCTATGGAAAACTCCGGAGGCTATACGTATT
ATGAAAATATTATGAATGGGCTTCCTATGGTGCGAACCAACAATACAGGA
TTGACAAAAACCGGTGGCATTCTGACGGATGATCCGATCATGGTAGTCGC
AGCGGTTTATATCAGCCAATCCGCTACATATTGTCGTCTTATAAGCTGGG
GATATAGTATTAATGAAGCATGGGATGTATATGCTGAGTTTTCTGGCGCG
TTGGTAAGATTTATATTTGTCACCGATACGGCGACGGCTGGGAGCGGTCC
TACTATAACCAGTGACTGGTTCAGTTATCCTCAGGGGTTTGTACTTGCCG
CATGGCAAGAGGATGACGAAACCATGCATTTCCGGATTATGGATGAAAGC
GGAAATGAGTACGATTATCCTGTAATTACCGGACGCGGGGCGGATTTTC
AAACTTCAGATTGTTCGATATTTATTATCCAAGTTACAACTGGGGATTTA
ATAATTATGTGGGAGAAATCATTGTTCACAATGATATATATATGGTTGAA
GACGTCTTTCATTATATGGCTTTCAAATGGGTGCCGGGATTAACCGGAAG
GGTGCGGATAAATCGCTTGTGGGAAAATCTTTATAAACCTGAATTATATA
CATCGCTCAATAGTGTTGTACTTATTACAGGCTCAACATCTTTTACCGGT
TCTATTATTAATAACGATCCAATTATTCTAACTTCAATAAATAACATAGA
TACACTACAATGGAACCCGCAATTTACCGGATCTATTGTCAATAACAACC
CAATCATCCTAACCCCGGTAAACAACATAGATACACTACAATGGAACCCG
CAATTTACCGGATCTATTGTCAATAACAACCCTGTTTTGTTAACAACGAT
AAGTAACGTATTACTTTTGATGTTTAATTAATAAAAAAACCACGAAAGCT
ATGCCTTATTATTTCGAGTTTAAAGTTAGAGAACTGGATCTTGAACCGGT
AAGTGTAACGCTCTCTCCGGCTCCAAGTTGGGTTTCGGTTTATAAATACA
```

FIG. 1Q

```
ACACCCAGCCTTTTGACCAATTTTACGGAACTTATGACATTACAGTGTTT
CTGGTAGCAAACCCACCCCCGGGAACACCGGATGGTACCTATTCGATAGG
GCTTACTTTGAGCGACGCGCTGGGCGGAATAACCACACATTCAGTCAATT
TCATAATCAACACTTCTGGAACCATTACATTTGATCCTGTTTCGGTGCCG
GGGCTCTGGGGTTGGTGGCAACCCGGAAACTGGCTTACTCAGAGCAGTGA
TACTTTCAATGATGTGGCTATATGGTATGACGCTTCTCCGGGGGCACATC
ATCTTACACTTGATAGGAGAATTACTATTTTACCATGGAATAGTACAGAT
GCTGGAAGTGCTTATGTCGGATCTTACATAAAACACTTTCGGATAATTC
ACTTCTGTTTTCATGGAGCCATGTCAATCACCAATTTGCCAATATGAATT
ATTCGTCGGGGCTGATAACTACAAACCCGAAAATGTTTTGATTACAAAA
GATACTTCTTTTTACTCCAATCAGTACTCTATTTTCTTTGTTTATAGAAA
TCATCTCGACTGGTTTTCTCATCGTATAACCGGAATGAGATTAACTATAA
ATCACTATGAATACTGGGCAACCAATATATGGGACTTTGATGTTGAACGG
GGTAATAATCATCTTGCAATGCCGGTCTATTCCCCGGTGGTGATTAACAG
AGCGGCGCCTTATACAACCGTCTCTTATGGATCATACTGGAATGACGATT
ATAATCACGGGTTTGTCGGCGGCTGGTTTATTGCGTTCTGTCTTCCTCCC
TATGCCGCTAATCCGTCAGCCAGAGACGCTTATTACTATGATGACGGGGG
CGGACTTACCACCATGAGCGTATTCAACTATGCCCCCGGCTATTACCAGA
ATAATGTTCCGCATCAACCTTATATTACCATATTCAAAGTTAATAAATAT
GCTTCTCAAACAGATGGGTCTCTCGGTATTCACCCTATTAAATTGTTTTA
TTACACCAATGAAGAATATGCGTCTATGTCGCTAATTGAAAGAAACAACA
GGTTCAGCAGATTTGTCTTTACTAAAGATCAGTGGAATGCTGTTGGATAT
ATTGTTGAGGAAAATCCCCTTATTTCCAACAGCGTTGTTATCGGTTATTC
CTACACTTACAGCATTTATTTCAACGAAACAACTTCCGTTACAAAATCTC
TGGAAGTAACATTTTATGACATAAATGGCAATTTCAGACCCCCGACAACT
TATGCTTATATTGACGGTTCAGACAACCAGCAGGCATATATAGACGTATA
TGGTGGGTTTGGCATAGGAACACGTTTTGCGACAGCTCAGAGTCAATATT
ATGCCAACACCGGTACTATAGGATGGAGAACTTATAACTTTACACCCGGG
GTGTTTTCTCTCTCTTTCAAGGAATGTCTGTTTTATACCCGCGCATTATG
GAACGAAGCGCCCCAGATCATGGATTATCTTATGAAAAAACACGGTATCC
CGTTTGTAAGCTGATATGCTGGAATTTACCTACAGTGGTACGTTTTCATA
CCCGGATAGTCAAACACTTTCCAGTTTTTACTGGATTATTAACGCCCCGT
CTGGAAGTGTTGTTACTTATTCCGAAATTTTAAACCCCCGCTTAAAGAA
ATCCCTATTGAAGTAACCATTTCCCTCGATACCACAAGTATACCGTCAGG
AAATGTAACATGGAGTGTTAACTTTTTTGCATATACAACCACCTCTATTA
CAGGAGAAGTTTATCTTTATATTTCCAATATCTCAGGATTGGAACCATAT
AGCATATCTATCTTTCTGACTTCAAGTTATGAGAAAGAAGGGCTCTGGAG
AAATCTCGGGTTGGGTGAATCTTTTTACTGCTATTCGCTTTCCACCACTC
CGAATGTACGATTTATCAAACACACCATTTCTCTTCAGAGTATCAGTTTG
ATACCAGCCGGTGGTAGTATCAAATGGGAAAAACCCCCGGAAAAACTTA
TTATTCTTTTTCGATTTTCGCCAAAGGGTTTTTCCTTAGAACAGTTGATT
TTGAGGGGTTGACTACAAGTCAGCTTAGCTGGTATAATGATATTCCATTT
GCTGTTTCAGGAGCCTATCTGTATACCGGATCAGGATTTCCGCTCATTAC
TTTTATCAACCAGAGTATGCTTTATCTGGTAACTTCATCGGGGGACTTCA
GTAACTTTGTTTTTAGAGATCTGACAACTAACACCGATGTGTTTTCTTTC
AGTGTGGAATATCCAACGCTTTCTCTTGCAAGAATATATATCACCTACGA
TGGGAATGATTTTGTCATAACATTCAGCAGTACTGTTAGTGATTATTACT
ATACCTATAATTTGCCCGGACTCAGTTTTTCTGATCATCTACTTATTGGG
AATTATCAATCTTTTTCGGGTCATTCCGCATGGAACTCTTTTATTGTACT
TGACTATAATGCGACAGGAAGTGCGTACCAGACAATAAGCAACCTGATAT
GAGCCATTTGATGAACTACACGAACATTACAGCACCACCACGCTCAGCG
TTAACGGGGTAGTGGTAAGTCATAGTTACAGAGCATTTCCTTCGCTTAGC
TACGTTGAAATTACGCTGTACAACGTACCTGCACCTACTGGATCAAATTA
TTTCTTTGTTTATGATCACGTTTACAATCAAAACATATTTCTTTATGCGC
TGAAACCTCAGGATATAGGGAAAGAAATTCTGGAAACGGTTAGTTTCAGG
ATTATTGTTGATTGATCATCAATAGATAATAAATTCTGGTTTTGTAAGCG
TAATATTGATCTCAAACCACCCGTCTTCGATAAACAGTGCCCCTGCTCCT
GAAAGTGTGTAATTTCCTGTAATTATATTGATTCTTCTGTTGAAATGGGA
TGTAGTCAATTCCCATATACTACCACCCGAAACAAACGTCTCAAATTCTT
CTTCCTCTATAACAGGTTGATGTTCTATCTCAACCAGACTCATAGAAGCA
ATTATGGTGCGCCTGTAGTTGAATTCAGATATATGATTCATTTCTATTGT
```

FIG. 1R

```
GCTGTAGGAAACGAGTCGGAATTGTTGATGTTCGGGAATGGTGATAACCG
AAAGAGATATCCCGTCTACTTTGTGAGAAAGAAAATTCTGTTTTGAGCG
AAGTTTGAGTAAATAGAGTCGTGGGTTTTGGTATATGTCCCAAGCCCGAT
ATATCTCAAATAATATCTTACCGGATATTCCAGACTACCGCTGAAGTTGT
AGATTTTATCAAGAATGCGTTCCTGAAGTGCAGCATATCGTATTTCACTT
GCTGTAAATACATAAGGTATGGTGGTGCGGATATACGGAATGTAATATA
ATCCAGTTCAGAGCCGGTAAGTGCTATGATACCTTTGAAAATCTCATTTG
GAAACGTGATATAACTTATAGATAATTGTGTATAGGTATAAAGATAGGTA
AGTCTCCTGTTTTCAAACGTTTCTACAAAGGAAATGGTATCCATTGAATG
GCTTGCGAAGAAAAGAGATAATTTTCAATCAGATGCTGTAAAGTAGCAT
TAACAAGAGATTTTGTTAAACGATTAAAATAGAGGGTTCTGTTGAAATGA
AAAGATACATAATCTAACCCGTAATTATTGGTTCGAAGTGCAATAAGATC
AGTGTTTTGCTCAACAGGAGCATTTACAAACCCTGAAAGCGTTCTAAAAA
GGGTATATATTTTCCCCGTCTGAAAAGCCTCTAAGTTCAATCCGATCGGA
TCGGTAAGATATCCCCTGAAATATTTTCATTGCGCAATTGTGTATTGAA
GCTTACGTAATAGCTGAAGGAGTAAAGGGTAGTTGGATCAACTGTATCGT
GAACAGGAGGAACAATCAAATCATAAGTCATGGGGAGAAAGTCTATTTTT
TCAATGCTGATTGGATCATAAAACTCATTTTTCCACCCAATGCGGTTGAA
CACAAAGAACGGAGGAACTCCTTCGGTGGAATAAGTGCCAGCGGGTATGG
AACCAGACAAAACGAATTCTGAATAAGTGGGTCTGTAGGTGTAAAGCCGA
TAGATGATAGATTGGGAATACTGAGATGTAGTAGACTGATGATATACCGA
AACGGTGAACGAATGGGTTCCGGATACGAACCCACTCATTGTGATATAAA
GAACCAATTCTTTGTATTCAGGATTTCCCTGATAGAAATTATCAATTATG
CTGTGCGAAAAAACAAAAGGTGGAAGGGATGATACCACTTCCACCTGATT
GAGAAATACCCTTCTTACAGGGTAAGAAACTGAATAAGTCATGGTTTCAT
ATCATCACTTAAGGATTACAAAGTGGTCAGCATGAACGTCTGCACGGTTC
ATAAGCGTGAAGCTACGCGCGGCAAGATACTGTTCAAGCAGGATAATATC
GCGCTCCGTCGGTGATTTGATAATAACCAGTTCGTAAATGCTACCGACAA
GCGGGCGCACGCCGTCGGTACCAATTGTGAGAATATTGATTCCGTCTGGA
CCCACCGCCACATTGTTCATCAAGGGGATACCGGAAATCCGGAGCGAACT
GTTCCCGCTGAACACACCCACTACCACCTGATCGCGGGTAGCGAGTGAAA
GCGTATATTCCGTGCTGGAGCCTCCGATTCCCCAGTTGTGGGCATTTCA
CAGAAAATATGGGGGTTGACAGAAAGTGTACCACCGGAGAACAACCCACC
GTTGGCGAAAGAACCCACAATACCGATAGCGAACGGCTGCTCGATTTCCA
GACCGGTACCTTCGAGACCCATCGACCGAAGCCATTCGTTTCCACGGAAC
ACCACCGCCGACAATCCGTTGTATGCATCCCGCACGAAAATGGGCTGGTT
ATCCGGGTTGGATTGTGTGAGGGAGTAAGATAGATAAGCCGATGTTGAAA
CATATGCTGGCACCCACGCATCAACCTTATCGCCCGTGTTGTAGGAAGCC
GTGAGGGTGTTCGCATCAAAGCGAAGCACCACTTTGGGCACCCAGCTTTC
AATGGTTTCCGCCGGATCGACAAAATAGGGGATGTTATATTTCTTAGCCA
GATAGTTTTCAACGTTCTGACGTTCAGCGTTGGTAAGTTTACGGTCAAAC
ACGCATAGCTCAGCAATATAGCCTCTCAGGTTCCACCCTATGAACATATT
CGATTCAACACGGTTACCGGTCTTACCTTCCATATACCGCACACCGTTGA
TGTAAATGCGGTCAAGCGGATATTTGGGGTGGGAAGTAGCAAAGCGAACA
TCGTTGGTTGTTGGCGAACCAGAGAGACCACTAATGTGGTACAGATTGAC
ATATGAACCTGTTTCATTTTCAAGTATCACCGTAATGATATTCCAGTCAT
TCAGGGGTACAAAAGCGTCTGCGGGTTGTGGAACAGTATTGTACCCACCG
TAAGAGTCCGGTAGTGCGTTGGAGACTCGAGGGTTGCGATATGAAGAGTT
CAAATAAATCCAGTGTTCAACCTGATTTTCTTTTACTTCAAGGCGGGGCA
CAATTACTGAATAACTGTGAACATTATTTTCATCAACCATTCTGAAATAA
GGTACATCCGTATCGTCTGTGTTGTGAGTATCCGACTTTGGTTGAGGATC
CCACATGGAGAACATCCACAGAAACCTACCCGGAATGTTCCGTAATTTA
CTGAATTGTTAGGAATGGGATTAGAAGAATTGGTTGTAATATTGCTGTAA
TTCGGATGATAAACCCACACCGATCCACTCTGCACAAACACCCCAGATGT
CGTATCCGGGAGTCTATCCAGTTTGGCAACCATGATAATGGTGCGTTCAG
TATTCTGAGAATAATCTCCGGTGCCCGGATAGTTAATACGCATAACCGAA
CCGGAACCGAAATACCAAGCCGGATAACCGTTGACAATATTTTCGACGAA
AATAGGTTTGCGGAAATCGTTAACCTGAGTAGCTTTAAATCCGGAATATG
CGGGAACAAGGTTGGGAATTTCGTCAACGTAATCGCCGGTTTCAAGCTGA
GGAGTGGAGCCGTCGGCGCTCATCCAGATTTTGCAGTTGGGGACGTCCGA
CGGCGAAGAATACGCATTGATCGTCTGAACATAAATGGGATAAGTGCGAA
```

FIG. 1S

```
CTGTTTCCGGGGTAACGCCATCGGTAGAGCGTACCGTAATGCTGTAGGTG
CCCGGCGCTACACCCGACAGATCACCGTATACACTCAGAATCCCTTCGGT
GCGCCCGTCGGGAAGAATGGACTGGGTAAAATCATATCCGGTAACCCAGC
TCGGGGCGGCGGAAACCGTAGCAGTAATCGTATTACCGTCGTTATCGTAG
ATATAAATGGAAAACGTTACGGTGTTAGAACTCTGGTAAGTCGGCATTGT
TTATCCCGGTTTTGTTTTAAATATTCTTATTTCACTCAAAATAAAAAGTC
AAATAGAGATAAGGCACAGAAATACTGCTATAGTCATTGATGGAGTCTAT
ATAGTCTTTTCCAATATACATGTGTGTGATAACATCTCCGCTATTATAGT
CATACATCAAGATGTATTCGGCTACATCGGGAGGAATGTTGTTCATAAAG
AACCCTGAAAATGTTATGGAGTAAATATTTCCGTCAAACTGTTCGTCAAT
CATACTGACAGTTTGCGTCAGATCCCCCCCCACTACCCGTTACAACATAC
AAACTGAAAGATGAGTGTGTAACGTTAAATTCCGGATAATAAGAATTAAC
CGGCACCACTGAAAGAGTTTTTCCATAGAAATATTTCTTACCGCTTCTT
TAAAAGCATTCATTATGGTTTCTTTTCGGTAAAAAGGTTCGGTGTTGTAA
GATAGATTGATAAATCCATAGATTTTATCTCTGTATAGAGAGTAACTGTA
ACCTACTCTATAGTTAATTAAGTTGTATTCCTGATTTAGTGTATGGTTAA
CAGGCTGACTGTATACCCATTTGTAAGCAAGCCAGCGGTGTTTTCATAC
ATGCTGGATATAAGCGGCTTTCGAGAGATCACAGGCGATGTGTTTCTTTG
AGTAGCATTTATCCAGTAATTGATAGGCGATTCCACCTTTCTGCTCATGA
TGTTTGTTCTATTTCCGGCAATGATCGCTCTTCTTAATGTGTGTTTATTA
ATCGTTTTGAACAATTGTCGATAGATAGTGCGGGTCTTGTTTTTGACAGT
GTTTCCGGTTCTATGATATGCTATAAGTATCTGTCGGAGTTGGTTGAGAT
CAAGGAGAAAATTTTGAGTTTTCTTTACAGAAGTGAGCAGGACGTTACCC
TGAAAACTTGGAAAGAAGTCTCTGGTGGTACGGATAACTTCCCGGATTTT
TAAAAGTCTCCGGTCAAAATGGGGGATATCATAGCTTGCATAAATGTTAG
TGCCCCTGAAGAACAATCCGATTATTCTATCAATGGTTGTTTTATAGTTT
AATTTTATTGTGCGTATGGTTAATTTTATCAAACGTTGCATCTGATTTGC
TATAAGGTTAAGGTACTTTTTAAAACTCAGAAGTCTGATGGTTACATATG
GCTCTAAGGTGGAATAAATGATTTTTCCAACAAATCTGACCTGTTTAATA
ATCTGTTGGTAAAAACGTAGCACATAGTTAACCGGTGTGTATCCGGTCAA
AGTTTTAAAGAAAGTTTTATTCACCAGAGTCGATTTAATGAGTGATCTGG
TCTTGATGATAGTTTTAATAAAAAAGTTTTTGATTGAATTCAACAGACTG
TTAAAGGAGGTAGATATATTTAAAACTTTAAAAAATTCTTCAGTGCTCCA
TACAAAAGCGGAAAGCAATTTATTGAAAGTTTTTAAATTGGGAAATCTCA
GTTTTAAAGTGGGGGTGTAGTTGACAGGTGTGTTTTTGTTTTCAAGATA
TACTTGAACTCATTAGAACTAAGAGGTTGGTTGACAGCATTATATCCATT
GAAAAGCGTAAGTGCGTAGGGGTTGTCGTAGTTGTTGTCAAGGAAAAGTC
GAAGTGCTGTCGGGTCATCATTTTCTATCAACAGCGGATCATCAATCGGG
TCTATATAAGGATCATAGGGAACGGAAAATATATCCCTGAAATCGTTTGT
CGAAGTATAAATATAAGATAATGTATAGTTAAAGATTACCGACTTTGTTT
CATATTTGTCAGTTGAATAAAACCTGAACCGTATACTTCCAGTATACCAG
TCAGGCGGAAAGGAAGATGCCGTTAAAAGATTGAGATAGGTTATAGTAGA
CCCGGAGTGCGATACACCAAACCAGAACTTATTGGGTGGGATTGTTGAA
CGATAAGTGGGCTGAATACTCCTCTTCCTTTGTGGTCTACTTTAAATCTC
ATTTTGTTCGTAGGTTATGTCATATTCGTCCAGTATCAAAGCGTTGTCAA
CAAATAGAGAATTTTCATATCCGTGCATGAATGGAATGGGTTCTCCATCG
AGTGATATGTCTTGAATACCAATGAATATGGGAAAATACAGACTGATCGA
TATATCCATTACTTCTATAATCGGATAATGATATTCGATAGTTATATTGA
ATACTGTTATTTCAGGGTAATTCAAACTTATGGTGAAGATAAACCCATAT
TCCATAAGAGGGTGATATAGATTAATTGAAATGGTGTTGAAGTTAATGTC
AAAATCGAGGGTGGATTCATATTGTGTGCTGAACGTTTTGCCGTTTATGT
CGCTGAGATCAGGTGAATAAAGATAAATATTAAAATCGAGGGGGTATCT
ATAATCAAAGCTTCCATATCTATATAATAGAGGTCTATATCGGCAATCTT
TTTTCCTTGATAATACACATCATATTCCAGATCTTTTGAAAAACTGGTAC
TGAAAAAATACCGGTAAGTGTCAAACAGATCAAGAATTATTGAAACTGTG
TGTTCGTTTTGGAAGACCAGACTATAACTGACATCTGAAACTAACGTCAG
ACTACTGGTACTTACAGGATATCTGAAATAAATGTCTCTATAACGTAAAT
ACCTGTCGGCTGATTCGGTATATACTTTTATTATGTAATCTGTATTAATA
CTCATAATTTATCGATATAAGTTCGTTTCCCTTTTTAACCAGAATAGTAC
TGATGGGTACATTTCCGTTCATGAATTCACCAAGCATATCGATAATAAAA
TCTACTTCTTCCCTCACTTCCAGCATAAGTGTGGGGGGTATTTCAAGATA
```

FIG. 1T

```
GACAATACCATCTTGATAGGAACCTTTTACATATTCACGGTTTTTATACC
AATTGATATATCGGCTCATAGAATGTTGAATTTTCCAATCGTCTTTTTTA
AAGGAAAACATTCCTTCATATTTGTTGAAGGGATCGTAAACGAAACCGAC
GTAGTCTTTCATGTTTTTCTTTAAATAAACAGGCGGTTGTGTTTTTATTC
AGAAAAAACTTATTTAAAGAAAAAAGATGTATACCGAACTGTTCAAGAAA
AGCAACCCGCACAACTCATATTACTATCATTACGTGCATTTTGACAGTAA
TTCAAACACACATTCAATCGATGTTCCCGGCGGAAATGCGCTCAAAAACA
TTCTTATTGTGGGTAACGCTTCTACCCCTTATTTTGTCTCTTTTAAAATC
TATACATCGCATAGCGGGTTTGTGCCGGTTCCAGTATCCTACGATTACGA
AGCGCTTGGAAACAATGCGCTGATTACCCCTAATATCTCTTCATTTGCAG
TTTTTTCCTCTATTCAAACCTCATCGCTTCGCATTAGCATTACCAATATC
ACCCCGTTTAGCGGAAGTGTTTACATACTGTTTAAAGTCGAGTAACGTAT
GTTTTACGAACCTTCTGTAAGCTTTTTTGCAGTATATCCTCAGTACAGCA
CCAGCGCGGCTTTTCTCACAGAATTCAATAAATCATCGGCGTGGGTGCTC
CACAAACTGGGCTACCCGGTGGTATCGGTGGAATTGACGAAAGATCAGCT
TATGTTTCTCTTTCACGAAGCATGGCAAGAATACTCTCAGTATATTTCAG
AATTTCTGATTCAGGAAAACTATGATAACGTTTTAATAAAAACATTTTC
CAGACGGAAGGGGAAATCTTTGAGAAGTTTCCCAAACCTAACAGTTCGCT
TATCATCGAGCTTTCTGATCGCTATGGAATGTACGACATGAACACCGAAT
ATGTAATCATTCCACTTACCGCTTCTCAATCGGTTTATGACTTGAAGAAT
TACATTACCGCATCCGGAAAAATTCACGTTCAGCAGGTGCTTGTCAATAG
ACCGCGCGTTGGTCTTGGTTCTACGCTGTACGGTAATGCTTTTGTCTTCA
ACAACTATTCTCCCTTCACCGTAGGATACGGCGCGGGCTGGAATATCGGT
CAGGTGCTCACGCCGCTTTCCTATCTTGCCACCACCATGCAGGCTACCGA
TCTTGCCTACAATATGTATCGCAAGCTCCACTTCTTTGAAATTGTCTCTG
GAAGTATGATTCGCATTTCTCCTGTTCCCGATTCCAACGACTCCCGGCTT
ACAATCAGATACAAACTGGAACGGGAAGAAGGTGATCTTATTGAAATGTA
CAATTCAATATTTTATACGAAAACAGGTCTCCTCGATCTGGAAAAACTAA
ATGAAAACTCCCTTATTGTGCTTCGGCATATCTTCCTCATGAAGGTGATC
GATACGCTTATTTTCATCCGCAAGAAGTACGACAACTACGCACTTCCCAA
TGCGGAACTTACGCTGAACGTCGACAACCTGAAGGAACTCAGGGAATCCA
CCAAGGAAAAGATCGACAAATACAAAGAGTGGCTTGACAACATGAAACTT
CACGCAAGGCTTCAGCGGAAAGGAGAAGAAGCAGAAGCGCTGGAGCGGGA
ACTCCAGCGCTATCCTATGGGGTTCCTATTTATGTAATCTCTCACCTGCA
ATCACTCAGCGTGCAGGCGCCCATGGGGTGATCTCCTCTACCGGGCTTTT
TGAACGGCGGTGGAATCTTATGTCCCGGTTTGTGGTGTGCAGTAACTTCC
TCAACCTTTCCATAGGTTGTGAGCATGGGGGTAATCCACCTTTTCATGGC
TTCTCCGATTTTTATTGTTGGTTCTTATAGATAAATAACCCTGTGGCAC
GCATCGTAAGTGAAAAACCACCCCAACAGCCACCACCGGTTCACATAACG
GAAAAATTCTTTGCCTTTTTTAAACTCTTTCATGATTGTTCTTCTTTTGG
AAGATTCAGCTTAATGGTGATATAATCCGAGTCGGGGAATTCTTTTCTTA
AATCCTCCAGCGACTCATACACAAAAATCATCCCGACGGCACCGGTGTTA
GCTATCTTAGAAAGTGGATAGACGACTTTCTGAACGCCGTTATTGATGAC
AACCTGCAGGTCATCCAGAAAGTTAAGCTGCATCGCGACGTAATACACGC
GCTCTTCGTTATTGTTGTCGTTCATGGCACACAGGGTTTTAAGGTTACGC
ATGGTAGTCTATTTTTACAATGTAGGTTTTGTCGTTATATTCTATCATGT
GATAATGCGCCTGATAAATATGGGTTCCTTCCAGAAATAGGGGCTCGTTA
CCTTCAAGGTAGACGAACACCATATCTTCGTCTCCACCCCCCTGAGAAAG
GCGGATAAAGGGAGTGTGCTGACTCTGGTGAGTAATACCGATAACAACAT
CGGGGTTTTTCTCGATAAAATCGAGAATTTCCCGCTCCTGTTCAGTGGGT
TCAAAATGCTTCCATTGATACACCCGGTAGGGGCGATTCGAAGCGATGTA
ATAGGGAAGAGAAGCTACATGTCGGTTATAAATATCCAGAACAATCTCTT
CAATATCAGTATTTTCTTTATTTTTAATTTCTTCCTCGAGTAGCATGTTA
AGATCAAGTATCATGTGAGCCAGCGTGCTGACTTCTGCTTCATGCATTTT
AATACCTTTCTTTTCAAGGATACGAACAATGCCTTCAGTGTCGAATTTGA
GAATCATGGCGCTAATGGGTTTAGTTTTCACTCTCTACAAGAAAACGAAT
AAGATCCTCAACGGTTTTATCTTTGTAGTATTTTCAACATACCCGAGAC
TTTTCAGCAGATCAATTGTTTTCTCTGAAATGATCTGACAGTATTTGTCT
CTATCTATGTATTTTTAACGATTTCAAGACCCTCCTCATCATCCTCACG
TATGCTAAGTGCGTGGATATTGCGGAGCCTGTTGATATGCGTTTTCTTTC
CCGCTTTCAGAATATCCCACACGCCGCTCCCATGTTCGGGGTTAACTTCT
```

FIG. 1U

```
TCCAGAGAAAGCGGGAGATTGGTTCTGGAAGGATCCAGCATGGTGCAGTA
GAACCAGTAGATCTTGTCTCCCATTTGCGGGGTTTGCATCCTATAATGG
AAGCGAAAAGCGCTCCCTTATAATGAATGGGAAGTGTATGGTCATACATT
TTTATGAATATCTCAGAGATTGGGACATTCTCCTTTTTCATCTTCATAAC
TTCCTCTACATACTCCACATATCTTTCGGCGCTGTCAGACGAAGATATTT
TCATTTTGTGATAGAGATCTTCAATAGACCAGAAATTCTTTTGAGACACA
AAGTTATTGTAGAACGCTATGGTGGCGGAAATGACATCGATGTCGGGTTG
GCTGATATACTTCAGGTAACCCCTGAAATACTTCTTGACAATTTCAGGCA
CCGAAGAGTTGATCACTTCGATTCCCTTCATCTCTTCTTTACCGTCTACA
GTAACCGCAAAGTAGCGGTTGATTTCTTTGATAAGAATGGATTTGAACAC
GAACTCCTGCTTTAACTCCAGCTTGAAATCTTCTCTTGCATTAAAGTTAT
TTTCCATATAGTCATTGATAAAAGAGTTGAGATGTTCTTGAAGCTCACCG
GCTTCCGCCACCGGATCATCCGTAAAAGCTTTGACGAAAATGGAGTCGGT
ATGCGAATAAATGAAGCGATCGCGAATCTGAGAAATCACGGAGCGAATAG
ACATGCGCCCGGCGGCGGTTACACTTTCCGCAATGGGAAGGCACCCCATG
TACACCGAACGGTTTCCGAAGATACCGTACATGGAGTTCATCATAATTTT
AAGTGCCCATTGACGGAAATGGTGTTCCATGTTGCCAGTTTCTTTGAAAA
GCTTACGTTCTTCCTTACGTCGGGTGAAAATCTCCCGAATGATAGAAGGA
AGCACGCCAACCGGCTCTTTCCTGTAAAACCAGCAGATACCCGACGGGTT
GGGCACCATAATGATATTTCGACTTTTTAAAAATTGCCGGAGTTCCTCAA
AGCTGTTGATGACAAAGAGGGGTTCACTCCGGTAAGAAGGGTTCATCCCT
GAATCGAAGATGTAGAGGGGAAACCCGAATTCCGGTTCTTCCTGATCTAC
CGGAATCACTTTGTTCTCCACCCGCATACACCCGTAAAACTCCGTTACGA
ACGTAGCGGGATCGATATTGAATTTGCTGATTACAGAGGGGTACAGCGAT
GTAAAATCAAGATCGAATACGTTGAAGTAAATATCGGGGTTGGTAAGTTC
AATGTAAGCACCGCGATAACGATACTTGTTGATGTTCATAGCAGAATACG
TTTGTTTTACATTGCGGGATCAAAATGGGTATCTTTCACCTCGATAAGGT
AGGTGTCTTTTAAATCACATTTGTATAATACGCCATCGAGTGGAGAAAGA
TCAATAATTCTCAAAACTTCATCCGTATAGAATTTTCGCTCGATAAGATT
ATGCGTTTCCAGACGTTTGCAGTACTCGAAGATAGCGTCTCCAACAACAT
AGCTTTCCAGGTGCCAGCAGGCAAGCCCATCATAATGATAAAGCCCCCAC
CAACCATTTGCTCTTTCCCTGACCACTGCAGGGATAACCCCCAGATCTTC
AAGAAATGCTTCAAGTTTATTTTCATCCATATAAAGCAAATCGCGTCGCA
TTATGTTTTTTCCCCGCTCCTCAAGAAACGCATCAACATACATCCACCCG
GTTTCATCCCGGATAAGCTTGCGAAGTGAAGGGTATGCCTCAACCGATGT
AAACCCGGTCTTCAAATCGGTAATAATATCCCGCGAAAACCGCATAACGA
ATAATAAGGGGTTTCGTAGTCGATAAGTTTTTCAATAATTTTAATGATT
TCGTACTTCATGGCTAAAACGCTACTTCATGGCTAATACGCTACGGTTAG
TTTAAGTGTCGGGTAAACCTTTCCATTAACTAATGCCACGCCCACCCCCC
CGTAAATGGATCCGAAAAATCTCTTCTGGAAAGAAAAGTCGTAATAATTG
AGCCCTACGGAAGCGCTGATAAGGTTGTGCGTTTTTCTAACCTTCAGCGC
AAAATCTTCCTGCATGAAACGTCCGGTTTCCGGGTTGAAAAACGTTACGC
GGAGCGTGTTGCCCTTCCACGTGGCATATCTTTCCGGAAGAAGCCCGTAG
AGTTTCATGTCCACCGGCTTCGGACACTCCACCGTGTCAATCTTCCCCAC
GGGCGCTCTCCGGTAAATGATCTGTTTGACCGGCTGGGCAAACTTCCCTT
CAACCTTCAATTCTGAAGGAAAAACTCTGTCCGAAAGTTCCACTCTGACT
TCCGGTCTGTAAACGGTGCGGTTGACGTAAAGATGTATGTTAACCGCGAT
CAGGATCAAAAGGAGTGCTTCTTTCCAGTACTTCATAAGTCTTCCTCTTC
TTGGAATTTGTCTTCTTCGTCTCTGATCATAGCGTATAGAATGATCAGAT
AGTTAATTGCGTCAATGATTCTACCTTCGACAGCATCCCGCTGGTTTTTA
ACCCCTCTGATCCAGCGTGCCACCCCTCTTAAATGTTTATCCAGAAATAC
ATACAGCACTTCTTCCCTTGAAATACCCAATCGCTTTGCAGTTTCTTCAA
AATTCTGAATACATTGTCGGTTTCGGCATACTCCTGTTGGGCTTGGAGT
CGGACACGATTTACTTCTCCAATAAGCTCTTTTACAATGCGTTCGAATTT
TGTGGTATTCATGGATTTCCTCCATTAAGTTTCTGGTATTTATCTTATTT
AAAGAAAAGATGAATACTCCCCGCAAAATATTTCTTAATCCACCCACCT
CAAGATCCCTACAGGATATTGAATACCTTTACCTCACCAACAAACACATC
ATTACCGGCGCGATAAATAAAGCGGTATGAGCATTGATGAAGCTTGTGA
ATGTGTTGTGGGGGGATCGTGCTCGAATATAAAGAAACACGGCATCA
ATATTTTTGATAATCTGACTATGGCGGTGGAGTATTTCATTAACAGGTAC
AAAGAGGATTTAAAAACCGGGCGCATTTAACTCATCATCTTTTCGTTGAT
```

FIG. 1V

```
AAATTGAATGAGTTCCTGTACGGAAGGATAAAACTGTTCCTCGAAAATCT
GGTGGTTTGTCTTTATCAATTCTTCAAGTTTATCCACATCCGCCCCGATC
TTTTCAAAAAAGGTACGGGCTTCGGAAAACAGTTCCCCTCTGGTTTCACA
TTCGGTATAAACCAGAAGAGGAACCATAACCCGGTAGAAAAATTCTTCCG
GTGCTTCCCTATCAACATACTCTTCAATAAGTTTCTCTGTAATAGGAACC
CCGCACGCCTCAAACACGTCATCCTGCACGGCGAAGTGAATGACGCCGTT
ATACAAAAGGTGCCGCAACCGCACCTTCCACATCAGGGAAGGGTCGGTTA
CGAACTCATACACCATTTGGAGAGCATTCTCGAGAGGAACCTCCTTTAAC
GGAAGCTCCTCAATTTCTTCTTCGATCGGGTAGAAGACGTTCTCTTCTTT
GGAGAACTTACGCTCCGGGGTAATTATAATCCAGAGCGCTTCTTTGACCT
GAGCAGCGTTCAAGTTGCCCATGTTGTACCTCCTTGTTTTTGTTAGTTAC
AGATTAAACAATTTGCTGGTTTTCTCGAACTCCTCGAACCACTGTTTCCG
GAGTTCATCCGAACCCCTGTATTTCAGGGGCTTGCTATCTTCTTTAACTT
TCGATTCCGGTTCAGGTTGCTCCTGGGTTTCGAGTTTCAGGGGAATTTCA
ACTTTCCCTTTGAGTTCTTTGAGCTTGTTCTCAATACCCGGCGGAACAAT
CCGATTTTTGAAGACCAGTTCCACCGCTTTGTTAATCACTTCATCAGCGG
CTTTACGGGTGCGCTGATAAATGGCATCCTGCTGAGCCTCTTTGAGTAAA
TACAAAGCGCGGCGTTTTAGATAATCCTCGCTGGCGCATCTCTGCATGGT
GAACTCCAGCGAACGTCGGTTGTGGATTTCGCTGTTAGCCATAAGGCTCT
CCCACCACATATACTCTTTTTCAGAATTGAGGATATAAGCCCCCTTGAAT
CTGACATAGGTATCCTCATCAAGCTTGAACCAGTATGCATCATAGAAACT
GTACCCCGCAAGGAATCGTCAATAACGTACCCGCAAGGGGTTCGACAA
AAACAAGCTCCAGATCGGCTACTGATAGTACATCGATCATATAGTCGCAT
CCTTTGTTCATAGCGTCTTTGAATTTTTCTCTAATCATGGCTTTTTCCTC
CTTTGGTTTATCGTTAAACCCACCAACGTCAAAAAGAGGGAGTTTGTTTT
TCGGATGGAGACAGAATTCGGAGTTTTTGGGCATACCCCGCTTCCAGTGT
TCCACCCAGCTATGACATACTTCCTCAAACATATCGGGGTATGTCTCTCT
GAACTTGGGAATTACGTATCGATAGAATTCGATATCGTATTTGAATAGCG
CATTTCTTATAACCGTAGGATCTTTTTCCATTGTGCTCTGTACGCGGAGA
TTTCTATGAAAATCAAGACTCTGGTACAGGAAGAAAAACGTTGCGTTCAC
AACAAAAAGATATGCTGTAAACTCGATCCAACTAAATGCTCTATATTCGG
TTGCAACAGGGTAAAATTTGTAAAGCCAGTAGCCCACGAAACCAAACGCC
ACAACCTTCAAAGGTTCGTGTACCTTGTTCACAACACGCGGGCTGTAAAG
CTTAAAACCCGAAAGCACGTTGTACGTGCCGGTAACGAACCACCTCCCAA
TCCAACACAAACCGATAGAACCCGATACAAGAATGGTGATCATTGTCTGG
CTCATGTGGGCGACGGCTTCGTGGTGCCCGAGCATAAACGGGAAACCAAT
AAACCGCCCGAATATTAGCAAGACCGGGAATGACAGAAGGTCCCCGGTTA
TAATGCAGACGGCGGCAATGAATGCAATCCACGCAATACCGGCGGCAAAC
GTAAACGACAGATAAAGGGCGTCGTTAAACGCTTCCGCCTCCTTGCGCCA
CAGCTTCAAATTATCTCCATAATAAAACCCCAGAACCGGAACCGCTACAA
GATAGCGATCCAGCCCCTCCACCACTTCCTTCTTGCTCAACTCAAGTTCG
CCCTTACCCCACTTGAGGAGCTTATCTCGATAAAGCTTGAAAGCTGTAAG
GGCGTACTTTCTTGTTACTCCGGCGTACATGGCTTTCCGGGTTTGAGTTA
TCAATCTGCTTATAACATACGCCGGAAATCCAGAAAAGTCAAGGGGATTA
CGTTAATTTTTTACGAAGAAGAAGACGTGCTACGTCGTCAAAGTAAATGG
CGGTTTTAGTGGCGTTGAGACGCTTGACTTTGAGCGGTTTATAAAGTCTG
TTCTTGATAAAAACGAAGCTCTGATAATTTTCCAGACGTTTACGTAAAA
ACTACTATTCTTTTCGTAAAAATGCAGAGGGCGATAAAATCGTCAGATT
GGGGGTTATAGACAAGCCGGTCATTTTCTGAAACACCCAAGACCTCTCT
ATTCTGGTGTATCTATATCTGGGTACATCCTCACAGGTTTTAACATGTAT
ATATCTACCCTCGCATATCAGATCAGCCGCATAGGATTTGTCTGAAGTGA
TAGTCAGATCGGGTGGGGTGCATTCATAACCAAGGTTGGTGAGATATTCA
TAAACGGCGAATTCTCCTATTTTACCAACAAAATAATTCCATTTTATTCT
TTCGGGGTTGTGCTGGTGGCGCTTTTTGTATTGCTCAAGCACAATCCCGT
CGTTTATCTGATTCTTAGCATATTCCATGCAGATGGGCACATACTGATCT
ACTTTTATCATCTTACCCACCCTTACCCAAGAGCGATACTTGTGGACGGA
TTGATAAGGTACATCACCGCCGTTTCACGGTAAAACGTTGATTTTGTGTA
ATGGATCCCAAGCGAAGAGACAAAGGGAGTTCCCGGATAAGCCATTTGTG
TGTTGTATCTATTGACACCGCTTTTCGGAAATGTATCTGCTACAATGGAA
AAGACCGCACCCTCGCGCTCTGTTGCTATACGGTCGACTGTAACGGTATC
CGGAATTGGAATTTCACCATCGAAAGATTTGAACATACTGAAAGAAAATT
```

FIG. 1W

```
GCTCAAAATGAGGGATTGACTGAGTCATCTGAAATGCGTAGAAAGGTTTA
CCTTCAATTACCACTCCCGCGAAGAAATTCTCTCCGGCAAAAAGCTGACG
AAGCAACAAGATAGCGTCGCGGGTTTTGTTTACCACCTCAAGCATATCCT
GATTGCGGGTTTCAATAACGTGTACATTATCCCCCTCCGCCAGATTTCTA
ACGCGGTTGGAAAGATTTCGCTGCAAAAACACCACGGCGGAATAAGGAGT
ATCTTCGAGTTTTTGAACAGGGTTTTCGGTAATGATATGATCCGGTTGAT
AAATCGAGCCTTCGAAAGCGTTATCCGTAATGACTCCGATATGTCTCAGA
TTGGATTCCATGTAGGAAAGCGTTGAAACATAATAACTGTAACTGATCGT
CGATGTGGTAACCTCTGGAAACATGCTGTAGGTGTGGTTGTCAATGAGCC
ACATTGAGATAGTACTGTCAGATGTACCTTTCAGGTAGAAATAAACCGAA
GTGGAAATAACAGTAGGCATTACCATCATCATGTAGCTCATGCTGTAAAG
CTGATCTATTCCGGGGAAAAGCAGCGTAATCACTTTCCCCTGAAGCACCA
CATTGAACGGAAGCAGCGAAAGACCATTTTCCAAATCTCTCATGTAGCAG
ACGCCGTGGAAATTCAGACTATCTACAACAAAACCGGAATTATCAATAAC
ATTTACAGAAACTGAAGTTATAAGCTCGCCGCGAGATGTATAGACCGGAT
AGTTAAAAGCCCCGGTTACATAATAGGGGTTGGCGTTGCTGACGGTAATG
GAGAAGGTAATAGAATCGAGAAAGCTATTGGCGGTAACTTCATAATATTC
TCTAATATCCTTATGTTCATTATAGGGAATGAACCCGTAAAACGTAAAT
AATTATTCAACACAATATCTTCCGGAGGAATGTTTTGACTTACCGGTATA
ATGTGTTCCGTGATGTAATACTGATCCCCCAGAAACGCGTCATGAATGAT
CACATCAAACTGATAATCTTTATTTCGTAAATCCAGCGATTCAGCCAGCG
TGTTTAACCATTTAACTTTCATTTTGCGATTGAAGGCGTGATAGGTAATA
CGATTGATCTGATCGTGCAGCGCGTCGAACGCATCGAGAAGTTTTCCGGT
AAGCTGCTCAAGCGTTTGAGACGGGTTCTGAGTTGTCGGTTCATTCAAAA
TATTTGTTTCCACAAACTGAAGATCATTGCGGAAGTAGAAAACATCCATG
ATATTCCCGATCATATCCATATAGGTGAGATATGAAGGATCGAACACTTC
TTCAGGAAGTCTTGAAGAAAGGCGATACGGGTTGGATACGTCGTATTCAG
TCGCAGCATAAAGGTGCATATCAAGAAGCACCTGATACGGATTGACGCCC
GGATAAATTGAAGAAAACGAAGGAAATACTTCTTCCCAGAAATGTATGGG
GAGCAGATAAAAGGTACCCGGAAGCGATGTCGAGTTGTAGTAGTAATCCA
GATATCCCAGCGCGTAACTCTGACGAATGGAGTCGTCTCTAAAGTAATGG
TTGATGTGCGTTACGTCTTCCGAAGCAAACCATTTAATGAATGGAAGGAA
GCTATCGTAGAGTTTATTTTTATTTCCTTATATTTTTCAGCCTTCTCCG
GATAAAAACCTGAAAGCGTGGTGATAATCTCATCATATTTCCTGAGCAGC
GTGATTCCTTTGAACGCCGCCTGAATGAGCGCTTCTGCTGACCCGAATTT
GACAAATCCGGAGAGCAGATGGAAATTGGATTTCTGCTCCATACTTCCGA
AGCTAAAAGACGGGATATAGGTGTTGATTCGATTGTATTCAATGTATTCC
AGTAGATCGACGGGACTCCTATCTTCAAATTCGAGATGAAACACGTTGTT
GGCAAACGCATCTTCCCTACCCCCAATGGCGCTGAAGGTAACCGTGTCTG
TTTCCGTGAGATTTACCGGAATGGATTCCTGCAAATCCACCTGACGCACA
AGATACACTTCTTTTGTCGAGTGAAGGAGTGATGAAGTTCCATATACATA
AAACGTTTCCTGATAATAAACCGGGGTACCCAGTTTATGAATATTCCCGT
TTACTTTAACCAGAATACTGTAGCTATTCTGGATTCGAGCGGTTACTTCA
GCGTAATAGTTGAACAGGTCTTCAAAAGTGATACTGGTGCTGATGTAGTT
TTCAAAAGCTTCGTTAATCTGGTTTTCAAGTTGTTCTATGGCTTCAGACGG
CAAATGAAATGGTGAGGAATATCTGATTGAGACCGGTTTGCGCAGAAAGG
TATTCTTTCGAAAGTGGTTCGGCTTCTTCAAGAACTTGCTGATAAGCGGA
AATTTCATTTTGATAAAAATTATTGAAAAACTCCTGTACATCGTTGAAAC
TGACGGTAGAGGTGAGTTCCAGCCGGGAGGTTGTAAAACTAAACGCCTGC
TCTTCTACGTAGCTGTAAGTTCCTAATTTTTTGAAATAAGCGTAGACGGG
ATAGGAGTCTACAGAGAAGGTATAAACAAACGGAAGCGAAATGGTGGGTT
TTTCAATTCCTTCAAAAACTTCAGCCGGAACAGAGTCAACCACCAGATAG
ACGTTTCCACTTCTTACATACTTGGAGGTTACTTTGCCAATAAAATCAAC
GGAATAAATGATTTCCCCGGCTGAAGAACCGCTGAAGTGTTCAATGTAAA
TGTAAGGATTTGTGTAGGAAGAGAATATGGAGTAAACCCGGCTACAATT
TGAGAACCCGAAATAATTATAAAATCTTGCATTCCTCTTTTTCTGTTAAA
TAATAACGCAATAAGTCAAGTGCATCTTTGGGATAGAAAGGCTGATAGTC
TTTCATGGAATGTGGATATTCGCCCCAGTCTTTGTAACCGGCGGGAGGAA
ACAGAAAACCAACTTTACATACGCCGCTATAGAGTTCCAACACTTTAGAA
ATTTCTTCAACGCTTACATCCGAATCAAAACAGAACACCAGTTCTTTAAC
CTTTAATTTTTGCACAACGTAGGAATCCGGAATACGATTCTTTCCACAGA
```

FIG. 1X

```
GTACGCACATTCCCACACCCAACCCATCCGTTGCATGGGGAAGCATATCG
AACATTCCCTCGAACAGATAAATCTTTCCTTTTCGAGCCGCTTCGTAGAA
ATAGACCGGGAGCTTACCCACCATATAGGAAAGATACCGAACCTTATCGA
AAGGTTGATAGAATTGAACGTTTCCTATGGAATCACCGAAGGCAACCCGC
TTTTCATCTACCACCTTGAAAAATCCTTTTGACGACATATAGCTGAGAAG
TTCCGGTTTTACCCGGCGCTCTTCAATGATGTGTTTGATAACCGGATATT
CGATATTTTCCTCTGAAAGAGGAGCCGCCTTTTTAAAAAGCGAGCGGTAG
TAAAAGTTTTTCTTGACGTTTGTCTGTTCAACATCCGTAAAATCGATATC
ACCCGAATTCTTATAATATGAATGAGTTCGACAGGTTTAAATCCGAAAA
TGCGCTCGAAGTCTCTATAAACGGTGCCTGAAAACCCACAACGGAAACAG
ATGAAAGAGGGGCGTCTATGGAAAAGTAAAGCGTGAGTCGGCGGTTGTT
TTTATGCGGGGCGCACTTAGGGCACAAACAGGCTACTTCTTTACCGCCCC
CGGCAACTTTAGCTTCGCTGAAGTATTTGGTGAGGATTTCTACAATCATG
GTTTTTTCTACAAAAACTCTAAGGAATCACAATGGTTCCCGGTGTAGTAA
TCACAGGATGATTTAAAGTAATGTTCACATCGGTTACCGTTATATCCGGC
GGAATCGTTGAAATGTCAATCGGGATATCGCAGTATTTGCTCTGAGAAAT
CTCTACGGCTTCGACGGTTACGGAAAAATTGAAATCATCGTCGGTATCGA
ATGCAGCCATGAAAAACTGTTCATCGGTACGTACGTTGACAATTTCATAC
CATCTTCTGGATTCCCCAAGCACCAGATCTCCCGGTTGTGGAAAATAGTC
GAATTCTTTCAGCACATTCCTAAGAAGATGAAGTCGGAGTTTCCGCACCG
ATCGCATTCCAACCTCCTCTGAAGCCGGTTCCCCAACCTCATATTCCACA
CGACAGGGGATCCGGTACATTTTATATTCTCTAATATCTTTCTTAGGAGA
CTCTCCATACAGATAGTGCAATACGTCGTTTTCGTCATCTTCCACCGCGT
TTTCAATAATACGAACAAAAAGGAAGTTGGCGTTGAGAATATCCTCAAGC
GCTTCAAGGGCAAAATGCTGAAGAAGATTGAGTTCCCGTCTTCCCCAGAA
AAGAGGATTACGCTTTTTATCATTTTTATTTAAATAACCCCTTTTCAAT
TCTCTCCGTTAGAAGCTTCTTTTCCGACTTTTGCATTTTCTCTTCGTCGC
CGTCAAGGCGGGCAAAAAACCAACTTTTATCATGATAATCCATAAGTCGA
AGAGCGAACCTTTTGCGAAACTCTCCGGGGTTTTCTTCCGGAGAAACCTG
TTCGGAAATCTCTTTATAAATCGTATCAAAAGATGACTCAAGCTGATTTC
GCATATCGGTATAAATTTCTTTGAGTTTCATCACGGTTTCCTGTTCATCC
GGGGTAAGTACAAAATCATCAAGTTTGTTTTCAAGAAAAAGATCGGCGAG
CTTCTCAGGAGTGATTGTAGTTTTAATCCGGTGGAGCTCCAGATATACCG
GGTGCTTGATCTTTGTGCGGTAATAAACACGCGGGGCAATTTCCTGTACG
GCTACAAATCCTTCATATACCACCTCATAACCGTCTCTCAGGCTTTTGAA
AAGCGGTGTAACTTCCTCAAATAGTTCCTGAAGGCGATTGGCACGAAAAA
GAGTATAGTTTTGCTCTTGAGACAGAACAGCCGGTAGCTTAAGATTTATT
TTTCCGCCACTTTCGTTGAAAATGCGTACGGCTTCTTCGGAGGGACCCAC
CTCGAAATATCCCTTCTCCGGATCCACCGAACGCACACCGATCAGAATGA
TATTTGGCTCCTCATAAGGAACCACCACTCGCGCGTCCGGATGAACCATT
TCAAATATGTAACAGTATGAGGAGTTCAAATGATAGAGAAGGTAAGGCGG
ATATTTCTTTTCAAAGGTTTCCCAGAACAATTCTCGATATGTTTTATCCA
TATGAGTGGTAACCATTCCGTTTTTGACAATGGATCCATTTGCGTCAATA
CTCCCAAGAGTGTGAATTTTCCACCCTTCATCATAATATAAAACCACACA
AGTACCATCCAGCTTTTCAACCAGTTTCATGGGAAGTTTGAACATGAAAC
CGGCTTTGCGCTTTTCATTCAGGGGAGACGCGTAACGAAGCGTCTGATAA
TAGTTTACGATTTCCGGCTGGAGTTCTTCCCCCCAGTTGAAAAATTTGTC
AAAGGGATAAGACAGAACTTTCCAACCACTATCCGTTTTGCGGAGAATCG
CCCCGCGACAGGCAAGGTGATATATCTTATCAAACTTACAACCAAGGTGA
TATTTGAACATGTATAGATCACCCCGGTTTTTGCACATAATCCCCTCCTT
GCGAAGGGATTCGACGGCTACTTCCGGAGACTCAAAAGAGTTCAGGTGTT
CGATAAGGTACTCAACCGGGTATTTACGTTCATCGATTCCATAGCGTAC
TATAAGTCTTGTTTTGAGTTTTCGGAAGCGTCGGTTGATCAGGGAGTTCG
TCTACAACTTCATAGTTTCCGGATAGGAAACCGTAGCAATCACACACCTC
CTTCGTAAATCTGTTTACGGGAATTGGTTACAAGTTTTTCAGCTACGCGC
AACATTTGTTACTCCACTTTTCAACCGGGGTTTCCACAAGGAAATGACC
AATACGGGTATCAAACCGGTTGAAGCCCACATTGTTGCGCTGAGCCGCGC
GGTCTTTATCCAGCGCCGCCACGATCGCCAGCTTCTGCTGAAGCTCCAGC
GCATAACCCCGCTCTTCCTCCGAAATGGTTTTACTTTCTTCTTCCTCCTC
CCGCTGCTGCTTCTGCTCAGACGTAGTAATCACATCGAGCAGAGATACAG
GCTTCTCAAGTTGAGTCTTCATACGCTCATGATTGAGTGCCTTTTCGATA
```

FIG. 1Y

```
ATTTCAATCTTGCGCGTCAGGTAATCGGCAAAGTTTTCATCCAGCGTATG
ACGCGCAACAATGTAGTGAATATCCACACATTCGGCTTCCTGACCAATGC
GGTGGAGACGATCTTCCGCCTGCAGGATATTGCCGGGTACCCAGTCCAAT
TCCACAAACACGGCGGTCTTAGCACGCGTCAGCGTAATGCCGACACCAGC
CGCCAGAATGCTGCAGAGCACCACGTCCACCTTACCACTCTGAAAATCCT
CCACCGCCTTTTGACGCTGCACCACATTTTCCTCGCCGGTAATGCGGGCG
TAGGTAATACCTTTAGCTTCAAGCACCTTCTGAATGATCTCGAACACATC
ATGATGGTGTGCAAACACAACCAACCCGTCCACTTCTTCCTCTTTCACAA
GAGAAACAATATAGTCAGCAGCGAACGGGGCTTTGTAATGGCATAAAAG
CGCCGCATTTCTGCAACGCGCTCAAACATAACCTTCATTTTTTCATCAAA
CTCCGCCATTGCCTCAGCCAGATCAGCGCTTTCAACCCCAACCCGCTCAA
ACTCGCGGAGAACGGAAATATAATTTTTGAGATTCTGGAGATCTTCAGCC
AGCTTGAAAATTTCTTCTTCAGCAAACATCTTATTAAGTTTTACAGGAAC
GATTTTACGGCTTTTCGGCGGAAGCTCCTTGAGCACATCTTTTTTCAAGC
GACGAATCATGATAGTGGAGCGAAGCTTTCCCTGAAGTTCTTCAAGGTTA
CTTGCACCACGAAAATCCCAACCATACCCATTATAGTAAGCGTTGCAATA
CCGCTTGGCGTAGCCCCAGAAATTACCAAACACCTTCGGAGCCGCCATCT
CAAGAATGGGATAAAGCTCAATCGGTCTATTGACGATAGGAGTACCGGTA
AGAAAGAGCACCTTCCCGCCCTGTTCTATGGAAGATTTGACAATAGATTT
TACAAACCCGGAGCGCTTCGTCTTCGGGTTTTTGATATAATGGCATTCGT
CTACGATCACAAGATCGTAAGCATAATCCTCTTCCGAAATGCGGTGGAGA
ATGTCATAATTGATAATGTAAATGGTGTTTTCAGAGAAAATCGACTTC
ATTGCCGTTAACCACAATAATTTCTTTTTCGTGAACCACCCAGCGCTTCA
ATTCCCGCTCCCAGTTGTACTTCAGAGAAGCGGGACACACTACCAGCACG
CGATCGGGGTTCATTACATTGATAACCCCGGCGCTCTGAATTGTTTTCC
GGTACCCATTTCGTCTGCAATGAGAGCACCCGGATATTCTTTAAAAACTT
CGGTAACAAAATGCACCCCCGCCTTCTGAAATGGGAAATAATCATATCCG
GTAGGTGCAGGTACGGCAAAATCGCTGCTGGTGACGCTGCTGAGCTCGAG
CTTGTGATTTTTTTCTTCCAGGAGAAGGTTGTACTGCTGAGCAGCCTTTT
CGTCGAAATAACCTTTCAGTTACTCGCATAATCGAGAATTGTCGTATAC
CATACCCTCTTATCCGGATCCCACTTCCACCCGGCATTTTTGGGGATCAG
ACGTTCTTCGTAGGTTCCTTTCCACTCGAACCGGTTGTTGTAAGTAACGT
AGCCCATGACCGCCCTGTCTTTGGCTGTCAATCTGCTGATAATATACGAC
ACTGAACAAGAAAAGTCAACCCCTTGACAGAAATTTCAATTAGAAGGGAA
ACGAAAGTTGAACAAACAGGTGATTGAAATGCTTCCGATAGCGCGTCGGA
AGATCAAAGGTGTCGTGGATAAACTTTTCAAATTCATCTTTTTCACCCTC
TAAAACATCATCAAGCCATAGTCTTCGACGTTCAAGGCTCCCAATAATCG
CCTCAATCGGATATGCTTCTATAAAAGCATTACCGGGATAATCATCTACA
ACACTCCTCACAACTTCTTCAATGTTTGTTGTATCTATCAATCCCCTTTC
CGTATAATACACTATATGTGGTTCTTCGTTTGATCCGTAATCTGATTCTA
AGTATACTATAACTTCATATTCTACTATATCTTTAACATACTCGATAATA
CTTTCTATTCCACTTTCAACCATTTCCTCTACTTTCTCCCCCCACTCTTC
ATCAAAATGATCTAAAATATCATCCGAGTTGATTATTTTTCTATAAGAT
CATAGTTTACATTTTCAGGTTTAATTGTGCTGTAAAAATATTCAAAACAG
CCGGTTGTCGACATATTTTATAAAGAGAAGCAACTACATCGGGATATGC
TTCGTGTTCCGCCCATTTACCAATATGTTGTTTGAAAAGAAAATAGGCGA
TACGATAAGAACCTCTGTTGGCTCTCCTTTTTTCTATATCTTCTGGCAAC
TCTATATTAAGATATTCATGAAGGTCTTTAATACCCTCCGCTTCCCCCAT
ATGATCAATTGCGATATCTACAAATTGTCTTATGAGATCGACAACCACCG
AAAGATTGATATATTCCTCGAATTTATTCTTCTGATAAAGCACAAATACC
TGCAGGGTTTCAGCGGGAATATAAACAGTATCATAATTATAAGCGAGGAC
GCTCCTTACACTGTCTAAAGCCATATTAATATAATATTCGATTGCATCTT
CTGAAGGTGCAAGATTTTCTACCAGATGGGGATATTTTTCAGCAATCACA
TCCAGCATCCGCGCCGCATAAGTAGCATAGGGTTCTTCGTCAATCGGTAC
CATTGTATTATCAGGAAGGTGAAATTCCTTTCCCTTACCAAATGTAGCGA
TTGCGTAAACAAGTCCGTCATACGGATTGCTACTATCGGCTTCGAAATCT
ATTCCCGGTTTGATCGCCGAAGGATGAAATACCCCCACGAACAAGGGATA
ATAATAGTTGAAATGTTGATCGCCAAGTCCCACACACACATGAATATGAT
TACCAATCATCCCGAGAATACGTCTGTTTTCCACCACATTTTGGGGGTGA
TATATGATCATAGAATTGTCTTCGTAGATAATCAAATCCGCATATTCTGT
GTGCATAAGCTGACGAAACTTCTCCCACAATGCCAGATAAGAAGCCCCCA
```

FIG. 1Z

```
CCTCTTCCACTTTTCCGGCGCGTTGATATGCCCCAACGACTTTTCCGGGA
TCGAGAAGCTGAAGGTTATCCGTAAGATCAAATTCCCTCAAAACGGAGGG
TTGGTGTCGCACCGAAAAATACCAGCGAAATGGCTCGATGTAAAGAGGGA
GATCGATCGGATCGATTTTGTCGCTCATCACCATACGATAAAAATATTCA
ACCAGCGCATTTGTCGAGATAAGGTTATATTCGGGATTGTTGCGAAGCGG
CTCAAAAATAGACTGAGCAACTTTGTGAAGAATATTTCCAAAAAATAAAA
TACGCTCCCCCGGATCACGGGGAACTTCTCCAAGATTTAATTGCTGAGCC
AGAAACCTGAGTTTGTTTTCGGAAGTTTTGCAAGTAGTTCTTTACCCCT
ACGGGACCCCGGAGCAGGAAAAGTAAACGCCATTTTTTTATTTTAAATAA
CTACGCCCCAAAATCCACATAAAGATAGCAAATTTTCCAGCTATCCTCCA
TCGAGATAGTATATTTTTATCCCCCTCTTTTTTAATCTGATAATCTTCC
TTACCGACATAATGTAAAAATTGCCTTATAAGTTGCCACAACCTATCATA
TTCCTCCGTTTCATCAGTGCAAGCCAGCTTGTACTGATAATCAACGAAGG
ACATATCGTTTATTTCATCATAAAAATTGTCATTGCCCCCCACAATGATA
ACTTCTGGATCAAATACAACCCATTCGATAAAATCAAGCATAAACTGGCT
TAATTCCGGATTTTTAAGAATATAACGCCAGTTCCAGCGCGATTCATGAT
CACATCGATCAAGCCTTTCTATCACCTTATAATCTTCATTATATCTGGCA
AGTAGAAAACGTCTCATTTCGGCAACGTTCATATCGTAGCTCAGATTATC
TGAAATATCGTTCAACATCTCCCGAAGTGCGTCTATAAAGAGACGCTTGA
TAGGCTCGCGTTCAAACATCAATTCTACAAACTTCACAACCACACAATCC
AGTTCTCTATGATTTTTCAGATAAGCGTCAATGTATATCCGACGCCGC
GTTGGCAATCAGATAGCACATCTTAGCCAGCGGCGTTTTGCAGACAAAAA
ATTCCCACCCGAAATCGCAAGGGTAAAAATCCTCCTTCACCTTATCAGGA
TAACGGCTGATAAGGATGGAGTGGGAAGACGATGAATTTGTGGAAAGACC
GAAACGAATGAATGCTTTCATGACTTCCTCCTTTGTTTGTCAATGGTTAC
ATAGACAACGTAAAAAACAACGGTAAGAATAAAAAGAAGTAAAAACTTTA
TGTTCAACCAGAAGGGATTCTCTCCTCTTAGCACCAGCGCTGCAGGGTTT
CTCAAGTATAATGAAAGATAAACCAAATACAGCGCAAGCGCCAGCGAAAT
AGAGCCTATCAGTATTTTGAACACTTTCATAGTTTTTTCCAGATGTTGAG
AAAAGTTACCGGATCGAACAGTTTTTCCCTCGACACCCTGAAACCCTTTT
CTTTCAAATAGGATCCCGGAGCAACAAGTGCTTCCGGCTCACTCATGTCG
ATGTAGCAGGAAAAAAGTCCTTCCTGATCGGTAGTGCTATGTGGAAATTC
TCTTTTGAACACCGGGTAAGTTTTAACAAAAAGGGAATCCACCGAAATGG
TGAGTTCTTTCATAAAATACTTCACCGCTTCCAGTGTCTTGTTTTCTGGA
ATTGGTATGTTATTATAAGTTTCTCCCCTCCCCACTTTCTTAAAACCAAG
TAGCAGAAGATGGCTCCCCTCTACCTGAGAAAGCATTTGCATCATTTCAA
TGGTTTCTTCAAAGGGAACGCTCCCCCATACGTGCTGAGCCACCAGTTGC
ACATTGGGGGGCTTCTGATTCAGAAGATCGATATACGACTCCACCGATTT
CAAACCATGCACGCTGAAACCTATCCCAAAAAGCCGATTCGGAAAATAAT
GCCGGTAGAACTTCATAAGCTTTCGGGCAAACGAAGCATTGAAGGTGGTT
ACGTTAACATAACCCCGGCTGAACGTTTTGACAATGCGATATAACTCTTC
CAGAAATCTCCCCTTCCAGAAAAAGCAGGGGTCTCCACCCCCTATGCTGA
GTTCGTAGGTACCCATTTCGTTTAACATTCGTGCGAACCGGATCATGTCA
CCCGGATCACACTCTGATCCCTCCGGGGTGGAGTTTTCATAACAGAAAGC
ACACCCAAAATTACACACGTTGGAGGGTTTGACATCAACGATATGCGGCA
CCTGAGTCTTAAACATGATTACCTCTGAGTTTTGTTTTCGGTGCGTATGT
TTTCCACAAAAACTACATAGGCTGAAAATACACCAAGAATAAAAATCTGA
GCAAACCCCACAACCCCCGTTTTGGATTTACTTCCGCTTTTACTTCAAA
AACGATACATATGATTCAAAGGTCTTTGATTTTCGGAATTTCTTCACAAA
CTGCTCAAGGGCTTCGTAAACGTCGGGGCGAACCAAGTTCTTCTCCTTCG
TGAACACCACCCGCCTTGACTCCCAGTCAACCCCGAAGTTAAAAAAGTTA
TTAAGGCTGACACAAAGCGAAGTGAGGGAAACTCATATATTTTTACAAT
TCCCCATTTCTGTCTATAAGCACCGAATAATATCCTCTAAAAGCGTCGC
ACAGGTTGCGCACAGTCTCCAGAAAATCCGAAACCGGCGCAAAGTCTTCA
AGCACATAGCAGGTTAGTTGAACGGCTTTTTCTTCATTCAGGTGCGTTAC
GGAATACATTACCGGCTTGACTACCATACTTCCTCCGTTTTTTTGACCGG
AAAACCGAATCAAAACACCAGAGTTCCATTCCACACAATACTAATTACCA
GTATTTAATTCCCTGTTATTTCACATACCCTCTGGATCATTCTGTTTTCT
TTCTTATATATTCCATTGTCAGTTGAAACCAAACAGATGAGCCATGCCGA
ACTTCATTACAAACATCAGGAATTCCCGTTTTAAGGAAGTTCTGACCGAA
ATGTACCATTGCCATCACGAAAGCGAGTACCACCTTGAGGGAAATGTTTT
```

FIG. 1A2

```
AAATCACACGCTTATGGTATTGCAGGTGGTAGATAAGATAACCGCTGATC
ACCGGGAGCAAACTAATCTATCCTTAACCGCCCTTCTTCATGATAGTGGG
AAACCCTATACCCGTGTTGTCGAAAGGGGAAGAGTAATGTTCCCCGGTCA
TGAAGGGGTGTCTACGTATATCGCTCCTCTTCTGCTGTGTGAAGTATTGA
GGGATTCCCTCATCACACCAAAAGACGCCATTCAAATCCTTTACGGCGTC
AATTACCATATGTTGCACTGGAAAAATCCAAACCTTTTTATGCGGCTTTT
CACCGAAATGGTTAATTATACCTGTTTATATAACTTCTTGAAAAAATTCA
ATCAGTGTGATCTAAAGGGTAGGGTTTCTACAAAACCCCAAAAGCAGGAA
TTCCCCGTAATCCATTATTTTGAGAATACCCCGATCGGTACTGTTGAGCG
CCATGTTTATTTTATGATCGGGGTTCCGGGGAGTGGAAAGAGCACGTTTC
TTCAGAAAGTTGGAGAGGGGCGATTGTATCCCGTGATGAAATCATGATG
GAATACGCCGCTGAAATAGGGATCACAGGAGACTACAATACTGTTTTCCG
GGAGATTCACAACAACCCTATGCATAAAACCAAGGTCAACAACCGCTACA
TGAACGCTTTCCGTAAGGCGGTTGAAGAGAATGAAAAGGTATTTGTAGAC
GCAACCAACATGAGTTATAAGAGCCGGAGACGTTTTTACAATGCGCTTCG
GCGGGATATTGCGGAAACCGTGGGTTACCATTATATCGTAATGCTTCCCG
ATTATTTTACGTGCATTGAACGCGCCGAAAATCGGGAAGGAAAGTCGATT
TCAAGGGAAGTGGTAACCGATATTGCGCGGAGTCTGCTTCTTCCGTGCAG
GGAACATCCCAACAGCATTGATACGACAATTTATATGTCTGATGGGCATG
ATGAACATGTGTTGAGAGTAGCTTGGTAGTTTTTAAGATTCGACGATGCT
CCCCCTGCTCAAGCGGGGGGATTTTTTATTTAATCAAAAGTGGAACCTT
TAGAGAAACTACTTGCCGTTCTCAAAAAGCTTGAAGCGTTTGAGGAATAT
CTTTCAAAGATAGATCTTGGAACGCTGGATCAGGTGATTACCCGGCTTAG
AAAGCTCCGGGAATCCAACGAAAACTGTACAAAGACTATCTTGAAGAAC
TTGAAAAAGCTTTTCAGCACCAATCAGGAAACGCTCGAAAAGCTGGTAGAC
GCCCTTTCGGAGTTTACGGAAGAGGAAAAGGAAAAACTTGAAAATTTCCT
TGAGACGCACCAGAAAGACGCCGCACGACTTCTTGGATATATTGACGTTT
TTGAAGCGTCGTGGAAACACATGAGCGCCGAACAACGGGCGGCATTTGAA
TCCTTTATCGACAGACTCAGAGAACTTCGTAGAAACCTCAATCTCGATCG
ATTCAAGACGGAAACAGCATTCGATGTTTTCGACAAAGCACGAAGAGACC
TTGGGGTGCCTTATGAATATATCAATCGGTTTGCATTAGACTTTATCAGA
TTTCGCCAGCGATCAGAAATTTTCTTCAAACAGATCATGGCATTTTTCAC
CTATGAAAGGGTGACAAGGTATACCGCTTATGGAATGGCAATTAATCTGG
TACAGGGGGCGCTTGAACGCTACATTGAAACTACTGATGAAGTGATCAGA
GTTACCGGTATTTACAACCGGCTGCTTAGGGATCAGGCGCTTCAGTTTTA
CCGCGCAAATATTGATCTGAGACGCTTCGGTGTTCAGCTCCGGGATACTA
CCCGCTTTATTGCCGAATTTTATGCATTTACGCGCACGCGCGATCCGTTC
GCGTTGATAGCTCAGACAGCAGCGGGTGCTGGAGACAACATCGACGGATT
CATGCGTCAGATGATTCTCTTGAATCAGCGCCTGAATATTGACAGCCGCA
CGCTAACACGTAACATGCTACTTGCAGCTACCACGCTGGAAGATAATATC
ATGCAACATATTCAGCTTATCACTGCTTTTGCAAATGAAGCAAATTTGAG
CGCTACCGAACTGGTCAGCGATCTTGTTGAAAGTTATTCAGAATTTGTCG
TGCTGCTTGGAAGCGGGGCGCGTCAGATCACGCAAACTCAGATTGCACTG
GCGCGGTGGAATATGTCGCTCAGAGACGGCATGAATATTCTGAAAGGTCT
CTATCAATCTCAGGAATCGGTGATCGACTCGCTCATTCAGATTCAGATTC
TCTCGCGCCAGCCGGTTGATTTCGAACGCTTCTTTGGAGCCATGCTCACC
GGCGACATTGAAGGAATCGTCGATCAGCTTGCGGAAATGGCAATGCAGAT
GCGGGGCATGATGGATGAACTCCCCATTTATCGTATGCAGTTTGAGCGGG
CACTTGAAGGGTTGGGCTTAACCTCCGAGCAGATCGCAACGATTCTTGGA
AAGTCCAGAGAGCAGCTTACAGGGTTCGGCACTATCGTGGAAGATTTCCG
CCGGAAGCTTTCACCTGAAATGCTTATCCAGACTTTTGATGAACTTCTGA
GACCCAACGAATGGGAAGAATTGAAGAATGCGGTGGATGCATTCTTCGAG
ACGTTTATGCTTTACGGCGCTGAACTCATTCGCAACATGATTCCGGTGCT
TAGAATTCTGACACAGGGAATGCAATTGATGTTCAAGTGGTCTCAGGCTA
TGACCGATCTTATCGATAAGGTTGGTAGCCTTGGTGGATTGTTGAAAGAC
AACGTTCTTGGAGATTTCTTCAAAAGCATTTTCGCGTTTCTTGGACCCGG
TGCCGCGCTTTACGCTATTGCGAATATCGGAAAGCTTGGAACTGCACTCA
AGATGTTATTTGATTTAATCATTTCCATTCCTCGCCGCATTGGGGGAGGG
GTTGTAAACCGTATTGGTTCCTTTTTCAGTCGTCTTGGAGATGTGTTCAA
GAAGTTCTTCGGTAGCCGGGAAATGAAACAGGTTGCGGAGGATGCAACTT
CAAGAAGAGGAATTCTCCGTCGAATCACCGGTGGAGTCAAAGATTTTACC
```

FIG. 1B2

```
AAAAACCTCTTTCAAAGCTTTTCGCTTGGATCGATCGTTCGTTTTACAGC
AGCGGTGGGGGTGCTGGTTGGTGGTATTTATCTTTTCGGAAAAGCTGTGA
AATCACTTCAGGGAATCGACTGGGGTGAGACTTCGAAAGGATTGCTTGCC
TTCTTTGGAGCGCTTACCACTACGGTAGGGTTGATCAGTCTTGGTGGTCT
TCTTTCACTTCCCGCACTTCTTACCGGTCTTGCAGCTTCCATAGGCGCTA
TTGCCGTGGTGGCGGGCGGTCTCTATCTCACCGGTGAAGCTATGGGAGTG
TTTGCCAGCAACCTTCAGAGACTTGCTTCCACGCTGGAAACCTACCCCAA
TCTGACTTCCGGTATATTCCGTCTGGCTGGAGCACTTGGTACGCTTGGTG
CCGTCGGTACGATTGCTGCTCCGGGCATGCTGGTTGGAGCTATTACCGAA
GCCGTAAGTGCGGCGATCAAACCCGATGTGGCTGTAAAAGCCATTATCGA
TCCAGATGTAATTACCGCCGGAGAAAAACTGATCGCAAACAAACTTGACC
GGATTATTGCGCTGCTTACGGAAATGCAAAATAGAACGGAGCCAAGAGTG
GTTACGCTGAATAAGCCGGAAAAGCCGGTTGAAAAACCAATCTTCAGCAC
ATTTAACTTTTAATCTTCATCCTTTTCTTCTCCCTTTTTCCAGACCGGAT
GATACCAGTCGTTTTCTTTCATCAGGTTGATGTAAAATACATATTTATAA
TTTTCAAATTTTTCATTCATGCGAAGCTTATAGAGATAATCATCTTTGAA
CTTTTGGATAGGTATTCTTCCTCCAACATAAAGCAGACCACCTTTTCCCA
CCACAAAGAACATATCTTCGGGGAAACGTTTGATCTGAAGCACTTCGATC
ACATCGTCAATGGTAAAAAACTTGTATGCGGTTTCTTTGGATGCGTTGTA
AATGTAATAATGATGCGCAACGTTGGATTTTCTGTTATCCGTAATCATAG
AAGTTTCTGCTTAAGTAGCTAAATATCACTATTAAATAACCGGATTTGAT
ATTTAAAGAAAAAGATGAAATTAACCGATCTCAGAAATAAAGTTACAAAC
GCATATAACCAGATTTCCAAGCAGAACCGCGAGTTAATCGCCGCCAAACT
TCGTAAAGACTCCAGTGCCACCATTTACTTCGGGGCTGCTGTCGAAAAAC
TTGACGACGCTACGATCAAAGAACGTATGATCGACGTTTTTGCCACGATC
ATTGCTCAGGCGTATGATCGCGCGATTTCCTTGCGCAAAGGAAAACCGAC
ACATCTACCCTCCCCTCAGTCAATGGTACTTACGCTGGCAAGATTTTACG
TGGAAAATGAAGACATTACGCTCAGCAAACTTAACGAAATTTCCATTGCG
CTGGGCTGGTATATCGCGCTGGTAAACGAACCGAATTTGCTTCAAAAATA
CAACCTCCCCAAACAGATCACGGAACTTGAGCCGGAGCAGCTTCTGCACA
CTTACAACCAGATCGCAAGATATTCCGACACCTATCAGGTGGAACTGGTA
AATCGCTATAAAGAAATTATCGATTTCCTGACGCAAAACGGTGAAGAGTT
CTGGGAAAAGAATACGGGGTTATTTTCAAACCTTCCTCTTACGAAATCA
ACGCCAAAGTGCTTCAGCTTGCCTCCGATCGTCTTTTTATCTGCACCGCA
CTTAACCCTATTTTCCACGACACCTATTATCCTTACTATGTGCTTGTAGT
CAACCCGGCTTACAAGGGAGACGGCAATGTTCACTATATCAAAGACGGCG
TCAAGGGATATTCAGGTATGGAGTTTTATCTTGCCACCTTCTCCGACAAA
CACCCCTACCAGAAGGGATTATTTGCTCAGTTTCGTAGCCAGTATAATAT
CGCCACCCCTCTCAGCTTTATCGAAAGCAGACTGTATCTGGGGGATTTTA
TGGAGTTTTTGTGGAAACGTAAAGATCTTCAGCCGCATATCTCTAAACTC
ATAAACCTTTACAAACAACACCCGGCTTATCTTTTCGATGAGAACGCAAT
GAAAAGGTTTGTGGAAAATGAGCTTTTCGATTTCAAAAATATCAACGACT
CACCCGGCGCACGCGAAGCCGTAGCTTATTTTATTCCAAGATCGACAAC
CGTTCTTTTATCGAGGGGCTGACTCCGCTGATCGGAGCCGCCGTTGAAAC
GGTTATGGAATCGGGAGAAGACCCCAATTACAAAAATGTACTTCCGGTGC
TGGTAGAGCTTATGGTCAAAAACAACTACGCTATGAAAAAGATTGAAGAA
GCTGTAATCGAAGCGGTGCATAGAAAAGCGGAAAACATTCTCAAATTCAC
CCCGGAAGACCATATCAGATATATGGCAATTCATTTCGCTCATAAAAATA
TTCCTTCAAATTCTGAAGAAGAAGGAAGAGATTTTGCCGAACAGATTTAT
TATAACATAATCAGACCTCAGATTACAGGCACCTCACCGTATGCTATTAT
GTTTAAACGTTTTATATATTCAATCATTCTTGCCGAAATGAAAGGTATTC
TCAAAAACAAGATAAATCAGGTGGTTAAAGAAATGGAAGAAGAATTCGGG
TTTGGAGACATTTCCCTTGCCGATTTCGACTGGGGGGCGGTGAAGAAGA
CGAAGATTCGTTCGAAATGGAACTTTAACTGGAAGTGTACACCGTTTCTC
CGACGATATAGAGACGCTGTCCACGAGATGTTCTTGAAACCTGAAAGGTG
GCATTGTAAATGTCGTGATCTTCAACCACTTCTTCAAGCTTTTTCTTAAT
ATCTCGATAAAGAAATGACTTTTCATCCACGTAGAAGAAGTACATCCACG
TCTGATACTCTTCTCCCCCATTTTTTCCGAAGAGTGATCTTCCTGATAC
AGGTGAAATCCGTAATCCTTTAAAATAGGTATATGTTTTTTGATGGCGTC
GGATGAAGCCTCGCTTCCGTCATAAAATACCTTGAGAATCATATTCTCCA
TTCCGGTGGAAGGAATGACAACTTTCCCTTCTTCCGTATACGCACCCTGA
```

FIG. 1C2

```
ATGGCAATAAGCAGCAGCCCCGGAGATATTTCATCAAAGAACTGGTAGGT
ATCCTCGACGGCGCGAATATCGGTAATCAATGTAATCTTGGTTTTACCTT
TTTTGACAAGGTTGCGAAGGGCAAAAATGGAAAGGAAAACAACCGCTTCG
AGAACCTGATCCGGAGACAAATCTTCCGATCTTCTTATGCTTAAGAAATA
CTCCCGGTGGTAGTCTCTCAGACGAAATCTCAGATCTTCCTCTTTCCTCA
AAACCCTCGCAATGCGACGGTCTGTTTCAACAATGAAGTCGGTATGCGTT
ATTTTTTTCTCCCATTCTCCGTCGAAAAATTCTACATCGTAAACAATAAA
ACCTATCGTGTTGTAGTGGTAGTTGATTTCTACTTCGATTCCCCATGAAC
TATCAGGCGCACGAAACAGAAAGTTTCGCGGGGTAAGCTTCCACTTCTCC
AGAACCGCGCTTTGAAAATTGACGAAGTTTGTAATGATTTTCCTGAGTGC
ATTCCTCAGTTCACTCATAAATAGCGATAAAGAGTTTTCTCAACCGTTTC
CAATATCTGAAGCGACTGTTTGGTTCCAAATCGAGATTCCTGAAGCACTC
TTGCACTTTGAAAAGAAGGAACGGCTACAACATCTATCGCTGTGATAAAG
AAGTCGTCAACAATTTCTACCCGTTTTTGCTGGCGGTAACCTACTTTGGT
TTTACCGCTCCCACGAAGGGAAAACCCGAAATTGATACCGTTTTCAAGAA
GCGATTTGACCAGATTTCCGTAAGGAGTTGGGAGAATGCGGAATTTTCCG
TACACTTTATTTCCTTCCATCCATACGTCTACCCACTGCACGGCAAGGCG
CTCAAGCGACACGAACCCGATTCGAAAATCGTTCTGGTAGGGGTGATCCA
GCTCGCCGTACATCTGACCCTTTTCAATCTCCTGCTTCATACGCTCCACT
GCTTTTTTTACGGCTTCCGGCGTGTAGAGTGTACCATTGTCGGAAATGAC
GTCGGCTTCCATAATCAGAGCCGTATAAGTTTTATCGTTAACTTCCATAG
CGGTTATTCTTCAGTTTATTGTTTTCTTCTTCCTTTTTGTCTTCGGCGT
ACAGGAAAACGGCTTCCACCGAAGGAAGCATTTCGCGAAGCCGCGCAAGC
ACATCGGTAAGCGCAACCAGCTTGGAAACACTTCCGCGAGAAGCTTCGAT
CGTGTTGATAAGCTCGCGAATGTAATTGCGATAGTTTTCATCCAGCGTAA
TCTTGTCAATGATCTCTTCGATCATTTCACACAATTCCTCGCTCACGCGG
GCAATATCCTTTTCCAGTTCTTCCGTGATTTTTTCGGCTTCTTTCACCCT
CTTTTCTTCGGGGATTTCATAACTATTCTGATCGTTTTCCTCCTCCATTA
ACACCTTTTCCTCTTCATCTTTCTTGTCCTGCTTGACATCTTTACGGATT
TTTTCCACATCACGGCTGGAGTAACCTACCGGCGCGTCATACCCCGCAAT
GTCGCCGGTGGTGGTCATCTCCTCGATCTGTTTCAACGCCGATTCATAAA
GGTGCGAGAGGATTGCCGCCACTTTAGCAGGTTTCCTTGCGCTCAGGAAA
AGCTCAGCCACACCAGCCGCGCGATAAATGCGGGGATCGATACGGGTTTC
GTAAACTTTTGAAAGCTGTTTTTCTCCAATGATCTTTTCCAGCGCTTCAT
GGAAACCGTTGTACTGGCGCTTTTTGCGGTATTCGTGGACGAAATAGGGA
ACCCTTTCATATTCCTGATCTATGCAGGCTTCGACAATTTTGGTAATGTA
ATAAACATCGTCAGATTCCACGAAATTCATCAATTCACTTGCGGAAGCCG
ACTCCAGCAATTTCTTGTCTTCCGAAGAAGCCTTCATGAACTGGAATAGA
AGGATTATATCCTTCTGCTTCATAACAACCTTTTTTTTCTTAAATAAATA
AAATCGAAGGAGAATTAAACAACTACGGTATTATAACCCCATCCACCGAT
ATAGTTGTAATTGTGGCTGGTTTTATATACGGGTAACAGTCATGAAATAC
TCTGTTTCTGATGTGGCGAATTTGTTCTTGTGTCATATCACCCGGTATTA
GAGTGGAATTCAGATAGGCTGCATCTTTAGTTATTGCTATGTGATACAAA
AGGGGCGCCATTTCACTGTAAGTGTGTGTATCTCTAAATATAAGTCTATT
ATTCAAATAAAATGAAACAGTAAGATCATTACTAAGAGGGTCCATTTCAT
AATGAAATTCATGGAACACAAAATAAGACCGGTTTGGATTATAAAATCCC
CATTCAGATACTGTTATACTATGAGTTACTTTCTTTGTTAAAAATGGGGT
AACTATAGTCGAATAAGTTACTCGAATACCCAGATTCCGGAAGATAATG
TAGAATAATATATTGAAATAATATTTTCACCACTTAAAATTCTACCTATG
TAACTAACATCTACATTGAACACCGAAGAGTCATCTGCATAACCGTCAAG
AAATATTGTCTGAAATAAATGGAATTTTTCTTTTTTACCATTTATAAAAA
GTTCGATATTGTTTACAGTTCCCCAATAATCCAAATCGTAAAAAAGACTA
AAAGAATAATTGGGGAAATGACTCTGATACGCCGCTTGACTACCACCAGC
ATAGCTATCTGCAATATAAAATTGATTCCATCTACTTATAGCTCCATAAT
TGATATTTGCCCTGGCAATAAAAGCATTATGACCAAAATCATAGAAAAAA
GAAGAATTAAAAAACTTTGTTCTAACTGATTGGGTACCATTTATTCCATC
TGTATATTCGGTTACTATATAATAGCCCGAACCGTTTCAATAGTGGGGT
GATCTGTTTTGATTAAATAATATACATCTCTGACGCTCATACTCCCTTTA
TATCCCCCAGCTACCAGATATTGATTGGAAACTGAAACCGTCAACCAGTC
GGGTAAAAAGGGTGTAACATCAACACCATTTATAGCCGAAACATAAGTGT
TCAAGACACTGATGTTATCTTGATCCGGGTCAAATAACGAAAATGAAATG
```

FIG. 1D2

```
GTAACATAGCCGTTTGCATCCGGGGTATATAAAATCTGGTATGCCATAAC
TTAAATGTTTTTTATTAAATATTACAAGCTGTAAATGAAGACTGCAGCCG
CAACCGAAGAAGTAAACCTGTCAAGTCTGAACAATTCGTAAATAAATTTA
ATATTATCACTTCCGGCAACTCCGCTGTATGAAAACACCCCCTGTCTGCG
TGTGATGATATTGTCGGTAAGCATATAAACATACATGCTGTTGGTAACAT
AAGGAGGGAAACCATCTGGATTGATCCAATTGACAACATAGCTATGGGTT
TCTCCCGGAGCAATTGATGAAGAGGGATAAGTGTACACCGTAGAGTTAGT
AACAAACTCAAAATAAGATGTACTGTTATACGTATCGGGTGTGGAACCGC
TCAATGTATAAAATAGAGAAAAAGTGTTGTTAATATGAGACATAATTGAA
AGGGTAAACGAAAATGTATACGGTTGTGTCGAAAGAGTCCCCATTAAAGA
CGGATAATCAACAGATCGACTGCTCAGTATGTTGAATGACTTACCTTCAT
ATAACAGCATATTGTACTTATACTTATGATAATAATATTTTCGAATCATA
GAGACTGTAGGAGCCGGGAGAGAAGTACTAAAAACAGCGATTTCGTAAAA
TTTAAAAGCAGGGTCTCCAGCATGATCTCTGATAAGCAATCTGTTAATAT
CTCGCCTTGTGTCTGTATTATACTTTTCACCAACAAAAACTCCGTTGATA
TAAAATGATGTTGTAGAATTGTTATGAGACACTTCAAAAAGAAGAGGATA
AGATAATACATCTGAGTAAGAAAACTCCAGACCATAGCCACTACACGTAT
ATGCGGTGCTCCCAACAGAAGAACCGCTATCAAGACTGAAAAGCACTACA
TTTAGTTTATTGTTGTTGTTTACAAACCCTGTTCCTATAAAGCGGTTGTT
GTCTGTACTGGTATTTAACATCATCACATCCATAAACTGGGAAATGCTAT
GTAGCATTGCAGGAGCAAAAACCATAAAAACATGGAATGGTGAATCTGGG
TTATTGTCTAACAGATTAACACTAAATGTGTTGTTATAATTATAACTATT
TATATGGCTGGCAAGATAAGAATAGCCTTTGTCCCAGTAATAATGCCAAC
CTTGCCCTGTTGAATATAAAGATACATGGCGATTACCCGTTAAAGACGGT
AAAACAGAAATGGTTGGGGTATATCCACTTTGTGTTATAGTTATATACTC
GACACTCCAAATTTCACTTAAACTACTCAAAGAAACAATTTCAAAATTGG
AAGTAAAAGAGACAGATTATAAAACTTTACGTTATTATCAAAATACACA
TAAACACCCATATCATACACACTTTCAAGGGAAAAAGACGGGTGTGTATG
GTCAAAAGATATTGTAACATCAATGACACTTCTGGTGCCGATGTAATATA
AAGAACTGGTAACAACCGTAAACCAGGGCGGTGTAACAGAAAAGATATA
TTATTTCTTTCAATATGGAAGCACTTACTGAAAAGGGTATTCCATAATC
ATCTTTCACTGAAAAGGTGATAATGATGGAGTTACTGCTTATTATGTAAT
CTCTGTTCATCTCATTCTTTAAAATTTAAACCTTAAATAATCAAGATCAA
CTTCGGGGGTTGTGGTTGGATAACTTTTATTGGCTGCTTTAAGCTCCCAT
TTAAACCCGGCATTAGAAAATGGTGGAACTTGAGAATATGTATCAAACGG
ATAATTTGCCGCCTTGAGTTCCCATTTAAACCCGGCATTAGAAAATGGTG
GAACTTGAGAATATGTATCAAACGGATAATTTGCCGCCTTGAGTTCCCAT
TTAAACCCGGCATTAGAAAATGGTGGAACTTGAGAATATGTATCATATGG
TATTTCAGATGATACAAGTTGGGTGTTAAGAGCAGCGGAAGGGGTTAACC
CTAAACTCTGGAAGGAATTTTTCATAGAAGAATTGCTATTAGTCAGATAA
ACGTTACTAACAGGCACATAATTTACCACCGGAGCAATCTGTCTGACAAA
TTTTGATACCGCTCCAATAAACGACACGCTTACACTCGATTTGGGAGATT
TGAAAAGTCCCCATGCACTTCCGGTTACCGCTGAAAAGAAAAGGAGATTG
ACCGGCTCATTCCAGACGTTTTCCCAATCGACTTCCAGCGCACCCATTTG
AGGAGATGAGTAGAAAGTCAGATTGTTACCCGTACTTTTGAGAACAACGT
TTGCTCCGGATGACGTCAGATAGAAATACTGAGTAGATGTAGAGACATAT
ACTGAGAAGTAAGAAAGATAACTTACCGTCAGAAATCCTGAATTAATTGG
GTTGAAGAAATAGGTGATGTGGTTGTATAACTGGCATATTTCAAATAAG
GTGTATTATCCGTGTAATACAGAACACTTGTCGAATAATTCAAATCCATG
AAAATGCTTGCCGTTCCGAAAAAGTCGGAGAAGGTGACTAAATAGGGTGA
TTTCCGAACCATGTATGTTCCATTATCAGCCGAAACGATAAAAACAGATT
TTGTTATATCGTAAAGTAATGCGTTGAATGTGGTGCTACCCTGATTGGAA
AATGTTATATAATCTTCAATATATCCGCCGCCAAGGAAAAGACGTTTGAT
TGAGACGGTTTCGGTGCTGGATGTCGTGTAATAATCCAACCAGAACACAT
CATATCCCCATGCAGCTACCCCACCGTATTGAATGCTGGTGGTGGTAACC
TGTTTATAACTTCCACTGGAATCCAGGAGTCCCACTTCTCCGGAAGATCC
ATCGTGCAGATTGAGAAAGAGTGCGGGAGATTGATCGTAAAAGAATCCAA
GCGATACGATTATATCCGAAGGGGTAGTAATATCCGGGAAGTAAAGAGAG
ATATTCGGGTCTGTAGTTGTAATGTTCGGGAAATACAGTTCTATATTAAC
GTCGGATGTAGTAATCGGAGGCGGTTCACTTGGGGATGGGGGCGGAGGAG
GAACATACGAATAAGAGGGGATCAGAATCTTCTGCACGAAAACATAAGCT
```

FIG. 1E2

```
TCATCCAGCTTGATCGGTTGAGAAAACTTCGATACAAACACCACGTCCCC
ATTCTGATTCATTCCATAGATTCCGCTGACATAAGGAGAAACCCCCGGAA
CAGCCGTGGGATTGGTGGTAAAGTTTTTGGCTACAAATTCGGCAACGAGA
AGCTTCAGAGGCTGCAATTCATAAAGCGTAAGGGTAAAGAAAAGCGGGGA
AATAGCCGGTACTTTCTTTCCCACAACCACAAACGATTCATTTCGAACAA
GGATAAAATCCGGGTGATCATAATAACTGTCATTCACAAGCGAGATAGGA
TTTCCTCCATACGTAATGGAATGTATGTGATAGTACTGTCGCTTGATTCT
CACAATTTCAAAAGTGAGCGCATCAAAATCGATATTCAGCTTACGAAAAA
GATCGATAAAAGCGCACGAATCTGAGCTTTGAGTTGATCATCCGGGGCA
ATTTCCAGTTTTATATTATCATTTTCGTAGCTACCGGGAGAAGGGAAACC
AACAACTTCGGTGAATACTTTTATATCGGTTTTATAAAAATCCTTCGCTC
TCATTTTATACTTGATGTTCTTCTCTATTAAATAAGAAAAGTTTATTCAG
GGGCTACCTTTGATAATATTCCCTGTACACCCAGCCGGTAAACCCAAGGT
CCAGAAGTTTGGGAATATCCCCTTCTCTTCCCCACTGCTTTTTCTGAAAT
ACATCCCCACGTTCAGATCAAAACTCATAACCGGATCCTGTAAATCTTC
AATGTAACGGCTGGCGAAACCGTTATCTCTGATCCTCAAAATTTCTTCAT
CGGTTATCTGATCATGAGGAAGATCATAAAGCTCTATCAGCTTACGACAG
GATTGAATATAGCGGTTATCTTCATAAAAATTAGGCGGATGTGGGTTAAT
CCAGCCGGATAAAATATCGGAATAAACCTTACCGGCAATCAGTTCGTGAG
CTTTGTTTTTCATATCGGGTTCGAGAATATCCAGAAGTATATAAAGCTCT
TGATAGGTTTTAACCGGCTCATAATACCTGAGTATGGAAGCGATCGCCAT
TCTGGTTTTTGTGTTCTCATAAAAAGCATGGAGTTCCGGTAGAATATACT
CCGCCGAAGAATGTCTTATTATATCCACTTCCGCCATATTCTGAGCCATA
CCCTTTTGATTGTATGCAATTTTTATAACATAAGGAGTTCCAACTATGCG
ATAAACCTTACGAGAAGAACCACCTCCTATATACTCCACAGAAGGCAATT
CATCCATCAAAGCTTTAAGTGCTCTGAAGGAAAGATGATTGTTCAGCAAC
TCTTCAAAATACTCAAATAAATCCTGATCTAACGATATGTTGTAACCGTA
AACAATTTTCTCTTTCATTACTTCTTCTTATTGTTTTTCTCCGTTCGCTT
AAGATAAGCGCGAGCCGATTTGAAAACCCGTTTATTACTGGTATTTGCTG
CAAAATTGATCATTTTCATAGCCCGATCTCTACCCACTTTTCTGATAAGG
GCACGCGCCAGCGATTCACCCGACTTGTACACATCATCAATATCTTTGTC
TTTGGGGATTCCAAGCACTTCATGCATTTTCCCGCGCTTGACTTTACCGC
TTTTGAATGCTTATTGAATCCACTTTTCTTCCTTTTTAGCCTCAGCCAGT
TTACGTTTCTTGAGTTCCTTGATATACTTCAGAGCGCGGTCATAAATATT
GTGTTCAGGGTTGACGTTGGCGGCAAAAACCAACATCCCCACGGCTTCTT
TGTACGAAACTTTCTTCAGGAGATCACGCACCAATTTGCGGTGATCTTTG
TAATGATCGACAATATCTTCATCTTCGGGGATTCCAAGCACTTCCTTCAT
GTGCCCGGCTTCACGCTTGACCTTGCTCACCCAGTCTTTTTCCCGCGCTT
CTGCAACGGTTTCCCCACCTTCATCCAGAAGTGCAATAGCTTCCGTATAG
AAGAAAGAATCCCCCTCCGTTTCTTCCAGAACGCGCAACGCTTCTTTCAG
AAGCTCCTTGTGTTCAATATGCATACGCTTTGCCATTTTCAACAAATCTT
TGACAAAAGACCGGGCATCATAACCGTAATACTTGGCGACAGAAACGACG
GAAGGAACTCCAAGATACTTACGCAACTTCATTGCTATGCGTTCAGCCGT
TGCCTCTGGATTACCCATCTTTTGAATGAGTTCTTCGCGGGTGACATTTT
CGGTCAGCAGTTTCTGGCGAAATTCGTTAAGCTTGGTTCTGGTCTCCTGC
AAAAGCCGCGCAACACGGAGAATTTCCTTTCGGTTCATATCTTATTCTCC
TTTTCTTTTAATTAAAGAAAAATAAAGACTCTATGAAAACAGAAGACAGA
AAAAAACTTGCTCAGGAAATCCTCGACAAAATCGTAAACAAAGCCATGCA
GCTTGAAACGTTGATTGACGATGAATACAACTATCTCAACAGAACCAGTG
TGCTGGTTGAAGAGGAGAGCAATCTGATGTCGGCAAAGGCTCGAATGCTT
GAGCTACATATTAAGATTCTCGACACGCTGCAGAAAGTGTATAAAGATCT
GAAAGAAGGGATTCAGGAAGAAGACGAAACGGAAAAGATTCTCATGGAGA
TTATCAATCAGAGCAAGGCTAACCTGTGAAAACAGGTAGTTCATTCAATT
TTTTAGCTATATTGATTCCCTGAGCTATCACCTGATCCATGTTGTAATAG
TTATAAGTAGCCAGTCTACCCACCAGTATAATCCCATGGCACTCCAGTTC
GTTCTTCATAGAAGCCGCCTTTTCTCTGTAGGTTTTCTTGTTAATCGGAT
AGGCTTTGAACGAATTTTCCTGAGGATGTTGAGAGGGATACTCTATGGTA
TAAACCCTGTCAAGATTCAGCCTGGAGTGATCGATAACGCGGGTAAAGGG
TTCTCTATCAGAGGAAAGATGAAATCCGATGGATTCGAGCGTACTCCACT
CTTTCAGTTTGCGAAGCACATAGGGATCGGAAGATATACCTTCAAGTTTT
TCTCTGGTTTCAATTCTGAGATGAATGTAAGGGAGATGTTCTTCTTTACC
```

FIG. 1F2

```
TGTTACTCTCTGGTAAAGCCTATCAAGGTCCCCGGTATAAATAAAAGGGT
TATTTTTTATGTCGTTTAGATGATCAAGCGCGTCTTCGGAATAAACTATA
TTGACTACCGGCACATAATTTCTGATATAATCAATCATCCGTATAATCAT
TTTCCAGTAACCATCAACCGGGAGCGCCACCATTTTATCGTCAAAATAAG
AGTGATATCTTTTCCAGTCGGTAAAGAAGGGAACGCGGGAAGCTACCGTT
TTTACCATCTCTTCATCCCAGTAATCTCCCCACACCTTTTTTGAGTAAGG
GGCATACCAGTTTTCATAGACGAAAGATTTAAGCGGTTCCGGGAGATTGC
CTACCGGAATTTTTCTGTTAAGAAGTTCTTCTTCCAGCTCAATTTCTCCA
AGATACAGCCGCACCCAGAAAAGAGATGAAGGAATAAATGAACATATATC
ATTTTCGGTAACAGCATAGGCATTGTAACTGATAGAGTAAAAGGAAGAGA
ATCGCGACACAAATTTGATCACTTCGGGGGAATTGGTATGAAAGATATGA
ACCCCGTATCGGTGATATTTTTCCCCCGGTCAAAATCCCAGACGTTCCC
ACCGGGGTGGTTGCGCTTTTCAAAAAAGTAATCTCTTCAAATCTGAAGC
CACGATCAAGGAGAGAAATAACGGTGCTGAGTGCCGCAAGACCTGTTCCC
CCTACAAACAACCGTTTCATAATTTTCTGACCTCCGGGTCTCTTAGCACT
TGAGGAAACATACCCTGTACCTGCTTTCCGACAAAATAATCCATGTTGAC
GCGCCGAACGGAGAATATCCGAGAAGGTCTGTACATATGTGCGTGAGATA
AATACGGAAGCGTGGCATATCTCCACTTGAACGCATGTGCCACATGGATT
AAAAAGTTTCCGTGTGGGTTGGAAGATAATCGTAATACTTTCTCAGAGA
TTCGAGATAATACCTGTTAATAACGTGCCCCCGTCAAGATGCATGAAAA
CGCCGCGCTTGTGCAGTTTGTTTGAAGTGAAATAATTGTAGACATAATCG
GCATATTCATTAAAAGCTTTACATCGAAATAATCGAGAAAATGTTCTTC
TCTGATAACAATCTCTCTCCAGTCTTTTTTTGCGAAAGTCTCCACATAAC
ATGCGGCGGCGTAAATGTAATATCCCTCAGGGGTTTTTAACCTTTCATCG
GCAAGATGATCGGGAAGCTCAATTCGCTCATACGGATCTTTGAAAGGTGT
TTCGTTTTGATAGGGAACAACCCCGTAAGGTTCTACCATGTTGGAGCAAA
TCATAAAATATTTATCGAAACACCCCTCCTCGAATGCTTTATCCAACCCT
TTCAGATATGCCGGGGGAATATAAACATCGTCGTGCACAAACACCCCGGC
TTCTACACCAAGAAGACCAAGTGCGTCAATAAATGCAGCAAACTGAGAGT
ACTGAATTTCATCTACAAGAAAAACATTAAGTTTGTGATGTTCCAGTTGA
TTTTTAAGCCACGATCTCCAAACTTCTTTATCTTTTACCGGTTGAAGGTT
GAAATGCTGGAGCAATTTATAATCCGGGTGAAAGCGCATTTCCGGATAAA
CAAAAATATAAAATAATCCCGAAGGTGTGAAATGTGTGGGTAAATATTT
TTAAGCCACACTTCGGGAATTTCCCCGAGCGTTATCATTACAAAGGCGAT
TTCCCCGCGATAAAAGAAGGGTTCGGGGAAGAAGAAATCTTCTCAACCT
TCATTGTTTCCGCAATTTTAATTACAACCCGGTTTTCTTCAAAGTTAAG
CTCGAATTCCTTTTCCGACGCATTGATTCCAAGTTCTTCCAGTTCCTTTT
GAAGTTCCCCCATGATCTTCATGCGCTCCCGCTTGGCTTTAAGCGCATGC
TCGAATACGTTCACATCGCCTTCATCGACGATTTCCACCAGCATATCAAA
GACAAGCACCGCCATTTCAATGTAGGCGTTGCGGAGTTGCATTTCACGAA
GTGCAAGGGATTTGAGCTGGTCAACCTTCTCTTTGTCTTCTACGACAATG
GTATTTTCAGAGCGTGTAACGGTAGGTTCACCCACTTTAATGAAATCTTT
CCCTTTCATGGCTTTTTTTGATGAAAAACGATCGGGTTCAAGAAAGGTT
TCAGAAGGTGTTAAGCGGATATTCTTCAGACGCCTGAGCTTCCGAAGCCG
CATCGTAATCGCCAACCGTAATATAAATATCCTCAATTCCAAAAAATTGG
GGCGGATAGCGAAATTCATAAAGCGTAAGTTCAGACGGCGTTACAACAAT
ATCAAATATCCACACACCACCTTCATCATTTCCAAGAATAATCGCTTTGC
AGTTGATCTTATCCGATTCGGTAAAGAAAGGTTTGCTTCTGAGAACAAAT
CTTCTCCCTACCGCAACAAAAAGGTTGGTGCCGCTTTCCGGGTAAAAATC
GACGTCGTTGTCTTCAGAATCAACGATGGTAAACACATTGGGTTGAATAT
AAAGCGTATAAGATTTGTTGACTCCATAAGCGGTTTGTGGTTCGATGATA
AAGTTCTGAGGATACTGTGTTTCATAGAGGATATTTACGTTTACGATCAT
CGGCATGAAATCCCTTCGATCCCCTTCATCCGTTTCATACAGCGTAACCA
GATGAAATTTGCTGTCAAAAATATTCCCCACTTCGCGAGGTTGACGAATG
ATAGAAACAGTTGGGGAGTATACATTATAAACCACTTCGTCATCTGAAAG
GGCGAATTTTCCCATCGTACGAAGATAATCGGCAATGGAGATTTTCTGGC
GAATGAGCTTTGCAATCAAACGCTGACCGTATTCTGTAAGAGACGCCGTA
ACAAGCATATCAGAATTCCACCTTCAGTTTAATCACGTATTCATCTTCGT
TGGTCTTACGAAGCGGAGAGGAAAGTCTTCCAAGCGCCACAAGCTGATTG
TTCTGATCATAGATTCCAACGGTGGTAATATAAGTACCCTGATCAGGATA
CAAAATGCGTCCGGAAGTGGGATCGTAGAATGTGGGATTGAGCGAGTAAT
```

FIG. 1G2

```
TGAATTCGCCAGCCTTTACGCGACAGAAAATAACCATAGAGTGAATGTTA
TCCACCATTGAAAGCGTCATGTCAAGAATAAGGTTGGCGATGTTTTCATG
AAGTTTCGCAACGCCACCGACCGGAGGATTGCTGTCAATCGGGAATCCGG
TTGGATCCAGCATGTAAAGCGAAGTGCTGTATCCCCCCGATCCAACCCCA
AGCGAATGAGAGACAAAATCGCCGCATGCATCCAGATCGATCAGAAGCAG
CGCCGACTGAGGGAATACGATTCCAAACACCTTCTGAGTTATGGAGTGGG
TTACAGGAACCGCCTTTCCACTCTGAAGTGAACCCGACACCAGATAGTAG
AACGGCTGCACCTGGGTGCGGATCGGAGTAGCGAGGTTGGTTTCGCCGCT
GTTGTCAACCAGAGACAGGGTTGCGCGGTTTGATCCGTCGGTGAAAGACA
GGTTAATCTGGAAATTACCAACATCAATTGTATCGGCAAAATTATGGAAG
GAGACTACCATGAAGTTCTTAAGTTCACTGAATCCGGCACCGGGATTTGC
GGGATCACGGGGAACAGTAATAACATCAGAAGCCAGATTGGTTTTGAATT
GATTGATAAAAGCCAGATAATGCTTTCGAGTAATTTCATTAGTTCCACCG
CCATAGTTCCCTTTGGAAGCAAACGCCACGGAAAACTCCGGATCGGTGGT
AAGCGATCCTTTGAAGATATTCACATAGTAATCGTTGTAATGATCGGGTT
GCGAAGAATAAGTTACAAAATCGTTTCGTGCAATAACTCCGCTTTTATCC
CAGAACCCCGGAACGGCTACATTTCTCGTGCTGTACACCACGTCGTCAAT
TTGCTTGAAGACAAACCCCTGAGGCTGCGGAGCCGTCTCAGCTTCCGTAG
CGATGTTGTTGACAACGTTTCGTATAGTTTCGAGCTCTTCCGTAGTGATA
GACAGATTCGATTGCAGATAGTTCAGAAATCCCTGCAAAATCTGTCGCTT
GGAATAATCGGTAACCGTTCCAAGTAGCGTGGTAATGTAGGAAATAAGTT
GCTCTCTCATAATCTTATGTAATCAGTTTTACTTTCAGTTCAGCTTGTGC
ACCACTTTCGTTGCCCCTGATAAGCACAATGGTTTCGGTGTTGGGCGTAG
CCGTTTGCGCCGGTTCGATCACAAACTTGCGCCCGGAAATCGCTTTATAG
TCGGGGTTGCTTGTCGGGAAGGGGAACGGCGCCTGTGTCGACGGTTCAGC
AACAGAAATGTTTAGCTGTTTGCTATCATAAAGCAATGAATAACCAAGAA
TCTTATCAAGTGCAACCACAAACTTTGTACTTGGGATGAAGAGATATCGG
CGAAGGTTATCTGTAGAAGTAACCCTGAGCACGATTTCACTCTGATCCAG
AAGCAAAATGGGAATTTCGTTGACAATGATATTCGGATCGCCTACCACAC
TGAAAAGATGATAGCGCGGCACTTCAAACGGCTTGGGTTCTACCAGCGAA
TAGCTCAGAATTTGCGGAGGGTTACCCGCGCTTGCAGAAAACACATATTC
ATAATCGATTCCGTCGTCAGAAAGTGCAAAGTAGGCAATATCGAAACTAC
CGGACGCAAACAACCTTCTACCGTATGCCGTGAGCGTGGCTACGGAATAT
ACCGTGTTTTCTGATTTGGTGGGGATAAACATTTTTTTCTTTAAATAAAG
TTTTCAGTTACCCACTACAAGTTTTAAAAGCTCAACCAGTATCGAAGGGT
CTACAATAGCCAGCGCAATGAAGGGAAAAAGTGGCAAAATCAACCCGACA
ATAAATCCGGTGAGTAGCAATTTGATGAACAGTTGTTGTTGATCTTTTCT
GTTCTGCAATGCATTGTCATAAGCGCCCTGCAATAGATCACGATATTTTT
CACCCACCTCCGTTTTATCTTTAAGAGACTCGATTTGAACGCTCAGTCGA
TTCAATATATCTTCTATATCATCAAGTTTTTCTCTAATGTTGTTTCTATC
CTGTACAACGGTTCTGAGCACATCTTTAATATCTTTAATCATTTCAATGA
TGTTCGATAGAATGAAACGTATCTGATAATCTCTGTCAAACTGTTCTTCG
TTCATCCCTGTTTTTAAATTAAATAAAAAGGGGAGACGACACGTAGTAC
ATCTCCCCCATAAAATTATTTTTTATGCGAATTAAGGCGTGCGCTTTTCC
AGAAGATACATCGTAAGAACATCGCCATTTACAGCAAGCAGTTTGGTACC
TTCCCGGTTGGGGAAAGGATTGATCCGGTTGAAATCAATGCGGCGCATTT
CCTGACGACTATCCTTTTCAAAATGGTTTCTCAGGAAATTCAGAGCATTT
AGCGTATAATACATGTCATTTTCTTTCCAGTAGTGCGCAATGATCTTGCG
TTTGTGGTTCAGCACGAAATCCTTTTCGCGGTGGAATTCCGGAACGGAAT
AAATGACATTATCCACCAGCGAGCAGTAATCGGCAAGATCCTGAAGATGA
GCATATTCAGTTGAAAGAATATCAGGAACCTCGCTGGGAATGTACGTGTC
ATAATCCCCGTAAACAATTCCCCGGATATTAGCCGCATTGTAAGTCGAAG
ACTCGACAAAATGCGTTTTCAACCGCTTGTCTGAGTAATCCTTGGAAAAC
AGAAATATCCGGCTTGGATTTTCAGGATCGTCGAACATTAAAAGCTTTTC
AGCCTTAACAAACCACTCATATTCCGACTTGAATACCGGCTTGAAATAGA
ACACGGTGCGGAATTGAGTGGAACGTCGAGAGCGTCTTGGTTTTGCCAAC
GTACCCATAGTCTTTCTCCTATTTTTTTTTGTTTGGTTTTAAATACATT
CTGTGTAACAATAAAAATTCATAAAGGTTTCAAAGATTTTTACAATTTCT
TATTTAAAGAAAAATGCCCGCAAAATCAAGAAAACAACAGAGATATATAT
TCTATCTCAGAAACAAATATGGATCACCGGAAAAAACCCCCAAGAAATAC
AAATGGATATGGCACAAAGATTGGGAGAAACTGGAGGAAGCCAAACGTAA
```

FIG. 1H2

```
AAA GAAAAAGAAGAAAAGACGTAAAAATAAACGCTCTTACCTGAAGCCGG
ATTCCTATTATAAGAAACCATACGGTTATTACGGAATCTGGTATTACCAT
TATGATGACGGTGTGGATGATGGGGGAGATGCGGGTGATGGTGGAAGTGG
TGCTGGTGTGGGTGAAGCTAAAGGTGCAAAACCTGCTAAGAAATCTAAAA
AAGAAGTGCTCCGCGATCTTGAGGTCAAACTGCACGACTTCAACAAGGAG
TTGAAAAAACTCCTCGAGAATCTCGGATTCTAAAAAAAGAAAGCCGGGGA
ATCAACCCCGGCATTTTTTGTTTCACCAAGGTAAATCGTTATTATCCGTC
TGACACGACTCAATCAATTCCTCTTCTTCCGGTTCTTCTTCTTCATAACT
GTAAAACCATATATGAAAGTAATATCCCCGCCCTTCTTCCCACTCTCGCA
TTTGCTGCTCTTCGAAGACGTCTTGCAAAAAACGCTTTGTCAAACTCATG
GCTCCCTCCTATTTTTGGTTGACAAATCGATTCTACTGGTAATATACGCA
TTGATCAGAGAAAGTCAAATGAAGAATCTGTTAAACAGAGATATATCCG
CACTCAGCGGAAGTGTAGATGTCAACCTCAGATACAATCTTATAAAGTTT
TTTCATTAGCACCACAAAGTCTTCTTCCGGAAGCTCTAATAGCAATTCCT
CATTATATTTGAGAAGGGGAAGCATAGCTTTACTTCCGCTACCCACCGAA
TAATAGGGATCACGAATGAACATTGTCGTGAAATTGTCGGATACCACAAA
CACCCCGTGCTGACTGATTCCCATAATTTTCCCGTTCATATCCCCATTAT
CATTCAGAAGATTCAACCCCTTCAGATGATCTCTCCACTTGTACGTAAAC
GTCTCTACAATCGTGTTTTTGCTGTAGGATTCTCTGTTAAAGATAAGCGG
CGAGGAAAATTTTGCAAAGGCGTTCTGATAGATTACCCTTCCGACAAAAC
CAAGCGGAATTCGATCCACCAGTTCGGACGGCGTCTGAATATCCAGAAAA
GCGGCTTTGGGGTCATCCCTGACCACCAGCATGCCGTCCATTGTGGTGGT
ATAGTCAAAAAAAACATACCGCTTATCGGCTCTGTCAATGGCTACTACCG
TGCTCATGATTATTTAAGGGTTTGCGTTAAGGTGTCTTTCAAATGATACA
CAATGTCTCTAATCTCAGCAGGTATAAGTTCTCTGATGGTAAAAAATTCG
TCAGGAAATATTATCTGTCTCAGATTAATATATCCTATTCGGTTGTGATA
GCGAACTCCGTTCCCCACCGCTACCACAATATGCTCGAAAGGTGAGCGGT
GTCCGTTTTTGTAAAGTCTTCTTGCAAGTTTTAAATTTTTATCTAAGTCG
GATTCATCAGAAGCATAGGAAACGCGGGCTATACGCGCCACCGATGTAAC
CAGTAGTTTGGAATTCAATTCCTCCGGTGAAATAACTCCCTGAAGAGGAT
CGACAATATCTCCGGGATTGGCTTCGAAAGCCGGGAGTTGTCGTAGATA
TAGCGAATCAGGAGCGCTATTTTTCGGAATTCGGGTTGTGCGTCGGAAGC
GCAACGAAGTCTGAAAAAGTTGTCAAGCGAATACGGATCGGCAATGGAAG
CGATGACATCTGTATATGCATAGGGTGAAAGTATTCGATTAGCGTGTTGC
TTGTGTACATTGAGTTTCTCGAGCACAAAATGCAACCCCGCTGATGTATA
TAACCCGGTATACCAACACCACCTTGCCAGCACATCTTTCCACCCTCCTA
TTTTTTTATCGGAAAACATTGCCCCTGAGTTTTCCACAAAATCATCTGGA
ACAAAGGGGTTTTCAAGTACACGCTTCCGGTATTTTTTCAAGGAAATGGC
TCTTGTAGAAGCGGCATTCCTCGAAAAGGCGCGATGTGTATTAAATTCAG
CCAGTATGACTGTGGGAATTTGAAAGCGAAAGCAGAAGAAGATATCGTTA
TTCGTCTTCGTTTTGATCAGATACCACACCATTGCTTTCTGAGTTTTTTC
CATTTAAAACCGATCCATTTAAACAAAGTTTCATTTCTCTGATTTCATCT
TTCAGGGTTTCAGAAAGGTGTAATATTTCATCCCACTCGCGAGTATTGCG
CTCAAAAATCTCAACTCCACTGGAAACATCACTCATCATTTTTTCCTCC
TTGTGTTTAATGTTGTGGTAAATCTATAATTTGCGGGTGTTGCCAGAAGC
GCATTTCATAGATACCCCACTTTCTTTTAAATAAAAGAAAAATAACTTTT
TTTAAAAAATTATTTACCCCGGTCGTCAAGTCTTCCAATATCCGGCTCTT
TATAGGGATGAATGCGATATTTCTTCTGGAAAAACTCCTTCCACTCCGGC
GATTTTTCAAATACGACATCCAGATTGTCGATAAGTGCCTTTGCCACCAT
GTGTTTGCAGATTCTCCCCCGGTAGTAATGATCCGGGCACGTACATTTGA
ATGTGCGGGTGTCAAAATTGACGCGCGTTACGTATTTTTTGTAGGAGCCG
CTTTCGAGAGTATCACGGGCGCGTTCAAGCAGCGTTCTCCCCTGTTTGTC
TTTCTGAGTCTGACACCATTTGAGAAAAGAGAGGAGTTGTTTATATCGCT
TATCGAACGTTTCAAGCCGCTTGCGCTCGCGTTCTTCAATAGAGCGCTTG
AGTTCTTCAGCCTTTTGCTGTCTCTCTTTTATACTTGGCGGCGGCATACG
CTCAGATGTTTAAAATTCTCCGAAGCAGACTTTCGATCTGATCTTCGGTA
AAATCTCTTTTGGATATATAAAGCACAAGATTGCGCTCCGTGTTGTTTTT
CGGTGGGTGTTTCCTTTGAGAAGGTTTCTGAAATATTCGATGAACTCTT
TTTTAAGCTCTTTTTTCCGACTTTCCGGTTTTATTCTGCACAAGTGTTTTT
TCGGTGGAAGTAGCCTCTTCTTCGTTGACGGCGACATTATATATAGAGAG
CATGAGAAACATCTCTACCGCCGGATCGGTAGCATGACGTGCAGCCATAT
```

FIG. 1I2

```
CGGCACTTCGGCGCTGAATGGCTTCATATAGCAGTGATTCCTCGCGGGTC
ATTCTTTTCTGTTAAATAAATGTGAATCCGTAGGAAAGGGAAAACATCAG
GGGAAAGCACACATATAAGAACCAGAACCCAGAACAAAAATAGGAGGAA
GGTTATGGGTAAGATCGATGTTTCGAACATCAAAACCGCCGTTGCCATCT
CCCAGAAAGCCAATGTTCCTCTTTATCTGTGGGTGGTGTGGGAATCTCC
AAAACCCAACAAATCTATCAGTATGCCACCAGCACCAATCAAAAATGTGC
TGTCGTTACGGGGTTGGCAATAGATCCAACCGACGTAGTGGGTCATTACA
TTGCCGACTTCAATAAACGTATCACCTACCAGACCAAACCCTATCTTTAT
GAACTCTTCGGTGAGGAAGAGCGGGGAATCATCTTCCTTGACGAATTCAA
CAACTCAGAAAGTGATGTGATGGGGTGTTTCTAAAGCTTCTCGACGAAA
AGAGGCTTGGAAGCTACAAACTCCCTGATGGAATTCACATCATTGCAGCC
GGTAATCCCCCCGAACTGGCTCCAAATGCTTCCTCGCTTCCGCTTGCCGT
CGCTACTCGATTTGCCCATCTTTATGTGGAAGCGGATTTCATCTCCCTTA
AGAGATGGTTGAAAGGAGCGGAAGATGAAGAGGATTATGTAAAGATTTTC
AATCTTGAAGTCGGGGAAGATGTTGTTCAGCAGGTGTTCGATATTTTCGT
TGACTACTGCATTGAAAACGGTCTTTTCCCGGCTTCAGAAGATTCTCGTA
GTTGCGAGTGGGAGGGGAGCCTGAATTACCGCACATTGCACTATGCAGCA
AAAATCGGGGCTGTATACAAAGTTGCTTACAAAAATGTATCAAATCAATC
GACACTGTATAATGTAACTGTAGAAATGATCCACGGTCTGGTTGGAACCA
TCGCTTCCAACCTGATGGAACATCTTGAAAACAAGTGGCTTCCATCGGCA
AAAGAGATTCTCGAAAACTATGATATTGTGCTCAAGCATCGAGACGCCTA
TGCCGCCCTTGCCTACAACCTTATGAGCGGCATTCAGGAAGAAGACTATC
CGAGGTTGGTGGATTTCATGCAATGGTTAGAAAAGAAAAACGAACTTGTA
ATGCTTGCGGCGATAGTGGAATCTTTCCAGTCGTTCATTCCGAAGAAAAG
GTTTCTGACAAGCCGGTTCGAATACTACAACCAGATTTTCAAAATCATTA
ATCGATCGCTGGACGTCTATAAGAAAGTCAAACCCACAAACAACAAGTGA
TTGATTATGGAACCGATTGTCGAAAAAAAGCTCTATGAACTGATTAACTG
CATTGTAAAAAATCATACCCCACTCGCCATGATTCTTTCCCGAATCAAAG
TGCGGGTAGGGGTAGGGATAAATACACACTGGGACTCTGCAAAGAACGG
GAAATCATTCTCAGCCGGTGTCTCTTTGATGATGAAATCGTTTATCCCAA
ACTTGTATTTATCAAAGACCCCGACACCGGCGAGATCGTAGACTATGATA
TTGAAGACTATGTTGCCAAAATCGATGATGAAGGGCGGTATCATACCCTG
CTGGAAGAAATCATTCATGCCGGTCTCATGCACCCCATGCGTGTAGACCG
GTTTCAGAAAACATATCAGGAGCTTTTGAAAAGAACAAGCGGCTGGTGA
ATTTTCTGTACCTTTGTCTTGAGGTTGAGCGTCATGCAATACATACCGCT
GTAGCCAACATCGATCTACTTAAGCCCGTGTTCAAAGACAACACGCGGGA
TGAAAAGATTGTGGAATTCATTAAAGTTATTCAACATGATCATCCCGATC
AAAAGCTGTTTGGGTTTACTTTTGAAAGACTGTTTTTGAAGTATCTCAAC
GATTTTGAGGGAGGTAAAATTGCAGCCCCCGCAATTTACGATCTGATGGA
ATACGACGGGAATACCGTTCCCGACAAGTTCATAGAAGCAATCGAAAAT
CTCTTCATAAAGGGAAAAAGTATGGAAATCAGACACTGGATGAAATCTTT
GAAATCCGGCGTGTGGATCAAAAGGGGTTGCAATTGACGCAACTCCTGAA
GCAGATTTGCTTCCGCAGGGCACGTAAAAAACCCTCGCTGCACGTGCTCG
ACAAAAAGCGGAAGCACTACGAACCGCTCAGGTTTGGGAAAATCAAAGAA
AAAACTTCAAATATCGCCATTATTCTGGATGTGTCGGAAGTATGCTTCG
TGATTTCAAAAGCATCGCCTGATTGACATCGCGACAAGTATGATCGTGG
AAACTTTCAAAAACGCACCCAATATCGATGTATACATCGGAGATACCGAA
ATCAAGGATAAAGCGAAGATCCGCACCCTGTTTTCCCGTTTCAAAGGGGG
CGGTGGAACCGATATGTCTAACATCTATAAACAACTGAAAGATCGATACC
AGAAAATACTGGTTGTTACCGACGGGAGACACCCTTCCCCGAACCAAAA
GACTACCGCCCTCAGGATACTTTTATCATCATTAATGATGAAATGCCCGA
AATTCCCAATTACATCAAAACCCTGAAGGTGAAACTATGAACGAAAAAGC
GTTCCAGTTCCGCAATCTTCTAAAGGAAGTGATCGGCATGCGAATCCTCG
AGCGATTCAACCACATAGAACCTGAAGGAAAAAGGAAATGGGTAATTTTA
TCCGCCTACATTCTAATAGTGGAAGAAGAAAATGCACCCCAGATCTGCAA
GGAACTTGTTCGAAACAATACAGAGATAGATCCTCTGGAATTTGTCAGAT
CTTTCAAAGAAGAACTTATAAACATGATCGAAAATCAAAATTATCGAAAT
GAATTTGAGAAATACGTTGCAAACTACGCGATAGAAACGAAATCAATTA
CAGAAACATGATAGCAAACTTTTTCTGATATAAAAAGGAAAACCCCCGGT
TCATCACCGGGGGCTTCCTCAGCGTCTATTCCCTATCGGGTAAGTTCCGC
CATTACGGCTGCAGGAGCTTCACATACAGCAGACCATAGAACTCTGGACG
```

FIG. 1J2

```
CACCACCTCCAGAGCGTAGCGGGTCATCAGACCACGCCGGTAAGAGAAGT
TAACGGGATCGACGATCGTCGGCGTGAACAGCAGCGGCACATACGGAGCG
TAAACCGCACCCGTTTGCCACGGCGTGTTCAGATCTTGATTACCCATGAT
GATCACCGGCTGGTTCTGATAGATGTTCTTGTACAGGCGGTAGCGTCCCT
GCACCATACCTACATAGAAGATACCGGTACCACCATCGCGGTTGTCGTTA
CCCGGCGTAAAGCCCGGCATCGACTCCAGCAGCGCAGCCACCTGTGGGCT
GGTAACAAGGAAGTTGGCACCCGCAACCGCCGTCTTCTGCTGAATGCGGT
TGCTGACCTTGTTCAGTTCGATCATCAGGGTAGCCAACCATTCCTGCTTC
GAGCCGTAGAAGTTGCCGGCAACAAAGTTACCCGACGTTTCATCGTAGTA
TTCACCGACCACTTCCGACCAGAAGCCATAGTTGTCAGTGCGCCGGGCAT
GCGCCATGATCGTCGACAGGATTTCCAGATCGATCTCACGGGCAATATAC
TGAGACATGAGCGTAACGATTTCGTTTTCAAGATCGACGCCCTTATGATA
GGCGGCGAGATCCTGCATCGCTTCCGGCGTCCAGGCGGCACGCAGCTTAC
GGGTCTTGGTAGCCACCGGACGGCTCCGAAGCTCAAGGTTGATCTCCGGA
ATATCCAGCGACTGGAATCCGGGATCCGGATAGTCAGGATCCGTCGACTG
GTCTTCGAAGTCGTTTCGAGCATCGATGTAGTAGACCAGATCAAGGTCTT
GAGTCGACGGAGTACCACCGGCAACGGTCGCAAAGTCAGAGCCGGTTACG
AAGAACAACCGCGCGTACAGCGCCGAACCGACGGCACCGACGATCCGGTT
GTAGCGCGGAAGCGGGTAAGCGACCGTGTTTTCAGGATCACCGGAAGCGT
CGTCATATTGCCAGAAGCGCACCGTATTCACATCGGCGACACCGGGAAGC
GACGCAACCGGCACATCCACATAGTACACCGCACCGCTCGAGACCAGTGA
AGCAATGCCGGTGTCAAAACCGACATCCCGCATCGTCGCCTGCTGGGCGG
TAGCCAGATCCACGGTGATCGTGGTCTCATACTCCCGACGCGACAGGCGA
GCGTTTTCATCATACAGACCGCCCGTAGCCGTGTCGGTGGTCAGACCGGT
ACCACCGTAGACCGAGCCGTTTCCGGGAAGCTCAGGCGACTTGAAATCCA
GATAGAAGACCAGACCTGTTGGGAGCGACAGCGGCTGCACCGACACCAGA
TCCGTCGCACGCAGGTTGGCGAACACACGGCGCACAATCGGAAGTGCCAG
ATTCCAGCCGTCAACCTCCGTGGTCTGGGTGGTCTCCATCAGGTGCTTCT
TAGCCTCGCGGTACTGGTTCTCCAGCAGGGTAGCGAGCGTATGCCGCTCC
CAGTCGTTACGGCAACCCTCCAGAAGCGGTTGCCACTTCTCGATAAGTTG
TTCGTTAATTTTCGGTTGGCTCATTTTACTCTTATTTTTTTTTGTTTTA
AATCTCTAAAAACATTCGGTATTTAACCGAATTAGAGTCCGGCAAGACGC
TTAATGCGCTCCAGATCCAACAGCGGATCCTCAACCGAACCCGACGTGCG
GGATTCGGCGACAGGTTTCACCACACGGGTTTCCTGCAGCTTGCGCTTGA
TCCGCTCACGAATGCGCTGGCGGGTAACTTCGTCAATGACGGGCTTCTTC
ACCCGGCTTTCCCGCATACGGCGCGGCGTCGGACACGAAGCAGCTTCCGC
CATTTCCTCCGTCTCCTCACCAGCCACCTTGCGAAGCAGTTCGATAGCCT
CCTCTACGCGCTCAAGAAGCGTGTGCAAAAGATCCATTTCTTCACGCACA
TGCTCCTCGCTTTCGACGGCACCCTTGATGTCAACATCAATATCGAGTTC
TTCGTCGTCCGAAAGATCGGCATCCTTTAACTCGATTTCGGCTTCCAGCT
CGCCGTCTTCGTCGACGTCTTCAACATCGATTTTGATGTCTTCGTCATCC
AGATCCAGTTCCAGATCCTCCTCATCGAGATCCAGTTCCAGATCTTCGTC
TTCGTGTTCGGCTTCGGTAATCCGACGCTTCATTTTGTGTTTAGCTTCTC
GCATTTCTTCCTGTTGTTTAGTTTCCCAGGCTTTTTGCAACGTTTGCGCG
ACTTCTTCGGCAAACGAAGCAAGCGTGTCATCGTCAGTTTCATCAACCTT
CGCTTCCGTCAGGGGATTACCTTCAGGCTCTTCCACCTGCTCAAGCTCTT
CTTCGAGTTCCTTCAAAGCCTCCCGAATTTCTTCGGTGATCGAGTGAATG
GAAGCTTCCTGAAGATGCCTCTTCTGCTTTTCCTGACGAAGCGACTCAAG
GTAACCCACAAAGTCTTTAAATTCCTGCATAACTCAAATTTAAATATATT
TAATCGCCATTCATTTTAAAAAATGGCACCTGCTACGTGGGAATATTAAA
CCCCACATCAAATTTAAATATATATTTTTCCGCACGAAATAAAAAAAAGG
GAGAGAAACTGATCTCTCCCCCAGGGGTAACATGTATTTTATAACTTGTG
AACTACCACCACCTATAGATGTGGATGGCTTCGTGGTCAAGGTAGCTCTT
GCTACCAGATTCCCCACGCTCAAAGGGCTGTTCCATCCCCGAATTTGCCA
ATTATTGGCTAATTAAATCACTTTCTTCTTCACAAGCGCCTCGCGCAATC
TATGGCGTGCTCTGTTGATTCGAGATTTGACGGTTCCGATAGGAATGTTG
TTTTTCTCAGCCAGCGCCTGCATGGCACATTTTCCTTCAACTCCATGTA
CTGTTTCATTATATTGTAAAACGGGTTATCGCCTTTTTCAAGTTCTTCCT
GAATCACCTCCACCGCACGTTTCAATTCATACTGCTCATCAAGCAGCGGC
TCTCCGGATTCAATTTCTACAGGGGTATCCCGATCTCCAAATGTAATTTC
TTCCATGTAAATCCTGGGACCACGTCGAGAATTGTATCGATAACGGGTAA
```

FIG. 1K2

```
TTACAACGGATTTGAATACAGTGTAAATATACGTAGCGAAAGAAGCTCCT
TCAACCACGCTATAGGAATCAAATCTAAGAAGCCTTAGAAACGTATCCTG
CACCATATCCTCGATTTCATGCTCCGACTTTGTATATTTCTTTCCGAAAT
TTTTGAGCCGCTCAGCATACCTACTGTAAAGCACTTCATAACGGATTTCG
AGCGGAACGTTCTGAAGGAAAAGTTCTTCGTCGGTCATCTGATAGTATTT
ACGCTTATCCATAACTTCTCCTCTGTTTTAAAGGTTGAAAATGATTTCGT
AGCCGTCAATGCGGTCATCAGTTATGAGCTTGTCATAAAGATCGTCAATC
TTTTCTATGTTGTCATAAATCATGAGCATTTCATCAATATCATGCACAAC
AACAGAAATGTAATAACCGTTTTCTTCATCAAAACAGAGTTCGGCGTAGC
TTTTATGAAGATCCCCCACACATTTTTTGATATTCTCTACAAATACTTCT
ACAGGATAATATCTAACCAGACAAAAATCGAGATGCGGAAGCACACTGTT
CATTATCTGCTCCAGCACCTCTTCATTAGAAATCAGCAGTTCATAATCGT
CAATGGTATTTACATTGTAGACAAGATGGTTGTTGGATGTAATAGTAGGA
ATGACTTCGTGAGTTGGGTTGAAATATGTGTTTACCAGATCTTGAACGGA
ATCGAGCGCGTCGCGATAATCAATTTTAGTCTCCATAGCCATATCCTAAA
AGGTTGGTTGATATATACCGGTTATGGAAAATAAAAAGGGGAGAGAGGG
TGTTTCCTTTCCCACACCCTCTCTCCGCGTTTATAGGGAAAGTCGTCATC
GAAGTAGCCCTCAATCTCCTCCATCGAATGAGATTCTTTTTCGGGAGAGA
TTCACCTTTTTCTTGGGGGGATTACAAAATTCCTCTTCCGCGGGATCAAA
GCCCCTAATGGAGAATCTCTTCCTGGCGGGAGCGGGTCATGCTTCCCCA
ATCATTGTTATTTCCCCAGACAAACATGGACGTCTCTTCCACCAACAA
AACGAACTTCTCCCGAATCGGCGGAGATGTTCGGGAGTTCACCGCGAACC
CGGATCAGGGATCCCACCCCGGCTTTCCGCACAAGATCGGAAGGTCCCGT
TGTAAAAGTAAATGTTGAACCACTCGGTGCTTTCTTGCTGACCGTCCCAC
CGACGGACCGCCAGCCGTACGGTGGTATAACTGTTTCCGCTACGGGTCTG
CTTTTCCTTCACGGACCCAATTCTCCGTGAAAGAAATACGACATTCATAC
TGCACCTCCTGGTTGGTTTAATTAGGGTTAATGTTATACCTTTTCAGGAA
CTTCGATCGCTTTAACTCCCTCTGATGAAGCACGGTTTCCACCGCGGCAA
AAATCACCAGCAGCAGAAACCACGCTCCTATCAGAAGCAGCGCCGTTTCA
AAATAAACCCACTTCATCACAAGCCCCGCCAGTACGAAGGCGGGCAAAAA
ACCTGTTATAACGTAAACAGCGCTCATGGTTCACCCCTGAGTCTGGAGTG
CAAAGGCACCTGTAATATCCACCCAACCCTCATGACGAAATACCGTCTTC
TTGACCACGGTTCCGTCGGGCTGCTGCTCCTCCACCGACACCCTCTTCGT
AAAGGAAAACAGAGGAATGATACAGAAAGCCATCAGAGCATTGACCAGAA
ACGGCATGAAGTAGGGCGCGCCTCCAATCATGGCGGCACCCAGCAAAATA
TCCTCCGTCTCCCCACTCTTCTTGAAAAACCCGGCGGCAAGAGCGGCAAT
CTCCCACGCGCGAGACATCATCTGATCGAAATCAGGAATTTCCTCGAACG
TAAGAAGCTCCTTCACCCGATTCCACTGATCATCAGGAAGGTTTACAACC
CCCGCCTCCATCTGTTCGGGAGTCGGATTGTGCTGGGTGAGATTCAGAAT
CGTCATGGCTTGTACCTCCGTTTGTTGTTAAGTGATCCACAGCCAGTAT
ACGCATAAAGCGGAAAAAAGTCAATCGGTATTTTCTTTCTTCATCTTAAT
TTCATTTTTTTCCTTGAGGGAAATATCCGCCGCATACATTTTTTCGGCTT
CCTTCAGCACCTCAGAGACTCTGCTGAAGATCTCCCTGAGCTGAACCATT
GACCACTCCGGATCGTCAAGCACCAGTGGAAGCGCGTAGCCGTCTTCATA
CGTTTCATAGTTATCCTCAAACAGATCTTCCAGCAGACGATCCAGCAGTG
CAGGAATTTCATATCGGTAACTCATAACTCCTCCGGCGGTTAACTTATCG
GTAAACCTTCACGGATGAAGGTCTCATGTGAATGAACACTTTTGCTCCCG
GATACACTTCATCCAGAACCATAAGCGCCACAAGCGAAGCAAGCGTCATG
TACACCCCTGGATACCTCCCACCGTCATATAATCCAGAAATCTGATCGT
ACCCGCCGAAATGGTATCTTCAAGCCCCCCATCCCAGATAAGATATTCCA
CGATGGAGGGAATCTGAACCCTGATCTTTTCCAGCTCCCGCTCGATATGG
ATATGCGGATCCGAACTACGCGCTGCTTCCCTGCAGATACCTTCCGCCAG
AACAAGCAACGTTTCATTTCGATTCTGATAAAAATAATTCAGAGCACCCT
CGAACAGCGCTTCAGGATCTGTAGCCGCACGCGGAACGCTTCTGGAAACG
TCTTTCAGAATCTGCATCATGACGCACCTCCATTTTTTCCAACATAACCT
TCTTATTTCCTTTTCGGTTCCACGCAATCCCAATTACCACTATTAATCTC
CATCAAGTCAGAAACCCGAATTCAATTTAAAACTTTTCTGTCTGAAATTC
CCTTATAACCCTTAAAACTTAACACTACCCTTTCAACACAATCCCAATCA
CCAGTAAAAACCTACCTGCATTAGATCTACTACTCCCCTTTGAAGCAAAA
AGGAAAAAACCAAAAATCAAATTCTATAACCCCTACAGGATACGCTCAG
CTTTAAGTCGCATATTACCCATTGGGATTTTAGAATTTTAAAATTTTGTT
```

FIG. 1L2

```
TTTCTTTAATCTCCATAGGGTACGCTTAGCATTGAGTCTTAATTTACCAT
TTGAGGGATTTTAATTTAGAAGTTTTTGTTTTTCTTTAATCTCCATAGGG
TACGCTTAGCATTGAGTCTTAATTTACCATTTGAGGGATTTTAATTTAGA
AATTCAAAAATTTAATTTTTTCATAACCTTGAGTGGCTTATTTACCTGTA
GAGCGTCATTCAAAAAACACCCCATTTCAAGAAACCTTCACATTGATCTG
TCGTTTTACAACATAAAACCTTTAAGTGGTATATGATCAGAAAGCGTAAA
AAATCTGAACATATCGGAGCGGATGCGATTCCAAAGGGATTGGTCTATGA
TGTTTTAAATCTTGGGTATACCGATAAGCTCAAATCCCGCATGATTGCTA
TACTGAGCATTCTTATCTACCATCGCCACCGGGAAGATCACACCTACGAG
ATTGAAACAGGATCGAAATGCAAGCGCATGGTGGAAGTTAAAAAAGGGGA
GTCCTGGATCAGCATTCCAACGCTTATTGAGCGGGTTTACAACACATTTG
GAATTAAGCTTACCAGGGAGCAGGTTAAATATGCCCTTCGTTTGCTTTTA
CAGCATGGTCTGATTTCGGTAAAGGAAGCAACCGGTGGGGTTTCGAAGG
TCATTTTGGAAACATTTATACATTCAGAGAAACGGATTTTGAAGGAGAGT
TTGTCGATCCTGTGGATTTGTGAGGGAAAATAGTGAAAGTGAAGAAGAA
ATCTGGTATGCAGATTATACGGAAAGTCGGTATTCGAATCGCGTAACCGT
CAGAGAAGGAGCATTTCATCCGATTATGAAAAGTAGGACACTTCTAAAAA
CGCATGTGCTTAGAAATCATCCAGATAGAGAAAAAGCTACGAAGTTTTAC
CCGAAAGAGATTGTTGTGGATATCGAAGCGGGTGGATATCGCTAGATGA
AACAGAGCGGTACAGACGCTTTAGACTCTTCGTGATAAACCGCGCTGCGA
AGTTTGCGAGAAAGTTCAGAGCACGCTACGGGGGAAAGTTGATATATGT
TTTACCGGAGGTAGGGGAATTCATCTGCATATTACGGGAAGTGTGCTCAA
TGTTCCAATGAACCGCAGTCAATTCGACAGGATTTTGAAAGAAGCAATTG
TTCGTATGCTTAAAGATACGGAACTATGGCGGTTTTTCGATCCTTCCACG
CTGAATCCTTTTCAGCTTGCCGGGGTTCGCGGAAAACTTCATGATAAGGC
TCCTTTTGACGACTGGGTGTATGTGAAGCGTACCTATCAAACGATTAAGC
CGCTCAAAGCCGGAAGTCTGCTTTCGAGTTTTGAGGAGGCGGCTTTCTGG
ATTTCGCGTAGCTTCGTCAGAAAAGCGGCTAAAGGCAATCCATTTAGAAC
GTACAGTCTGGTAAAGGAAGGGCTACTGGAAGGGGAGCCGTGGAGCGATC
ACCATGCGGGAAGAGATACGGCTGCTTTCTGCATGGCATGCGATCTTCTG
GAAGCCGGATACATGACGGATCAGGTGTTGCTGTTTCTGAAAGATTGGGA
TAAGAAAAACAAACCTTCTCTTGGAGATAAGATTATCGCGCAGAAGGTAA
GATCGGCGCGGCGGCTTCTGCGCGAAAAGGAAAGCTTAAAGCAAACCCT
TCTCTACAGCTTCTCTAATTGTTTTGAAAAAGTGATAGAATCTTTCCGGG
GAAAAGCTGTATCCGATCATGTCGGTGATAACGCTCATCACATTGAAAAA
TCGTTGGACTTCATCCGGATTTCTTCTGTCGATTTTGATAAGAAGTTCGA
TTATACGTTTAAACGATTTAGGATAATCGTACCACAGAAAGGAAAGATAT
GCACCCGACGATCCTTCTTCCTCTTCTTTTTTCATGTAAGAACGAATATC
TTCATACAGATACCATATATCCACAATGCTTTGAGCGAGTTTCTCCATAA
TTCTGGTGGCGGTGTTGCTGAACGTATTGATATACTCACAGGTAACAACA
TACATATTCTTTTTGATTTCTTCGATAATTTCAACATGAATATTTGTTTC
CAGAAGATAAACAGGGAAAGAAATTGAAAGTTTTTCAAGCTGCACAATTT
TATGCAGAAAGGTGTTTTCGCGCACTTCCCAATCCCACAGACATTTCACA
GTCAGATATATTTCATTTCTTATAACTTTCTCCAGTTCGACGAAAATATA
CGATTTATTTTCTATAAAGCCGGGTAACTCTTCATGAATGATGCGGTTTA
AGTTGCTGTGTTTTTTCATACGGGTGTTATCTCTCAGCAATTTTCTTTTA
GCATTTGCCACAAATCTCTGATATCTTTCTTCAAAATCTTCTTTTTTGAA
TTGGATGTTGCTTCATTTTGCAATTGTCTGGTTCTTATAGCAAGCGTCT
CAATGAACGTTTTGATTAGAAGTATTGCTCCCTTAGCCATATCCTGAATG
GTGGAATCGGCGGGTAAATCCACACGAAAGATTTTCGAGTTTCTTCGTT
TTTGATCAGTGCGACGTTCCATCCCATTCTCTTTTCCATGAAAAACCTGA
GCGCCCAGACCAGATATTCGTAGAAGTTTTCAGTCATTTATTTTAAATA
TTCCCTTATCTGTATTCCACTTCCGGAGATTCTATATGGATGTAAAGTAT
ATTTTTTCGTGGTATAAAATTCATCTGAGCGTGCACCGCAATTTTCAGGT
CGTTCTCGCTCAAATGATGCTCGCCCCACCTGAACGATCCGATAAACTGC
AGCGTGATATGGTGCGTGATCAAATCCGTAGAAAACTCCAGCTTATCATC
TGTTTCGGGTGGAAGCACATCGGTAGAGGGAAACCGGGATTTCACATCAA
GACGTGCAAGCACCAGATAATGATGGTAATTCTCGACGTTTGATGCCGGT
GATATGTTTTTGAGTTTGTCGTTTAATGTGCGGATTACTTCTTTCATTTC
CTTTTCGATGGTGGTATCCTCTGATTCTTTTCTGGAGAAATGTTTTTAT
AAGAGGGTCCTTTTTTGATATGTTCTACCGGGGAAATGGCTTTAAGCAGT
```

FIG. 1M2

```
CTGTAGGCATAATGCAACGTGTCGTTTATCATCTTTATGAATTTTCTGAT
CGCAACGCTTACAGGTGTATCCTCAGAGATGCTCAGGTAGACCAGATCGG
GGTGTTTTCTCAAATGATAATCAGGTGGAGAGAAGCCGGGATATTTTCC
AGATAGTTTTTGATGGTGTTTGTAAGCAGTTCCTGATACGATGGCATTTT
ATTTTAAATAAGTGTTGATAAACAAACAGGCTTTTTTCACATATTCGAAC
AATTCATCTTTGGAAAGATGGTGTGGTTTGTACTGACGATGCATAAACTT
ATAAGCAATATCAAACAATACCCTACCCTTTTCCTCACTTTCTTTAATAA
TATCTATAATGCTGTCTATTTCCTCTTTCAGTTCTCTGTAAATGGTTCGG
TATCGGTTTATGTCCTGCTCTGTCAGGTGTTCACTATTTTCATATTTTAT
CCCGAATACAGACATAATACCTATTGTTCCTCCGATAAATTCCAGTGTTC
CATTCCGGGTAGAGGCGCTTACAAATGAGTTGCGAATCTTCAATGTTTTA
TCTGAAACGAAACTTTTAAAACTTAAGTCAAGGAGCATTTCTGTAACAAA
CAGAGGAGCATTCAGGTGGAAAATTTTTGCAAATTTTGAATTTTCTCGGG
GAAACCATTTAACAAAACCGATTATCATTATACCAAGATGAGCTTCCTTT
GCAAAAACCGGCATAATGTAAAGATGAATTTCGTTTCGAAATTCTATTTC
GTCTGTGAAGTGGGTGATTAATTTTTTATCGATATTATTGTAGTGTATAG
TATCGTCTTTAAGTTCTTTCATTTTTTTCTGAAGTTTCTTTAATGCCTGT
TGAAACTTCTCCTCAATTTGATCTACAGCTATTTTTCAACTCCGATATC
TTCTTCGAAGTGTCTGATTTTGGTAAGTGATAGTTCTATAGTCTTTTTAA
GCGTATGAACATACATCCGCGTAAAATCTCTGGGTAACTGCTTTTCGGCG
GGAATAAGACGCACTTTTACATAAGAAGGTCGTTTCTCTATAATTTCTAC
ACTGGAAAATTCCGATCTTTTTTTAAAATATTCAATGATGTTCATTGCA
AGTAGTGCTTCAACAACGCCTTCCATAGTTTTTTTAGCTAAGGTTTTTTG
TTTACAGTTTTGTAGTTTTCGTTAATTAAGGTGTTTAATGCTATTGGTTT
TTTTAACTATTCCCCACGAACTATCTGTTTCAATACACGATATCTTTCCA
CCATATCGAGGTTTATAATATCCAGCGCTCTACCTATTTCATCAAACATT
TCGATCACGCGTTCATCCTGATTGTTTTGCTGTGTTCGATAAGGTTTCT
GAGTTCAAAAGCTCCCCGTATACCACTGGAATACAGAAATGCGATTTTG
GAATATCAGGGTGTCCGGGATTAATAAGAGATAGAAAATGTTCAATGTTT
TTTATGAGTTCATGAAGGCGATTATACTGCATGTTGAAATAAGCGTGGGC
TTTTGTCAGCCTGATGTTTTCTTCTATCATGGGGCGCACGTAAAAACTCC
CATGCAGAGCGGTTCCGATATTGGTAAAAACTGTCTCGTGAAACAGAATA
GCGGAAAGTGCGGCGTTTTTAACCGGATAGAGAGAACTTGCACCAATAAC
CGATATATCAAACAGAGCAGGAAAAAACTCGAAAAGACTCTGATCATTAA
AGAAAATATGCATTTCGTTTTTTCGATATACCAGATCAGGGTATTTATGT
GTGGTGTTAAATATTTTCTGTATTTTCTGAACCGTTTCTTTCTCCTTATT
TATTTTTTCTTTAAACTTCTCAATAGCCTGCTGGTACTTATCATTTATTT
TGCTGTCTACAGAAAACCCGGAATAAATGGTTCGTGTCTTTTTTATAAAA
AACTCGATCAGTTCTTTGAACATGCGCGGCGTTTCTTTTATAATCTCTTT
TGCGGTTGCGTTTTCACCGATGTCAAGGATTATGGTTACATGTTTATCGC
CGGCGTCTATGTTACCGGATACTTTTTTTGAAATCTGTAATACTGCTGA
ATTGCACTTAAAATCTCTTTACGGTATTTTTTCGGAGTCATAAGGTGTCG
GGTTTGATTTTATTAAATCACTCAGGTTTTTAAGTCGTGCATGTTTAACC
CAGTTTTTTAACCACCCTGTTATTCCACCATATGACTTTTCCATCTGATC
TTACGATTCCTCCGTATCCCATGCGGCTCAGGATCTCATTGATTTTCCG
TTTTGAGGAACGTTGAGTGCACCAAAATAGAGTTCAGTAAGTTGCTTCAT
AAAACGGTTTCTATCCTGATTCAGATCTTCTTCTATCATCATCTGAATGC
GGGTTGGAAATGTATCTACGATCAGGTTACGACGTAGACTCTATCGCTG
GCTTCCCATCTTGAAAGGAAAAAGGAATCATATCGAAGCAACCGGTCAAA
CGTTTCGTCAACGACGGTTTTGACAAATGTCGCAAGTTTCGGGTGAAAA
CGGCTCCGGTTTGCTCGAAAGTGATAAGCAACCCTTTGAAAAGCATTTTT
CGGAGTGCGGAGAGGCTGTAGGGAACGTCAAAATGAATTCCCCTTTCGAC
GAATCCATATGGCGGCTTTCCAAATACCCCTGAAGTTTCATTCGGTGAA
GTTCCCAGCCGCTTCAAGAAATTCGTCAATCTGAAGTTTTTTAAGTTTT
TTGAGATCGGAGGAGTTAAGGTGCACGCCGAAATAGTTAAGTGCGCCCCC
GGTGGACGCGAAAAGGGGGAGGTTGTAAAAATCTTTTGGATAATCGTTTT
CCTTTTTGACGTTGAGAAATTCCTCCGGCTCGATGATATAGTAGAGGTGA
TACCCGCGCTCCAAGATTTCCCGAAGGGTTTTTTCGTTTAACGGGATTTC
GCTCATAAGGAGTCCGTTTCCCTCCACAGAAGACACAATCAGGTTTGAGG
GATCAAGCGTTTCGATTTTTTCAAGGAGCTCTTTCATACGGGTATCTGCA
GGGTTATCTGTTCGCGGTTAATCTGCACAACGATTTTGAGAAGGTGTGTG
```

FIG. 1N2

```
GCTTCGTCAAAACTCACGTCTATAGTATCTATGTCGTAGGGTTCGAGGTT
GGAGGCAATCAGGTTGAACAGTTCATCATAATCATAATTCTCGAAAAGAA
TGTTGCGAATACCGATCCCTCTTTCTGGATCGTAGGGATATTCCCCCGGC
TCGATGAAAAGCAGGAGTTTTATCTTATCGATCAGGAGTTTTACCGGGTC
ATCAGGAAATCTGAATTCGGTGCAGTGTCGTTCAGATAGAACATTTCAT
TTTTGTTTAAATAAATCCTCGAGGAATCTTCAAATAAAGAGGGGCGTTAA
TGGATGAAAAGACTGAGGAATATGGTCAATCTTATCGATCTCAAAAATCA
GTATTATGCTTACTCTTTCAAGTTTTTCGACTCCTATCAGATCAGCTGGG
ATAATTACCCGCATCTTAAAGAGTTCGTCATTGAAAACTATCCCGGCACT
TATTTTTCATGCTACGCTCCGGGGATTCTGTACAAGCTTTTCCTCAAATG
GAAGCGGGGTATGATCATTGACGACTATGACCGACACCCGCTCCGAAAGA
AGTTACTTCCTCAGTACAAAGAGCACCGCTATGAATACATTGAGGGAAAA
TACGGTGTGGTTCCTTTCCCCGGGTTTCTGAAATATCTGAAGTTCCACTT
TGAGGACTTGCGGTTTAAAATGCGCGATCTTGGAATCACCGATTTCAAAT
ATGCACTTGCCATTTCTCTTTTTTACAACCGGGTAATGCTCAGAGATTTT
CTGAAAAACTTTACCTGTTATTACATTGCCGAATATGAAGCTGACGATGT
AATCGCACATCTGGCGCGTGAGATTGCACGAAGCAATATCGACGTAAACA
TCGTCTCAACGGATAAAGATTATTACCAGCTATGGGATGAAGAGGATATA
AGAGAAAGGGTTTATATCAATTCTCTTTCATGTAGTGATGTGAAGACACC
CCGCTACGGATTTCTTACCATTAAAGCACTTCTTGGAGACAAAAGCGATA
ACATTCCCAAATCTCTGGAAAAAGGAAAAGGCGAAAAGTATCTTGAAAAG
AAAGGATTTGCGGAGGAAGATTACGATAAGGAACTATTCGAGAATAATCT
GAAGGTGATCAGGTTTGGAGACGAATATCTTGGAGAAAGGGATAAAAGCT
TTATAGAAAATTTTTCTACGGGGATACTCTGTGGAACTTTTATGAATTT
TTTTACTATGACCCTTTGCATGAACTTTTCCTCAGAAATATAAGAAAGAG
GAGACTATGAAAGTACTCGCATTTACCGATGCACCTACGTTTCCCACGGG
GGTGGGTCATCAGCTTCACAACATTATCAATTACGGGTTTGACGCAACCG
ATCGCTGGGTTGTGGTGCACCCGCCCCGGTCGCCAAGGGCTGGAGAGACT
AAAAACGTCGTTATTGGAAACACTCCAGTCAAGCTTATCAATTCTCCGCG
AGGATATGCGGATGATCCGGCGTTTGTGATGAAGGTGGTGGAAGATGAAA
AGCCGGATGTGCTTGTAATTTTTACCGATCCGTGGGCTTACCACCCCTTT
ATGCAACAACTTTCTTACTGGATTATCGAGCGGAATCTCCCGCTGGTATA
TTATCATGTGTGGGATAATTTTCCGGCTCCTCTGTACAACATCCCCTTCT
GGCACACCTGCAATGAAGTGATAGGAATTTCGATGAAATCGACGATCAAC
GTGCAGCTTGCGAAGGAGTATGTGGAGGCGTATGAAATCACCATGTATCG
CGATCCGGAGGTATTCTATCTTCCGCATGCGGTCGAACCCAATGTATTCA
AACGCATGGATCGCAAGAAGCACGTGAATTTGTGCGGGGACTTGTCGGA
GATAGGATGTTTGATGACAGCGTGATCTGGCTTTACAACAATCGAAATAT
TTCACGCAAGAATCTGATGGATACCATTTATGCTTTTCTGGTATACATGC
TCAAAAACTACAGGAAACATCACCTTTTGATTATAAAGTCTGACCCGGTT
GTACCGGTGGGAACGGATATTCCCGCGTTTCTTGCCGATATTAATTCGTT
TTTCCACTACCGGGATATTGACCTTCGGGAACACATTGTTTTCATTTCCA
ATGACGAAGTATTTCACAACGGCGGATTTTCAAGGGAGGAAATCGCATTG
CTTTATAACGGCGCCGATGTGGTGCTGCAGCTTTCATCTAATGAGGGGTT
CGGGATCGCTTCGCTTGAGGCGTCGCTGTGTGGAGCCCCGGTGGTTGCTA
CTATGACGGGTGGTATTGCAGATCAGTACTCCCTCTACGAAATGGATTAT
GAGGTGGCGGATGGAAGTGATGAAGATATAATCTGCAAGATTTATGAGGA
AGTGCACCGTCAGGTGCTCAATCAGTATCTCGATATGCTCCGTCAAAACG
GAAAGGATCCGGAAAGCGCTCCCCGCAAAAATCATATGATGCGGATGGTG
AAACCTTATCGTCATTATCAGGGATCGCCGGCTACTCCCTACATTCTTGA
CGACAGGGTTCCTATCCGGGACGTATTCCCGAAGTTCGATGAAGCGCTGG
CGCTGAGGAATCGTGAGGATTACGAAAAACTTTATGAAGAATCGGTTGAG
TACATCACCATGCACTTCGATGTAGAGGTGCTCGGAAAAGAGTTCAAGAA
ATCCCTTAGCCGTGCCATTAAGAATAACCAGAAAACCACAAGACAGGTTG
TCGTGCTATGAAGAAGAAAGTGCTTCTTGTTTCGCCGCTTCGTTCCGTTA
GCGGCTATGGAACCGTAAGTCGCGGAATTTATCGCATTCTGAAGCGAATG
GAAAAAGAGGGGTTGATCGATTTTGATGTGATGGTATTGCGGTGGGGTAC
GTTTTCGGAAACCACCCACCTTGATGATGAAATCAAGAAGAGAATTCAGG
AGAAGTATGATCAGGTGTACGATGTTGCGATCATGGTTTCTTCTCCCTAC
GACTATCGCTACTGGAACAACATCTTCAGAGCGAAACACCTGCTCTTTTT
CAATGCGATGGTGGAAACGAAACCGTTCCATCCGAATCTGTTCCAGCAGC
```

FIG. 102

```
TTTTCAACTTCATGCTTCAGGTTCCCACCGCGCACCTTGTGTTTCCTTCT
TCCGAAATCAAGAGGATCTGGGAAGAAATCATCAATTCCCAACCCATCCA
TCCGGCAATGGGTGCTGCAGTGCTCTCCGCATTCATGTAGTACCCAACC
CGGTAGATGAAGTTTACTATACTTCGAACTTCGGGAATAAAAACGTTCGT
AAAAATGTGATCGGCGCGATTCGAAAGAAGATTGAGGAAATCCGTCGATC
CTATGAACTGGAGCGGGTGTTTCTGACTTTTGCGCCTATGGGAGTAGATC
GAAAGAACACCAGGGTTTTACCCGAACTTATCGAAATGGTGGGCGGGTT
GGAATTCTGGCGCTGGCGGGCGGAACAAATTCTTTTATACTTTACGACTT
TCAGCGGCTTATCTGGATGGAAGGTGAGAAAGCCTATAAGCGGCTTCCGC
TTCACCGATCGATCGACGTTACCCCGGAAGAGCTTATGTTCGTTTTTGGA
TCGCTGACGGTGGAAGAGCTGAGTGCGGTGATGGATATGGTGGATGGTGG
AATCAACCTTTCGCATGGAGAATCGTGGGATTACCTGTTGCACAACATGA
TGCTACTGGGCAAACCCTGTCTTTACGTCGACTTCTTCCGTCGGGATTAT
ATCCCTTCGGAGCTTCGTGATGTGCTGGGGTGGATTTCAATATGGTACC
CCTCCCGAAGGTGGTTCCCAACATTCCGCACGATCATCCGTTCTTCCACC
CGCAAACGATGGTGGCGGAACCCAATTTGCAGGATGCAGCGGAAAAGCTC
GACTGGGTGTTGCGGAACTACGGTGAAGTCTCAAAGATGATTACCAGCCA
TAGAGACGCTTTCAAAACCGACGATACGATCTATGAATTTCTGGTTGACG
CACTGGAGTCGATCGAAGAACCACAGGCGGCATAAAAATTTCACATTCTG
GATAAACCGGGGGAATTCGGGCATTTATCCCGAAAATCCCCCTTTTTTGT
CTCAAAACCGTTTTGGCGGGGTAGATATTTAATATCACCCCGTGGAAAGT
TTAACCCCAAAACAGGAGTGGATATGTCGTACTATACTGAAGTCGGCGCA
CCCTACTTTACACGTGAAGAGCAGTTTGTTCGGAATTTGCTGTTCGACGT
AACTTTTAATTCCAAATATTCTTTCTTCGATCTGACGCTGCAGCGTCGTC
TTACCTTTGAGGAAGTGCTGGAAGAGGTGCTGGCGGTGTTTCATGCCCGA
ATCGAGGAAGTCTGCAAACCCATTTATCGCCAGCAGGCGCACCAGTACGT
GGAGAAGTTCGGCGAGTATTTCCGCCAGCGCAAGCTTTTTCCCTCGATGC
GCCTTGTGCAGTTTTCGCGCATGGTTCCTTACAACCACACCCGTCTTTAC
AATTGCTCTTATACTCCCGTTGATTCCATTGATTCGATCGCGGAGCTTTT
CTACCTGATGTTGTGTGGCGTGGGTGTGGGATACAGCGTGGAGCGTAAAT
ATATCGAACAGCTTCCTGTTGTATATCCCGAAAGTGAGGGGCAGACAATC
ACCTATCAGGTGGAGGATTCGATCGAGGGATGGTGCTCGGCGCTCAAGCG
TTATCTCTATGCGCGGTTTACGCCCAACCACCCGAAGATTGTATTTGACT
ATTCTCTTTTGAGACCGGAGGGAAGTGTGATTGGAAAGCGTTACAATGCT
GCATTTGGTTATACTAAAAACAATCCCATCAAAGAAGCAATCGAGGCGGT
AAAGGGGATTTTCGACAAAGCAGTAGGAAGGAAACTCAAGCCGATCGAGG
TACATGATCTCATTACAACGTTCGGCATGATTATCAATCGTGCGAACGTG
CGCGGAATGGCGGCGATCGTCTTTTTCGATTATGATGATGAAGAAATGCT
TCGCTGCAAGGATTTCACGCGCGGCGAAGTCCCTCAGAACCGCTGGTATG
CCAACAACTCTGTCGTGTTGTATAGAGACGGCGATAAACTTCGCGGAGTG
CGCGGGGAAATCGTCGATCTTCGGGATATTTTCATGGAAGCCTATTGTGG
GAAGTCTGGTGAACCCGGCGTCTTTGTAACCAACGACGAACATTATCGCA
CGAACCCGTGTGGTGAAGCTTCTCTTTATCGCAATTTCTGCAACCTTACG
GAGATCGCCATTCCCCGTGTTCATCAGAGTGAGATCGCGGATGTGTTGAA
CACAGCTATCTTCATTGGTGTGCTTCAGTCTACGTTTACCGACTTTAAGT
TCCTTCGCGATGTGTGGAAAGAGCGCACCGAAGAAGACAACTTGCTTGGC
GTTTCGCTGACCGGCATTTACGAAAATCTGGATGCGCTCAAAGAGTACAT
GAAGCTTTCTTCGAAAGGTCATGTCAAATTCATGGCGGCTCAATTTGCCG
GTTGGTTCGGGTTGAACAACCCGGCTCGCATTACGCTGGTCAAGCCCTCC
GGCACGGTGTCGCTGCTTGCCGGGGTTTCTCCGGGTTGCCACCCACCCTA
TTCCGAATATTTTATCCGGAGAAACCGGGTGGATATGAATCACATGCTGG
TTGAAGTTTTGAAGGATTATCCGTTTATCATTGATGATGAAGTGTATCCC
GATAAGAAAGTGATCGAATTTCCGCTTCGGGCGCAACGCCACTTTACGCA
CGATCCCATGTTTCAGGTGCGTCTTCGCAACCAGATCATGAGGGCTGGG
TGGAACCCTCGCATAATCGCGGCAAAAACACACACAACGTATCGATTACG
GTTTATGTAAGAGATGAAGGGGAAGTGGAGATTGTAAGTCGCGAACTCAA
AAATGAGCGAAACATTTCGGGAATCACGATTCTTCCGGTGGTTGAGAATG
GCTATAAACTGGCACCATTCGAAGCAATTCCCAGGGAAAAGTATGCCGAC
ATGATGGGCGAAATCCACGTGTACCTTGATAGAATCAAACACCAGCTAAA
CGGCACGCCCGACTCCCCGCGTCTGAAACTGATCTCCGATTCCGACGTTT
TTGAGGGAGAGAAAGGTTGTGCCGGTCTGCAATGCTATTTCGACATGTAA
```

FIG. 1P2

```
CATGAAACTCGTACTTAAACACTCCAGAGAAGAGTCTTTCTATCCTGAAA
CAATAAAAACTCTTGATCATCTTAGAGAGAATGGGTGGGAAATCGTTCTC
CTACAGGATAATCGTTTTAATATCATAGAAGGTTACGATTTCGATATGGT
GATTACCACGTCGAACCCTCAATACAGCTTTGCGGATTTCCACAATGAAG
CATTGAAATTTGCCAAGCACGGGGAGTGGCTTTTTTATCTTGATTTCGAT
GAATATTTATGTGATAATTTTTGTGAAAGGGTTAAAAAATATATCAACAG
AGATGTTCATTGTTACAACATCGCACGCATAAACATTATAATTCCTCAGG
AGAAAACGGGTGATGTGTGCGGGATGTACGGATGGCGTAGTTTTAATATC
AATATACCTGAGGAAGGGAGTGTAAAAGCGATAAATTTCCCCGATTACCA
GACGCGTCTGGTTCGCGCCGGAACCGGCAAATGGTACGGGAACGCCCACG
AACGCTTTGTGTGCGATAATGCTTTTAAACACAAAACGTTACCGTTTGAT
GGTGGATATATTATCCACCGTAAATCTTTTGAGAAACAGATTACCGATAA
CGCGCTCTGGTCAACCTATACACCGTGATATATGTTCAGCGTAATTCTCA
TACACGGAAACGAGGATCTTATCAATAAGAACTGATAGATAATCTTAAT
GAATTCAGGGAAGCAGGATGTGAACTCATTTGCTGCAGGATGATCGTTT
TTCACCGCCCGACTTTTTCAAATTTGATATTGTTATAAAACATTCCGTTT
CCGAAGGGATGGACCGTCATCGAAATTTTGCCAATCAACATGCTTCTTTT
GAATGGGTGTTGTGGTTGGATTTTGACGAATATCTATTCCCCGGATTTAC
AGAACGAGCTCCTGAATACATGAAAAGGGATATATGGGGGTATGGATTTT
ACAGATTGAACATGATCGTTCCACCTGAAAAAACTTCATGGTTCGTTCAG
AATTATGGCTGGTATGAAATGGTTGGTGGGTTTCAACCATATCGATCAG
GGGGGTTTCTTATCAGGCTATAAATTACCCGGAGGTTCATTATCGTTTTG
TTCGAAGAGATTGCGGCAAGTGGGTTGGTAAAAGACATGAATACTGGTAT
TCAGGTGATTTTCGTAAAAAAGCCATATTTCCGGCGGATCGAGAAACACT
TTTCCACGTTAAACCCATTGACAAAGCAATAAGAGACAACTATAAATGGA
GGGCACTATGATGAACCCCGAAATGAAAGAGATTCTGAAGAAGCTTATGA
AACCCTTCCACCCTGATCGCCATTCCTATCGCGTTACCGGAACCTTCCGG
ACTCGGGAAGGGCGGAACATGGGGGTGGTGGCATTTTACATTTCATCACG
CGACGTGATGGATCGGTTGGATGCGGTGGTGGGACCAGAGAACTGGCGAG
ACGAATATGAAGTGCCGGCTCCGGGGTGATGAAGTGTGTGCTTTATTTG
CGTATAGGTGGGGAGTGGGTTGGAAAGAGTGATGTGGGGACCGGCAACAT
AGAAAACCCTGAAAGTGGATGGAAAGGCGCCGCTTCTGACGCCTTGAAGC
GAGCGGCGGTCAAGTGGGGAATCGGGCGTTATCTCTATGCACTTCCCAAA
TGCTATGTGGAGGTGGATGATAGAAAGCGTATTGTTAATGAAGAGGCGGT
CAAGTCTTTTCTCCATAAGCATGTTACCGAACTGCTGAAGAATTATCAGT
AACCCAAACCTAAACCCGAAAAATATATGGAAACGATTGTAATTTCCCAA
AACAATACGACGGAGATGACGGAACCCCCCAGAACATTTCCGATTCGGT
TAAAAGCGGGTTTATCTATCTTATCGAAAAGTCTCATTTCCTTGAAAAGA
AAAACTTCCTTAAAATCATATCGAACATGGACCCCCGCCGCATTTCCAAT
CCGGAGGTGCGCGTGGTGGCGGAGTACATATATGATTATTTCAAAAGTCA
TAGTAATTTCCCTTCTAAAAGAAATCTTTGCCATCACTTTGAGTGGAGCG
AAGATCTGGAAGGAGACCCCGCCGATTATCAGCGTATCATTCAGTATCTC
AAATCTTCTTACATTCGATCCTCTATAACAAAAACGCTTTCATATCTTGA
GAAGGATGACCTTTCCGCGTTGAAAGAAATTGTCAGAGCCATTCGGGTGG
TGGAGGATAGTGGGGTGTCGCTGGTGGAGGAATTCGATCTTGCAACCAGC
GAGTTTAATGAACTTTTTGTTAAAGAAGAACGCATTCCCACCCCCTGGGA
GAGTGTAAACAAAATATGGCGGGCGGTCTTGGTCGGGAGAGCTTGGAA
TCGTTATGCTTCCTTCGGGGTGGGGTAAGTCATGGTTCCTTGTTTCACTT
GGTCTTCATGCCTTTCGAACGGGTAAGCGCGTGATTTATTTCACTCTGGA
GCTTGACCAAAAATATGTGATGAAGCGGTTTTTAAAGATGTTTGCACCTT
ATTGCAAAGGACGCGCTTCTTCCTATCGCGACGTTTATCAAATAATGAAA
GAGCTTATGTTTTCTCAGGATAATCTTTTGAAGATTGTTTTCTGTAATGC
GATGGAAGATATTGAGCACTATATTGCGCTGTATAACCCCGACGTTGTGC
TGATTGACTATGCCGATCTTATTTATGATGTGGAAACCGACAAAGAGAAA
AATTATCTGCTTTTGCAAAAAATTTATAGGAAACTTCGTCTCATTGCAAA
GGTATATAATACAGCAGTATGGAGCGCCTCTCAGCTTAATCGCGGTTCCC
TTTCAAAGCAAGCCGACGTCGATTTCATTGAGAAATACATTGCCGATTCA
TTTGCAAAAGTTGTTGAAATCGACTTCGGG
```

FIG. 1Q2

| 1 Locus | 2 start | 3 stop | 4 nt | 6 aa | 5 dir | 7 confidenc | 8 Partial %ident | 9 putative protein | 10 protein (genbank) | 11 aa | 12 Match organism | 13 identity match |
|---|---|---|---|---|---|---|---|---|---|---|---|---|
| Transc.fact. | | | | | | | | | | | | |
| 1 | 133 | 744 | 611 | 204 | 1 | 4 | | | | | | |
| 2 | 290 | 715 | 425 | 142 | -3 | 5 | | | | | | |
| 3 | 1086 | 1505 | 419 | 140 | 3 | 5 | | | | | | |
| 3.1 | 2091 | 3476 | 1385 | 462 | 3 | 1 | | | | | | |
| 5 | 3446 | 4396 | 950 | 317 | -3 | 5 | | | | | | |
| 6 | 3490 | 3885 | 395 | 132 | 1 | 5 | | | | | | |
| repl | 4415 | 5056 | 641 | 214 | -3 | 5 | | | | | | |
| 7 | 5056 | 5823 | 767 | 256 | -2 | 4 | 45% | "Rec N" | | | | |
| 58=61? | 6064 | 6948 | 884 | 295 | -2 | 5 | | | | | | |
| das=rnh | 7004 | 7846 | 842 | 281 | -3 | 5 | 24% | "helicase-primase" "RNAseH" | gi:4490554 | 305 | Herpes-virus T4 | |
| 8 | 8212 | 9168 | 956 | 319 | 1 | 1 | | | | | | |
| 9 | 9111 | 9683 | 572 | 191 | -1 | 5 | 27% | "Unknown" | gi:2447052 | 289 | Chlorella virus | 74/268 |
| 10 | 9165 | 10619 | 1454 | 485 | 3 | 1 | | | | | | |
| 11 | 10489 | 11094 | 605 | 202 | -2 | 5 | | | | | | |
| 12 | 10616 | 11893 | 1277 | 426 | 2 | 5 | | | | | | |
| | 11992 | 13671 | 1679 | 560 | -2 | 5 | | | | | | |
| GP50-myco | 12026 | 14008 | 1982 | 661 | 2 | 3 | 24% | "Ribonucleotide | gi:465365 | 682 | Mycob.-phage | 146/603 |
| 13 | 13977 | 14636 | 659 | 220 | 2 | 5 | 26% | glucosyltransferase" | | | | |
| a-gt | 14640 | 15269 | 629 | 210 | 3 | 5 | | | | | | |
| 14 | 15254 | 15760 | 506 | 169 | 1 | 5 | | | | | | |
| 15 | 15403 | 16041 | 638 | 213 | -1 | 3 | 23% | "T4-primas-helicase" | P04530 | | T4 | 55/237 |
| GP41 | 15785 | 17035 | 1250 | 417 | 2 | 3 | 42% | "DNA-polymerse??" | | | diverse | 19/42 |
| dnapol? | 17032 | 17826 | 794 | 265 | 1 | 4 | | | | | | |
| 16 | 17847 | 20267 | 2420 | 807 | 1 | 5 | | | | | | |
| 17 | 20254 | 20619 | 365 | 122 | 1 | 5 | 45% | "unknown" | | | Aquiex | |
| ExoU | 20276 | 21241 | 965 | 322 | -3 | 3 | | | | | | |
| 18 | 21255 | 21989 | 734 | 245 | -1 | 5 | | | | | | |
| 19 | 21351 | 21719 | 368 | 123 | 3 | 5 | 27% | "Polymerase**" | gi:3511205 | | diverse | 67/245 |
| GP43a=pol(exo) | 21993 | 23042 | 1049 | 350 | -1 | 1 | | | | | | |
| 20 | 22497 | 22955 | 458 | 153 | 3 | 5 | | | | | | |
| 21 | 23375 | 24301 | 926 | 309 | 2 | 5 | | | | | | |
| Capsid? | 24310 | 25056 | 746 | 249 | 1 | 4 | | "Capsid-protein??" | | | | |
| 22 | 25794 | 26471 | 677 | 226 | 3 | 5 | | | | | | |
| GP3 | 26647 | 27153 | 506 | 169 | -2 | 1 | 19% | "Tail-sheath protein" | CAA32952 | 184 | T4 | 23/117 |
| GP18 | 27253 | 29481 | 2228 | 743 | 1 | 2 | 35% | "Tail sheath-protein" | P13332 | 659 | T4 | 84/185 |
| 22.1 | 30258 | 30920 | 662 | 221 | -1 | 4 | 34% | | | | Tomato-virus | |
| 23 | 30997 | 33342 | 2345 | 782 | -2 | 5 | | | | | | |
| 24 | 33362 | 33955 | 593 | 198 | -3 | 5 | | | | | | |

FIG. 2A

| Label | Start | End | Length | AA | Frame | ? | % | Description | Accession | # | Organism | Ratio |
|---|---|---|---|---|---|---|---|---|---|---|---|---|
| 25 | 33724 | 34224 | 500 | 167 | 1 | 5 | | | | | | |
| GP20 | 33948 | 35576 | 1628 | 543 | -1 | 1 | 33% | "Tail-tube-protein" | P13334 | | T4 | 45/135 |
| 26 | 35631 | 37496 | 1865 | 622 | 3 | 5 | | | | | | |
| 27 | 38627 | 39085 | 458 | 153 | 2 | 5 | | | | | | |
| 28 | 39213 | 40106 | 893 | 298 | 3 | 3 | | | | | | |
| Transpos. | 44821 | 45708 | 887 | 296 | -3 | 5 | 30% | "Transposase" | gi3676289 | 348 | Ifl-virus | 77/252 |
| 29 | 44882 | 45646 | 764 | 255 | 2 | 5 | | | | | | |
| 30 | 45740 | 47158 | 1418 | 473 | 1 | 5 | | | | | | |
| 31 | 47211 | 47630 | 419 | 140 | 2 | 5 | | | | | | |
| 32 | 47805 | 49211 | 1406 | 469 | 3 | 5 | | | | | | |
| 33 | 49594 | 50577 | 983 | 328 | -2 | 5 | | | | | | |
| 34 | 50661 | 52241 | 1580 | 527 | -1 | 1 | | | | | | |
| 35 | 52498 | 53364 | 866 | 289 | 1 | 5 | | | | | | |
| GP17 | 53361 | 54887 | 1526 | 509 | 3 | 5 | 26% | "T4-DNA-packaging-" | P17312 | | T4 | 121/459 |
| 36 | 53475 | 54128 | 653 | 218 | -1 | 5 | | | | | | |
| 37 | 54965 | 56341 | 1376 | 459 | 2 | 5 | | | | | | |
| 38 | 56567 | 59419 | 2852 | 951 | 2 | 5 | | | | | | |
| 39 | 56710 | 57381 | 671 | 224 | 2 | 5 | | | | | | |
| 40 | 58087 | 58959 | 872 | 291 | -2 | 5 | | "Unknown" | | | Chlorella- | |
| e | 59429 | 60130 | 701 | 234 | 2 | 5 | 37% | "Lyzozyme" | gi:3337264 | 165 | P2-phage | 37/99 |
| 41 | 60122 | 61324 | 1202 | 401 | -3 | 1 | | | | | | |
| tk | 61647 | 62339 | 692 | 231 | -1 | 5 | 22-28% | "Thymidine kinase" | | | diverse | |
| 42 | 62338 | 63030 | 692 | 231 | -2 | 5 | | | | | | |
| 43 | 63034 | 64413 | 1379 | 460 | 2 | 5 | | | | | | |
| 44 | 64825 | 66276 | 1451 | 484 | -1 | 5 | | | | | | |
| 45 | 66276 | 67547 | 1271 | 424 | 3 | 5 | | | | | | |
| 46 | 66504 | 66992 | 488 | 163 | -1 | 5 | | | | | | |
| 47 | 67567 | 69180 | 1613 | 538 | 2 | 5 | | | | | | |
| 48 | 69182 | 70168 | 986 | 329 | -3 | 5 | | | | | | |
| 49 | 70436 | 71959 | 1523 | 508 | -3 | 5 | | | | | | |
| 50 | 71972 | 74014 | 2042 | 681 | 1 | 5 | | | | | | |
| 51 | 73372 | 74106 | 734 | 245 | -3 | 5 | | | | | | |
| 52 | 74259 | 75965 | 1706 | 569 | 3 | 4 | | | | | | |
| 53 | 75959 | 76672 | 713 | 238 | -2 | 1 | | | | | | |
| 54 | 76660 | 76977 | 317 | 106 | 3 | 5 | | | | | | |
| GP13 | 77415 | 78503 | 1088 | 363 | -1 | 5 | 39% | "Neck-protein" | P11110 | 309 | T4 | 13/39 |
| GP43b=dnapol | 79584 | 81152 | 1568 | 523 | 3 | 5 | 25% | "polymerase" | | | diverse | |
| 55 | 79779 | 80381 | 602 | 201 | -1 | 5 | | | | | | |
| 56 | 80448 | 80846 | 398 | 133 | 3 | 5 | | | | | | |
| 57 | 81748 | 82251 | 503 | 168 | -2 | 5 | | | | | | |
| 58 | 83464 | 85047 | 1583 | 528 | -2 | 3 | | | | | | |

| # | Label | Start | End | Len | ? | Str | Sc | Description | Accession | Size | Organism | Ratio |
|---|---|---|---|---|---|---|---|---|---|---|---|---|
| 59 | | 86099 | 88750 | 2651 | 884 | -3 | 5 | | | | | |
| 60 | | 88731 | 89663 | 932 | 311 | -1 | 5 | "RNA-ligase" | | 374 | T4 | 20/152 |
| 61 | GP63=malig? | 89687 | 90292 | 605 | 202 | -3 | 5 | "helicase" | | 866 | diverse | 142/460 |
| 62 | Helicase | 90291 | 91607 | 1316 | 439 | -1 | 2 | | | | | |
| 63 | | 91704 | 93671 | 1967 | 656 | -1 | 5 | | | | | |
| 64 | | 91812 | 93722 | 1910 | 637 | 3 | 5 | | | | | |
| 65 | capsid | 93758 | 95551 | 1793 | 598 | -3 | 5 | "capsid-p??" | | 230 | Chlorella virus | |
| 65.1 | | 94693 | 95415 | 722 | 241 | 1 | 3 | | | | | |
| 65.2 | | 95565 | 96335 | 770 | 257 | -1 | 5 | | | | | |
| 66 | | 96545 | 97384 | 839 | 280 | -3 | 5 | "Minor tail protein" | | 837 | T4 | 24/71 |
| 67 | | 98061 | 99146 | 1085 | 362 | 3 | 5 | | | | | |
| 68 | GP21 | 99163 | 101880 | 2717 | 906 | 3 | 1 | "Prohead-core" "RNA-enzyme" "Capsid-protein" | P=6807 | 212 | T4 | 41/139 |
| 69 | capsid? | 102281 | 103895 | 1613 | 538 | 3 | 5 | | | | | |
| 70 | | 103895 | 104784 | 893 | 298 | -2 | 5 | | | | | |
| 71 | | 104784 | 105316 | 533 | 178 | -3 | 5 | | | | | |
| 72 | kinase? | 105316 | 106187 | 869 | 290 | -1 | 5 | "Kinase" | | 380 | diverse | |
| 73 | UDP-gal-mut | 106241 | 107365 | 1124 | 375 | -3 | 5 | "UDP-gal.-pyranose" | gi:2621401 | | Met.thermoaut | 100/379 |
| 74 | | 107390 | 108928 | 1538 | 513 | -3 | 5 | | | | | |
| 74.1 | | 108933 | 110918 | 1985 | 662 | 3 | 5 | | | | | |
| 75 | | 110122 | 110948 | 827 | 276 | -3 | 3 | | | | | |
| 76 | | 110972 | 111736 | 764 | 255 | -3 | 1 | | | | | |
| 77 | | 112217 | 112683 | 467 | 156 | 1 | 5 | | | | | |
| 78 | | 112988 | 114139 | 1151 | 384 | -3 | 5 | | | | | |
| 79 | | 113104 | 113487 | 383 | 128 | 1 | 5 | | | | | |
| 80 | | 114133 | 115169 | 1037 | 346 | 3 | 5 | | | | | |
| 81 | | 114624 | 115049 | 425 | 142 | 3 | 5 | | | | | |
| td | | 115539 | 116165 | 626 | 209 | -1 | 5 | "Thymidylate synthetase" | gi:279686 | 521 | | |
| 82 | | 115566 | 116273 | 707 | 236 | -3 | 5 | | | | | |
| 83 | | 116278 | 117529 | 1250 | 417 | -3 | 3 | | | | | |
| 84 | Transcr-reg. | 116962 | 117495 | 533 | 178 | -1 | 5 | | | | | |
| 85 | | 117532 | 118149 | 617 | 206 | -2 | 5 | | | | | |
| 86 | GP23 | 118647 | 119273 | 626 | 209 | -1 | 5 | "Capsid-protein" | CAA25911 | | | |

```
              20      40
DPOL_VACCC : ------------------------QNATMDEFLNISWFYISN-GISPDGCYSLD : 29
DPOL_VACCV : ------------------------QNATMDEFLNISWFYISN-GISPDGCYSLD : 29
DPOL_VARV/ : ------------------------QNATMDEFLNISWFYISN-GISPDGCYSLD : 29
DPOL_FOWPV : ------------------------EKQYLQEYLDITWFYLLN-NITPDGCYKID : 29
DPOD_BOVIN : ----------------------PSFAPYEANVDFEIRFMVDT-DIVGCNWLELP : 31
DPOD_HUMAN : ----------------------PSFAPYEANVDFEIRFMVDT-DIVGCNWLELP : 31
DPOD_CANAL : ----------------------IDPCITYDNINYLLRLMIDC-KITGMSWITLP : 31
DPOD_YEAST : ----------------------SNGTTTYDNIAYTLRLMVDC-GIVGMSWITLP : 31
DPOD_SCHPO : ----------------------VGVTTFESNTQYLLRFMIDC-DVVGMNWIHLP : 31
DPOD_PLAFK : ----------------------IGGIVYEANLPFILRYIIDH-KITGSSWINCK : 31
DPOL_CHVN2 : -----------------------EYQIYESSVDPIIRIFHLR-NINPADWMHVS : 30
DPOL_CHVP1 : ------------------------YQIYESSVDPIIRVFHLR-NINPADWIRVS : 29
DPOL_EBV/2 : -----------------------GCRIFEANVDATRRFVLDN-DFVTFGWYSCR : 30
DPOL_HSVSA : -----------------------GCEVFETNVDAIRRFVIDN-DFSTFGWYTCK : 30
DPOL_HSV11 : -----------------------PAIKKYEGGVDATTRFILDNPGFVTFGWYRLK : 32
DPOL_HSV21 : -----------------------PAIRKYEGGVDATTRFILDNPGFVTFGWYRLK : 32
DPOL_HSVEB : -----------------------PEITKFEGSVDVTTRLLLDNENFTSFGWYRLR : 32
DPOL_VZVD/ : -----------------------PELKKYEGRVDATTRFLMDNPGFVSFGWYQLK : 32
DPOL_HCMVA : -----------------------GFPVYEVRVDPLTRLVIDR-RITTFGWCSVN : 30
DPOL_MCMVS : -----------------------GRKVYELGVDPLARFLIDR-KIPSFGWCLAR : 30
DPOL_HSV6U : -----------------------GFVVYEIDVDVLTRFFVDN-GFLSFGWYNVK : 30
DPOA_HUMAN : ------------------------SHVFGTNTSSLELFLMNR-KIKGPCWLEVK : 29
DPOA_MOUSE : ------------------------SHVFGTNTSSLELFLMNR-KIKGPCWLEVK : 29
DPOA_DROME : ------------------------AHIFGATTNALERFLLDR-KIKGPCWLQVT : 29
DPOA_SCHPO : ------------------------SHVFGTNTALFEQFVLSR-RVMGPCWLKIQ : 29
DPOA_YEAST : ------------------------YHVFGGNSNIFESFVIQN-RIMGPCWLDIK : 29
DPOA_TRYBB : ------------------------QVVVGASRSLLELFLIKK-RLMGPSYLEIE : 29
DPOL_NPVAC : -----------------------NAACLDKFLHNVNRVHMQT-PFVEGAYMRFK : 30
DPOL_NPVLD : -----------------------DKNCLDGYLADVNRVHMQT-SLLEGQYVRFK : 30
DPOZ_YEAST : -----------------------NKVPSMGNKKTESQISMHTPHSKFLYKFASDVS : 33
DPOL_PYRFU : ------------------------FKIEHDRTFRPYIYALLRDDSKIEEVKKITGE : 32
DPO1_SULSO : ------------------------FNNYMYDIGLIPGMPYVVKN-GKLESVYLSLD : 31
DPO2_ECOLI : ------------------------AQHILQGEQGFRLTPLALKDFHRQPVYGLYCR : 32
DPol_Dtok  : MILDADYITEDGKPVIRVFKKEKGEFKIDYDRDFEPYIYALLKDDSAIEDIKKITAE : 57
RM378      : ------------------------MKITLSASVYPRSMKIYGVELIEGKKHLFQS : 31
RB69       : MKEFYLTVEQIGDSIFERYIDSNGRERTREVE-YKPSLFAHCPESQAT--------- : 47
```

FIG. 3A

```
                        60         .         80         .         100         .
DPOL_VACCC  : ----------EQYLTKINNGC-YHCDDPRNCFAKKIPRFDIP---------------  :  60
DPOL_VACCV  : ----------EQYLTKINNGC-YHCDDPRNCFAKKIPRFDIP---------------  :  60
DPOL_VARV/  : ----------DQYLTKINNGC-YHCGDPRNCFAKEIPRFDIP---------------  :  60
DPOL_FOWPV  : ----------IEHLTPIKKDC-YHCDDVSKVFIQEIPIFEVK---------------  :  60
DPOD_BOVIN  : --------AGKYILRP-EGKA-TLCQLEADVLWSDVISHPPEGEW------------  :  66
DPOD_HUMAN  : --------AGKYALRL-KEKA-TQCQLEADVLWSDVVSHPPEGPW------------  :  66
DPOD_CANAL  : --------RDKYKIVN--NKI-STCQIECSIDYRDLISHPPEGEW------------  :  65
DPOD_YEAST  : --------KGKYSMIEPNNRV-SSCQLEVSINYRNLIAHPAEGDW------------  :  67
DPOD_SCHPO  : --------ASKYQFRY-QNRV-SNCQIEAWINYKDLISLPAEGQW------------  :  66
DPOD_PLAFK  : --------KGHYYIRNKNKKI-SNCTFEIDISYEHVEPITLENEY------------  :  67
DPOL_CHVN2  : --------KAFPVETR----I-SNSDIEVETSFQHLGPS----DL------------  :  58
DPOL_CHVP1  : --------KAYPAQTR----I-SNSDIEVETSFQHLGPV----ED------------  :  57
DPOL_EBV/2  : --------R--AIPRLQHRD--SYAELEYDCEVGDLSVRRED---------------  :  60
DPOL_HSVSA  : --------S--ACPRITNRD--SHTDIEFDCGYYDLEFHADR---------------  :  60
DPOL_HSV11  : PG----RNNTLAQPAAPMAFG-TSSDVEFNCTADNLAIEGGM---------------  :  69
DPOL_HSV21  : PG----RGNAPAQPRPPTAFG-TSSDVEFNCTADNLAVEGAM---------------  :  69
DPOL_HSVEB  : PG----THGERVQLRPVERHV-TSSDVEINCTPDNLEPIPDE---------------  :  69
DPOL_VZVD/  : PG----VDGERVRVRPASRQL-TLSDVEIDCMSDNLQAIPND---------------  :  69
DPOL_HCMVA  : --------R--YDWRQQGRA--STCDIEVDCDVSDLVAVPDD---------------  :  60
DPOL_MCMVS  : --------R--YSVRAAGYV--SRAQLEIDCDVADILPIEEQ---------------  :  60
DPOL_HSV6U  : --------K--YIPQDMGKG--SNLEVEINCHVSDLVSLED----------------  :  59
DPOA_HUMAN  : -----------KSTALNQP-V-SWCKVEAMALKPDLVNVIKD--------VSPPPLV :  65
DPOA_MOUSE  : -----------NPQLLNQP-I-SWCKFEVMALKPDLVNVIKD--------VSPPPLV :  65
DPOA_DROME  : -----------GFKVSPTP-M-SWCNTEVTLTEPKNVELVQDKGK----PAPPPPLT :  69
DPOA_SCHPO  : -----------QPNFDAVKNA-SWCRVEIGCSSPQNISVSFEKNEI---TSKTPPMT :  71
DPOA_YEAST  : -----------GADFNSIRNA-SHCAVEVSVDKPQNITPTTTKT-------MPNLR  :  66
DPOA_TRYBB  : -----------HLVTAMDR-V-SHCKTEFLVPSPKDIKVYNSS-------KPPPPFT :  66
DPOL_NPVAC  : KT----QRCQNNYVGGSTTRMFNLQHFNEDFELVDEMTLTSG---------------  :  68
DPOL_NPVLD  : NA----HACRDYRLSHTAK---DVHEFESMLERVQVSALSHE---------------  :  65
DPOZ_YEAST  : ----------GKQKRKKSSVHDSLTHLTLEIHANTRSDKIPD---------------  :  65
DPOL_PYRFU  : RH---GKIVRIVDVEKVEKKFLGKPITVWKLYLEHPQDVPTIREKV-REHPAVVDIF :  85
DPO1_SULSO  : ----------EKDVEEIKKAFADSDEMTRQMAVDWLPIFET----------------  :  62
DPO2_ECOLI  : ----------AHRQLMNYEKRLREGGVTVYEADVRPPERYLMER------FITSPVWV :  74
DPol_Dtok   : RHG---TTVRVTRAERVKKKFLGRPVEVWKLYFTHPQDVPAIRDKIREHPAVVDIYE : 111
RM378       : ---------------------------------------PVPPHLKRI------AQQNR :  45
RB69        : --------------KYFDIY--GKPCTRKLFANMRDASQWIKRMEDI---GLEAL  :  83
```

FIG. 3B

```
                        120           .         140          .         160           .
DPOL_VACCC  : ------------------------RSYLFLDIECHFDKKFPSVFINPISHTSYCYID  :  93
DPOL_VACCV  : ------------------------RSYLFLDIECHFDKKFPSVFINPISHTSYCYID  :  93
DPOL_VARV/  : ------------------------RSYLFLDIECHFDKKFPSVFINPISHTSYCYID  :  93
DPOL_FOWPV  : ------------------------FTYLLFDIECQFDKKFPSVFVNPISHISCWIID  :  93
DPOD_BOVIN  : -------------------QRIAPLRVLSFDIECAGRKG----IFPEPE--RDPVIQ  :  98
DPOD_HUMAN  : -------------------QRIAPLRVLSFDIECAGRKG----IFPEPE--RDPVIQ  :  98
DPOD_CANAL  : -------------------LKMAPLRILSFDIECAGRKG----VFPEAE--HDPVIQ  :  97
DPOD_YEAST  : -------------------SHTAPLRIMSFDIECAGRIG----VFPEPE--YDPVIQ  :  99
DPOD_SCHPO  : -------------------SKMAPLRIMSFDIECAGRKG----VFPDPS--IDPVIQ  :  98
DPOD_PLAFK  : -------------------QQIPKLRILSFDIECIKLDGK---GFPEAK--NDPIIQ  : 100
DPOL_CHVN2  : -------------------KEVPPLIIASWDIETYSKDR----KFPLAENPADYCIQ  :  92
DPOL_CHVP1  : -------------------KTVPPLVIASWDIETYSKDR----KFPLAENPTDYCIQ  :  91
DPOL_EBV/2  : -------------------SSWPSYQALAFDIECLG-----EEGFPTATNEADLILQ  :  93
DPOL_HSVSA  : -------------------TEWPPYNIMSFDIECIG-----EKGFPCAKNEGDLIIQ  :  93
DPOL_HSV11  : -------------------SDLPAYKLMCFDIECKAGGE-DELAFPVAGHPEDLVIQ  : 106
DPOL_HSV21  : -------------------CDLPAYKLMCFDIECKAGGE-DELAFPVAERPEDLVIQ  : 106
DPOL_HSVEB  : -------------------AAWPDYKLMCFDIECKAGTG-NEMAFPVATNQEDLVIQ  : 106
DPOL_VZVD/  : -------------------DSWPDYKLLCFDIECKSGGS-NELAFPDATHLEDLVIQ  : 106
DPOL_HCMVA  : -------------------SSWPRYRCLSFDIECMSG----EGGFPCAEKSDDIVIQ  :  94
DPOL_MCMVS  : -------------------SNWPFYRCLSFDIECMSG----TGAFPAAENVDDIIIQ  :  94
DPOL_HSV6U  : -------------------VNWPLYGCWSFDIECLGQ----NGNFPDAENLGDIVIQ  :  93
DPOA_HUMAN  : VMAFSMKTMQNAKNHQNEIIAMAALVHHSFALDKAAPKPP-------FQSHFCVVSK  : 115
DPOA_MOUSE  : VMSFSMKTMQNVQNHQHEIIAMAALVHHSFALDKAPPEPP-------FQTHFCVVSK  : 115
DPOA_DROME  : LLSLNVRTSMNPKTSRNEICMISMLTHNRFHIDRPAPQPA-------FNRHMCALTR  : 119
DPOA_SCHPO  : VMSLAFRTLINKEQNKQEVVMISARIFENVDIEKGLPAND-------MPSYSFSLIR  : 121
DPOA_YEAST  : CLSLSIQTLMNPKENKQEIVSITLSAYRNISLDSPIPENI-------KPDDLCTLVR  : 116
DPOA_TRYBB  : VASIQLHAQLDSDGVKNEVIAASIALYGDVSIDGE-RKPN--------ITECFTGVR  : 114
DPOL_NPVAC  : -------------------IMPVLSCYDIETHSD------GHNMSKASVDCIMS    :  97
DPOL_NPVLD  : -------------------ILPVVACYDIETHSD------GQRFSAPDADFIIS    :  94
DPOZ_YEAST  : -------------------PAIDEVSMIIWCLEEETFPL-----------DLDIAYE :  92
DPOL_PYRFU  : EYDIPFAKRYLIDKGLIPMEGEEELKILAFDIETLYHE----------GEEFGKGP  : 131
DPO1_SULSO  : -------------------EIPKIKRVAIDIEVYTPVKG---RIPDSQKAEFPIIS  :  96
DPO2_ECOLI  : EGDMHNGTIVNARLKPHPDYR-PPLKWVSIDIETTRHG------ELYCIGLEGCGQR : 124
DPol_Dtok   : YDIPFAKRYLIDRGLIPMEGDEE-LRMLAFDIETLYHE----------GEEFGEGP  : 156
RM378       : GKIEAEAISYYIREQKSHITPEALSQCVFIDIETISPKK-------SFPDPWRDPVY :  95
RB69        : GMDDFKLAYLSDTYNYEIKYDHTKIRVANFDIEVTSPDG--------FPEPSQAKHP : 132

Exo I

FIG. 3C
```

```
                       180         .         200         .         220
DPOL_VACCC  :  LSGKRLLFT---------LINEEMLTEQEIQ---EAVDRGCLRIQSLMEMD------  :  132
DPOL_VACCV  :  LSGKRLLFT---------LINEEMLTEQEIQ---EAVDRGCLRIQSLMEMD------  :  132
DPOL_VARV/  :  LSGKRLLFT---------LINEEMLTEQEIQ---EAVDRGCLRIQSLMEMD------  :  132
DPOL_FOWPV  :  KVT-EYKFT---------LINTDILPDKEP------------SILHHKDFS------  :  122
DPOD_BOVIN  :  ICSLGLRWG----------EPEP-FLR------------LALTLRPCAPIL------  :  126
DPOD_HUMAN  :  ICSLGLRWG----------EPEP-FLR------------LALTLRPCAPIL------  :  126
DPOD_CANAL  :  IANVVQKSG----------ESKP-FVR------------NVFTVNTCSSII------  :  125
DPOD_YEAST  :  IANVVSIAG----------AKKP-FIR------------NVFTLNTCSPIT------  :  127
DPOD_SCHPO  :  IASIVTQYG----------DSTP-FVR------------NVFCVDTCSQIV------  :  126
DPOD_PLAFK  :  ISSILYFQG----------EPIDNCTK------------FIFTLLECASIP------  :  129
DPOL_CHVN2  :  IATTFQKYG----------EPEP-YRR------------VVVCYKQTASVE------  :  120
DPOL_CHVP1  :  IATTFQKYG----------EPEP-YRR------------VVVCYKQTAPVE------  :  119
DPOL_EBV/2  :  ISCVLWSTG----------EEAGRYRR-----------ILLTLGTCEDIEG-----  :  123
DPOL_HSVSA  :  ISCVFWHAG----------ALD-TTRN-----------MLLSLGTCSAVEN-----  :  122
DPOL_HSV11  :  ISCLLYDLS----------TTA-LEHV-----------LLFSLGSCDLPESHLN-E  :  139
DPOL_HSV21  :  ISCLLYDLS----------TTA-LEHI-----------LLFSLGSCDLPESHLS-D  :  139
DPOL_HSVEB  :  ISCLLYSLA----------TQN-HEHT-----------LLFSLGSCDISEEYSF-A  :  139
DPOL_VZVD/  :  ISCLLYSIP----------RQS-LEHI-----------LLFSLGSCDLPQRYVQ-E  :  139
DPOL_HCMVA  :  ISCVCYETGGNTAVDQGIPNGNDGRGCTSEGVIFGHSGLHLFTIGTCGQVG------  :  145
DPOL_MCMVS  :  ISCVCFGVG------EMVHHAYDVHADLSTPAVPEN---HLFTIGPCAPI-------  :  135
DPOL_HSV6U  :  ISVISFDTE-----------G-DRDER-----------HLFTLGTCEKI-------  :  119
DPOA_HUMAN  :  PKDCIFPYA----------FKEVIEK-------------------------------  :  131
DPOA_MOUSE  :  PKDCIFPCD----------FKEVISK-------------------------------  :  131
DPOA_DROME  :  PAVVSWPLD----------LNFEMAKY------------------------------  :  136
DPOA_SCHPO  :  PLKQIFPNG----------FEKLARQH------------------------------  :  138
DPOA_YEAST  :  PPQSTSFPL----------GLAALAKQK-----------------------------  :  134
DPOA_TRYBB  :  QLSPDAPLPLDLETYCLSK--------------------------------------  :  133
DPOL_NPVAC  :  IGFVVYKND-------EYAKFCFMYH-------------KLPTQIPETYDD-----  :  128
DPOL_NPVLD  :  IAVVVRRDA--------ADTRICLFYSP-----------DDPVDLSSSSSSPPA-A  :  130
DPOZ_YEAST  :  GIMIVHKASEDS----------------T----------FPTKIQHCIN------  :  115
DPOL_PYRFU  :  IIMISYADE--------NEAKVITWKN------------------------------  :  150
DPO1_SULSO  :  IALAGSDGLK----------KVLVLNR-----------NDVNEGSVKLDG------  :  125
DPO2_ECOLI  :  IVYMLGPEN-----------GDASS-------------------------------  :  138
DPol_Dtok   :  ILMISYADE--------EGARVITWK-------------NIDLPY----------  :  180
RM378       :  SISIKPYGKP--------VVVVLLLIT-----------NPEAHIDNFN------KFTT  :  128
RB69        :  IDAITHYDSIDDR------FYVFDLLN------SPYGNVEEWSIEIAAKLQEQGGDE  :  177
```

FIG. 3D

```
                    .        240         .        260         .        280
DPOL_VACCC  : -------YERELVLCSEIVLLRIAKQLLELTFDYVVTFNGHNFDLRYITNR----- : 176
DPOL_VACCV  : -------YERELVLCSEIVLLRIAKQLLELTFDYVVTFNGHNFDLRYITNR----- : 176
DPOL_VARV/  : -------YERELVLCSEIVLLQIAKQLLELTFDYIVTFNGHNFDLRYITNR----- : 176
DPOL_FOWPV  : --------PKDRITYCTEIVMLLIMKKILEHRFDFVITFNGNNFDIRYISGR----- : 166
DPOD_BOVIN  : -------GAKVQSYEREEDLLQAWSTFIRIMDPDVITGYNIQNFDLPYLISR----- : 171
DPOD_HUMAN  : -------GAKVQSYEKEEDLLQAWSTFIRIMDPDVITGYNIQNFDLPYLISR----- : 171
DPOD_CANAL  : -------GSQIFEHQREEDMLHWKEFITKVDPDVIIGYNTANFDIPYVLNR----- : 170
DPOD_YEAST  : -------GSMIFSHATEEEMLSNWRNFIIKVDPDVIIGYNTTNFDIPYLLNR----- : 172
DPOD_SCHPO  : -------GTQVYEFQNQAEMLSSWSKFVRDVDPDVLIGYNICNFDIPYLLDR----- : 171
DPOD_PLAFK  : -------GSNVIWFNDEKTLLEAWNEFIIRIDPDFLTGYNIINFDLPYILNR----- : 174
DPOL_CHVN2  : -------GVEIISCAEEADVMNTWMTILQDEITDVSIGYNLWQYDLRYIHGRSMMCV : 170
DPOL_CHVP1  : -------GVEIISCLEESDVMNTWMKILQDEKTDVSIGYNTWQYDLRYVHGRTQMCV : 169
DPOL_EBV/2  : --------VEVYEFPSELDMLYAFFQLIRDLSVEIVTGYNVANFDWPYILDR----- : 167
DPOL_HSVSA  : --------TEVYEFPSEIDMLHGFFSLIRDFNVEIITGYNISNFDLPYLIDR----- : 166
DPOL_HSV11  : LAARGLPTPVVLEFDSEFEMLLAFMTLVKQYGPEFVTGYNIINFDWPFLLAK----- : 191
DPOL_HSV21  : LASRGLPAPVVLEFDSEFEMLLAFMTFVKQYGPEFVTGYNIINFDWPFVLTK----- : 191
DPOL_HSVEB  : CVQRGEPRPTVLEFDSEYELLVAFLTFLKQYSPEFATGYNIVNFDWAYIVNK----- : 191
DPOL_VZVD/  : MKDAGLPEPTVLEFDSEFELLIAFMTLVKQYAPEFATGYNIVNFDWAFIMEK----- : 191
DPOL_HCMVA  : ------PDVDVYEFPSEYELLLGFMLFFQRYAPAFVTGYNINSFDLKYILTR----- : 191
DPOL_MCMVS  : ------PDVKIYTFPSEYEMLRGFFIFLSWYSPEFITGYNINGFDIKYILTR----- : 181
DPOL_HSV6U  : ------DGVHIYEFASEFELLLGFFIFLRIESPEFITGYNINNFDLKYLCIR----- : 165
DPOA_HUMAN  : ------KNVKVEVAATERTLLGFFLAKVHKIDPDIIVGHNIYGFELEVLLQR----- : 177
DPOA_MOUSE  : ------KNMKVEIAATERTLIGFFLAKVHKIDPDILVGHNICSFELEVLLQR----- : 177
DPOA_DROME  : ------KSTTVHKHDSERALLSWFLAQYQKIDADLIVTFDSMDCQLNVITDQ----- : 182
DPOA_SCHPO  : ------KS-SIFCERSEVSLLNNFLNKVRTYDPDVYFGHDFEMCYS-VLLSR----- : 182
DPOA_YEAST  : ------LPGRVRLFNNEKAMLSCFCAMLKVEDPDVIIGHRLQNVYLDVLAHR----- : 180
DPOA_TRYBB  : ------RMPGVHRFINERALLTWFAETLAALDPDIIVGHNIIGYTVETLLNR----- : 179
DPOL_NPVAC  : -------DTYVVMFQNEIDMITAFFDMIKITNPDVILDFNGDVFDLPYILGR----- : 173
DPOL_NPVLD  : ------PDTAAVHFRAERDMIAAFFQLLPLLNADVVLDFNGDKFDLPFLTGR----- : 176
DPOZ_YEAST  : ----EIPVMFYESEFEMFEALTDLVLLLDPDILSGFEIHNFSWGYIIER-------C : 161
DPOL_PYRFU  : -----IDLPYVEVVSSEREMIKRFLRIIREKDPDIIVTYNGDSFDFPYLAKR----- : 197
DPO1_SULSO  : --------ISVERFNTEYELLGRFFDILLEYP--IVLTFNGDDFDLPYIYFR----- : 167
DPO2_ECOLI  : ---------LDFELEYVASRPQLLEKLNAWFANYDPDVIIGWNVVQFDLRMLQKH----- : 184
DPol_Dtok   : ----------VESVSTEKEMIKRFLKVIQEKDPDVLITYNGDNFDFAYLKKR----- : 222
RM378       : SVGDNTFEIHYRTFLSEKRLLEYFWNVLKPKFT-FMLAWNGYQFDYPYLLIR----- : 179
RB69        : VPSEIIDKIIYMPFDNEKELLMEYLNFWQQKTPVILTGWNVESFDIPYVYNR----- : 229
                                                            Exo II
```

FIG. 3E

```
                         .         300         .         320         .         340
DPOL_VACCC  : LELLTGE----KIIFRSPDKKEAVHLCIYERNQSSHKG-----VGGMAN--------  : 216
DPOL_VACCV  : LELLTGE----KIIFRSPDKKEAVYLCIYERNQSSHKG-----VGGMAN--------  : 216
DPOL_VARV/  : LELLTGE----KIIFRSPDKKEAVHLCIYERNQSSHKG-----VGGMAN--------  : 216
DPOL_FOWPV  : LEILEKS----FIYFSLPDATETVKLKIFER-FVTG--------GTFTN--------  : 202
DPOD_BOVIN  : --AQTLK----VPGFPLLGRVIGLRSNIRESS--FQ-------SRQTG--------R : 205
DPOD_HUMAN  : --AQTLK----VQTFPFLGRVAGLCSNIRDSS--FQ-------SKQTG--------R : 205
DPOD_CANAL  : --AKALG----LNDFPFFGRLKRVKQEIKDAV--FS-------SRAYG--------T : 204
DPOD_YEAST  : --AKALK----VNDFPYFGRLKTVKQEIKESV--FS-------SKAYG--------T : 206
DPOD_SCHPO  : --AKSLR----IHNFPLLGRIHNFFSVAKETS--FS-------SKAYG--------T : 205
DPOD_PLAFK  : --GTALN----LKKLKFLGRIKNVASTVKDSS--FS-------SKQFG--------T : 208
DPOL_CHVN2  : DDITGED----NVRLKNLGRLLVGGGEVIERD--LS-------SNAFG--------Q : 206
DPOL_CHVP1  : DDMTGED----KVKLSNLGRLLSGGGEVVERD--LS-------SNAFG--------Q : 205
DPOL_EBV/2  : --ARHIY----SINPASLGKIR--AGGVCEVRRPHDAG-----KGFLR--------- : 202
DPOL_HSVSA  : --ATQIY----NIKLSDYSRVK--TGSIFQVHTPKDTG-----NGFMR--------- : 201
DPOL_HSV11  : --LTDIY----KVPLDGYGRMN--GRGVFRVW---DIG-----QSHFQ--------- : 223
DPOL_HSV21  : --LTEIY----KVPLDGYGRMN--GRGVFRVW---DIG-----QSHFQ--------- : 223
DPOL_HSVEB  : --VTSVY----NIKLDGYGKFN--KGGLFKVW---DIA-----TNHFQ--------- : 223
DPOL_VZVD/  : --LNSIY----SLKLDGYGSIN--RGGLFKIW---DVG-----KSGFQ--------- : 223
DPOL_HCMVA  : --LEYLY----KVDSQRFCKLPTAQGGRFFLHSP-AVGFKRQYAAAFPSASHNNPAS : 241
DPOL_MCMVS  : --AEKLY----KMDVGQFTKLR--RGGRMFVFSP-EKG-----KAGFG--------T : 216
DPOL_HSV6U  : --MDKIY----HYDIGCFSKLK---NGKIGISVP-HEQ----YRKGFL--------- : 199
DPOA_HUMAN  : --INVCK----APHWSKIGRLK--RSNM-PKLGGRS---------GFG--------- : 207
DPOA_MOUSE  : --INECK----VPYWSKIGRLR--RSNM-PKLGSRS---------GFG--------- : 207
DPOA_DROME  : --IVALK----IPQWSRMGRLR--LS---QSFGKR---------------------- : 206
DPOA_SCHPO  : --LKERK----IHNWSSIGRLR--RSEWPRSFNRSS--------QQFV--------- : 214
DPOA_YEAST  : --MHDLN----IPTFSSIGRRL--RRTWPEKFGRGNSN-----MNHFF--------- : 215
DPOA_TRYBB  : --YQELN----IVRWSTIGRLD--VRRFPRIQGNNFN--------LAI--------- : 211
DPOL_NPVAC  : --LNKTK--------MLLKRYDLPAAPTTKLFINKLG------------------- : 201
DPOL_NPVLD  : --ANKLCGPAEAARATKIARYDLSPVNVVTQQSYDKFS------------------ : 212
DPOZ_YEAST  : QKIH------QFDIVRELARVKCQIKTKLS-----------DTWG----------Y : 190
DPOL_PYRFU  : --AEKLG------IKLTIGRDG--SEPKMQRIG----------------------- : 220
DPO1_SULSO  : --ALKLG------YFPEEIPIDVAGKDEAKYLAG---------------------- : 193
DPO2_ECOLI  : --AERYR------LPLRLGRDN--SELEWREHG------------FKN-------- : 210
DPol_Dtok   : --SEMLG------VKFILGRDG--SEPKIQRMG----------------------- : 245
RM378       : SHIHEVN----VISDKLLPDWKLVRKISDRNLP----------------------- : 208
RB69        : --IKNIFG---ESTAKRLS--P--HRKTRVKVIEN------------------MY : 257
```

FIG. 3F

```
                         .       360         .       380         .       40
DPOL_VACCC : TTFHVNNNNGTIFFDLYSFIQKSEK---LDSYKLDSISKNAFSCMGKVLNRGVREMT : 270
DPOL_VACCV : TTFHVNNNNGTIFFDLYSFIQKSEK---LDSYKLDSISKNAFSCMGKVLNRGVREMT : 270
DPOL_VARV/ : TTFHVNNNNGTIFFDLYSFIQKSEK---LDSYKLDSISKNAFSCMGKVLNRGVREMT : 270
DPOL_FOWPV : KTYHINNNNGVMFFDLYAFIQKTER---LDSYKLDSISKNIFNCNVAIKEIDDTILT : 256
DPOD_BOVIN : RDSKVVSMVGRVQMDMLQVLLREYK---LRSYTLNAVSFHFLGE----QKEDVQHSI : 255
DPOD_HUMAN : RDTKVVSMVGRVQMDMLQVLLREYK---LRSHTLNAVSFHFLGE----QKEDVQHSI : 255
DPOD_CANAL : RENKVVNIDGRMQLDLLQFIQREYK---LRSYTLNSVSAHFLGE----QKEDVQHSI : 254
DPOD_YEAST : RETKNVNIDGRLQLDLLQFIQREYK---LRSYTLNAVSAHFLGE----QKEDVHYSI : 256
DPOD_SCHPO : RESKTTSIPGRLQLDMLQVMQRDFK---LRSYSLNAVCSQFLGE----QKEDVHYSI : 255
DPOD_PLAFK : HETKEINIFGRIQFDVYDLIKRDYK---LKSYTLNYVSFEFLKE----QKEDVHYSI : 258
DPOL_CHVN2 : NKFFLLDMPGVMQIDLLQWFRKNRN---LESYSLNNVSKLYLGD----QKNDLPAMQ : 256
DPOL_CHVP1 : NKFFLLDMPGVMQIDLLQWFRKNRN---LESYSLNNVSKLYLGD----QKNDLPAMQ : 255
DPOL_EBV/2 : -ANTKVRITGLIPIDMYAVCRDKLS---LSDYKLDTVARHLLGA----KKEDVHYKE : 251
DPOL_HSVSA : -SVSKIKISGIIAIDMYIVCKDKLS---LSNYKLDTVANHCIGA----KKEDVSYKD : 250
DPOL_HSV11 : -KRSKIKVNGMVNIDMYGIITDKIK---LSSYKLNAVAEAVLKD----KKKDLSYRD : 272
DPOL_HSV21 : -KRSKIKVNGMVNIDMYGIITDKVK---LSSYKLNAVAEAVLKD----KKKDLSYRD : 272
DPOL_HSVEB : -KKSKVKINGLISLDMYSVATEKLK---LPSYKLDAVVGDVLGE----HKIDLPYKE : 272
DPOL_VZVD/ : -RRSKVKINGLISLDMYAIATEKLK---LSSYKLDSVAREALNE----SKRDLPYKD : 272
DPOL_HCMVA : TAATKVYIAGSVVIDMYPVCMAKTN---SPNYKLNTMAELYLRQ----RKDDLSYKD : 291
DPOL_MCMVS : SNTVKVFWSGTVVLDMYPVCTAKAS---SPNYKLDTMAEIYLKK----KKDDLSYKE : 266
DPOL_HSV6U : QAQTKVFTSGVLYLDMYPVYSSKIT---AQNYKLDTIAKICLQQ----EKEQLSYKE : 249
DPOA_HUMAN : ---ERNATCGRMICDVEISAKELIR---CKSYHLSELVQQILKT----ERVVIPMEN : 254
DPOA_MOUSE : ---ERNATCGRMICDVEISAKELIH---CKSYHLSELVQQILKT----ERIVIPTEN : 254
DPOA_DROME : ---LLEHFVGRMVCDVKRSAEECIR---ARSYDLQTLCKQVLKLK-ESERMEVNADD : 256
DPOA_SCHPO : ---EKQIIAGRLMCDLSNDFGRSMI-K-AQSWSLSEIVLKELDI----KRQDINQEK : 262
DPOA_YEAST : ---ISDICSGRLICDIANEMGQSLTPK-CQSWDLSEMYQVTCEK----EHKPLDIDY : 264
DPOA_TRYBB : ---EKEACVGRLVVDTYLLAREYYKSTNYKLLSLSTQMEIKGITD-NRGHFEPGSTV : 264
DPOL_NPVAC : NKVDTYYFNYYIHIDLYKFFSSDSNQHKVENFQLNTISSYYLGE----NKIDLPWTE : 254
DPOL_NPVLD : NKLHSHYLTYYIHIDLYQFLSTDSEHNDLENFQLNTVAEHYLKK----SKVDLPIHD : 265
DPOZ_YEAST : AHSSGIMITGRHMINIWRALRSDVN---LTQYTIESAAFNILHK----RLPHFSFES : 240
DPOL_PYRFU : -DMTAVEVKGRIHFDLYHVITRTIN---LPTYTLEAVYEAIFGK----PKEKVYADE : 269
DPO1_SULSO : ---LHIDLYKFFFNKAVRNYAFEGK---YNEYNLDAVAKALLGT------SKVKVDT : 238
DPO2_ECOLI : -GVFFAQAKGRLIIDGIEALKSAFWN--FSSFSLETVAQELLGEG---KSIDNPWDR : 261
DPol_Dtok  : -DRFAVEVKGRIHFDLYPVIRRTI---NLPTYTLETVYEPVFGQ----PKEKVYAEE : 294
RM378      : FYFNPRTPVEFVFFDYMRLYRSFVAYKELESYRLDYIAREEIGE----GKVDFDVRF : 261
RB69       : GSREIITLFGISVLDYIDLYKKFSFT-NQPSYSLDYISEFELNV-GKLKYDGPISKL : 312
```

FIG. 3G

```
              0            420           440           .
DPOL_VACCC  : FIGDDTTDAKGKAAAFAKVLTTGNYVTVDEDIICKVIRK--DIWENGFKVVLLCPT- : 324
DPOL_VACCV  : FIGDDTTDAKGKAAAFAKVLTTGNYVTVDEDIICKVIRK--DIWENGFKVVLLCPT- : 324
DPOL_VARV/  : FIGDDTTDAKGKAAVFAKVLTTGNYVTVDD-IICKVIHK--DIWENGFKVVLSCPT- : 323
DPOL_FOWPV  : LEATVKDNSKDKLSIFSRVLETGNYITIGDNNVSKIVYK--DINQDSFIIKVISNRD : 311
DPOD_BOVIN  : ITDLQNGNDQT------RRRLAVYCLKDAFLPLRLLER--LMVLVNAMEMARVTG- : 302
DPOD_HUMAN  : ITDLQNGNDQT------RRRLAVYCLKDAYLPLRLLER--LMVLVNAVEMARVTG- : 302
DPOD_CANAL  : ITDLQNGTKET------RRRLAVYCLKDAFLPLRLLDK--LMCLVNYTEMARVTG- : 301
DPOD_YEAST  : ISDLQNGDSET------RRRLAVYCLKDAYLPLRLMEK--LMALVNYTEMARVTG- : 303
DPOD_SCHPO  : ITDLQNGTADS------RRRLAIYCLKDAYLPQRLMDK--LMCFVNYTEMARVTG- : 302
DPOD_PLAFK  : MNDLQNESPES------RKRIATYCIKDGVLPLRLIDK--LLFIYNYVEMARVTG- : 305
DPOL_CHVN2  : IFEKFEGGADD------RAIIAAYARKDTDLPLKLLKK--MAILEDITEMANAVK- : 303
DPOL_CHVP1  : IFEKFEGNAED------RAIIAAYAAKDTDLPLKLLKK--MAILEDLTEMANAVK- : 302
DPOL_EBV/2  : IPRLFAAGPEG------RRRLGMYCVQDSALVMDLLNH--FVIHVEVAEIAKIAH- : 298
DPOL_HSVSA  : IMPLFMSGPEG------RAKIGLYCVIDSVLVMKLLKF--FMIHVEISEIAKLAK- : 297
DPOL_HSV11  : IPAYYAAGPAQ------RGVIGEYCIQDSLLVGQLFFK--FLPHLELSAVARLAG- : 319
DPOL_HSV21  : IPAYYASGPAQ------RGVIGEYCVQDSLLVGQLFFK--FLPHLELSAVARLAG- : 319
DPOL_HSVEB  : IPSYYAGGPDR------RGVIGEYCIQDSRLVGKLFFK--YLPHLELSAVAKLAR- : 319
DPOL_VZVD/  : IPGYYASGPNT------RGIIGEYCIQDSALVGKLFFK--YLPHLELSAVARLAR- : 319
DPOL_HCMVA  : IPRCFVANAEG------RAQVGRYCLQDAVLVRDLFNT--INFHYEAGAIARLAK- : 338
DPOL_MCMVS  : IPVQFSAGDEG------RAPGGKYCLQDAVLVRELFEM--LAFHFEAAAIARLAR- : 313
DPOL_HSV6U  : IPKKFISGPSG------RAVVGKYCLQDSVLVVRLFKQ--INYHFEVAEVARLAH- : 296
DPOA_HUMAN  : IQNMYSESSQ-------LLYLLEHTWKDAKFILQIMCE--LNVLPLALQITNIAG- : 300
DPOA_MOUSE  : IRNMYSESSY-------LLYLLEHIWKDARFILQIMCE--LNVLPLALQITNIAG- : 300
DPOA_DROME  : LLEMYEKGES-------ITKLISLTMQDNSYLLRLMCE--LNIMPLALQITNICG- : 302
DPOA_SCHPO  : ALQSWTDTAHG------LLDYLVHCEIDTFFIAAVAFK--IQMLQLSKNLTNIAG- : 309
DPOA_YEAST  : QNPQYQNDVNS------MTMALQENITNCMISAEVSYR--IQLLTLTKQLTNLAG- : 311
DPOA_TRYBB  : LVKDSMMSSEA------LCPILLQLLNCAVLSFNVASF--LDVIPLTKRLTLLAG- : 311
DPOL_NPVAC  : MVKMYNTRRLD--------VIAKYNVQDCMLPIKLFVK--LKMADSVYSQCILHR- : 299
DPOL_NPVLD  : MLQMYGEKRLS--------RIVEYNVQDCVLPVELFLK--LEIADYMYTQCMLLY- : 310
DPOZ_YEAST  : LTNMWNAKKST-----TELKTVLNYWLSRAQINIQLLRK--QDYIARNIEQARLIG- : 289
DPOL_PYRFU  : IAKAWESGEN--------LERVAKYSMEDAKATYELG----KEFLPMEIQLSRLVG- : 313
DPO1_SULSO  : LISFLDVEK-----------LIEYNFRDAEITLQLTTFNNDLTMKLIVLFSRISR- : 282
DPO2_ECOLI  : MDEIDRRFAED-------KPALATYNLKDCELVTQIFHK--TEIMPFLLERATVNG- : 308
DPol_Dtok   : IARAWESGEG--------LERVARYSMEDAKATYELGK----EFFPMEAQLSRLVG- : 338
RM378       : YHEIPVYPDK----------KLVEYNAVDAILMEEIENK--NHILPTLFEIARLSN- : 305
RB69        : RE------SN--------HQRYISYNIIDVYRVLQIDA--KRQFINLSLDMGYYAK- : 352

Exo III
```

FIG. 3H

```
                    460         .        480          .        500        .
DPOL_VACCC  : -LPNDTYKLSFGKDDVDLAQMYKDYNLNIALDMARYCIHDACLCQYLWEYYG----- : 375
DPOL_VACCV  : -LPNDTYKLSFGKDDVDLAQMYKDYNLNIALDMARYCIHDACLCQYLWEYYG----- : 375
DPOL_VARV/  : -LTNDTYKLSFGKDDVDLAQMYKDYNLNIALDMARYCIHDACLCQYLWEYYG----- : 374
DPOL_FOWPV  : YEIGSVHNISFGKDDVDLKDMYKNYNLEIALDMERYCIHDACLCKYIWDYYR----- : 363
DPOD_BOVIN  : --------VPLGYLLSRGQQVKVVSQLLRQAMRQGLLMPVVK--------------- : 336
DPOD_HUMAN  : --------VPLSYLLSRGQQVKVVSQLLRQAMHEGLLMPVVK--------------- : 336
DPOD_CANAL  : --------VPFSYLLSRGQQIKVISQLFRKCLQEDIVIPNLK--------------- : 335
DPOD_YEAST  : --------VPFSYLLARGQQIKVVSQLFRKCLEIDTVIPNMQ--------------- : 337
DPOD_SCHPO  : --------VPFNFLLARGQQIKVISQLFCKALQHDLVVPNIR--------------- : 336
DPOD_PLAFK  : --------TPFVYLLTRGQQIKVTSQLYRKCKELNYVIPSTY--------------- : 339
DPOL_CHVN2  : --------VPVDYINFRGQQVRAFSCLVGKARQMNYAIPDDK--------------- : 337
DPOL_CHVP1  : --------VPVDYINFRGQQIRAFSCLVGKARQMNYAIPDDK--------------- : 336
DPOL_EBV/2  : --------IPCRRVLDDGQQIRVFSCLLAAAQKENFILPMPS--------------- : 332
DPOL_HSVSA  : --------IPTRRVLTDGQQIRVFSCLLAAARAENYILPVSN--------------- : 331
DPOL_HSV11  : --------INITRTIYDGQQIRVFTCLLRLADQKGFILPDTQGR---FRGAGGEAPK : 365
DPOL_HSV21  : --------INITRTIYDGQQIRVFTCLLRLAGQKGFILPDTQGR---FRGLDKEAPK : 365
DPOL_HSVEB  : --------ITLTRVIFDGQQIRVYTCLLKLARERNFILPDNRRR---FDSQADAASE : 365
DPOL_VZVD/  : --------ITLTKAIYDGQQVRIYTCLLGLASSRGFILPDGG-----YP-------- : 355
DPOL_HCMVA  : --------IPLRRVIFDGQQIRIYTSLLDECACRDFILPNHYSKGTTVPETNSVAVS : 387
DPOL_MCMVS  : --------IPLRKVIFDGQQIRIYTCLLEECSGRDMILPNMPSLG-----------H : 351
DPOL_HSV6U  : --------VTARCVVFEGQQKKIFPCILTEAKRRNMILP------------------ : 327
DPOA_HUMAN  : --------NIMSRTLMGGRSERNEFLLLHAFYENNYIVPDKQIF------------- : 336
DPOA_MOUSE  : --------NIMSRTLMGGRSERNEFLLLHAFYENNYIVPDKQIF------------- : 336
DPOA_DROME  : --------NTMTRTLQGGRSERNEFLLLHASTEKNYIVPDKKPV------------- : 338
DPOA_SCHPO  : --------NSWARTLTGTRAERNEYILLHEFKKNGYIVPDKQQS------------- : 345
DPOA_YEAST  : --------NAWAQTLGGTRAGRNEYILLHEFSRNGFIVPDKE-G------------- : 346
DPOA_TRYBB  : --------NLWSRTLYGARSERIEYLLLHAFHNLKFVTPDKK--------------- : 345
DPOL_NPVAC  : --------LCTDDVICNISHLISVACFYAAITNTRINESTGK--------------- : 333
DPOL_NPVLD  : --------LCTDDLLRNISHKITVAYFHLALTNTVARRPD----------------- : 342
DPOZ_YEAST  : --------IDFHSVYYRGSQFKVESFLIRICKSESFILLSPG--------------- : 323
DPOL_PYRFU  : --------QPLWDVSRSSTGNLVEWFLLRKAYERNEVAPNKP--------------- : 347
DPO1_SULSO  : --------LGIEELTRTEISTWVKNLYYWEHRKRNWLIPLKEEILAK---------- : 321
DPO2_ECOLI  : ---------LPVDRHGGSVAAFGHLYFPRMHRAGYVAPNLG---------------- : 340
DPol_Dtok   : --------QSLWDVSRSSTGNLVEWFLLRKAYERNDVAPNKP--------------- : 372
RM378       : -LTPALALNASNILIGNVTGKLGVKFV-DYIKKIDTINTMFK--------------- : 345
RB69        : --------IQIQSV--FSPIKTWDAIIFNSLKEQNKVIPQGR--------------- : 384
```

FIG. 31

```
                520         .         540         .         560         .
DPOL_VACCC  : ------------------------------------VETKTDA--GASTYVLPQSMVF : 395
DPOL_VACCV  : ------------------------------------VETKTDA--GASTYVLPQSMVF : 395
DPOL_VARV/  : ------------------------------------VETKTDA--GASTYVLPQSMVF : 394
DPOL_FOWPV  : ------------------------------------VPSKINA--ASSTYLLPQSLAL : 383
DPOD_BOVIN  : -----------------------------T----------E--G--GED-------- : 342
DPOD_HUMAN  : -----------------------------S----------E--G--GED-------- : 342
DPOD_CANAL  : -----------------------------S----------E--GS-NEE-------- : 342
DPOD_YEAST  : -----------------------------S----------Q--AS-DDQ-------- : 344
DPOD_SCHPO  : -----------------------------V----------N--GT-DEQ-------- : 343
DPOD_PLAFK  : -------------------------M--------------K--VNTNEK-------- : 347
DPOL_CHVN2  : -------------------------M--------------W--TV-DGK-------- : 344
DPOL_CHVP1  : -------------------------A--------------W--AT-EGK-------- : 343
DPOL_EBV/2  : -----------------------------------AS-DRD---------------- : 337
DPOL_HSVSA  : -----------------------------------DV-NAD---------------- : 336
DPOL_HSV11  : RPAAAREDEERP-------------------EEEGEDEDE--REEGGGEREP-EG : 398
DPOL_HSV21  : RPAVPRGEGERPGDGNG--------------DEDKDDDED--GDEDGDERE--EV : 402
DPOL_HSVEB  : TSELAMDSQSHAFDSTD--------------EPDGVDGTP--DAAGSGATSENGG : 404
DPOL_VZVD/  : ---ATFEYKDVIPDVGD--------------VEEEMDEDE--SVSPTGTSS---- : 387
DPOL_HCMVA  : PNAAIISTAAVPGDAGSVAAMFQMSPPLQSAPSSQDGVSPGS--GSNSSSSVGV--- : 439
DPOL_MCMVS  : GAAAAIEEAAAGGE-G---------------DETSEGE--NSNNSR-------- : 379
DPOL_HSV6U  : ---------------------------SMVS--S--HNRQG-------- : 337
DPOA_HUMAN  : ---------------------------RKPQQKL--GDEDEEIDGD--- : 353
DPOA_MOUSE  : ---------------------------RKPQQKL--GDEDEEIDGD--- : 353
DPOA_DROME  : ---------------------------SK-RSGA--GDTDRTLSGA--- : 354
DPOA_SCHPO  : ---------------------------IRRHAEA--FGAEDGLQ----- : 360
DPOA_YEAST  : ---------------------------NRSRAQK--QRQNEENA----- : 361
DPOA_TRYBB  : ---------------------------KRDLKR--GREDDDDE----- : 359
DPOL_NPVAC  : -------------------EEPDPYFFNKNDLSIIS--GQFKADKAAAG-- : 361
DPOL_NPVLD  : -------------------PTPDPYFFNKYDLSVTS--GASAPSTSRPANA : 372
DPOZ_YEAST  : ------------------------------KKDVRKQK----- : 331
DPOL_PYRFU  : ------------------------------SE--EEYQRRLR----- : 357
DPO1_SULSO  : ------------------------------SSNIRT--SALIKGK------ : 334
DPO2_ECOLI  : ------------------------------E--VPPHAS------- : 347
DPol_Dtok   : ------------------------------DE-------RELARRTES---- : 383
RM378       : ------------------------------KIPEMN--INKYR-------- : 356
RB69        : ------------------------------S--HPVQP-------- : 390
                                 End of ORF056e-|-Beginning of ORF632e
```

FIG. 3J

```
                    580              600              620
DPOL_VACCC : EYRASTVIKGPLLKLLLETKTILVRSETKQKFPYEGGKVFAPKQKMFSNNVLIFDYN : 452
DPOL_VACCV : EYRASTVIKGPLLKLLLETKTILVRSETKQKFPYEGGKVFAPKQKMFSNNVLIFDYN : 452
DPOL_VARV/ : GYKASTVIKGPLLKLLLETKTILVRSETKQKFPYEGGKVFAPKQKMFSNNVLIFDYN : 451
DPOL_FOWPV : EYRASTLIKGPLLKLLLEERVIYTRKITKVRYPYIGGKVFLPSQKTFENNVMIFDYN : 440
DPOD_BOVIN : ------------------------------YTGATVIEPLKGYYDVPIATLDFS : 366
DPOD_HUMAN : ------------------------------YTGATVIEPLKGYYDVPIATLDFS : 366
DPOD_CANAL : ------------------------------YEGATVIEPERGYYDVPIATLDFS : 366
DPOD_YEAST : ------------------------------YEGATVIEPIRGYYDVPIATLDFN : 368
DPOD_SCHPO : ------------------------------YEGATVIEPIKGYYDTPIATLDFS : 367
DPOD_PLAFK : ------------------------------YEGATVLEPIKGYYIEPISTLDFA : 371
DPOL_CHVN2 : ------------------------------YEGATVLDAKKGAYFTSIAALDFA : 368
DPOL_CHVP1 : ------------------------------YEGATVLDAKKGAYFTPIAALDFA : 367
DPOL_EBV/2 : ---------G--------------------YQGATVIQPLSGFYNSPVLVVDFA : 362
DPOL_HSVSA : ---------G--------------------FQGATVINPIPGFYNNAVLVVDFA : 361
DPOL_HSV11 : ARETAGRHVG--------------------YQGARVLDPTSGFHVNPVVVFDFA : 432
DPOL_HSV21 : ARETGGRHVG--------------------YQGARVLDPTSGFHVDPVVVFDFA : 436
DPOL_HSVEB : GKPGVGRAVG--------------------YQGAKVLDPVSGFHVDPVVVFDFA : 438
DPOL_VZVD/ : -----GRNVG--------------------YKGARVFDPDTGFYIDPVVVLDFA : 416
DPOL_HCMVA : ------FSVGSGSSGGVGVSNDNHGAGGTAAVSYQGATVFEPEVGYYNDPVAVFDFA : 490
DPOL_MCMVS : --------TVG-------------------YQGATVLEPECGFHHVPVCVFDFA : 406
DPOL_HSV6U : ---------IG-------------------YKGATVLEPKTGYYAVPTVVFDFQ : 363
DPOA_HUMAN : -----TNKYKKG------------------RKKGAYAGGLVLDPKVGFYDKFILLLDFN : 389
DPOA_MOUSE : -----TNKYKKG------------------RKKATYAGGLVLDPKVGFYDKFILLLDFN : 389
DPOA_DROME : -----DATMQT-------------------KKKAAYAGGLVLEPMRGLYEKYVLLMDLN : 389
DPOA_SCHPO : -----EESLGK-------------------KKDKYKGGLVFEPQKGLYETCILVMDFN : 394
DPOA_YEAST : -----DAPVNS-------------------KKAKYQGGLVFEPEKGLHKNYVLVMDFN : 395
DPOA_TRYBB : ---------GK-------------------RKTKYQGGMVLEPKSGLYSEYILLLDFN : 389
DPOL_NPVAC : ----ISNLKRKLIPLKNIPKDAINLGPANQTVKYKGGKVLKPRAGIYKN-AFSLDFN : 413
DPOL_NPVLD : --IDLSQLKRTPVDAARIPPSAVKLCSTRQSCTYKGGKVLSPKPGFNRW-VATLDFN : 426
DPOZ_YEAST : ------------------------------ALECVPLVMEPESAFYKSPLIVLDFQ : 357
DPOL_PYRFU : ---------ES-------------------YTGGFVKEPEKGLWEN-IVYLDFR : 382
DPO1_SULSO : ---------G--------------------YKGAVVIDPPAGIFFN-ITVLDFA : 358
DPO2_ECOLI : ------------------------------PGGYVMDSRPGLYDS-VLVLDYK : 369
DPol_Dtok  : ------------------------------YAGGYVKEPEKGLWEN-IVYLDYK : 406
RM378      : ------------------------------YRGAYIELTNPDIYFN-VFDLDFT : 379
RB69       : ------------------------------YPGAFVKEPIPNRYKY-VMSFDLT : 413
                                                                  *
```

FIG. 3K

```
                    640             660             680
DPOL_VACCC  : SLYPNVCIFGNLSPE-TLVGVVVSTNRLEE----EINNQLLLQKYPPPRYITVH---  : 501
DPOL_VACCV  : SLYPNVCIFGNLSPE-TLVGVVVSTNRLEE----EINNQLLLQKYPPPRYITVH---  : 501
DPOL_VARV/  : SLYPNVCIFGNLSPE-TLVGVVVSSNRLEE----EINNQLLLQKYPPPRYITVH---  : 500
DPOL_FOWPV  : SLYPNVCIYGNLSPE-KLVCILLNSNKLES----EINMRTIKSKYPYPEYVCVS---  : 489
DPOD_BOVIN  : SLYPSIMMAHNLCYT-TLLRP---GAAQKL----GLT-EDQFIKTP-----------  : 403
DPOD_HUMAN  : SLYPSIMMAHNLCYT-TLLRP---GTAQKL----GLT-EDQFIRTP-----------  : 403
DPOD_CANAL  : SLYPSIMMAHNLCYT-TLLNK---NSIKAF----GLT-EDDYTKTP-----------  : 403
DPOD_YEAST  : SLYPSIMMAHNLCYT-TLCNK---ATVERL----NLKIDEDYVITP-----------  : 406
DPOD_SCHPO  : SLYPSIMQAHNLCYT-TLLDS---NTAELL----KLKQDVDYSVTP-----------  : 405
DPOD_PLAFK  : SLYPSIMIAHNLCYS-TLIKS---NHEVSD----LQNDDITTIQGK-----------  : 409
DPOL_CHVN2  : SLYPSIIRAHNMSPE-TLVMD---KRFENL----PGIEYYEIETGL-----------  : 406
DPOL_CHVP1  : SLYPSIIRAHNMSPE-TLVME---KRFENV----PGVEYYEIETGL-----------  : 405
DPOL_EBV/2  : SLYPSIIQAHNLCYS-TMITPGEEHRLAGL----RPGEDYESFRLT-----------  : 403
DPOL_HSVSA  : SLYPSIIQAHNLCYS-TLIPHHALHNYPHL----KSS-DYETFMLS-----------  : 401
DPOL_HSV11  : SLYPSIIQAHNLCFS-TLSLR--ADAVAHL----EAGKDYLEIEVG-----------  : 471
DPOL_HSV21  : SLYPSIIQAHNLCFS-TLSLR--PEAVAHL----EADRDYLEIEVG-----------  : 475
DPOL_HSVEB  : SLYPSIIQAHNLCFT-TLALD--EVDLAGL----QPSVDYSTFEVG-----------  : 477
DPOL_VZVD/  : SLYPSIIQAHNLCFT-TLTLN--FETVKRL----NPS-DYATFTVG-----------  : 454
DPOL_HCMVA  : SLYPSIIMAHNLCYS-TLLVP---GGEYPV----DPA-DVYSVTLEN----------  : 528
DPOL_MCMVS  : SLYPSIIMSNNLCYS-TLLVE---GS-PEV----PEK-DVLRVEIG-----------  : 442
DPOL_HSV6U  : SLYPSIMMAHNLCYS-TLVLDE--RQIAGL----SES-DILTVKLG-----------  : 401
DPOA_HUMAN  : SLYPSIIQEFNICFT-TVQRVA--SEAQKV----TEDGEQEQIP-------------  : 426
DPOA_MOUSE  : SLYPSIIQEFNICFT-TVQRVT--SEVQKA----TEDEEQEQIP-------------  : 426
DPOA_DROME  : SLYPSIIQEYNICFN-PVQ---------QP-------VDADELP-------------  : 416
DPOA_SCHPO  : SLYPSIIQEYNICFT-TVDRS--------P----SNSDSDDQIP-------------  : 425
DPOA_YEAST  : SLYPSIIQEFNICFT-TVDR--------------NKEDIDELP-------------- : 423
DPOA_TRYBB  : SLYPSLIQEFNVCYT-TIDR---------D----ENTVSAEVPPPESL---------  : 423
DPOL_NPVAC  : SLYLTIMIAICACLS-NLILCE----------------------------------- : 434
DPOL_NPVLD  : ALYPTIMMWEGVCMSSNVFIAS----------------------------------- : 448
DPOZ_YEAST  : SLYPSIMIGYNYCYSTMIGRVREINLTENN----LGVSKFSLPRNILALLKNDV--- : 407
DPOL_PYRFU  : ALYPSIIITHNVSPD-TLN---------L----EGCKNYDIAP-------------  : 411
DPO1_SULSO  : SLYPSIIRTWNLSYE-TVDIQQ-------C----KKPYEVKDETG------------  : 391
DPO2_ECOLI  : SLYPSIIRTFLIDPVGLVEG-------------MAQPDPEHSTEG------------  : 401
DPol_Dtok   : SLYPSIIITHNVSPD-TLNR-------------EGCREYDVAP-------------  : 435
RM378       : SLYPSVISKFNIDPATFVTEFYGCMRVENK----VIPVDQEEPEFGFPLYIFDSGMN  : 432
RB69        : SLYPSIIRQVNISPETIAGTFKVAPLHDYINAVAERPSDVYSCSPNGMMYYKDRDGV  : 470
              **
              motif A
```

FIG. 3L

```
                         .       700        .       720         .       740
DPOL_VACCC : ----------CEPRLPNLISEIAIFDRSIE------------GTIPRLLRTFLAE : 534
DPOL_VACCV : ----------CEPRLPNLISEIAIFDRSIE------------GTIPRLLRTFLAE : 534
DPOL_VARV/ : ----------CEPRLPNLISEIAIFDRSIE------------GTIPRLLRTFLAE : 533
DPOL_FOWPV : ----------CESRLSDYYSEIIVYDRREK------------GIIPKLLEMFIGK : 522
DPOD_BOVIN : ---------------TGDEFVKAS----VRK-----------GLLPQILENLLSA : 428
DPOD_HUMAN : ---------------TGDEFVKTS----VRK-----------GLLPQILENLLSA : 428
DPOD_CANAL : ---------------NGDYFVHSN----LRK-----------GILPTILDELLTA : 428
DPOD_YEAST : ---------------NGDYFVTTK----RRR-----------GILPIILDELISA : 431
DPOD_SCHPO : ---------------NGDYFVKPH----VRK-----------GLLPIILADLLNA : 430
DPOD_PLAFK : ---------------NNLKFVKKN----VKK-----------GILPLIVEELIEA : 434
DPOL_CHVN2 : ---------------GTFKYPQKNDETGEGQ-----------GVVPALLDDLAKF : 435
DPOL_CHVP1 : ---------------GKFKYAQKNDETGEGQ-----------GVVPALLDDLAKF : 434
DPOL_EBV/2 : ---------------GGVYHFVKKH----VHE-----------SFLASLLTSWLAK : 429
DPOL_HSVSA : ---------------SGPIHFVKKH----IQA-----------SLLSRLLTVWLSK : 427
DPOL_HSV11 : ---------------GRRLFFVKAH----VRE-----------SLLSILLRDWLAM : 497
DPOL_HSV21 : ---------------GRRLFFVKAH----VRE-----------SLLSILLRDWLAM : 501
DPOL_HSVEB : ---------------DQKLFFVHAH----IRE-----------SLLGILLRDWLAM : 503
DPOL_VZVD/ : ---------------GKRLFFVRSN----VRE-----------SLLGVLLKDWLAM : 480
DPOL_HCMVA : ---------------GVTHRFVRAS----VRV-----------SVLSELLNKWVSQ : 554
DPOL_MCMVS : ---------------DQCHRFVREN----VHR-----------SLLAELLVRWLTQ : 468
DPOL_HSV6U : ---------------DETHRFVKPC----IRE-----------SVLGSLLKDWLAK : 427
DPOA_HUMAN : -----------------ELPDPS---LEM-------------GILPREIRKLVER : 448
DPOA_MOUSE : -----------------ELPDPN---LEM-------------GILPREIRKLVER : 448
DPOA_DROME : -----------------TLPDSK---TEP-------------GILPLQKRLVES : 438
DPOA_SCHPO : -----------------DTPSAS---ANQ-------------GIFPRLIANLVER : 447
DPOA_YEAST : -----------------SVPPSE---VDQ-------------GVLPRLLANLVDR : 445
DPOA_TRYBB : -----------ICLSCRAAGLPSPC---LHK-----------CILPKVIRGLVDS : 453
DPOL_NPVAC : ---------------DGNVYLHN-----SR-----------AIVVKLLLKLLSE : 458
DPOL_NPVLD : ---------------DGNVYLDKN-----VN-----------AVNPKLLKTLSEM : 472
DPOZ_YEAST : ----------TIAPNGVVYAKTS----VRK-----------STLSKMLTDILDV : 436
DPOL_PYRFU : ---------------QVGHKFCKDIP------------------GFIPSLLGHLLEE : 435
DPO1_SULSO : ---------------EVLHIVCMD-----RP-----------GITAVITGLLRDF : 415
DPO2_ECOLI : ------------------FLDAWFS--REK-----------HCLPEIVTNIWHG : 424
DPol_Dtok  : ---------------QVGHRFCKDFP------------------GFIPSLLGDLLEE : 459
RM378      : PSYRSEPLFVINSFEELRQFLKSRNIIMVPNPSGICWFYRKEPVGVLPSIIREIFTR : 489
RB69       : VPTEITKVFNQRKEHKGYMLAAQRNGEIIKEALHN-PNLSVDEPLDVDYRFDFSDEI : 526
```

FIG. 3M

```
                760           780              8
DPOL_VACCC : RARYKKMLKQAT---SSTEKAIYDSM---------QYTYKIVANSVYGLMGFRNS-A : 578
DPOL_VACCV : RARYKKMLKQAT---SSTEKAIYDSM---------QYTYKIVANSVYGLMGFRNS-A : 578
DPOL_VARV/ : RARYKKMLKQAT---SSTEKAIYDSM---------QYTYKIIANSVYGLMGFRNS-A : 577
DPOL_FOWPV : RKEYKNLLKTAS---TTIESTLYDSL---------QYIYKIIANSVYGLMGFSNS-T : 566
DPOD_BOVIN : RKRAKAELAKET---DPLRRQVLDGR---------QLALKVSANSVYGFTGAQVG-R : 472
DPOD_HUMAN : RKRAKAELAKET---DPLRRQVLDGR---------QLALKVSANSVYGFTGAQVG-K : 472
DPOD_CANAL : RKKAKADLKKET---DPFKKDVLNGR---------QLALKISANSVYGFTGATVG-K : 472
DPOD_YEAST : RKRAKKDLRDEK---DPFKRDVLNGR---------QLALKISANSVYGFTGATVG-K : 475
DPOD_SCHPO : RKKAKADLKKET---DPFKKAVLDGR---------QLALKVSANSVYGFTGATNG-R : 474
DPOD_PLAFK : RKKVKLLIKNEK---NNITKMVLNGR---------QLALKISANSVYGYTGASSGGQ : 479
DPOL_CHVN2 : RKQAKKHMAEAKKNDDEFREALYDAQ---------QRSYKIVMNSVYGFLGASRG-F : 482
DPOL_CHVP1 : RKLAKKHMAEAKRNGDDFKEALYDAQ---------QRSFKVVMNSVYGFLGASKG-F : 481
DPOL_EBV/2 : RKAIKKLLAACE---DPRQRTILDKQ---------QLAIKCTCNAVYGFTGVANG-L : 473
DPOL_HSVSA : RKAIRQKLAECE---DLDTKTILDKQ---------QLAIKVTCNAVYGFTGVASG-L : 471
DPOL_HSV11 : RKQIRSRIPQS----SPEEAVLLDKQ---------QAAIKVVCNSVYGFTGVQHG-L : 540
DPOL_HSV21 : RKQIRSRIPQS----PPEEAVLLDKQ---------QAAIKVVCNSVYGFTGVQHG-L : 544
DPOL_HSVEB : RKAVRARIPTS----TPEEAVLLDKQ---------QSAIKVICNSVYGFTGVANG-L : 546
DPOL_VZVD/ : RKAIRARIPGS----SSDEAVLLDKQ---------QAAIKVVCNSVYGFTGVAQG-F : 523
DPOL_HCMVA : RRAVRECMRECQ---DPVRRMLLDKE---------QMALKVTCNAFYGFTGVVNG-M : 598
DPOL_MCMVS : RKLVREAMKQCT---NEMQRMIMDKQ---------QLALKVTCNAFYGFTGVAAG-M : 512
DPOL_HSV6U : RREVKAEMQNCS---DPMMKLLLDKK---------QLALKTTCNSVYGVTGAAHG-L : 471
DPOA_HUMAN : RKQVKQLMKQQDL--NPDLILQYDIR---------QKALKLTANSMYGCLGFSYS-R : 493
DPOA_MOUSE : RKQVKQLMKQQDL--NPDLVLQYDIR---------QKALKLTANSMYGCLGFSYS-R : 493
DPOA_DROME : RKEVKKLMAAPDL--SPELQMQYHIR---------QMALKLTANSMYGCLGFAHS-R : 483
DPOA_SCHPO : RRQIKGLLKDNSA--TPTQRLQWDIQ---------QQALKLTANSMYGCLGYTKS-R : 492
DPOA_YEAST : RREVKKVMK-TET--DPHKRVQCDIR---------QQALKLTANSMYGCLGYVNS-R : 489
DPOA_TRYBB : RREIKRMMK-SEK--DPGNLAMLEIR---------QLALKLTANSMYGCLGFEYS-R : 497
DPOL_NPVAC : RCKFKKNRDNQSE--SAFLYDLYDQK---------QNSVKRTANSIYGYYGIFYK-- : 502
DPOL_NPVLD : RVRYKGLRDQCEY--NSFYYKLYDKI---------QNALKRIANSIYGYYGIFFK-- : 516
DPOZ_YEAST : RVMIKKTMNEIGDD-NTTLKRLLNNK---------QLAKILLANSFYGYYGYAKA-R : 483
DPOL_PYRFU : RQKIKTKMKETQ---DPIEKILLDYR---------QKAIKLLANSFYGYYGYAKA-R : 479
DPO1_SULSO : RVKIYKKKAKNPNN-SEEQKLLYDVV---------QRAMKVFINATYGVFGAETFP- : 461
DPO2_ECOLI : RDEAKRQGNKP---------------L--------SQALKIIMNAFYGVLGTTAC-R : 457
DPol_Dtok  : RQKVKKKMKAT---VDPIERKLLDYR---------QRAIKILANSYYGYYAYANA-R : 503
RM378      : RKEERKLFKET-----GNMEHHFR-----------QWALKIMMNSMYGIFGNRSV-Y : 529
RB69       : KEKIKKLSAKS-----LNEMLFRAQRTEVAGMTAQINRKLLINSLYGALGNVWF-R : 576
                                                      *    *  **
                                                         motif B
```

FIG. 3N

```
                    00            820             840            .
DPOL_VACCC  : LYSYASAKSCTSIGRRMILYLESVLNGAELSNGML--RFANPLSNP-------FYMD : 626
DPOL_VACCV  : LYSYASAKSCTSIGRRMILYLESVLNGAELSNGML--RFANPLSNP-------FYMD : 626
DPOL_VARV/  : LYSYASAKSCTSIGRRMILYLESVLNGAELSNGML--RFANPLSNP-------FYMD : 625
DPOL_FOWPV  : LYSYSSAKTCTTIGRNMITYLDSIMNGAVWENDKL--ILADFPRN--------IFSG : 613
DPOD_BOVIN  : LPCLEISQSVTGFGRQMIEKTKQLVETKYTV------ENGYS--------------- : 508
DPOD_HUMAN  : LPCLEISQSVTGFGRQMIEKTKQLVESKYTV------ENGYS--------------- : 508
DPOD_CANAL  : LPCLAISSSVTAFGREMIEKTKNEVQEYYSK------KNGHP--------------- : 508
DPOD_YEAST  : LPCLAISSSVTAYGRTMILKTKTAVQEKYCI------KNGYK--------------- : 511
DPOD_SCHPO  : LPCLAISSSVTSYGRQMIEKTKDVVEKRYRI------ENGYS--------------- : 510
DPOD_PLAFK  : LPCLEVAVSITTLGRSMIEKTKERVESFYCK------SNGYE--------------- : 515
DPOL_CHVN2  : IPCVPIAASVTATGRKMIEHTAKRVTELLP---------G----------------- : 513
DPOL_CHVP1  : IPCVPIAASVTATGRKMIEHTAKRAVELLP---------G----------------- : 512
DPOL_EBV/2  : FPCLSIAETVTLQGRTMLERAKAFVEA--LSPANL--QALAPSP------------- : 513
DPOL_HSVSA  : LPCISIAETVTLQGRTMLEKSKIFIEA--MTPDTL--QEIVP--------------- : 509
DPOL_HSV11  : LPCLHVAATVTTIGREMLLATREYVHARWAAFEQL--LADFPEA------------- : 582
DPOL_HSV21  : LPCLHVAATVTTIGREMLLATRAYVHARWAEFDQL--LADFPEA------------- : 586
DPOL_HSVEB  : LPCLRIAATVTTIGRDMLLKTRDYVHSRWATRELL--EDNFPGA------------- : 588
DPOL_VZVD/  : LPCLYVAATVTTIGRQMLLSTRDYIHNNWAAFERF--ITAFPDI------------- : 565
DPOL_HCMVA  : MPCLPIAASITRIGRDMLERTARFIKDNFSEPCFL--HNFFNQEDYVVGTREGDSEE : 653
DPOL_MCMVS  : LPCLPIAASITKIGRDMLLATAGHIEDRCNRPDFL--RTVLGLP------------- : 554
DPOL_HSV6U  : LPCVAIAASVTCLGREMLCSTVDYVNSKMQSEQFF--CEEFGLT------------- : 513
DPOA_HUMAN  : FYAKPLAALVTYKGREILMHTKEMVQKMN---------------------------- : 522
DPOA_MOUSE  : FYAKPLAALVTYKGREILMHTKDMVQKMN---------------------------- : 522
DPOA_DROME  : FFAQHLAALVTHKGRD-LTNTQQLVQKMN---------------------------- : 511
DPOA_SCHPO  : FYARPLAVLITYKGREALMNTKELADQMG---------------------------- : 521
DPOA_YEAST  : FYAKPLAMLVTNKGREILMNTRQLAESMN---------------------------- : 518
DPOA_TRYBB  : FYAQPLAELVTRQGRLALQNTVELIPQISPS-------------------------- : 528
DPOL_NPVAC  : ----VLANYITRVGRNQLRLAISLIEGLSNDPEIL--EKFNLG-------------- : 539
DPOL_NPVLD  : ----PLANYITKMGRGKLKEVVGKVEAMSDDPRIL--REFGLS-------------- : 553
DPOZ_YEAST  : MPCSDLADSIVQTGRETLEKAIDIIEKDETWN------------------------- : 515
DPOL_PYRFU  : WYCKECAESVTAWGRKYIELVWKELEEKFG--------------------------- : 509
DPO1_SULSO  : LYAPRVAESVTALGRYVITSTVKKAREE-G--------------------------- : 490
DPO2_ECOLI  : FFDPRLASSITMRGHQIMRQTKALIEAQG---------------------------- : 486
DPol_Dtok   : WYCRECAESVTAWGRQYIETTMREIEEKFG--------------------------- : 533
RM378       : MGCLPIAESVTAAGRMSIRSVISQIRDR----------------------------- : 557
RB69        : YYDLRNATAITTFGQMALQWIERKVNEYLNEVCG---TEG----------------- : 613
                                     *
```

FIG. 30

```
              860            880           900
DPOL_VACCC : DRDINPIVKTSLP--IDYRFRFRSVYGDTDSVFTEIDSQD-------VDKSIEIAKE : 674
DPOL_VACCV : DRDINPIVKTSLP--IDYRFRFRSVYGDTDSVFTEIDSQD-------VDKSIEIAKE : 674
DPOL_VARV/ : DRDINPIVKTSLP--IDYRFRFRSVYGDTDSVFTEIDSQD-------VDKSIEIAKE : 673
DPOL_FOWPV : ETMFNKELEVPN---MNESFKFRSVYGDTDSIFSEISTKD-------IEKTAKIAKH : 660
DPOD_BOVIN : --------TS-----------AKVVYGDTDSVMCRFGVSS-------VAEAMALGRE : 539
DPOD_HUMAN : --------TS-----------AKVVYGDTDSVMCRFGVSS-------VAEAMALGRE : 539
DPOD_CANAL : --------YD-----------AKVIYGDTDSVMVKFGYQD-------LETCMKLGEE : 539
DPOD_YEAST : --------HD-----------AVVVYGDTDSVMVKFGTTD-------LKEAMDLGTE : 542
DPOD_SCHPO : --------HD-----------AVVIYGDTDSVMVKFGVKT-------LPEAMKLGEE : 541
DPOD_PLAFK : --------HN-----------STVIYGDTDSVMVKFGTNN-------IEEAMTLGKD : 546
DPOL_CHVN2 : ---------------------SEVIYGDTDSVMIRMKLPDDKIHD--MDEQFKMAKW : 547
DPOL_CHVP1 : ---------------------SEVIYGDTDSVMVKMKLPDDKVHD--MDEQFKMAKW : 546
DPOL_EBV/2 : ----DAWAPLN------PEGQLRVIYGDTDSLFIECRGFS-------ESETLRFADA : 553
DPOL_HSVSA : -----HIVKHE------PDAKFRVIYGDTDSLFVECVGYS-------VDTVVKFGDF : 548
DPOL_HSV11 : ----AD-MRAP------GPYSMRIIYGDTDSIFVLCRGLT-------AAGLTAVGDK : 621
DPOL_HSV21 : ----AG-MRAP------GPYSMRIIYGDTDSIFVLCRGLT-------GEALVAMGDK : 625
DPOL_HSVEB : ----IG-FRNH------KPYSVRVIYGDTDSVFIKFVGLT-------YEGVSELGDA : 627
DPOL_VZVD/ : ----ESSVLSQ------KAYEVKVIYGDTDSVFIRFKGVS-------VEGIAKIGEK : 605
DPOL_HCMVA : SSALPEGLETSSGGSNERRVEARVIYGDTDSVFVRFRGLT-------PQALVARGPS : 703
DPOL_MCMVS : ----PEAIDP-------EALRVKIIYGDTDSVFAAFYGID-------KEALLKAVGA : 593
DPOL_HSV6U : ----SSDFTG-------DLEVEVIYGDTDSIFMSVRNMV--------NQSLRRIAPM : 551
DPOA_HUMAN : ---------------------LEVIYGDTDSIMINTNSTN------LEEVFKLGNK : 551
DPOA_MOUSE : ---------------------LEVIYGDTDSIMINTNSTN------LEEVFKLGNK : 551
DPOA_DROME : ---------------------YDVVYGDTDSLMINTNITD------YDQVYKIGHN : 540
DPOA_SCHPO : ---------------------LQVIYGDTDSVMLNTNVTD------KNHALRIGNE : 550
DPOA_YEAST : ---------------------LLVVYGDTDSVMIDTGCDN------YADAIKIGLG : 547
DPOA_TRYBB : ---------------------IRVIYGDTDSVMIQTGIKDD-----IVKVRNLGFE : 558
DPOL_NPVAC : ----------------SITFKVVYGDTDSTFVLPTFNYNEISN--ETDTLK--QI : 574
DPOL_NPVLD : ----------------KINFSVIYGDTDSCFIRVLFDEAEWRR--TAARPRSAPS : 590
DPOZ_YEAST : --------------------AKVVYGDTDSLFVYLPGKT-------AIEAFSIGHA : 544
DPOL_PYRFU : --------------------FKVLYIDTDGLYATIPGGE-------SEEIKKKALE : 538
DPO1_SULSO : --------------------LTVLYGDTDSLFLLNPPKN--------SLENIIKWV : 518
DPO2_ECOLI : --------------------YDVIYGDTDSTFVWLKGAHS------EEEAAKIGRA : 516
DPol_Dtok  : --------------------FKVLYADTDGFFATIPGAD-------AETVKNKAKE : 562
RM378      : --------------------FIYSHTDSIFVKAFTDDP--------VAEAGELQEH : 585
RB69       : --------------------EAFVLYGDTDSIYVSADKIIDKVGESKFRDTNHWVDF : 650
                                 *  **
                                motif C
```

FIG. 3P

```
                920            940            960
DPOL_VACCC  : LERLINNR--V----------LFN----NFKIEFEAVYKNLIMQ--------SKKK : 706
DPOL_VACCV  : LERLINNR--V----------LFN----NFKIEFEAVYKNLIMQ--------SKKK : 706
DPOL_VARV/  : LERLINSR--V----------LFN----NFKIEFEAVYKNLIMQ--------SKKK : 705
DPOL_FOWPV  : LEHIINTK--I----------LHA----NFKIEFEAIYTQLILQ--------SKKK : 692
DPOD_BOVIN  : AADWVS-G--H----------FPS----PIRLEFEKVYFPYLLI--------SKKR : 570
DPOD_HUMAN  : AADWVS-G--H----------FPS----PIRLEFEKVYFPYLLI--------SKKR : 570
DPOD_CANAL  : AANYVS-T--K----------FKN----PIKLEFEKVYFPYLLI--------NKKR : 570
DPOD_YEAST  : AAKYVS-T--L----------FKH----PINLEFEKAYFPYLLI--------NKKR : 573
DPOD_SCHPO  : AANYVS-D--Q----------FPN----PINWSFS--TFPYLLI--------SKKR : 570
DPOD_PLAFK  : AAERIS-K--E----------FLS----PIKLEFEKVYCPYLLL--------NKKR : 577
DPOL_CHVN2  : LAGEIT-K--D----------FKA----PNDLEFEKIYYPYILY--------SKKR : 578
DPOL_CHVP1  : LAGEIT-K--D----------FRA----PNDLEFEKIYYPYILY--------SKKR : 577
DPOL_EBV/2  : LAAHTTRS--L----------FVA----PISLEAEKTFSCLMLI--------TKKR : 585
DPOL_HSVSA  : LAAFTSEK--L----------FNA----PIKLESEKTFQCLLLL--------AKKR : 580
DPOL_HSV11  : MASHISRA--L----------FLP----PIKLECEKTFTKLLLI--------AKKK : 653
DPOL_HSV21  : MASHISRA--L----------FLP----PIKLECEKTFTKLLLI--------AKKK : 657
DPOL_HSVEB  : MSRQISAD--L----------FRA----PIKLECEKTFQRLLLI--------TKKR : 659
DPOL_VZVD/  : MAHIISTA--L----------FCP----PIKLECEKTFIKLLLI--------TKKR : 637
DPOL_HCMVA  : LAHYVTAC--L----------FVE----PVKLEFEKVFVSLMMI--------CKKR : 735
DPOL_MCMVS  : LAANVTNA--L----------FKE----PVRLEFEKMFVSLMMI--------CKKR : 625
DPOL_HSV6U  : IAKHITDR--L----------FKS----PIKLEFEKILCPLILI--------CKKR : 583
DPOA_HUMAN  : VKSEVN----K----------LYK----LLEIDIDGVFKSLLLL--------KKKK : 581
DPOA_MOUSE  : VKSEVN----K----------LYK----LLEIDIDAVFKSLLLL--------KKKK : 581
DPOA_DROME  : IKQSVN----K----------LYK----QLELDIDGVFGCLLLL--------KKKK : 570
DPOA_SCHPO  : FKEKVN----E----------RYS----KLEIDIDNVYQRMLLH--------AKKK : 580
DPOA_YEAST  : FKRLVN----E----------RYR----LLEIDIDNVFKKLLLH--------AKKK : 577
DPOA_TRYBB  : IKGKVN----Q----------RYQ----SLELDIDGVFRAMLLL--------RKKK : 588
DPOL_NPVAC  : CTHVETRVNNS----------FTD----GYKMAFENLMKVLILL--------KKKK : 608
DPOL_NPVLD  : CRTTCAKRSTT----------LWC----GYKMSLENIMLSLILL--------KKKK : 624
DPOZ_YEAST  : MAERVTQN-------------NPK----PIFLKFEKVYHPSILI--------SKKR : 575
DPOL_PYRFU  : FVKYIN---SK----------LPG----LLELEYEGFYKRGFFV--------TKKR : 569
DPO1_SULSO  : KTTFN------------------------LDLEVDKTYKFVAFSG-------LKKN : 543
DPO2_ECOLI  : LVQHVNAWWAETLQK-----QRLTS----ALELEYETHFCRFLMPTIRGADTGSKKR : 564
DPol_Dtok   : FLNYIN---PR----------LPG----LLELEYEGFYRRGFFV--------TKKK : 593
RM378       : LNSFINDYMENN---------FNAREDFKLELKQEFVFKSILIK--------EINR : 624
RB69        : LDKFARERMEPAIDRGFREMCEYMNNKQHLMFMDREAIAGPPLGSKGIGGFWTGKKR : 707
```

FIG. 3Q

```
                        .         980          .        1000          .        1020
DPOL_VACCC  : YTTMKYSASSNSKSVPERINKGTSETRRDVSKFHKNMIKTYKTRLSE-MLSEGRMNS : 762
DPOL_VACCV  : YTTMKYSASSNSKSVPERINKGTSETRRDVSKFHKNMIKTYKTRLSE-MLSEGRMNS : 762
DPOL_VARV/  : YTTMKYSASSNSKSVPERINKGTSETRRDVSKFHKNMIKIYKTRLSE-MLSEGRMNS : 761
DPOL_FOWPV  : YTTIKYLANYKPGDKPIRVNKGTSETRRDVALFHKHMIQRYKDMLMK-LLMQSKGQ- : 747
DPOD_BOVIN  : YAGLLFSS---RPDAHDRMDCKGLEAVRRDNCPLVANLVTASLRRLLI-DRDPSGAVA : 624
DPOD_HUMAN  : YAGLLFSS---RPDAHDRMDCKGLEAVRRDNCPLVANLVTASLRRLLI-DRDPEGAVA : 624
DPOD_CANAL  : YAGLYWT---RPEKFDKMDTKGIETVRRDNCQLVQNVITKVLEFILE-ERDVPKAQR : 623
DPOD_YEAST  : YAGLFWT---NPDKFDKLDQKGLASVRRDSCSLVSIVMNKVLKKILI-ERNVDGALA : 626
DPOD_SCHPO  : YAGLFWT---RTDTYDKMDSKGIETVRRDNCPLVSYVIDTALRKMLI-DQDVEGAQL : 623
DPOD_PLAFK  : YAGLLYT---NPNKHDKMDCKGIETVRRDFCILIQQMMETVLNKLLI-EKNLNSAIE : 630
DPOL_CHVN2  : YAAIKFE---DPDEKGKVDVKGLALVRRDFSPITREILKESLDTILF-KKDTPTAVT : 631
DPOL_CHVP1  : YAAVKFE---EPDEKGKVDVKGLALVRRDFSPITRDILKESLDTILY-KKDTPTAVS : 630
DPOL_EBV/2  : YVGVLTD-------G-KTLMKGVELVRKTACKFVQTRCRRVLDLVLA-DARVKEAAS : 633
DPOL_HSVSA  : YIGILSN-------D-KLLMKGVDLVRKTACKFVQNTSSKILNLILK-DPEVKAAAQ : 628
DPOL_HSV11  : YIGVIYG-------G-KMLIKGVDLVRKNNCAFINRTSRALVDLLFY-DDTVSGAAA : 701
DPOL_HSV21  : YIGVICG-------G-KMLIKGVDLVRKNNCAFINRTSRALVDLLFY-DDTVSGAAA : 705
DPOL_HSVEB  : YIGVING-------G-KMLMKGVDLVRKNNCSFINLYARHLVDLLLY-DEDVATAAA : 707
DPOL_VZVD/  : YIGVIYG-------G-KVLMKGVDLVRKNNCQFINDYARKLVELLLY-DDTVSRAAA : 685
DPOL_HCMVA  : YIGKVEG-------ASGLSMKGVDLVRKTACEFVKGVTRDVLSLLFE-DREVSEAAV : 784
DPOL_MCMVS  : YIGKVHG-------SQNLSMKGVDLVRRTACGFVKAVVSDVLHMVFN-DETVSEGTM : 674
DPOL_HSV6U  : YIGRQDD-------S-LLIFKGVDLVRKTSCDFVKGVVKDIVDLLFF-DEEVQTAAV : 631
DPOA_HUMAN  : YAALVVEPTSDGNYVTKQELKGLDIVRRDWCDLAKDTGNFVIGQILS-DQSRDTIVE : 637
DPOA_MOUSE  : YAALVVEPTSDGNYITKQELKGLDIVRRDWCDLAKDTGNFVIGQILS-DQSRDTIVE : 637
DPOA_DROME  : YAAIKLSKDSKGNLRREQEHKGLDIVRRDWSQLAVMVGKAVLDEVLS-EKPLEEKLD : 626
DPOA_SCHPO  : YAALQLDS----QGKPNLDVKGLDMKRREFCTLAKEASKFCLDQILS-GELTETVIE : 632
DPOA_YEAST  : YAALTVNLDKNGNGTTVLEVKGLDMKRREFCPLSRDVSIHVLNTILS-DKDPEEALQ : 633
DPOA_TRYBB  : YAALSVVDWQGEGKVYKREVKGLDMVRRDWCPLSQHVSDAVLKRILN-AEGGEDILD : 644
DPOL_NPVAC  : YCYLNSE---------NKIVYKGWLVKKDMPVFMRIAFRTAVEQILR-HLDMDKCLQ : 655
DPOL_NPVLD  : YCYLNNE---------QRTKYKGWLIKRDMPLFMRKAFRATVDSFS--AATRRVRAR : 670
DPOZ_YEAST  : YVGFSYES--PSQTLPIFDAKGIETVRRDGIPAQQKIIEKCIRLLFQ-TKDLSKIKK : 629
DPOL_PYRFU  : YAVIDEE-------GKVITRGLEIVRRDWSEIAKETQARVLETILK-HGDVEEAVR : 617
DPO1_SULSO  : YFGVYQD-------GKVDIKGMLVKKRNTPEFVKKVFNEVKELMIS-INSPNDVKE : 591
DPO2_ECOLI  : YAGLIQE-----GDKQRMVFKGLETVRTDWTPLAQQFQQELYLRIFR-NEPYQEYVR : 615
DPol_Dtok   : YAVIDEE-------DKITTRGLEIVRRDWSEIAKETQARVLEAILK-HGDVEEAVR : 641
RM378       : YFAVTVD-------G-KEEMKGIEVINSSVPEIVKKYFRGYLKYISQPDIDVISATI : 673
RB69        : YALNVWDMEGTRYAEPKLKIMGLETQKSSTPKAVQKALKECIRRMLQ--EGEESLQE : 762
                                    *
```

FIG. 3R

```
                    1040           1060            1080
DPOL_VACCC  : NQVCID----------------ILRSLETDLRSEFDSRSSPLELFMLSRMHHSN- : 800
DPOL_VACCV  : NQVCID----------------ILRSLETDLRSEFDSRSSPLELFMLSRMHHSN- : 800
DPOL_VARV/  : NQVCID----------------ILRSLETDLRSEFDSRSSPLELFMLSRMHHLN- : 799
DPOL_FOWPV  : QEITRL----------------ILQSLETDMISEFTHN-REFEKYLLSRKHHNN- : 784
DPOD_BOVIN  : HAQDV----------IS------------DLLCN-RIDISQLVITKELTRAAA-- : 654
DPOD_HUMAN  : HAQDV----------IS------------DLLCN-RIDISQLVITKELTRAAS-- : 654
DPOD_CANAL  : FVKQT----------IA------------DLLQN-RIDLSQLVITKAYSKHD--- : 652
DPOD_YEAST  : FVRET----------IN------------DILHN-RVDISKLIISKTLAPN---- : 654
DPOD_SCHPO  : FTKKV----------IS------------DLLQN-KIDMSQHVITKALSKTD--- : 652
DPOD_PLAFK  : YTKSK----------IK------------ELLTN-NIDMSLLVVTKSLGKTD--- : 659
DPOL_CHVN2  : ETVEC----------IR------------KVLDN-EYPMEKFTMSKTLKTG---- : 659
DPOL_CHVP1  : ETLER----------IR------------KVLDN-EYPMEKFMMSKLLKTG---- : 658
DPOL_EBV/2  : LLSHRPFQESFTQGLPVGFLPVIDILNQAYTDLREG-RVPMGELCFSTELSRKLSA- : 688
DPOL_HSVSA  : LLSTKDPDYAFREGLPDGFLKVIDILNESHKNLRTG-QVPVEELTFSTELSRPISS- : 683
DPOL_HSV11  : ALAERPAEEWLARPLPEGLQAFGAVLVDAHRRITDP-ERDIQDFVLTAELSRHPRA- : 756
DPOL_HSV21  : ALAERPAEEWLARPLPEGLQAFGAVLVDAHRRITDP-ERDIQDFVLTAELSRHPRA- : 760
DPOL_HSVEB  : EVTDVPPAEWVGRPLPSGFDKFGRVLVEAYNRITAP-NLDVREFVMTAELSRSPES- : 762
DPOL_VZVD/  : EASCVSIAEWNRRAMPSGMAGFGRIIADAHRQITSP-KLDINKFVMTAELSRPPSA- : 740
DPOL_HCMVA  : RLSRLSLDEVKKYGVPRGFWRILRRLVQARDDLYLH-RVRVEDLVLSSVLSKDISL- : 839
DPOL_MCMVS  : KLSRMTFDDLKKNGIPCEFGPVVSRLCRARDDLHLK-KVPVPELTLSSVLSQELSC- : 729
DPOL_HSV6U  : EFSHMTQTQLREQGVPVGIHKILRRLCEAREELFQN-RADVRHLMLSSVLSKEMAA- : 686
DPOA_HUMAN  : NIQKR-------------------LIEIGENVLNG-SVPVSQFEINKALTKDPQD- : 672
DPOA_MOUSE  : NIQKR-------------------LIEIGENVLNG-SVPVSQFEINKALTKDPQD- : 672
DPOA_DROME  : AVHAQ-------------------LEKIKTQIAEG-VVPLPLFVITKQLTRTPQD- : 661
DPOA_SCHPO  : NIHSY-------------------LMDFSEKMRNG-KFPANKFIIFNRLGKNPED- : 667
DPOA_YEAST  : EVYDY-------------------LEDIRIKVETN-NIRIDKYKINMKLSKDPKA- : 668
DPOA_TRYBB  : FVIKY-------------------MKGVAQDVRSGNVYPLEEFVISKSLTKEPES- : 680
DPOL_NPVAC  : SLQTS-------------------FYEYYDEFAKS-K-SLTDYSFSMTYNDNPGK- : 689
DPOL_NPVLD  : PARRE-------------------MLRYYREFGAP-RENLVDYCFSMSYNETSTT- : 705
DPOZ_YEAST  : YLQN--------------------EFFKIQIG-KVSAQDFCFAKEVKLGAYK-    : 660
DPOL_PYRFU  : IVKEV-------------------IQKLANYEIPPEKLAIYEQITRPLHE-      : 648
DPO1_SULSO  : IKRKIVD-----------------VVKGSYEKLKNKGYNLDELAFKVMLSKPLDA- : 629
DPO2_ECOLI  : ETID--------------------KLMAG-ELD-ARLVYRKRLRRPLSE-       : 642
DPol_Dtok   : IVKEVT------------------EKLSRHEVPPEKLVIYEQITRDLRS-       : 672
RM378       : AFYNN-------------------FVSQKNFWSIEDLYHKMKISSSDSAERYVEY  : 709
RB69        : YFKEF-------------------EKEFRQLNYISIASVSSANNIAKYDVGG     : 795
```

FIG. 3S

```
                              1100          1120           1140
DPOL_VACCC  : YKS----------ADNPNMYLVTEYNKNN-----PETIELGERYYFAYICPAN----  : 838
DPOL_VACCV  : YKS----------ADNPNMYLVTEYNKNN-----PETIELGERYYFAYICPAN----  : 838
DPOL_VARV/  : YKS----------ADNPNMYLVTEYNKNN-----PETIELGERYYFAYICPAN----  : 837
DPOL_FOWPV  : YKS----------ATHSNFELVKRYNLEN-----TEKIEIGERYYYIYICDIS----  : 822
DPOD_BOVIN  : DYA----------GKQAHVELAERMRKRDP----GSAPSLGDRVPYVIISA------  : 691
DPOD_HUMAN  : DYA----------GKQAHVELAERMRKRDP----GSAPSLGDRVPYVIISA------  : 691
DPOD_CANAL  : -YS----------AKQAHVELAERMRKRDP----GSAPTLGDRVAYYVIIKT------  : 688
DPOD_YEAST  : -YT----------NPQPHAVLAERMKRRE-----GVGPNVGDRVDYVIIG-------  : 688
DPOD_SCHPO  : -YA----------AKMAHVELAERMRKRDA----GSAPAIGDRVAYYVIIKG------  : 688
DPOD_PLAFK  : -YE----------TRLPHVELAKKLKQRDS----ATAPNVGDRVSYIIVKG------  : 695
DPOL_CHVN2  : YKN----------ECQPHLHVSNKIFERT-----GFPVPSGARVPFVYIED------  : 695
DPOL_CHVP1  : YKN----------ECQPHLHVANKIYERT-----GFPVPSGARVPFVYIED------  : 694
DPOL_EBV/2  : YKS----------TQMPHLAVYQKFVERN-----EELPQIHDRIQYVFVEPK-----  : 725
DPOL_HSVSA  : YKT----------ENLPHLTVYKKIITRH-----EEPPQVHDRIPYVFV--------  : 717
DPOL_HSV11  : YTN----------KRLAHLTVYYKLMARR-----AQVPSIKDRIPYVIVAQTREVEE  : 798
DPOL_HSV21  : YTN----------KRLAHLTVYYKLMARR-----AQVPSIKDRIPYVIVAQTREVEE  : 802
DPOL_HSVEB  : YTN----------KRLPHLTVYFKLAMRN-----EELPSVKERIPYVIVAQTEAAER  : 804
DPOL_VZVD/  : YIN----------RRLAHLTVYYKLVMRQ-----GQIPNVRERIPYVIVAPTDEVEA  : 782
DPOL_HCMVA  : YRQ----------SNLPHIAVIKRLAARS-----EELPSVGDRVFYVLTAPGVRTAP  : 881
DPOL_MCMVS  : YKQ----------KNLPHLAVIRRLAARK-----EELPAVGDRVEYVLTLP------  : 765
DPOL_HSV6U  : YKQ----------PNLAHLSVIRRLAQRK-----EEIPNVGDRIMYVLIAP------  : 722
DPOA_HUMAN  : YPDK---------KSLPHVHVALWINSQG-----GRKVKAGDTVSYVICQDGSN---  : 712
DPOA_MOUSE  : YPDR---------KSLPHVHVALWINSQG-----GRKVKAGDTVSYVICQDGSN---  : 712
DPOA_DROME  : YRNS---------ASLPHVQVALRMNRER-----NRRYKKGDMVDLCDCLDGTT---  : 701
DPOA_SCHPO  : YPNG---------KTMPFVQVALKKKAR------GENVRVGDVIPFIIAGSDAD---  : 706
DPOA_YEAST  : YPGG---------KNMPAVQVALRMRKA------GRVVKAGSVITFVITKQDEI---  : 707
DPOA_TRYBB  : YHG----------TGYPHAVVALRMKQR------KEGVRVGDLIPYVICEGDE----  : 717
DPOL_NPVAC  : KRKSTDDN-EGPSPKRRVITVARHCREILVNKGTDFVPGNGDRIPYLLIDIEG----  : 741
DPOL_NPVLD  : AKRRKEED----PARKPVITIAKHCRELLANPGVDFLPGNGDRIQYVLVDVKE----  : 754
DPOZ_YEAST  : SEK----------TAPAGAVVVKRRINEDH-----RAEPQYKERIPYLVVKG------  : 697
DPOL_PYRFU  : YKAIG-----------PHVAVAKKLAAKG------VKIKPGMVIGYIVLRGDG----  : 684
DPO1_SULSO  : YKK----------NTPQHVKAALQLRPFG------VNVLPRDIIYYVKVRS------  : 664
DPO2_ECOLI  : YQR----------NVPPHVRAARLADEEN------Q--KRGRPLQYQNRGT------  : 675
DPol_Dtok   : YRATG-----------PHVAVAKRLAARG------IKIRPGTVISYIVLKG------  : 706
RM378       : VEE----------VMKMKKENVPISEIFIKMYDHTLPIHYKGALFASIIG--CKPP  : 753
RB69        : FPGP----------KCPFHIRGILTYNRAIKGNIDAPQVVEGEKVYVLPLR---EGN  : 839
```

FIG. 3T

```
                         .         1160          .        1180            .     1
DPOL_VACCC  : ----------------------------VPWTKKLVN----------------IKT : 850
DPOL_VACCV  : ----------------------------VPWTKKLVN----------------IKT : 850
DPOL_VARV/  : ----------------------------VPWTKKLVN----------------IKT : 849
DPOL_FOWPV  : ----------------------------LPWQKKLCN----------------ILS : 834
DPOD_BOVIN  : --------------------------------AK-------------------GVAA : 697
DPOD_HUMAN  : --------------------------------AK-------------------GVAA : 697
DPOD_CANAL  : --------------------------------G--------------------GDKN : 693
DPOD_YEAST  : --------------------------------G--------------------NDKL : 693
DPOD_SCHPO  : --------------------------------AQ-------------------GDQF : 694
DPOD_PLAFK  : --------------------------------VK-------------------GQAQ : 701
DPOL_CHVN2  : ------------------------------KKNL-------------------DTKQ : 703
DPOL_CHVP1  : ------------------------------KKNP-------------------DIKQ : 702
DPOL_EBV/2  : ------------------------------GGVKG------------------ARK  : 733
DPOL_HSVSA  : ------------------------------GKTT-------------------SCI  : 724
DPOL_HSV11  : TVARLAALRELDAAAPGDEPAPPAALPSPAKRPRETP---SPADPPGGASKPRKLLV : 852
DPOL_HSV21  : TVARLAALRELDAAAPGDEPAPPAALPSPAKRPRETP---SHADPPGGASKPRKLLV : 856
DPOL_HSVEB  : EAGVVNSMR----------G--TAQNPVVTKTARP-----QPK-------RKLLV : 835
DPOL_VZVD/  : DAKSVALLR----------G--DPLQNTAGKRCG------EAK-------RKLII : 812
DPOL_HCMVA  : QGSSDNGDSVTAGVVSRSDAIDGTDDDADGGGVEESNRRGGEPAKKRARKPPSAVCN : 938
DPOL_MCMVS  : ---------------------------DGCKKN--------------------VPN  : 774
DPOL_HSV6U  : -------------------------SIGNKQ----------------------THN  : 731
DPOA_HUMAN  : -------------------------LTASQ-----------------------R    : 718
DPOA_MOUSE  : -------------------------LTATQ-----------------------R    : 718
DPOA_DROME  : -------------------------NAAMQ-----------------------R    : 707
DPOA_SCHPO  : -------------------------GHPAD-----------------------R    : 712
DPOA_YEAST  : -------------------------DNAADTPA------------LSVAER       : 721
DPOA_TRYBB  : -------------------------HIDD------------------------K    : 722
DPOL_NPVAC  : ---------------------------------------------------KV     : 743
DPOL_NPVLD  : ---------------------------------------------------KI     : 756
DPOZ_YEAST  : -------------------------KQGQ------------------------LLR  : 704
DPOL_PYRFU  : -------------------------P---------------------------I    : 686
DPO1_SULSO  : ------------------------------------------------------    :  -
DPO2_ECOLI  : ---------------------------------------------------IKY    : 678
DPol_Dtok   : -------------------------PG--------------------------RV   : 710
RM378       : QMGDKIYWFYCTMLDPSRTNLPLSLEEVNPEHGSGVWDILKAGKKTHINRLRNIHAL : 810
RB69        : PFGDKCIAWPSG-----------------------------------------TEIT : 855
```

FIG. 3U

```
                   200         .        1220        .        1240           .
DPOL_VACCC  : YETIIDRSFKLGSDQRIFYEVYFK-RLTSEIVNLLDNKVLCIS--------------- : 892
DPOL_VACCV  : YETIIDRSFKLGSDQRIFYEVYFK-RLTSEIVNLLDNKVLCIS--------------- : 892
DPOL_VARV/  : YETIIDRSFKLGSDQRIFYEVYFK-RLTSEIVNLLDNKVLCIS--------------- : 891
DPOL_FOWPV  : YEVIADSKFYLPKDKRIFYEIYFK-RIASEVVNLLTDKTQC----------------- : 874
DPOD_BOVIN  : YMKSEDPLFVLEHSLPIDTQYYLEQQLAKPLLRIFEPILGE----------------- : 738
DPOD_HUMAN  : YMKSEDPLFVLEHSLPIDTQYYLEQQLAKPLLRIFEPILGE----------------- : 738
DPOD_CANAL  : YEKSEDPLYVLENSLPIDVKYYLDQQLTKPLERIFIPILGE----------------- : 734
DPOD_YEAST  : YNRAEDPLFVLENNIQVDSRYYLTNQLQNPIISIVAPIIGD----------------- : 734
DPOD_SCHPO  : YMRSEDPIYVLENNIPIDAKYYLENQLSKPLLRIFEPILGE----------------- : 735
DPOD_PLAFK  : YERAEDPLYVLDNNLAIDYNHYLD-AIKSPLSRIFEVIMQN----------------- : 741
DPOL_CHVN2  : SFRAEDPTFAQENDLIVDRLFYIEHQLMKPICSLFEPLLDD----------------- : 744
DPOL_CHVP1  : SFKAEDPTFAQDNGLIVDRLFYIEHQLLKPICSLFEPLLDD----------------- : 743
DPOL_EBV/2  : TEMAEDPAYAERHGVPVAVDHYFD-KLLQGAANILQCLFDN----------------- : 773
DPOL_HSVSA  : SNMAEDPTYTVQNNIPIAVDLYFD-KLIHGVANIIQCLFKD----------------- : 764
DPOL_HSV11  : SELAEDPAYAIAHGVALNTDYYFS-HLLGAACVTFKALFGN----------------- : 892
DPOL_HSV21  : SELAEDPGYAIARGVPLNTDYYFS-HLLGAACVTFKALFGN----------------- : 896
DPOL_HSVEB  : SDLAEDPTYVSENDVPLNTDYYFS-HLLGTISVTFKALFGN----------------- : 875
DPOL_VZVD/  : SDLAEDPIHVTSHGLSLNIDYYFS-HLIGTASVTFKALFGN----------------- : 852
DPOL_HCMVA  : YEVAEDPSYVREHGVPIHADKYFE-QVLKAVTNVLSPVFPG----------------- : 978
DPOL_MCMVS  : YEIAEDPRHVVEAKLSINAEKYYE-QVVKAVTNTLMPVFPR----------------- : 814
DPOL_HSV6U  : YELAEDPNYVIEHKIPIHAEKYFD-QIIKAVTNAISPIFPK----------------- : 771
DPOA_HUMAN  : AYAPEQLQKQDN--LTIDTQYYLAQQIHPVVARICEPIDGI----------------- : 757
DPOA_MOUSE  : AYAPEQLQKLDN--LAIDTQYYLAQQIHPVVARICEPIDGI----------------- : 757
DPOA_DROME  : AYHLDELKTSEDKKLQLDTNYYLGHQIHPVVTRMVEVLEGT----------------- : 748
DPOA_SCHPO  : AYSPQEIMNTNST-LVIDYNYYLSHQILPPIERVIAPIEGT----------------- : 752
DPOA_YEAST  : AHALNEVMIKSNN-LIPDPQYYLEKQIFAPVERLLERIDSF----------------- : 761
DPOA_TRYBB  : AYHIDEVRRSDG--LSVDVEWYLSSQLYPPVMRLCEHIQGF----------------- : 761
DPOL_NPVAC  : TEKAYPLRLFDP--VKMRISWIKHMGILCTFMNELLEIFGD----------------- : 782
DPOL_NPVLD  : TQKAFPLKLFDPDSPTLQISWLKHMNILCTFMNELIQVFGN----------------- : 797
DPOZ_YEAST  : ERCVSPEEFLEGENLELDSEYYINKILIPPLDRLFNLIGIN----------------- : 745
DPOL_PYRFU  : SNRAILAEEYDPKKHKYDAEYYIENQVLPAVLRILEGFGYR----------------- : 727
DPO1_SULSO  : --KDGVKPVQLAKVTEIDAEKYLE-ALRSTFEQILRAFGVS----------------- : 702
DPO2_ECOLI  : VWTTNGPEPLDYQRSPLDYEHYLTRQLQPVAEGILPFIEDN----------------- : 719
DPol_Dtok   : GDRAIPFDEFDPAKHRYDAEYYIENQVLPAVERILRAFGYRKEDLRYQKTKQAGLGA  : 767
RM378       : SIREDDEEGLEIVKKYIDRDKYCQIISEKTIDLLKSLGYVENTTKIKTVEDLIRFLV  : 867
RB69        : DLIKDDVLHWMDYTVLLEKTFIKPLEGFTSAAKLDYEKKASLF--------------- : 898
```

FIG. 3V

```
              1260
DPOL_VACCC : ------ :  -
DPOL_VACCV : ------ :  -
DPOL_VARV/ : ------ :  -
DPOL_FOWPV : ------ :  -
DPOD_BOVIN : ------ :  -
DPOD_HUMAN : ------ :  -
DPOD_CANAL : ------ :  -
DPOD_YEAST : ------ :  -
DPOD_SCHPO : ------ :  -
DPOD_PLAFK : ------ :  -
DPOL_CHVN2 : ------ :  -
DPOL_CHVP1 : ------ :  -
DPOL_EBV/2 : ------ :  -
DPOL_HSVSA : ------ :  -
DPOL_HSV11 : ------ :  -
DPOL_HSV21 : ------ :  -
DPOL_HSVEB : ------ :  -
DPOL_VZVD/ : ------ :  -
DPOL_HCMVA : ------ :  -
DPOL_MCMVS : ------ :  -
DPOL_HSV6U : ------ :  -
DPOA_HUMAN : ------ :  -
DPOA_MOUSE : ------ :  -
DPOA_DROME : ------ :  -
DPOA_SCHPO : ------ :  -
DPOA_YEAST : ------ :  -
DPOA_TRYBB : ------ :  -
DPOL_NPVAC : ------ :  -
DPOL_NPVLD : ------ :  -
DPOZ_YEAST : ------ :  -
DPOL_PYRFU : ------ :  -
DPO1_SULSO : ------ :  -
DPO2_ECOLI : ------ :  -
DPol_Dtok  : WLKPKT : 773
RM378      : ESEN-- : 871
RB69       : ------ :  -
```

FIG. 3W

```
                  .        20         .        40         .
T4-RNAlig  : MQELFNNLMELCKDSQRKFFYSDDVSASG-RTYRIFSYN-----YASYS---DWLLP :  48
ACNV-RNAli : ---MLHVSRLLANGGVKNLCDKFKVKIKNYTEHDLMVLN-----YESFER--DRDHP :  47
ORF-739f   : -MSMNVKYPVEYLIEHLNSFESPEVAVESLRKEGIMCKNRGDLYMFKYHLGCKFDKI :  56
                                  *                *

.        60         .        80         .       100         .
T4-RNAlig  : DALECRGIMFEMDGEKPVRIASRPMEKFFNLNENPFTMNI----------DLNDVDY :  95
ACNV-RNAli : VVVECRGLILNS---RTYAVVSRSFDRFFNFQELLQNIGG------------EDAHH :  89
ORF-739f   : YHLACRGAILRKT-DSGWKVLSYPFDKFFNWGEELQPEIVNYYQTLRYASPLNEKRK : 112
                 ***                *     ***  *

.       120         .       140         .       160         .
T4-RNAlig  : ----------ILTKEDGSLVSTYLDGDEILFKSKGSIKSE-----------QALMA : 130
ACNV-RNAli : KLFQSKENFKFYEKIDGSLIKIYKYNGEWHASTRGSAFAENLCVSD---VTFKRLVL : 143
ORF-739f   : AGFMFKLPMKLVEKLDGTCVVLYYDEG-WKIHTLGSIDANGSIVKNGMVTTHMDKTY : 168
                         * **       *              **

KX(D/N)G

.       180         .       200         .       220         .
T4-RNAlig  : NGILMNINHHRLRDRLKELAEDGFTANFEFVAPTNRIVLAYQEMK-IILLNVR---- : 182
ACNV-RNAli : QALQLDEAHNQFQALCNEYLDCASTHMFELTSKHNRIVTVYDEQPTLWYLASR---- : 196
ORF-739f   : RELFWETFEKKYPPYLLYHLNSSYCYIFEMVHPDARVVVPYEEPN-IILIGVRSVDP : 224
                                       **       *  *  * *        *

.       240         .       260         .       280         .
T4-RNAlig  : ---------------ENETGEYISYDDIYKDATLRPYLVERYEIDSPKWIEEAKNA : 223
ACNV-RNAli : ---------------NNETGDYFYCSNLPFCKYPKCYEFT----SVQECVEHAAQL : 233
ORF-739f   : EKGYFEVGPSEEAVRIFNESGGKINLKLPAVLSQEQNYTLFRANRLQELFEEVTPLF : 281
                             ** *                  *            *

.       300         .       320         .       340         .
T4-RNAlig  : ENIEGYVAVMK-----------DGSHFKIKSDWYVSLHSTKSSLDNPEKLFKTIID : 268
ACNV-RNAli : KNLEEGFVVYDK---------NNAPLCKIKSDVYLNMHKNQSRAENPTKLAQLVIN : 280
ORF-739f   : KSLRDGYEVVYEGFVAVQEIAPRVYYRTKIKHPVYLELHRIKTTIT-PEKLADLFLE : 337
                  *                    ***    *   *       * **

.       360         .       380         .        40         .
T4-RNAlig  : GASDDLKAMYADDEYSYRKIEAFETTYLKYLDRALFLVLDCHNKHCGKDRKTYAMEA : 325
ACNV-RNAli : GEHDDFLALFPHLKSVIKPYVDARNTFTNESTINIMVSGLTLNQQR-FNELVQTLPW : 336
ORF-739f   : NKLDDF-VLTPDEQETVMKLKEIYTDMRNQLESSFDTIYKEISEQVSPEENPGEFRK : 393
                  **

0         .       420         .       440         .
T4-RNAlig  : QGVAKGAGMDHLFGIIMSLYQGYDSQEKVMCEIEQNFLKNYKKF---------IPEG : 373
ACNV-RNAli : KCLAYRCRKAQTIDVESEFLKLTEPEKIKMIKNIIKFVSTKQALNNKLAPTIKLPSS : 393
ORF-739f   : R-FALR--LMDYHDKS-WFFARLDGDEEKMQKSEKKLLTERIEKG--------LFK- : 437
                      *                     *

T4-RNAlig  : Y : 374
ACNV-RNAli : K : 394
ORF-739f   : - : -
```

FIG. 4

```
                         .        20         .        40         .
Ecoli-polI  : --------MVQIPQNP-----LILVDGSSYLYR----AYHAFPPLTNSAGEPTGAMY   :  40
Taq-polI    : ---MRGMLPLFEPKGR-----VLLVDGHHLAYR----TFHALKGLTTSRGEPVQAVY   :  45
ORF_1218a   : MKRLRNMVNLIDLKNQYYAYSFKFFDSYQISWD----NYPHLKEFVIENYPGTYFSC   :  53
T4-RNaseH   : ----MDLEMMLDEDYKEG---ICLIDFSQIALSTALVNFPDKEKINLSMVRHLILNS   :  50
T7-gp6exo   : -MALLDLKQFYELREGCDDKGILVMDGDWLVFQAMS-AAEFDASWEEEIWHRCCDHA   :  55
                                                 *

.        60         .        80         .       100         .
Ecoli-polI  : GVLNMLRSLIMQYKP------THAAVVFDAKGKTFRDELFE-HYKSHR---------   :  81
Taq-polI    : GFAKSLLKALKEDG-------DAVIVVFDAKAPSFRHEAYG-GYKAGR---------   :  85
ORF_1218a   : YAPGILYKLFLKWK-------RGMIIDDYDRHPLRKKLLP-QYKEHRYEYIEGKYG   : 101
T4-RNaseH   : IKFNVKKAKTLGYT-------KIVLCIDNAKSGYWRRDFAY-YYKKNR-----GKAR   :  94
T7-gp6exo   : KARQILEDSIKSYETRKKAWAGAPIVLAFTDSVNWRKELVDPNYKANR--------K   : 104
                                         *                 **  *

.       120         .       140         .       160         .
Ecoli-polI  : -PPMP---DDLRAQIEPLHAMVKAMGLPLLA-------------------------V   : 109
Taq-polI    : -APTP---EDFPRQLALIKELVDLLGLARLE-------------------------V   : 113
ORF_1218a   : VVPFPGFLKYLKFHFEDLRFKMRDLGITDFKYALAISLFYNRVMLRDFLKNFTCYYI   : 158
T4-RNaseH   : EESTWDWEGYFESSHKVIDELKAYMPYIVMD-------------------------I   : 126
T7-gp6exo   : AVKKP------VGYFEFLDALFEREEFYCIR-------------------------E   : 130

.       180         .       200         .       220
Ecoli-polI  : SGVEADDVIGTLAREAEKA-GRPVLISTGDKDMAQLVTPNITLINTMTNTILGPEEV   : 165
Taq-polI    : PGYEADDVLASLAKKAEKE-GYEVRILTADKDLYQLLSDRIHVLHPEG-YLITPAWL   : 168
ORF_1218a   : AEYEADDVIAHLAREIARS-NIDVNIVSTDKDYYQLWDEEDIRERVYINSLSCSDVK   : 214
T4-RNaseH   : DKYEADDHIAVLVKKFSLE-GHKILIISSDGDFTQLHKYP--NVKQWS--PMHKKWV   : 178
T7-gp6exo   : PMLEGDDVMGVIASNPSAFGARKAVIISCDKDFKTIPNCDFLWCTTGN--------I   : 179
                *  **                    *         *   *

.       240         .       260         .       280
Ecoli-polI  : VNKYGVPPELIIDFLALMGDSSDNIPGVPGVGEKTAQALLQGLGG--LDTLYAEPEK   : 220
Taq-polI    : WEKYGLRPDQWADYRALTGDESDNLPGVKGIGEKTARKLLEEWGS--LEALLKNLDR   : 223
ORF_1218a   : TPRYG-----FLTIKALLGDKSDNIP--KSLEKGKGEKYLEKKG-------FAEEDY   : 257
T4-RNaseH   : KIKSG-SAEIDCMTKILKGDKKDNVASVKVRSDFWFTRVEGERTPSMKTSIVEAIAN   : 234
T7-gp6exo   : LTQTEESADWWHLFQTIKGDITDGYSGIAGWGDTAEDFLNNPFITEPKTSVLKSGKN   : 236
                             **    *

.       300         .       320         .       340
Ecoli-polI  : IAGLSFRGAKTMAAKLEQNKEVAYLSYQLATIKTDVELELTCEQLEVQQPAAEELLG   : 277
Taq-polI    : LK----P---AIREKILAHMDDLKLSWDLAKVRTDLPLEVDFAK--RREPDRERLRA   : 271
ORF_1218a   : DK----------ELFENNLKVIRFGDEYLGERDKSFIENFSTG--------DTLWN   : 295
T4-RNaseH   : DR--------EQAKVLLTESEYNRYKENLVLIDFDYIPDNIASN-------IVNYYN   : 276
T7-gp6exo   : KG-------------QEVTKWVKRDPEPHETLWDCIKSIGAKAG--------MTEED   : 272

.       360
Ecoli-polI  : LFKKYEFKRWTADVEAGKWLQAK------   : 300
Taq-polI    : FLERLEFGSLLHEFGLLESPKALEEAPWP   : 300
ORF_1218a   : FYEFFYYDPLHELFLRNIRKRRL------   : 318
T4-RNaseH   : SYKLPPRGKIYSYFVKAGLSKLTNSINEF   : 305
T7-gp6exo   : IIKQGQMARILRFNEYNFIDKEIYLWRP-   : 300
```

FIG. 5

```
                          .         20         .         40         .
DnaB_Ecoli  : VLDATVARIEQLFQQP-HDGVTGVNTGYDDLNKKTAG-LQPSDLIIVAARPSMGKTT :  55
DnaB-Hinfl  : VLESTIEKIDILSKLENHSGVTGVTTGFTDLDKKTAG-LQPSDLIIVAARPSMGKTT :  56
DnaB-Ctrac  : ALQERQEAFQASAHDSSSPMLSGFPTHFLDLDKMISG-FSPSNLIILAARPAMGKTA :  56
DnaB-Bstea  : ILVQTYDNIEMLHNRD--GEITGIPTGFTELDRMTSG-FQRSDLIIVAARPSVGKTA :  54
DnaB-Hpylo  : VLESAMDLITENQRKG-SLEVTGIPTGFVQLDNYTSG-FNKGSLVIIGARPSMGKTS :  55
DnaB-Mgeni  : EIANQEEALIKKVHRG-ELIISGLSSGFLKLDQLTSG-WKPGELIVIAARPGRGKTA :  55
DnaB-Bburg  : IAERVHNEIYERSMKK-KEANFGIPSGFRKVDSLIGG-FRNSDFIIVGARPSIGKTA :  55
T4-gp41     : YVGHDWMDDYEARWLSYMNKARKVPFKLRILNKITKGGAETGTLNVLMAGVNVGKSL :  57
T7-gp4      : VVSALSLRERIREHLSSEESVGLLFSGCTGINDKTLG-ARGGEVIMVTSGSGMGKST :  56
ORF1293b    : VSLVEEFDLATSEFNELFVKEERIPTPWESVNKNMAGGLGRGELGIVMLPSGWGKSW :  57
                                *                               **
                                                                motif H1

60         .         80         .        100         .
DnaB_Ecoli  : FAMNLVENAAMLQD---KPVLIFSLEMPSEQIMMRSLASLSRVDQTKIRTGQ-LDDE : 108
DnaB-Hinfl  : FAMNLCENAAMASE---KPVLVFSLEMPAEQIMMRMIASLARVDQTKIRTGQNLDEI : 110
DnaB-Ctrac  : LALNIVENFCFDSR---LPVGIFSLEMTVDQLIHRIICSRSEVEAKKISVGD-ISGR : 109
DnaB-Bstea  : FALNIAQNVATKTN---ENVAIFSLEMSAQQLVMRMLCAEGNINAQNLRTGK-LTPE : 107
DnaB-Hpylo  : LMMNMVLS-ALNDD---RGVAVFSLEMSAEQLALRALSDLTSINMHDLESGR-LDDD : 107
DnaB-Mgeni  : LLINFMASAAKQIDPKTDVVLFFSLEMRNREIYQRHLMHESQTSYTLTNRQR--INN : 110
DnaB-Bburg  : FALNIASYIALRKEEK-KKVGFFSLEMTADALIKRIISSQSCIDSFKVQNSI-LSGQ : 110
T4-gp41     : GLCSLAAD-YLQLG---HNVLYISMEMAEEVCAKRIDANMLDVSLDDIDDGH-ISYA : 109
T7-gp4      : FVRQQALQWGTAMG---KKVGLAMLEESVEETAEDLIGLHNRVRLRQSDSLK-REII : 109
ORF1293b    : FLVSLGLH-AFRTG---KRVIYFTLELDQKYVMKRFLKMFAPYCKGRASSYR----D : 106
                                  *      *
                                     motif H1a 120         .        140         .        160         .
DnaB_Ecoli  : DWARISGTMGILLEKRNIYIDDSSG--LTPTEVRSRARRIAR-EH-GGIGLIMIDYL : 161
DnaB-Hinfl  : EWNKIASVVGMFKQKNNLFIDDSSG--LTPTDVRSRARRVYR-EN-GGLSMIMVDYL : 163
DnaB-Ctrac  : DFQRVVSVVREMEEHT-LLIDDYPG--LKITDLRARARRMK--ES-YDIQFLVIDYL : 160
DnaB-Bstea  : DWGKLTMAMGSLSNAG-IYIDDTPS--IRVSDIRAKCRRLKQ-ES--GLGMIVIDYL : 158
DnaB-Hpylo  : QWENLAKCFDHLSQKK-LFFYDKSY--VRIEQIRLQLRKLKS-QH-KELGIAFIDYL : 159
DnaB-Mgeni  : VFEELMEASSRIKNLP-IKLFDYSS--LTLQEIRNQITEVSK-TS--NVRLVIIDYL : 161
DnaB-Bburg  : EIKSLNDIINEISDSE-LYIEDTPN--ISLLTLATQARKLKR-FY--GIDIIFVDYI : 161
T4-gp41     : EYKGKMEKWREKSTLGRLIVKQYPTGGADANTFRSLLNELKLKKN-FVPTIIIVDYL : 165
T7-gp4      : ENGKFDQWFDELFGNDTFHLYDS----FAEAETDRLLAKLAYMRSGLGCDVIILDHI : 162
ORF1293b    : VYQIMKELMFSQDNLLKIVFCN------AMEDIEHYIALYN-------PDVVLIDYA : 150
                                                                         *
                                                                motif H2

180         .        200         .        220
DnaB_Ecoli  : QLMRVP---ALSDNRTLEIAEISRSLKALAKELNVPVVALSQLNR---SLEQRADKR : 212
DnaB-Hinfl  : QLMRAP---AFSDNRTLEIAEISRSLKALAKELQVPVVALSQLNR---TLEQRGDKR : 214
DnaB-Ctrac  : QLISSSGNLRNSDSRNQEISEISRMLKNLARELNIPILCLSQLSR---KVEDRANHR : 214
DnaB-Bstea  : QLIQGSG--RSKENRQQEVSEISRSLKALARELEVPVIALSQLSR---SVEQRQDKR : 210
DnaB-Hpylo  : QLMSGS---KATKERHEQIAEISRELKTLARELEIPIIALVQLNR---SLENRDDKR : 210
DnaB-Mgeni  : QLVNALKN-NYGLTRQQEVTMISQSLKAFAKEFNTPIIAAAQLSR---RIEERKDSR : 214
DnaB-Bburg  : SLISFET---KNLPRHEQVASISKSLKELARELEIPIVALSQLTR---DTEGRE--- : 209
T4-gp41     : GICKSCRIRVYSENSYTTVKAIAEELRALAVETETVLWTAAQVGK---QAWDSSD-- : 217
T7-gp4      : SIVVSAS---GESDERKMIDNLMTKLKGFAKSTGVVLVVICHLKNPDKGKAHEEGRP : 216
ORF1293b    : DLIYDVET--DKEKNYLLLQKIYRKLRLIAKVYNTAVWSASQLNRG--SLSKQADVD : 203
                                 *  *
                                                                motif H3
```

FIG. 6A

```
                    .        240          .        260         .        280
DnaB_Ecoli  : PVNSDLRESGSIEQDADLIMFIYRDEVYHENSDLK-------------------- : 247
DnaB-Hinfl  : PVNSDLRESGSIEQDADLIMFIYRDEVYNDNSEDK-------------------- : 249
DnaB-Ctrac  : PLMSDLRESGSIEQDADQIMFLLRREYYDPN-DKP-------------------- : 248
DnaB-Bstea  : PMMSDIRESGSIEQDADIVAFLYRDDYYNKDSENK-------------------- : 245
DnaB-Hpylo  : PILSDIKDSGGIEQDADIVLFLYRGYIYQMRAEDNKIDKLKKEGKIEEAQELYLKVN : 267
DnaB-Mgeni  : PILSDLRESGSIEQDADMVLFIHRTNDDKKEQEEENTN----------------- : 252
DnaB-Bburg  : PNLASLRESGALEQDADIVILLHRDKDFKFESSAEIEP----------------- : 247
T4-gp41     : VNMSDIAESAGLPATADFMLAVIETEELAAAEQQLIKQIKSRYGDKNKWNKFLMG-- : 272
T7-gp4      : VSITDLRGSGALRQLSDTIIALERNQQGDMPNLVLVR------------------ : 253
ORF1293b    : FIEKYIADSFAKVVEIDFGMAFIPDSENSTPDIHVG------------------- : 239
                           *        *
                        motif H4

.        300          .        320         .        340
DnaB_Ecoli  : ------------GIAEIIIGKQRNGPIGTVRLTFNGQWSRFDNYAGP-QYDDE---- : 287
DnaB-Hinfl  : ------------GVAEIIIGKQRNGPIGRVRLKFNGQFSRFDNLAEQREYRDDY--- : 291
DnaB-Ctrac  : ------------GTAELIVAKNRHGSIGSVQLVFEKDFARFRNYAGC-EFPG----- : 287
DnaB-Bstea  : ------------NIIEIIIAKQRNGPVGTVQLAFIKEYNKFVNLERR--FDEAQIPP : 288
DnaB-Hpylo  : EERRIHKQNGSIEEAEIIVAKNRNGATGTVYTRFNAPFTRYEDMPIDSHLEEGQETK : 324
DnaB-Mgeni  : ------------LFEVELILEKNRNGPNGKVKLNFRSDTSSFISQYSP-SFDDQYS-- : 295
DnaB-Bburg  : ------------IETKVIVAKHRNGPTGRADILFLPHITKFVNKDHQY--------- : 283
T4-gp41     : ---------VQKGNQKWVEIEQDSTPTEVNEVAGSQQIQAEQNRYQRNESTRAQLDA : 320
T7-gp4      : -------------ILKCRFTGDTGIAGYMEYNKETGWLEPSSYSGEEESHSESTDW : 296
ORF1293b    : --------------FGKIFKNRMGAVRKLEYTINFENYTVDVAVK----------- : 270

.
DnaB_Ecoli  : -------- :  -
DnaB-Hinfl  : -------- :  -
DnaB-Ctrac  : -------- :  -
DnaB-Bstea  : GA------ : 290
DnaB-Hpylo  : VDYDIVTT : 332
DnaB-Mgeni  : -------- :  -
DnaB-Bburg  : -------- :  -
T4-gp41     : LANELKF- : 327
T7-gp4      : SNDTDF-- : 302
ORF1293b    : -------- :  -
```

FIG. 6B

```
      -------|----------|----------|----------|----------|----------|---
    1 attttctgttttttcacaggcaagtattcgacatgctcgaaacccgcgaagcttattatcagt 63

-------|----------|----------|----------|----------|----------|------
   64 tgcttcaatcgttaaacgatttcctcgaagaagacctgaaggagaattatgaagatcacgcta 126
                                                        M  K  I  T  L    5

---|----------|----------|----------|----------|----------|---------
  127 agcgcaagcgtataccccgatcgatgaaaatttacggagtggagctaatcgaggggaaaaaa 189
    6 S  A  S  V  Y  P  R  S  M  K  I  Y  G  V  E  L  I  E  G  K  K   26

|----------|----------|----------|----------|----------|----------|--
  190 cacttatttcaatcacccgtaccccacatttgaagcgcatcgctcagcagaatcgagggaag 252
   27 H  L  F  Q  S  P  V  P  P  H  L  K  R  I  A  Q  Q  N  R  G  K   47

-------|----------|----------|----------|----------|----------|-----
  253 attgaggctgaggctatatcctattacatcagagaacaaaaaagccacatcacgccggaagct 315
   48 I  E  A  E  A  I  S  Y  Y  I  R  E  Q  K  S  H  I  T  P  E  A   68

----|----------|----------|----------|----------|----------|--------
  316 ttgtctcagtgcgtctttatcgatattgagacgatttccccgaaaaaaagctttcccgacccg 378
   69 L  S  Q  C  V  F  I  D  I  E  T  I  S  P  K  K  S  F  P  D  P   89

-|----------|----------|----------|----------|----------|----------|-
  379 tggagagacccagtttattccatttccatcaaaccgtatggaaaaccggtggtggtagtgctt 441
   90 W  R  D  P  V  Y  S  I  S  I  K  P  Y  G  K  P  V  V  V  V  L  110

--------|----------|----------|----------|----------|----------|----
  442 ctccttatcaccaacccggaggctcatatcgataactttaacaaatttaccaccagcgtaggg 504
  111 L  L  I  T  N  P  E  A  H  I  D  N  F  N  K  F  T  T  S  V  G  131

------|----------|----------|----------|----------|----------|-------
  505 gataacacatttgaaattcattacagaacattcctttcggaaaaaagattgctcgagtatttc 567
  132 D  N  T  F  E  I  H  Y  R  T  F  L  S  E  K  R  L  L  E  Y  F  152

--|----------|----------|----------|----------|----------|----------|
  568 tggaatgtgctgaaaccaaaatttactttcatgctcgcatggaacggttatcagttcgattat 630
  153 W  N  V  L  K  P  K  F  T  F  M  L  A  W  N  G  Y  Q  F  D  Y  173

----------|----------|----------|----------|----------|----------|---
  631 ccctacctgctcattcgtagtcatatccatgaggtgaatgtcattagtgataagttgcttccg 693
  174 P  Y  L  L  I  R  S  H  I  H  E  V  N  V  I  S  D  K  L  L  P  194

------|----------|----------|----------|----------|----------|------
  694 gactggaagctggtgcggaaaatttccgatcgaaacctaccattctatttcaatccccgtacc 756
  195 D  W  K  L  V  R  K  I  S  D  R  N  L  P  F  Y  F  N  P  R  T  215

---|----------|----------|----------|----------|----------|---------
  757 cctgtagaatttgtgttttttgattacatgcggctttatcgctcctttgtggcatacaaagag 819
  216 P  V  E  F  V  F  F  D  Y  M  R  L  Y  R  S  F  V  A  Y  K  E  236

|----------|----------|----------|----------|----------|----------|--
  820 ttggagtcctaccggctcgactatattgcgcgagaggaaataggagaaggtaaggtggatttc 882
  237 L  E  S  Y  R  L  D  Y  I  A  R  E  E  I  G  E  G  K  V  D  F  257

-------|----------|----------|----------|----------|----------|-----
  883 gacgtaagattctatcatgagattcctgtctacccggataaaaagttggtggaatacaacgcc 945
  258 D  V  R  F  Y  H  E  I  P  V  Y  P  D  K  K  L  V  E  Y  N  A  278
```

FIG. 7A

```
         ----|---------|---------|---------|---------|---------|--------
     946 gtagacgccattttgatggaagaaatcgaaaataaaaaccatattctcccgacgctgtttgaa 1008
     279 V   D   A   I   L   M   E   E   I   E   N   K   N   H   I   L   P   T   L   F   E  299

-|---------|---------|---------|---------|---------|---------|-
    1009 attgcaagactttcaaatctgactcccgcactggcattgaacgcttccaatattcttatcgga 1071
     300 I   A   R   L   S   N   L   T   P   A   L   A   L   N   A   S   N   I   L   I   G  320

---------|---------|---------|---------|---------|---------|----
    1072 aatgttacaggaaaacttggtgtcaaattcgttgattacatcaagaaaatcgacaccattaat 1134
     321 N   V   T   G   K   L   G   V   K   F   V   D   Y   I   K   K   I   D   T   I   N  341

-----|---------|---------|---------|---------|---------|-------
    1135 acaatgttcaaaaaaatacctgagtaaactatgaatatgcagaccattgacgaaacgctttat 1197
     342 T   M   F   K   K   I   P   E   *  350
```

FIG. 7B

```
          ----------|----------|----------|----------|----------|----------|---
  1 ctatacggatgaagttttgagaattattgatctttctccactcgatggcgtattatacaaatg 63

-------|----------|----------|----------|----------|----------|------
 64 tgatttaaaagacacctaccttatcgaggtgaaagatacccattttgatcccgcaatgtaaaa 126

---|----------|----------|----------|----------|----------|----------
127 caaacgtattctgctatgaacatcaacaagtatcgttatcgcggtgcttacattgaacttacc 189
                    M  N  I  N  K  Y  R  Y  R  G  A  Y  I  E  L  T    16

|----------|----------|----------|----------|----------|----------|--
190 aaccccgatatttacttcaacgtattcgatcttgatttacatcgctgtacccctctgtaatc 252
 17 N  P  D  I  Y  F  N  V  F  D  L  D  F  T  S  L  Y  P  S  V  I    37

--------|----------|----------|----------|----------|----------|-----
253 agcaaattcaatatcgatcccgctacgttcgtaacggagttttacgggtgtatgcgggtggag 315
 38 S  K  F  N  I  D  P  A  T  F  V  T  E  F  Y  G  C  M  R  V  E    58

----|----------|----------|----------|----------|----------|--------
316 aacaaagtgattccggtagatcaggaagaaccggaattcgggtttcccctctacatcttcgat 378
 59 N  K  V  I  P  V  D  Q  E  E  P  E  F  G  F  P  L  Y  I  F  D    79

-|----------|----------|----------|----------|----------|----------|-
379 tcagggatgaacccttcttaccggagtgaacccctctttgtcatcaacagctttgaggaactc 441
 80 S  G  M  N  P  S  Y  R  S  E  P  L  F  V  I  N  S  F  E  E  L   100

---------|----------|----------|----------|----------|----------|----
442 cggcaattttttaaaaagtcgaaatatcattatggtgcccaacccgtcgggtatctgctggttt 504
101 R  Q  F  L  K  S  R  N  I  I  M  V  P  N  P  S  G  I  C  W  F   121

-----|----------|----------|----------|----------|----------|-------
505 tacaggaaagagccggttggcgtgcttccttctatcattcgggagattttcacccgacgtaag 567
122 Y  R  K  E  P  V  G  V  L  P  S  I  I  R  E  I  F  T  R  R  K   142

--|----------|----------|----------|----------|----------|----------|
568 gaagaacgtaagcttttcaaagaaactggcaacatggaacaccatttccgtcaatgggcactt 630
143 E  E  R  K  L  F  K  E  T  G  N  M  E  H  H  F  R  Q  W  A  L   163

---------|----------|----------|----------|----------|----------|---
631 aaaattatgatgaactccatgtacggtatcttcggaaaccgttcggtgtacatggggtgcctt 693
164 K  I  M  M  N  S  M  Y  G  I  F  G  N  R  S  V  Y  M  G  C  L   184

-------|----------|----------|----------|----------|----------|------
694 cccattgcggaaagtgtaaccgccgccgggcgcatgtctattcgctccgtgatttctcagatt 756
185 P  I  A  E  S  V  T  A  A  G  R  M  S  I  R  S  V  I  S  Q  I   205

---|----------|----------|----------|----------|----------|----------
757 cgcgatcgcttcatttattcgcataccgactccatttttcgtcaaagcttttacggatgatccg 819
206 R  D  R  F  I  Y  S  H  T  D  S  I  F  V  K  A  F  T  D  D  P   226

|----------|----------|----------|----------|----------|----------|--
820 gtggcggaagccggtgagcttcaagaacatctcaactcttttatcaatgactatatggaaaat 882
227 V  A  E  A  G  E  L  Q  E  H  L  N  S  F  I  N  D  Y  M  E  N   247

-------|----------|----------|----------|----------|----------|-----
883 aactttaatgcaagagaagatttcaagctggagttaaagcaggagttcgtgttcaaatccatt 945
248 N  F  N  A  R  E  D  F  K  L  E  L  K  Q  E  F  V  F  K  S  I   268
```

FIG. 8A

```
          ----|----------|----------|----------|----------|----------|--------
  946 cttatcaaagaaatcaaccgctactttgcggttactgtagacggtaaagaagagatgaaggga 1008
  269  L  I  K  E  I  N  R  Y  F  A  V  T  V  D  G  K  E  E  M  K  G  289

-|----------|----------|----------|----------|----------|----------|-
 1009 atcgaagtgatcaactcttcggtgcctgaaattgtcaagaagtatttcaggggttacctgaag 1071
  290  I  E  V  I  N  S  S  V  P  E  I  V  K  K  Y  F  R  G  Y  L  K  310

---------|----------|----------|----------|----------|----------|----
 1072 tatatcagccaacccgacatcgatgtcatttccgccaccatagcgttctacaataactttgtg 1134
  311  Y  I  S  Q  P  D  I  D  V  I  S  A  T  I  A  F  Y  N  N  F  V  331

-----|----------|----------|----------|----------|----------|-------
 1135 tctcaaaagaatttctggtctattgaagatctctatcacaaaatgaaaatatcttcgtctgac 1197
  332  S  Q  K  N  F  W  S  I  E  D  L  Y  H  K  M  K  I  S  S  S  D  352

--|----------|----------|----------|----------|----------|----------|
 1198 agcgccgaaagatatgtggagtatgtagaggaagttatgaagatgaaaaaggagaatgtccca 1260
  353  S  A  E  R  Y  V  E  Y  V  E  E  V  M  K  M  K  K  E  N  V  P  373

---------|----------|----------|----------|----------|----------|---
 1261 atctctgagatattcataaaaatgtatgaccatacacttcccattcattataagggagcgctt 1323
  374  I  S  E  I  F  I  K  M  Y  D  H  T  L  P  I  H  Y  K  G  A  L  394

-------|----------|----------|----------|----------|----------|------
 1324 ttcgcttccattataggatgcaaaccccccgcaaatgggagacaagatctactggttctactgc 1386
  395  F  A  S  I  I  G  C  K  P  P  Q  M  G  D  K  I  Y  W  F  Y  C  415

---|----------|----------|----------|----------|----------|---------
 1387 accatgctggatccttccagaaccaatctcccgctttctctggaagaagttaaccccgaacat 1449
  416  T  M  L  D  P  S  R  T  N  L  P  L  S  L  E  E  V  N  P  E  H  436

|----------|----------|----------|----------|----------|----------|--
 1450 gggagcggcgtgtgggatattctgaaagcgggaaagaaaacgcatatcaacaggctccgcaat 1512
  437  G  S  G  V  W  D  I  L  K  A  G  K  K  T  H  I  N  R  L  R  N  457

--------|----------|----------|----------|----------|----------|-----
 1513 atccacgcacttagcatacgtgaggatgatgaggagggtcttgaaatcgttaaaaaatacata 1575
  458  I  H  A  L  S  I  R  E  D  D  E  E  G  L  E  I  V  K  K  Y  I  478

----|----------|----------|----------|----------|----------|--------
 1576 gatagagacaaatactgtcagatcatttcagagaaaacaattgatctgctgaaaagtctcggg 1638
  479  D  R  D  K  Y  C  Q  I  I  S  E  K  T  I  D  L  L  K  S  L  G  499

-|----------|----------|----------|----------|----------|----------|-
 1639 tatgttgaaaatactacaaagataaaaaccgttgaggatcttattcgttttcttgtagagagt 1701
  500  Y  V  E  N  T  T  K  I  K  T  V  E  D  L  I  R  F  L  V  E  S  520

---------|----------|----------|----------|----------|----------|----
 1702 gaaaactaaacccattagcgccatgattctcaaattcgacactgaaggcattgttcgtatcct 1764
  521  E  N  *  523
```

FIG. 8B

```
          ----------|----------|----------|----------|----------|----------|---
      1   ccggtttgatacccgtattggtcatttccttgtggaaaccccggttgaaaagtggagtaacaa   63

------|----------|----------|----------|----------|----------|------
     64   aatgttgcgcgtagctgaaaaacttgtaaccaattcccgtaaacagatttacgaaggaggtgt   126

---|----------|----------|----------|----------|----------|---------
    127   gtgattgctacggtttcctatccggaaactatgaagttgtagacgaactccctgatcaaccga   189

|----------|----------|----------|----------|----------|----------|--
    190   cgcttccgaaaactcaaaacaagacttatagtacgctatggaatcgatgaacgtaaaataccc   252
                                                            M  N  V  K  Y  P    6

-------|----------|----------|----------|----------|----------|-----
    253   ggttgagtaccttatcgaacacctgaactcttttgagtctccggaagtagccgtcgaatccct   315
      7    V  E  Y  L  I  E  H  L  N  S  F  E  S  P  E  V  A  V  E  S  L       28

----|----------|----------|----------|----------|----------|--------
    316   tcgcaaggaggggattatgtgcaaaaacggggtgatctatacatgttcaaatatcaccttgg   378
     29    R  K  E  G  I  M  C  K  N  R  G  D  L  Y  M  F  K  Y  H  L  G      49

-|----------|----------  ----------|----------|----------|---------|-
    379   ttgtaagtttgataagatatatcaccttgcctgtcgcggggcgattctccgcaaaacggatag   441
     50    C  K  F  D  K  I  Y  H  L  A  C  R  G  A  I  L  R  K  T  D  S      70

--------|----------|----------|----------|----------|----------|----
    442   tggttggaaagttctgtcttatccctttgacaaattttttcaactgggggggaagaactccagcc   504
     71    G  W  K  V  L  S  Y  P  F  D  K  F  F  N  W  G  E  E  L  Q  P      91

-----|----------|----------|----------|----------|----------|-------
    505   ggaaatcgtaaactattatcagacgcttcgttacgcgtctcccctgaatgaaaagcgcaaagc   567
     92    E  I  V  N  Y  Y  Q  T  L  R  Y  A  S  P  L  N  E  K  R  K  A     112

--|----------|----------|----------|----------|----------|----------|
    568   cggtttcatgttcaaacttcccatgaaactggttgaaaagctggatggtacttgtgtggtttt   630
    113    G  F  M  F  K  L  P  M  K  L  V  E  K  L  D  G  T  C  V  V  L     133

----------|----------|----------|----------|----------|----------|---
    631   atattatgatgaagggtggaaaattcacactcttggagtattgacgcaaatggatccattgt   693
    134    Y  Y  D  E  G  W  K  I  H  T  L  G  S  I  D  A  N  G  S  I  V     154

------|----------|----------|----------|----------|----------|------
    694   caaaaacggaatggttaccactcatatggataaaacatatcgagaattgttctgggaaacctt   756
    155    K  N  G  M  V  T  T  H  M  D  K  T  Y  R  E  L  F  W  E  T  F     175

---|----------|----------|----------|----------|----------|---------
    757   tgaaaagaaatatccgccttaccttctctatcatttgaactcctcatactgttacatatttga   819
    176    E  K  K  Y  P  P  Y  L  L  Y  H  L  N  S  S  Y  C  Y  I  F  E     196

|----------|----------|----------|----------|----------|----------|--
    820   aatggttcatccggacgcgcgagtggtggttccttatgaggagccaaatatcattctgatcgg   882
    197    M  V  H  P  D  A  R  V  V  V  P  Y  E  E  P  N  I  I  L  I  G     217

-------|----------|----------|----------|----------|----------|-----
    883   tgtgcgttcggtggatccggagaagggatatttcgaggtgggtccctccgaagaagccgtacg   945
    218    V  R  S  V  D  P  E  K  G  Y  F  E  V  G  P  S  E  E  A  V  R     238
```

FIG. 9A

```
      ----|---------|---------|---------|---------|---------|--------
 946  cattttcaacgaaagtggcggaaaaataaatcttaagctaccggctgttctgtctcaagagca  1008
 239   I  F  N  E  S  G  G  K  I  N  L  K  L  P  A  V  L  S  Q  E  Q   259

-|---------|---------|---------|---------|---------|---------|-
1009  aaactatactctttttcgtgccaatcgccttcaggaactatttgaggaagttacaccgctttt  1071
 260   N  Y  T  L  F  R  A  N  R  L  Q  E  L  F  E  E  V  T  P  L  F   280

--------|---------|---------|---------|---------|---------|----
1072  caaaagcctgagagacggttatgaggtggtatatgaaggatttgtagccgtacaggaaattgc  1134
 281   K  S  L  R  D  G  Y  E  V  V  Y  E  G  F  V  A  V  Q  E  I  A   301

-----|---------|---------|---------|---------|---------|-------
1135  cccgcgtgtttattaccgcacaaagatcaagcacccggtatatctggagctccaccggattaa  1197
  P    R  V  Y  Y  R  T  K  I  K  H  P  V  Y  L  E  L  H  R  I  K   322

--|---------|---------|---------|---------|---------|---------|
1198  aactacaatcactcctgagaagctcgccgatctttttcttgaaaacaaacttgatgatttttgt  1260
 323   T  T  I  T  P  E  K  L  A  D  L  F  L  E  N  K  L  D  D  F  V   343

---------|---------|---------|---------|---------|---------|---
1261  acttaccccggatgaacaggaaaccgtgatgaaactcaaagaaatttataccgatatgcgaaa  1323
 344   L  T  P  D  E  Q  E  T  V  M  K  L  K  E  I  Y  T  D  M  R  N   364

------|---------|---------|---------|---------|---------|------
1324  tcagcttgagtcatcttttgatacgatttataaagagatttccgaacaggtttctccggaaga  1386
 365   Q  L  E  S  S  F  D  T  I  Y  K  E  I  S  E  Q  V  S  P  E  E   385

---|---------|---------|---------|---------|---------|---------
1387  aaaccccggagagtttcgcaaaaggttcgctcttcgacttatggattatcatgataaaagttg  1449
 386   N  P  G  E  F  R  K  R  F  A  L  R  L  M  D  Y  H  D  K  S  W   406

|---------|---------|---------|---------|---------|---------|--
1450  gttttttgcccgccttgacggcgacgaagagaaaatgcaaaagtcggaaaagaagcttctaac  1512
 407   F  F  A  R  L  D  G  D  E  E  K  M  Q  K  S  E  K  K  L  L  T   427

-------|---------|---------|---------|---------|---------|-----
1513  ggagagaattgaaaagggttatttaaataaaaatgataaaaaagcgtaatcctcttttctgg  1575
 428      E  R  I  E  K  G  L  F  K  *  437

----|---------|---------|---------|---------
 576  ggaagacgggaactcaatcttcttcagcattttgcccttgaagc  1619
```

FIG. 9B

```
        ---------|---------|---------|---------|---------|---------|---
  1 gcttcgtcaaaactcacgtctatagtatctatgtcgtagggttcgaggttggaggcaatcagg 63

------|---------|---------|---------|---------|---------|------
 64 ttgaacagttcatcataatcataattctcgaaaagaatgttgcgaataccgatccctctttct 126

---|---------|---------|---------|---------|---------|---------
127 ggatcgtagggatattccccggctcgatgaaaagcaggagttttatcttatcgatcaggagt 189

|---------|---------|---------|---------|---------|---------|--
190 tttaccgggtcatcaggaaatctgaaattcggtgcagtgtcgttcagatagaacatttcattt 252

-------|---------|---------|---------|---------|---------|-----
253 ttgtttaaataaatcctcgaggaatcttcaaataaagagggcgttaatggatgaaaagactg 315
                                                    M  K  R  L    4

----|---------|---------|---------|---------|---------|--------
316 aggaatatggtcaatcttatcgatctcaaaaatcagtattatgcttactctttcaagttttc 378
  5  R  N  M  V  N  L  I  D  L  K  N  Q  Y  Y  A  Y  S  F  K  F  F   25

-|---------|---------|---------|---------|---------|---------|-
379 gactcctatcagatcagctgggataattacccgcatcttaaagagttcgtcattgaaaactat 441
 26  D  S  Y  Q  I  S  W  D  N  Y  P  H  L  K  E  F  V  I  E  N  Y   46

--------|---------|---------|---------|---------|---------|----
442 cccggcacttattttcatgctacgctccggggattctgtacaagcttttcctcaaatggaag 504
 47  P  G  T  Y  F  S  C  Y  A  P  G  I  L  Y  K  L  F  L  K  W  K   67

-----|---------|---------|---------|---------|---------|-------
505 cggggtatgatcattgacgactatgaccgacacccgctccgaaagaagttacttcctcagtac 567
 68  R  G  M  I  I  D  D  Y  D  R  H  P  L  R  K  K  L  L  P  Q  Y   88

--|---------|---------|---------|---------|---------|---------|
568 aaagagcaccgctatgaatacattgagggaaaatacggtgtggttccttttccccgggtttctg 630
 89  K  E  H  R  Y  E  Y  I  E  G  K  Y  G  V  V  P  F  P  G  F  L   109

---------|---------|---------|---------|---------|---------|---
631 aaatatctgaagttccactttgaggacttgcggtttaaaatgcgcgatcttggaatcaccgat 693
110  K  Y  L  K  F  H  F  E  D  L  R  F  K  M  R  D  L  G  I  T  D   130

------|---------|---------|---------|---------|---------|------
694 ttcaaatatgcacttgccatttctctttttttacaacccgggtaatgctcagagattttctgaaa 756
131  F  K  Y  A  L  A  I  S  L  F  Y  N  R  V  M  L  R  D  F  L  K   151

---|---------|---------|---------|---------|---------|---------
757 aactttacctgttattacattgccgaatatgaagctgacgatgtaatcgcacatctggcgcgt 819
152  N  F  T  C  Y  Y  I  A  E  Y  E  A  D  D  V  I  A  H  L  A  R   172

|---------|---------|---------|---------|---------|---------|--
820 gagattgcacgaagcaatatcgacgtaaacatcgtctcaacggataaagattattaccagcta 882
173  E  I  A  R  S  N  I  D  V  N  I  V  S  T  D  K  D  Y  Y  Q  L   193

-------|---------|---------|---------|---------|---------|-----
883 tgggatgaagaggatataagagaaagggtttatatcaattctctttcatgtagtgatgtgaag 945
194  W  D  E  E  D  I  R  E  R  V  Y  I  N  S  L  S  C  S  D  V  K   214
```

FIG. 10A

```
        ----|---------|---------|---------|---------|---------|--------
     946 acaccccgctacggatttcttaccattaaagcacttcttggagacaaaagcgataacattccc 1008
     215 T  P  R  Y  G  F  L  T  I  K  A  L  L  G  D  K  S  D  N  I  P  235

-|---------|---------|---------|---------|---------|---------|-
    1009 aaatctctggaaaaaggaaaaggcgaaaagtatcttgaaaagaaaggatttgcggaggaagat 1071
     236 K  S  L  E  K  G  K  G  E  K  Y  L  E  K  K  G  F  A  E  E  D  256

--------|---------|---------|---------|---------|---------|----
    1072 tacgataaggaactattcgagaataatctgaaggtgatcaggtttggagacgaatatcttgga 1134
     257 Y  D  K  E  L  F  E  N  N  L  K  V  I  R  F  G  D  E  Y  L  G  277

-----|---------|---------|---------|---------|---------|-------
    1135 gaaagggataaaagctttatagaaaattttctacgggggatactctgtggaactttatgaa 1197
     278 E  R  D  K  S  F  I  E  N  F  S  T  G  D  T  L  W  N  F  Y  E  298

--|---------|---------|---------|---------|---------|---------|
    1198 ttttttactatgacccttttgcatgaacttttcctcagaaatataagaaagaggagacta tga 1260
     299 F  F  Y  Y  D  P  L  H  E  L  F  L  R  N  I  R  K  R  R  L  *  319

---------|---------|---------|---------|---------|---------|---
    1261 aagtactcgcatttaccgatgcacctacgtttcccacgggggtgggtcatcagcttcacaaca 1323

------|---------|---------|---------|---------|---------|------
    1324 ttatcaattacgggtttgacgcaaccgatcgctgggttgtggtgcaccgccccggtcgccaa 1386

---|---------|---------|---------|---------|---------|
    1387 gggctggagagactaaaaacgtcgttattggaaacactccagtcaagcttatca 1440
```

FIG. 10B

```
         ----------|----------|----------|----------|----------|----------|---
       1 acttcccaaatgctatgtggaggtggatgatagaaagcgtattgttaatgaagaggcggtcaa  63

------|----------|----------|----------|----------|----------|------
      64 gtctttctccataagcatgttaccgaactgctgaagaattatcagtaacccaaacctaaacc 126

---|----------|----------|----------|----------|----------|----------
     127 cgaaaaatatatggaaacgattgtaatttcccaaaacaatacgacggagatgacggaacccc 189
                       M  E  T  I  V  I  S  Q  N  N  T  T  E  M  T  E  P  P   18

|----------|----------|----------|----------|----------|----------|--
     190 ccagaacatttccgattcggttaaaagcgggtttatctatcttatcgaaaagtctcatttcct 252
      19  Q  N  I  S  D  S  V  K  S  G  F  I  Y  L  I  E  K  S  H  F  L   39

--------|----------|----------|----------|----------|----------|-----
     253 tgaaaagaaaaacttccttaaaatcatatcgaacatggaccccgccgcatttccaatccgga 315
      40  E  K  K  N  F  L  K  I  I  S  N  M  D  P  R  R  I  S  N  P  E   60

----|----------|----------|----------|----------|----------|--------
     316 ggtgcgcgtggtggcggagtacatatatgattatttcaaaagtcatagtaatttcccttctaa 378
      61  V  R  V  V  A  E  Y  I  Y  D  Y  F  K  S  H  S  N  F  P  S  K   81

-|----------|----------|----------|----------|----------|----------|-
     379 aagaaatctttgccatcactttgagtggagcgaagatctggaaggagaccccgccgattatca 441
      82  R  N  L  C  H  H  F  E  W  S  E  D  L  E  G  D  P  A  D  Y  Q  102

----------|----------|----------|----------|----------|----------|----
     442 gcgtatcattcagtatctcaaatcttcttacattcgatcctctataacaaaaacgctttcata 504
     103  R  I  I  Q  Y  L  K  S  S  Y  I  R  S  S  I  T  K  T  L  S  Y  123

-----|----------|----------|----------|----------|----------|-------
     505 tcttgagaaggatgacctttccgcgttgaaagaaattgtcagagccattcgggtggtggagga 567
     124  L  E  K  D  D  L  S  A  L  K  E  I  V  R  A  I  R  V  V  E  D  144

--|----------|----------|----------|----------|----------|----------|
     568 tagtgggtgtcgctggtggaggaattcgatcttgcaaccagcgagtttaatgaacttttgt 630
     145  S  G  V  S  L  V  E  E  F  D  L  A  T  S  E  F  N  E  L  F  V  165

----------|----------|----------|----------|----------|----------|---
     631 taaagaagaacgcattcccaccccctgggagagtgtaaacaaaaatatggcggcggtcttgg 693
     166  K  E  E  R  I  P  T  P  W  E  S  V  N  K  N  M  A  G  G  L  G  186

------|----------|----------|----------|----------|----------|------
     694 tcggggagagcttggaatcgttatgcttccttcggggtggggtaagtcatggttccttgtttc 756
     187  R  G  E  L  G  I  V  M  L  P  S  G  W  G  K  S  W  F  L  V  S  207

---|----------|----------|----------|----------|----------|----------
     757 acttggtcttcatgcctttcgaacgggtaagcgcgtgatttatttcactctggagcttgacca 819
     208  L  G  L  H  A  F  R  T  G  K  R  V  I  Y  F  T  L  E  L  D  Q  228

|----------|----------|----------|----------|----------|----------|--
     820 aaaatatgtgatgaagcggttttttaaagatgtttgcaccttattgcaaaggacgcgcttcttc 882
     229  K  Y  V  M  K  R  F  L  K  M  F  A  P  Y  C  K  G  R  A  S  S  249

-------|----------|----------|----------|----------|----------|-----
     883 ctatcgcgacgtttatcaaataatgaaagagcttatgttttctcaggataatcttttgragat 945
     250  Y  R  D  V  Y  Q  I  M  K  E  L  M  F  S  Q  D  N  L  L  K  I  270
```

FIG. 11A

```
         ----|---------|---------|---------|---------|---------|--------
   946 tgttttctgtaatgcgatggaagatattgagcactatattgcgctgtataaccccgacgttgt 1008
   271  V  F  C  N  A  M  E  D  I  E  H  Y  I  A  L  Y  N  P  D  V  V  291

-|---------|--------- ---------|---------|---------|---------|-
  1009 gctgattgactatgccgatcttatttatgatgtggaaaccgacaaagagaaaaattatctgct 1071
   292  L  I  D  Y  A  D  L  I  Y  D  V  E  T  D  K  E  K  N  Y  L  L  312

---------|---------|---------|---------|---------|---------|----
  1072 tttgcaaaaaatttataggaaacttcgtctcattgcaaaggtatataatacagcagtatggag 1134
   313  L  Q  K  I  Y  R  K  L  R  L  I  A  K  V  Y  N  T  A  V  W  S  333

-----|---------|---------|---------|---------|---------|-------
  1135 cgcctctcagcttaatcgcggttccctttcaaagcaagccgacgtcgatttcattgagaaata 1197
   334  A  S  Q  L  N  R  G  S  L  S  K  Q  A  D  V  D  F  I  E  K  Y  354

--|---------|---------|---------|---------|---------|---------|
  1198 cattgccgattcatttgcaaaagttkttgaaatcgacttcgggatggcgtttattccggatag 1260
   355  I  A  D  S  F  A  K  V  V  E  I  D  F  G  M  A  F  I  P  D  S  375

---------|---------|---------|---------|---------|---------|---
  1261 cgagaactcaacccccgatattcacgtcggattcggtaaaatcttcaaaaaccgtatgggtgc 1323
   376  E  N  S  T  P  D  I  H  V  G  F  G  K  I  F  K  N  R  M  G  A  396

------|---------|---------|---------|---------|---------|------
  1324 ggtaagaaagctggaatatacaattaactttgaaaactatacggtagacgttgctgttaaatg 1386
   397  V  R  K  L  E  Y  T  I  N  F  E  N  Y  T  V  D  V  A  V  K  *  417

---|---------|---------|---------|---------|---------|---------
  1387 acacaagttaagacaaaagggcttaaagacatcagaataggtagaaaggagggtaagttcaca 1449

|---------|---------|---------|---------|---------|--------
  1450 catgtaaatacaacaaagaaaggaaagaataagaaatatttcagggcggaacatgaacg 1508
```

BACTERIOPHAGE RM 378 OF A THERMOPHILIC HOST ORGANISM

RELATED APPLICATION

This application claims the benefit of U.S. Provisional Application No. 60/137,120, filed Jun. 2, 1999, the entire teachings of which are incorporated herein by reference.

BACKGROUND OF THE INVENTION

The use of thermophilic enzymes has revolutionized the field of recombinant DNA technology. Polymerases (DNA and RNA), ligases, exonucleases, reverse transcriptases, polynucleotide kinases and lysozymes, as well as many other thermophilic enzymes, are of great importance in the research industry today. In addition, thermophilic enzymes are also used in commercial settings (e.g., proteases and lipases used in washing powder, hydrolidic enzymes used in bleaching). Identification of new thermophilic enzymes will facilitate continued DNA research as well as assist in improving commercial enzyme-based products.

SUMMARY OF THE INVENTION

This invention pertains to a novel bacteriophage of *Rhodothermus marinus*, bacteriophage RM 378, which can be isolated from its native environment or can be recombinantly produced. The invention additionally pertains to the nucleic acids of the genome of bacteriophage RM 378 as deposited, as well as to the nucleic acids of a portion of the genome of bacteriophage RM 378 as shown in FIG. 1; to isolated nucleic acid molecules containing a nucleotide sequence of an open reading frame (or more than one open reading frame) of the genome of bacteriophage RM 378, such as an open reading frame as set forth in FIG. 2; to isolated nucleic acid molecules encoding a polypeptide obtainable from bacteriophage RM 378 or an active derivative or fragment of the polypeptide (e.g., a DNA polymerase, such as a DNA polymerase lacking exonuclease domains; a 3'-5' exonuclease, such as a 3'-5' exonuclease lacking DNA polymerase domain; a 5'-3' exonuclease (RNase H); a DNA helicase; or an RNA ligase); to DNA constructs containing the isolated nucleic acid molecule operatively linked to a regulatory sequence; and also to host cells comprising the DNA constructs. The invention further pertains to isolated polypeptides encoded by these nucleic acids, as well as active derivatives or fragments of the polypeptides.

Because the host organism of the RM 378 bacteriophage is a thermophile, the enzymes and proteins of the RM 378 bacteriophage are expected to be significantly more thermostable than those of other (e.g., mesophilic) bacteriophages, such as the T4 bacteriophage of *Escherichia coli*. The enhanced stability of the enzymes and proteins of RM 378 bacteriophage allows their use under temperature conditions which would be prohibitive for other enzymes, thereby increasing the range of conditions which can be employed not only in DNA research but also in commercial settings.

BRIEF DESCRIPTION OF THE DRAWINGS

FIGS. 1A–1Q2 are a depiction of the nucleic acid sequence (SEQ ID NO:1) of the genome of bacteriophage RM 378.

FIGS. 2A–2C delineate the open reading frames (ORFs) in the genome of bacteriophage RM 378.

FIGS. 3A–3W depict a sequence alignment of the predicted gene products of ORF056e and ORF632e and sequences of DNA polymerases of family B. The sequence marked RM378 (SEQ ID NO:36) is the combined sequences of the gene products of ORF056e and ORF632e in bacteriophage RM378. The end of one sequence and the beginning of another is indicated. Other sequences are: Vaccinia virus (strain Copenhagen) DNA polymerase (DPOL_VACCC) (SEQ ID NO:2); Vaccinia virus (strain WR) DNA polymerase (DPOL_VACCV) (SEQ ID NO:3); Variola virus DNA polymerase (DPOL_VARV) (SEQ ID NO:4); Fowlpox virus DNA polymerase (DPOL_FOWPV) (SEQ ID NO:5); *Bos taurus* (Bovine) DNA polymerase delta catalytic chain (DPOD_BOVIN) (SEQ ID NO:6); Human DNA polymerase delta catalytic chain (DPOD_HUMAN) (SEQ ID NO:7); *Candida albicans* (Yeast) DNA polymerase delta large chain (DPOD_CANAL) (SEQ ID NO:8); *Saccharomyces cerevisiae* DNA polymerase delta large chain (DPOD_YEAST) (SEQ ID NO:9); *Schizosaccharomyces pombe* DNA polymerase delta large chain (DPOD_SCHPO) (SEQ ID NO:10); *Plasmodium falciparum* DNA polymerase delta catalytic chain (DPOD_PLAFK) (SEQ ID NO:11); *Chlorella* virus NY-2A DNA polymerase (DPOL_CHVN2) (SEQ ID NO:12); *Paramecium bursaria chlorella* virus 1 DNA polymerase (DPOL_CHVP1) (SEQ ID NO:13); Epstein-barr virus (strain B95-8) DNA polymerase (DPOL_EBV) (SEQ ID NO:14); *Herpesvirus saimiri* (strain 11) DNA polymerase (DPOL_HSVSA) (SEQ ID NO:15); Herpes simplex virus (type 1/strain 17) DNA polymerase (DPOL_HSV11) (SEQ ID NO:16); Herpes simplex virus (type 2/strain 186) DNA polymerase (DPOL_HSV21) (SEQ ID NO:17); Equine herpesvirus type 1 (strain Ab4p) (EHV-1) DNA polymerase (DPOL_HSVEB) (SEQ ID NO:18); *Varicella-zoster* virus (strain Dumas) (VZV) DNA polymerase (DPOL_VZVD) (SEQ ID NO:19); Human cytomegalovirus (strain AD169) DNA polymerase (DPOL_HCMVA) (SEQ ID NO:20); Murine cytomegalovirus (strain Smith) DNA polymerase (DPOL_MCMVS) (SEQ ID NO:21); Herpes simplex virus (type 6/strain Uganda-1102) DNA polymerase (DPOL_HSV6U) (SEQ ID NO:22); Human DNA polymerase alpha catalytic subunit (DPOA_HUMAN) (SEQ ID NO:23); Mouse DNA polymerase alpha catalytic subunit (DPOA_MOUSE) (SEQ ID NO:24); *Drosophila melanogaster* DNA polymerase alpha catalytic subunit (DPOA_DROME) (SEQ ID NO:25); *Schizosaccharomyces pombe* DNA polymerase alpha catalytic subunit (DPOA_SCHPO) (SEQ ID NO:26); *Saccharomyces cerevisiae* DNA polymerase alpha catalytic subunit (DPOA_YEAST) (SEQ ID NO:27); *Trypanosoma brucei* DNA polymerase alpha catalytic subunit (DPOA_TRYBB) (SEQ ID NO:28); *Autographa californica* nuclear polyhedrosis virus DNA polymerase (DPOL_NPVAC) (SEQ ID NO:29); *Lymantria dispar* multicapsid nuclear polyhedrosis virus DNA polymerase (DPOL_NPVLD) (SEQ ID NO:30); *Saccharomyces cerevisiae* DNA polymerase zeta catalytic subunit (DPOZ_YEAST) (SEQ ID NO:31); *Pyrococcus woesei* DNA polymerase (DPOL_PYRFU) (SEQ ID NO:32);. *Sulfolobus solfataricus* DNA polymerase I (DPO1_SULSO) (SEQ ID NO:33); *Escherichia coli* DNA polymerase II (DPO2_ECOLI) (SEQ ID NO:34); Desilforococcus strain Tok DNA polymerase (Dpol_Dtok) (SEQ ID NO:35); and bacteriophage RB69 DNA polymerase (RB69) (SEQ ID NO:37). Most of the sequences are partial as found in the Protein Family Data Base of Alignments and IIMMs (Sanger Institute), family DNA pol_B, accession no. PF00136.

FIG. 4 depicts a sequence alignment of the predicted gene product of ORF739f from bacteriophage RM378 (ORF-739f) (SEQ ID NO:40), *Autographa californica* nucleopolyhedrovirus putative bifunctional polynucleotide kinase and RNA ligase (ACNV-RNAlig) (SEQ ID NO:38); and bacteriophage T4 RNA ligase (T4-RNAlig) (SEQ ID NO:39).

FIG. 5 depicts a sequence alignment of the predicted gene product of ORF1218a from bacteriophage RM378 (ORF-1218a) (SEQ ID NO:43) with proteins or domains with 5'-3' exonuclease activity, including: *Escherichia coli* DNA polymerase I (*Ecoli*-polI) (SEQ ID NO:41), *Thermus aquaticus* DNA polymerase I (Taq-polI) (SEQ ID NO:42), bacteriophage T4 ribonuclease H (T4-RNaseH) (SEQ ID NO:44) and bacteriophage T7 gene6 exonuclease (T7-gp6exo) (SEQ ID NO:45). Conservation of acidic residues mainly clustered at the proposed active site are seen.

FIGS. 6A–6B depict a sequence alignment of the predicted gene product of ORF1293b (SEQ ID NO:55) from bacteriophage RM378 (ORF1293b) with sequences of replicative DNA helicases of the DnaB family, including: *Escherichia coli* (DnaB-*Ecoli*) (SEQ ID NO:46), *Haemophilus influenza* (DnaB-*Hinflu*) (SEQ ID NO:47), *Chlamydomonas trachomatis* (DnaB-*Ctracho*) (SEQ ID NO:48), *Bacillus stearothermophilus* (DnaB-*Bstearo*) (SEQ ID NO:49), *Halobacter pylori* (DnaB-*Hpylor*) (SEQ ID NO:50), *Mycoplasma genitalium* (DnaB-*Mgenital*) (SEQ ID NO:5 1), *Borrelia burgdorferi* (DnaB-*Bburgdor*) (SEQ ID NO:52), bacteriophage T4 gene 41 (T4-gp41) (SEQ ID NO:53), bacteriophage T7 gene 4 (T7-gp4) (SEQ ID NO:54) (from the Protein Family Data Base of Alignments and IIMMs (Sanger Institute), family DnaB, accession no. PF00772). The sequences have been truncated at the N-termini, and conserved sequence motifs are indicated.

FIGS. 7A–7B depict the nucleic acid sequence of open reading frame ORF 056e (nucleotides 21993–23042 of the genome) (SEQ ID NO:56) with flanking sequences, and the putative encoded polypeptide (SEQ ID NO:57) which displays amino acid sequence similarity to polymerase 3'-5' exonucleases.

FIGS. 8A–8B depict the nucleic acid sequence of open reading frame ORF 632e (nucleotides 79584–81152 of the genome) (SEQ ID NO:58) with flanking sequences, and the putative encoded polypeptide (SEQ ID NO:59) which displays amino acid sequence similarity to polymerases.

FIGS. 9A–9B depict the nucleic acid sequence of open reading frame ORF 739f (nucleotides 90291–91607 of the genome) (SEQ ID NO:60) with flanking sequences, and the putative encoded polypeptide (SEQ ID NO:40) which displays amino acid sequence similarity to RNA ligase.

FIGS. 10A–10B depict the nucleic acid sequence of open reading frame ORF 1218a (nucleotides 8212–9168 of the genome) (SEQ ID NO:61) with flanking sequences, and the putative encoded polypeptide (SEQ ID NO:43) which displays amino acid sequence similarity to 5'-3' exonuclease of DNA polymerase I and T4 RNase H.

FIGS. 11A–11B depict the nucleic acid sequence of open reading frame ORF 1293b (nucleotides 15785–17035 of the genome) (SEQ ID NO:62) with flanking sequences, and the putative encoded polypeptide (SEQ ID NO:55) which displays amino acid sequence similarity to T4 DNA helicase.

DETAILED DESCRIPTION OF THE INVENTION

The present invention relates to a bacteriophage, the nucleic acid sequence of the bacteriophage genome as well as portions of the nucleic acid sequence of the bacteriophage genome (e.g., a portion containing an open reading frame), and proteins encoded by the nucleic acid sequences, as well as nucleic acid constructs comprising portions of the nucleic acid sequence of the bacteriophage genome, and host cells comprising such nucleic acid constructs. As described herein, Applicants have isolated and characterized a novel bacteriophage active against the slightly halophilic, thermophilic eubacterium *Rhodothermus marinus*. The bacteriophage, RM 378, is a member of the Myoviridae family, with an A2 morphology. RM 378, which is completely stable up to about 65° C., appears to consist of approximately 16 proteins with one major protein of molecular weight of 61,000 daltons. RM 378 can be replicated in *Rhodothermus marinus* species ITI 378.

*RHODOTHERMUS MARINUS* ITI 378

Accordingly, one embodiment of the invention is the bacterium, *Rhodothermus marinus* species ITI 378. *Rhodothermus marinus*, and particularly species ITI 378, can be cultured in a suitable medium, such as medium 162 for Thermus as described by Degryse et al. (*Arch. Microbiol.* 117:189–196 (1978)), with ⅒ buffer and with 1% NaCl. *Rhodothermus marinus* species ITI 378 can be used in replication of bacteriophage RM 378, as described herein, or in replication or identification of other bacteriophages, particularly thermophilic bacteriophages. *Rhodothermus marinus* species ITI 378 can also used in the study of the relationship between the bacteriophages and their host cells (e.g., between bacteriophage RM 378 and *Rhodothermus marinus* species ITI 378).

BACTERIOPHAGE RM 378

Another embodiment of the invention is isolated RM 378 bacteriophage. "Isolated" RM 378 bacteriophage refers to bacteriophage that has been separated, partially or totally, from its native environment (e.g., separated from *Rhodothermus marinus* host cells) ("native bacteriophage"), and also refers to bacteriophage that has been chemically synthesized or recombinantly produced ("recombinant bacteriophage"). A bacteriophage that has been "recombinantly produced" refers to a bacteriophage that has been manufactured using recombinant DNA technology, such as by inserting the bacteriophage genome into an appropriate host cell (e.g., by introducing the genome itself into a host cell, or by incorporating the genome into a vector, which is then introduced into the host cell).

Isolated bacteriophage RM 378 can be used in the study of the relationship between the bacteriophages and their host cells (e.g., *Rhodothermus marinus*, such as *Rhodothermus marinus* species ITI 378). Isolated bacteriophage RM 378 can also be used as a vector to deliver nucleic acids to a host cell; that is, the bacteriophage can be modified to deliver nucleic acids comprising a gene from an organism other than the bacteriophage (a "foreign" gene). For example, nucleic acids encoding a polypeptide (e.g., an enzyme or pharmaceutical peptide) can be inserted into the genome of bacteriophage RM 378, using standard techniques. The resultant modified bacteriophage can be then used to infect host cells, and the protein encoded by the foreign nucleic acids can then be produced.

Bacteriophage RM 378 can be produced by inoculating appropriate host cells with the bacteriophage. Representative host cells in which the bacteriophage can replicate include *Rhodothermus marinus*, particularly species isolated in a location that is geographically similar to the location where bacteriophage RM 378 was isolated (e.g., northwest Iceland). In a preferred embodiment, the host cell is *Rhodothermus marinus* species ITI 378. The host cells are cultured in a suitable medium (e.g., medium 162 for Thermus as described by Degryse et al., *Arch. Microbiol.* 11 7:189–196 (1978), with ⅒ buffer and with 1% NaCl). In addition, the host cells are cultured under conditions suitable for replication of the bacteriophage. For example, in a preferred embodiment, the host cells are cultured at a temperature of at least approximately 50° C. In a more preferred embodiment, the host cells are cultured at a temperature between about 50° C. and about 80° C. The bacteriophage can also be stored in a cell lysate at about 4° C.

NUCLEIC ACIDS OF THE INVENTION

Another embodiment of the invention pertains to isolated nucleic acid sequences obtainable from the genome of bacteriophage RM 378. As described herein, approximately 130 kB of the genome of bacteriophage RM 378 have been sequenced. The sequence of this 130 kB is set forth in FIG. 1. There are at least approximately 200 open reading frames (ORFs) in the sequence; of these, at least approximately 120 putatively encode a polypeptide of 100 amino acids in length or longer. These 120 are set forth in FIG. 2. FIG. 2 sets forth the locus of each ORF; the start and stop nucleotides in the sequence of each ORF; the number of nucleotides in the ORF, and the expected number of amino acids encoded therein; the direction of the ORF; the identity of the putative protein encoded therein; the protein identified by a BLAST search as being the closest match to the putative protein; the percentage identity at the amino acid level of the putative protein (based on partial sequence similarity; the overall similarity is lower); the organism from which the closest matching protein is derived; and other information relating to the ORFs.

The invention thus pertains to isolated nucleic acid sequence of the genome ("isolated genomic DNA") of the bacteriophage RM 378 that has been deposited with the Deutsche Sammlung Von Mikroorganismen und Zellkulturen GmbH (DSMZ) as described below. The invention also pertains to isolated nucleic acid sequence of the genome of bacteriophage RM 378 as is shown in FIG. 1 (SEQ ID NO:1).

The invention additionally pertains to isolated nucleic acid molecules comprising the nucleotide sequences of each of the ORFs described above or fragments thereof, as well as nucleic acid molecules comprising nucleotide sequences of more than one of the ORFs described above or fragments of more than one of the ORFs. The nucleic acid molecules of the invention can be DNA, or can also be RNA, for example, mRNA. DNA molecules can be double-stranded or single-stranded; single stranded RNA or DNA can be either the coding, or sense, strand or the non-coding, or antisense, strand. Preferably, the nucleic acid molecule comprises at least about 100 nucleotides, more preferably at least about 150 nucleotides, and even more preferably at least about 200 nucleotides. The nucleotide sequence can be only that which encodes at least a fragment of the amino acid sequence of a polypeptide; alternatively, the nucleotide sequence can include at least a fragment of a coding sequence along with additional non-coding sequences such as non-coding 3' and 5' sequences (including regulatory sequences, for example).

In certain preferred embodiments, the nucleotide sequence comprises one of the following ORFs: ORF 056e, 632e, 739f, 1218a, 1293b. For example, the nucleotide sequence can consist essentially of one of the ORFs and its flanking sequences, such as are shown in FIGS. 7–11 (e.g., ORF 056e (SEQ ID NO:56), 632e (SEQ ID NO:58), 739f (SEQ ID NO:60), 1218a (SEQ ID NO:61), 1293b (SEQ ID NO:62)).

Additionally, the nucleotide sequence(s) can be fused to a marker sequence, for example, a sequence which encodes a polypeptide to assist in isolation or purification of the polypeptide. Representative sequences include, but are not limited to, those which encode a glutathione-S-transferase (GST) fusion protein. In one embodiment, the nucleotide sequence contains a single ORF in its entirety (e.g., encoding a polypeptide, as described below); or contains a nucleotide sequence encoding an active derivative or active fragment of the polypeptide; or encodes a polypeptide which has substantial sequence identity to the polypeptides described herein. In a preferred embodiment, the nucleic acid encodes a polymerase (e.g., DNA polymerase); DNA polymerase accessory protein; dsDNA binding protein; deoxyriboncleotide-3-phosphatase; DNA topoisomerase; DNA helicase; an exonuclease (e.g., 3'-5' exonuclease, 5'-3' exonuclease (RNase H)); RNA ligase; site-specific RNase inhibitor of protease; endonuclease; exonuclease; mobility nuclease; reverse transcriptase; single-stranded binding protein; endolysin; lysozyme; helicase; alpha-glucosyltransferase; or thymidine kinase, as described herein. In a particularly preferred embodiment, the nucleic acid encodes a DNA polymerase, 3'-5' exonuclease, 5'-3 exonuclease (RNase H), DNA helicase or RNA ligase. In another particularly preferred embodiment, the nucleic acid encodes a DNA polymerase that lacks exonuclease domains, or a 3'-5' exonuclease that lacks DNA polymerase domain, as described below.

The nucleic acid molecules of the invention are "isolated;" as used herein, an "isolated" nucleic acid molecule or nucleotide sequence is intended to mean a nucleic acid molecule or nucleotide sequence which is not flanked by nucleotide sequences which normally (in nature) flank the gene or nucleotide sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Thus, an isolated nucleic acid molecule or nucleotide sequence can include a nucleic acid molecule or nucleotide sequence which is synthesized chemically or by recombinant means. Therefore, recombinant DNA contained in a vector are included in the definition of "isolated" as used herein. Also, isolated nucleotide sequences include recombinant DNA molecules in heterologous organisms, as well as partially or substantially purified DNA molecules in solution. In vivo and in vitro RNA transcripts of the DNA molecules of the present invention are also encompassed by "isolated" nucleotide sequences.

The present invention also pertains to nucleotide sequences which are not necessarily found in nature but which encode the polypeptides described below. Thus, DNA molecules which comprise a sequence which is different from the naturally-occurring nucleotide sequence but which, due to the degeneracy of the genetic code, encode the polypeptides of the present invention are the subject of this invention. The invention also encompasses variations of the nucleotide sequences of the invention, such as those encoding active fragments or active derivatives of the polypeptides as described below. Such variations can be naturally-occurring, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide or amino acid variations are silent or conserved; that is, they do not alter the characteristics or activity of the encoded polypeptide.

The invention described herein also relates to fragments of the isolated nucleic acid molecules described herein. The term "fragment" is intended to encompass a portion of a nucleotide sequence described herein which is from at least about 25 contiguous nucleotides to at least about 50 contiguous nucleotides or longer in length; such fragments are useful as probes and also as primers. Particularly preferred primers and probes selectively hybridize to the nucleic acid molecule encoding the polypeptides described herein. For example, fragments which encode polypeptides that retain activity, as described below, are particularly useful.

The invention also pertains to nucleic acid molecules which hybridize under high stringency hybridization conditions, such as for selective hybridization, to a nucleotide sequence described herein (e.g., nucleic acid molecules which specifically hybridize to a nucleotide sequence encoding polypeptides described herein, and, optionally, have an activity of the polypeptide). Hybridization probes are oligonucleotides which bind in a base-specific manner to a complementary strand of nucleic acid. Suitable probes include polypeptide nucleic acids, as described in (Nielsen et al., Science 254, 1497–1500 (1991)).

Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity.

"High stringency conditions", "moderate stringency conditions" and "low stringency conditions" for nucleic acid hybridizations are explained on pages 2.10.1–2.10.16 and pages 6.3.1–6 in *Current Protocols in Molecular Biology* (Ausubel, F. M. et al., "*Current Protocols in Molecular Biology*", John Wiley & Sons, (1998)) the teachings of which are hereby incorporated by reference. The exact conditions which determine the stringency of hybridization depend not only on ionic strength (e.g., 0.2×SSC, 0.1×SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined.

Exemplary conditions are described in Krause, M. H. and S. A. Aaronson, *Methods in Enzymology*, 200:546–556 (1991). Also, in, Ausubel, et al., "*Current Protocols in Molecular Biology*", John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each °C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

For example, a low stringency wash can comprise washing in a solution containing 0.2×SSC/0.1% SDS for 10 min at room temperature; a moderate stringency wash can comprise washing in a prewarmed solution (42° C.) solution containing 0.2×SSC/0.1% SDS for 15 min at 42° C.; and a high stringency wash can comprise washing in prewarmed (68° C.) solution containing 0.1×SSC/0.1%SDS for 15 min at 68° C. Furthermore, washes can be performed repeatedly or sequentially to obtain a desired result as known in the art.

Equivalent conditions can be determined by varying one or more of the parameters given as an example, as known in the art, while maintaining a similar degree of identity or similarity between the target nucleic acid molecule and the primer or probe used. Hybridizable nucleic acid molecules are useful as probes and primers, e.g., for diagnostic applications.

Such hybridizable nucleotide sequences are useful as probes and primers for diagnostic applications. As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

The invention also pertains to nucleotide sequences which have a substantial identity with the nucleotide sequences described herein; particularly preferred are nucleotide sequences which have at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, with nucleotide sequences described herein. Particularly preferred in this instance are nucleotide sequences encoding polypeptides having an activity of a polypeptide described herein. For example, in one embodiment, the nucleotide sequence encodes a DNA polymerase, 3'-5' exonuclease, 5'-3' exonuclease (RNase H), DNA helicase, or RNA ligase, as described below. In a preferred embodiment, the nucleotide encodes a DNA polymerase lacking exonuclease domains, or a 3'-5' exonuclease lacking DNA polymerase domain, as described below.

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent identity between two sequences can be accomplished using a mathematical algorithm. A preferred, non-limiting example of a mathematical algorithm utilized for the comparison of two sequences is the algorithm of Karlin et al., *Proc. Natl. Acad. Sci. USA*, 90:5873–5877 (1993). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al., *Nucleic Acids Res*, 25:3389–3402 (1997). When utilizing BLAST and Gapped BLAST programs, the default parameters of the respective programs (e.g., NBLAST) can be used. See the programs provided by National Center for Biotechnology Information, National Library of Medicine, National Institutes of Health. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

The invention also provides expression vectors containing a nucleic acid sequence encoding a polypeptide described herein (or an active derivative or fragment thereof), operably linked to at least one regulatory sequence. Many expression vectors are commercially available, and other suitable vectors can be readily prepared by the skilled artisan. "Operably linked" is intended to mean that the nucleotide sequence is linked to a regulatory sequence in a manner which allows expression of the nucleic acid sequence. Regulatory sequences are art-recognized and are selected to produce the polypeptide or active derivative or fragment thereof. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to bacteriophage RM 378 can be employed. It should be understood that the design of the expression vector may depend on such factors as the choice of the host cell to be transformed and/or the type of polypeptide desired to be expressed. For instance, the polypeptides of the present invention can be produced by ligating the cloned gene, or a portion thereof, into a vector suitable for expression in an appropriate host cell (see, for example, Broach, et al., *Experimental Manipulation of Gene Expression*, ed. M. Inouye (Academic Press, 1983) p. 83; *Molecular Cloning: A Laboratory Manual*, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Thus, prokaryotic and eukaryotic host cells transformed by the described expression vectors are also provided by this invention. For instance, cells which can be transformed with the vectors of the present invention include, but are not limited to, bacterial cells such as *Rhodothermus marinus*, *E. coli* (e.g., *E. coli* K12 strains), Streptomyces, Pseudomonas, Bacillus, *Serratia marcescens* and *Salmonella typhimurium*,. The host cells can be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host. The nucleic acid molecules of the present invention can be produced, for example, by replication in such a host cell, as described above. Alternatively, the nucleic acid molecules can also be produced by chemical synthesis.

The isolated nucleic acid molecules and vectors of the invention are useful in the manufacture of the encoded polypeptide, as probes for isolating homologous sequences (e.g., from other bacteriophage species), as well as for detecting the presence of the bacteriophage in a culture of host cells.

The nucleotide sequences of the nucleic acid molecules described herein (e.g., a nucleic acid molecule comprising any of the open reading frames shown in FIG. 2, such as a nucleic acid molecule comprising the open reading frames depicted in FIGS. 7–11 (SEQ ID NO:56, 58, 60, 61 and 62, respectively)) can be amplified by methods known in the art. For example, this can be accomplished by e.g., PCR. See generally *PCR Technology: Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (eds. McPherson et al., IRL Press, Oxford); and U.S. Pat. No. 4,683,202.

Other suitable amplification methods include the ligase chain reaction (LCR) (see Wu and Wallace, *Genomics* 4, 560 (1989), Landegren et al., *Science* 241, 1077 (1988), transcription amplification (Kwoh et al., *Proc. Natl. Acad. Sci. USA* 86, 1173 (1989)), and self-sustained sequence replication (Guatelli et al., *Proc. Nat. Acad. Sci. USA*, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA can be radiolabelled and used as a probe for screening a library or other suitable vector to identify homologous nucleotide sequences. Corresponding clones can be isolated, DNA can be obtained following in vivo excision, and the cloned insert can be sequenced in either or both orientations by art recognized methods, to identify the correct reading frame encoding a protein of the appropriate molecular weight. For example, the direct analysis of the nucleotide sequence of homologous nucleic acid molecules of the present invention can be accomplished using either the dideoxy chain termination method or the Maxam Gilbert method (see Sambrook et al., *Molecular Cloning, A Laboratory Manual* (2nd Ed., CSHP, New York 1989); Zyskind et al., *Recombinant DNA Laboratory*

*Manual,* (Acad. Press, 1988)). Using these or similar methods, the protein(s) and the DNA encoding the protein can be isolated, sequenced and further characterized.

POLYPEPTIDES OF THE INVENTION

The invention additionally relates to isolated polypeptides obtainable from the bacteriophage RM 378. The term, "polypeptide," as used herein, includes proteins, enzymes, peptides, and gene products encoded by nucleic acids described herein. In one embodiment, the invention pertains to the polypeptides encoded by the ORFs as described above. In addition, as described in detail below, bacteriophage RM 378 is similar to the well-known *E. coli* bacteriophage T4. Thus, it is expected that bacteriophage RM 378 comprises additional polypeptides that are homologous to those found in bacteriophage T4.

For example, representative proteins expected to be encoded by genes of bacteriophage RM 378 include the following: DNA topoisomerase; exonuclease (e.g., 3'-5' exonuclease, 5'-3' exonuclease (RNase H)); helicase; enzymes related to DNA or RNA synthesis (e.g., dCTPase, dUTPase, dCDPase, dUDPase, GTPase, dGTPase, ATPase, dATPase); transposase; reverse transcriptase; polymerase (e.g., DNA polymerase, RNA polymerase); DNA polymerase accessory protein; DNA packaging protein; DNA topoisomerase; RNA polymerase binding protein; RNA polymerase sigma factor; site-specific RNase inhibitor of protease; recombinant protein; alpha-glucosyltransferase; mobility nuclease; endonuclease (e.g., endonuclease II, endonuclease V, endonuclease VII); inhibitor of Lon protease; thymidine kinase; site-specific RNase; N-glycosidase; endolysin; lysozyme; dNMP kinase; DNA ligase; deoxyribonucleotide-3'-phosphatase; ssDNA binding protein; dsDNA binding protein; and RNA ligase.

In a particularly preferred embodiment, the polypeptide is polymerase (e.g., DNA polymerase); DNA polymerase accessory protein; dsDNA binding protein; deoxyriboncleotide-3-phosphatase; DNA topoisomerase; RNA ligase; site-specific RNase inhibitor of protease; endonuclease; exonuclease (e.g., 3'-5' exonuclease, 5'-3' exonuclease (RNase H)); nobility nuclease; reverse transcriptase; single-stranded binding protein; enolysin; lysozyme; helicase; alpha-glucosyltransferase; or thymidine kinase. In an especially preferred embodiment, the polypeptide is a DNA polymerase, a 3'-5' exonuclease, a 5'-3' exonuclease (RNase H), a DNA helicase, or an RNA ligase, such as those shown in FIGS. 7–11 (e.g., for a DNA polymerase, SEQ ID NO:58; a 3'-5' exonuclease, SEQ ID NO:56; a 5'-3' exonuclease (RNase H) (SEQ ID NO:61); a DNA helicase (SEQ ID NO:62), or an RNA ligase (SEQ ID NO:60)). In a most preferred embodiment, the polypeptide is a DNA polymerase that lacks exonuclease domains, or a 3'-5' exonuclease that lacks DNA polymerase domain, as described in the examples below. As used herein, the term, "lacking exonuclease domains," indicates that the polypeptide does not contain an amino acid domain (e.g., a consecutive or closely spaced series of amino acids) homologous to domains where such exonuclease activity resides in other similar polymerases (such as polymerases in the same family); it does not refer to the presence of a non-functional domain homologous to domains where exonuclease activity resides. Similarly, the term, "lacking DNA polymerase domain," indicates that the polypeptide does not contain an amino acid domain (e.g., a consecutive or closely spaced series of amino acids) homologous to domains where such DNA polymerase activity resides in other similar exonucleases (such as exonucleases in the same family); it does not refer to the presence of a non-functional domain homologous to domains where DNA polymerase activity resides.

These polypeptides can be used in a similar manner as the homologous polypeptides from bacteriophage T4; for example, polymerases and ligases of bacteriophage RM 378 can be used for amplification or manipulation of DNA and RNA sequences. The polymerases and ligases of bacteriophage RM 378, however, are expected to be much more thermostable than those of bacteriophage T4, because of the thermophilic nature of the host of bacteriophage RM 378 (in contrast with the mesophilic nature of *E. coli*, the host of bacteriophage T4).

The polypeptides of the invention can be partially or substantially purified (e.g., purified to homogeneity), and/or are substantially free of other polypeptides. According to the invention, the amino acid sequence of the polypeptide can be that of the naturally-occurring polypeptide or can comprise alterations therein. Polypeptides comprising alterations are referred to herein as "derivatives" of the native polypeptide. Such alterations include conservative or non-conservative amino acid substitutions, additions and deletions of one or more amino acids; however, such alterations should preserve at least one activity of the polypeptide, i.e., the altered or mutant polypeptide should be an active derivative of the naturally-occurring polypeptide. For example, the mutation(s) can preferably preserve the three dimensional configuration of the binding site of the native polypeptide, or can preferably preserve the activity of the polypeptide (e.g., if the polypeptide is a DNA polymerase, any mutations preferably preserve the ability of the enzyme to catalyze combination of nucleotide triphosphates to form a nucleic acid strand complementary to a nucleic acid template strand). The presence or absence of activity or activities of the polypeptide can be determined by various standard functional assays including, but not limited to, assays for binding activity or enzymatic activity.

Additionally included in the invention are active fragments of the polypeptides described herein, as well as fragments of the active derivatives described above. An "active fragment," as referred to herein, is a portion of polypeptide (or a portion of an active derivative) that retains the polypeptide's activity, as described above.

Appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al. (*Science* 247:1306–1310(1990)). For example, conservative amino acid replacements can be those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine or a similar conservative replacement of an amino acid with a structurally related amino acid will not have a major effect on activity or functionality.

The polypeptides of the invention can also be fusion polypeptides comprising all or a portion (e.g., an active fragment) of the native bacteriophage RM 378 polypeptide amino acid sequence fused to an additional component, with optional linker sequences. Additional components, such as radioisotopes and antigenic tags, can be selected to assist in the isolation or purification of the polypeptide or to extend the half life of the polypeptide; for example, a hexahistidine tag would permit ready purification by nickel chromatography. The fusion protein can contain, e.g., a glutathione-S-transferase (GST), thioredoxin (TRX) or maltose binding protein (MBP) component to facilitate purification; kits for expression and purification of such fusion proteins are commercially available. The polypeptides of the invention can also be tagged with an epitope and subsequently purified using antibody specific to the epitope using art recognized methods. Additionally, all or a portion of the polypeptide can be fused to carrier molecules, such as immunoglobulins, for many purposes, including increasing the valency of protein binding sites. For example, the polypeptide or a portion thereof can be linked to the Fc portion of an immunoglobulin; for example, such a fusion could be to the Fc portion of an IgG molecule to create a bivalent form of the protein.

Also included in the invention are polypeptides which are at least about 90% identical (i.e., polypeptides which have substantial sequence identity) to the polypeptides described herein. However, polypeptides exhibiting lower levels of identity are also useful, particular if they exhibit high, e.g., at least about 90%, identity over one or more particular domains of the polypeptide. For example, polypeptides sharing high degrees of identity over domains necessary for particular activities, such as binding or enzymatic activity, are included herein. Thus, polypeptides which are at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, are encompassed by the invention.

Polypeptides described herein can be isolated from naturally-occurring sources (e.g., isolated from host cells infected with bacteriophage RM 378). Alternatively, the polypeptides can be chemically synthesized or recombinantly produced. For example, PCR primers can be designed to amplify the ORFs from the start codon to stop codon, using DNA of RM378 or related bacteriophages or respective recombinant clones as a template. The primers can contain suitable restriction sites for an efficient cloning into a suitable expression vector. The PCR product can be digested with the appropriate restriction enzyme and ligated between the corresponding restriction sites in the vector (the same restriction sites, or restriction sites producing the same cohesive ends or blunt end restriction sites).

Polypeptides of the present invention can be used as a molecular weight marker on SDS-PAGE gels or on molecular sieve gel filtration columns using art-recognized methods. They are particularly useful for molecular weight markers for analysis of proteins from thermophilic organisms, as they will behave similarly (e.g., they will not denature as proteins from mesophilic organisms would).

The polypeptides of the present invention can be isolated or purified (e.g., to homogeneity) from cell culture (e.g., from culture of host cells infected with bacteriophage RM 378) by a variety of processes. These include, but are not limited to, anion or cation exchange chromatography, ethanol precipitation, affinity chromatography and high performance liquid chromatography (HPLC). The particular method used will depend upon the properties of the polypeptide; appropriate methods will be readily apparent to those skilled in the art. For example, with respect to protein or polypeptide identification, bands identified by gel analysis can be isolated and purified by HPLC, and the resulting purified protein can be sequenced. Alternatively, the purified protein can be enzymatically digested by methods known in the art to produce polypeptide fragments which can be sequenced. The sequencing can be performed, for example, by the methods of Wilm et al. (*Nature* 379(6564):466–469 (1996)). The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice*, 2nd Edition, Springer-Verlag, New York (1987); and Deutscher (ed), *Guide to Protein Purification, Methods in Enzymology*, Vol. 182 (1990).

The following Examples are offered for the purpose of illustrating the present invention and are not to be construed to limit the scope of this invention. The teachings of all references cited are hereby incorporated herein by reference in their entirety.

EXAMPLE 1

Isolation, Purification and Characterization of Bacteriophage

A. Materials and Methods

Bacterial strains and growth media

The thermophilic, slightly halophilic eubacterium, *Rhodothermus marinus* was first isolated from shallow water submarine hot springs in Isafjardardjup in northwest Iceland (Alfredsson, G. A. et al., *J. Gen. Microbiol.* 134:299–306 (1988)). Since then Rhodothermus has also been isolated from two other areas in Iceland (Petursdottir et al., in prep.), from the Azores and the Bay of Naples in Italy (Nunes, O. C. et al., *Syst. Appl. Microbiol.* 15:92–97 (1992); Moreira, L. et al., *Syst. Appl. Microbiol.* 19:83–90 (1996)). Rhodothermus is distantly related to the group containing Flexibacter, Bacterioides and Cytophaga species (Anderson, O. S. and Fridjonsson, O. H., *J. Bacteriol.* 176:6165–6169 (1994)).

Strain ITI 378 (originally R-21) is one of the first Rhodothermus strains isolated from submarine hot springs in Isafjardardjup in northwest Iceland. The strain was grown at 65° C. in medium 162 for Thermus (Degryse et al., *Arch. Microbiol.* 117:189–196 (1978)), with ¹/₁₀ the buffer and with 1% NaCl. Strain ITI 378 is phenotypically and phylogenetically similar (over 99% similarity in 16s rRNA sequence) to type strain DSM 4252.

Bacteriophage Isolation

A water sample with some sand and mud was collected from a hot spring (62° C.) appearing at low tide in Isafjardardjup at the same site as the bacterium was originally isolated. The same kind of samples were collected from the Blue Lagoon and the Salt factory on Reykjanes in southwest Iceland.

After mixing a sample in a Waring blender, the sample was filtered through a Buchner funnel, followed by centrifugation, before filtering the water through a 0.45 μm membrane. After centrifuging again, the sample was filtered through a sterile 0.2 μm membrane. This filtrate was used for infecting 18 different Rhodothermus strains (8 from Isafjardardjup in northwest Iceland, and 10 from Reykjanes in southwest Iceland). The sample (4 ml) was mixed with 5 ml of soft agar A (the above growth medium with 2% agar) and 1 ml of overnight culture of different Rhodothermus strains. After pouring the sample onto a thin layer agar plate, the plates were incubated for 1–2 days at 65° C. A single, well-isolated plaque was stabbed with a sterile Pasteur pipette and dissolved in 100 µl of 10 mM MgCl$_2$ solution (forming the plaque solution).

The bacteriophage is sensitive to freezing; it can be stored in a cell lysate at 4° C. (e.g., as described below under "Liquid Lysate").

Plate Lysate

Overnight culture (0.9 ml) was mixed with 100 µl of the plaque solution and incubated for 15 minutes at 65° C. before adding 3 ml of soft agar B (same as A, but 1% agar and 10 mM MgCl$_2$). After mixing and pouring onto thin layer agar plates, the plates were incubated for 1–2 days at 65° C. To nearly totally lysed plates was added 1 ml of 10 mM MgCl$_2$, and after incubating at 4° C. for a few hours, the top layer was scraped off and put into a sterile tube. After adding 100 µl chloroform and mixing it, the sample was centrifuged and the supernatant collected. The sample was centrifuged again and filtered through a 0.2 µm filter; the filtrate was stored at 4° C. This lysate was used for testing host specificity.

Liquid Lysate

Liquid cultures were infected when they had reached an absorbance of 0.5 at 600 nm (expected to contain $2.5 \times 10^8$ cells/ml). The phage ratio was 0.1 pfu/cell culture. The cultures were incubated at high shaking (300 rpm) and growth was followed by measuring absorbance at 600 nm. When lysis had occurred, chloroform was added to the cultures (10 µl/ml) and shaking continued for 1 hour. Cell debris was removed by centrifugation and titer estimation was performed on the supernatant. large-scale purification from 300 ml culture was undertaken for DNA isolation and for protein composition analysis, as well as for electron microcopy.

Bacteriophage Purification

For electron microscopy, the bacteriophages were precipitated using PEG 8000 (Sambrook, J. et al., Molecular Cloning, Cold Spring Harbor Laboratory Press, Cold Spring Harbor, N.Y., 1989) and resuspended in SM buffer (Sambrook, J. et al., Molecular Cloning, Cold Spring Harbor Laboratory Press, Cold Spring Harbor, N.Y., 1989) before loading on the top of CsCl (0.75 g/ml). This sample was centrifuged for 23 hours at 38,000 rpm in TY-64 rotor (Sorvall Ultracentrifuge). The layer of bacteriophage was collected using a syringe.

Protein Determination and DNA Isolation

Purified bacteriophage supernatant with a titer of approximately $10^{13}$ pfu/ml was boiled for 5 minutes in SDS and β-mercaptoethanol loading puffer according to the method of Laemmli (Laemmli, U. K., *Nature* 227:680–685 (1970)) using 10% polyacrylamide gel, and stained with Coomassie brilliant blue. Bio-Rad pre-stained low molecular weight standards (7.7–204 kDa) were used as size markers. Bacteriophage DNA was isolated from a purified phage lysate containing approximately $10^{13}$ pfu/ml using the Qiagen lambda kit (Cotolog No. 12543, Qiagen) according to manufacturer's instructions.

Temperature and Chloroform Sensitivity

Bacteriophage RM 378 at approximately $10^{11}$ pfu/ml was incubated for 30 minutes over a temperature range of 50–96° C. before the remaining bacteriophage titer was determined. The bacteriophage lysate at approximately $10^{11}$ pfu/ml was mixed with an equal volume of chloroform, and incubated at room temperature. After 30 minutes, the remaining viable bacteriophage were titrated with strain ITI 378 as a host.

Determination of G+C Content

The mole percent guanine plus cytosine content of the bacteriophage was determined by CSM with HPLC according to Mesbah (Mesbah, M. U. et al., *Int. J Syst. Bacteriol.* 39:159–167 (1989)).

Estimation of Genome Size

Bacteriophage DNA was digested individually with a variety of restriction endonucleases, and the fragments separated by electrophoresis on 0.5–0.8% (w/v) agarose gel. Pulsed-field gel electrophoresis (PFGE) was also used for size estimation. Pulsed Field Certified Agarose from BioRad (Catalog No. 162–0137, Bio Rad) (1%) was used for the gel, and low-melt agarose (Catalog No. 162–0017, Bio Rad) (1%) for filling the wells when using marker plugs. Samples of 1.0 and 0.5 µg DNA were used and Bio Rad low range marker (#350) as well as λ-ladder (Catalog No. 170–3635, Bio Rad) was employed. The running buffer was 0.5×TBE (Sambrook, J. et al., Molecular Cloning, Cold Spring Harbor Laboratory Press, Cold Spring Harbor, N.Y., 1989). Bio Rad Pulsed Field Electrophoresis system (CHEF-DRIII) was used with an initial switch time of 60 seconds, final switch time of 60 seconds, 6 V/cm angle of 120° and 21 hour run time. Gels were stained with ethidium bromide and washed in distilled water for 3 hours before photographing under a UV light illuminator.

Electron Microscopy

The bacteriophage was stained with 2.5% phosphotungstic acid and the grids examined with a Philips EM 300 electron microscope. Bacteriophage samples from CsCl purification, as well as directly from a liquid lysed culture with titer of $10^3$ pfu/ml, were used for microscopy studies.

DNA Sequencing and Genome Analysis

The phage genome was sequenced using the "shot gun sequencing" technique (see, e.g., Fleischmann, R. D. et al., *Science* 269:496–512 (1995)). The sequences were aligned (Ewing, B., et al., *Genome Research* 8:175–185 (1998)); Ewing, B. and Green, P., *Genome Research* 8:186–194 (1998)). The consensus sequence of 130,480 bp was visualized with the program XBB-Tools (Sicheritz-Ponten, T., Department of Molecular Evolution, Uppsala, Sweden) for open reading frames (ORFs).

B. Results

Bacteriophage Isolation

The phage sample from the southwest area of Iceland, prepared as described above, infected 4 strains of Rhodothermus, all from Reykjanes in southwest Iceland. The phage sample from the northwest area of Iceland, prepared as described above, infected 7 strains of Rhodothermus, all from Isafjardardjup in northwest Iceland. Bacteriophages were isolated from two of the strains infected with the sample from the southwest, and from all 7 of the strains infected with the sample from the northwest. Of these, one of the bacteriophages from the sample from the northwest was isolated from strain ITI 378 and designated RM 378. The titer of this bacteriophage was estimated; in liquid culture it repeatedly gave titers of $5-8 \times 10^{13}$ pfu/ml.

Attempts to isolate the bacteriophages from Rhodothermus by subjecting it to stress such as ultraviolet (UV) exposure did not succeed. Because such stress would have excised a prophage from the chromosome and have initiated a lytic response, the failed attempts suggest that Rhodothermus did not contain prophages.

Bacteriophage Morphology

Bacteriophage RM 378 is a tailed phage with a moderately elongated head. It is a T4-like phage, resembling the T4 phage of *Escherichia coli* both in morphology and genome size, and has a double-stranded DNA genome. RM 378 belongs to the Myoviridae family and has the A2 morphology (Ackermann, H. W., *Arch. Virol.* 124:201–209 (1992)). The bacteriophage head measures 85 nm on one side and 95 nm on the other. The tail is 150 nm in length, with a clear right-handed spiral to the tail sheath. The head/tail ratio is 0.63 and the total length is 245 nm.

Host Specificity and Infection

RM 378 concentrated bacteriophage was tested against 9 different Rhodothermus strains from the two different areas (Isafjardardjup in northwest Iceland, and Reykjanes in southwest Iceland). It infected 5 strains from the northwest, but no strains from the southwest. Thus, the bacteriophage infected only strains of Rhodothermus from the same geographical area from which the bacteriophage was isolated. It did not infect any of the 6 Thermus strains that were tested.

Growth of bacteria was followed at 65° C. in a liquid. Uninfected culture was used as control, and growth was followed until the control culture had reached stationary phase. Cell lysis started 9 hours after infection of the culture, and stationary phase in the control was reached about 14 hours after infection.

Stability of the Bacteriophage

Bacteriophage RM 378 was stable to 30 minutes exposure to chloroform, indicating that it probably does not contain lipids. Heat stability of the phage was tested at 50° C.–96° C. by incubating the phage concentrate for 30 minutes, followed by estimation of titer. There was no change of the titer up to 65° C., but at 70° C. and 80° C. a 100-fold drop in pfu/ml was measured. Linear decrease of the titer was observed up to 96° C., where it was 10,000 times lower after 30 minutes than in the starting solution. After 3 months of storage at 4° C. the titer dropped 100-fold (down to $10^{11}$ pfu/ml). After 27 months of storage the titer had fallen from $10^{11}$ pfu/ml to $10^5$ pfu/ml in a CsCl-purified sample.

Composition of Bacteriophage RM 378

Purified bacteriophage was subjected to SDS-PAGE analysis for examination of its protein composition. The phage was composed of at least 16 proteins with apparent molecular weights from 23–150 kDa. The five main bands were at 92, 61, 52, 50 and 26 kDa, and were in a ratio of 0.14:0.45:0.21:0.13:0.06. The major protein band of 61 kDa accounted for about 20% of the total protein; the five main bands together represented about 50% of total proteins.

The average G+C mol % of the RM 378 phage was 42.0±0.1. The DNA was digested with a variety of restriction enzymes (HindIII, XhoI, ClaI, AluI, NotI, SacI, PstI, BamHI, SmaI, SpeI, EcoRV). Three of the enzymes (NotI, SmaI, SpeI) did not cleave RM 378, and the rest resulted in multiple fragments. Because the addition of the fragment sizes resulted in a variable amount for the total genome size, the phage DNA was also run on PFGE, which estimated the size of the DNA to be about 150 kb.

Characteristics of the Bacteriophage

The RM 378 bacteriophage is a virulent bacteriophage following a lytic cycle of infection. Very high titer lysates of up to $10^{13}$ pfu/ml could be obtained, which indicated a large burst size of more than 100. Because no bacteriophages have been reported against this bacterial genus, RM 378 represents a new species.

Genome Analysis and Comparison to T4 Bacteriophage

The nucleic acid sequence of RM 378 is set forth in FIG. 1. The nucleic acid sequence of RM 378 contains at least 200 open reading frames (ORFs); see, for example, the ORFs described in FIG. 2. Of these, five were identified in more detail, as described in Example 2, including the ORFs expected to encode DNA polymerase, 3'-5' exonuclease, 5'-3' exonuclease, RNA ligase and DNA helicase.

RM 378 belongs in the T-even family, in that it is similar to bacteriophage T4 of *Escherichia coli*. Bacteriophage T4 of *E. coli* is a well-studied phage which, together with T2 and T6, belongs to the family of bacteriophages known as T-even phages. T-even phages are nearly identical not only in structure and composition, but also in properties. Several enzymes isolated from bacteriophage T4 are used in the field of recombinant DNA technology as well as in other commercial applications. For example, T4 DNA polymerase, T4 DNA ligase and T4 RNA ligase are frequently used in the research industry today.

The genome of RM 378 was aligned in a consensus sequence, and the open reading frames (ORFs) were analyzed and compared to the T4 bacteriophage genome. The overall genome arrangement seemed to be different and the overall similarity to known proteins was low. However, despite this apparently high genetic divergence, several structural and morphological features were highly conserved. Furthermore, homologs to proteins in T4 were identified in the RM 378 bacteriophage. These similarities are set forth in Table 1, below.

In view of the similarities between bacteriophage T4 and bacteriophage RM 378, it is reasonable to expect that bacteriophage RM 378 comprises genes that are homologous to those found in bacteriophage T4, and that these genes in bacteriophage RM 378 encode proteins and enzymes that correlate to those proteins and enzymes found in bacteriophage T4.

EXAMPLE 2

Detailed Analysis of Five Open Reading Frames (ORFs)

A. Selection of Reading Frames for Analysis

Five open reading frames (ORFs) of the numerous ORFs described above in the genome of bacteriophage RM378, have been further characterized and the corresponding genes cloned and expressed. The genes include a DNA polymerase, 3'-5' exonuclease, 5'-3'-exonuclease (RNase H), replicative DNA helicase and RNA ligase. These genes were chosen as examples of the many valuable genes encoded by the bacteriophage genome. The corresponding polypeptide products of these genes are mainly components of the bacteriophage replication machinery and can be utilized in various molecular biology applications as evident by the current use of homologous counterparts from other sources. The sequences of the five ORFs show low similarity to sequences in public databases indicative of distant relationship to known proteins; however, probable homology to known sequences can be established by comparison with families of sequences showing overall sequence similarity as well as conservation of shorter regions, sequence motifs and functionally important residues, in some cases aided by three-dimensional structural information. The limited sequence similarity or these sequences to publicly available sequences suggests that these gene products have functional properties very different from corresponding proteins currently in use in molecular biology applications. Together with the presumed thermostability, the properties of these gene products render them valuable in various applications in molecular biology.

DNA Polymerase

DNA polymerases have evolved to accommodate the varied tasks required for replication and repair. DNA replication involves 1) local melting of the DNA duplex at an origin of the replication, 2) synthesis of a primer and Okazaki fragment, 3) DNA melting and unwinding at the replication fork, 4) extension of the primer on the leading strand and discontinuous synthesis of primers followed by extension of the lagging strand, 5) removal of RNA primers and 6) sealing of nicks. (Perler et al., *Adv Protein Chem* 48:377–435 (1996)).

The different types of DNA polymerases have been grouped into Families A, B, C and X corresponding to similarity with *E. coli* pol I, II and III and pol b respectively (Braithwaite, D. K. and Ito, J., *Nucleic Acids Res.* 21:787–802 (1993)). Each of these Families contains conserved sequence regions (Perler et al., *Adv Protein Chem.* 48:377–435 (1996); Blanco L., et al., *Gene* 100:27–38 (1991); Morrison A. et al., *Proc Natl Acad Sci USA.* 88:9473–9477 (1991)). Family B DNA polymerasese are also called Pol α Family DNA polymerases.

The DNA polymerases of family B type include bacteriophage T4 and bacteriophage RB69 DNA polymerase as well as archaeal polymerases and *E. coli* polymerase II. Polymerases of this type normally have two activities, the polymerase activity and the proofreading 3'-5' exonuclease activity, found in different domains within the same polypeptide with the exonuclease domain being N-terminal to the polymerase domain (Steitz, T. A., *J Biol Chem* 274:17395–8 (1999); Kornberg, A. and Baker, T. A., DNA Replication, Freeman, New York (1992); Brautigam, C. A. and Steitz, T. A., *Curr.Opin.Struct.Biol.* 8:45–63 (1998)). Polymerases of family B have an overall domain architecture different from polymerases of family A and do not have a 5'-3' exonuclease activity which is normally found in polymerases in family A. The determined structure of RB69 DNA polymerase is a representative structure of family B type polymerase and shows clearly the modular organization of the enzyme with separate domains (Wang, J. et al., *Cell* 89:1087–99 (1997), Protein data bank (PDB) accession code 1WAJ). The structure of the archaeal DNA polymerase from Desulfurococcus strain Tok was shown to have the same overall structure (Zhao, Y. et al., *Structure Fold Des* 7:1189–99 (1999), PDB accession code 1QQC). The alignment of polymerases in this family indicates the presence of several conserved region in the sequences with characteristic sequence motifs both belonging to both the exonuclease domain and the polymerase domain (Hopfner, K. P. et al., *Proc Natl Acad Sci USA* 96:3600–3605 (1999)).

Exonucleases

Besides the basic polymerization function, DNA polymerases may contain 5'-3' and a 3'-5' exonuclease activity. The 3'-5' exonuclease activity is required for proofreading. In general the family B polymerases have 3'-5' exonuclease activity, but not 5'-3 ' exonuclease activity. If both exonucleases are present, the 5'-3' exonuclease domain is at the N-terminal followed by the 3'-5' exonuclease domain and the C-terminal polymerase domain. The structure of the polymerases can be defined further in terms of domain structure. The polymerase domain is thus composed of a number of smaller domains, often referred to as the palm, fingers and thumb, and although these parts are not homologous across families, they do show analogous structural features (Steitz, T. A., *J. Biol Chem* 274:17395–8 (1999); Komberg, A. & Baker, T. A., DNA Replication, Freeman, New York (1992); Brautigam, C. A. & Steitz, T. A., *Curr.Opin.Struct.Biol.* 8:45–63 (1998) ).

RNase H (Ribonuclease H), e.g. from bacteriophage T4, removes the RNA primers that initiate lagging strand fragments, during DNA replication of duplex DNA. The enzyme has a 5'-3' exonuclease activity on double-stranded DNA and RNA-DNA duplexes. Further, T4 RNase H has a flap endonuclease activity that cuts preferentially on either side of the junction between single and double-stranded DNA in flap and fork DNA structures. Besides replication, T4 RNase H also plays a role in DNA repair and recombination. (Bhagwat, M., et al., *J. Biol. Chem.* 272:28531–28538 (1997); Bhagwat, M., et al. *J. Biol. Chem.* 272:28523–28530 (1997)).

T4 RNase H shows sequence similarity to other enzymes with a demonstrated role in removing RNA primers, including phage T7 gene 6 exonuclease, the 5'-3' nuclease domain of *E. coli* DNA polymerase I, and human FEN-1 (flap endonuclease). These enzymes have 5'-3'-exonuclease activity on both RNA-DNA and DNA-DNA duplexes and most of them have a flap endonuclease activity that removes the 5-ssDNA tail of flap or fork structures. The T4 enzyme homologous to members of the RAD2 family of prokaryotic and eukaryotic replication and repair nucleases (Mueser T. C., et al., *Cell.* 85:1101–1112 (1996)).

RNase H is a part of the reverse transcriptase complex of various retroviruses. The HIV-1 RT associated ribonuclease H displays both endonuclease and 3'-5' exonuclease activity (Ben-Artzi, H., et al., *Nucleic Acids Res.* 20:5115–5118 (1992); Schatz, O., etal., *EMBO J.* 4:1171–1176 (1990)).

In molecular biology, RNase H is applied to the replacement synthesis of the second strand of cDNA. The enzyme produces nicks and gaps in the mRNA strand of the cDNA:mRNA hybrid, creating a series of RNA primers that are used by the corresponding DNA polymerase during the synthesis of the second strand of cDNA (Sambrook, J., et al., Molecular cloning: a laboratory manual, 2nd ed. Cold Spring Harbour Laboratory Press (1989)). The RNase H of *E. coli* can promote the formation and cleavage of RNA-DNA hybrid between an RNA site and a base paired strand of a stable hairpin or duplex DNA at temperature below their Tm (Li. J., and R. M. Wartell, *Biochemistry* 37:5154–5161 (1998); Shibahara, S., et al., *Nucleic Acids Res.* 15:4403–4415 (1987)). Thus, the enzyme has been used for site-directed cleavage of RNA using chimeric DNA splints (presence of complementary chimeric oligonucleotides) (Inoue, H., et al., *Nucleic Acids Symp Ser.* 19:135–138 (1988)) or oligoribonucleotide capable of forming a stem and loop structure (Hosaka H., et al., *J. Biol. Chem.* 269: 20090–20094 (1994)).

DNA helicase

DNA helicases use energy derived from hydrolysis of nucleoside triphosphate to catalyze the disruption of the hydrogen bonds that hold the two strands of double-stranded DNA together. The reaction results in the formation of the single-stranded DNA required as a template or reaction intermediate in DNA replication, repair or recombination (Matson, S. W., et al., *BioEssays.* 16:13–21 (1993)).

The bacteriophage T4 Gp41 is a highly processive replicative helicase (similar to the DNA B protein of *E. coli*) and has been shown to form hexamer in the presence of ATP (Dong, F., and P. H. von Hippel, *J. Biol. Chem.* 271:19625–19631 (1996)). The enzyme facilitates the unwinding of DNA helix ahead of the advancing DNA polymerase and accelerates the movement of the replication fork. It has been suggested that gp41 interacts with the polymerase holoenzyme at the replication fork (Schrock R. D. and B. Alberts, *J. Biol. Chem.* 271:16678–16682 (1996)). Gp41 has a 5'-3' polarity and requires a single stranded region on the 5' side of the duplex to be unwound. The ATP-activated helicase binds to a single gp61 primase molecule on appropriate DNA template (Morris, P. D., and K. D. Raney, *Biochemistry.* 38:5164–5171 (1999)) to reconstitute a stable primosome (Richardson, R. W. and N. G. Nossal, *J. Biol Chem.* 264:4725–4731 (1989)). Although the gp41 alone does not form a stable complex with DNA template, this helicase by itself can carry out moderately processive ATP-driven translocation along single strand DNA (Dong, F., and P. H. von Hippel. *J. Biol. Chem.* 271:19625–19631 (1996)). The T4 gene 59 protein accelerates the loading of gp41 onto DNA, when it is covered with 32 protein (the T4 single strand binding protein), and stimulates the helicase activity to catalyze replication fork movement through a DNA double helix, even through a promoter-bound RNA polymerase molecule (Barry, J., and B. Alberts. *J. Biol. Chem.* 269:33063–33068 (1994); Tarumi, K., and T. Yonesaki, *J Biol Chem.* 270:2614–2619 (1995)). The T4 gp41 helicase has also been disclosed to participate in DNA recombination. Following exonuclease nicking of ds DNA and further expansion into a gap, gp41 creates a free 3' end, which is required as a substrate by recombination proteins (RecA like) (Tarumi, K., and T. Yonesaki. *J Biol Chem.* 270:2614–2619 (1995)).

RNA Ligase

RNA ligase is abundant in T4-infected cells and has been purified in high yields. Bacteriophage T4 RNA ligase catalyzes the ATP-dependent ligation of a 5'-phosphoryl-terminated nucleic acid donor (i.e. RNA or DNA) to a 3'-hydroxyl-terminated nucleic acid acceptor. The reaction can be either intramolecular or intermolecular, i.e., the enzyme catalyzes the formation of circular DNA/RNA, linear DNA/RNA dimers, and RNA-DNA or DNA-RNA block co-polymers. The use of a 5'-phosphate, 3'-hydroxyl terminated acceptor and a 5'-phosphate, 3'-phosphate terminated donor limits the reaction to a unique product. Thus, the enzyme can be an important tool in the synthesis of DNA of defined sequence (Marie I., et al., *Biochemistry* 19:635–642 (1980), Sugion, A. et al., *J. Biol. Chem.* 252:1732–1738 (1977)).

The practical use of T4 RNA ligase has been demonstrated in many ways. Various ligation-anchored PCR amplification methods have been developed, where an anchor of defined sequence is directly ligated to single strand DNA (following primer extension, e.g. first strand cDNA). The PCR resultant product is amplified by using primers specific for both the DNA of interest and the anchor (Apte, A. N., and P. D. Siebert, *BioTechniques.* 15:890–893 (1993); Troutt, A. B., et al., *Proc. Natl. Acad. Sci. USA.* 89: 9823–9825 (1992); Zhang, X. H., and V. L. Chiang, *Nucleic Acids Res.* 24:990–991(1996)). Furthermore, T4 RNA ligase has been used in fluorescence-, isotope- or biotin-labeling of the 5'-end of single stranded DNA/RNA molecules (Kinoshita Y., et al., *Nucleic Acid Res.* 25: 3747–3748 (1997)), synthesis of circular hammer head ribozymes (Wang, L., and D. E. Ruffner. *Nucleic Acids Res* 26: 2502–2504 (1998)), synthesis of dinucleoside polyphosphates (Atencia, E. A., et al. *Eur. J. Biochem.* 261: 802–811 (1999)), and for the production of composite primers (Kaluz, S., et al., *BioTechniques.* 19: 182–186 (1995)).

B. DNA Polymerase Activity and 3'-5' Exonuclease Activity Are Found in Gene Products of Separate Genes in the Phage RM378 Genome The predicted gene products of two open reading frames (ORF056e and ORF632e), which are widely separated in the genome of phage RM378, both showed similarity to family B type polymerases as shown below.

Identification of the ORF056e gene product as 3'-5' exonuclease

The predicted gene product of ORF056e (locus GP43a) was run against a sequence database (NCBI nr) in a similarity search using BLAST (Altschul, S. F. et al., *J. Mol. Biol.* 215:403–410 (1990)) (Table 2). Out of 64 hits with E value lower (better) than 1, all sequences were of DNA polymerases of family B type including DNA polymerase from bacteriophage RB69, archaeal DNA polymerases and *E. coli* polymerase II. Importantly, all these sequences are DNA polymerase sequences having the sequence characteristics of the DNA polymerase domain as well as the 3'-5' exonuclease domain and are considerably longer (excluding partial sequences) than the predicted gene product of ORF056e which has a length of 349 residues. The similarity is restricted to the N-terminal halves of these sequences corresponding to the part of the protein where the 3'-5' proofreading exonuclease domain is located.

Table 2 lists the 20 sequences with strongest similarity to the ORF056e sequence together with the length and E-value according to BLAST search. The sequence identity with the ORF056e sequence ranges from 21 to 27%. Of the 64 sequences identified in the sequence database, 34 are of viral origin and 15 of archaeal origin. Out of the twenty top scoring sequences, 16 are of viral origin.

Identification of the ORF632e gene product as DNA polymerase

The sequence similarity program BLAST (Altschul, S. F. et al., *J. Mol. Biol.* 215:403–410 (1990)) was also used to identify potential homologues of the ORF632e (locus GP43b) gene product. The 100 sequences in the sequence database (NCBI nr) with the strongest similarity to the ORF632e sequence were all defined as DNA polymerase sequences. These sequences all had an E value lower than 10–5 and are considerably longer (excluding partial sequences) than the predicted gene product of ORF632e which has a length of 522 residues (Table 3). Sequence alignments between the ORF632e sequence and the sequences identified in the database shows that the similarity is restricted to a domain with the DNA polymerase activity as characterized by conserved sequence motifs such as DxxSLYPS (Hopfner, K. P. et al., *Proc Natl Acad Sci USA* 96:3600–3605 (1999)). In these sequences this domain is always preceded by a long N-terminal region where the 3'-5' exonuclease activity normally is found. The corresponding N-terminal region is lacking in ORF362e which consists only of the DNA polymerase domain (family B type polymerases ). The sequence motif DXXSLYPS (SEQ ID NO:63) in the ORF632e sequence is found very close to its N-terminus unlike its location in all the 100 analyzed sequences in the public database.

Table 3 lists the 20 sequences with strongest similarity to the ORF632e sequence together with the length and E-value according to a BLAST search. The sequence identity with the ORF632e sequence rages from 23 to 28% within aligned regions of 300 to 428 residues. The majority of these 20 sequences are of archaeal DNA polymerases of family B type.

The results of the similarity searches indicated that gene products of ORF056e and ORF632e correspond to the exonuclease domain and the polymerase domain of family B type polymerases, respectively. Partial alignment of sequences of a number of members of this family was obtained from the Protein Families Data Base of Alignments and HMMs (Sanger Institute), accession number PF00136. The sequences of ORF056e and ORF632e could be combined as one continuous polypeptide and aligned to the previous set of sequences. The coordinates of the three-dimensional structures of DNA polymerases from bacteriophage RB69 (PDB ID 1WAJ), the archaea *Thermococcus gorgonarius* (PDB ID 1TGO) and the archaea Desulforococcus strain Tok (PDB ID 1QQc) were structurally aligned and the sequence alignment produced from the structural alignment. The corresponding sequences were added to the previous alignment and the alignment adjusted, guided by the alignment from the structural superposition, mainly in regions which are less conserved. The resulting alignment, shown in FIG. 3, strongly supports the previous interpretation that 3'-5' proofreading activity and DNA polymerase activity are found in two proteins encoded by separate genes in bacteriophage RM378. As seen in the alignment (FIG. 3), the major conserved regions in this protein family in the 5'-3' exonuclease domain and in the polymerase domain are also conserved in the gene products of ORF056e and ORF632e, respectively. As defined by Hopfner et al. (Hopfnier, K. P. et al., *Proc Natl Acad Sci USA* 96:3600–3605 (1999)), this includes regions exo I, -II and -III in the exonuclease domain and motifs A, -B and -C in the polymerase protein. Motif A corresponds to the DxxSLYPS motif mentioned above and includes an aspartic acid residue, involved in coordinating one of the two Mg2+ ions which are essential for the polymerase activity, and a tyrosine residue which stacks it side chain against an incoming nucleotide in the polymerase reaction. Another aspartic residue which also acts as Mg2+ ion ligand (motif C), and is essential for the catalytic mechanism, is also found in the sequence of ORF632e (D215). Inspection of the three-dimensional structure of bacteriophage RM69 DNA polymerase (PDB ID 1WAJ), with respect to the alignment, shows that the end of the ORF056e sequence and the beginning of the ORF632e sequence are found between the 3'-5' exonuclease domain and the DNA polymerase domain.

The polymerase activity encoded by bacteriophage RM378 thus resides in an enzyme which is relatively short corresponding only to the polymerase domain of other members in this family and unlike those relatives does not have an 3'-5' exonuclease domain. The 3'-5' exonuclease is found as another protein encoded by a separate gene elsewhere in the genome. The natural form of DNA polymerase from *Thermus aquaticus* (Taq) also lacks the proofreading 3'-5' exonuclease activity but this polymerase differs from the polymerase of RM378 in several aspects: i) it belong to a different family of polymerase (family A) which have a different general architecture, ii) the lack of 3'-5' exonuclease activity is due to a non-functional domain since it still contains a structural domain homologous to a domain where this activity resides in other polymerase in this family, and iii) naturally occurring Taq has 5'-3' exonuclease activity besides its polymerase activity (Kim, Y. et al., *Nature* 376:612–616 (1995)). Thus, the current protein is the only known example of a DNA polymerase which by nature lacks proofreading activity and the corresponding structural domain present in other polymerases of this type, and therefore represents the discovery of a unique compact type of DNA polymerase found in nature lacking both 3'-5' and 5'-3' exonuclease activity.

C. ORF739f Encodes an RNA Ligase

Several sequences of RNA ligases in a protein sequence database showed similarity to the ORF739f sequence (locus GP63) as identified in a similarity search using BLAST (Altschul, S. F. et al., *J. Mol. Biol.* 215:403–410 (1990)). The top scoring sequences found in the BLAST search are show in Table 4. Only 3 sequences showed a score with E-value below 1.0. The two most significant and extensive similarities were found to the sequences of RNA ligases from *Autographa californica* nucleopolyhedrovirus and bacteriophage T4. The similarity to the third sequence, that of a DNA helicase, is much less extensive and has considerable higher E-value. The sequence identity between the ORF739f sequence and the two RNA ligase sequences is 23% over regions of 314 and 381 residues. A sequence alignment of these three sequences is shown in FIG. 4.

The site of covalent reaction with ATP (adenylation) has been located at residue K99 in bacteriophage T4 RNA ligase (Thogersen H C, et al., *Eur J Biochem* 147:325–9 (1985) ;Heaphy, S., Singh, M. and Gait, M. J., *Biochemistry* 26:1688–96 (1999)). A corresponding Lysine residue (K126) is also found in the sequence of ORF739f. An aspartic residue close to the adenylation site in T4 RNA ligase has also been implied as important for the catalytic mechanism (Heaphy, S., Singh, M. and Gait, M. J., *Biochemistry* 26:1688–96 (1999)). This residue is also conserved in ORF739f (D128). It has been suggested that the motif KX(D/N)G may be a signature element for covalent catalysis in nucleotidyl transfer (Cong, P., and Shuman, S., *J Biol Chem* 268:7256–60 (1993)). The conservation of these active site residues supports the interpretation of ORF739f gene product as RNA ligase having catalytic mechanism in common with other RNA ligases and involving covalent reaction with ATP.

Table 4 shows sequences with strongest similarity (E-value cutoff of 1.0) to the ORF739f sequence together with their length and E-value according to BLAST search.

D. Orf 1218a Encodes a Gene Product with 5'-3' Exonuclease Activity

A BLAST search (Altschul, S. F. et al., *J. Mol. Biol.* 215:403–410 (1990)) identified about 60 sequences in the database (NCBI nr) with significant similarity (corresponding to E-value lower than 1) to the sequence of the predicted gene product of ORF 1218a (locus DAS). Almost all the identified sequences are of DNA polymerase I from bacterial species (DNA polymerase family A) and the similarity is restricted to the N-terminal halves of these sequences and the ORF 1218a sequence is much shorter, 318 residues, compared to the identified sequences which usually are between 800 and 900 residues (Table 5).

Structural and functional studies of DNA polymerases of this type (family A) have defined the different structural domains and how these correlate with the different activities of the enzyme. Polymerases of this type normally have a polymerase activity located in a C-terminal domain and two exonuclease activities, a 3'-5' exonuclease proofreading activity in a central domain and a 5'-3 exonuclease activity in an N-terminal domain (Kornberg, A. and Baker, T. A., DNA Replication, Freeman, New York (1992); Brautigarn, C. A. and Steitz, T. A., *Curr.Opin.Struct.Biol.* 8:45–63 (1998)). The sequence of ORF 1218a corresponds to the 5'-3' exonuclease domain of these polymerases.

The 5'-3' exonuclease domain of DNA polymerase I belongs to a large family of proteins which also include ribonuclease H (RNase H) including bacteriophage T4 RNase H. The analysis of the structure of bacteriophage T4 RNase H revealed the conservation of a several acidic residues in this family of proteins. These residues are clustered at the active site, some of which help coordinate two functionally important Mg2+ ions (Mueser, T. C.,et al., *Cell* 85:1101–12 (1996)). The corresponding alignment shown in FIG. 5, including the sequence of the ORF 1218a gene product, shows that these acidic residues (possibly with the exception of one) are also found in the gene product of ORF1218a thus further supporting its proposed activity as 5'-3' exonuclease.

The 5'-3' exonuclease of polymerase I and RNase H both remove RNA primers that have been formed during replication but T4 DNA polymerases and other polymerases of the same type (family B), including the identified polymerase of phage RM378 identified here (see above), lack the 5'-3' exonuclease activity. T4 RNase H (305 residues) and the ORF1218a gene product (318 residues) are of similar size with conserved regions scattered throughout most of the sequences (FIG. 5). These proteins are likely to have a very similar structure given the structural similarity between T4 RNase H and 5'-3' exonuclease domain of polymerase I (Mueser, T. C., et al., *Cell* 85:1101–12 (1996)). The gene product of ORF1218a probably has a function analogous to the function of RNase H in bacteriophage T4.

Table 5 sets forth the 21 sequences with strongest similarity to the ORF 1218a sequence together with the length and E-value according to BLAST search. The sequence identity with the ORF1218a sequence ranges from 31 to 41% within aligned regions of 82 to 145 residues.

E. A Replicative DNA Helicase is Part of the Replication Machinery of Phage RM378

Several sequences of replicative DNA helicases were identified in a similarity search using BLAST (Altschul, S. F., et al., *J. Mol. Biol.* 215:403–410 (1990)) with the ORF1293b (locus GP41) sequence as query sequence. 15 sequences had an E-value lower than 1.0 with the sequence of bacteriophage T4 replicative DNA helicase (product of gene 41, accession number P04530) having by far the lowest E-value. Some of the sequences found in the similarity search are hypothetical proteins and some are defined as RAD4 repair protein homologues. However, the most extensive similarity was found with the replicative helicase sequences, with sequence identity of 20–23% spanning 210–295 residues, and these sequences are all of length similar to the length of the ORF1293b gene product (416 residues). Table 6 shows the identified sequences of the similarity search.

The replicative DNA helicases with similarity to the ORF1293b sequence are of the same protein family often named after the corresponding helicase in *E. coli* encoded by the DnaB gene (e.g. DnaB-like helicases). The Protein Families Data Base of Alignments and HMMs (Sanger Institute), holds 37 sequences in this family (family DnaB, accession number PF00772) and the alignment of these sequences shows clearly several regions with conserved sequence motifs. One of this motif is characteristic for ATPases and GTPases (Walker A motif, P-loop) and forms a loop that is involved in binding the phosphates of the nucleotide (Sawaya, M. R. et al., *Cell* 99:167–77 (1999)). The replicative helicases bind single stranded DNA (at the replication fork) and translocate in the 5'-3' direction with ATP (GTP) driven translocation (Matson, S. W., et al., *BioEssays* 16:13–22 (1993)). The significant similarity found in the BLAST search to sequences other than helicase sequences is partly due to the presence of an ATP/GTP binding sequence motif in these sequences.

FIG. 6 shows the sequence alignment of some members of the DnaB protein family together with the sequence of ORF 1293b. Sawaya et al. have shown how several conserved motifs and functionally important residues of the DnaB family relate to the crystal structure of the helicase domain of the T7 helicase-primase (Sawaya, M. R. et al., Cell 99:167–77 (1999)). The alignment in FIG. 6 shows how these conserved motifs are present in the ORF1293b sequence thereby supporting its role as replicative helicase.

The bacteriophage T4 replicative helicase sequence was indicated as most closely related to the ORF1293b sequence in the similarity search. The structure and function of the corresponding helicases may be very similar in these two bacteriophages and, together with the similarity of numerous other components of these phages, may be indicative of other similarities of their replication machinery. T4 replicative helicase is known to be an essential protein in the phage replication and interact with other proteins at the replication fork such as the primase to form the primosome (Nossal, N. G., *FASEB J.* 6:871–8 (1992)). Similarly, the helicase encoded by ORF1293b may have an essential function in bacteriophage RM378. Other homologues of components of the T4 replication system have been detected as well as shown above and still others may also be expected to be encoded by the bacteriophage genome.

Table 6 sets forth sequences with strongest similarity (E-value cutoff of 1.0) to the ORF1293b sequence together with the length and E-value according to BLAST search.

F. Subcloning of Selected ORFs from RM378

Plasmids were designated pSH1, pGK1, pOL6, pJB1 and pJB2, were generated for the genes encoding the 3'-5' exonuclease, the DNA polymerase, the RNA-ligase gene, the RNaseH gene and the helicase gene, respectively. The correct insertion of the ORFs into the expression vector was verified by DNA sequencing, and the expression of the genes was verified by SDS gel electrophoresis of respective host strain crude extracts.

*E. coli* strain JM109 [supE44Δ(lac-proAB), hsdR17, recA1, endA1, gyrA96, thi-1, relA1 (F'traD36, proAB, lacIqZΔM15)] (Viera and Messing, *Gene,* 19:259–268 (1982)) and strain XL10-Gold [TetrΔ(mcrA)183 Δ(mcrCB-hsdSMR-nrr)173 endA1 supE44 thi-1 recA1 gyrA96 relA1 lac Hte (F' proAB lacIqZΔM15 Tn10 (Tetr) Amy Camr)] (Stratagene) were used as hosts for expression plasmids.

Restriction enzyme digestions, plasmid preparations, and other in vitro manipulation of DNA were performed using standard protocols (Sambrook et al., Molecular Cloning 2nd Ed. Cold Spring Harbor Press, 1989).

The PCR amplification of the nucleic acids sequence containing the open reading frame (ORF) 056e, which displayed similarity to 3'-5' exonuclease domain of family B polymerase genes was as follows. The forward primer exo-f: CACGAGCTC ATG AAG ATC ACG CTA AGC GCA AGC (SEQ ID NO:64), spanning the start codon (underlined) and containing restriction enzyme site, was used with the reverse primer exo-r: ACAGGTACC TTA CTC AGG TAT TTT TTT GAA CAT (SEQ ID NO:65), containing restriction site and spanning the stop codon (underlined, reverse complement) [codon 350 of ORF 056E shown in FIG. 7]. The PCR amplification was performed with 0.5 U of Dynazyme DNA polymerase (Finnzyme), 10 ng of RM378 phage DNA, a 1 μM concentration of each synthetic primer, a 0.2 mM concentration of each deoxynucleoside triphosphate, and 1.5 mM $MgCl_2$ in the buffer recommended by the manufacturer. A total of 30 cycles were performed. Each cycle consisted of denaturing at 94° C. for 50 s, annealing at 50° C. for 40 s, and extension at 72° C. for 90 s. The PCR products were digested with Kpn I and Sac I and ligated into Kpn I and Sac I digested pTrcHis A (Invitrogen) to produce pSH1. Epicurian Coli XL10-Gold (Stratagene) were transformed with pSH1 and used for induction of protein expression, although any host strain carrying a lac repressor could be used.

The PCR amplification of the nucleic acids sequence containing ORF 632e, which exhibited similarity to DNA polymerase domain of family B polymerase genes was similar as described above for the putative 3'-5' exonuclease gene except that other PCR-primers were used. The forward primer pol-f: CACGAGCTC ATGAACATCAACAAGTATCGTTAT (SEQ ID NO:66), spanning the start codon (underlined) and containing restriction enzyme sites was used with the reverse primer pol-r: ACAGGTACCTTAGTTTTCACTCTCTACAAG (SEQ ID NO:67), containing restriction site and spanning the stop codon (underlined reverse complement) [codon 523 of ORF 632e shown in FIG. 8]. The PCR products were digested with Kpn I and Sac I and ligated into Kpn I and Sac I digested pTrcHis A (Invitrogen) to produce pGK1. Epicurian Coli XL10-Gold (Stratagene) were transformed with pGK1 and used for induction of protein expression. The expressed protein was observed with Anti-Xpress Antibody (Invitrogen) after Western Blot.

The PCR amplification of the nucleic acid sequence containing ORF 739f, (which displayed similarity to the T4

RNA ligase gene) was similar to the procedure described above for the putative 3'-5' exonuclease gene. The forward primer Rlig-f: GGG AAT TCT TAT GAA CGT AAA ATA CCC G (SEQ ID NO:68), spanning the start codon (underlined) and containing restriction enzyme sites was used with the reverse primer Rlig-r: GGA GAT CTT ATT TAA ATA ACC CCT TTT C (SEQ ID NO:69), containing restriction site and spanning the stop codon (underlined reverse complement) [codon 437 of the ORF shown in FIG. 9]. The PCR products were digested with EcoRI and Bg/II. Subsequently the amplified products were cloned into EcoRI and BamHI digested pBTac1 (Amann et al., *Gene* 25:167–178 (1983)) to produce pOL6. Cells of *E. coli* strain JM109 were transformed with pOL6 and used for induction of protein expression, although any host strain carrying a lac repressor could be used.

The PCR amplification of the nucleic acid sequence containing ORF 1218a, (which displayed similarity to the T4 RNaseH gene) was similar to the procedure described above for the putative 3'-5' exonuclease gene except that other PCR-primers were used. The forward primer RnH-f: GGGAATTCTT ATG AAA AGA CTG AGG AAT AT (SEQ ID NO:70), spanning the start codon (underlined) and containing restriction enzyme sites was used with the reverse primer RnH-r: GGA GAT CTC ATA GTC TCC TCT TTC TT (SEQ ID NO:71), containing restriction site and spanning the stop codon (underlined reverse complement) [codon 319 of the ORF shown in FIG. 10]. The PCR products were digested with EcoRI and Bg/II and ligated into EcoRI and BamHI digested pBTac1 (Amann et al. *Gene* 25:167–178. 1983) to produce pJB1. As for the RNA ligase clone, cells of *E. coli* strain JM109 were transformed with pJB1 and used for induction of protein expression.

The PCR amplification of the nucleic acid sequence containing ORF 1293b, which displayed similarity to the dnaB like helicase genes was as described above for the putative 3'-5' exonuclease gene except other PCR-primers were used. The forward primer HelI-f: GGGCAATTGTT ATG GAA ACG ATT GTA ATT TC (SEQ ID NO:72), spanning the start codon (underlined) and containing restriction enzyme sites was used with the reverse primer HelI-r: CGGGATCC TCA TTT AAC AGC AAC GTC (SEQ ID NO:73), containing restriction site and spanning the stop codon (underlined reverse complement) [codon 417 of the ORF shown in FIG. 11]. The PCR products were digested with EcoRI and Bg/II and ligated into EcoRI and BamHI digested pBTac1 (Amann et al. *Gene* 25:167–178 (1983)) to produce pJB2. Cells of *E. coli* strain JM109 were transformed with pJB2 and used for induction of protein expression.

Deposit of Biological Material

A deposit of *Rhodothermus marinus* strain ITI 378, and a deposit *Rhodothermus marinus* strain ITI 378 infected with bacteriophage RM 378, was made at the following depository under the terms of the Budapest Treaty:

Deutsche Sammlung Von Mikroorganismen und Zellkulturen GmbH (DSMZ)

Mascheroder Weg 1b

D-38124 Braunschweig, Germany.

The deposit of *Rhodothermus marinus* strain ITI 378 received accession number DSM 12830, with an accession date of May 28, 1999. The infected strain (*Rhodothermus marinus* strain ITI 378 infected with bacteriophage RM 378) received accession number DSM 12831, with an accession date of May 31, 1999.

During the pendency of this application, access to the deposits described herein will be afforded to the Commissioner upon request. All restrictions upon the availability to the public of the deposited material will be irrevocably removed upon granting of a patent on this application, except for the requirements specified in 37 C.F.R. 1.808(b) and 1.806. The deposits will be maintained in a public depository for a period of at least 30 years from the date of deposit or for the enforceable life of the patent or for a period of five years after the date of the most recent request for the furnishing of a sample of the biological material, whichever is longer. The deposits will be replaced if they should become nonviable or nonreplicable.

TABLE 1

Comparison of Structural Features of T4 and RM 378

| Feature | T4 | RM 378 |
|---|---|---|
| Phage type | T-even, A2 morphology | T-even, A2 morphology |
| Family | Myoviridae | Myoviridae |
| Genome size | 168,900 bases | ca 130,480 bases |
| Number of ORFs | ca 300 | >200 |
| Characteristic structural proteins | GP3, GP13, GP17, GP18, GP20, GP21, GP23 | Putative homologs of the same were identified |
| Arrangement of structural proteins | All of the above genes are on the same strand and clustered in a region covering 35 kb | All of the above genes were dispersed over the whole genome and found on both strands |
| Representative enzymes | lysozyme and thymidine kinase (on same strand) | lysozyme and thymidine kinase (on different strands) |

TABLE 2

| Source: | Accession #: | Definition: | Length: | E-value*: |
|---|---|---|---|---|
| *Spodoptera litura* nucleopolyhedrovirus | AAC33750.1 | DNA polymerase | 603 (partial) | 9e-08 |
| *Spodoptera littoralis* nucleopolyhedrovirus | AAF61904.1 | DNA polymerase | 998 | 9e-08 |
| *Sulfurisphaera ohwakuensis* | O050607 | DNA POLYMERASE I (DNA POLYMERASE B1) | 872 | 3e-07 |
| *Xestia c-nigrum* | AAC06350.1 | DNA polymerase | 1098 | 4e-07 |

TABLE 2-continued

| Source: | Accession #: | Definition: | Length: | E-value*: |
|---|---|---|---|---|
| granulovirus | | | | |
| *Lymantria dispar* nucleopolyhedrovirus | T30431 | DNA-directed DNA polymerase | 1014 | 5e-07 |
| *Lymantria dispar* nucleopolyhedrovirus | P30318 | DNA POLYMERASE | 1013 | 5e-07 |
| nucleopolyhedrovirus | AAC33747.1 | DNA polymerase | 647 (partial) | 8e-07 |
| *Sulfolobus acidocaldarius* | P95690 | DNA POLYMERASE I | 875 | 4e-06 |
| *Bacteriophage RB69* | Q38087 | DNA POLYMERASE | 903 | 5e-06 |
| *Spodoptera exigua* nucleopolyhedrovirus | AAC33749.1 | DNA polymerase | 636 | 2e-04 |
| *Spodoptera exigua* nucleopolyhedrovirus | AAF33622.1 | DNA polymerase | 1063 | 2e-04 |
| *Mamestra brassicae* nucleopolyhedrovirus | AAC33746.1 | DNA polymerase | 628 (partial) | 9e-04 |
| *Melanoplus sanguinipes* entomopoxvirus | AAC97837.1 | putative DNA polymerase | 1079 | 9e-04 |
| *Orgyia anartoides* nucleopoluhedrovirus | AAC33748.1 | DNA polymerase | 658 | 0.003 |
| *Sulfolobus solfataricus* | AAB53090.1 | DNA polymerase | 882 | 0.003 |
| *Sulfolobus solfataricus* | P26811 | DNA POLYMERASE I | 882 | 0.003 |
| Human herpesvirus 7 | AAC40752.1 | catalytic subunit of replicative DNA polymerase | 1013 | 0.004 |
| Human herpesvirus 7 | AAC40752.1 | catalytic subunit of replicative DNA polymerase | 1013 | 0.004 |
| *Methanococcus voltae* | P52025 | DNA POLYMERASE | 824 | 0.010 |
| *Bombyx mori* nuclear polyhedrosis virus | P41712 | DNA POLYMERASE | 986 | 0.013 |
| *Bombyx mori* nuclear polyhedrosis virus | BAA03756.1 | DNA polymerase | 986 | 0.051 |

*An E-value of 1 assigned to a hit can be interpreted as meaning that in a database of the current size one might expect to see 1 match with a similar score simply by chance.

TABLE 3

| Source: | Accession #: | Definition: | Length: | E-value*: |
|---|---|---|---|---|
| *Aeropyrum pernix* | O93745 | DNA POLYMERASE I | 959 | 4e-20 |
| *Aeropyrum pernix* | BAA75662.1 | DNA polymerase | 923 | 4e-20 |
| *Aeropyrum pernix* | BAA75663.1 | DNA polymerase II | 772 | 7e-14 |
| *Aeropyrum pernix* | O93746 | DNA POLYMERASE II | 784 | 7e-14 |
| *Pyrodictium occultum* | BAA07579.1 | DNA polymerase | 914 | 2e-16 |
| *Pyrodictium occultum* | A56277 | DNA-directed DNA polymerase | 879 | 2e-16 |
| *Pyrodictium occultum* | B56277 | DNA-directed DNA polymerase | 803 | 6e-11 |
| *Sulfolobus acidocaldarius* | P95690 | DNA POLYMERASE I | 875 | 5e-16 |
| *Archaeoglobus fulgidus* | O29753 | DNA POLYMERASE | 781 | 1e-14 |
| *Chlorella virus* NY2A | P30320 | DNA POLYMERASE | 913 | 3e-14 |
| *Thermococcus gorgonarius* | P56689 | DNA POLYMERASE | 773 | 4e-14 |
| *Paramecium bursaria* Chlorella virus I | A42543 | DNA-directed DNA polymerase | 913 | 9e-14 |
| *Paramecium bursaria* Chlorella virus I | P30321 | DNA POLYMERASE | 913 | 4e-13 |
| *Pyrobaculum islandicum* | AAF27815.1 | family B DNA polymerase | 785 | 9e-14 |
| *Homo sapiens* | P09884 | DNA POLYMERASE ALPHA CATALYTIC SUBUNIT | 1462 | 1e-13 |
| *Homo sapiens* | NP_002682.1 | polymerase (DNA directed), delta 1, catalytic subunit | 1107 | 6e-07 |
| *Homo sapiens* | S35455 | DNA-directed DNA polymerase delta 1 | 107 | 9e-07 |
| Chlorella virus K2 | BAA35142.1 | DNA polymerase | 913 | 3e-13 |
| *Sulfolobus solfataricus* | AAB53090.1 | DNA polymerase | 882 | 3e-13 |
| *Sulfolobus solfataricus* | P26811 | DNA POLYMERASE I | 882 | 3e-13 |

*An E-value of 1 assigned to a hit can be interpreted as meaning that in a database of the current size one might expect to see 1 match with a similar score simply by chance.

TABLE 4

| Source: | Accession #: | Definition: | Length: | E-value*: |
|---|---|---|---|---|
| *Autographa californica* nucleopolyhedrovirus | P41476 | PUTATIVE BIFUNCTIONAL POLYNUCLEOTIDE KINASE/RNA LIGASE | 694 | 3e-07 |
| Coliphage T4P | 00971 | RNA LIGASE | 374 | 0.002 |
| *Aquifex aeolicus* | D70476 | DNA helicase | 530 | 0.25 |

*An E-value of 1 assigned to a hit can be interpreted as meaning that in a database of the current size one might expect to see 1 match with a similar score simply by chance.

TABLE 5

| Source: | Accession #: | Definition: | Length: | E-value*: |
|---|---|---|---|---|
| *Streptococcus pneumoniae* | P13252 | DNA POLYMERASE I | 877 | 2e-08 |
| *Lactococcus lactis* subsp. *cremoris* | O32801 | DNA POLYMERASE I | 877 | 2e-06 |
| *Bacillus stearothermophilus* | AAB52611.1 | DNA polymerase I | 876 | 1e-05 |
| *Bacillus stearothermophilus* | AAB62092.1 | DNA polymerase I | 877 | 2e-05 |
| *Bacillus stearothermophilus* | S70368 | DNA polymerase I | 876 | 2e-05 |
| *Bacillus stearothermophilus* | P52026 | DNA POLYMERASE I | 876 | 2e-05 |
| *Bacillus stearothermophilus* | JC4286 | DNA-directed DNA polymerase | 879 | 4e-05 |
| *Bacillus stearothermophilus* | AAA85558.1 | DNA polymerase | 954 | 4e-05 |
| *Thermus thermophilus* | 2113329A | DNA polymerase | 834 | 3e-05 |
| *Thermus thermophilus* | P52028 | DNA POLYMERASE I | 834 | 3e-05 |
| *Thermus thermophilus* | BAA85001.1 | DNA polymerase | 834 | 3e-05 |
| *Bacillus subtilis* | O34996 | DNA POLYMERASE I | 880 | 4e-05 |
| *Bacillus caldotenax* | Q04957 | DNA POLYMERASE I | 877 | 4e-05 |
| *Deinococcus radiodurans* | A40597 | DNA-directed DNA polymerase | 921 | 4e-05 |
| *Deinococcus radiodurans* | P52027 | DNA POLYMERASE I | 956 | 4e-05 |
| *Aquifex aeolicus* | D70440 | DNA polymerase I 3'-5' exo domain | 289 | 7e-05 |
| *Thermus filiformis* | O52225 | DNA POLYMERASE I | 833 | 7e-05 |
| *Anaerocellum thermophilum* | Q59156 | DNA POLYMERASE I | 850 | 3e-04 |
| *Rickettsia felis* | CAB56067.1 | DNA polymerase I | 922 | 3e-04 |
| *Rhodothermus* sp. 'ITI 518' | AAC98908.I | DNA polymerase type I | 924 | 4e-04 |
| *Thermus aquaticus* | P19821 | DNA POLYMERASE I | 832 | 4e-04 |

*An E-value of 1 assigned to a hit can: be interpreted as meaning that in a database of the current size one might expect to see 1 match with a similar score simply by chance.

TABLE 6

| Source: | Accession #: | Definition: | Length: | E-value*: |
|---|---|---|---|---|
| coliphage T4 | P04530 | PRIMASE-HELICASE (PROTEIN GP41) | 475 | 3E-06 |
| *Campylobacter jejuni* | CAB75198.1 | replicative DNA helicase | 458 | 0.003 |
| *Listeria monocytogenes* | Q48761 | DNA REPAIR PROTEIN RADA HOMOLOG | 452 | 0.003 |
| *Listeria monocytogenes* | AAC33293.1 | Rada homolog | 457 | 0.016 |
| *Mycoplasma arthritidis* bacteriophage MAV | 1AAC33767.1 | putative replication protein | 276 | .007 |
| *Aeropyrum pernix* | B72665 | hypothetical protein | 726 | 0.016 |
| *Porphyra purpurea* | P51333 | PROBABLE REPLICATIVE DNA HELICASE | 568 | 0.027 |
| *Escherichia coli* | P03005 | REPLICATIVE DNA HELICASE | 471 | 0.047 |
| *Saccharomyces cerevisiae* | NP_011861.1 | SH3 domain | 452 | 0.047 |
| *Chlamydia trachomatis* | O84300 | DNA REPAIR PROTEIN RADA HOMOLOG | 454 | 0.14 |

TABLE 6-continued

| Source: | Accession #: | Definition: | Length: | E-value*: |
|---|---|---|---|---|
| Haemophilus influenzae | P45256 | REPLICATIVE DNA HELICASE | 504 | 0.14 |
| Caenorhabditis elegans | T16375 | hypothetical protein | 566 | 0.18 |
| Pyrococcus horikoshii | B71133 | hypothetical protein | 483 | 0.18 |
| Cyanidium caldarium | AAF12980.1 | unknown; replication helicase subunit | 489 | 0.53 |
| Rickettsia prowazekii | Q9ZD04 | DNA REPAIR PROTEIN RADA HOMOLOG | 448 | 0.69 |

*An E-value of 1 assigned to a hit can be interpreted as meaning that in a database of the current size one might expect to see 1 match with a similar score simply by chance.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated nucleic acid molecule comprising the genome of bacteriophage RM 378, which is deposited in *Rhodethermus marinus* strain ITI 378 infected with bacteriophage RM 378 in the Deutsche Sammlung Von Mikroorganismen und Zellkulturen GmbH (DSMZ), accession number DSM 12831.

2. An isolated nucleic acid molecule comprising the nucleotide sequence SEQ ID NO:1, shown in FIG. 1.

3. A DNA construct comprising an isolated nucleic acid molecule comprising the nucleotide sequence SEQ ID NO: 1, operatively linked to a regulatory sequence.

4. A host cell comprising a DNA construct of claim 3.

* * * * *

SEQUENCE LISTING

<160> NUMBER OF SEQ ID NOS: 73

<210> SEQ ID NO 1
<211> LENGTH: 129908
<212> TYPE: DNA
<213> ORGANISM: Bacteriophage RM378

<400> SEQUENCE: 1

```
cgggtctgct tttccttcac ggacccaatt ctccgtgaaa gaaatacgac attcatactg      60
cacctcctgg ttggtttaat tagggttaat gttataccct ttcaggaact tcgatcgctt     120
taactccctc tgatgaagca cggtttccac cgcggcaaaa atcaccagca gcagaaacca     180
cgctcctatc agaagcagcg ccgtttcaaa ataaaccac ttcatcacaa gccccgccag      240
tacgaaggcg ggcaaaaaac ctgttataac gtaaacagcg ctcatggttc acccctgagt     300
ctggagtgca aaggcacctg taatatccac ccaaccctca tgacgaaata ccgtcttctt     360
gaccacggtt ccgtcgggct gctgctcctc caccgacacc ctcttcgtaa aggaaaacag     420
aggaatgata cagaaagcca tcagagcatt gaccagaaac ggcatgaagt agggcgcgcc     480
tccaatcatg gcggcaccca gcaaaatatc ctccgtctcc ccactcttct tgaaaaaccc     540
ggcggcaaga gcggcaatct cccacgcgcg agacatcatc tgatcgaaat caggaatttc     600
ctcgaacgta agaagctcct tcacccgatt ccactgatca tcaggaaggt ttacaacccc     660
cgcctccatc tgttcgggag tcggattgtg ctgggtgaga ttcagaatcg tcatggcttg     720
tacctccgtt tgtttgttaa gtgatccaca gccagtatac gcataaagcg gaaaaaagtc     780
aatcggtatt ttctttcttc atcttaattt cattttttc cttgagggaa atatccgccg     840
catacatttt ttcggcttcc ttcagcacct cagagactct gctgaagatc tccctgagct     900
gaaccattga ccactccgga tcgtcaagca ccagtggaag cgcgtagccg tcttcatacg     960
tttcatagtt atcctcaaac agatcttcca gcagacgatc cagcagtgca ggaatttcat    1020
atcggtaact cataactcct ccggcggtta acttatcggt aaaccttcac ggatgaaggt    1080
ctcatgtgaa tgaacacttt tgctcccgga tacacttcat ccagaaccat aagcgccaca    1140
agcgaagcaa gcgtcatgta caccccctgg atacctccca ccgtcatata atccagaaat    1200
ctgatcgtac ccgccgaaat ggtatcttca agccccccat cccagataag atattccacg    1260
```

-continued

```
atggagggaa tctgaaccct gatcttttcc agctcccgct cgatatggat atgcggatcc    1320
gaactacgcg ctgcttccct gcagatacct ccgccagaa caagcaacgt tcatttcga     1380 ttctgataaa aataattcag agcaccctcg aacagcgctt caggatctgt agccgcacgc    1440
ggaacgcttc tggaaacgtc tttcagaatc tgcatcatga cgcacctcca ttttttccaa    1500
cataaccttc ttatttcctt tcggttcca cgcaatccca attaccacta ttaatctcca    1560
tcaagtcaga aacccgaatt caatttaaaa cttttctgtc tgaaattccc ttataaccct    1620
taaaacttaa cactacccct tcaacacaat cccaatcacc agtaaaaacc tacctgcatt    1680
agatctacta ctccccttg aagcaaaaag gaaaaaacca aaaatcaaaa ttctataacc    1740
cctacaggat acgctcagct ttaagtcgca tattacccat tgggatttta gaattttaaa    1800 atttttgtttt tctttaatct ccatagggta cgcttagcat tgagtcttaa tttaccattt    1860
gagggatttt aatttagaag ttttttgtttt tctttaatct ccatagggta cgcttagcat    1920
tgagtcttaa tttaccattt gagggatttt aatttagaaa ttcaaaaatt taattttttc    1980
ataaccttga gtggcttatt tacctgtaga gcgtcattca aaaaacaccc catttcaaga    2040
aaccttcaca ttgatctgtc gttttacaac ataaaaccctt taagtggtat atgatcagaa    2100
agcgtaaaaa atctgaacat atcggagcgg atgcgattcc aaagggattg gtctatgatg    2160
ttttaaatct tgggtatacc gataagctca atcccgcat gattgctata ctgagcattc    2220
ttatctacca tcgccaccgg gaagatcaca cctacgagat tgaaacagga tcgaaatgca    2280
agcgcatggt ggaagttaaa aaaggggagt cctggatcag cattccaacg cttattgagc    2340
gggtttacaa cacatttgga attaagctta ccagggagca ggttaaatat gcccttcgtt    2400
tgcttttaca gcatggtctg atttcggtaa aggaagcaac cggtgggtt tcgaaaggtc    2460 attttggaaa catttataca ttcagagaaa cggattttga aggagagttt gtcgatcctg    2520
tggattttgt gagggaaaat agtgaaagtg aagaagaaat ctggtatgca gattatacgg    2580
aaagtcggta ttcgaatcgc gtaaccgtca gagaaggagc atttcatccg attatgaaaa    2640
gtaggacact tctaaaaacg catgtgctta gaaatcatcc agatagagaa aaagctacga    2700
agttttaccc gaaagagatt gttgtggata tcgaagcggg tggatatcgc gtagatgaaa    2760
cagagcggta cagacgcttt agactcttcg tgataaaccg cgctgcgaag tttgcgagaa    2820
agttcagagc acgctacggg gggaaagttg atatatgttt taccggaggt aggggaattc    2880
atctgcatat tacgggaagt gtgctcaatg ttccaatgaa ccgcagtcaa ttcgacagga    2940
ttttgaaaga agcaattgtt cgtatgctta agatacgga actatggcgg ttttttcgatc    3000 cttccacgct gaatcctttt cagcttgccg gggttcgcgg aaaacttcat gataaggctc    3060
cttttgacga ctgggtgtat gtgaagcgta cctatcaaac gattaagccg ctcaaagccg    3120
gaagtctgct ttcgagtttt gaggaggcgg cttttctgga ttcgcgtagc ttcgtcagaa    3180
aagcggctaa aggcaatcca tttagaacgt acagtctggt aaaggaaggg ctactggaag    3240
gggagccgtg gagcgatcac catgcgggaa gagatacggc tgctttctgc atggcatgcg    3300
atcttctgga agccggatac atgacggatc aggtgttgct gtttctgaaa gattgggata    3360
agaaaaacaa accttctctt ggagataaga ttatcgcgca aaggtaaga tcggcgcggc    3420 ggcttcttgc gcgaaaagga aagcttaaag caaacccttc tctacagctt ctctaattgt    3480
tttgaaaaag tgatagaatc tttccgggga aaagctgtat ccgatcatgt cggtgataac    3540
gctcatcaca ttgaaaaatc gttggacttc atccggattt cttctgtcga ttttgataag    3600
aagttcgatt atacgtttaa acgatttagg ataatcgtac cacagaaagg aaagatatgc    3660
```

```
acccgacgat ccttcttcct cttctttttt catgtaagaa cgaatatctt catacagata   3720
ccatatatcc acaatgcttt gagcgagttt ctccataatt ctggtggcgg tgttgctgaa   3780
cgtattgata tactcacagg taacaacata catattcttt ttgatttctt cgataatttc   3840
aacatgaata tttgtttcca gaagataaac agggaaagaa attgaaagtt tttcaagctg   3900
cacaatttta tgcagaaagg tgttttcgcg cacttcccaa tcccacagac atttcacagt   3960
cagatatatt tcatttctta taactttctc cagttcgacg aaaatatacg atttattttc   4020
tataaagccg ggtaactctt catgaatgat gcggtttaag ttgctgtgtt ttttcatacg   4080
ggtgttatct ctcagcaatt ttcttttagc atttgccaca aatctctgat atctttcttc   4140
aaaatcttct ttttgaatt ggatgttggc ttcattttgc aattgtctgg ttcttatagc    4200
aagcgtctca atgaacgttt tgattagaag tattgctccc ttagccatat cctgaatggt   4260
ggaatcggcg ggtaaatcca cacgaaagat ttttcgagtt tcttcgtttt tgatcagtgc   4320
gacgttccat cccattctct tttccatgaa aaacctgagc gcccagacca gatattcgta   4380
gaagttttca gtcattttat tttaaatatt cccttatctg tattccactt ccggagattc   4440
tatatggatg taaagtatat ttttcgtgg tataaaattc atctgagcgt gcaccgcaat    4500
tttcaggtcg ttctcgctca aatgatgctc gccccacctg aacgatccga taaactgcag   4560
cgtgatatgg tgcgtgatca aatccgtaga aaactccagc ttatcatctg tttcgggtgg   4620
aagcacatcg gtagagggaa accgggattt cacatcaaga cgtgcaagca ccagataatg   4680
atggtaattc tcgacgtttg atgccggtga tatgtttttg agtttgtcgt ttaatgtgcg   4740
gattacttct ttcatttcct tttcgatggt ggtatcctct gattcttttc tggagaaaat   4800
gtttttataa gagggtcctt ttttgatatg ttctaccggg gaaatggctt taagcagtct   4860
gtaggcataa tgcaacgtgt cgtttatcat ctttatgaat tttctgatcg caacgcttac   4920
aggtgtatcc tcagagatgc tcaggtagac cagatcgggg tgttttctca aatgataatc   4980
aggtggagag aagccgggat attttttccag atagttttg atggtgtttg taagcagttc    5040
ctgatacgat ggcattttat tttaaataag tgttgataaa caaacaggct ttttttcacat   5100 attcgaacaa ttcatctttg gaaagatggt gtggtttgta ctgacgatgc ataaacttat   5160
aagcaatatc aaacaatacc ctaccctttt cctcactttc tttaataata tctataatgc   5220
tgtctatttc ctcttcagt tctctgtaaa tggttcggta tcggtttatg tcctgctctg    5280
tcaggtgttc actatttca tattttatcc cgaatacaga cataatacct attgttcctc    5340
cgataaattc cagtgttcca ttccgggtag aggcgcttac aaatgagttg cgaatcttca   5400
atgttttatc tgaaacgaaa cttttaaaac ttaagtcaag gagcatttct gtaacaaaca   5460
gaggagcatt caggtggaaa attttttgcaa attttgaatt ttctcgggga aaccatttaa    5520
caaaaccgat tatcattata ccaagatgag cttcctttgc aaaaaccggc ataatgtaaa   5580
gatgaatttc gtttcgaaat tctatttcgt ctgtgaagtg ggtgattaat tttttatcga   5640
tattattgta gtgtatagta tcgtctttaa gttctttcat ttttttctga gtttctttta   5700
atgcctgttg aaacttctcc tcaatttgat ctacagctat tttttcaact ccgatatctt   5760
cttcgaagtg tctgattttg gtaagtgata gttctatagt cttttttaagc gtatgaacat   5820 acatccgcgt aaaatctctg ggtaactgct tttcggcggg aataagacgc acttttacat   5880
aagaaggtcg tttctctata atttctacac tggaaaattc cgatcttttt tttaaaatat   5940
tcaatgatgt tcattgcaag tagtgcttca acaacgcctt ccatagtttt tttagctaag    6000
```

-continued

```
gttttttgtt tacagttttg tagttttcgt taattaaggt gtttaatgct attggttttt    6060
ttaactattc cccacgaact atctgtttca atacacgata tctttccacc atatcgaggt    6120
ttataatatc cagcgctcta cctatttcat caaacatttc gatcacgcgt tcatcctgat    6180 tgttttgct gtgttcgata aggtttctga gttcaaaagc tccccgtata ccactggaat     6240
acagaaatgc gattttgga atatcagggt gtccgggatt aataagagat agaaaatgtt    6300
caatgttttt tatgagttca tgaaggcgat tatactgcat gttgaaataa gcgtgggctt    6360
ttgtcagcct gatgttttct tctatcatgg ggcgcacgta aaaactccca tgcagagcgg    6420
ttccgatatt ggtaaaaact gtctcgtgaa acagaatagc ggaaagtgcg gcgttttaa     6480 ccggatagag agaacttgca ccaataaccg atatatcaaa cagagcagga aaaactcga     6540 aaagactctg atcattaaag aaaatatgca tttcgttttt tcgatatacc agatcagggt    6600
atttatgtgt ggtgttaaat attttctgta ttttctgaac cgtttctttc tccttattta    6660
ttttttcttt aaacttctca atagcctgct ggtacttatc atttattttg ctgtctacag    6720
aaaacccgga ataaatggtt cgtgtctttt ttataaaaaa ctcgatcagt tctttgaaca    6780
tgcgcggcgt ttcttttata atctcttttg cggttgcgtt ttcaccgatg tcaaggatta    6840
tggttacatg tttatcgccg gcgtctatgt ttaccggata ctttttttga aatctgtaat    6900
actgctgaat tgcacttaaa atctctttac ggtatttttt cggagtcata aggtgtcggg    6960 tttgattta ttaaatcact caggttttta agtcgtgcat gtttaaccca gttttttaac     7020
caccctgtta ttccaccata tgacttttcc atctgatctt acgattcctc cgtatcccat    7080
gcggctcagg atctcattga ttttccgtt ttgaggaacg ttgagtgcac caaaatagag     7140
ttcagtaagt tgcttcataa aacggtttct atcctgattc agatcttctt ctatcatcat    7200
ctgaatgcgg gttggaaatg tatctacgat caggtttacg acgtagactc tatcgctggc    7260
ttcccatctt gaaggaaaa aggaatcata tcgaagcaac cggtcaaacg tttcgtcaac     7320
gacggttttg acaaatgtcg caagttttcg ggtgaaaacg gctccggttt gctcgaaagt    7380
gataagcaac ccttttgaaaa gcattttccg gagtgcggag aggctgtagg gaacgtcaaa   7440
atgaattccc ctttcgacga atccatatgg cggctttcca ataccccct gaagtttcat    7500 tcggtgaagt tccagccgc ttccaagaaa ttcgtcaatc tgaagttttt taagttttt     7560 gagatcggag gagttaaggt gcacgccgaa atagttaagt gcgccccgg tggacgcgaa    7620 aaggggagg ttgtaaaaat cttttggata atcgttttcc tttttgacgt tgagaaattc    7680
ctccggctcg atgatatagt agaggtgata cccgcgctcc aagatttccc gaagggtttt    7740 tcgtttaac gggattcgc tcataaggag tccgttcc tccacagaag acacaatcag        7800
gtttgaggga tcaagcgttt cgatttttc aaggagctct ttcatacggg tatctgcagg    7860
gttatctgtt cgcggttaat ctgcacaacg attttgagaa ggtgtgtggc ttcgtcaaaa    7920
ctcacgtcta tagtatctat gtcgtagggt tcgaggttgg aggcaatcag gttgaacagt    7980
tcatcataat cataattctc gaaagaatg ttgcgaatac cgatccctct ttctggatcg     8040
tagggatatt cccccggctc gatgaaaagc aggagttta tcttatcgat caggagtttt    8100
accgggtcat caggaaatct gaattcggt gcagtgtcgt tcagatagaa catttcattt    8160
ttgtttaaat aaatcctcga ggaatcttca ataaagagg ggcgttaatg gatgaaaaga     8220
ctgaggaata tggtcaatct tatcgatctc aaaaatcagt attatgctta ctcttcaag   8280 tttttcgact cctatcagat cagctggat aattaccgc atcttaaaga gttcgtcatt      8340
gaaaactatc ccggcactta tttttcatgc tacgctccgg ggattctgta caagcttttc    8400
```

-continued

```
ctcaaatgga agcggggtat gatcattgac gactatgacc gacacccgct ccgaaagaag    8460
ttacttcctc agtacaaaga gcaccgctat gaatacattg agggaaaata cggtgtggtt    8520
cctttccccg ggtttctgaa atatctgaag ttccactttg aggacttgcg gtttaaaatg    8580
cgcgatcttg gaatcaccga tttcaaatat gcacttgcca tttctctttt ttacaaccgg    8640
gtaatgctca gagattttct gaaaaacttt acctgttatt acattgccga atatgaagct    8700
gacgatgtaa tcgcacatct ggcgcgtgag attgcacgaa gcaatatcga cgtaaacatc    8760
gtctcaacgg ataaagatta ttaccagcta tgggatgaag aggatataag agaaagggtt    8820
tatatcaatt ctctttcatg tagtgatgtg aagacacccc gctacggatt tcttaccatt    8880
aaagcacttc ttggagacaa aagcgataac attcccaaat ctctgaaaaa aggaaaaggc    8940
gaaaagtatc ttgaaaagaa aggatttgcg gaggaagatt acgataagga actattcgag    9000
aataatctga aggtgatcag gtttggagac gaatatcttg gagaaaggga taaaagctttt   9060 atagaaaatt tttctacggg ggatactctg tggaactttt atgaattttt ttactatgac    9120
cctttgcatg aacttttcct cagaaatata agaaagagga gactatgaaa gtactcgcat    9180
ttaccgatgc acctacgttt cccacggggg tgggtcatca gcttcacaac attatcaatt    9240
acgggtttga cgcaaccgat cgctgggttg tggtgcaccc gccccggtcg ccaagggctg    9300
gagagactaa aaacgtcgtt attggaaaca ctccagtcaa gcttatcaat tctccgcgag    9360
gatatgcgga tgatccggcg tttgtgatga aggtggtgga agatgaaaag ccggatgtgc    9420
ttgtaatttt taccgatccg tgggcttacc accccttttat gcaacaactt tcttactgga   9480
ttatcgagcg gaatctcccg ctggtatatt atcatgtgtg ggataatttt ccggctcctc    9540
tgtacaacat ccccttctgg cacacctgca atgaagtgat aggaatttcg atgaaatcga    9600
cgatcaacgt gcagcttgcg aaggagtatg tggaggcgta tgaaatcacc atgtatcgcg    9660
atccggaggt attctatctt ccgcatgcgg tcgaacccaa tgtattcaaa cgcatggatc    9720
gcaagaaagc acgtgaattt gtgcggggac ttgtcggaga taggatgttt gatgacagcg    9780
tgatctggct ttacaacaat cgaaatattt cacgcaagaa tctgatggat accatttatg    9840
cttttctggt atacatgctc aaaaactaca ggaaacatca ccttttgatt ataaagtctg    9900
acccggttgt accggtggga acggatattc ccgcgtttct tgccgatatt aattcgtttt    9960
tccactaccg ggatattgac cttcgggaac acattgtttt catttccaat gacgaagtat   10020
ttcacaacgg cggattttca agggaggaaa tcgcattgct ttataacggc gccgatgtgg   10080
tgctgcagct ttcatctaat gaggggttcg ggatcgcttc gcttgaggcg tcgctgtgtg   10140
gagccccggt ggttgctact atgacgggtg gtattgcaga tcagtactcc ctctacgaaa   10200
tggattatga ggtggcggat ggaagtgatg aagatataat ctgcaagatt tatgaggaag   10260
tgcaccgtca ggtgctcaat cagtatctcg atatgctccg tcaaaacgga aaggatccgg   10320
aaagcgctcc ccgcaaaaat catatgatgc ggatggtgaa accttatcgt cattatcagg   10380
gatcgccggc tactccctac attcttgacg acagggttcc tatccgggac gtattcccga   10440
agttcgatga agcgctggcg ctgaggaatc gtgaggatta cgaaaaactt tatgaagaat   10500
cggttgagta catcaccatg cacttcgatg tagaggtgct cggaaaagag ttcaagaaat   10560
cccttagccg tgccattaag aataaccaga aaccacaag acaggttgtc gtgctatgaa    10620
gaagaaagtg cttcttgttt cgccgcttcg ttccgttagc ggctatggaa ccgtaagtcg   10680
cggaatttat cgcattctga agcgaatgga aaagagggg ttgatcgatt ttgatgtgat   10740
```

```
ggtattgcgg tggggtacgt tttcggaaac cacccacctt gatgatgaaa tcaagaagag    10800
aattcaggag aagtatgatc aggtgtacga tgttgcgatc atggtttctt ctccctacga    10860
ctatcgctac tggaacaaca tcttcagagc gaaacacctg ctcttttca atgcgatggt    10920
ggaaacgaaa ccgttccatc cgaatctgtt ccagcagctt tcaacttca tgcttcaggt     10980
tcccaccgcg caccttgtgt ttccttcttc gaaatcaag aggatctggg aagaaatcat    11040
caattcccaa cccatccatc cggcaatggg tgctgcagtg ctctcccgca ttcatgtagt    11100
acccaacccg gtagatgaag tttactatac ttcgaacttc gggaataaaa acgttcgtaa    11160
aaatgtgatc ggcgcgattc gaaagaagat tgaggaaatc cgtcgatcct atgaactgga    11220
gcgggtgttt ctgactttg cgcctatggg agtagatcga aagaacacca gggttttacc     11280
cgaacttatc gaaatggtgg ggcgggttgg aattctggcg ctggcgggcg aacaaattc     11340
ttttatactt tacgactttc agcggcttat ctggatggaa ggtgagaaag cctataagcg    11400
gcttccgctt caccgatcga tcgacgttac cccggaagag cttatgttcg ttttggatc     11460
gctgacggtg gaagagctga gtgcggtgat ggatatggtg gatggtggaa tcaacctttc    11520
gcatggagaa tcgtgggatt acctgttgca caacatgatg ctactgggca aaccctgtct    11580
ttacgtcgac ttcttccgtc gggattatat cccttcggag cttcgtgatg tgctgggggt    11640
ggatttcaat atggtacccc tcccgaaggt ggttcccaac attccgcacg atcatccgtt    11700
cttccacccg caaacgatgg tggcggaacc caatttgcag gatgcagcgg aaaagctcga    11760
ctgggtgttg cggaactacg gtgaagtctc aaagatgatt accagccata gagacgcttt    11820
caaaaccgac gatacgatct atgaatttct ggttgacgca ctggagtcga tcgaagaacc    11880
acaggcggca taaaaatttc acattctgga taaaccgggg gaattcgggc atttatcccg    11940
aaaatccccc ttttttgtct caaaaccgtt ttggcggggt agatatttaa tatcaccccg    12000
tggaaagttt aaccccaaaa caggagtgga tatgtcgtac tatactgaag tcggcgcacc    12060
ctactttaca cgtgaagagc agtttgttcg gaatttgctg ttcgacgtaa cttttaattc    12120
caaatattct ttcttcgatc tgacgctgca gcgtcgtctt acctttgagg aagtgctgga    12180
agaggtgctg gcggtgtttc atgcccgaat cgaggaagtc tgcaaaccca tttatcgcca    12240
gcaggcgcac cagtacgtgg agaagttcgg cgagtatttc cgccagcgca agcttttcc     12300
ctcgatgcgc cttgtgcagt tttcgcgcat ggttccttac aaccacaccc gtctttacaa    12360
ttgctcttat actcccgttg attccattga ttcgatcgcg gagcttttct acctgatgtt    12420
gtgtggcgtg ggtgtgggat acagcgtgga gcgtaaatat atcgaacagc ttcctgttgt    12480
atatcccgaa agtgagggc agacaatcac ctatcaggtg gaggattcga tcgagggatg     12540
gtgctcggcg ctcaagcgtt atctctatgc gcggtttacg cccaaccacc cgaagattgt    12600
atttgactat tctcttttga gaccggaggg aagtgtgatt ggaaagcgtt acaatgctgc    12660
atttggttat actaaaaaca atcccatcaa agaagcaatc gaggcggtaa aggggatttt    12720
cgacaaagca gtaggaagga aactcaagcc gatcgaggta catgatctca ttacaacgtt    12780
cggcatgatt atcaatcgtg cgaacgtgcg cggaatggcg gcgatcgtct ttttcgatta    12840
tgatgatgaa gaaatgcttc gctgcaagga tttcacgcgc ggcgaagtcc ctcagaaccg    12900
ctggtatgcc aacaactctg tcgtgttgta tagagacggc gataaacttc gcggagtgcg    12960
cggggaaatc gtcgatcttc gggatatttt catggaagcc tattgtggga agtctggtga    13020
acccggcgtc tttgtaacca acgacgaaca ttatcgcacg aacccgtgtg gtgaagcttc    13080
tctttatcgc aatttctgca accttacgga gatcgccatt cccgtgttc atcagagtga     13140
```

```
gatcgcggat gtgttgaaca cagctatctt cattggtgtg cttcagtcta cgtttaccga  13200
ctttaagttc cttcgcgatg tgtggaaaga gcgcaccgaa gaagacaact tgcttggcgt  13260
ttcgctgacc ggcatttacg aaaatctgga tgcgctcaaa gagtacatga agctttcttc  13320
gaaaggtcat gtcaaattca tggcggctca atttgccggt tggttcgggt tgaacaaccc  13380
ggctcgcatt acgctggtca agccctccgg cacggtgtcg ctgcttgccg gggtttctcc  13440
gggttgccac ccaccctatt ccgaatattt tatccggaga aaccgggtgg atatgaatca  13500
catgctggtt gaagttttga aggattatcc gtttatcatt gatgatgaag tgtatcccga  13560
taagaaagtg atcgaatttc cgcttcgggc gcaacgccac tttacgcacg atcccatgtt  13620
tcaggtgcgt cttcgcaacc agatcatgag gggctgggtg gaaccctcgc ataatcgcgg  13680
caaaaacaca cacaacgtat cgattacggt ttatgtaaga gatgaagggg aagtggagat  13740
tgtaagtcgc gaactcaaaa atgagcgaaa catttcggga atcacgattc ttccggtggt  13800
tgagaatggc tataaactgg caccattcga agcaattccc agggaaaagt atgccgacat  13860
gatgggcgaa atccacgtgt accttgatag aatcaaacac cagctaaacg gcacgcccga  13920
ctccccgcgt ctgaaactga tctccgattc cgacgttttt gagggagaga aaggttgtgc  13980
cggtctgcaa tgctatttcg acatgtaaca tgaaactcgt acttaaacac tccagagaag  14040
agtctttcta tcctgaaaca ataaaaactc ttgatcatct tagagagaat gggtgggaaa  14100
tcgttctcct acaggataat cgttttaata tcatagaagg ttacgatttc gatatggtga  14160
ttaccacgtc gaaccctcaa tacagctttg cggatttcca caatgaagca ttgaaatttg  14220
ccaagcacgg ggagtggctt ttttatcttg atttcgatga atatttatgt gataattttt  14280
gtgaaagggt taaaaaatat atcaacagag atgttcattg ttacaacatc gcacgcataa  14340
acattataat tcctcaggag aaaacgggtg atgtgtgcgg gatgtacgga tggcgtagtt  14400
ttaatatcaa tatacctgag gaagggagtg taaaagcgat aaatttcccc gattaccaga  14460
cgcgtctggt tcgcgccgga accggcaaat ggtacgggaa cgcccacgaa cgctttgtgt  14520
gcgataatgc ttttaaacac aaaacgttac cgtttgatgg tggatatatt atccaccgta  14580
aatcttttga gaaacagatt accgataacg cgctctggtc aacctataca ccgtgatata  14640
tgttcagcgt aattctcata cacggaaacg aggatcttat caataaagaa ctgatagata  14700
atcttaatga attcagggaa gcaggatgtg aactcatttt gctgcaggat gatcgttttt  14760
caccgcccga cttttttcaaa tttgatattg ttataaaaca ttccgtttcc gaagggatgg  14820
accgtcatcg aaattttgcc aatcaacatg cttcttttga atgggtgttg tggttggatt  14880
ttgacgaata tctattcccc ggatttacag aacgagctcc tgaatacatg aaaagggata  14940
tatgggggta tggattttac agattgaaca tgatcgttcc acctgaaaaa acttcatggt  15000
tcgttcagaa ttatggctgg tatgaaatgg ttgggtgggt ttcaaccata tcgatcaggg  15060
gggtttctta tcaggctata aattacccgg aggttcatta tcgttttgtt cgaagagatt  15120
gcggcaagtg ggttggtaaa agacatgaat actggtattc aggtgatttt cgtaaaaaag  15180
ccatatttcc ggcggatcga gaaacacttt tccacgttaa acccattgac aaagcaataa  15240
gagacaacta taaatggagg gcactatgat gaaccccgaa atgaaagaga ttctgaagaa  15300
gcttatgaaa cccttccacc ctgatcgcca ttcctatcgc gttaccggaa ccttccggac  15360
tcgggaaggg cggaacatgg gggtggtggc atttacatt tcatcacgcg acgtgatgga  15420
tcggttggat gcggtggtgg gaccagagaa ctggcgagac gaatatgaag tgccggctcc  15480
```

-continued

| | |
|---|---|
| gggggtgatg aagtgtgtgc tttatttgcg tataggtggg gagtggggttg gaaagagtga | 15540 |
| tgtggggacc ggcaacatag aaaaccctga aagtggatgg aaaggcgccg cttctgacgc | 15600 |
| cttgaagcga gcggcggtca agtggggaat cgggcgttat ctctatgcac ttcccaaatg | 15660 |
| ctatgtggag gtggatgata gaaagcgtat tgttaatgaa gaggcggtca agtcttttct | 15720 |
| ccataagcat gttaccgaac tgctgaagaa ttatcagtaa cccaaaccta aacccgaaaa | 15780 |
| atatatggaa acgattgtaa tttcccaaaa caatacgacg gagatgacgg aacccccca | 15840 |
| gaacatttcc gattcggtta aaagcgggtt tatctatctt atcgaaaagt ctcatttcct | 15900 |
| tgaaaagaaa aacttcctta aaatcatatc gaacatggac ccccgccgca tttccaatcc | 15960 |
| ggaggtgcgc gtggtggcgg agtacatata tgattatttc aaaagtcata gtaatttccc | 16020 |
| ttctaaaaga aatctttgcc atcactttga gtggagcgaa gatctggaag gagacccccgc | 16080 |
| cgattatcag cgtatcattc agtatctcaa atcttcttac attcgatcct ctataacaaa | 16140 |
| aacgctttca tatcttgaga aggatgacct ttccgcgttg aaagaaattg tcagagccat | 16200 |
| tcgggtggtg gaggatagtg gggtgtcgct ggtggaggaa ttcgatcttg caaccagcga | 16260 |
| gtttaatgaa cttttttgtta aagaagaacg cattcccacc ccctgggaga gtgtaaacaa | 16320 |
| aaatatggcg gcggtcttg gtcggggaga gcttggaatc gttatgcttc cttcggggtg | 16380 |
| gggtaagtca tggttccttg tttcacttgg tcttcatgcc tttcgaacgg gtaagcgcgt | 16440 |
| gatttatttc actctggagc ttgaccaaaa atatgtgatg aagcggtttt taaagatgtt | 16500 |
| tgcaccttat tgcaaaggac gcgcttcttc ctatcgcgcg gtttatcaaa taatgaaaga | 16560 |
| gcttatgttt tctcaggata atcttttgaa gattgttttc tgtaatgcga tggaagatat | 16620 |
| tgagcactat attgcgctgt ataaccccga cgttgtgctg attgactatg ccgatcttat | 16680 |
| ttatgatgtg gaaaccgaca aagagaaaaa ttatctgctt ttgcaaaaaa tttataggaa | 16740 |
| acttcgtctc attgcaaagg tatataatac agcagtatgg agcgcctctc agcttaatcg | 16800 |
| cggttcccctt tcaaagcaag ccgacgtcga tttcattgag aaatacattg ccgattcatt | 16860 |
| tgcaaaagtt gttgaaatcg acttcgggat ggcgtttatt ccggatagcg agaactcaac | 16920 |
| ccccgatatt cacgtcggat tcggtaaaat cttcaaaaac cgtatgggtg cggtaagaaa | 16980 |
| gctggaatat acaattaact ttgaaaaacta tacggtagac gttgctgtta atgacacaa | 17040 |
| gttaagacaa aagggcttaa agacatcaga ataggtagaa aggagggtaa gttcacacat | 17100 |
| gtaaatacaa caaagaaagg aaagaataag aaatatttca gggcggaaca tgaacgcctg | 17160 |
| tttctcaacc ttattcgagc acttcaggtt ggggattatg ccgaaatcaa ttctctttttt | 17220 |
| cctcttgtcg aaaagcaact ccgatggatg gtacgaaaga tagtgaaccg actcaatctc | 17280 |
| acttcacttg tttcatatta tgaccacggc gaatgggagc atgatattgt aagttatgtg | 17340 |
| ttctccaaac tcgataacta ttctcccgaa aagggaaggg tgttcagtta tatcagtgtt | 17400 |
| atcatagtca attatgctat caatttgaac aataaaattt attataaccg ggtgggtat | 17460 |
| cattcagatt tctatgcaga taatcctacc accgaagact acaagggtct ggatgaaaag | 17520 |
| gaagagttga gttatgaaat agacgatcag attaatctga agattgattt tgagcatttc | 17580 |
| tgcaatctgt ttttaaatgc ttccgaagaa actttactca agcattttca ggaagacgaa | 17640 |
| gttttttattg ttaaaaatat tgcgctttct ctgaaatatg atccggatat tatcacgacg | 17700 |
| ccttttctgg gggttgtaca tcggatgatc tgtgagtttt gtggggtgga attttcccgc | 17760 |
| tataagttttt ccaaagtgtt caagaaaatg gttcaactat accacgaagt ttttaacggg | 17820 |
| gggtaaaggt tatttaaata aaaaatatgt tttcggcttc tgattataaa ggaaacgtaa | 17880 |

```
cttttagttt tcacttccct tcgcttctca ccaatgccgg atcgcaccca aataaggcat   17940
atgtgtatta cgactatatg ggtagtgatc tggtgttcac ttttttctcga ataagattca  18000 gcctgtcggc acccggcacc tacgatgctt attttgacgc tcatattcag gatgttgaca   18060
ccattacctt cgattcaaac ggataccgtg agctttattt cattttcagc gtttcctggg   18120
aaggatccaa cacttcgggc accatttcgg gtgccaatct tatcagcgta tcttcctttg   18180
ttactggata ccccgaaaac agttttcttg cctatacgct ttccgtttac tctgcttccg   18240
ccacaaccta tcttaacctt aatgatgctt acagaattta cgtagggaac attttcggca   18300
ccccgcaatg ggaagttggt tttaccggta gtttcacggt ttctgctacg ccttcaattt   18360
ctcacaaccg tttcaggatt ttacttcttt ctaactttga tagtgcactt aattactata   18420
ttactacgtt cagcgcacca gcattcgcct cacattcatt tcaggttatc aggaaaatat   18480
atgaagttga gccactttct gcttacacag taccgtctat cgtgttttc tacacggttt    18540 cagctactaa cagcttcggg tggagctatt ccaatataga aatgggtct ctttacagaa    18600 tatcaactat gtccattcta agttatcctt acccctacac ggcaccggct ataacgtata   18660
tcactttttc tggcggaatt gtttcggatg aagaatttat tgtaaaggtg cccataaccc   18720
tttcttatat taacaacata ataccgtatt tcatcggcaa ccccactacc acttcaaaca   18780
ttgacgatgt gaatgctact gaagataaaa ttatccctac ttcgataagt aactttaaaa   18840 caacccttc atttcaggtt tttgcttttc cgaacacact ccctgttaaa acggaacaag    18900
tatcaattcc cgttaccttc agtccggaaa cgggcaacat ttctattcct gtttccatct   18960
catttcctgc gtttgtaaga actgctgcgg ctacaatgga taatccgggc aattttttcca  19020 cttctgtcgg aaatggtatc gtggttagcg atcttgtgtg tcagaataca gggaatatac   19080
ctattacatt tagtggtgtc agtcttgcaa tagacgatgg taactggtat gtggacaccc   19140
cctccgtggg atatggtttt aacccgaaca gcgggttttg gttcgatgtt cactttatgc   19200
cttatgggga tgtaaactac agtcaatcca tttattttac gttttcgttc aattatccaa   19260
caaattatgg aaatatattg tcaggtagtt ttgttgaatc catttctttc catgcggttg   19320
ctacaggaac cgccccttcc ggtcaggtgg gtattacggt gtccaactgg aatgtggaca   19380
accctaacac cgttatggtt ggtaaatatg ttaccggttc cttcagcatc acggcaagtg   19440
ctacaaacaa tcagatcgct caggttaccc tgacttcatc aaccccccaat ctgtatttca    19500 cgacggtttc aggtgttggt attaacaatc ttcatgctac ggcggtaaat tctctggcgc   19560
tacaggttgc tcccggagct tctctttctg tttatacccca gtggtatatg aatatggttt   19620
atacggcttc ggctcctgat gtaaccatat cggtaacgtc ttctaatgct acggaaatga   19680
acggcgtgcc gggattgacg gaagttaagc gatcgcattc gctgacgaac cctgctcgat   19740
atgcaaattt gaatatagga atttttttcac tcagtgctta tggtcccttc tatcaatcaa   19800
ccgcctctat tttgccgttc ccttattctt ttagtcttgg gggcatcaac gtcgttagaa   19860
atgttggttt ggcttggctt gattttatc caacgaacag cactcattct gaatgtatg    19920 ttaaattgac catgtctctg acaggatcgg ctttaaatgt tcatagcgta gtaacttcat   19980 cgtattttc tgatccttct aatttcgagt gggaagtcaa cactttgcag catactctgt    20040
tcagcccccc ttatggatat tttcttcata ttagaataag accgactcca agtgatatta   20100
acataatacc gacttcaagt gcatatggat atggtacgtt tgttgtaagt tggagcatga   20160
gtcttatttc ccatataaat ggggtaagcg tggcttctct tggacagggg tattcaaatg   20220
```

```
ctttgagttt gtggtttgat catactgttt tctatgaagc accatagtaa tttcttatct   20280
atacgacaca tacttgataa aattgccgct ttctcccatt tcaaaatatt ttctgagcgt   20340
agaaggagta aaatccgtgg cgtctccaag ctttcgagtg ggggtgatca gtgttgcgtt   20400
gattttgaca tagtggcttt tgatcatttt gttgtggggg aaaagcaggt tgtaaagcgc   20460
catctggttt acgtcgttca aaagatgttc atgccagaga atatcgtaag tgcgggtaag   20520
cagcgcaaga agattggtgt agtagttccg ttcttcctta atggtgtaaa gcggcgtgca   20580
ggaaatgatg atcgcttgaa tttcctcacc cggctttaat tctttaagtt taataaggtt   20640
ttcaatggta aacccaagcg gaatcacttc tcttacccca ccgtctacat aggtgttgtc   20700
tccgatttta accggaggaa agaccagcgg aatgctacaa gaagcaagaa tggatttgag   20760
aagaagttcc tcttttttgct cttccgggat ttcctgatct tcaaaaaggt agttaccgtc   20820
ttttacaacg attccggtgg atttgccgtt ttgcaaattc acagaacaat tgatatagat   20880
tttattgaaa ttcagaagcg ggagcacgtt tttctcaagg tatttcccaa gaggggaaaa   20940
atcatacaga taatttcgtt tgagaataag tgttttgaga agggcaaacc actcaggctg   21000
ctgtttgtaa acctgtttcg gggaaagaga agccacatt tgcttcatga gatcggtacc   21060
tttcggggta agcgccgcgc gggaagcaca ccacacgccg ttgatacttc ccaccgaagt   21120
tccggctaca gcaagaattt cgttgtcttt aagcgctcct tccctcacca gacaggaaat   21180
gacgcccgcc tgaaaagcac ctttggctcc tcccccgac aggatcagca gttttttcat   21240
ttttaattaa ataatgctca ttttcccgat ggaagcatgg aaatccactt caatttggca   21300
aatccgtctt ccgttttccc gttgatcata tatgcgtagg ctccaaagac gtgagctatc   21360
ttgcaatact cctcttcgtt gtcaataaag attgtatagt ggttgggtgg aatgattcca   21420
tagatgagtt cgtttacttt cccgattttt ttgcccccga caatgcggtt gggaagtgga   21480
agattatgtt ttttcaaata cgactcgatg ttttcccggt ggtttgcgct caggatgtaa   21540
aggcggtgat agttcggatt tctttttacc agatcgtaaa gataggtgta caggttatga   21600
aatttcgtaa tcgttccgtc gaagtctata cacaccgcca ccttgattgg tttgacaaga   21660
atccgggaga gcaatatatg agcggatttg tgcatagtca tagacacctg atccggtgaa   21720
agatcgataa tgcggggaaa tttgtaaatg cggcggagac ggttggtaag gtagcggatg   21780
tatctatcca ttcccatgta cttctcgata atatcaaggt attccggatt ttttccttaca   21840 aacacctctt tcatcaggtg tttaatatga atggtttccc gtcgggtgag aagaagtttt   21900
gttaaacctc tcacccgcaa ctcttcgaga atctccggag ataaatcttc gaactggaga   21960
taaagcgttt cgtcaatggt ctgcatattc atagtttact caggtatttt tttgaacatt   22020
gtattaatgg tgtcgatttt cttgatgtaa tcaacgaatt tgacaccaag ttttcctgta   22080
acatttccga taagaatatt ggaagcgttc aatgccagtg cgggagtcag atttgaaagt   22140
cttgcaattt caaacagcgt cgggagaata tggttttat tttcgatttc ttccatcaaa   22200
atggcgtcta cggcgttgta ttccaccaac tttttatccg ggtagacagg aatctcatga   22260
tagaatctta cgtcgaaatc caccttacct tctcctattt cctctcgcgc aatatagtcg   22320
agccggtagg actccaactc tttgtatgcc acaaaggagc gataaagccg catgtaatca   22380
aaaaacacaa attctacagg ggtacgggga ttgaaataga atggtaggtt tcgatcggaa   22440
attttccgca ccagcttcca gtccggaagc aacttatcac taatgacatt cacctcatgg   22500
atatgactac gaatgagcag gtagggataa tcgaactgat aaccgttcca tgcgagcatg   22560
aaagtaaatt ttggtttcag cacattccag aaatactcga gcaatctttt ttccgaaagg   22620
```

```
aatgttctgt aatgaatttc aaatgtgtta tccctacgc tggtggtaaa tttgttaaag   22680
ttatcgatat gagcctccgg gttggtgata aggagaagca ctaccaccac cggttttcca   22740
tacggtttga tggaaatgga ataaactggg tctctccacg ggtcgggaaa gcttttttc   22800 ggggaaatcg tctcaatatc gataaagacg cactgagaca aagcttccgg cgtgatgtgg   22860
cttttttgtt ctctgatgta ataggatata gcctcagcct caatcttccc tcgattctgc   22920
tgagcgatgc gcttcaaatg tggggtacg ggtgattgaa ataagtgttt tttcccctcg   22980
attagctcca ctccgtaaat tttcatcgat cgggggtata cgcttgcgct tagcgtgatc   23040
ttcataattc tccttcaggt cttcttcgag gaaatcgttt aacgattgaa gcaactgata   23100
ataagcttcg cgggtttcga gcatgtcgaa tacttgcctg tgaaaaaaca gaaatctct   23160 tatcttgcgc gtggctccga tcagaagacg gtgtttccgc tggaggatgt tatacccttat  23220 gatataagta atcagcaccc cacttacggt tgccgcaata gcaaccccca accagaaata   23280
tacttcctgc atggtttctt ttttcttca aaaaaacctt tccgtgaaaa aatagtttca   23340
actggtaact gcaaacaaac ataaggagag agtcatgctc gacttttatc gctgctttgt   23400
caaaatcttt cagaatagct acttcgccaa cccaacaaaa taccggtttg gcgaaaaggt   23460
cagagaagca gtgttcaact ggggagcacg cgtggcacac cacgcatca attcgcgaga   23520 aaccgaaatc gttgcagatc cggagatgga tgattatttc agaagatcat ttttctccga   23580 aaaccctat atgcttgtta aaattaccca tcccgatgaa tcgatgataa atacggtaat   23640
atggcaaagc aagcgatatg aaaacttttc ccgcgtctat caactcattc gcacaattgc   23700
acagatgaga gaagaagaag tcgataacta catgaatcag atcatgccgt ttattgcgtt   23760
gaatctcaat acgatcaatc gctatatgaa caaaacaaat cttctctttc aaacccctta   23820
tgatgagtta tacggtttca ctctgctttt caagtcggta attcgcattg ccgaagaaga   23880
aaacgaactg gagtatcttg cgaataaaga tgtcattgat agttataata agaagattga   23940 ggaattttc aataccgatg aaaatatcgc tacatttgga tatgttctaa aagatatgct   24000
gtctcactgc attattgcca tcggtatgat cctgctggaa gcgaaggata aaacacacat   24060
gaagttttat gaggaacttg gtgagtttat ggcggaaata ggtaaggtat acttaaaagt   24120
gatagaggaa ggtgagaaag atatgaatgc gctgacgcat ttatacctct ggtgtatgat   24180
tgccggttgt atcattaaca tgttgaacgt caggattccg gatgaattgc ggttggctgc   24240
tatcatggtt gaagaaacgc ttgcctcgca ccaactgcaa cccttattt cgttaaactg   24300 aagagggta tgatacagaa acaaccccg tataaaaact acaaaaagta catggatcag   24360
cggggagaag tgctgagacc gcaccccgc aagaaggtat atatcccatt tcttattgcg   24420
gaatgtggaa cttatctatg gaacgacata agaaacatga tgtttgcgct tccggggtgg   24480
aaagatgtgg tgaaaaaata cggtgtgggg gaaaaatcca ccccggagcc tttctatgat   24540
ttcctttcgc tttttatcaa gaatactacg ctttacagtg attatagaac caaacaaacg   24600 cttttttcaat cgcgaataga gcgcataaaa atggaagagg aagtctggaa tctttccaat   24660
gcactgatca atctgttcct ttatctgaaa gagcattatc cctattattt ctcaaaagag   24720
tttgtctttt actttgacat taatttctat ttcaggaagc tcacatttta tgatattctt   24780
gccggggaag atttgcggaa taaaatcaac gacacatttc agaaaatgct ctctaaaggt   24840
tacacggtac accttttcaaa aatgaaacct cagagtagag aagattatct atgtttgcgt   24900
tatgccgaat atatggaagc tattatggct cgagatgagt tcaagcagga aatggatatg   24960
```

```
aaagggagtg ggaatctttt ttatcttatt gatggtttta aatgggggtt gataaataga   25020
aaagatgaag tagaatttgt tgtactggta aggtaaaaac tatataaata aaggggtta    25080 gtttatggcg agctggactt acgataccac ttcgcgtatt ctgtcaatta ccgttagtgt   25140
ggtggatctc gacaataacg atgtactggt ttacaccggt agcaattatc ctacatggtt   25200
gagtccgccg accacttcgt acgtttccgg ttcgttgtct ccaaagcagt ttgatgtgta   25260
tatcagcggt agcacgctca acgttcagac agggtcttat caggttgatt tgcttgccat   25320
tgaacagggt gtgtcgttcc cgctccacctc ttcggcaagc ttcacgatta cggttacggc   25380
ggtttaacaa attttaggca agaagtctcc atcctctaca gggtggagat gaattgccta   25440
ttgacaaaat tcagtggtgt attacaataa agcaagatg tttagagcat acaaatacag     25500
gatatatcct aacaaaaaac aaaagaacc cttagagaaa actttggtt gtgtggggtt       25560 ctactggaac agggcattag aaatcaaact caaagcttta ggaataaag agaaatacc      25620 acaggtcttg cccgccttaa gggtggtagg gtcggaacga cccgaactta tgcctgtgga   25680
ggagcgggta gctccgatga agcaggaagc tccatcttct acaagatgga gtagttcact   25740
tcacagaaac tttatttctg ttttatcgtt ttttccgtaa aaaaaagaa attatggttg     25800 taaaactacc gctgcatgat ttttaccctg aaggttcacc tttcaaaacc gaaactttta   25860
cggtaaaaga ccccaccatt gaagacgaag accgcctttt caacccggat cgcatcaagg   25920
ggggatatgc tctggatgat tttgtgagag gactccttcc cgaagaggct cagcgccagt   25980
acggaaacat gttcctcatt gacaggaatt tcattctgta tgccgtcagg gtggcaatgt   26040
tcggagacac cattgaattt cgggaaaaca tcgaatgttc tcattgcggc gcttcgcttc   26100
gggaggctac catagacagc gaggtttta ttcccgaaaa tcgtaagttt gagttaaaag      26160
aagggggtta ttttatccgt tttaagttgc ttaccgtttc agatcagaat gttatgagaa    26220
aagatccact catgaaaagc aactttctga cgcgcacgct ttattacgta atcgatacga   26280
ttgaaaaaga agagagcgac attaccgaca aatatgcgct tatccgttct attcctatt    26340 cacttggcac caagatcaga gagtttctga atacacaata tcctcgattt gatattttca   26400
tcaaatgcgg ttcgtgcgaa agcaccatcc cctttgagat gaacgaatcc tttttttga    26460 ataagttatg attcagaaga agagcttgaa aaaatcgtgg tagaacggta tgaagcccga   26520
aggaaattgc ttctctttct gaaagaactg gataccatt ccagtttaaa aacgaaaatt    26580
tctatatcag aactccgggt aattgcctat atgtataccc agcaactgga agagcaggaa   26640
agagagttca agcgttttcg gggaccgcac tgaagtcaag cgtggcgtag tcaaattgaa   26700
gggtaagctg cacgttcaca agacccgaag catcggagaa gtcgagcgag tcgccgttga   26760
tgtcggcaac ccaggctccg tggaaagtcc attgttcaat tacggcaccc tgaggatcaa   26820
gaagcagaag ctggatatt ttcttgtaaa catcctgata gccgtcgcgc ccggtggtag    26880
gatcgtggtg tgcaagtacc cactggtaaa ccgccatcat ccccgattcc tcgattggat   26940
cataaagcgt caggttgatt gggttccagc taattttcc cttatatttg aagtaggtgt   27000
taatgtggtg cacttcgccg acggcaaagc tgaaattagg acgcgccgaa gcgtagacca   27060
tgtaggcggg aatcccgtcg atctgcatga ggaaaaggcg tttctgcttg ggttcaaaac   27120
gccggaaaag catgttttca acaacgcgtg ccatatcgtt cctttttctt taaatatgta   27180
taaatcgttt ttcaaaaaaa tgacaggaa aaatatttaa agttgacaat taacaacaaa     27240
accgaaaaaa atatgtatag ggtaaacgta aaagaagtag acctttcgat taccccctgaa   27300 gtcgggacac cggtccaaac ggcgcttgta ggtgcgttcg atctaccgat tcccagcgaa   27360
```

```
cttccggtat cggtaacccc cgatgaattc cgccgcgtcg gatcaaccga actcagtctc   27420
attgcagatt cgctggtggg tggtcaggag gttacggtga tcagaccgcg aggagaaacg   27480
caatcgctga atgcggcatt tgttgtggtg ggtggttata atgtaaccct tggtgccttc   27540
aacgttttct atctgatgtt tctggggtat gatcctcaga aaggatatac tgatgtgtct   27600
tatgtagatg tgcaattggc tggtacccca acggatacca ttctgttcag ctactcgctg   27660
gacggttctt cgacaacgca ttcacttacc ataaatctaa acgccccag tgttacgcta   27720 ccttctaata tcgtaccgct ctttttctac tatgaacctt atacgggttc gattacgctc   27780
cagagttccg ttaactatag tggattaaca ctgaattata cggtcagcaa agcgaccact   27840
ccttgggtgt attttgctga atatggcacg ccaacatctt ctcttacgct ttataaagga   27900
ttttatctgg aaggaattga cctgaacagc tttaacaaac aatttgttgt atctatcgaa   27960
aatattacgg taaatagaga aaaaggtcag gtgctttatc cttcgtttga tgtggtggta   28020
cacttccggg atattagggg ggtcagtgcc aataccgaat atattcgctt ccgtcaggtc   28080
aatctcaacc ctgaatctcc gaattatatc gagcgcgtaa ttggcaacat gacctttgag   28140
tttgacggtg agcgcattgt tacaggcggt gaataccccca atcaggtacc cttcctccgc   28200
gtggtggtct ctcaggatat taagcaaaac gtcgccgggg ttgaaaagtg ggttccggtt   28260
ggatttgaag gtatttattc tgtaggcgac ttcactgtta ttgttaacga attgaccaat   28320
gtgtcaatcc cggttacgga ttcggctatt attccgccca tgcggtttac ccgcattgaa   28380
cagattacgc tgtcgggcgg tgcttcgttc agcgtgatca gcaatcaacc gtatggtttc   28440
aatattcagg attctcgtca tagctactgg ctctcacctt tcaaagatga tgaactgata   28500
atcggaaccg aactggtact tccggctctg gatgtttcaa cggaattcgg agtttcaagt   28560
tgggaagaag cacttcctga attcagcttc ctgatgccgt tccagggcgg ttcagacgga   28620
tacattcgcg ttgatgaaaa tgagccggat acaatcgggc gcgtgaagat cactccggca   28680
ttgcttgcca actatgaaag gttgcttccg cttctgacgg aagatcaatt cgatctggtg   28740
ctcacgccct atctgacgtt tgctgatcat gccggaacgg tgaatgcttt catcaatcgc   28800
gccgaaaaca ggttcctata tctgtttgac attgccggag atgatgatac cgaaaatctg   28860
gctatttcgc ttgctggata tatcaactcc agcttcgcaa ctacgttctt tccgtgggtg   28920
cgtcgtctga ccaataaggg aatgcgtacg gttccggctt ctcttgcagc ctaccggagc   28980
attcgcacca ccgatccgga gacgggtctg gctccggtgg gagcgcggcg cggcgtggta   29040
acgggcgagc cggtgcgtca ggtggattgg gaagacctgt acaacaaccg aatcaacccg   29100
atcgttcgcg tcgaaaacga tgtgcttctc ttcggtcaga agacgatgct caatgtcaat   29160
tcggcgctca atcgaatcaa cgtgcgtcga ctcctgattg ttatgcgcaa tcggatttct   29220
cagattcttt ccagctacct gtttgagaac aacaccagtg aaaaccggct tcgtgccgaa   29280
gcgctggtgc gccagtattt ggaatcactc cgtctccggg gcgctgtaac cgactatgag   29340
gtggcgatcg attcggttac cacaccgacg gatatcgaca caacacgct ccgcgcacgg   29400 gttacggtgc agcccgcccg ctcgatcgaa tacatcgata ttacctttgt tatcacgccg   29460
acaggcgtag aaatccacctg agaaataaac ctttcaaaat ataaacccgc ctatcaaaag   29520
gggcgggttt ttttatttaa aataaaatga agtttaacaa ctgggttgag tataccgacg   29580
acgtactccg acttgagtat taccttgagt acgaaattcg ccggtggaga tatcagtatt   29640
gtgatccgtt ccccactttt gaagatttca aagaggcggt caaaaaagcc cctcgaatta   29700
```

```
tcgtaacgcc ggaacttgat aaaattataa gaaatcgttc tcgaaccgc acgtttgacg     29760 aactgcttgc attgattaaa acttaccggg gatatccgaa atttcgcaat gaaaagacgc     29820
ttcaggctat atatgacggg tttaaaaaca ataaacccat gaaaatgccg atcgtgttgg     29880
agcttcccga cggaacatta cgggttatgt ctggaaatac ccgtatggat gtggcattcc     29940
agctcgggat aaaccccaaa gttattctgg tgaaggttcc tgataggtgc cattaatcca     30000
cactttccat atcaccatac tgatctacaa tgtaaatctt gttgcagaat tctttaaatt     30060
tattcagcgg aaccactttg gggttggtga tagcccattc gtttacgata aatgcgtgga     30120
gacgcgatcc catttctttc aaatccctct ggatttgttc aacttcatca tcccattccc     30180
catcacttat cttatggatt cctccacttg gtacgggttt gccaagatag tgaaaaatga     30240
aagggtggga ggagtcgttt ttaagccgct gcaggatttt ctgacctgct ttcgaggaaa     30300
cgctgaacat tttcttttaa ataagattca taatcttcaa ttagcggaaa gtgttcaagc     30360
tgtttgagca gggtgttaac ttcataggca aaacgaaagc gggagttctg gtagaagtct     30420
ccgattgtta ccggaattct gaaatcagga atgttttttga tttcattgtc ttcaatattg     30480
aagacgaaat agcagtgaat gagcgggttt tgaagctctt gcttgataac ataacgatcg     30540
aacattttga tatatttcca gatcacttcc cggttgttca aatagatttc ttttgcccga     30600 tcgggagaa actttgttat gaagaaatcg tcaagcagct cttcgatctc acttagtgca     30660
ctggtctgct tgttaataaa gctttttaatt actccgttga aatccccaag cacacattcg     30720
gagctatcgt gcatgagcac acaatagccg aaaagcgcat cgctacacac ttcgcgagcc     30780
acgtcgtaaa caatcagact atgttcgagc acggaataaa aatattttcc tccgtttccc     30840
tgatagcggc aaatgttgga gagccttgca gcaacatctt caatggtaat acggtgaagg     30900
ctcgggtgca attcgagttt catggtgtta tgactgtttg gttcacacga cacaatcctt     30960
aaagaggata aggttaaaag aggttccctt ccttcaatta aaattcaaaa atgtcaatat     31020
caatgtcaag atcagtgtcg tcttcggttt tacgttttcg aagaacataa tcgacgtaat     31080
ctatatggac cacaaagtag gaggtatcgt aaatctgaac caaaatcgca ttgacaaacc     31140
gttcaacata cttttttggag gaaaagaaag catttatcaa aatatctaac atcatcttat     31200 aataccccatc gtctgtgttc attacatttt taacaagtac atctttaatt tcatctaata     31260
tagatttgtt ttgaggtata gttttttattg cttgatctgt gatagctttc aataattcat     31320
cgtcattaag tattgttatt acagttttcc ataaatttgt aatcatattg ctgttatttg     31380
aagagaaaaa gttgcgtggg tcacttaaat gcaaaactac acttggtata aataaacggt     31440
aagtattact tacattatct tttaatccat tatcttttaa tcccagaaga gatttatagg     31500
tatcgataat tatagaaatt ttgtcaacat ccattataat atctttgtat ttaagtatat     31560
tttctctggt ggcgtcatta aaatctcttg tcggggtacc aaacagcgtt ttaataatct     31620
catctttcag tttaggtata atctcattta aaatttcctc tcttttttgat tcgtattgtt     31680 ttactttgtt ttctataact aaagacgcga gaaatgtaga aaaaaggtca aatactgttt     31740
ttttggtctt ttcattatta ggtctcacca gatcttgata tttataatct ataaaaaatt     31800
tcaaattgtt ttctattttt tttctgttta tgttaataaa tttatctctg agcgttttat     31860
atacgacttc gttttgaaga tggaaatctc ccacaagatc tatggctgac gaactttctg     31920
gtggtatgaa ttgaagtttg acgttcttca caagggggaga atcctcttca tagttggctt     31980
ctgcaattct aaacgtttcg gagctaatta tatctgaaat aacttccagt tgggactctc     32040
tgataaagaa ggaaataaaa tcttttatttt tatctttcaa ttgattccag agatcgtaac     32100
```

```
cgggtacgta ttcctgaaaa tctgtattca accatatatt aagtactttt cccacacttt    32160
ctattccctc ctttatttcc ttactattaa cagataaacc aatgactttg ttaataacat    32220
tttgtgcaat agtttaact ataccctcaa tgacttttc atccaaactc tgagagggtt     32280
gaagaatata gatgttagat acaaggttct ggagtaatag tagggcttcg ggggaaacat    32340
ttttcatgaa tttatctaaa gtggagtaaa gctcttcgag ttctttcttt gctttatcac    32400
tgagaccgat tatttccgct attttaaagt taatctcttt aataatgggc aaaggtagcg    32460
aaagtgtttc gagattttga ttgaactggt ttttatactc tctgatatcg gttgatttgt    32520
aagtaatgac atgggcaatg acgccgctgg tttcaattgt tccggtaaat gtggatactt    32580
ttattttatg gtaaaagtca tttctcgggt gtataaagaa aataaaaaca taatcatgtt    32640
tataattatc ccaatagcta tcgttttgag caatacagac ggtggtactt ttgttggtgt    32700
tggtttcggt taacatttct ttgattcctt gataggatat ttcaggtaaa agtcgaacaa    32760
gtacggcatc gctatcttcc atttccggtt tattatgata gacaagttct atgtccccgt    32820
tcttgatata ttttctgacg gcttccatgg tgttgttcca gcgatccagg tagcgaaccg    32880
tataagaggg gaggtatgta tcgatgatct gctcgagatc gataaagctt ttaataaact    32940
tgaacttcat agaatgaagt tcgtcttttc ttccctcctg actcaatttt ttattgataa    33000
caaaaagagc cgccagttta tctacattgc tgagcatgtt atgataataa aaacgattct    33060
ccaccggaat atgactttca tccgatcgat ttgtatacat tgctacaata ccctgtagaa    33120
taaaaacctg agcctgctcc ggaagaggtg tgttgtaggt ggttttgcc gattgcataa     33180 ttcgatcgac aagttctttt ttgacccttat cttttacaaa actgaaaaac atactttaa    33240 gctcttgctc tgtagccgtt tccggatcaa tttctatatt gagtgtgggg tcttcgttta    33300
ttttttgtgc cagcttacgt gcaaaattaa tatcgaattg catatttgta gacttttatt    33360
ttaaataact tttcgttttc gggtataaaa aggtctggtt ttgctggtgg attcctccac    33420
ctgaatgttc agcgagaagt tcggatcacg cggaaattcc tgatagtttt ccatatgcat    33480
taaaattttc aggtgatagt ttatttccgc cacaaatacc agttcatcag acgacgggtt    33540
gatcatacga tcggaaattc cttctacgac aatatcccat accgccgcat tgtctttggt    33600
aaggataaga tcgggtctta cgtttgagag aatctgagtg atctcgcttt cttttgtaag    33660
ataataaaaa gcacgatagt tgactttata gggaaccggc accctgtact gaatggtgga    33720
ttggtgttga ttttccgtaa aggtaagaaa agcaggaaaa ttctgtataa cttcgattcc    33780
ttctcgcatg acaacaacga agggatactc cactttgaac atatccgtta ccatcgattt    33840
cctttgcgcc tgagatttgt cgaaataat gcgcggtttg gtgccaagag ccttttgata    33900
gatttctttt gcaaaaacta cggcaaagta atcggctgta ataatttcgt tcattcttct    33960
tcagggaatg gaagttcttc ttcaccacca cccgtttctt cttcgaattc ttcgaaggct    34020
ccgccaagat taagttcgcc gcccagttct tctccgcctt ccgttccgaa atcgaattcc    34080
gttcttcctc ttggcgattc gatcggggag ccgcgctcgc caaggaagtc ggcggggtt    34140 gtttcctcac cgaatccgcc cgtgtcgaaa agaccgccgc caccggctgc ttccgccact    34200
tcctcctggg gcttgagatc gtagggaatc tgaagaatgt tactataaat ccagtcttca    34260
cgaacccagc ctttgaggcg ttcggcaata ccgattcgct gctcaatcac ggcaaagcgc    34320
tcaccttcca caatcgaatt cgagcggttc attaccaggc ggaaatcctg atcggcaaac    34380
tctttgttca tgcgcaccat gcgttcgagt tcttccacaa agaaccctg aatgcgtttg      34440
```

```
atcgtgttgt tgaatttgat atcctgagta gccagtgtgt ttttagcatt cacgtctcct    34500
tcataaccaa tgaacgcctt tggtaccttg agtgcggaga tgagtcggtt gagcatgtat    34560
tccacatctt cagcaagatc tactttggaa ccctgaagaa tatcgatttc caccgcacga    34620
cgatctccgc gccggggaat gaagtaatct ttgagaatgc tttcgataga aaagtagtta    34680
tcgattccga gaaattgatt ctgattattt cttacccaat agtctcgctt atactgcatg    34740
gcaatattgg tcagatattc gttgatcttg tcggcggca cgtttccgac atctacgtaa    34800
aacacccgtc tatcgacact acgaaccaca cggtaaagca tgagcgcatc ttccatgagt    34860
cgaagctggt tccatatcgc tcgagcactt tcaaggtagc ttctaccata ggggaagaag    34920
ttggtgtcga ttttgtgaga aaagtgaatg acatcttcct caggaatatc ttcgttaaag    34980
tatccgctta caacgttacg gtaaacgtcg gtaataacat aataccaggt atccgtttcg    35040
gggttatatc gctttgagaa aatgtaagga gagaccacct gaaattttc gatcgtgcca    35100 tccgaacctt tttcaagaat atgaagaaac atatctccgt atttgatcat gttgcgaatg    35160
ataggatagg cgttctttc aatatttata acataatcca gataggagag tattgctttt    35220
gcaagctcaa tgtcttttgt taccacatcc acaatattac cgttttcgtt gggaatcgtg    35280
cattcatctg caatgatatc cagcaccgtg gaaataagcg gatcggtata atccatgcga    35340
tcgtacatat cgtagaggaa aaaccggttg aattctattc ctccgtagaa cctgctcgca    35400
taccccgctg tcgcaaacgg gtggtacatg ttaatcggaa tcatggaaga gccacccgca    35460
ccgtgcggcg ctcccatacc atacatcgga gaaggaaat tggtgaagtt gacagcttcg    35520
ttcagttttt tatattttc cagagacggc atattctcca cttttttgtt aaataacatt    35580
aacctaataa tgtaccaaat aacgaaatgg tttcgtttat ttaaaagaaa atgacctatc    35640
gggaagccag agcacttttc aacaagatca aaacactccc tgattataga accgcgttg    35700 tcattcggat gtctgaaatc agagaaagac ccaccttcaa ccctcgagga caatataata    35760
ccacaccccc cggcacttat gcctatccac ttggcttcgt actggacatc gggggtgggg    35820
gcgaggattt tgtcgatttt attgcgggta ttatgctttt gccctacgct tcacatgccg    35880
aatgggtaca tatcttttac ataaaagaca tgggttgttt tctgaatctt ggggataaag    35940
aggatacaga ggaattcctg agaaagtatg cagagaaaaa tccttttata aatactttaa    36000
tagagcacat tcgcatttat cagccgataa atgataatac gctctttccc attctaaacc    36060
gctatcttgt cggaatgcct tatgaaaaca tatcaagcga agagtttcac cagagtttca    36120
acagggttct ggaaaagctg aaagaaggat acatagacat tttcaaaggt gtttaccagc    36180
atatcacccc agatgacgca cctgctgttg ctttcgtgaa cgaattcaga gattttattt    36240
ccaatctggg ggattatcac actggaaaaa atatactgga agtggcaata gcccgaattg    36300
tgttcgccgt tttcagacgt catgaactta agaaatgat cgaagcaatg atcggtaatg    36360
caccgggaga aattacctcc tcacgcttta tcaactatct tccggttttct gattccagaa    36420 gtctgagtgc atttacccga tggttttgcca ttacacatcg cctgttttac tatgcttttca    36480 ataaagggt aatcagagag caatatcttg aagaatcggc tacgctgtttt gtggatatga    36540 ttttcaccat tgccttttca aaggaaaaaa taagagctgc tatggataca atgttcagaa    36600
tgttaataga tcaaatcaaa gataaaggta tacccaaatc ctatcgggtt tacagcgaac    36660
ttggttattg cggaatatac gatccgggaa ccggcggtgt gcatgaagcc gaacctgctc    36720
aggtggtctg gtgggatccc tccgtggtgg aatactacgg ggcgattccc aacataggga    36780
tgcgagaacg taaaattcag aacctgaagg attatataac cgcccttgac gtggtcagat    36840
```

```
tttttgtcaa ggtgtttata tacaataaac atttacttac acaagaaccc cgtttgttta   36900
atcaatcggc tgaggatatt gcttggcatt ttaaaagaat attttataag aaagaattca   36960
tttacctttt tgaaaaaggt ttgcggatga ttagtagatt tatcaaaaca ggaaatgtaa   37020
atcagttgat gtctcttatt catgatgtac tcatgttgca ccttagaaca gatctcctcg   37080
cgagggtatc tgcagtttat agatcatact ctcttgaaga ttattataac gaagaactca   37140
aacatatgaa gagggtggta ggtgatattg ccgataacat ggttgcactt cttacaaatt   37200
acgccgtgga tattctgacc ggtaaagagc aggttaagga tatagacagc gcattttccc   37260
attatctcga tcatctcaga gaaaaacttc aagaattgtt agataagtct gctttagagt   37320
tgcgcggaaa agcaggtaca aaaacactat tgcaaagatc tttagcagta gagtcgggga   37380
tagagtctat tctttcagga attatcttca tgagaaagtt tctggaagct tatgattcgg   37440
atagagagaa gattgaggaa gcgttcaggg tggtaaaaga aagactaagg gattaaatac   37500
tggtaattgg gattgtgtgg aatgggtatt tttgaaaaga aggtgaatct gaaagagggg   37560
tggatccacc ttacaacatt tccgtagaaa gaggcaaaaa ggggagaatg ctatgaagat   37620
caaaaaggta attatagcgc tgctgtttct actcacagcc ttccagcttg ggggattat   37680 ggcattgtat cttttttccgc gataagcgcc tgtagctcaa ccggaaagag caccagcctt   37740
ctaagctggt ggttgtgggt tcgagtccca ccggcgctc aggtgtaatc agaaacaaaa   37800
aaagggaggg agtcatgaca gtcatatggg caatcttttt tatagtcatg gtgttgatgg   37860
aaattcgaac ctttcgggta agaggtatc tggaagatca ctccacccga caaggttctt   37920
atgcaaccga atggtattac cggtggtga atgaaaagga ggaacgtaaa aaaccgggtt   37980
cgcaatggga tttgtaagaa aaaagagcg ccttattatc aagcgtgatt tcgacgcgct   38040
taaatttgaa gacgcgttcg atcttgagat cgtgtttcac gtcaacccg aagttgaaat   38100 tattgatcgg ggagaagacg tggttgtcgt atatgccccg cttggcattt tgggaagcgg   38160
ggaaacagtt gaagaggcaa tgaatagttt gcttcttcag gctgtaaagg aatataaaga   38220
gagcacttat gaaggagagc gagagatact tcgttccttt ataaagttgt acacgtcgtt   38280
tctcccgccc gactgaaaaa gtcgggtttg agtaataggg cattcgtctg ctctcatgag   38340
taaccgataa ccaaacaaac ggaggtagcc atgaaagagg tcagcgtcac ccatgtcgtc   38400
gtttgcccct tctgtggcaa gacgggcgaa gtcaccatta cggcggatgg gagtggtccc   38460
cgcctcgtgg aaatggagcg catttgcccc cacgtagata ctgaatacga cgaaagaaag   38520
cgggggattt acgtacattt cagtgacggc gaaaggggggg actacgtctt cctatacgcc   38580
ccccttgcgc tgtacgtccg ggagggcgat ccccatctga tcgcccgtgc gctccgccgg   38640 cggggctta aggtacgggt cgacgggcgc cacatcatct tcaagacacc cgtctacccg   38700
tatccggtgg acttggcgct taggcagtat atgcttaacg ccgggcgcac ggtctcatac   38760
aaacacgtgc atctgtgaag attatgtgag ggggttgcgc ggcgcttggc attttcgtat   38820
attagaactg tcaccaacca aacaaaccaa ggaggtagcc acgaaagcga ttgacgttct   38880
caagacattc ccagccccgg acagcttcga gggcgtctat tactgtccgg agcatccaga   38940
ggttgaaatc aaagaaaccg tccgttggac ggaggttcca aacccaacc ccgacgcccg   39000 caacccggtc gcagtacacc gggttgtgga ccgctggtgc ccggtctgcg ggagaccggc   39060
tgttctggga gctcgatccg catgacgggt gtttcggcga tattcgcaat cttcgcaacg   39120
ccgaagcaaa gcttgcccgc cacattttaa agtaatttcc gtttatattt acttatattt   39180
```

```
acatagggt ttagaacaaa ccggaagata ttatgaagtg gtttaaacga cttacgacgc    39240
tggagatttc ccttcttatt cctctcttta tttccttgag cgtttacttc tccactcagg    39300
gagtcgccaa atttgtggcg cttcctgtgt gggtggtggc actggtaata gcggctattg    39360
acgtggcaaa gttcgtaagt gtgggtctcc ttgttaccac aaggggatgg ctgctcaaaa    39420
caattctgat tccggtcatc ctgtgcgccg tcttgccac ttctttcagt ttttatgcgg    39480
cacttgttta ttcacacgcg gagtcggtgt cttcagagaa agttgaaaac atcacagaag    39540
ctaccataac tcgtgaaacc gttcagcgtc agatcgcgcg ttatgagcag cttcttgagg    39600
aggttgaccg ttctattgaa aatatgaaca acacaaccac agagagcatc tggcaagaac    39660
gtctccgcaa gcgagagttg gagtcgctgg tgaatcgaaa ggaggagtac cttgccgcta    39720
ttgactctct tgaagccgtt cttgtaagca gcacggtgga atcgaatcag cgtcaaaatc    39780 tattttttcct caactatatt actcccaact tctatttcgt gcttcttacg atcattttcg    39840
atccgcttgc cgttcttctt tacgcgctgt tgtgcgcat gctgaagcaa aatgcgcgtg    39900
aggaagatga aaagaagtg aaagaggaaa aaacgggagt ggaggttgtg aaacctaatg    39960
aacccgaaga gcaggatttc gtttccaagc aagaggaagc ggagcagctg ctgatggata    40020 aagttttca aaccaaacgc tttgcatttg atccaacccg aatgcaaccc cagaaggtgg    40080
ttatacggga aaaaaggagg aggtgatatg tacattgtaa aaaagtcag gatattgagt    40140 gagacggcaa cggtaatcgt cgaatattca gattacaggg caaatgtatg ggttgggaag    40200
ggaatctcct gtagagcctt tctcaaaagc aaagaggtta gaacagggt aatcccttac    40260 ctgaccattt acaaaagata ccccagaaat ggaaagctac tggaagattt cttaaaatcg    40320
atggaacaac aatatgtaca acatacgcgt caacacatat agtgtaggc tgcattcgca    40380 ccaagttccg attctcaaag cagccaacga tccttccatt gttgatcaca acatgtatct    40440
gtacattacc gcccgccacc ccttttttgcg gctcaagata gatttcacgt ttaacggcaa    40500
caaaagggtg gcgtcatcgg caattatttc catgcacaac aggggaaag atctgattaa    40560 agaatataag ctgttcgatc ttgatatata caaaccgaca actgcttcgt ataaaccctc    40620
agataagacc aagactgtaa agttgattta aactttttaa atgataatag acgttgggtg    40680
attatgtatt gtcttcgata taaaatagca gatatacgtt gtgccgccct taacgtacat    40740
gcgtcgaaag tggcaccccc ctcctatgta gacatagtga ttaagggggt ttttaagata    40800
aaaaaagggg cgctcagtat cgcggttcat cctgatacac ctgtgggaga cataaggttt    40860
gattgtctca tgaaggttta tggaagcgga gatgtgtttg aaatacactg ttttaaaatc    40920
atttttcatt tgaatgatat taaaaagagg tgttatcgga atcttttaaa gttggttata    40980
agttagtgta aatatgtggg ttctaaaacg gcaagagcag gaaatagga taaagagtca    41040 ggatacgccg attctggctc ctattaatgc tgaggtggaa atacacatag aaaagtatat    41100
aggcggattt ccgaagacaa aaggcttgta tgcagaagtg atctatgcgt caaaatataa    41160
caaaccggtt gtttttgcgc aaaaccttaaa tgcgaactac gaaatgtact tatgttctat    41220
tggtatttat aaaaacgtcg gaagacagaa taacattata aacatcttaa aactttatgt    41280
aaacctgtaa caccatgtac gttttaaaaa ttaaaaaata cagctttcat accggatttt    41340
acaaaattcc ggcaaatggt atggtacggg atcctgagaa tgggtatatt gatctttgtc    41400
tcaaaacgga actcccgtta tgtgctttct ttgtaaacta tgaggaagaa gatgaaccgc    41460 gcgttttgt tataaaagag gctggaaaag atcctcagga aactatcgta gaattattg    41520 taagtaaaaa ctttcccatt aataggaatt tcaacataat caaactgata tttgcgccat    41580
```

```
gatggttgtt gccggtagaa attacaagct ggaatccagc gaaatgctga ttcccaacgt   41640
ggtggttaca tccaaaaacc gaatctataa cgtttcgata tgggttatag acatcggata   41700
tttctatgcg ggaaatgaac gggggtatct tggattaaga tgtggggttg aaaaaacgtt   41760
tactggcttt aaaattaatg tctataaaac cacaaatcgc gggaagtgat atgtatatga   41820
taagattgaa atgccacgat tatcccaata cggtcaacag caaaaaaatg gttaattaca   41880
aaataactct gaaatcagaa cacccatcaa acacacttac cattctgata aactgggttt   41940
caaccaatat cgaaagatat ggcaaccata ttatgtttca gcgtcccggt tattacctga   42000
gcgctacgtt tttgtttaaa aaacatcttt atttcaaagg cggttaccat ctacaaagct   42060
ttcgactgta aaaaatgtaa accgatatgt atctcataag acatagtctc aaaaataggg   42120
ttgcctatcc agaggatcct tactacaaac caccggtttc caccggcggg aaatgggtta   42180
cgcatctggg aaagctttgt aaaatagaat ttcacgcact ggttttgcag aaggaaatgt   42240
gggaagagat aagaagtagg aacaaatcac tattcaacga tcggattcgc aaagtacttt   42300
tgtacgatac tgaagaaaac ctatttgcca tatataagat aatctgatgt ttctgcttaa   42360
gacaacaccg cgcaatcaca atccgcgtca ggtatggttg aaactacctg accagagacg   42420
ggtgtttttt gaggtttcct acagattcgt agaaatttca catgcgactg gaaaccgtgt   42480
taacagaatt ctattacaac tcctgtcgga atatcatttt acatttgtaa aaaaggcgga   42540
ctatgctgct ggtcaaaaac agccacatcg atcccaatga tggtgaaatg cggctaaaat   42600
acagccgcgt tatggatgtt aaaatttatc ttggggcgtt tgggaaatac ccaaaccccc   42660
gaagggtgtc ttatagtctg gcacccttg atgaactgtt tgagtttgca agctggatgt   42720
cacttttgat gatagaaaag cacataaacc ggaaaaagta atatgtacgt gtttaaagta   42780
agttatttta tgaacggcga gccgataggc atacgtaccc tttcaaggtg ggtgcaggtt   42840
gaaattgcct actggggtaa agaaggtaca cgttataaaa gagttaccgg tgggagattt   42900
gaggaaaatg attactggta cgaaatagag ataaaaaaat agaatgtgtc attatgtatc   42960
ttatgagaat gaataaaagt gtaccaataa cacccatttc cgggaggggg agtacactga   43020
gcgggcatag cgagattaga ataggagccg cgtgttttcg cgccatgcac tggacttata   43080
taataagtgt acacataccg aacaatcagt ttagtgtttg tttaatggaa aaaagagaat   43140
taataaacgt attttttagac aagcatataa aatgtacgta ttaagtacag gtgttgatga   43200
tccactattt atgaccggaa cttctacacc gggtgtgatc actcccaaag agggtttttta   43260 tacaacccag aagtttattc gtgtgtggtt ttttgtacgc tactacagtg ttcccccaaa   43320
atcccacaac gttgtacatt ttaccagcgc caaccattat aaacttataa aaaattcta    43380 ttatgtatac tattaaatta acaaaggggg ttaaaaacaa cgaatgtttt gtggttgtcg   43440
gaaacgaaat tctctccaat gaccccattg taaactataa tatatttagc aaacaggatg   43500
atctgttcgc atttacaatt caatactggc atagcttaag aacactggga ccagaaggca   43560
caccacttga tctggaactg acgtctaatg cgataaatct tggaaggatt tataacgaag   43620
aagatgaacc cttcccggat ttcattttg aaaaactgat atataaagac tttcaagaaa    43680
gctctaaatt tgggtggtga tgtatataac aatcagaaaa caaatcgaat cggtagtata   43740
cgtagaacct gaattgctat atcatatgtt cgtagaaatg ctgggatacg atgtggtagt   43800
ttatacgcta tatgccgccc aatgtaccaa atatcccgat aataaaacgg gggtggttaa   43860
gatgtttagt aaaaagaagg tgtttttatgt gctgaaggtg ataaaagtga gcaggaaacc   43920
```

```
ttctttctgg aaacgtcttt tagaatgggt aaaagctatt atcaggggt gatatgtatt   43980 acctcaagtt gccggtagca agcactcac cctttgattg tatctgggtg ttgtttatga   44040
tacattactt tcctgtaagt gtttctttaa acaccccgaa cgctgtatat tttaacatca   44100
aaaattttaa acttattaag agaatttatc aaaggttata atgtggaaca atcaactttg   44160
gggtgatcac aatgattgta cttaaaaacac cgatactcag agttacttcg tggttagata   44220
ttagaaccgt tttgtacgtt gaggggattg gatttgttac cagaatcccc tggatgtggg   44280
atattatctt tgaaattgtt tacgtttata ataaaattga gcgtaatgct tgttattata   44340
ccaattacat caatttcact ttgaatcttg attcagtagg cggtaaagcg tttgctgtgt   44400
tgaaaggggg cgcaccagaa caggtttttt ccattattat ggtggttaga agatagaaag   44460
gtgtcatgtt cgtattgaaa atgcgtgttg tcgaaaagat tagagatcat tatgtacctt   44520
ccgactatag atcttttata cgtcttggta actatacttg gttctatctt ttttatcatg   44580
acacccatga cataccgttg acaccggcgc ataatacctt cccacaaacg tttgccgcca   44640
tgcagacgct cacggtcaaa tgcaagctgg tcctctctaa ggagcagcga gaagcacttg   44700
acaccaccat gcgagcgttt gccgccgcgt gcaacgatgc aatcgccgtc ggtcgaagac   44760
tgaataccgc gtcgaacatt cgcatccacc gcgtctgcta cagcgacctc agagcaaggc   44820
atggtcttac agccaacctt gccgtccgtg ccattgcccg agcagcaggc attctcaaag   44880
tcaagaagcg ccagtgcagt acagtacgcc cgacaagcat cgactacgac gcccgcatct   44940
tctccttccg agaagccaac aagcgccgtg gtctggaaga cgcggcaagg agactactac   45000
atcggtatcc acattaacgt agagacgccc ccacctgaag atgagcacgg gtggattggc   45060
gtcgaccttg gaatcgcgag cattgccacg ctgagcgacg gcacggtgtt cagcggcgac   45120
cagatagagc gggtccgtgc tcggtatgaa agaacccgcc gctccctcca gcgaaaaggc   45180
acgaggggcg caaagcgcgt cctgaaacgg ctctcgggaa gggagcggcg cttccagcag   45240
gcgatcaacc acaccatcag tcgccgtatc gtagaccggg ctatcgccga gggtaagggt   45300
gtccggctcg aagacctcag cggcattcgc aaaagtgtgc gcgttcgaaa atcgcagcgc   45360
agaagaatcc accgctgggc gttctatgat ttgcgcatta aaatcgcgta caagtgcgcc   45420
cttgccgggg tgcccttcga gctgattgat ccccgatata cgtctcagcg ctgtccggtc   45480
tgcgggcata ccgagagggc aaaccgcaag agccagagca gtttgtctg ccgctcgtgc   45540 ggattggaag cgaacgccga tgtggttggc gcaattaaca ttgcactcgg gggcgttgtc   45600
aaccgtcccg aagtagcgcc cgatgatgtc gaagcggtgt tgcatggtca cgccgaact   45660 gagacggagg gcagctacaa gcccacgact gaagtcgtgg gtagttgatg aatatccata   45720
gccatttatt taatcaaaaa tgcttctcga aagccgaaaa ggagaattcc tacaacagga   45780 aattcttcg ttgtataaaa cctatgggga tcgtcttctg gtaagatttt ccagcgccga   45840
acgcgaaacc ttcaatcccg acgccgacta tttcacaacg cctatcggta cttacgccta   45900
tcctgtcggt gctatcttcc acatttcgga agacgatgtg gtgatcgatc ccgacatgta   45960
cggggtttcc gaaagaaaat atatttattt ttttgtggca agtaaagatg cttcttggct   46020
taacatatcc tctcaacatc cggcgtttga aattccccctt gttttgtaca accagttcag   46080
aaattatgcc gatctctatg acgtttcact ggatgatgtt ttccggaatc gaaacagtat   46140
ggaaagctat cttacctact ggtgctttgc cattgcatcc cgtgtttttct ccgatcttac   46200 agagacactc aagcagaact tgatggaatt gcttcgaaaa gatcttcccc gtatgcgggg   46260
atattatcag gagctttcaa atatttgcag ggaatttgac gtcgatgttt caagattcta   46320
```

```
tcatgcacgt aacaatcccg aagaatggct caatttgctg attgcagaac ttcttgaccg   46380
gctcaacagc ggcttcagac acatgaaatc agccggggat gtaaagcata agtatttcat   46440
gtatcctctg atcgttttta taacattgct tcacaacagg tatgcacctt atccgaattc   46500
cattgaagcg gcttataata taggagccaa aaaagaccct gttgttctga cgggtttcct   46560
tcgaaaggtg ggatatgatg gaatctggga tcatggcacc ggagccattc actccaatga   46620
acccgctcag gtggtctggt ggaaacccac tgctgcaagg ctggtgaaca aaatggataa   46680
ccctctttat gtttcgcctt cctccatagg attcggttat cttgcgtttg ccgatgaagg   46740
ggttgcaccc tccaatgaaa aacagaaaaa atatttatgg aatctgattt taagtggtaa   46800
aatggatgag tttattgaaa tcatggatat gatcatgtac cgtaagtatc ttgcagcgct   46860
tttcaacgcg tttttgaatg aaagacgggt ggctctcaaa cacgctatcg gattcaaggc   46920
attcaaggaa tatctcaagc aaaatgcaga ggaaatcaga aacttttttca gagtgagcag   46980 caatgcgccg gtgcagcttg tatgggaccg gttcagaaaa gcattcagaa tttctgaatt   47040
acttcgaaac tacgaagaat tgattgaccg gcacccttat gaggtggatg attttgccca   47100
caagcttctt ggtaatttta acttttttgaa agaactgatt aagcccacca gactataaaa   47160
cgcaaaataa ttaaaaaaat gaaagttaat taaaataaaa ggaggtcaaa atgaagaggt   47220
tgacaaaaga acagtttatt aacaattttc acgagcccaa ctcgctgcat ttgttcccat   47280
ctatagagga tttcattaac cctcgacaag gagatattac tcaatcctac tgttatgtat   47340
tacctgttca ggatttaaaa atcgacaaca aaatgggcat accggtaaat tttgatttat   47400
cacaggcttt aaataagatg ataggttcta aaggtgagtt gaacaaaaat ttgatcaaac   47460
aaaaaaactc ggcacttaag gaattaaaaa atatattaca gaagtttcac aaaattttac   47520
aatcattaaa atctaatttt aatgaaggga tagcactggt ttttcattcc ttttttttta   47580
tgaaaaagtg cactcctttg atcatgctcg cgcatcgtat gattatgtaa aaagcaaccc   47640
caaaagtgtt ttagagccac tcaatgaagc attaaaatac gatgaagaaa tcgtcgagga   47700
agctattaga gaaacagtat cagattatct ggaaagtgga gactggtatg atatgattga   47760
aaatgcagtc gaaaagtatt tgaggggtta attaaaagaa aaccatgctt gatcagcttc   47820
tttctctttc cgggctttac tttgatcaac agcttttgc gggttcaccg ggagagttgt   47880
ttttgcggtt ggtggcggaa gcactcgatg aagcggagtt caatgtaagg agtctgcaga   47940
accgaagcta tccgctgact gtagagaata ctgatgatct gctgagactg gcacacctga   48000
acggtgtaag tattaccccc tacgttcagg gaattgtcaa agcagaactt cttgttactt   48060 tcccccatttc ggttaccaca tctgttcctg acttgacaac acatgcaccg gaaattctct   48120
acatggatat tcttgccgat acggattatt tctatctgga ttataccgat ttccgccaga   48180
ccgatacccg tatcattacc accagcacca atcttatcta ctcaagagac gtagtctttc   48240
gtcatggtag ggttgagcgg agaagctatc cggtaagtca gacgatcccc ttcatgatgt   48300
tagaacttga ggaagatgtg gtggatgtta agaacgtttt cgtggaatac cctgatggaa   48360
ggctggtcaa gttttaccgc tcacgtaatc ttcatgaaaa tctggtggtt gaaaatgcgg   48420
taatttacaa cacccgccac atttacgacg tggtgttttc ctcggggaga gtgcatttgc   48480
ttttcggtag aaagatttct ctggaagacc cgatttcaca taccggctat acttttcccg   48540
ccggaagcac catatatgtc gacacggttg caatcgatcc gactaccctg aacagcttca   48600
ttccggaact tgaagcagat atcaaaaccg ttaagatcaa caaccgtatt ggggcaaccc   48660
```

-continued

```
ctcagattca ggtgctcacc gaaggtggat acacttcccg tcttaaagac atcgaatatc    48720
tcaaacggga actgcttgtc gctcttcaga aagacgaact ggaaagagaa atcgcaaaat    48780
atttcgataa atacagattc gttcgagaag atgatattgt ctatgtggaa ggagccatat    48840
accgcaacgg tagattcacc ttccacgaag ccgatcgatt ctatatgcag aaagtggttt    48900
ccacctacaa ccgcaacatg atcgtcagga aaattccgat cacccccctc aagatcatca    48960
ttcgcgcttc caacattctg aaccccggag aactgatcac tttcgtaaaa gattatatca    49020
gaaaacttcc gatcggtgga acgtggatca caaatgaact tgtggggtta ataaaagaaa    49080
aattcaatgt cgtatgtgtg ctggaaattt attttggaga aacttatgcc cgaaaggttt    49140
cggaagatat tatcatctac gacggcgtac tcgacgttga agtgtagaa gtcaaacccg    49200 tactggtttg atgggcgct atgcaaaaac caagggaagg aaatttcaga actttgtaaa    49260
atcgctgctt gaatccacct tcaaaaattg gagcttcaag acagcaatca tgggcgaatc    49320
aggttcagat gtcaagatat ttccggagca gatttttcg gttgaagtaa aacaccacaa    49380
aaacggattg atcagaaagg atgatatgcc ttctgaaacc gtactcaagc aagcacgcga    49440
gcttatccgt aaggaaaaca gtcatttctg tttgatcgtt ttgaaggaga attacaaaac    49500
cccacaatat tttgtgctttt atcgaaacgg aaagctgaga aagctggaag atatatcgga    49560
gcttaaggaa attgtaaaaa gatataaatg atagttactt tgagagaaag accgtattgg    49620
agatatattt acctgttgaa aattccatag cggcgcttaa gcaaaaactg gcaaggttag    49680
ccgctgcaaa cgaaaccgca ggtggaacgc ctggaccccc cattttgctg aactcctgag    49740
caaacttgcg catcatcttc gtcatgaaag aattgaaaga ttttccaaga agcgcatttt    49800
cggtagcgct actggtattg cctatataaa ccctgtctcc atgtagatac atccgttcgg    49860
tggaaatcct cacctttctc tccgcaccca ttagcaattc ttcctgcatg gcaaggtgca    49920 attttttgc agccacaagg attcgctcac gttgcagcag gtgcagtgaa tccgatctta    49980
ttttaacaac gtaaccgcca ctttcttcat ccaccgactc attcttgaaa gatattttat    50040
atgatttcag atttacctga tcgccgtcta ttttaccata gattccatac ggggatttat    50100
cttcgtcgac agaagtggtt aaatcgtcag agacttcatc actgtacttt ccaagaaaca    50160
gatttccctc ttcgtcaaac catagcgcct gcattccctt tccgttgaga aaatattcac    50220
ccggaaacga tcttatccgt gcccgtttca attgattaat cgtaacacca ctttcattgt    50280
cgttggtggt ttgaaggtag tttgacatgt tgacggggaa ggggaaatac cagagccttc    50340
cattgatttc cacataagca aggagatcac ccacctcagg ataaaatcct atgtgcacga    50400
aaaatggata ggctacacca atcacttctt cagaaatgtc tttgattctg accgccatgt    50460
atctttcggg agtatcgaca tcatctactt ccagtaccaa tccgaatttt accggagatg    50520
aaaagaaaga tattttgctg cttttgttag aaaagaattc ctgagtgttg aaccccattt    50580
tttattttat ttttgttagt taaacatata aactatatag ttttcttttaa aataaaacac    50640 caaatgattt ttaacacttc atactattga agatttttca gaatacgatc cacgacctgt    50700 ttccatttc ggttatcctt atattcacca acaatctctc ctgctatctc gaataccgct    50760
tctccaaaat accacaaatg ttttttccagt tctacgtgca catgatattc gttcctttca    50820
atatagtctt caattaatcg tttgataaaa tgatgtaaaa cgtattcacc ttcgaatctt    50880
tctttaacat aaaacaccac aatttctgct cccagagata ccgcatctgt acctctttga    50940
ctgataggtt catcataacg cattccaacc acaatactca taagaacttc tgagggtaat    51000
ggatgacctt catgagagtg gaaagatag tggttagtta ttttagtcag cagcttttt    51060
```

```
accgtctctc tatccagaaa gtgtgtgtag ttattgattc tatcttcaat atagtcaacg   51120
aattccaatt gcagtttggt gaatataaat tcttcttggg cgtatagttt atcatataca   51180
aaatctacaa gatcatcatt ttgttcattg tactgatcaa taatggaagt aacaattttt   51240
tctatcttat tctctataaa tttatctacg ttcaatgcgt gttttaaacc ttcctttata   51300
atctctaaaa tttcggggtc tgataaataa tcttcccaca aatcatcttt aagcatatct   51360
ttataaacaa tgaaggcaat cgcatctttt accggttcgg gaatgtgtgg aataaggtct   51420
tcaggttcat ttatgcgtat tgctctttcg atcaacaaac gaatataaaa atctatagat   51480 tcggggttt gaatattaaa gtcaagtatc ctatcaaggt ctgttctgtc atcaatgcca    51540
tattttagca acagtctctg cttataagat ggaatagacg gcacctgttc cacaataaat   51600
tcataaagag gagaaccctc tttaagattg attacaaaaa ggtctctcaa ataattagca   51660
gccgtcatct ttactcgagc attgacaaac gccatttta taacgtgggg ttcattatag    51720
ttttgaacaa cattaaaaag tgaatggaaa tgttcagttg attcggctac tattagtttc   51780
ccatttctgg ttcccactat cataaaagaa taaaacaggg atgtgaaata ttccttgccg   51840
gttatgctgt atggaaaatt agactttcgt agtccacaaa aaacaagggc tacgcccctg   51900
tcaacaattg atttcaactt gtttaatatt tgcgaacctt tggtttttat ctcattttgt   51960
ttatgaataa tgaagtttct aagttgcaaa aattgatctt gggtgaccct tgatgaatgc   52020
ttatagatat aattgaatgt ttctaataag tggtgattca agggaatgcc ttcttgggga   52080
tgaaaactaa gttttttctac gggtaaaaca taacaccttta aaaacagcga atcccccacta  52140 tcgtttggta aaacatacat gaaccagtta attgaagaaa aaaagcttaa cgcctctttg   52200
ctgtggaagt tatccgcaaa ttgttctctt gtcagtatca gcatataacc taagcaaagt   52260
ttattataca aggtaaattt ggattaaata ataaccagac ttctcagatg taattattcg   52320
tcttttccaa ccacatcaga ataaaacgtt tctatttcgt taagatcttt gttgatcaga   52380
gtttcaattt gttttttttca gccccatgac acaccctcca ttttttggca tactaaacaa   52440
ggcaaaaccc agacagttcc atagccgccg acttatttaa agaaaaataa atgaaaaatg   52500
cttcaagtac tgaaagacac ctatttaaac agcgcttccc cgcataacaa ctatggagcc   52560
gacgaaattc tccggctcaa tgccacttcc agcattgcat tgcagtttga aacccgatt    52620 ggaacgggtt atgagattcg cctgtttgtt gccgacgcgt ggattcccca tgtagaatat   52680
ctgggtgggg gaagctatca ccggctgctc ctcaccgttt cgctctacag cttttctatg   52740
gatgaaggat atggaaccga agtagaaccg cttataagcc agagtttcaa ctatgcgtcg   52800
ctgtcaacgc ttcctttacc actggaagtt cgcacggtaa gcgcatttat tcatctggca   52860
ccgctcaagc ggcgtatggt aagcattcca cttacaaact ttttcaacgc cggaaacttt   52920
gttcttatcg aatcggctga ggaaatggcg gtcaacttttt tcagcagaca gacgcgcacg   52980
gctttcattc cctatactat tccgacagta tccttgcagc cccggcgct ttcagacttc     53040 gtatacgata cccgcataga cgactacgga gtatatctgc aggcttggga gcggaagatt   53100
cccattgcgg taagggtta tctcatgcag acgctgtcat acatagacct ctcaaccgta    53160
tggtttgaag tatacgtgtt cgacatgatc accggtgagg aacactatta tacatcgctg   53220
cttcccactc ccgttgggaa taactggtac tatattgaca tgagccgtgt caatatgaaa   53280
agaacccagt atgtgagact caaaccggtt ggaagcacca acgacatttt cctttccttc   53340
cacaaccgct atctgagact atgaacaccc aacagattat aaaacaggag cttgaaaaat   53400
```

-continued

| | | | | | |
|---|---|---|---|---|---|
| gtaaaaacga | tccgatttat | ttcattcgta | aatatgtgaa | aatccagcac | ccgatcaagc | 53460 |
| gcgtcatacc | gttcgatcta | tacccgattc | aggagaaact | cattaacttt | tatcatacac | 53520 |
| accgatatgt | aatcacggaa | aaaccccgcc | agatgggtgt | aacgtggtgt | gcagtggcgt | 53580 |
| atgcacttca | tcagatgatc | ttcaactcca | actacaaggt | actgattgca | gccaacaagg | 53640 |
| aagccacggc | aaaaacgtg | ctggaacgta | tcaagtttgc | ttatgagcag | cttcccagat | 53700 |
| ttcttcagat | taaaaacgt | acatggaata | aaacctatat | cgaattttcc | aactattctt | 53760 |
| ccgcaagagc | cgtctcttcc | aaagtgatt | ctggacgttc | ggaaagtatt | acgcttctga | 53820 |
| ttgtggaaga | agccgcgttc | atttccaaca | tggaggaact | ctgggcttcg | gtgcagcaga | 53880 |
| cgcttgccac | cggtggtaaa | tgtatcgtca | actccaccta | caacgggtt | ggaaactggt | 53940 |
| acgaacgcac | aatccgagcc | gccaaggaag | gaaaagcga | attcaagtat | tttggtatca | 54000 |
| aatggagtga | tcatcctgag | cgagatgaaa | atggtttga | ggagcaaaaa | agattgcttc | 54060 |
| ccccacgtgt | gtttgctcag | gagattctct | gcattcctca | gggttcggga | gaaaacgtca | 54120 |
| ttccgttcca | tttgatcaga | gaagaagaat | ttatcgatcc | gtttgtggta | aaatacggtg | 54180 |
| gagattactg | ggagtggtac | cgcaaacccg | gttattactt | tatcagcgta | gaccctgctt | 54240 |
| cgggtagagg | ggaagatcga | tccgccgtag | gtgtgcaggt | gctgtgggta | gaccctcaga | 54300 |
| cgctcaccat | tgaacaggtg | gcggaattcg | cctccgataa | aacctcgctt | cccgtcatgc | 54360 |
| gtcaggtgat | caagcagatt | tatgacgaat | tcaaaccaca | actcattttc | atcgagacaa | 54420 |
| acggtatcgg | catgggctc | tatcagttca | tggaagctta | cacgcccagt | attgtaggat | 54480 |
| actataccac | acagcggaaa | aaggtgcacg | gatcggacct | tctggcaaaa | ctctacgaag | 54540 |
| acggtagatt | gattctgaga | tcgaaaagac | tcttggagca | gcttcagcgc | acaacatggg | 54600 |
| ttaaaaacaa | agtggaaaca | gcaggaagaa | atgacccttta | catggcgctt | atcaacggtc | 54660 |
| tcatggctat | cgctactcac | gaaatcatgg | aagccaaccc | tgaatgggaa | aagattaacg | 54720 |
| taaccttcaa | cagttatctt | gggaataagg | taaccccag | cacgctcgac | atcaaccaag | 54780 |
| agtttggagg | agaatttacc | tatatcgcca | caccgaaggt | aaatcctgat | ctgaacaaaa | 54840 |
| atctattaat | tcaaaaaaaa | tccgaagatt | tcatctggta | tatctgaaaa | cggctttcca | 54900 |
| cacaatccca | attaccagta | tttaatatcc | ctctctgata | tactcccccg | ttatttaaaa | 54960 |
| gaaaatgcca | ctgagtagag | acatcataaa | tcgaatcaaa | gagaaacagg | atactctcag | 55020 |
| agagaatatt | acctacagcg | caaagcttct | caagaagatt | acagaaacca | accttcagaa | 55080 |
| attcttttca | gagacgctta | catgggggat | aagggaagcc | aaaaaccttg | tactggcaca | 55140 |
| acttcctcct | gaatacagaa | ctcaaaatct | aaacaacccc | acacttactc | ttcactggtt | 55200 |
| taccttcaat | ttcaatccct | ttgtttacaa | acgcgaagtt | aaaagcaaac | tttatgattc | 55260 |
| tccgactccc | aaggtttatc | ctcttaaaag | ccatgattat | gggtatagaa | cggagctttt | 55320 |
| gagtgggtct | ccggttcctg | ctcccaacct | tcgctatatt | gtcagataca | atcctgaaac | 55380 |
| cgatcgtctt | gaagctcgca | cggtggatat | taccaccgaa | gaaggaatca | gatatgtgtg | 55440 |
| gggtgcgtcg | ggtaatattc | ctcaggatac | gctcgagttt | acatcgctac | gtggtcttgg | 55500 |
| taaagacgat | atgatcgatc | tggctcgagag | cggcgttccc | tatgagaact | cgctggtgca | 55560 |
| gcttttccga | aacagagctt | ccattggggtt | tcagtatgat | gaagaccttc | gcaaacccat | 55620 |
| tcaggtggat | cgtatcaata | tggaaggatt | tactcagaac | gaatcggaga | ttatcaatga | 55680 |
| ttatgttacg | ttctatttca | agagcgtagt | gagcggctgg | atatgtcagt | tcagagcttt | 55740 |
| tatcaacagt | tttggtgaat | ccaccaacgc | ttcatacaac | actcaggatt | atatcttcaa | 55800 |

```
catcatcaaa atgtattcgt atatcaatgt agagaccacc tataacattt cgttcaccct    55860
gtttcctatg agtaagcagg agctttcaaa aatatggggt aagctctcat ttctcaaagc    55920
acacctgttt ccggcaaagc gggtaacacc cggcggcaac tttgtacctc cggtacttga    55980
agtaacgctt ggcaacgtct ggagaaaaag gaaggtgctt cttacttctc tcaatatctc    56040
attcggggaa gataccgtat gggaactgga tccaggtatg caacttcccc agtggatcaa    56100
agtggatctg aatttgattt tgctgtacga acagaatatt accacggaag actggcttca    56160
aaaccgcgtt aaaatgttcg attatacgac aaacaagccg ccttctacgc ttgccgcctc    56220
cgactccatg atcgatcccg caacaggcgt ggcacttgac atttcgacgt tcaaataccc    56280
ggaacccgaa agttttaacc tgaaacttgc aaaactcgat atacttaaaa accttggata    56340
aattatgaaa gtatattctt tttcgggaac gcgacgcgct cagaacatag ccgtacagga    56400
atatggagat tactcctact ggcaagatat gctgcttgca aacggtattt actccggatc    56460
gatcattccc ccgtatgttc cgtcgctttc catttacacc ccggaggaac tcgagaaccg    56520
tctggtagat aaataccata ttcccgatct gaaatatttt taacctatgc tgataagaag    56580
cctgcaccct tccgttgtaa agtatatcag acaatttgct tcgacatcga cggttcagaa    56640
gatttccgca aggcttgtgt tcatggtgcg cgtgagagac gccgcacctt tcagagcgta    56700
caacattgtc ttaaacaaca taaatttcta taccattgaa aacgaaatca ctcctgatct    56760
ccagtcgtac tacgattatc ttccggctcc agctattctt tcggtggacg tcgatccggc    56820
tcctgacggg atatacggta tgatggcgcg tgccaccgtc aatgtgcgtt gcttttctct    56880
caaacaactt cgggaactgg agtggagcct gtttccggga attacggcgc tcattgaagt    56940
agtgcgcaca aacaatgaaa ttcccgtgga ttttatttct gatcgctatg tgcgaaatcc    57000
ttcgcttctg aaagacattc tttttagccc gcaatcggta atcaaactcc atgagagaga    57060
tgaaggcaat aggatatttt tccccggaat acttaaaaga acaaatgttt cgtataacaa    57120 caatacccttt gacattacct ttgagtttag taattttagt atagcttccg tattttttc    57180 tcgaaactac gatattaagg atgtagagac ggctcgaaaa acgctggctg gtttctacaa    57240
tgagcgctgg agtacgcttt ccagccagaa gaaagtcaga tcgggtcagg atctgaacct    57300
tgacagaacc tatcagatgt tcggtggggg gaataaagca tttcccgccg aaaagggtat    57360
tgaagtgggc gtgggtactc atttcgatac aggcgacaaa actttcgccc cttcgcttcc    57420
ttccaacacc ttcgagtcgc tggaatatat tcgttttgaa gatttcctga aggaaattct    57480
gattccctat attcgggaca cctacccgga agatgttcct ccggaaatgg caattctacc    57540
gatcgacata gacaactcct atatgttcat tcataaacac ttgagaacca acaacgtaga    57600
tatcattttc ccaaccgaat acatggtgtt cgattctacg aatatgacgc cggattacat    57660
tatgggattt tcagattatg aggatcatgc agagtggttc gagaagaatt tcgggaaacc    57720
ttacacccgt cacccgattg gatcagttgg taaagtgggg aaagtgatgt tggctcgaaa    57780
gtatctttcc gaactgatcg gagaattcga acgcggcgac gacaagccgt tcagtttcat    57840
tattgataga atcattcagg atataataaa atccacctat ggcttttctc agcttttcct    57900
gatgaaggtg ggagagcaat acgtcattta tgataataga cttctggatg tagagacgcc    57960
tgttcagcag gtggaaaaca aatcccgtct tgaaccggaa gaaatcaaga tatgggaact    58020
tcacgacatc agctatacgc tggatattcc tgaatatctt gcgatggcgg taatgatgaa    58080
gcgtctttca gactcgctga ataccctacgt caacgatcca gtggatttcc ttattcccgg    58140
```

```
ttccgttgag gatgtggtgc tgaagacgct taccggagag cgtgtgaaag gaaccgcgct    58200
ggaagatacc acggaaagtt cggatgtggt tgttaccaag gtgaacctga gcgctgaagt    58260
aatccgtgca ctcatgaaca atcccaattt cagagcgctc atgaatgtaa tcaaagaaaa    58320
tgaatcgggg ggcaactacg aagccattga aatagaacat attatagcaa aacacggaag    58380
ttatgataac gcttttgcgc tggcgcggct ggcgaacacc cgctttgcgc ggggtaaagt    58440
gtggtatcgg gtaagaggcg atcagaaaga ggaaattacc ggagagcttg taagaaaggt    58500
cgaacaggct tccagcttca gcgatctggt tacgcacccg ttcgtcgatg tgccgaaatc    58560
tcaggtgtcg cttccggttt ctcccggaag atataccacc gcctgtggcg cttaccagtt    58620
tacgaaaaca acatggcggt ggatcgagag agagtacgcc gatctgtggc gggagcttag    58680
taagaaagcg gatgtggcgg tggattccgc cggaaatgaa atggtggtta ccggtcttcc    58740
acccgctacg gtatatgaat atcaggcggt tgtcgacact accgttcagt ctcgaattgt    58800
ggttcctccc acccccgtca atcaggatta catggtggca atttatctca cgatcattct    58860
caacaacgca aaccttaccg aagaagagtg gaatctgttt ttgaacgaag gattcgggtt    58920
taagcgtgag gaaatagtta aagaaaaact taccacccat tttgcttccc tcagaaaagt    58980
caatctcaat gcttcaatca gaagagacgc gtttgagcgc aaaggaaatg tcagtacatt    59040
tttgagtata aaacataagg atctgagcga aacaaaaagt gttaaatcta ttacatttga    59100
tgtaacgaag gttgacgata gatatgtagc ctacattccc atgcacctgt caacctatta    59160
caaagtgctt ctttatatgg gcacgctccc ggaaagacag cggggaagg gtgctcagta    59220 tctgaccggt attacactca acataacggt tccgggtaat tcgctctgga ggattttga    59280 cacgttcaaa atagaaggta ttcccgaaat ctattatgaa aacggctatt tcattgtaac    59340
gaaaatctcc cacaacatat caggcggaac atggaccacc ggggttacgg caaaatactt    59400
ttacacgggc aaaacgtaaa aaaaactat gagcaagtac tttctaaaac caacttctta    59460
cgcttccgac gtttatcttg caccacacgt tcccgaactg gaatacgttc caaaggaact    59520
gataaaaggg tttgacatgc tcctcaactg gatcagtgca ctggaaacaa atcatctgtt    59580
ttacagcgca atcaactatc tggctaaaga ttaccatgta aagaaacacc gcgaatatgt    59640
gatccatttc atttatccta aattcaatct ttcggaaaag gattatccag aaaaagatga    59700 agattcccctt attatgcttc ccgatcaccc ttttgctcgg caccgcaaag aggaaatctt    59760
aaaccatttt aagggtagat atcttgcgtt taccgcttcc ggaagatatc agtttattcg    59820
atccacatgg aaacatcttg taatgaatta tcacactcag aaaattaccg ccttttcttc    59880
gctaaatcag gattatcttg cgctgtgtct tgtaagggaa gccttaatgc gcgttaaggc    59940
aacggggaat aaacggtata tgaacctctg ggagtatttt atagactacg gatatattca    60000
tttcgatgaa ttcatgcacc ataaacaggt agtatatgcc ctttcaatgg tatgggaagc    60060
tttccagaaa tttcctgagg ggcttcagag tgatgaattt attaaagaat atgaaaagct    60120
ctatcgctga cgagtttctg ttacataccc cgtcgatttg atctgcataa tcgcttctct    60180
tctggtagag tcgtacagga tagaagtctc atgatccatg taacccaact ctccggcttt    60240
ttcatgaagg ataccgctca gcgtctgcgc caggttcgag ttgggaagaa tacccggcgt    60300
gatttcgata agatatttc ctccctgttt cgatccgttg agtttgccgc ccccaagacc    60360
aaattcccgc aaaacagatt tcaacctttc gacgttaatt tctttgcttt gagccgtaac    60420
gtatatcgag atcgtattcc gctctttttc ctgctggtat ttgtggttga acaccacttc    60480
gatcttttca gggtttcaa aagcagtttg cagtctggag acaaaacgct caagtaccgg    60540
```

-continued

```
aatgcggagc gcggctttta caagttgacg cgttcccttc ttctggataa ttttgtgaga  60600
gcgctgaatg atgaatgaaa gatgctgaag cacttccaca gtgaattcgg caatgctttc  60660
gtctacttcg gcaagctgat cgtcgggtaa attgtcggct tcttccagcg attgataaag  60720
tgcgttaatg tattgcctta cttcatcagg gatatagaaa tgcatgaccg gctcaactct  60780
gaaaggtagc gtgccgtaaa aaagtacggc atgaccgttt tctctgttaa tttcgatcat  60840
ggtggtaccg atattctgta aataattacc ttcaatcggc acccttcttt tggacgcccg  60900
ctccagagga atctccatct cctcctgttc gatttcttcc tcttcttcct cctcttcttc  60960
ctgagctaaa acaagcatgt catcttcttc ttcctcgaca taagcaggct caccggtggt  61020
cttgaagaat tggagcgtaa tgattgccac ctcttgcggc tgaggaagtc tgatcacacc  61080
accttctccc caccccggcg gcggctcaaa acccatgcga atcagcgctt gcatttcctc  61140
cggggttgga gccggaagtt ccatacccccc ttcggtaatc tgacagataa ttgaaagctc  61200
cgggggattg atgcgcctta cgtaaacgat gcgatcgtaa gggctgtacg caccgacgta  61260
ttcgtgctcc tgcaaagtgg aaaaatagga agaaatgtc tgtattccct ttagcggatt  61320
cattttcttt taaatatatg cttcttcagg aacaagcgaa atggtgggag gagacgtgat  61380
tcgggaaaaa tctttaaatt cataatcatt cccacgatac agtagatatg gagagattcc  61440
ccctacaggc aaaggtggtg tgggttttct tgggggagta ccaccgccgc cgggttcatc  61500
ttcatcgtca tccatatctt tgtttctttt tccaccaaac agattttggc ggtattttgc  61560
ctcgaaaata atttcaataa tgtagtaaag aacaacgcac atgacgatac aggcgagcag  61620
aaaaacgctg acgacaaata tgtactggat caggtactcc atgttacaaa ccgttcaaaa  61680
caacttttac atacgggttt ataatggctt acctccggca caattaaata agggtcttcc  61740
agagggttca ggtaacccat tcccctcaaa tccacacttc cattcacaaa tcgtatgttg  61800
tattgcgttg gattaccgca ctcacaacga ctggaaatgt ttattttaat gggattgtat  61860
ttttcttcga tctgtttcca taccggaaat tctcttccaa gatagtcggt tctgagaccg  61920
ctgagcacca cttctatttt ccacgaaaaa ataaattcga tctcttcagg tgttgcaaac  61980
tggaattcat caacggctat gagcgaacac ctaccggttt taagctggag atattcggct  62040
tcataaaatg tggggttttg aatgaagtcg gtaagattgt aaacgcaaga atgggtaaat  62100
ccgcttcgag atttcaaggt agggggaatag ccgtaaatgc ttccgggttt aaagacaaga  62160
taatcgtcaa agttttctaa aagttttata agaaaatgag ttttacccga tgccatcgcc  62220
ccgttgatga cggtaacgga gcgggttgag cgttccttca gaaattttat aacagcctta  62280
tccagttcga tattgtgcag ggtggtatct ccggaaagcg tctcagggaa atcgtacttc  62340
atagttgatt tattttttaag ccgaagtctc tgaccacaag gggtttgtca tcggttctac  62400
cccagttgtc gatcagggta aaatcctcac ccagcagatt gaattgccga atcagcctta  62460
cggtttcccg gattacagga tttttaagaa cggtgaagta aaaagtgtgc ctatcttcta  62520
cgcttacgtt gtcaagcgtg agtctattaa tggcatttcc aaatatatcg gcaaaacgcc  62580
tatcataagc agaaaccacc tcgaaaccct cgaacgttgc gtcttcccgt aagtagcgtt  62640
tccggataaa cccttcaatc agaacactat aaacatcaaa gtcaatatca gcgacacttt  62700
caaaataggc ttcattgaca ggtgcgacaa attcggtgat tagaaccccca ccttctttga  62760 aaacctgagc gtagtcgacg gcgatttcac ttcctgacct acgcaccacc tcatattcgg  62820
taatgttctg tttgattcca ttgtcattat gagcaatttt caaaaccagt tcggtgtcgg  62880
```

```
gtattctgaa tacttctctc cctcttcccc ttttgacggg ttcaaggtat ttcttttgag    62940
ccagaaggta agccgcgcga agcgggtttt cacttcgctg aaagtaagtc agaatatccc    63000
ggagcgtgtc tgtttctttt aaggttatca taggctaatc cagtgttata tcatacatga    63060
tttgtgcggc aaccacttct ttaaaatatt caacgaaatc tctgtcgtct ctaacgtcct    63120
ttaaatactt ttctatttcc ggttttacat attcaaaaaa ctcatccata taacttgtt    63180 tgataaataa tgtaaaatga tcccctctt catccatatt gagtttgtta atgataacac    63240
cataagcaat tcgtataaag gtttgtacat ctattacgtg gcgaaggtct ttctgaataa    63300
ggatattttc tatcttatgc tttattggaa aatatccgga agaaaccga atcgcttcct    63360 caagattttt gctgacaaaa gctataatat cgctctgcag ttttcgcaaa atataatgat    63420
aatgtgcatc ttcgatttta taataagccg catctctgag ataatcgtat atctgatccg    63480
cgatattaag atgatctatt gcttccttta tggcttttgc tttgaaattt ctgtcaaaga    63540
aaattgggtg ttgccttctt tcctcttctt caaatttacg tacaacatat tgtgcgatcg    63600
gatttaaatg atcttgcccg taatgataag ccgcgaatct tatgacattt gaccagaaat    63660
attcgatttg gggaggaaaa agcacattta ttagactggt tccaccgtat tcttcataaa    63720
gaaaagagcg aacacaccag cggataatgt cttcgttatt tttataatcc gacagaatca    63780
aataaacctg attggtggga tcgaagccgc caagtacatc tcgagtcaat tttgagattg    63840 tctcttcag ttcaaaagaa ggggtggttt cttttagcag gaatatcatt ccgtccccgc     63900
ggggtatttt accttcgtgg atgtaaaaat agtagtacat ttcacgggtt acaatgatat    63960
tccagagagg agtagccacc cattgataaa cttcgtcatc ataccgcgcc cctataagta    64020
tagaacccat aaacagaaaa tctatatctc gatactttc attgagcgtg cttacctcaa     64080
taatcacaaa aaaatggtct gtcatggact tcaattttct ttccaataac accaatgttt    64140
ttcctgtttt tatcaacgct ttccgtgttt cttcaagtag ttcacccgcc cattggtgct    64200
gtcttaattt ttcttcaatg aaatttttgt aaatctgttg gtacataaca tttgacaggc    64260
ttgttctggt aagatcctct gaagtcaata tgaaatagtt ggtgttgtaa taatatgggg    64320
tgtttggggg caaattggtt ttaataaact gttgacttaa cccgttgaac aacggtttat    64380
taagaacaaa ggtatcggtg tttatcgttt ccattggttt ttatttaaat aaaaagaacg    64440
tatgagagaa ccttttctgt ttcgagatcc gacaatcgaa agctttggaa gcttttatt     64500 ggaatacctt gacattcagg aagttcgtgt taaaaccgaa tttttcggcg gtaaactgca    64560
aaaactcaaa gatggttatc attttccgga tgtaaaactt aaacccggta agatgtcga     64620 aaagttccga actctgtgca acgcattcgg gtttgatgtg gaaatatccg aaaacgggat    64680
aacgttcaca aaaagacagg aatattgttt tatcgaggag gctctgaaaa aggcgacaga    64740
gaaatatcag attttcgttc ttgcaccaat agaagttgat cttgttttta catgttgcaa    64800
ccagatattt gtcgaatatg aaatatgagc actgttaaaa taccttagc cgttaacata     64860 tacgacccca agggcgacga atgggaattt atctacagca actatgcggt agaagttgta    64920
ggaagtgaat atctggttcc ggttgtaaca ctgaaaaccg gatcggttaa ctatttcaga    64980
ttcaatgtgc ttctaaccta ctctcagacc gggtctttcc cccttatct gaattttctg     65040 aacaaaaaca ccaatcagat caatgtagtt taccgaaata tcagttacag ttatatcagt    65100
tccagcaatg tgaactggta tcccacaagt atatccggtc ttcttggttg gtggcaagca    65160
tatcatccgt cacgtgttaa agattacatc atagaccgca ctgaaaacca gagccatctg    65220
gtaaaaattg aaaggtatac ctataatgat cagtggctta accctacaac aacattcgtt    65280
```

-continued

```
tctcatgaga gtaataggat aaaaatgatg cttccaatga atgatttgat tgataatcac    65340
gggaataact gggtgtcaga accccgaaat tcttatgtag gatatgtttc acaatctcag    65400
aaattcctgt cgaaggaata cacttttttc tatgtttttt cggtagttga aaaaaacccc    65460
tatgtaacag taagtgggga gccgctgata ccgggtgctg catatcccgc cctttcaaca    65520
agctattact ctattattcc caagggtggc gaatatctgg ctggtttaca tatatttcgt    65580
tctaaaactt atagttctgt aaacgataaa atgaatacgg cttctcttat gattcttttt    65640
accacctatc ccgttataag tagttctacg tttgctccgg aatataaggg ggataatgaa    65700
aacgcttttt ccaatacaca atatcgcata caccccgcta tagcggctat cggagagaaa    65760
gatttaaagt ctcattatgt tccgggaata agaatagtct atcatacaga atctacaatg    65820
aacccgggag ttcagcttta tgagctttat cttggttata agaataccac ttcactttat    65880
gaactggaag taacttcttc agatatagca cgttttgatg tacctaccat tgtagggtac    65940
cgcattaaac aaagtggtag cgttatttct tattctgtta ctttgaacaa tgaaccgccg    66000
gtatggtatg taattacggc aagcattcct tccatcgatc tttctgatcc gatttttacc    66060
gatcatagaa acgaagccgg cattattata gggtcgctgt acgggtatct atatgattat    66120
cagcttggag atgtcggaaa tctttcggct atttatcggt ggggatccaa gggtatttac    66180
ttttatgaag cactgttata tacccgctcg cttgacgatg cagaatacca gcaagtgaac    66240
gaacaccttg ttaagaaata ccgattcggg ctgtaatggg aagaataaat acgacatatt    66300
ttatttatct gtatttcccg cgtatagata taagcggtct tgataatata catattgaaa    66360
tagaaatatt gggtggcttt agttttacac ccgtttctta tacctacaat acatctggct    66420 ctttttattac aacagaaacc cccgttgtca gggtgatgga aaatcgcaca ccggatatat    66480
accttcatgt tgtgagttta agtgctttat atagtaattt cgaccctct cttcattctt    66540 ggcatatctg gcttgatttc acaaggctta cggcttctaa aaccgacggt caacctgttt    66600
atacatcgga tatacaatcc attcagagtg atatatctat ggaaaactcc ggaggctata    66660
cgtattatga aaatattatg aatgggcttc ctatggtgcg aaccaacaat acaggattga    66720
caaaaaccgg tggcattctg acggatgatc cgatcatggt agtcgcagcg gtttatatca    66780
gccaatccgc tacatattgt cgtcttataa gctggggata tagtattaat gaagcatggg    66840
atgtatatgc tgagttttct ggcgcgttgg taagatttat atttgtcacc gatacggcga    66900
cggctgggag cggtcctact ataaccagtg actggttcag ttatcctcag gggtttgtac    66960
ttgccgcatg gcaagaggat gacgaaacca tgcatttccg gattatggat gaaagcggaa    67020
atgagtacga ttatcctgta attaccggac gcggggcgg attttcaaac ttcagattgt    67080
tcgatattta ttatccaagt tacaactggg gatttaataa ttatgtggga gaaatcattg    67140
ttcacaatga tatatatatg gttgaagacg tctttcatta tatggctttc aaatgggtgc    67200
cgggattaac cggaagggtg cggataaatc gcttgtggga aaatctttat aaacctgaat    67260
tatatacatc gctcaatagt gttgtactta ttacaggctc aacatctttt accggttcta    67320
ttattaataa cgatccaatt attctaactt caataaataa catagataca ctacaatgga    67380
acccgcaatt taccggatct attgtcaata acaacccaat catcctaacc ccgtaaaaca    67440
acatagatac actacaatgg aacccgcaat ttaccggatc tattgtcaat aacaaccctg    67500
ttttgttaac aacgataagt aacgtattac ttttgatgtt taattaataa aaaaaccacg    67560
aaagctatgc cttattattt cgagtttaaa gttagagaac tggatcttga accggtaagt    67620
```

```
gtaacgctct ctccggctcc aagttgggtt tcggtttata aatacaacac ccagccttt   67680
gaccaatttt acggaactta tgacattaca gtgtttctgg tagcaaaccc accccggga   67740
acaccggatg gtacctattc gatagggctt actttgagcg acgcgctggg cggaataacc  67800
acacattcag tcaatttcat aatcaacact tctggaacca ttacatttga tcctgtttcg  67860
gtgccgggc tctggggttg gtggcaaccc ggaaactggc ttactcagag cagtgatact  67920
ttcaatgatg tggctatatg gtatgacgct ctccggggg cacatcatct tacacttgat  67980
aggagaatta ctattttacc atggaatagt acagatgctg gaagtgctta tgtcggatct  68040
tacataaaaa cactttcgga taattcactt ctgttttcat ggagccatgt caatcaccaa  68100
tttgccaata tgaattattc gtcggggct gataactaca aacccgaaaa tgttttgatt  68160
acaaaagata cttctttta ctccaatcag tactctattt tctttgttta tagaaatcat  68220
ctcgactggt tttctcatcg tataaccgga atgagattaa ctataaatca ctatgaatac  68280
tgggcaacca atatatggga ctttgatgtt gaacgggta ataatcatct tgcaatgccg  68340
gtctattccc cggtggtgat taacagacg gcgccttata caaccgtctc ttatggatca  68400
tactggaatg acgattataa tcacgggttt gtcggcggct ggtttattgc gttctgtctt  68460
cctccctatg ccgctaatcc gtcagccaga gacgcttatt actatgatga cgggggcgga  68520
cttaccacca tgagcgtatt caactatgcc cccggctatt accagaataa tgttccgcat  68580
caaccttata ttaccatatt caaagttaat aaatatgctt ctcaaacaga tgggtctctc  68640
ggtattcacc ctattaaatt gttttattac accaatgaag aatatgcgtc tatgtcgcta  68700
attgaaagaa acaacaggtt cagcagattt gtctttacta aagatcagtg gaatgctgtt  68760
ggatatattg ttgaggaaaa tccccttatt tccaacagcg ttgttatcgg ttattcctac  68820
acttacagca tttatttcaa cgaaacaact tccgttacaa aatctctgga agtaacattt  68880
tatgacataa atggcaattt cagacccccg acaacttatg cttatattga cggttcagac  68940
aaccagcagg catatataga cgtatatggt gggtttggca taggaacacg ttttgcgaca  69000
gctcagagtc aatattatgc caacaccggt actataggat ggagaactta taactttaca  69060
cccggggtgt tttctctctc tttcaaggaa tgtctgtttt atacccgcgc attatggaac  69120
gaagcgcccc agatcatgga ttatcttatg aaaaaacacg gtatcccgtt tgtaagctga  69180
tatgctggaa tttacctaca gtggtacgtt ttcatacccg gatagtcaaa cactttccag  69240
tttttactgg attattaacg ccccgtctgg aagtgttgtt acttattccg aaattttaaa  69300
ccccccgctt aaagaaatcc ctattgaagt aaccatttcc ctcgatacca caagtatacc  69360
gtcaggaaat gtaacatgga gtgttaactt ttttgcatat acaaccacct ctattacagg  69420
agaagtttat ctttatattt ccaatatctc aggattggaa ccatatagca tatctatctt  69480
tctgacttca agttatgaga aagaagggct ctggagaaat ctcgggttgg gtgaatcttt  69540
ttactgctat tcgctttcca ccactccgaa tgtacgattt atcaaacaca ccatttctct  69600
tcagagtatc agtttgatac cagccggtgg tagtatcaaa tgggaaaaac ccccggaaaa  69660
aacttattat tcttttttcga ttttcgccaa agggttttc cttagaacag ttgatttga  69720
gggggttgact acaagtcagc ttagctggta taatgatatt ccatttgctg tttcaggagc  69780
ctatctgtat accggatcag gatttccgct cattactttt atcaaccaga gtatgcttta  69840
tctggtaact tcatcggggg acttcagtaa cttttgtttttt agagatctga caactaacac  69900
cgatgtgttt tctttcagtg tggaatatcc aacgctttct cttgcaagaa tatatatcac  69960
ctacgatggg aatgattttg tcataacatt cagcagtact gttagtgatt attactatac  70020
```

-continued

```
ctataatttg cccggactca gttttctga tcatctactt attgggaatt atcaatcttt    70080
ttcgggtcat tccgcatgga actcttttat tgtacttgac tataatgcga caggaagtgc    70140
gtaccagaca ataagcaacc tgatatgagc cattttgatg aactcacga acattacagc     70200 accaccacgc tcagcgttaa cggggtagtg gtaagtcata gttacagagc atttccttcg    70260
cttagctacg ttgaaattac gctgtacaac gtacctgcac ctactggatc aaattatttc    70320
tttgtttatg atcacgttta caatcaaaac atatttcttt atgcgctgaa acctcaggat    70380
atagggaaag aaattctgga aacggttagt ttcaggatta ttgttgattg atcatcaata    70440
gataataaat tctggttttg taagcgtaat attgatctca aaccaccgt cttcgataaa     70500 cagtgcccct gctcctgaaa gtgtgtaatt tcctgtaatt atattgattc ttctgttgaa    70560
atgggatgta gtcaattccc atatactacc acccgaaaca aacgtctcaa attcttcttc    70620
ctctataaca ggttgatgtt ctatctcaac cagactcata gaagcaatta tggtgcgcct    70680
gtagttgaat tcagatatat gattcatttc tattgtgctg taggaaacga gtcggaattg    70740
ttgatgttcg ggaatggtga taaccgaaag agatatcccg tctactttgt gagaaaagaa    70800
aattctgttt tgagcgaagt ttgagtaaat agagtcgtgg gttttggtat atgtcccaag    70860
cccgatatat ctcaaataat atcttaccgg atattccaga ctaccgctga agttgtagat    70920
tttatcaaga atgcgttcct gaagtgcagc atatcgtatt tcacttgctg taaatacata    70980
aggtatggtg gtgcggatat acgggaatgt aatataatcc agttcagagc cggtaagtgc    71040
tatgatacct ttgaaaatct catttggaaa cgtgatataa cttatagata attgtgtata    71100
ggtataaaga taggtaagtc tcctgttttc aaacgtttct acaaaggaaa tggtatccat    71160
tgaatggctt gcgaagaaaa agagataatt ttcaatcaga tgctgtaaag tagcattaac    71220
aagagatttt gttaaacgat taaaatagag ggttctgttg aaatgaaaag atacataatc    71280
taacccgtaa ttattggttc gaagtgcaat aagatcagtg ttttgctcaa caggagcatt    71340
tacaaaccct gaaagcgttc taaaaagggt atatattttc cccgtctgaa aagcctctaa    71400
gttcaatccg atcggatcgg taagatatcc cctgaaatat ttttcattgc gcaattgtgt    71460
attgaagctt acgtaatagc tgaaggagta aagggtagtt ggatcaactg tatcgtgaac    71520
aggaggaaca atcaaatcat aagtcatggg gagaaagtct atttttttcaa tgctgattgg   71580 atcataaaac tcatttttcc acccaatgcg gttgaacaca aagaacggag gaactccttc    71640
ggtggaataa gtgccagcgg gtatggaacc agacaaaacg aattctgaat aagtgggtct    71700
gtaggtgtaa agccgataga tgatagattg ggaatactga gatgtagtag actgatgata    71760
taccgaaacg gtgaacgaat gggttccgga tacgaaccca ctcattgtga tataaagaac    71820
caattctttg tattcaggat ttccctgata gaaattatca attatgctgt gcgaaaaaac    71880
aaaaggtgga agggatgata ccacttccac ctgattgaga aataccttc ttacagggta     71940 agaaactgaa taagtcatgg tttcatatca tcacttaagg attacaaagt ggtcagcatg    72000
aacgtctgca cggttcataa gcgtgaagct acgcgcggca agatactgtt caagcaggat    72060
aatatcgcgc tccgtcggtg atttgataat aaccagttcg taaatgctac cgacaagcgg    72120
gcgcacgccg tcggtaccaa ttgtgagaat attgattccg tctggaccca ccgccacatt    72180
gttcatcaag gggataccgg aaatccggag cgaactgttc ccgctgaaca cacccactac    72240
cacctgatcg cgggtagcga gtgaaagcgt atattccgtg ctggagcctc cgattcccca    72300
gttgtggggc atttcacaga aaatatgggg gttgacagaa agtgtaccac cggagaacaa    72360
```

```
cccaccgttg gcgaaagaac ccacaatacc gatagcgaac ggctgctcga tttccagacc   72420
ggtaccttcg agacccatcg accgaagcca ttcgtttcca cggaacacca ccgccgacaa   72480
tccgttgtat gcatcccgca cgaaaatggg ctggttatcc gggttggatt gtgtgaggga   72540
gtaagataga taagccgatg ttgaaacata tgctggcacc cacgcatcaa ccttatcgcc   72600
cgtgttgtag gaagccgtga gggtgttcgc atcaaagcga agcaccactt tgggcaccca   72660
gctttcaatg gtttccgccg gatcgacaaa ataggggatg ttatatttct tagccagata   72720
gttttcaacg ttctgacgtt cagcgttggt aagtttacgg tcaaacacgc atagctcagc   72780
aatatagcct ctcaggttcc accctatgaa catattcgat tcaacacggt taccggtctt   72840
accttccata taccgcacac cgttgatgta aatgcggtca agcggatatt tggggtggga   72900
agtagcaaag cgaacatcgt tggttgttgg cgaaccagag agaccactaa tgtggtacag   72960
attgacatat gaacctgttt cattttcaag tatcaccgta atgatattcc agtcattcag   73020
gggtacaaaa gcgtctgcgg gttgtggaac agtattgtac ccaccgtaag agtccggtag   73080
tgcgttggag actcgagggt tgcgatatga agagttcaaa taaatccagt gttcaacctg   73140
attttctttt acttcaaggc ggggcacaat tactgaataa ctgtgaacat tattttcatc   73200
aaccattctg aaataaggta catccgtatc gtctgtgttg tgagtatccg actttggttg   73260
aggatcccac atggagaaca tccacagaaa cctacccgga atgtttccgt aatttactga   73320
attgttagga atgggattag aagaattggt tgtaatattg ctgtaattcg gatgataaac   73380
ccacaccgat ccactctgca caaacacccc agatgtcgta tccgggagtc tatccagttt   73440
ggcaaccatg ataatggtgc gttcagtatt ctgagaataa tctccggtgc ccggatagtt   73500
aatacgcata accgaaccgg aaccgaaata ccaagccgga taaccgttga caatattttc   73560
gacgaaaata ggtttgcgga aatcgttaac ctgagtagct ttaaatccgg aatatgcggg   73620
aacaaggttg ggaatttcgt caacgtaatc gccggtttca agctgaggag tggagccgtc   73680
ggcgctcatc cagattttgc agttggggac gtccgacggc gaagaatacg cattgatcgt   73740
ctgaacataa atgggataag tgcgaactgt ttccggggta acgccatcgg tagagcgtac   73800
cgtaatgctg taggtgcccg gcgctacacc cgacagatca ccgtatacac tcagaatccc   73860
ttcggtgcgc ccgtcgggaa gaatggactg ggtaaaatca tatccggtaa cccagctcgg   73920
ggcggcggaa accgtagcag taatcgtatt accgtcgtta tcgtagatat aaatggaaaa   73980
cgttacggtg ttagaactct ggtaagtcgg cattgtttat cccggttttg ttttaaatat   74040
tcttatttca ctcaaaataa aaagtcaaat agagataagg cacagaaata ctgctatagt   74100
cattgatgga gtctatatag tcttttccaa tatacatgtg tgtgataaca tctccgctat   74160
tatagtcata catcaagatg tattcggcta catcgggagg aatgttgttc ataaagaacc   74220
ctgaaaatgt tatggagtaa atatttccgt caaactgttc gtcaatcata ctgacagttt   74280
gcgtcagatc cccccccact acccgttaca acatacaaac tgaaagatga gtgtgtaacg   74340
ttaaattccg gataataaga attaaccggc accactgaaa gagttttttcc atagaaaata   74400 tttcttaccg cttcttttaaa agcattcatt atggtttctt ttcggtaaaa aggttcggtg   74460
ttgtaagata gattgataaa tccatagatt ttatctctgt atagagagta actgtaacct   74520
actctatagt taattaagtt gtattcctga tttagtgtat ggttaacagg ctgactgtat   74580
acccatttgt aagcaagcca gcggtgtttt tcatacatgc tggatataag cggctttcga   74640
gagatcacag gcgatgtgtt tctttgagta gcatttatcc agtaattgat aggcgattcc   74700
acctttctgc tcatgatgtt tgttctattt ccggcaatga tcgctcttct taatgtgtgt   74760
```

```
ttattaatcg ttttgaacaa ttgtcgatag atagtgcggg tcttgttttt gacagtgttt    74820
ccggttctat gatatgctat aagtatctgt cggagttggt tgagatcaag gagaaaattt    74880
tgagttttct ttacagaagt gagcaggacg ttaccctgaa aacttggaaa gaagtctctg    74940
gtggtacgga taacttcccg gattttaaaa agtctccggt caaaatgggg gatatcatag    75000
cttgcataaa tgttagtgcc cctgaagaac aatccgatta ttctatcaat ggttgtttta    75060
tagtttaatt ttattgtgcg tatggttaat tttatcaaac gttgcatctg atttgctata    75120
aggttaaggt acttttaaa actcagaagt ctgatggtta catatggctc taaggtggaa    75180
taaatgattt ttccaacaaa tctgacctgt ttaataatct gttggtaaaa acgtagcaca    75240
tagttaaccg gtgtgtatcc ggtcaaagtt ttaaagaaag ttttattcac cagagtcgat    75300
ttaatgagtg atctggtctt gatgatagtt ttaataaaaa agtttttgat tgaattcaac    75360
agactgttaa aggaggtaga tatatttaaa actttaaaaa attcttcagt gctccataca    75420
aaagcggaaa gcaatttatt gaaagttttt aaattgggaa atctcagttt taaagtgggg    75480
gtgtagttga caggtgtgtt ttttgttttc aagatatact tgaactcatt agaactaaga    75540
ggttggttga cagcattata tccattgaaa agcgtaagtg cgtaggggtt gtcgtagttg    75600
ttgtcaagga aaagtcgaag tgctgtcggg tcatcatttt ctatcaacag cggatcatca    75660
atcgggtcta tataaggatc atagggaacg gaaaatatat ccctgaaatc gtttgtcgaa    75720 gtataaaatat aagataatgt atagttaaag attaccgact ttgtttcata tttgtcagtt    75780
gaataaaacc tgaaccgtat acttccagta taccagtcag gcggaaagga agatgccgtt    75840
aaaagattga gataggttat agtagacccg gagtgcgata caccaaacca gaacttattg    75900 ggtgggggatt gttgaacgat aagtgggctg aatactcctc ttcctttgtg gtctacttta    75960
aatctcattt tgttcgtagg ttatgtcata ttcgtccagt atcaaagcgt tgtcaacaaa    76020
tagagaattt tcatatccgt gcatgaatgg aatgggttct ccatcgagtg atatgtcttg    76080
aataccaatg aatatgggaa aatacagact gatcgtatata tccattactt ctataatcgg    76140
ataatgatat tcgatagtta tattgaatac tgttatttca gggtaattca aacttatggt    76200
gaagataaac ccatattcca taagagggtg atatagatta attgaaatgg tgttgaagtt    76260
aatgtcaaaa tcgagggtgg attcatattg tgtgctgaac gttttgccgt ttatgtcgct    76320
gagatcaggt gaataaagat aaatattaaa atcgagggg gtatctataa tcaaagcttc    76380
catatctata taatagaggt ctatatcggc aatcttttt ccttgataat acacatcata    76440
ttccagatct tttgaaaaac tggtactgaa aaaataccgg taagtgtcaa acagatcaag    76500
aattattgaa actgtgtgtt cgttttggaa gaccagacta taactgacat ctgaaactaa    76560
cgtcagacta ctggtactta caggatatct gaaataaatg tctctataac gtaaatacct    76620
gtcggctgat tcggtatata ctttattat gtaatctgta ttaatactca taattttatcg    76680 atataagttc gtttcccttt ttaaccagaa tagtactgat gggtacattt ccgttcatga    76740 attccaccaag catatcgata ataaaatcta cttcttccct cacttccagc ataagtgtgg    76800
ggggtatttc aagatagaca ataccatctt gataggaacc ttttacatat tcacggtttt    76860
tataccaatt gatatatcgg ctcatagaat gttgaatttt ccaatcgtct tttttaaagg    76920
aaaacattcc ttcatatttg ttgaagggat cgtaaacgaa accgacgtag tctttcatgt    76980
ttttctttaa ataaacaggc ggttgtgttt ttattcagaa aaaacttatt taagaaaaa    77040 agatgtatac cgaactgttc aagaaaagca acccgcacaa ctcatattac tatcattacg    77100
```

```
tgcattttga cagtaattca aacacacatt caatcgatgt tcccggcgga aatgcgctca   77160
aaaacattct tattgtgggt aacgcttcta cccctatttt tgtctctttt aaaatctata   77220
catcgcatag cgggtttgtg ccggttccag tatcctacga ttacgaagcg cttggaaaca   77280
atgcgctgat taccctaat atctcttcat ttgcagtttt ttcctctatt caaacctcat    77340
cgcttcgcat tagcattacc aatatcaccc cgtttagcgg aagtgtttac atactgttta   77400
aagtcgagta acgtatgttt tacgaacctt ctgtaagctt ttttgcagta tatcctcagt   77460
acagcaccag cgcggctttt ctcacagaat tcaataaatc atcggcgtgg gtgctccaca   77520
aactgggcta cccggtggta tcggtggaat tgacgaaaga tcagcttatg tttctctttc   77580
acgaagcatg gcaagaatac tctcagtata tttcagaatt tctgattcag gaaaactatg   77640
ataacgtttt aataaaaaac attttccaga cggaagggga aatctttgag aagtttccca   77700
aacctaacag ttcgcttatc atcgagcttt ctgatcgcta tggaatgtac gacatgaaca   77760
ccgaatatgt aatcattcca cttaccgctt ctcaatcggt ttatgacttg aagaattaca   77820
ttaccgcatc cggaaaaatt cacgttcagc aggtgcttgt caatagaccg cgcgttggtc   77880
ttggttctac gctgtacggt aatgcttttg tcttcaacaa ctattctccc ttcaccgtag   77940 gatacgcgc gggctggaat atcggtcagg tgctcacgcc gctttcctat cttgccacca    78000
ccatgcaggc taccgatctt gcctacaata tgtatcgcaa gctccacttc tttgaaattg   78060
tctctggaag tatgattcgc atttctcctg ttcccgattc caacgactcc cggcttacaa   78120
tcagatacaa actggaacgg gaagaaggtg atcttattga aatgtacaat tcaatatttt   78180
atacgaaaac aggtctcctc gatctggaaa aactaaatga aaactccctt attgtgcttc   78240
ggcatatctt cctcatgaag gtgatcgata cgcttatttt catccgcaag aagtacgaca   78300
actacgcact tcccaatgcg gaacttacgc tgaacgtcga caacctgaag gaactcaggg   78360
aatccaccaa ggaaaagatc gacaaataca agagtggct tgacaacatg aaacttcacg    78420
caaggcttca gcggaaagga gaagaagcag aagcgctgga gcgggaactc cagcgctatc   78480
ctatggggtt cctatttatg taatctctca cctgcaatca ctcagcgtgc aggcgcccat   78540
ggggtgatct cctctaccgg gcttttgaa cggcggtgga atcttatgtc ccggtttgtg    78600
gtgtgcagta acttcctcaa ccttttccata ggttgtgagc atgggggtaa tccacctttt  78660
catggcttct ccgattttt attgttggtt cttatagata aataaccctg tggcacgcat    78720
cgtaagtgaa aaaccacccc aacagccacc accggttcac ataacggaaa aattctttgc   78780
cttttttaaa ctctttcatg attgttcttc ttttggaaga ttcagcttaa tggtgatata   78840
atccgagtcg gggaattctt ttcttaaatc ctccagcgac tcatacacaa aaatcatccc   78900
gacggcaccg gtgttagcta tcttagaaag tggatagacg actttctgaa cgccgttatt   78960
gatgacaacc tgcaggtcat ccagaaagtt aagctgcatc gcgacgtaat acacgcgctc   79020
ttcgttattg ttgtcgttca tggcacacag ggttttaagg ttacgcatgg tagtctattt   79080
ttacaatgta ggttttgtcg ttatattcta tcatgtgata atgcgcctga taaatatggg   79140
ttccttccag aaatagggc tcgttacctt caaggtagac gaacaccata tcttcgtctc    79200 caccccctg agaaggcgg ataaaggag tgtgctgact ctggtgagta ataccgataa      79260
caacatcggg gttttctcg ataaaatcga gaatttcccg ctcctgttca gtgggttcaa    79320
aatgcttcca ttgatacacc cggtagggc gattcgaagc gatgtaatag ggaagagaag    79380
ctacatgtcg gttataaata tccagaacaa tctcttcaat atcagtattt tctttatttt   79440
taatttcttc ctcgagtagc atgttaagat caagtatcat gtgagccagc gtgctgactt   79500
```

```
ctgcttcatg cattttaata cctttctttt caaggatacg aacaatgcct tcagtgtcga   79560
atttgagaat catggcgcta atgggtttag ttttcactct ctacaagaaa acgaataaga   79620
tcctcaacgg ttttatctt tgtagtattt tcaacatacc cgagactttt cagcagatca    79680
attgttttct ctgaaatgat ctgacagtat ttgtctctat ctatgtattt tttaacgatt   79740
tcaagaccct cctcatcatc ctcacgtatg ctaagtgcgt ggatattgcg gagcctgttg   79800
atatgcgttt tctttcccgc tttcagaata tcccacacgc cgctcccatg ttcggggtta   79860
acttcttcca gagaaagcgg gagattggtt ctggaaggat ccagcatggt gcagtagaac   79920
cagtagatct tgtctcccat ttgcgggggt ttgcatccta taatggaagc gaaaagcgct   79980
cccttataat gaatgggaag tgtatggtca tacatttta tgaatatctc agagattggg    80040
acattctcct ttttcatctt cataacttcc tctacatact ccacatatct ttcggcgctg   80100
tcagacgaag atattttcat tttgtgatag agatcttcaa tagaccagaa attcttttga   80160
gacacaaagt tattgtagaa cgctatggtg gcggaaatga catcgatgtc gggttggctg   80220
atatacttca ggtaacccct gaaatacttc ttgacaattt caggcaccga agagttgatc   80280
acttcgattc ccttcatctc ttctttaccg tctacagtaa ccgcaaagta gcggttgatt   80340
tctttgataa gaatggattt gaacacgaac tcctgctttta actccagctt gaaatcttct   80400
cttgcattaa agttattttc catatagtca ttgataaaag agttgagatg ttcttgaagc   80460
tcaccggctt ccgccaccgg atcatccgta aaagctttga cgaaaatgga gtcggtatgc   80520
gaataaatga agcgatcgcg aatctgagaa atcacggagc gaatagacat gcgcccggcg   80580
gcggttacac tttccgcaat gggaaggcac cccatgtaca ccgaacggtt tccgaagata   80640
ccgtacatgg agttcatcat aattttaagt gcccattgac ggaaatggtg ttccatgttg   80700
ccagtttctt tgaaaagctt acgttcttcc ttacgtcggg tgaaaatctc ccgaatgata   80760
gaaggaagca cgccaaccgg ctctttcctg taaaaccagc agatacccga cgggttgggc   80820
accataatga tatttcgact tttaaaaat tgccggagtt cctcaaagct gttgatgaca    80880 aagagggtt cactccggta agaagggttc atccctgaat cgaagatgta gagggaaac     80940 ccgaattccg gttcttcctg atctaccgga atcactttgt tctccacccg catacacccg   81000
taaaactccg ttacgaacgt agcgggatcg atattgaatt tgctgattac agagggtac    81060 agcgatgtaa aatcaagatc gaatacgttg aagtaaatat cggggttggt aagttcaatg   81120
taagcaccgc gataacgata cttgttgatg ttcatagcag aatacgtttg ttttacattg   81180
cgggatcaaa atgggtatct ttcacctcga taaggtaggt gtcttttaaa tcacatttgt   81240
ataatacgcc atcgagtgga gaaagatcaa taattctcaa aacttcatcc gtatagaatt   81300
ttcgctcgat aagattatgc gtttccagac gtttgcagta ctcgaagata gcgtctccaa   81360
caacatagct ttcaggtgc cagcaggcaa gcccatcata atgataaagc ccccaccaac    81420
catttgctct ttccctgacc actgcaggga taaccccag atcttcaaga aatgcttcaa    81480
gtttattttc atccatataa agcaaatcgc gtcgcattat gttttttccc cgctcctcaa   81540
gaaacgcatc aacatacatc cacccggttt catcccggat aagcttgcga agtgaagggt   81600
atgcctcaac cgatgtaaac ccggtcttca aatcggtaat aatatcccgc gaaaccgca    81660 taacgaaata ataaggggtt tcgtagtcga taagttttc aataattta atgatttcgt     81720 acttcatggc taaaacgcta cttcatggct aatacgctac ggttagttta agtgtcggt    81780 aaaccttcc attaactaat gccacgccca ccccccgta aatggatccg aaaatctct      81840
```

```
tctggaaaga aaagtcgtaa taattgagcc ctacggaagc gctgataagg ttgtgcgttt    81900
ttctaacctt cagcgcaaaa tcttcctgca tgaaacgtcc ggtttccggg ttgaaaaacg    81960
ttacgcggag cgtgttgccc ttccacgtgg catatctttc cggaagaagc ccgtagagtt    82020
tcatgtccac cggcttcgga cactccaccg tgtcaatctt ccccacgggc gtctcccggt    82080
aaatgatctg tttgaccggc tgggcaaact tcccttcaac cttcaattct gaaggaaaaa    82140
ctctgtccga aagttccact ctgacttccg gtctgtaaac ggtgcggttg acgtaaagat    82200
gtatgttaac cgcgatcagg atcaaaagga gtgcttcttt ccagtacttc ataagtcttc    82260
ctcttcttgg aatttgtctt cttcgtctct gatcatagcg tatagaatga tcagatagtt    82320
aattgcgtca atgattctac cttcgacagc atcccgctgg tttttaaccc ctctgatcca    82380
gcgtgccacc cctcttaaat gtttatccag aaatacatac agcacttctt cccttgaaat    82440
acccaatcgc tttgcagttt cttcaaaatt ctgaaataca ttgtcggttt cggcatactc    82500
ctgttgggct tggagtcgga cacgatttac ttctccaata agctctttta caatgcgttc    82560
gaattttgtg gtattcatgg atttcctcca ttaagtttct ggtatttatc ttatttaaag    82620 aaaagatga atactccccg caaatatttt cttaatccac ccacctcaag atccctacag    82680
gatattgaat acctttacct caccaacaaa cacatcatta ccggcgcgat aaataaagcc    82740
ggtatgagca ttgatgaagc ttgtgaatgt gttgtggggg ggatcgtgct cgaatataaa    82800
gaaacacacg gcatcaatat ttttgataat ctgactatgg cggtggagta tttcattaac    82860
aggtacaaag aggatttaaa aaccgggcgc atttaactca tcatcttttc gttgataaat    82920
tgaatgagtt cctgtacgga aggataaaac tgttcctcga aaatctggtg gtttgtcttt    82980
atcaattctt caagtttatc cacatccgcc ccgatctttt caaaaaaggt acgggcttcg    83040 gaaacagtt cccctctggt ttcacattcg gtataaacca gaagaggaac cataacccgg    83100
tagaaaaatt cttccggtgc ttccctatca acatactctt caataagttt ctctgtaata    83160
ggaaccccgc acgcctcaaa cacgtcatcc tgcacggcga agtgaatgac gccgttatac    83220
aaaaggtgcc gcaaccgcac cttccacatc agggaagggt cggttacgaa ctcatacacc    83280
atttggagag cattctcgag aggaacctcc tttaacggaa gctcctcaat ttcttcttcg    83340
atcgggtaga agacgttctc ttctttggag aacttacgct ccggggtaat tataatccag    83400
agcgcttctt tgacctgagc agcgttcaag ttgcccatgt tgtacctcct tgttttgtt    83460 agttacagat taaacaattt gctggttttc tcgaactcct cgaaccactg tttccggagt    83520
tcatccgaac ccctgtattt cagggcttg ctatcttctt taactttcga ttccggttca    83580
ggttgctcct gggtttcgag tttcagggga atttcaactt tccctttgag ttctttgagc    83640
ttgttctcaa tacccggcgg aacaatccga ttttgaaga ccagttccac cgctttgtta    83700
atcacttcat cagcggcttt acgggtcgcg tgataaatgg catcctgctg agcctctttg    83760
agtaaataca aagcgcggcg ttttagataa tcctcgctgg cgcatctctg catggtgaac    83820
tccagcgaac gtcggttgtg gatttcgctg ttagccataa ggctctccca ccacatatac    83880 tcttttttcag aattgaggat ataagccccc ttgaatctga cataggtatc ctcatcaagc    83940
ttgaaccagt atgcatcata gaaactgtac ccccgcaagg aatcgtcaat aacgtacccc    84000
gcaaggggtt cgacaaaaac aagctccaga tcggctactg atagtacatc gatcatatag    84060
tcgcatcctt tgttcatagc gtctttgaat ttttctctaa tcatggcttt ttcctcccttt    84120 ggtttatcgt taaacccacc aacgtcaaaa agagggagtt tgttttttcgg atggagacag    84180 aattcggagt ttttgggcat accccgcttc cagtgttcca cccagctatg acatacttcc    84240
```

-continued

```
tcaaacatat cggggtatgt ctctctgaac ttgggaatta cgtatcgata gaattcgata    84300
tcgtatttga atagcgcatt tcttataacc gtaggatctt tttccattgt gctctgtacg    84360
cggagatttc tatgaaaatc aagactctgg tacaggaaga aaaacgttgc gttcacaaca    84420
aaaagatatg ctgtaaactc gatccaacta aatgctctat attcggttgc aacagggtaa    84480
aatttgtaaa gccagtagcc cacgaaacca aacgccacaa ccttcaaagg ttcgtgtacc    84540
ttgttcacaa cacgcgggct gtaaagctta aaacccgaaa gcacgttgta cgtgccggta    84600
acgaaccacc tcccaatcca acacaaaccg atagaacccg atacaagaat ggtgatcatt    84660
gtctggctca tgtgggcgac ggcttcgtgg tgcccgagca taaacgggaa accaataaac    84720
cgcccgaata ttagcaagac cgggaatgac agaaggtccc cggttataat gcagacggcg    84780
gcaatgaatg caatccacgc aataccggcg gcaaacgtaa acgacagata aagggcgtcg    84840
ttaaacgctt ccgcctcctt gcgccacagc ttcaaattat ctccataata aaaccccaga    84900
accggaaccg ctacaagata gcgatccagc ccctccacca cttccttctt gctcaactca    84960
agttcgccct taccccactt gaggagctta tctcgataaa gcttgaaagc tgtaagggcg    85020
tactttcttg ttactccggc gtacatggct ttccgggttt gagttatcaa tctgcttata    85080
acatacgccg gaaatccaga aaagtcaagg ggattacgtt aattttttac gaagaagaag    85140
acgtgctacg tcgtcaaagt aaatggcggt tttagtggcg ttgagacgct tgactttgag    85200
cggtttataa agtctgttct tgataaaaaa cgaagctctg ataattttcc agacgtttac    85260
gtaaaaacta ctattctttt cgtaaaaaat gcagagggcg ataaaatcgt cagattgggg    85320
gttatagaca agccggtcat tttttctgaaa cacccaagac ctctctattc tggtgtatct    85380
atatctgggt acatcctcac aggttttaac atgtatatat ctaccctcgc atatcagatc    85440
agccgcatag gatttgtctg aagtgatagt cagatcgggt ggggtgcatt cataaccaag    85500
gttggtgaga tattcataaa cggcgaattc tcctatttta ccaacaaaat aattccattt    85560
tattctttcg gggttgtgct ggtggcgctt tttgtattgc tcaagcacaa tcccgtcgtt    85620
tatctgattc ttagcatatt ccatgcagat gggcacatac tgatctactt ttatcatctt    85680
acccacccct tacccaagagc gatacttgtg gacggattga taaggtacat caccgccgtt    85740
tcacggtaaa acgttgattt tgtgtaatgg atcccaagcg aagagacaaa gggagttccc    85800
ggataagcca tttgtgtgtt gtatctattg acaccgcttt tcggaaatgt atctgctaca    85860
atggaaaaga ccgcaccctc gcgctctgtt gctatacggt cgactgtaac ggtatccgga    85920
attggaattt caccatcgaa agatttgaac atactgaaag aaaattgctc aaaatgaggg    85980
attgactgag tcatctgaaa tgcgtagaaa ggtttacctt caattaccac tcccgcgaag    86040
aaattctctc cggcaaaaag ctgacgaagc aacaagatag cgtcgcgggt tttgtttacc    86100
acctcaagca tatcctgatt gcgggtttca ataacgtgta cattatcccc ctccgccaga    86160
tttctaacgc ggttggaaag atttcgctgc aaaaacacca cggcggaata aggagtatct    86220
tcgagttttt gaacagggtt ttcggtaatg atatgatccg gttgataaat cgagccttcg    86280
aaagcgttat ccgtaatgac tccgatatgt ctcagattgg attccatgta ggaaagcgtt    86340
gaaacataat aactgtaact gatcgtcgat gtggtaacct ctggaaacat gctgtaggtg    86400
tggttgtcaa tgagccacat tgagatagta ctgtcagatg tacctttcag gtagaaataa    86460
accgaagtgg aaataacagt aggcattacc atcatcatgt agctcatgct gtaaagctga    86520
tctattccgg ggaaaagcag cgtaatcact ttcccctgaa gcaccacatt gaacggaagc    86580
```

```
agcgaaagac cattttccaa atctctcatg tagcagacgc cgtggaaatt cagactatct  86640
acaacaaaac cggaattatc aataacattt acagaaactg aagttataag ctcgccgcga  86700
gatgtataga ccggatagtt aaaagccccg gttacataat aggggttggc gttgctgacg  86760
gtaatggaga aggtaataga atcgagaaag ctattggcgg taacttcata atattctcta  86820
atatccttat gttcattata gggaatgaac ccgtaaaacg taaaataatt attcaacaca  86880
atatcttccg gaggaatgtt ttgacttacc ggtataatgt gttccgtgat gtaatactga  86940
tcccccagaa acgcgtcatg aatgatcaca tcaaactgat aatctttatt tcgtaaatcc  87000
agcgattcag ccagcgtgtt taaccattta actttcattt tgcgattgaa ggcgtgatag  87060
gtaatacgat tgatctgatc gtgcagcgcg tcgaacgcat cgagaagttt ccggtaagc  87120 tgctcaagcg tttgagacgg gttctgagtt gtcggttcat tcaaatatt tgtttccaca  87180 aactgaagat cattgcggaa gtagaaaaca tccatgatat tcccgatcat atccatatag  87240
gtgagatatg aaggatcgaa cacttcttca ggaagtcttg aagaaaggcg atacgggttg  87300
gatacgtcgt attcagtcgc agcataaagg tgcatatcaa gaagcacctg atacggattg  87360
acgcccggat aaattgaaga aaacgaagga aatacttctt cccagaaatg tatggggagc  87420
agataaaagg tacccggaag cgatgtcgag ttgtagtagt aatccagata tcccagcgcg  87480
taactctgac gaatggagtc gtctctaaag taatggttga tgtgcgttac gtcttccgaa  87540
gcaaaccatt taatgaatgg aaggaagcta tcgtagagtt tattttttat ttccttatat  87600
ttttcagcct tctccggata aaaacctgaa agcgtggtga taatctcatc atatttcctg  87660
agcagcgtga ttcctttgaa cgccgcctga atgagcgctt ctgctgaccc gaatttgaca  87720
aatccggaga gcagatggaa attggatttc tgctccatac ttccgaagct aaaagacggg  87780
atataggtgt tgattcgatt gtattcaatg tattccagta gatcgacggg actcctatct  87840
tcaaattcga gatgaaacac gttgttggca aacgcatctt ccctacccc aatggcgctg  87900 aaggtaaccg tgtctgtttc cgtgagattt accggaatgg attcctgcaa atccacctga  87960
cgcacaagat acacttcttt tgtcgagtga aggagtgatg aagttccata tacataaaac  88020
gtttcctgat aataaaccgg ggtacccagt ttatgaatat tcccgtttac tttaaccaga  88080
atactgtagc tattctggat tcgagcggtt acttcagcgt aatagttgaa caggtcttca  88140
aaagtgatac tggtgctgat gtagtttca aaagcttcgt taatctggtt ttcaagttgt  88200
tctatggctt cgacggcaaa tgaaatggtg aggaatatct gattgagacc ggtttgcgca  88260
gaaaggtatt cttcgaaag tggttcggct tcttcaagaa cttgctgata agcggaaatt  88320
tcattttgat aaaaattatt gaaaaactcc tgtacatcgt tgaaactgac ggtagaggtg  88380
agttccagcc gggaggttgt aaaactaaac gcctgctctt ctacgtagct gtaagttcct  88440
aattttttga ataagcgta gacgggatag gagtctacag agaaggtata aacaaacgga  88500
agcgaaatgg tgggttttc aattccttca aaaacttcag ccggaacaga gtcaaccacc  88560
agatagacgt ttccacttct tacatacttg gaggttactt tgccaataaa atcaacgaa  88620 taaatgattt ccccggctga agaaccgctg aagtgttcaa tgtaaatgta aggatttgtg  88680
taggaaagag aatatggagt aaacccggct acaatttgag aacccgaaat aattataaaa  88740
tcttgcattc ctctttttct gttaaataat aacgcaataa gtcaagtgca tctttgggat  88800 agaaggctg atagtcttc atggaatgtg atattcgcc ccagtctttg taaccggcgg  88860
gaggaaacag aaaaccaact ttacatacgc cgctatagag ttccaacact ttagaaattt  88920
cttcaacgct tacatccgaa tcaaaacaga acaccagttc tttaaccttt aattttttgca  88980
```

```
caacgtagga atccggaata cgattctttc cacagagtac gcacattccc acacccaacc    89040
catccgttgc atgggaagc atatcgaaca ttccctcgaa cagataaatc tttccttttc     89100
gagccgcttc gtagaaatag accggagct tacccaccat ataggaaaga taccgaacct     89160
tatcgaaagg ttgatagaat tgaacgtttc ctatggaatc accgaaggca acccgctttt    89220
catctaccac cttgaaaaat ccttttgacg acatatagct gagaagttcc ggttttaccc    89280
ggcgctcttc aatgatgtgt ttgataaccg gatattcgat atttcctct gaaagaggag     89340 ccgccttttt aaaagcgag cggtagtaaa agttttctt gacgtttgtc tgttcaacat      89400
ccgtaaaatc gatatcaccc gaattcttat aatatgaaat gagttcgaca ggtttaaatc    89460
cgaaaatgcg ctcgaagtct ctataaacgg tgcctgaaaa cccacaacgg aaacagatga    89520 aaagagggc gtctatggaa aagtaaagcg tgagtcggcg gttgttttta tgcgggggcgc    89580 acttagggca caaacaggct acttctttac cgcccccggc aactttagct tcgctgaagt    89640
atttggtgag gatttctaca atcatggttt tttctacaaa aactctaagg aatcacaatg    89700
gttcccggtg tagtaatcac aggatgattt aaagtaatgt tcacatcggt taccgttata    89760
tccggcggaa tcgttgaaat gtcaatcggg atatcgcagt atttgctctg agaaatctct    89820
acggcttcga cggttacgga aaaattgaaa tcatcgtcgg tatcgaatgc agccatgaaa    89880
aactgttcat cggtacgtac gttgacaatt tcataccatc ttctggattc cccaagcacc    89940
agatctcccg gttgtggaaa atagtcgaat tctttcagca cattcctaag aagatgaagt    90000
cggagtttcc gcaccgatcg cattccaacc tcctctgaag ccggttcccc aacctcatat    90060
tccacacgac agggatccg gtacatttta tattctctaa tatcttctt aggagactct      90120 ccatacagat agtgcaatac gtcgttttcg tcatcttcca ccgcgttttc aataatacga    90180
acaaaaagga agttggcgtt gagaaatatcc tcaagcgctt caagggcaaa atgctgaaga   90240
agattgagtt cccgtcttcc ccagaaaaga ggattacgct ttttatcat ttttatttaa     90300 ataccccctt ttcaattctc tccgttagaa gcttcttttc cgacttttgc attttctctt    90360
cgtcgccgtc aaggcgggca aaaaccaac ttttatcatg ataatccata agtcgaagag     90420
cgaacctttt gcgaaactct ccggggtttt cttccggaga aacctgttcg gaaatctctt    90480
tataaatcgt atcaaaagat gactcaagct gatttcgcat atcggtataa atttctttga    90540
gtttcatcac ggtttcctgt tcatccgggg taagtacaaa atcatcaagt ttgttttcaa    90600
gaaaaagatc ggcgagcttc tcaggagtga ttgtagtttt aatccggtgg agctccagat    90660
ataccgggtg cttgatcttt gtgcggtaat aaacacgcgg ggcaatttcc tgtacggcta    90720
caaatccttc atataccacc tcataaccgt ctctcaggct tttgaaaagc ggtgtaactt    90780
cctcaaatag ttcctgaagg cgattggcac gaaaaagagt atagttttgc tcttgagaca    90840
gaacagccgg tagcttaaga tttatttttc cgccactttc gttgaaaatg cgtacggctt    90900
cttcggaggg acccacctcg aaatatccct tctccggatc caccgaacgc acaccgatca    90960
gaatgatatt tggctcctca taaggaacca ccactcgcgc gtccggatga accatttcaa    91020
atatgtaaca gtatgaggag ttcaaatgat agagaaggta aggcggatat ttcttttcaa    91080
aggtttccca gaacaattct cgatatgttt tatccatatg agtggtaacc attccgtttt    91140
tgacaatgga tccatttgcg tcaatactcc caagagtgtg aattttccac ccttcatcat    91200
aatataaaac cacacaagta ccatccagct tttcaaccag tttcatggga agtttgaaca    91260
tgaaaccggc tttgcgcttt tcattcaggg gagacgcgta acgaagcgtc tgataatagt    91320
```

```
ttacgatttc cggctggagt tcttccccec agttgaaaaa tttgtcaaag ggataagaca   91380
gaactttcca accactatcc gttttgcgga gaatcgcccc gcgacaggca aggtgatata   91440
tcttatcaaa cttacaacca aggtgatatt tgaacatgta tagatcaccc cggttttgc    91500
acataatccc ctccttgcga agggattcga cggctacttc cggagactca aaagagttca   91560
ggtgttcgat aaggtactca accgggtatt ttacgttcat cgattccata cgtactata    91620
agtcttgttt tgagttttcg gaagcgtcgg ttgatcaggg agttcgtcta caacttcata   91680
gtttccggat aggaaaccgt agcaatcaca cacctccttc gtaaatctgt ttacgggaat   91740
tggttacaag tttttcagct acgcgcaaca ttttgttact ccacttttca accggggttt   91800
ccacaaggaa atgaccaata cgggtatcaa accggttgaa gcccacattg ttgcgctgag   91860
ccgcgcggtc tttatccagc gccgccacga tcgccagctt ctgctgaagc tccagcgcat   91920
aaccccgctc ttcctccgaa atggttttac tttcttcttc ctcctcccgc tgctgcttct   91980
gctcagacgt agtaatcaca tcgagcagag atacaggctt ctcaagttga gtcttcatac   92040
gctcatgatt gagtgccttt tcgataattt caatcttgcg cgtcaggtaa tcggcaaagt   92100
tttcatccag cgtatgacgc gcaacaatgt agtgaatatc cacacattcg gcttcctgac   92160
caatgcggtg gagacgatct tccgcctgca ggatattgcc gggtaccag tccaattcca    92220
caaacacggc ggtcttagca cgcgtcagcg taatgccgac accagccgcc agaatgctgc   92280
agagcaccac gtccaccta ccactctgaa aatcctccac cgccttttga cgctgcacca    92340
cattttcctc gccggtaatg cgggcgtagg taataccttt agcttcaagc accttctgaa   92400
tgatctcgaa cacatcatga tggtgtgcaa acacaaccaa cccgtccact tcttcctctt   92460
tcacaagaga aacaatatag tcagcagcga acggggcttt gtgaatggca taaagcgcc    92520
gcatttctgc aacgcgctca aacataacct tcatttttc atcaaactcc gccattgcct    92580
cagccagatc agcgctttca accccaaccc gctcaaactc gcggagaacg gaaatataat   92640
ttttgagatt ctggagatct tcagccagct tgaaaatttc ttcttcagca aacatcttat   92700
taagttttac aggaacgatt ttacggcttt tcggcggaag ctccttgagc acatcttttt   92760
tcaagcgacg aatcatgata gtggagcgaa gctttccctg aagttcttca aggttacttg   92820
caccacgaaa atcccaacca tacccattat agtaagcgtt gcaataccgc ttggcgtagc   92880
cccagaaatt accaaacacc ttcggagccg ccatctcaag aatgggataa agctcaatcg   92940
gtctattgac gataggagta ccggtaagaa agagcacctt cccgccctgt tctatggaag   93000
atttgacaat agattttaca aacccggagc gcttcgtctt cgggtttttg atataatggc   93060
attcgtctac gatcacaaga tcgtaagcat aatcctcttc cgaaatgcgg tggagaatgt   93120
cataattgat aatgtaaatg gtgttttca gagaaaatc gacttcattg ccgttaacca     93180
caataatttc ttttcgtga accacccagc gcttcaattc ccgctcccag ttgtacttca    93240
gagaagcggg acacactacc agcacgcgat cggggttcat tacattgata accccggcgc   93300
tctgaattgt ttttccggta cccatttcgt ctgcaatgag agcacccgga tattctttaa   93360
aaacttcggt aacaaaatgc accccgcct tctgaaatgg gaaataatca tatccggtag    93420
gtgcaggtac ggcaaaatcg ctgctggtga cgctgctgag ctcgagcttg tgatttttt    93480
cttccaggag aaggttgtac tgctgagcag ccttttcgtc gaaataacct tcagtttac    93540
tcgcataatc gagaattgtc gtataccata ccctcttatc cggatcccac ttccacccgg   93600
cattttggg gatcagacgt tcttcgtagg ttcctttcca ctcgaaccgg ttgttgtaag    93660
taacgtagcc catgaccgcc ctgtcttgg ctgtcaatct gctgataata tacgacactg    93720
```

```
aacaagaaaa gtcaacccct tgacagaaat ttcaattaga agggaaacga aagttgaaca    93780
aacaggtgat tgaaatgctt ccgatagcgc gtcggaagat caaaggtgtc gtggataaac    93840
ttttcaaatt catctttttc accctctaaa acatcatcaa gccatagtct tcgacgttca    93900
aggctcccaa taatcgcctc aatcggatat gcttctataa aagcattacc gggataatca    93960
tctacaacac tcctcacaac ttcttcaatg tttgttgtat ctatcaatcc cctttccgta    94020
taatacacta tatgtggttc ttcgtttgat ccgtaatctg attctaagta tactataact    94080
tcatattcta ctatatcttt aacatactcg ataatacttt ctattccact ttcaaccatt    94140
tcctctactt tctccccca ctcttcatca aaatgatcta aaatatcatc cgagttgatt    94200
attttttcta taagatcata gtttacattt tcaggtttaa ttgtgctgta aaaatattca    94260
aaacagccgg ttgtcgacat attttataa agagaagcaa ctacatcggg atatgcttcg    94320
tgttccgccc atttaccaat atgttgtttg aaaagaaaat aggcgatacg ataagaacct    94380
ctgttggctc tccttttttc tatatcttct ggcaactcta tattaagata ttcatgaagg    94440
tctttaatac cctccgcttc ccccatatga tcaattgcga tatctacaaa ttgtcttatg    94500
agatcgacaa ccaccgaaag attgatatat tcctcgaatt tattcttctg ataaagcaca    94560
aatacctgca gggtttcagc gggaatataa acagtatcat aattataagc gaggacgctc    94620
cttacactgt ctaaagccat attaatataa tattcgattg catcttctga aggtgcaaga    94680
ttttctacca gatggggata ttttcagca atcacatcca gcatccgcgc cgcataagta    94740
gcatagggtt cttcgtcaat cggtaccatt gtattatcag gaaggtgaaa ttcctttccc    94800
ttaccaaatg tagcgattgc gtaaacaagt ccgtcatacg gattgctact atcggcttcg    94860
aaatctattc ccggtttgat cgccgaagga tgaaataccc ccacgaacaa gggataataa    94920
tagttgaaat gttgatcgcc aagtcccaca cacacatgaa tatgattacc aatcatcccg    94980
agaatacgtc tgttttccac cacattttgg gggtgatata tgatcataga attgtcttcg    95040
tagataatca aatccgcata ttctgtgtgc ataagctgac gaaacttctc ccacaatgcc    95100
agataagaag ccccacctc ttccactttt ccggcgcgtt gatatgcccc aacgacttt    95160 ccgggatcga gaagctgaag gttatccgta agatcaaatt ccctcaaaac ggagggttgg    95220
tgtcgcaccg aaaaatacca gcgaaatggc tcgatgtaaa gagggagatc gatcggatcg    95280
attttgtcgc tcatcaccat acgataaaaa tattcaacca gcgcatttgt cgagataagg    95340
ttatattcgg gattgttgcg aagcggctca aaaatagact gagcaacttt gtgaagaata    95400
tttccaaaaa ataaaatacg ctccccccgga tcacggggaa cttctccaag atttaattgc    95460
tgagccagaa acctgagttt gttttcggga agttttgcaa gtagttcttt accctacgg    95520 gaccccggag caggaaaagt aaacgccatt ttttatttt aaataactac gccccaaaat    95580
ccacataaag atagcaaatt ttccagctat cctccatcga gatagtatat tttttatccc    95640
cctctttttt aatctgataa tcttccttac cgacataatg taaaaattgc cttataagtt    95700
gccacaacct atcatattcc tccgtttcat cagtgcaagc cagcttgtac tgataatcaa    95760
cgaaggacat atcgtttatt tcatcataaa aattgtcatt gccccccaca atgataactt    95820
ctggatcaaa tacaacccat tcgataaaat caagcataaa ctggcttaat tccggatttt    95880
taagaatata acgccagttc cagcgcgatt catgatcaca tcgatcaagc ctttctatca    95940
ccttataatc ttcattatat ctggcaagta gaaaacgtct catttcggca acgttcatat    96000
cgtagctcag attatctgaa atatcgttca acatctcccg aagtgcgtct ataaagagac    96060
```

```
gcttgatagg ctcgcgttca aacatcaatt ctacaaactt cacaaccaca caatccagtt   96120
ctctatgatt tttcagataa gcgtcaatgt atatatccga cgccgcgttg gcaatcagat   96180
agcacatctt agccagcggc gttttgcaga caaaaaattc ccacccgaaa tcgcaagggt   96240
aaaaatcctc cttcacctta tcaggataac ggctgataag gatggagtgg aagacgatg    96300 aatttgtgga aagaccgaaa cgaatgaatg ctttcatgac ttcctccttt gtttgtcaat   96360
ggttacatag acaacgtaaa aaacaacggt aagaataaaa agaagtaaaa actttatgtt   96420
caaccagaag ggattctctc ctcttagcac cagcgctgca gggtttctca agtataatga   96480
aagataaacc aaatacagcg caagcgccag cgaaatagag cctatcagta ttttgaacac   96540
tttcatagtt ttttccagat gttgagaaaa gttaccggat cgaacagttt ttccctcgac   96600
accctgaaac cctttcttt caaataggat cccggagcaa caagtgcttc cggctcactc    96660
atgtcgatgt agcaggaaaa aagtccttcc tgatcggtag tgctatgtgg aaattctctt   96720
ttgaacaccg ggtaagtttt aacaaaaagg gaatccaccg aaatggtgag ttctttcata   96780
aaatacttca ccgcttccag tgtcttgttt tctggaattg gtatgttatt ataagtttct   96840
cccctcccca ctttcttaaa accaagtagc agaagatggc tcccctctac ctgagaaagc   96900
atttgcatca tttcaatggt ttcttcaaag ggaacgctcc cccatacgtg ctgagccacc   96960
agttgcacat tgggggggctt ctgattcaga agatcgatat acgactccac cgatttcaaa   97020
ccatgcacgc tgaaacctat cccaaaaagc cgattcggaa aataatgccg gtagaacttc   97080
ataagctttc gggcaaacga agcattgaag gtggttacgt taacataacc ccggctgaac   97140
gttttgacaa tgcgatataa ctcttccaga aatctcccct tccagaaaaa gcaggggtct   97200
ccacccccta tgctgagttc gtaggtaccc atttcgttta acattcgtgc gaaccggatc   97260
atgtcacccg gatcacactc tgatccctcc ggggtggagt tttcataaca gaaagcacac   97320
ccaaaattac acacgttgga gggtttgaca tcaacgatat gcggcacctg agtcttaaac   97380
atgattacct ctgagttttg ttttcggtgc gtatgttttc cacaaaaact acataggctg   97440
aaaatacacc aagaataaaa atctgagcaa accccacaac cccgtttttt ggatttactt   97500
ccgcttttac ttcaaaaacg atacatatga ttcaaaggtc tttgattttc ggaatttctt   97560
cacaaactgc tcaagggctt cgtaaacgtc ggggcgaacc aagttcttct ccttcgtgaa   97620
caccacccgc cttgactccc agtcaacccc gaagttaaaa aagttattaa ggctgacaca   97680
aagcgaagtg aggggaaact catatatttt tacaatttcc ccatttctgt ctataagcac   97740
cgaataatat cctctaaaag cgtcgcacag gttgcgcaca gtctccagaa aatccgaaac   97800
cggcgcaaag tcttcaagca catagcaggt tagttgaacg gcttttcttt cattcaggtg   97860
cgttacggaa tacattaccg gcttgactac catacttcct ccgtttttttt gaccggaaaa   97920 ccgaatcaaa acaccagagt tccattccac acaatactaa ttaccagtat ttaattccct   97980
gttatttcac atacctctg gatcattctg ttttctttct tatatattcc attgtcagtt   98040
gaaaccaaac agatgagcca tgccgaactt cattacaaac atcaggaatt cccgttttaa   98100
ggaagttctg accgaaatgt accattgcca tcacgaaagc gagtaccacc ttgagggaaa   98160
tgttttaaat cacacgctta tggtattgca ggtggtagat aagataaccg ctgatcaccg   98220
ggagcaaact aatctatcct taaccgccct tcttcatgat agtgggaaac cctatacccg   98280
tgttgtcgaa aggggaagag taatgttccc cggtcatgaa ggggtgtcta cgtatatcgc   98340
tcctcttctg ctgtgtgaag tattgaggga ttccctcatc acaccaaaag acgccattca   98400 aatccttttac ggcgtcaatt accatatgtt gcactggaaa aatccaaacc ttttttatgcg  98460
```

```
gcttttcacc gaaatggtta attatacctg tttatataac ttcttgaaaa aattcaatca   98520
gtgtgatcta aagggtaggg tttctacaaa accccaaaag caggaattcc ccgtaatcca   98580
ttattttgag aatacccccga tcggtactgt tgagcgccat gtttatttta tgatcggggt  98640
tccggggagt ggaaagagca cgtttcttca gaaagttgga gaggggggcga ttgtatcccg  98700 tgatgaaatc atgatggaat acgccgctga aataggggatc acaggagact acaatactgt   98760
tttccgggag attcacaaca accctatgca taaaaccaag gtcaacaacc gctacatgaa   98820
cgctttccgt aagcggttg aagagaatga aaaggtattt gtagacgcaa ccaacatgag   98880
ttataagagc cggagacgtt tttacaatgc gcttcggcgg gatattgcgg aaaccgtggg   98940
ttaccattat atcgtaatgc ttcccgatta ttttacgtgc attgaacgcg ccgaaaatcg   99000
ggaaggaaag tcgatttcaa gggaagtggt aaccgatatt gcgcggagtc tgcttcttcc   99060
gtgcagggaa catcccaaca gcattgatac gacaatttat atgtctgatg ggcatgatga  99120
acatgtgttg agagtagctt ggtagttttt aagattcgac gatgctcccc ctgctcaagc   99180 gggggggattt tttatttaat caaaagtgg aaccttagga gaaactactt gccgttctca   99240
aaaagcttga agcgtttgag gaatatcttt caaagataga tcttgaacg ctggatcagg    99300 tgattacccg gcttagaaag ctccgggaat ccaacgaaaa actgtacaaa gactatcttg   99360
aagaacttga aaagcttttc agcaccaatc aggaaacgct cgaaaagctg gtagacgccc   99420
tttcggagtt tacggaagag gaaaaggaaa aacttgaaaa tttccttgag acgcaccaga   99480
aagacgccgc acgacttctt ggatatattg acgtttttga agcgtcgtgg aaacacatga   99540
gcgccgaaca acgggcggca tttgaatcct ttatcgacag actcagagaa cttcgtagaa   99600
acctcaatct cgatcgattc aagacggaaa cagcattcga tgttttcgac aaagcacgaa   99660
gagaccttgg ggtgccttat gaatatatca atcggtttgc attagacttt atcagatttc   99720
gccagcgatc agaaatttc ttcaaacaga tcatggcatt tttcacctat gaaagggtga   99780 caagtatac cgcttatgga atggcaatta atctggtaca gggggcgctt gaacgctaca   99840
ttgaaactac tgatgaagtg atcagagtta ccggtattta caaccggctg cttagggatc   99900
aggcgcttca gttttaccgc gcaaatattg atctgagacg cttcggtgtt cagctccggg   99960
atactacccg ctttattgcc gaatttatg catttacgcg cacgcgcgat ccgttcgcgt  100020
tgatagctca gacagcagcg ggtgctggag acaacatcga cggattcatg cgtcagatga  100080
ttctcttgaa tcagcgcctg aatattgaca gccgcacgct aacacgtaac atgctacttg  100140
cagctaccac gctggaagat aatatcatgc aacatattca gcttatcact gcttttgcaa  100200
atgaagcaaa tttgagcgct accgaactgg tcagcgatct tgttgaaagt tattcagaat  100260
ttgtcgtgct gcttggaagc ggggcgcgtc agatcacgca aactcagatt gcactggcgc  100320
ggtggaatat gtcgctcaga gacggcatga atattctgaa aggtctctat caatctcagg  100380
aatcggtgat cgactcgctc attcagattc agattctctc gcgccagccg gttgatttcg  100440
aacgcttctt tggagccatg ctcaccgcg acattgaagg aatcgtcgat cagcttgcgg   100500
aaatggcaat gcagatgcgg ggcatgatgg atgaactccc catttatcgt atgcagtttg  100560
agcgggcact tgaagggttg ggcttaacct ccgagcagat cgcaacgatt cttggaaagt  100620
ccagagagca gcttacaggg ttcggcacta tcgtggaaga tttccgccgg aagctttcac  100680
ctgaaatgct tatccagact tttgatgaac ttctgagacc caacgaatgg gaagaattga  100740
agaatgcggt ggatgcattc ttcgagacgt ttatgcttta cggcgctgaa ctcattcgca  100800
```

```
acatgattcc ggtgcttaga attctgacac agggaatgca attgatgttc aagtggtctc 100860
aggctatgac cgatcttatc gataaggttg gtagccttgg tggattgttg aaagacaacg 100920
ttcttggaga tttcttcaaa agcattttcg cgtttcttgg acccggtgcc gcgctttacg 100980
ctattgcgaa tatcggaaag cttggaactg cactcaagat gttatttgat ttaatcattt 101040
ccattcctcg ccgcattggg ggaggggttg taaaccgtat tggttccttt ttcagtcgtc 101100
ttggagatgt gttcaagaag ttcttcggta gccgggaaat gaaacaggtt gcggaggatg 101160
caacttcaag aagaggaatt ctccgtcgaa tcaccggtgg agtcaaagat tttaccaaaa 101220
acctctttca aagcttttcg cttggatcga tcgttcgttt tacagcagcg gtggggtgc 101280 tggttggtgg tatttatctt ttcggaaaag ctgtgaaatc acttcaggga atcgactggg 101340
gtgagacttc gaaaggattg cttgccttct ttggagcgct taccactacg gtagggttga 101400
tcagtcttgg tggtcttctt tcacttcccg cacttcttac cggtcttgca gcttccatag 101460
gcgctattgc cgtggtggcg ggcggtctct atctcaccgg tgaagctatg ggagtgtttg 101520
ccagcaacct tcagagactt gcttccacgc tggaaaccta ccccaatctg acttccggta 101580
tattccgtct ggctggagca cttggtacgc ttggtgccgt cggtacgatt gctgctccgg 101640
gcatgctggt tggagctatt accgaagccg taagtgcggc gatcaaaccc gatgtggctg 101700
taaaagccat tatcgatcca gatgtaatta ccgccggaga aaaactgatc gcaaacaaac 101760
ttgaccggat tattgcgctg cttacggaaa tgcaaaatag aacggagcca agagtggtta 101820
cgctgaataa gccggaaaag ccggttgaaa aaccaatctt cagcacattt aacttttaat 101880
cttcatcctt ttcttctccc ttttttccaga ccggatgata ccagtcgttt tctttcatca 101940
ggttgatgta aaatacatat ttataatttt caaattttc attcatgcga agcttataga 102000
gataatcatc tttgaacttt tggataggta ttcttcctcc aacataaagc agaccacctt 102060
ttcccaccac aaagaacata tcttcgggga aacgtttgat ctgaagcact tcgatcacat 102120
cgtcaatggt aaaaaacttg tatgcggttt cttttggatgc gttgtaaatg taataatgat 102180
gcgcaacgtt ggattttctg ttatccgtaa tcatagaagt ttctgcttaa gtagctaaat 102240
atcactatta aataaccgga tttgatattt aaagaaaaag atgaaattaa ccgatctcag 102300
aaataaagtt acaaacgcat ataaccagat ttccaagcag aaccgcgagt taatcgccgc 102360
caaacttcgt aaagactcca gtgccaccat ttacttcggg gctgctgtcg aaaaacttga 102420
cgacgctacg atcaaagaac gtatgatcga cgttttttgcc acgatcattg ctcaggcgta 102480
tgatcgcgcg atttccttgc gcaaaggaaa accgacacat ctaccctccc ctcagtcaat 102540
ggtacttacg ctggcaagat tttacgtgga aaatgaagac attacgctca gcaaacttaa 102600
cgaaatttcc attgcgctgg gctggtatat cgcgctggta aacgaaccga atttgcttca 102660
aaaatacaac ctccccaaac agatcacgga acttgagccg gagcagcttc tgcacactta 102720
caaccagatc gcaagatatt ccgacaccta tcaggtggaa ctggtaaatc gctataaaga 102780
aattatcgat ttcctgacgc aaaacggtga agagttctgg gaaaaagaat acggggttat 102840
tttcaaacct tcctcttacg aaatcaacgc caaagtgctt cagcttgcct ccgatcgtct 102900
ttttatctgc accgcactta accctatttt ccacgcacacc tattatcctt actatgtgct 102960
tgtagtcaac ccggcttaca agggagacgg caatgttcac tatatcaaag acggcgtcaa 103020
gggatattca ggtatggagt tttatcttgc caccttctcc gacaaacacc cctaccagaa 103080
gggattattt gctcagtttc gtagccagta taatatcgcc ccccctctca gctttatcga 103140
aagcagactg tatctggggg attttatgga gttttttgtgg aaacgtaaag atcttcagcc 103200
```

```
gcatatctct aaactcataa acctttacaa acaacacccg gcttatcttt tcgatgagaa    103260
cgcaatgaaa aggtttgtgg aaaatgagct tttcgatttc aaaaatatca acgactcacc    103320
cggcgcacgc gaagccgtag cttatttta ttccaagatc gacaaccgtt cttttatcga     103380
ggggctgact ccgctgatcg gagccgccgt tgaaacggtt atggaatcgg gagaagaccc    103440
caattacaaa aatgtacttc cggtgctggt agagcttatg gtcaaaaaca actacgctat    103500
gaaaaagatt gaagaagctg taatcgaagc ggtgcataga aaagcggaaa acattctcaa    103560
attcaccccg gaagaccata tcagatatat ggcaattcat ttcgctcata aaatattcc     103620 ttcaaattct gaagaagaag gaagagattt tgccgaacag atttattata acataatcag    103680
acctcagatt acaggcacct caccgtatgc tattatgttt aaacgtttta tatattcaat    103740
cattcttgcc gaaatgaaag gtattctcaa aacaagata aatcaggtgg ttaaagaaat     103800
ggaagaagaa ttcgggtttg gagacatttc ccttgccgat ttcgactggg ggggcggtga    103860
agaagacgaa gattcgttcg aaatggaact ttaactggaa gtgtacaccg tttctccgac    103920
gatatagaga cgctgtccac gagatgttct tgaaacctga aggtggcat tgtaaatgtc      103980 gtgatcttca accacttctt caagcttttt cttaatatct cgataaagaa atgacttttc    104040
atccacgtag aagaagtaca tccacgtctg atactcttct ccccccattt tttccgaaga    104100
gtgatcttcc tgatacaggt gaaatccgta atcctttaaa ataggtatat gttttttgat    104160
ggcgtcggat gaagcctcgc ttccgtcata aaataccttg agaatcatat tctccattcc    104220
ggtggaagga atgacaactt tcccttcttc cgtatacgca ccctgaatgg caataagcag    104280
cagccccgga gatatttcat caaagaactg gtaggtatcc tcgacggcgc gaatatcggt    104340
aatcaatgta atcttggttt tacctttttt gacaaggttg cgaagggcaa aaatggaaag    104400
gaaaacaacc gcttcgagaa cctgatccgg agacaaatct tccgatcttc ttatgcttaa    104460
gaaatactcc cggtggtagt ctctcagacg aaatctcaga tcttcctctt tcctcaaaac    104520
cctcgcaatg cgacggtctg tttcaacaat gaagtcggta tgcgttattt ttttctccca    104580
ttctccgtcg aaaaattcta catcgtaaac aataaaacct atcgtgttgt agtggtagtt    104640
gatttctact tcgattcccc atgaactatc aggcgcacga aacagaaagt ttcgcgggt      104700 aagcttccac ttctccagaa ccgcgctttg aaaattgacg aagtttgtaa tgatttcct      104760 gagtgcattc ctcagttcac tcataaatag cgataaagag ttttctcaac cgtttccaat    104820
atctgaagcg actgtttggt tccaaatcga gattcctgaa gcactcttgc actttgaaaa    104880
gaaggaacgg ctacaacatc tatcgctgtg ataaagaagt cgtcaacaat ttctacccgt    104940
ttttgctggc ggtaacctac tttggtttta ccgctcccac gaagggaaaa cccgaaattg    105000
ataccgtttt caagaagcga tttgaccaga tttccgtaag gagttgggag aatgcggaat    105060
tttccgtaca ctttatttcc ttccatccat acgtctaccc actgcacggc aaggcgctca    105120
agcgacacga acccgattcg aaaatcgttc tggtagggt  gatccagctc gccgtacatc      105180 tgacccttttt caatctcctg cttcatacgc tccactgctt tttttacggc ttccggcgtg    105240
tagagtgtac cattgtcgga aatgacgtcg gcttccataa tcagagccgt ataagtttta    105300
tcgttaactt ccatagcggt tattcttcag ttttattgtt ttcttcttcc tttttgtctt    105360
cggcgtacag gaaaacggct tccaccgaag gaagcatttc gcgaagccgc gcaagcacat    105420
cggtaagcgc aaccagcttg gaaacacttc cgcgagaagc ttcgatcgtg ttgataagct    105480
cgcgaatgta attgcgatag ttttcatcca gcgtaatctt gtcaatgatc tcttcgatca    105540
```

```
tttcacacaa ttcctcgctc acgcgggcaa tatcctttc cagttcttcc gtgatttttt   105600
cggcttcttt caccctcttt tcttcgggga tttcataact attctgatcg ttttcctcct   105660
ccattaacac cttttcctct tcatctttct tgtcctgctt gacatcttta cggattttt    105720 ccacatcacg gctggagtaa cctaccggcg cgtcataccc cgcaatgtcg ccggtggtgg   105780
tcatctcctc gatctgtttc aacgccgatt cataaaggtg cgagaggatt gccgccactt   105840
tagcaggttt ccttgcgctc aggaaaagct cagccacacc agccgcgcga taaatgcggg   105900
gatcgatacg ggtttcgtaa acttttgaaa gctgttttc tccaatgatc ttttccagcg    105960
cttcatggaa accgttgtac tggcgctttt tgcggtattc gtggacgaaa tagggaaccc   106020
tttcatattc ctgatctatg caggcttcga caatttggt aatgtaataa acatcgtcag    106080
attccacgaa attcatcaat tcacttgcgg aagccgactc cagcaatttc ttgtcttccg   106140
aagaagcctt catgaactgg aatagaagga ttatatcctt ctgcttcata caacctttt    106200 ttttcttaaa taaataaat cgaaggagaa ttaaacaact acgtattat aaccccatcc     106260 accgatatag ttgtaattgt ggctggtttt atatacgggt aacagtcatg aaatactctg   106320
tttctgatgt ggcgaatttg ttcttgtgtc atatcacccg gtattagagt ggaattcaga   106380
taggctgcat ctttagttat tgctatgtga tacaaaaggg gcgccatttc actgtaagtg   106440
tgtgtatctc taaatataag tctattattc aaataaaatg aaacagtaag atcattacta   106500
agagggtcca tttcataatg aaattcatgg aacacaaaat aagaccggtt tggattataa   106560
aatccccatt cagatactgt tatactatga gttactttct ttgttaaaaa tggggtaact   106620
atagtcgaat aagttactcg aatacccaga ttcccggaag ataatgtaga ataatatatt   106680
gaaataatat tttcaccact taaaattcta cctatgtaac taacatctac attgaacacc   106740
gaagagtcat ctgcataacc gtcaagaaat attgtctgaa ataaatggaa tttttctttt   106800
ttaccattta taaaaagttc gatattgttt acagttcccc aataatccaa atcgtaaaaa   106860
agactaaaag aataattggg gaaatgactc tgatacgccg cttgactacc accagcatag   106920
ctatctgcaa tataaaattg attccatcta cttatagctc cataattgat atttgccctg   106980
gcaataaaag cattatgacc aaaatcatag aaaaagaag aattaaaaaa ctttgttcta    107040
actgattggg taccatttat tccatctgta tattcggtta ctatataata gcccgaaccc   107100
gtttcaatag tggggtgatc tgttttgatt aaataatata catctctgac gctcatactc   107160
cctttatatc ccccagctac cagatattga ttggaaactg aaaccgtcaa ccagtcgggt   107220
aaaaagggtg taacatcaac accatttata gccgaaacat aagtgttcaa gacactgatg   107280
ttatcttgat ccgggtcaaa taacgaaaat gaaatggtaa catagccgtt tgcatccggg   107340
gtatataaaa tctggtatgc cataacttaa atgtttttta ttaaatatta caagctgtaa   107400
atgaagactg cagccgcaac cgaagaagta aacctgtcaa gtctgaacaa ttcgtaaata   107460
aatttaatat tatcacttcc ggcaactccg ctgtatgaaa acaccccctg tctgcgtgtg   107520
atgatattgt cggtaagcat ataaacatac atgctgttgg taacataagg agggaaacca   107580
tctggattga tccaattgac aacatagcta tgggtttctc ccggagcaat tgatgaagag   107640
ggataagtgt acaccgtaga gttagtaaca aactcaaaat aagatgtact gttatacgta   107700
tcgggtgtgg aaccgctcaa tgtataaaat agagaaaaag tgttgttaat atgagacata   107760
attgaaaggg taaacgaaaa tgtatacggt tgtgtcgaaa gagtcccat taaagacgga    107820 taatcaacag atcgactgct cagtatgttg aatgacttac cttcatataa cagcatattg   107880
tacttatact tatgataata atattttcga atcatagaga ctgtaggagc cgggagagaa   107940
```

```
gtactaaaaa cagcgatttc gtaaaattta aaagcagggt ctccagcatg atctctgata 108000
agcaatctgt taatatctcg ccttgtgtct gtattatact tttcaccaac aaaaactccg 108060
ttgatataaa atgatgttgt agaattgtta tgagacactt caaaagaag aggataagat 108120 aatacatctg agtaagaaaa ctccagacca tagccactac acgtatatgc ggtgctccca 108180
acagaagaac cgctatcaag actgaaaagc actacattta gtttattgtt gttgtttaca 108240
aaccctgttc ctataaagcg gttgttgtct gtactggtat ttaacatcat cacatccata 108300
aactgggaaa tgctatgtag cattgcagga gcaaaaacca taaaaacatg gaatggtgaa 108360
tctgggttat tgtctaacag attaacacta aatgtgttgt tataattata actatttata 108420
tggctggcaa gataagaata gcctttgtcc cagtaataat gccaaccttg ccctgttgaa 108480
tataaagata catggcgatt acccgttaaa gacggtaaaa cagaaatggt tggggtatat 108540
ccactttgtg ttatagttat atactcgaca ctccaaattt cacttaaact actcaaagaa 108600
acaatttcaa aattggaagt aaaaagagac agattataaa actttacgtt attatcaaaa 108660
tacacataaa cacccatatc atacacactt tcaaggaaa aagacgggtg tgtatggtca 108720
aaagatattg taacatcaat gacacttctg gtgccgatgt aatataaaga actggtaaca 108780
accgtaaacc agggcggtgt aacagaaaaa gatatattat tttctttcaa tatgaaagca 108840
cttactgaaa agggtattcc ataatcatct ttcactgaaa aggtgataat gatggagtta 108900
ctgcttatta tgtaatctct gttcatctca ttctttaaaa tttaaccctt aaataatcaa 108960
gatcaacttc gggggttgtg gttggataac ttttattggc tgctttaagc tcccatttaa 109020
acccggcatt agaaaatggt ggaacttgag aatatgtatc aaacggataa tttgccgcct 109080
tgagttccca tttaaacccg gcattagaaa atggtggaac ttgagaatat gtatcaaacg 109140
gataatttgc cgccttgagt tcccatttaa acccggcatt agaaaatggt ggaacttgag 109200
aatatgtatc atatggtatt tcagatgata caagttgggt gttaagagca gcggaagggg 109260
ttaaccctaa actctggaag gaattttca tagaagaatt gctattagtc agataaacgt 109320
tactaacagg cacataattt accaccggag caatctgtct gacaaatttt gataccgctc 109380
caataaacga cacgcttaca ctcgatttgg gagatttgaa aagtccccat gcacttccgg 109440
ttaccgctga aaagaaaagg agattgaccg gctcattcca gacgttttcc caatcgactt 109500
ccagcgcacc catttgagga gatgagtaga aagtcagatt gttacccgta cttttgagaa 109560
caacgtttgc tccggatgac gtcagataga aatactgagt agatgtagag acatatactg 109620
agaagtaaga aagataactt accgtcagaa atcctgaatt aattgggttg aagaaatagg 109680
gtgatgtggt tgtataactg gcatatttca ataaggtgt attatccgtg taatacgaa 109740 cacttgtcga ataattcaaa tccatgaaaa tgcttgccgt tccgaaaaag tcggagaagg 109800
tgactaaata gggtgatttc cgaaccatgt atgttccatt atcagccgaa acgataaaaa 109860
cagattttgt tatatcgtaa agtaatgcgt tgaatgtggt gctaccctga ttggaaaatg 109920
ttatataatc ttcaatatat ccgccgccaa ggaaaagacg tttgattgag acggtttcgg 109980
tgctggatgt cgtgtaataa tccaaccaga acacatcata tccccatgca gctaccccac 110040
cgtattgaat gctggtggtg gtaacctgtt tataacttcc actggaatcc aggagtccca 110100
cttctccgga agatccatcg tgcagattga gaaagagtgc gggagattga tcgtaaaaga 110160
atccaagcga tacgattata tccgaagggg tagtaatatc cggaagtaa agagagatat 110220 tcgggtctgt agttgtaatg ttcgggaaat acagttctat attaacgtcg gatgtagtaa 110280
```

-continued

```
tcggaggcgg ttcacttggg gatggggggcg gaggaggaac atacgaataa gagggggatca 110340
gaatcttctg cacgaaaaca taagcttcat ccagcttgat cggttgagaa aacttcgata 110400
caaacaccac gtccccattc tgattcattc catagattcc gctgacataa ggagaaaccc 110460
ccggaacagc cgtgggattg gtggtaaagt ttttggctac aaattcggca acgagaagct 110520
tcagaggctg caattcataa agcgtaaggg taaagaaaag cggggaaata gccggtactt 110580
tctttcccac aaccacaaac gattcatttc gaacaaggat aaaatccggg tgatcataat 110640
aactgtcatt cacaagcgag ataggatttc ctccatacgt aatggaatgt atgtgatagt 110700
actgtcgctt gattctcaca atttcaaaag tgagcgcatc aaaatcgata ttcagcttac 110760
gaaaaagatc gataaaaagc gcacgaatct gagctttgag ttgatcatcc ggggcaattt 110820
ccagttttat attatcattt tcgtagctac cgggagaagg gaaaccaaca acttcggtga 110880
atactttttat atcggtttta taaaaatcct tcgctctcat tttatacttg atgttcttct 110940
ctattaaata agaaaagttt attcaggggc tacctttgat aatattccct gtacacccag 111000
ccggtaaacc caaggtccag aagtttggga atatccccct tctcttcccca ctgcttttttc 111060
tgaaatacat cccccacgtt cagatcaaaa ctcataaccg gatcctgtaa atcttcaatg 111120
taacggctgg cgaaaccgtt atctctgatc ctcaaaattt cttcatcggt tatctgatca 111180
tgaggaagat cataaagctc tatcagctta cgacaggatt gaatatagcg ttatcttca 111240
taaaaattag gcggatgtgg gttaatccag ccgataaaa tatcggaata aaccttaccg 111300
gcaatcagtt cgtgagcttt gttttttcata tcgggttcga gaatatccag aagtatataa 111360
agctcttgat aggttttaac cggctcataa tacctgagta tggaagcgat cgccattctg 111420
gttttttgtgt tctcataaaa agcatggagt tccggtagaa tatactccgc cgaagaatgt 111480
cttattatat ccacttccgc catattctga gccatacccct tttgattgta tgcaattttt 111540
ataacataag gagttccaac tatgcgataa accttacgag aagaaccacc tcctatatac 111600
tccacagaag gcaattcatc catcaaagct ttaagtgctc tgaaggaaag atgattgttc 111660
agcaactctt caaaatactc aaataaatcc tgatctaacg atatgttgta accgtaaaca 111720
attttctctt tcattacttc ttcttattgt ttttctccgt tcgcttaaga taagcgcgag 111780
ccgatttgaa aacccgtttta ttactggtat ttgctgcaaa attgatcatt ttcatagccc 111840
gatctctacc cacttttctg ataagggcac gcgccagcga ttcacccgac ttgtacacat 111900
catcaatatc tttgtctttg gggattccaa gcacttcatg catttttcccg cgcttgactt 111960
taccgctttt gaatgcttat tgaatccact tttcttcctt tttagcctca gccagtttac 112020
gtttcttgag ttccttgata tacttcagag cgcggtcata aatattgtgt tcaggggttga 112080
cgttggcggc aaaaaccaac atccccacgg cttctttgta cgaaactttc ttcaggagat 112140
cacgcaccaa tttgcggtga tctttgtaat gatcgacaat atcttcatct tcggggattc 112200
caagcacttc cttcatgtgc ccggcttcac gcttgacctt gctcacccag tcttttttccc 112260
gcgcttctgc aacggtttcc ccaccttcat ccagaagtgc aatagcttcc gtatagaaga 112320
aagaatcccc ctccgtttct tccagaacgc gcaacgcttc tttcagaagc tccttgtgtt 112380
caatatgcat acgctttgcc attttcaaca aatctttgac aaaagaccgg gcatcataac 112440
cgtaatactt ggcgacagaa acgacggaag gaactccaag atacttacgc aacttcattg 112500
ctatgcgttc agccgttgcc tctgattac ccatctttttg aatgagttct tcgcgggtga 112560
catttttcggt cagcagtttc tggcgaaatt cgttaagctt ggttctggtc tcctgcaaaa 112620
gccgcgcaac acggagaatt cccttcggt tcatatctta ttctcctttt cttttaatta 112680
```

```
aagaaaaata aagactctat gaaaacagaa gacagaaaaa aacttgctca ggaaatcctc    112740
gacaaaatcg taaacaaagc catgcagctt gaaacgttga ttgacgatga atacaactat    112800
ctcaacagaa ccagtgtgct ggttgaagag gagagcaatc tgatgtcggc aaaggctcga    112860
atgcttgagc tacatattaa gattctcgac acgctgcaga aagtgtataa agatctgaaa    112920
gaagggattc aggaagaaga cgaaacgaaa aagattctca tggagattat caatcagagc    112980
aaggctaacc tgtgaaaaca ggtagttcat tcaattttt agctatattg attccctgag    113040
ctatcacctg atccatgttg taatagttat aagtagccag tctacccacc agtataatcc    113100
catggcactc cagttcgttc ttcatagaag ccgccttttc tctgtaggtt ttcttgttaa    113160
tcggataggc tttgaacgaa ttttcctgag gatgttgaga gggatactct atggtataaa    113220
ccctgtcaag attcagcctg gagtgatcga taacgcgggt aaagggttct ctatcagagg    113280
aaagatgaaa tccgatggat tcgagcgtac tccactcttt cagtttgcga agcacatagg    113340
gatcggaaga tataccttca agttttctc tggtttcaat tctgagatga atgtaaggga    113400
gatgttcttc tttacctgtt actctctggt aaagcctatc aaggtccccg gtataaataa    113460
aagggttatt ttttatgtcg tttagatgat caagcgcgtc ttcggaataa actatattga    113520
ctaccggcac ataatttctg atataatcaa tcatccgtat aatcattttc cagtaaccat    113580
caaccgggag cgccaccatt ttatcgtcaa aataagagtg atatctttc cagtcggtaa    113640 agaagggaac gcgggaagct accgttttta ccatctcttc atcccagtaa tctccccaca    113700 cctttttga gtaaggggca taccagtttt catagacgaa agatttaagc ggttccggga    113760
gattgcctac cggaattttt ctgttaagaa gttcttcttc cagctcaatt tctccaagat    113820
acagccgcac ccagaaaaga gatgaaggaa taaatgaaca tatatcattt tcggtaacag    113880
cataggcatt gtaactgata gagtaaaagg aagagaatcg cgacacaaat ttgatcactt    113940
cgggggaatt ggtatgaaag atatgaaccc cgtatcggtg atattttttc ccccggtcaa    114000
aatcccagac gttcccaccg gggtggttgc gcttttcaaa aaaagtaatc tcttcaaatc    114060
tgaagccacg atcaaggaga gaaataacgg tgctgagtgc cgcaagacct gttccccta    114120 caaacaaccg tttcataatt ttctgacctc cgggtctctt agcacttgag gaaacatacc    114180
ctgtacctgc tttccgacaa aataatccat gttgacgcgc cgaacggaga atatccgaga    114240
aggtctgtac atatgtgcgt gagataaata cggaagcgtg gcatatctcc acttgaacgc    114300
atgtgccaca tggattaaaa aagtttccgt gtgggttgga agataatcgt aatactttct    114360
cagagattcg agataatacc tgttaataac gtgccccccg tcaagatgca tgaaaacgcc    114420
gcgcttgtgc agtttgtttg aagtgaaata attgtagaca taatcggcat attcattaaa    114480
aagctttaca tcgaaataat cgagaaaatg ttcttctctg ataacaatct ctctccagtc    114540 ttttttttgcg aaagtctcca cataacatgc ggcggcgtaa atgtaatatc cctcaggggt    114600
ttttaacctt tcatcggcaa gatgatcggg aagctcaatt cgctcatacg gatctttgaa    114660
aggtgtttcg ttttgatagg gaacaacccc gtaaggttct accatgttgg agcaaatcat    114720
aaaatattta tcgaaacacc cctcctcgaa tgctttatcc aacccttca gatatgccgg    114780 gggaatataa acatcgtcgt gcacaaacac cccggcttct acaccaagaa gaccaagtgc    114840
gtcaataaat gcagcaaact gagagtactg aatttcatct acaagaaaaa cattaagttt    114900
gtgatgttcc agttgatttt taagccacga tctccaaact tctttatctt ttaccggttg    114960
aaggttgaaa tgctggagca atttataatc cgggtgaaag cgcatttccg gataaacaaa    115020
```

```
aatataaaaa taatcccgaa ggtgtgaaat gtgtgggtaa atatttttaa gccacacttc  115080
gggaatttcc ccgagcgtta tcattacaaa ggcgatttcc ccgcgataaa agaagggtt   115140 cggggaagaa gaaatcttct caaccttcat tgttttccgc aatttttaatt acaacccggt 115200 tttcttcaaa gttaagctcg aattcctttt ccgacgcatt gattccaagt tcttccagtt  115260 cctttttgaag ttcccccatg atcttcatgc gctcccgctt ggctttaagc gcatgctcga 115320
atacgttcac atcgccttca tcgacgattt ccaccagcat atcaaagaca agcaccgcca  115380
tttcaatgta ggcgttgcgg agttgcattt cacgaagtgc aagggatttg agctggtcaa  115440
ccttctcttt gtcttctacg acaatggtat tttcagagcg tgtaacggta ggttcaccca   115500 cttaatgaa atctttccct ttcatggctt tttttgatga aaaaacgatc gggttcaaga    115560
aaggtttcag aaggtgttaa gcggatattc ttcagacgcc tgagcttccg aagccgcatc  115620
gtaatcgcca accgtaatat aaatatcctc aattccaaaa aattgggggcg atagcgaaa   115680 ttcataaagc gtaagttcag acggcgttac aacaatatca aatatccaca caccaccttc   115740
atcatttcca agaataatcg ctttgcagtt gatcttatcc gattcggtaa agaaaggttt   115800
gcttctgaga acaaatcttc tccctaccgc aacaaaaagg ttggtgccgc tttccgggta  115860
aaaatcgacg tcgttgtctt cagaatcaac gatggtaaac acattgggtt gaatataaag  115920
cgtataagat ttgttgactc cataagcggt ttgtggttcg atgataaagt tctgaggata  115980
ctgtgtttca tagaggatat ttacgtttac gatcatcggc atgaaatccc ttcgatcccc  116040
ttcatccgtt tcatacagcg taaccagatg aaatttgctg tcaaaaatat tccccacttc   116100
gcgaggttga cgaatgatag aaacagttgg ggagtataca ttataaacca cttcgtcatc   116160
tgaaagggcg aatttttccca tcgtacgaag ataatcggca atggagattt tctggcgaat  116220
gagctttgca atcaaacgct gaccgtattc tgtaagagac gccgtaacaa gcatatcaga  116280
attccacctt cagtttaatc acgtattcat cttcgttggt cttacgaagc ggagaggaaa  116340
gtcttccaag cgccacaagc tgattgttct gatcatagat tccaacggtg gtaatataag  116400
taccctgatc aggatacaaa atgcgtccgg aagtgggatc gtagaatgtg ggattgagcg  116460
agtaattgaa ttcgccagcc tttacgcgac agaaaataac catagagtga atgttatcca  116520
ccattgaaag cgtcatgtca agaataaggt tggcgatgtt ttcatgaagt ttcgcaacgc  116580
caccgaccgg aggattgctg tcaatcggga atccggttgg atccagcatg taaagcgaag  116640
tgctgtatcc ccccgatcca accccaagcg aatgagagac aaaatcgccg catgcatcca  116700
gatcgatcag aagcagcgcc gactgaggga atacgattcc aaacaccttc tgagttatgg  116760
agtgggttac aggaaccgcc tttccactct gaagtgaacc cgacaccaga tagtagaacg  116820
gctgcacctg ggtgcggatc ggagtagcga ggttggtttc gccgctgttg tcaaccagag  116880
acagggttgc gcggtttgat ccgtcggtga aagacaggtt aatctggaaa ttaccaacat  116940
caattgtatc ggcaaaatta tggaaggaga ctaccatgaa gttcttaagt tcactgaatc   117000
cggcaccggg atttgcggga tcacggggaa cagtaataac atcagaagcc agattggttt   117060
tgaattgatt gataaaagcc agataatgct ttcgagtaat ttcattagtt ccaccgccat   117120
agttcccttt ggaagcaaac gccacggaaa actccggatc ggtggtaagc gatcctttga   117180
agatattcac atagtaatcg ttgtaatgat cgggttgcga agaataagtt acaaaatcgt   117240
ttcgtgcaat aactccgctt ttatcccaga accccggaac ggctacattt ctcgtgctgt   117300
acaccacgtc gtcaatttgc ttgaagacaa accccctgagg ctgcggagcc gtctcagctt   117360
ccgtagcgat gttgttgaca acgtttcgta tagtttcgag ctcttccgta gtgatagaca   117420
```

-continued

```
gattcgattg cagatagttc agaaatccct gcaaaatctg tcgcttggaa taatcggtaa   117480
ccgttccaag tagcgtggta atgtaggaaa taagttgctc tctcataatc ttatgtaatc   117540
agttttactt tcagttcagc ttgtgcacca ctttcgttgc ccctgataag cacaatggtt   117600
tcggtgttgg gcgtagccgt ttgcgccggt tcgatcacaa acttgcgccc ggaaatcgct   117660
ttatagtcgg ggttgcttgt cgggaagggg aacggcgcct gtgtcgacgg ttcagcaaca   117720
gaaatgttta gctgtttgct atcataaagc aatgaataac caagaatctt atcaagtgca   117780
accacaaact ttgtacttgg gatgaagaga tatcggcgaa ggttatctgt agaagtaacc   117840
ctgagcacga tttcactctg atccagaagc aaaatgggaa tttcgttgac aatgatattc   117900
ggatcgccta ccacactgaa aagatgatag cgcggcactt caaacggctt gggttctacc   117960
agcgaatagc tcagaatttg cggagggtta cccgcgcttg cagaaaacac atattcataa   118020
tcgattccgt cgtcagaaag tgcaaagtag gcaatatcga aactaccgga cgcaaacaac   118080
cttctaccgt atgccgtgag cgtggctacg gaatataccg tgttttctga tttggtgggg   118140
ataaacattt ttttctttaa ataaagtttt cagttaccca ctacaagttt taaaagctca   118200
accagtatcg aagggtctac aatagccagc gcaatgaagg gaaaaagtgg caaaatcaac   118260
ccgacaataa atccggtgag tagcaatttg atgaacagtt gttgttgatc ttttctgttc   118320
tgcaatgcat tgtcataagc gccctgcaat agatcacgat attttcacc cacctccgtt    118380 ttatctttaa gagactcgat ttgaacgctc agtcgattca atatatcttc tatatcatca   118440
agtttttctc taatgttgtt tctatcctgt acaacggttc tgagcacatc tttaatatct   118500
ttaatcattt caatgatgtt cgatagaatg aaacgtatct gataatctct gtcaaactgt   118560
tcttcgttca tccctgtttt taaattaaat aaaaagggg agacgacacg tagtacatct    118620
cccccataaa attattttt atgcgaatta aggcgtgcgc ttttccagaa gatacatcgt    118680
aagaacatcg ccatttacag caagcagttt ggtaccttcc cggttgggga aaggattgat   118740
ccggttgaaa tcaatgcggc gcatttcctg acgactatcc ttttcaaaat ggtttctcag   118800
gaaattcaga gcatttagcg tataatacat gtcattttct ttccagtagt gcgcaatgat   118860
cttgcgtttg tggttcagca cgaaatcctt ttcgcggtgg aattccggaa cggaataaat   118920
gacattatcc accagcgagc agtaatcggc aagatcctga agatgagcat attcagttga   118980
aagaatatca ggaacctcgc tgggaatgta cgtgtcataa tccccgtaaa caattccccg   119040
gatattagcc gcattgtaag tcgaagactc gacaaaatgc gttttcaacc gcttgtctga   119100
gtaatccttg gaaaacagaa atatccggct tggattttca ggatcgtcga acattaaaag   119160
cttttcagcc ttaacaaacc actcatattc cgacttgaat accggcttga aatagaacac   119220
ggtgcggaat tgagtggaac gtcgagagcg tcttggtttt gccaacgtac ccatagtctt   119280
tctcctattt ttttttgtt tggttttaaa tacattctgt gtaacaataa aaattcataa    119340
aggtttcaaa gattttaca atttcttatt taaagaaaaa tgcccgcaaa atcaagaaaa    119400
caacagagat atatattcta tctcagaaac aaatatggat caccgaaaaa accccccaag   119460
aaatacaaat ggatatggca caaagattgg gagaaactgg aggaagccaa acgtaaaaag   119520
aaaaagaaga aagacgtaaa aataaacgc tcttacctga agccggattc ctattataag    119580
aaaccatacg gttattacgg aatctggtat taccattatg atgacggtgt ggatgatggg   119640
ggagatgcgg gtgatggtgg aagtggtgct ggtgtgggtg aagctaaagg tgcaaaacct   119700
gctaagaaat ctaaaaaaga agtgctccgc gatcttgagg tcaaactgca cgacttcaac   119760
```

-continued

```
aaggagttga aaaaactcct cgagaatctc ggattctaaa aaaagaaagc cggggaatca  119820
acccggcat  tttttgtttc accaaggtaa atcgttatta tccgtctgac acgactcaat  119880
caattcctct  tcttccggtt cttcttcttc ataactgtaa aaccatatat gaaagtaata  119940
tccccgccct  tcttcccact ctcgcatttg ctgctcttcg aagacgtctt gcaaaaaacg  120000
ctttgtcaaa  ctcatggctc cctcctattt ttggttgaca aatcgattct actggtaata  120060
tacgcattga  tcagagaaaa gtcaaatgaa gaatctgtta aacagagata tatccgcact  120120
cagcggaagt  gtagatgtca acctcagata caatcttata aagttttttc attagcacca  120180
caaagtcttc  ttccggaagc tctaatagca attcctcatt atatttgaga aggggaagca  120240
tagctttact  tccgctaccc accgaataat agggatcacg aatgaacatt gtcgtgaaat  120300
tgtcggatac  cacaaacacc ccgtgctgac tgattcccat aatttttccg ttcatatccc  120360
cattatcatt  cagaagattc aaccccttca gatgatctct ccacttgtac gtaaacgtct  120420
ctacaatcgt  gttttttgctg taggattctc tgttaaagat aagcggcgag gaaaattttg  120480
caaaggcgtt  ctgatagatt acccttccga caaaaccaag cggaattcga tccaccagtt  120540
cggacggcgt  ctgaatatcc agaaaagcgg ctttggggtc atccctgacc accagcatgc  120600
cgtccattgt  ggtggtatag tcaaaaaaaa cataccgctt atcggctctg tcaatggcta  120660
ctaccgtgct  catgattatt taagggtttg cgttaaggtg tcttcaaat  gatacacaat  120720
gtctctaatc  tcagcaggta taagttctct gatggtaaaa aattcgtcag gaaatattat  120780
ctgtctcaga  ttaatatatc ctattcggtt gtgatagcga actccgttcc ccaccgctac  120840
cacaatatgc  tcgaaaggtg agcggtgtcc gttttttgtaa agtcttcttg caagttttaa  120900
attttttatct  aagtcggatt catcagaagc ataggaaacg cgggctatac gcgccaccga  120960
tgtaaccagt  agtttggaat tcaattcctc cggtgaaata actccctgaa gaggatcgac  121020
aatatctccg  ggattggctt cgaaagccgg ggagttgtcg tagatatagc gaatcaggag  121080
cgctatttt   cggaattcgg gttgtgcgtc ggaagcgcaa cgaagtctga aaaagttgtc  121140
aagcgaatac  ggatcggcaa tggaagcgat gacatctgta tatgcatagg gtgaaagtat  121200
tcgattagcg  tgttgcttgt gtacattgag tttctcgagc acaaaatgca accccgctga  121260
tgtatataac  ccggtatacc aacaccacct tgccagcaca tctttccacc ctcctatttt  121320
tttatcggaa  aacattgccc ctgagttttc cacaaaatca tctggaacaa agggggttttc  121380
aagtacacgc  ttccggtatt ttttcaagga aatggctctt gtagaagcgg cattcctcga  121440
aaaggcgcga  tgtgtattaa attcagccag tatgactgtg ggaatttgaa agcgaaagca  121500
gaagaagata  tcgttattcg tcttcgtttt gatcagatac cacaccattg ctttctgagt  121560
tttttccatt  taaaaccgat ccatttaaac aaagtttcat ttctctgatt tcatctttca  121620
gggtttcaga  aaggtgtaat atttcatccc actcgcgagt attgcgctca aaaatctcaa  121680
ctccactgga  aacatcactc atcatttttt tcctccttgt gtttaatgtt gtggtaaatc  121740
tataatttgc  gggtgttgcc agaagcgcat ttcatagata cccactttc  ttttaaataa  121800
aagaaaaata  acttttttta aaaaattatt taccccggtc gtcaagtctt ccaatatccg  121860
gctctttata  gggatgaatg cgatatttct tctggaaaaa ctccttccac tccggcgatt  121920
tttcaaatac  gacatccaga ttgtcgataa gtgcctttgc caccatgtgt ttgcagattc  121980
tccccggta   gtaatgatcc gggcacgtac atttgaatgt gcgggtgtca aaattgacgc  122040
gcgttacgta  ttttttgtag gagccgcttt cgagagtatc acgggcgcgt tcaagcagcg  122100
ttctcccctg  tttgtctttc tgagtctgac accatttgag aaaagagagg agttgtttat  122160
```

-continued

```
atcgcttatc gaacgtttca agccgcttgc gctcgcgttc ttcaatagag cgcttgagtt 122220
cttcagcctt ttgctgtctc tcttttatac ttggcggcgg catacgctca gatgtttaaa 122280
attctccgaa gcagactttc gatctgatct tcggtaaaat ctcttttgga tatataaagc 122340
acaagattgc gctccgtgtt gttttcggt ggggtgtttc ctttgagaag gtttctgaaa 122400
tattcgatga actctttttt aagctctttt tccgactttc cggttttatt ctgcacaagt 122460
gtttttcgg tggaagtagc ctcttcttcg ttgacggcga cattatatat agagagcatg 122520
agaaacatct ctaccgccgg atcggtagca tgacgtgcag ccatatcggc acttcggcgc 122580
tgaatggctt catatagcag tgattcctcg cgggtcattc ttttctgtta aataaatgtg 122640
aatccgtagg aaagggaaaa catcagggga aagcacacat ataagaacca gaacccagaa 122700
caaaaaatag gaggaaggtt atgggtaaga tcgatgtttc gaacatcaaa accgccgttg 122760
ccatctccca gaaagccaat gttcctcttt atctgtgggg tggtgtggga atctccaaaa 122820
cccaacaaat ctatcagtat gccaccagca ccaatcaaaa atgtgctgtc gttacggggt 122880
tggcaataga tccaaccgac gtagtgggtc attacattgc cgacttcaat aaacgtatca 122940
cctaccagac caaaccctat ctttatgaac tcttcggtga ggaagagcgg ggaatcatct 123000
tccttgacga attcaacaac tcagaaagtg atgtgatggg ggtgtttcta aagcttctcg 123060
acgaaaagag gcttggaagc tacaaactcc ctgatggaat tcacatcatt gcagccggta 123120
atcccccga actggctcca aatgcttcct cgcttccgct tgccgtcgct actcgatttg 123180
cccatcttta tgtggaagcg gatttcatct cccttaagag atggttgaaa ggagcggaag 123240
atgaagagga ttatgtaaag attttcaatc ttgaagtcgg ggaagatgtt gttcagcagg 123300
tgttcgatat tttcgttgac tactgcattg aaaacggtct tttcccggct tcagaagatt 123360
ctcgtagttg cgagtgggag gggagcctga attaccgcac attgcactat gcagcaaaaa 123420
tcggggctgt atacaaagtt gcttacaaaa atgtatcaaa tcaatcgaca ctgtataatg 123480
taactgtaga aatgatccac ggtctggttg gaaccatcgc ttccaacctg atggaacatc 123540
ttgaaaacaa gtggcttcca tcggcaaaag agattctcga aaactatgat attgtgctca 123600
agcatcgaga cgcctatgcc gcccttgcct acaaccttat gagcggcatt caggaagaag 123660
actatccgag gttggtggat ttcatgcaat ggttagaaaa gaaaaacgaa cttgtaatgc 123720
ttgcggcgat agtggaatct ttccagtcgt tcattccgaa gaaaggttt ctgacaagcc 123780
ggttcgaata ctacaaccag attttcaaaa tcattaatcg atcgctggac gtctataaga 123840
aagtcaaacc cacaaacaac aagtgattga ttatggaacc gattgtcgaa aaaagctct 123900
atgaactgat taactgcatt gtaaaaaatc ataccccact cgccatgatt cttccccgaa 123960
tcaaagtgcg ggtaggggt agggataaat acacactggg actctgcaaa gaacgggaaa 124020
tcattctcag ccggtgtctc tttgatgatg aaatcgttta tcccaaactt gtatttatca 124080
aagaccccga caccggcgag atcgtagact atgatattga agactatgtt gccaaaatcg 124140
atgatgaagg gcggtatcat accctgctgg aagaaatcat tcatgccggt ctcatgcacc 124200
ccatgcgtgt agaccggttt cagaaaacat atcaggagct ttttgaaaag aacaagcggc 124260
tggtgaattt tctgtacctt tgtcttgagg ttgagcgtca tgcaatacat accgctgtag 124320
ccaacatcga tctacttaag cccgtgttca agacaacac gcgggatgaa agattgtgg 124380
aattcattaa agtattcaa catgatcatc ccgatcaaaa gctgtttggg tttacttttg 124440
aaagactgtt tttgaagtat ctcaacgatt ttgagggagg taaaattgca gccccgcaa 124500
```

```
tttacgatct gatggaatac gacgggaata ccgttcccga caagttcata gaagcaatcg   124560
aaaaatctct tcataaaggg aaaaagtatg gaaatcagac actggatgaa atctttgaaa   124620
tccggcgtgt ggatcaaaag gggttgcaat tgacgcaact cctgaagcag atttgcttcc   124680
gcagggcacg taaaaaaccc tcgctgcacg tgctcgacaa aaagcggaag cactacgaac   124740
cgctcaggtt tgggaaaatc aaagaaaaaa cttcaaatat cgccattatt ctggatgtgt   124800
cgggaagtat gcttcgtgat ttcaaaaagc atcgcctgat tgacatcgcg acaagtatga   124860
tcgtggaaac tttcaaaaac gcacccaata tcgatgtata catcggagat accgaaatca   124920
aggataaagc gaagatccgc accctgtttt cccgtttcaa aggggggcggt ggaaccgata   124980 tgtctaacat ctataaacaa ctgaaagatc gataccagaa aatactggtt gttaccgacg   125040
gggagacacc cttccccgaa ccaaaagact accgccctca ggatactttt atcatcatta   125100
atgatgaaat gcccgaaatt cccaattaca tcaaaaccct gaaggtgaaa ctatgaacga   125160
aaaagcgttc cagttccgca atcttctaaa ggaagtgatc ggcatgcgaa tcctcgagcg   125220
attcaaccac atagaacctg aaggaaaaag gaaatgggta atttatccg cctacattct   125280 aatagtggaa gaagaaaatg cacccccagat ctgcaaggaa cttgttcgaa acaatacaga   125340
gatagatcct ctggaatttg tcagatcttt caaagaagaa cttataaaca tgatcgaaaa   125400
tcaaaattat cgaaatgaat ttgagaaata cgttgcaaac tacgcgatag aaaacgaaat   125460
caattacaga aacatgatag caaacttttt ctgatataaa aaggaaaacc cccggttcat   125520
caccgggggc ttcctcagcg tctattccct atcgggtaag ttccgccatt acggctgcag   125580
gagcttcaca tacagcagac catagaactc tggacgcacc acctccagag cgtagcgggt   125640
catcagacca cgccggtaag agaagttaac gggatcgacg atcgtcggcg tgaacagcag   125700
cggcacatac ggagcgtaaa ccgcacccgt ttgccacggc gtgttcagat cttgattacc   125760
catgatgatc accggctggt tctgatagat gttcttgtac aggcggtagc gtccctgcac   125820
catacctaca tagaagatac cggtaccacc atcgcggttg tcgttacccg gcgtaaagcc   125880
cggcatcgac tccagcagcg cagccacctg tgggctggta acaaggaagt tggcacccgc   125940
aaccgccgtc ttctgctgaa tgcggttgct gaccttgttc agttcgatca tcagggtagc   126000
caaccattcc tgcttcgagc cgtagaagtt gccggcaaca aagttacccg acgtttcatc   126060
gtagtattca ccgaccactt ccgaccagaa gccatagttg tcagtgcgcc gggcatgcgc   126120
catgatcgtc gacaggattt ccagatcgat ctcacgggca atatactgag acatgagcgt   126180
aacgatttcg ttttcaagat cgacgccctt atgataggcg gcgagatcct gcatcgcttc   126240
cggcgtccag gcggcacgca gcttacgggt cttggtagcc accggacggc tccgaagctc   126300
aaggttgatc tccggaatat ccagcgactg gaatccggga tccggatagt caggatccgt   126360
cgactggtct tcgaagtcgt ttcgagcatc gatgtagtag accagatcaa ggtcttgagt   126420
cgacggagta ccaccggcaa cggtcgcaaa gtcagagccg gttacgaaga caaccgcgc   126480 gtacagcgcc gaaccgacgg caccgacgat ccggttgtag cgcggaagcg ggtaagcgac   126540
cgtgttttca ggatcaccgg aagcgtcgtc atattgccag aagcgcaccg tattcacatc   126600
ggcgacaccg ggaagcgacg caaccggcac atccacatag tacaccgcac cgctcgagac   126660
cagtgaagca atgccggtgt caaaaccgac atcccgcatc gtcgcctgct gggcggtagc   126720
cagatccacg gtgatcgtgg tctcatactc ccgacgcgac aggcgagcgt tttcatcata   126780
cagaccgccc gtagccgtgt cggtggtcag accggtacca ccgtagaccg agccgtttcc   126840
gggaagctca ggcgacttga aatccagata gaagaccaga cctgttggga gcgacagcgg   126900
```

```
ctgcaccgac accagatccg tcgcacgcag gttggcgaac acacggcgca caatcggaag   126960
tgccagattc cagccgtcaa cctccgtggt ctgggtggtc tccatcaggt gcttcttagc   127020
ctcgcggtac tggttctcca gcagggtagc gagcgtatgc cgctcccagt cgttacggca   127080
accctccaga agcggttgcc acttctcgat aagttgttcg ttaattttcg gttggctcat   127140
tttactctta ttttttttt gttttaaatc tctaaaaaca ttcggtattt aaccgaatta   127200
gagtccggca agacgcttaa tgcgctccag atccaacagc ggatcctcaa ccgaacccga   127260
cgtgcgggat tcgcgacag gtttcaccac acgggtttcc tgcagcttgc gcttgatccg   127320
ctcacgaatg cgctggcggg taacttcgtc aatgacgggc ttcttcaccc ggctttcccg   127380
catacggcgc ggcgtcggac acgaagcagc ttccgccatt tcctccgtct cctcaccagc   127440
caccttgcga agcagttcga tagcctcctc tacgcgctca agaagcgtgt gcaaagatc   127500 catttcttca cgcacatgct cctcgctttc gacggcaccc ttgatgtcaa catcaatatc   127560
gagttcttcg tcgtccgaaa gatcggcatc ctttaactcg atttcggctt ccagctcgcc   127620
gtcttcgtcg acgtcttcaa catcgatttt gatgtcttcg tcatccagat ccagttccag   127680
atcctcctca tcgagatcca gttccagatc ttcgtcttcg tgttcggctt cggtaatccg   127740
acgcttcatt ttgtgtttag cttctcgcat ttcttcctgt tgtttagttt cccaggcttt   127800
ttgcaacgtt tgcgcgactt cttcggcaaa cgaagcaagc gtgtcatcgt cagtttcatc   127860
aaccttcgct tccgtcaggg gattaccttc aggctcttcc acctgctcaa gctcttcttc   127920
gagttccttc aaagcctccc gaatttcttc ggtgatcgag tgaatggaag cttcctgaag   127980
atgcctcttc tgcttttcct gacgaagcga ctcaaggtaa cccacaaagt ctttaaattc   128040
ctgcataact caaatttaaa tatatttaat cgccattcat tttaaaaaat ggcacctgct   128100
acgtgggaat attaaacccc acatcaaatt taaatatata ttttccgca cgaaataaaa   128160 aaaagggaga gaaactgatc tctcccccag gggtaacatg tattttataa cttgtgaact   128220
accaccacct atagatgtgg atggcttcgt ggtcaaggta gctcttgcta ccagattccc   128280
cacgctcaaa gggctgttcc atccccgaat ttgccaatta ttggctaatt aaatcacttt   128340
cttcttcaca agcgcctcgc gcaatctatg gcgtgctctg ttgattcgag atttgacggt   128400
tccgatagga atgttgtttt tctcagccag cgcctgcatg gcacattttt ccttcaactc   128460
catgtactgt ttcattatat tgtaaaacgg gttatcgcct tttcaagtt cttcctgaat   128520 cacctccacc gcacgtttca attcatactg ctcatcaagc agcggctctc cggattcaat   128580
ttctacaggg gtatcccgat ctccaaatgt aatttcttcc atgtaaatcc tgggaccacg   128640
tcgagaattg tatcgataac gggtaattac aacggatttg aatacagtgt aaatatacgt   128700
agcgaaagaa gctccttcaa ccacgctata ggaatcaaat ctaagaagcc ttagaaacgt   128760
atcctgcacc atatcctcga tttcatgctc cgactttgta tatttcttc cgaaattttt   128820 gagccgctca gcatacctac tgtaaagcac ttcataacgg atttcgagcg aacgttctg   128880 aaggaaaagt tcttcgtcgg tcatctgata gtatttacgc ttatccataa cttctcctct   128940
gttttaaagg ttgaaaatga tttcgtagcc gtcaatgcgg tcatcagtta tgagcttgtc   129000
ataaagatcg tcaatctttt ctatgttgtc ataaatcatg agcatttcat caatatcatg   129060
cacaacaaca gaaatgtaat aaccgttttc ttcatcaaaa cagagttcgg cgtagctttt   129120
atgaagatcc cccacacatt ttttgatatt ctctacaaat acttctacag gataaatatct   129180 aaccagacaa aaatcgagat gcggaagcac actgttcatt atctgctcca gcacctcttc   129240
```

```
attagaaatc agcagttcat aatcgtcaat ggtatttaca ttgtagacaa gatggttgtt  129300
ggatgtaata gtaggaatga cttcgtgagt tgggttgaaa tatgtgttta ccagatcttg  129360
aacggaatcg agcgcgtcgc gataatcaat tttagtctcc atagccatat cctaaaaggt  129420
tggttgatat ataccggtta tggaaaataa aaaagggag agagggtgtt tcctttccca  129480
caccctctct ccgcgtttat agggaaagtc gtcatcgaag tagccctcaa tctcctccat  129540
cgaatgagat tctttttcgg gagagattca ccttttttctt gggggattca caaaattcct  129600
cttccgcggg atcaaagccc ctaatggaga atctcttcct ggcgggagcg ggttcatgct  129660
tccccaatca ttgttatttc cccagacaaa cacatggacg tctcttccac caacaaaacg  129720
aacttctccc gaatcggcgg agatgttcgg gagttcaccg cgaacccgga tcagggatcc  129780
caccccggct ttccgcacaa gatcggaagg tcccgttgta aaagtaaatg ttgaaccact  129840
cggtgctttc ttgctgaccg tcccaccgac ggaccgccag ccgtacggtg gtataactgt  129900
ttccgcta                                                           129908

<210> SEQ ID NO 2
<211> LENGTH: 892
<212> TYPE: PRT
<213> ORGANISM: Vaccinia virus (strain Copenhagen)

<400> SEQUENCE: 2

Gln Asn Ala Thr Met Asp Glu Phe Leu Asn Ile Ser Trp Phe Tyr Ile
 1               5                  10                  15

Ser Asn Gly Ile Ser Pro Asp Gly Cys Tyr Ser Leu Asp Glu Gln Tyr
                20                  25                  30

Leu Thr Lys Ile Asn Asn Gly Cys Tyr His Cys Asp Asp Pro Arg Asn
            35                  40                  45

Cys Phe Ala Lys Lys Ile Pro Arg Phe Asp Ile Pro Arg Ser Tyr Leu
        50                  55                  60

Phe Leu Asp Ile Glu Cys His Phe Asp Lys Lys Phe Pro Ser Val Phe
 65                  70                  75                  80

Ile Asn Pro Ile Ser His Thr Ser Tyr Cys Tyr Ile Asp Leu Ser Gly
                85                  90                  95

Lys Arg Leu Leu Phe Thr Leu Ile Asn Glu Glu Met Leu Thr Glu Gln
            100                 105                 110

Glu Ile Gln Glu Ala Val Asp Arg Gly Cys Leu Arg Ile Gln Ser Leu
        115                 120                 125

Met Glu Met Asp Tyr Glu Arg Glu Leu Val Leu Cys Ser Glu Ile Val
    130                 135                 140

Leu Leu Arg Ile Ala Lys Gln Leu Leu Glu Leu Thr Phe Asp Tyr Val
145                 150                 155                 160

Val Thr Phe Asn Gly His Asn Phe Asp Leu Arg Tyr Ile Thr Asn Arg
                165                 170                 175

Leu Glu Leu Leu Thr Gly Glu Lys Ile Ile Phe Arg Ser Pro Asp Lys
            180                 185                 190

Lys Glu Ala Val His Leu Cys Ile Tyr Glu Arg Asn Gln Ser Ser His
        195                 200                 205

Lys Gly Val Gly Gly Met Ala Asn Thr Thr Phe His Val Asn Asn Asn
    210                 215                 220

Asn Gly Thr Ile Phe Phe Asp Leu Tyr Ser Phe Ile Gln Lys Ser Glu
225                 230                 235                 240

Lys Leu Asp Ser Tyr Lys Leu Asp Ser Ile Ser Lys Asn Ala Phe Ser
                245                 250                 255
```

-continued

```
Cys Met Gly Lys Val Leu Asn Arg Gly Val Arg Glu Met Thr Phe Ile
        260                 265                 270
Gly Asp Asp Thr Thr Asp Ala Lys Gly Lys Ala Ala Ala Phe Ala Lys
            275                 280                 285
Val Leu Thr Thr Gly Asn Tyr Val Thr Val Asp Glu Asp Ile Ile Cys
        290                 295                 300
Lys Val Ile Arg Lys Asp Ile Trp Glu Asn Gly Phe Lys Val Val Leu
305                 310                 315                 320
Leu Cys Pro Thr Leu Pro Asn Asp Thr Tyr Lys Leu Ser Phe Gly Lys
                325                 330                 335
Asp Asp Val Asp Leu Ala Gln Met Tyr Lys Asp Tyr Asn Leu Asn Ile
            340                 345                 350
Ala Leu Asp Met Ala Arg Tyr Cys Ile His Asp Ala Cys Leu Cys Gln
        355                 360                 365
Tyr Leu Trp Glu Tyr Tyr Gly Val Glu Thr Lys Thr Asp Ala Gly Ala
    370                 375                 380
Ser Thr Tyr Val Leu Pro Gln Ser Met Val Phe Glu Tyr Arg Ala Ser
385                 390                 395                 400
Thr Val Ile Lys Gly Pro Leu Leu Lys Leu Leu Glu Thr Lys Thr
                405                 410                 415
Ile Leu Val Arg Ser Glu Thr Lys Gln Lys Phe Pro Tyr Glu Gly Gly
                420                 425                 430
Lys Val Phe Ala Pro Lys Gln Lys Met Phe Ser Asn Asn Val Leu Ile
            435                 440                 445
Phe Asp Tyr Asn Ser Leu Tyr Pro Asn Val Cys Ile Phe Gly Asn Leu
    450                 455                 460
Ser Pro Glu Thr Leu Val Gly Val Val Ser Thr Asn Arg Leu Glu
465                 470                 475                 480
Glu Glu Ile Asn Asn Gln Leu Leu Leu Gln Lys Tyr Pro Pro Arg
                485                 490                 495
Tyr Ile Thr Val His Cys Glu Pro Arg Leu Pro Asn Leu Ile Ser Glu
                500                 505                 510
Ile Ala Ile Phe Asp Arg Ser Ile Glu Gly Thr Ile Pro Arg Leu Leu
            515                 520                 525
Arg Thr Phe Leu Ala Glu Arg Ala Arg Tyr Lys Lys Met Leu Lys Gln
            530                 535                 540
Ala Thr Ser Ser Thr Glu Lys Ala Ile Tyr Asp Ser Met Gln Tyr Thr
545                 550                 555                 560
Tyr Lys Ile Val Ala Asn Ser Val Tyr Gly Leu Met Gly Phe Arg Asn
                565                 570                 575
Ser Ala Leu Tyr Ser Tyr Ala Ser Ala Lys Ser Cys Thr Ser Ile Gly
                580                 585                 590
Arg Arg Met Ile Leu Tyr Leu Glu Ser Val Leu Asn Gly Ala Glu Leu
        595                 600                 605
Ser Asn Gly Met Leu Arg Phe Ala Asn Pro Leu Ser Asn Pro Phe Tyr
            610                 615                 620
Met Asp Asp Arg Asp Ile Asn Pro Ile Val Lys Thr Ser Leu Pro Ile
625                 630                 635                 640
Asp Tyr Arg Phe Arg Phe Arg Ser Val Tyr Gly Asp Thr Asp Ser Val
                645                 650                 655
Phe Thr Glu Ile Asp Ser Gln Asp Val Asp Lys Ser Ile Glu Ile Ala
            660                 665                 670
```

```
Lys Glu Leu Glu Arg Leu Ile Asn Asn Arg Val Leu Phe Asn Asn Phe
            675                 680                 685

Lys Ile Glu Phe Glu Ala Val Tyr Lys Asn Leu Ile Met Gln Ser Lys
    690                 695                 700

Lys Lys Tyr Thr Thr Met Lys Tyr Ser Ala Ser Ser Asn Ser Lys Ser
705                 710                 715                 720

Val Pro Glu Arg Ile Asn Lys Gly Thr Ser Glu Thr Arg Arg Asp Val
                725                 730                 735

Ser Lys Phe His Lys Asn Met Ile Lys Thr Tyr Lys Thr Arg Leu Ser
            740                 745                 750

Glu Met Leu Ser Glu Gly Arg Met Asn Ser Asn Gln Val Cys Ile Asp
            755                 760                 765

Ile Leu Arg Ser Leu Glu Thr Asp Leu Arg Ser Glu Phe Asp Ser Arg
            770                 775                 780

Ser Ser Pro Leu Glu Leu Phe Met Leu Ser Arg Met His His Ser Asn
785                 790                 795                 800

Tyr Lys Ser Ala Asp Asn Pro Asn Met Tyr Leu Val Thr Glu Tyr Asn
                805                 810                 815

Lys Asn Asn Pro Glu Thr Ile Glu Leu Gly Glu Arg Tyr Tyr Phe Ala
                820                 825                 830

Tyr Ile Cys Pro Ala Asn Val Pro Trp Thr Lys Lys Leu Val Asn Ile
            835                 840                 845

Lys Thr Tyr Glu Thr Ile Ile Asp Arg Ser Phe Lys Leu Gly Ser Asp
            850                 855                 860

Gln Arg Ile Phe Tyr Glu Val Tyr Phe Lys Arg Leu Thr Ser Glu Ile
865                 870                 875                 880

Val Asn Leu Leu Asp Asn Lys Val Leu Cys Ile Ser
                885                 890

<210> SEQ ID NO 3
<211> LENGTH: 892
<212> TYPE: PRT
<213> ORGANISM: Vaccinia virus (strain WR)

<400> SEQUENCE: 3

Gln Asn Ala Thr Met Asp Glu Phe Leu Asn Ile Ser Trp Phe Tyr Ile
1               5                   10                  15

Ser Asn Gly Ile Ser Pro Asp Gly Cys Tyr Ser Leu Asp Glu Gln Tyr
                20                  25                  30

Leu Thr Lys Ile Asn Asn Gly Cys Tyr His Cys Asp Asp Pro Arg Asn
            35                  40                  45

Cys Phe Ala Lys Lys Ile Pro Arg Phe Asp Ile Pro Arg Ser Tyr Leu
50                  55                  60

Phe Leu Asp Ile Glu Cys His Phe Asp Lys Lys Phe Pro Ser Val Phe
65                  70                  75                  80

Ile Asn Pro Ile Ser His Thr Ser Tyr Cys Tyr Ile Asp Leu Ser Gly
                85                  90                  95

Lys Arg Leu Leu Phe Thr Leu Ile Asn Glu Glu Met Leu Thr Glu Gln
            100                 105                 110

Glu Ile Gln Glu Ala Val Asp Arg Gly Cys Leu Arg Ile Gln Ser Leu
        115                 120                 125

Met Glu Met Asp Tyr Glu Arg Glu Leu Val Leu Cys Ser Glu Ile Val
    130                 135                 140

Leu Leu Arg Ile Ala Lys Gln Leu Leu Glu Leu Thr Phe Asp Tyr Val
145                 150                 155                 160
```

-continued

```
Val Thr Phe Asn Gly His Asn Phe Asp Leu Arg Tyr Ile Thr Asn Arg
            165                 170                 175
Leu Glu Leu Leu Thr Gly Glu Lys Ile Ile Phe Arg Ser Pro Asp Lys
        180                 185                 190
Lys Glu Ala Val Tyr Leu Cys Ile Tyr Glu Arg Asn Gln Ser Ser His
        195                 200                 205
Lys Gly Val Gly Gly Met Ala Asn Thr Thr Phe His Val Asn Asn Asn
        210                 215                 220
Asn Gly Thr Ile Phe Phe Asp Leu Tyr Ser Phe Ile Gln Lys Ser Glu
225                 230                 235                 240
Lys Leu Asp Ser Tyr Lys Leu Asp Ser Ile Ser Lys Asn Ala Phe Ser
                245                 250                 255
Cys Met Gly Lys Val Leu Asn Arg Gly Val Arg Glu Met Thr Phe Ile
                260                 265                 270
Gly Asp Asp Thr Thr Asp Ala Lys Gly Lys Ala Ala Phe Ala Lys
                275                 280                 285
Val Leu Thr Thr Gly Asn Tyr Val Thr Val Asp Glu Asp Ile Ile Cys
        290                 295                 300
Lys Val Ile Arg Lys Asp Ile Trp Glu Asn Gly Phe Lys Val Val Leu
305                 310                 315                 320
Leu Cys Pro Thr Leu Pro Asn Asp Thr Tyr Lys Leu Ser Phe Gly Lys
                325                 330                 335
Asp Asp Val Asp Leu Ala Gln Met Tyr Lys Asp Tyr Asn Leu Asn Ile
                340                 345                 350
Ala Leu Asp Met Ala Arg Tyr Cys Ile His Asp Ala Cys Leu Cys Gln
                355                 360                 365
Tyr Leu Trp Glu Tyr Tyr Gly Val Glu Thr Lys Thr Asp Ala Gly Ala
                370                 375                 380
Ser Thr Tyr Val Leu Pro Gln Ser Met Val Phe Glu Tyr Arg Ala Ser
385                 390                 395                 400
Thr Val Ile Lys Gly Pro Leu Leu Lys Leu Leu Leu Glu Thr Lys Thr
                405                 410                 415
Ile Leu Val Arg Ser Glu Thr Lys Gln Lys Phe Pro Tyr Glu Gly Gly
                420                 425                 430
Lys Val Phe Ala Pro Lys Gln Lys Met Phe Ser Asn Asn Val Leu Ile
                435                 440                 445
Phe Asp Tyr Asn Ser Leu Tyr Pro Asn Val Cys Ile Phe Gly Asn Leu
                450                 455                 460
Ser Pro Glu Thr Leu Val Gly Val Val Ser Thr Asn Arg Leu Glu
465                 470                 475                 480
Glu Glu Ile Asn Asn Gln Leu Leu Gln Lys Tyr Pro Pro Arg
                485                 490                 495
Tyr Ile Thr Val His Cys Glu Pro Arg Leu Pro Asn Leu Ile Ser Glu
                500                 505                 510
Ile Ala Ile Phe Asp Arg Ser Ile Glu Gly Thr Ile Pro Arg Leu Leu
                515                 520                 525
Arg Thr Phe Leu Ala Glu Arg Ala Arg Tyr Lys Lys Met Leu Lys Gln
        530                 535                 540
Ala Thr Ser Ser Thr Glu Lys Ala Ile Tyr Asp Ser Met Gln Tyr Thr
545                 550                 555                 560
Tyr Lys Ile Val Ala Asn Ser Val Tyr Gly Leu Met Gly Phe Arg Asn
                565                 570                 575
```

-continued

```
Ser Ala Leu Tyr Ser Tyr Ala Ser Ala Lys Ser Cys Thr Ser Ile Gly
            580                 585                 590

Arg Arg Met Ile Leu Tyr Leu Glu Ser Val Leu Asn Gly Ala Glu Leu
        595                 600                 605

Ser Asn Gly Met Leu Arg Phe Ala Asn Pro Leu Ser Asn Pro Phe Tyr
        610                 615                 620

Met Asp Asp Arg Asp Ile Asn Pro Ile Val Lys Thr Ser Leu Pro Ile
625                 630                 635                 640

Asp Tyr Arg Phe Arg Phe Arg Ser Val Tyr Gly Asp Thr Asp Ser Val
                645                 650                 655

Phe Thr Glu Ile Asp Ser Gln Asp Val Asp Lys Ser Ile Glu Ile Ala
                660                 665                 670

Lys Glu Leu Glu Arg Leu Ile Asn Asn Arg Val Leu Phe Asn Asn Phe
        675                 680                 685

Lys Ile Glu Phe Glu Ala Val Tyr Lys Asn Leu Ile Met Gln Ser Lys
        690                 695                 700

Lys Lys Tyr Thr Thr Met Lys Tyr Ser Ala Ser Asn Ser Lys Ser
705                 710                 715                 720

Val Pro Glu Arg Ile Asn Lys Gly Thr Ser Glu Thr Arg Arg Asp Val
                725                 730                 735

Ser Lys Phe His Lys Asn Met Ile Lys Thr Tyr Lys Thr Arg Leu Ser
                740                 745                 750

Glu Met Leu Ser Glu Gly Arg Met Asn Ser Asn Gln Val Cys Ile Asp
        755                 760                 765

Ile Leu Arg Ser Leu Glu Thr Asp Leu Arg Ser Glu Phe Asp Ser Arg
        770                 775                 780

Ser Ser Pro Leu Glu Leu Phe Met Leu Ser Arg Met His His Ser Asn
785                 790                 795                 800

Tyr Lys Ser Ala Asp Asn Pro Asn Met Tyr Leu Val Thr Glu Tyr Asn
                805                 810                 815

Lys Asn Asn Pro Glu Thr Ile Glu Leu Gly Glu Arg Tyr Tyr Phe Ala
                820                 825                 830

Tyr Ile Cys Pro Ala Asn Val Pro Trp Thr Lys Lys Leu Val Asn Ile
        835                 840                 845

Lys Thr Tyr Glu Thr Ile Ile Asp Arg Ser Phe Lys Leu Gly Ser Asp
        850                 855                 860

Gln Arg Ile Phe Tyr Glu Val Tyr Phe Lys Arg Leu Thr Ser Glu Ile
865                 870                 875                 880

Val Asn Leu Leu Asp Asn Lys Val Leu Cys Ile Ser
                885                 890
```

<210> SEQ ID NO 4
<211> LENGTH: 891
<212> TYPE: PRT
<213> ORGANISM: Variola virus

<400> SEQUENCE: 4

```
Gln Asn Ala Thr Met Asp Glu Phe Leu Asn Ile Ser Trp Phe Tyr Ile
1               5                   10                  15

Ser Asn Gly Ile Ser Pro Asp Gly Cys Tyr Ser Leu Asp Asp Gln Tyr
            20                  25                  30

Leu Thr Lys Ile Asn Asn Gly Cys Tyr His Cys Gly Asp Pro Arg Asn
        35                  40                  45

Cys Phe Ala Lys Glu Ile Pro Arg Phe Asp Ile Pro Arg Ser Tyr Leu
    50                  55                  60
```

-continued

```
Phe Leu Asp Ile Glu Cys His Phe Asp Lys Lys Phe Pro Ser Val Phe
 65                  70                  75                  80

Ile Asn Pro Ile Ser His Thr Ser Tyr Cys Tyr Ile Asp Leu Ser Gly
                 85                  90                  95

Lys Arg Leu Leu Phe Thr Leu Ile Asn Glu Glu Met Leu Thr Glu Gln
                100                 105                 110

Glu Ile Gln Glu Ala Val Asp Arg Gly Cys Leu Arg Ile Gln Ser Leu
            115                 120                 125

Met Glu Met Asp Tyr Glu Arg Glu Leu Val Leu Cys Ser Glu Ile Val
    130                 135                 140

Leu Leu Gln Ile Ala Lys Gln Leu Leu Glu Leu Thr Phe Asp Tyr Ile
145                 150                 155                 160

Val Thr Phe Asn Gly His Asn Phe Asp Leu Arg Tyr Ile Thr Asn Arg
                165                 170                 175

Leu Glu Leu Leu Thr Gly Glu Lys Ile Ile Phe Arg Ser Pro Asp Lys
                180                 185                 190

Lys Glu Ala Val His Leu Cys Ile Tyr Glu Arg Asn Gln Ser Ser His
            195                 200                 205

Lys Gly Val Gly Gly Met Ala Asn Thr Thr Phe His Val Asn Asn Asn
    210                 215                 220

Asn Gly Thr Ile Phe Phe Asp Leu Tyr Ser Phe Ile Gln Lys Ser Glu
225                 230                 235                 240

Lys Leu Asp Ser Tyr Lys Leu Asp Ser Ile Ser Lys Asn Ala Phe Ser
                245                 250                 255

Cys Met Gly Lys Val Leu Asn Arg Gly Val Arg Glu Met Thr Phe Ile
                260                 265                 270

Gly Asp Asp Thr Thr Asp Ala Lys Gly Lys Ala Ala Val Phe Ala Lys
            275                 280                 285

Val Leu Thr Thr Gly Asn Tyr Val Thr Val Asp Asp Ile Ile Cys Lys
    290                 295                 300

Val Ile His Lys Asp Ile Trp Glu Asn Gly Phe Lys Val Val Leu Ser
305                 310                 315                 320

Cys Pro Thr Leu Thr Asn Asp Thr Tyr Lys Leu Ser Phe Gly Lys Asp
                325                 330                 335

Asp Val Asp Leu Ala Gln Met Tyr Lys Asp Tyr Asn Leu Asn Ile Ala
                340                 345                 350

Leu Asp Met Ala Arg Tyr Cys Ile His Asp Ala Cys Leu Cys Gln Tyr
            355                 360                 365

Leu Trp Glu Tyr Tyr Gly Val Glu Thr Lys Thr Asp Ala Gly Ala Ser
    370                 375                 380

Thr Tyr Val Leu Pro Gln Ser Met Val Phe Gly Tyr Lys Ala Ser Thr
385                 390                 395                 400

Val Ile Lys Gly Pro Leu Leu Lys Leu Leu Glu Thr Lys Thr Ile
                405                 410                 415

Leu Val Arg Ser Glu Thr Lys Gln Lys Phe Pro Tyr Glu Gly Gly Lys
                420                 425                 430

Val Phe Ala Pro Lys Gln Lys Met Phe Ser Asn Asn Val Leu Ile Phe
            435                 440                 445

Asp Tyr Asn Ser Leu Tyr Pro Asn Val Cys Ile Phe Gly Asn Leu Ser
    450                 455                 460

Pro Glu Thr Leu Val Gly Val Val Ser Ser Asn Arg Leu Glu Glu
465                 470                 475                 480
```

-continued

```
Glu Ile Asn Asn Gln Leu Leu Leu Gln Lys Tyr Pro Pro Arg Tyr
            485                 490                 495

Ile Thr Val His Cys Glu Pro Arg Leu Pro Asn Leu Ile Ser Glu Ile
            500                 505                 510

Ala Ile Phe Asp Arg Ser Ile Glu Gly Thr Ile Pro Arg Leu Leu Arg
            515                 520                 525

Thr Phe Leu Ala Glu Arg Ala Arg Tyr Lys Lys Met Leu Lys Gln Ala
    530                 535                 540

Thr Ser Ser Thr Glu Lys Ala Ile Tyr Asp Ser Met Gln Tyr Thr Tyr
545                 550                 555                 560

Lys Ile Ile Ala Asn Ser Val Tyr Gly Leu Met Gly Phe Arg Asn Ser
                565                 570                 575

Ala Leu Tyr Ser Tyr Ala Ser Ala Lys Ser Cys Thr Ser Ile Gly Arg
            580                 585                 590

Arg Met Ile Leu Tyr Leu Glu Ser Val Leu Asn Gly Ala Glu Leu Ser
            595                 600                 605

Asn Gly Met Leu Arg Phe Ala Asn Pro Leu Ser Asn Pro Phe Tyr Met
            610                 615                 620

Asp Asp Arg Asp Ile Asn Pro Ile Val Lys Thr Ser Leu Pro Ile Asp
625                 630                 635                 640

Tyr Arg Phe Arg Phe Arg Ser Val Tyr Gly Asp Thr Asp Ser Val Phe
                645                 650                 655

Thr Glu Ile Asp Ser Gln Asp Val Asp Lys Ser Ile Glu Ile Ala Lys
            660                 665                 670

Glu Leu Glu Arg Leu Ile Asn Ser Arg Val Leu Phe Asn Asn Phe Lys
            675                 680                 685

Ile Glu Phe Glu Ala Val Tyr Lys Asn Leu Ile Met Gln Ser Lys Lys
    690                 695                 700

Lys Tyr Thr Thr Met Lys Tyr Ser Ala Ser Ser Asn Ser Lys Ser Val
705                 710                 715                 720

Pro Glu Arg Ile Asn Lys Gly Thr Ser Glu Thr Arg Arg Asp Val Ser
                725                 730                 735

Lys Phe His Lys Asn Met Ile Lys Ile Tyr Lys Thr Arg Leu Ser Glu
            740                 745                 750

Met Leu Ser Glu Gly Arg Met Asn Ser Asn Gln Val Cys Ile Asp Ile
    755                 760                 765

Leu Arg Ser Leu Glu Thr Asp Leu Arg Ser Glu Phe Asp Ser Arg Ser
770                 775                 780

Ser Pro Leu Glu Leu Phe Met Leu Ser Arg Met His His Leu Asn Tyr
785                 790                 795                 800

Lys Ser Ala Asp Asn Pro Asn Met Tyr Leu Val Thr Glu Tyr Asn Lys
                805                 810                 815

Asn Asn Pro Glu Thr Ile Glu Leu Gly Glu Arg Tyr Tyr Phe Ala Tyr
            820                 825                 830

Ile Cys Pro Ala Asn Val Pro Trp Thr Lys Lys Leu Val Asn Ile Lys
            835                 840                 845

Thr Tyr Glu Thr Ile Ile Asp Arg Ser Phe Lys Leu Gly Ser Asp Gln
    850                 855                 860

Arg Ile Phe Tyr Glu Val Tyr Phe Lys Arg Leu Thr Ser Glu Ile Val
865                 870                 875                 880

Asn Leu Leu Asp Asn Lys Val Leu Cys Ile Ser
                885                 890
```

-continued

```
<210> SEQ ID NO 5
<211> LENGTH: 874
<212> TYPE: PRT
<213> ORGANISM: Fowlpox virus

<400> SEQUENCE: 5

Glu Lys Gln Tyr Leu Gln Glu Tyr Leu Asp Ile Thr Trp Phe Tyr Leu
 1               5                  10                  15

Leu Asn Asn Ile Thr Pro Asp Gly Cys Tyr Lys Ile Asp Ile Glu His
            20                  25                  30

Leu Thr Pro Ile Lys Lys Asp Cys Tyr His Cys Asp Asp Val Ser Lys
        35                  40                  45

Val Phe Ile Gln Glu Ile Pro Ile Phe Glu Val Lys Phe Thr Tyr Leu
 50                  55                  60

Leu Phe Asp Ile Glu Cys Gln Phe Asp Lys Lys Phe Pro Ser Val Phe
 65                  70                  75                  80

Val Asn Pro Ile Ser His Ile Ser Cys Trp Ile Ile Asp Lys Val Thr
                85                  90                  95

Glu Tyr Lys Phe Thr Leu Ile Asn Thr Asp Ile Leu Pro Asp Lys Glu
            100                 105                 110

Pro Ser Ile Leu His His Lys Asp Phe Ser Pro Lys Asp Arg Ile Thr
        115                 120                 125

Tyr Cys Thr Glu Ile Val Met Leu Leu Ile Met Lys Lys Ile Leu Glu
130                 135                 140

His Arg Phe Asp Phe Val Ile Thr Phe Asn Gly Asn Asn Phe Asp Ile
145                 150                 155                 160

Arg Tyr Ile Ser Gly Arg Leu Glu Ile Leu Glu Lys Ser Phe Ile Tyr
                165                 170                 175

Phe Ser Leu Pro Asp Ala Thr Glu Thr Val Lys Leu Lys Ile Phe Glu
            180                 185                 190

Arg Phe Val Thr Gly Gly Thr Phe Thr Asn Lys Thr Tyr His Ile Asn
        195                 200                 205

Asn Asn Asn Gly Val Met Phe Phe Asp Leu Tyr Ala Phe Ile Gln Lys
210                 215                 220

Thr Glu Arg Leu Asp Ser Tyr Lys Leu Asp Ser Ile Ser Lys Asn Ile
225                 230                 235                 240

Phe Asn Cys Asn Val Ala Ile Lys Glu Ile Asp Asp Thr Ile Leu Thr
                245                 250                 255

Leu Glu Ala Thr Val Lys Asp Asn Ser Lys Asp Lys Leu Ser Ile Phe
            260                 265                 270

Ser Arg Val Leu Glu Thr Gly Asn Tyr Ile Thr Ile Gly Asp Asn Asn
        275                 280                 285

Val Ser Lys Ile Val Tyr Lys Asp Ile Asn Gln Asp Ser Phe Ile Ile
290                 295                 300

Lys Val Ile Ser Asn Arg Asp Tyr Glu Ile Gly Ser Val His Asn Ile
305                 310                 315                 320

Ser Phe Gly Lys Asp Asp Val Asp Leu Lys Asp Met Tyr Lys Asn Tyr
                325                 330                 335

Asn Leu Glu Ile Ala Leu Asp Met Glu Arg Tyr Cys Ile His Asp Ala
            340                 345                 350

Cys Leu Cys Lys Tyr Ile Trp Asp Tyr Tyr Arg Val Pro Ser Lys Ile
        355                 360                 365

Asn Ala Ala Ser Ser Thr Tyr Leu Leu Pro Gln Ser Leu Ala Leu Glu
370                 375                 380
```

-continued

```
Tyr Arg Ala Ser Thr Leu Ile Lys Gly Pro Leu Leu Lys Leu Leu Leu
385                 390                 395                 400

Glu Glu Arg Val Ile Tyr Thr Arg Lys Ile Thr Lys Val Arg Tyr Pro
                405                 410                 415

Tyr Ile Gly Gly Lys Val Phe Leu Pro Ser Gln Lys Thr Phe Glu Asn
                420                 425                 430

Asn Val Met Ile Phe Asp Tyr Asn Ser Leu Tyr Pro Asn Val Cys Ile
            435                 440                 445

Tyr Gly Asn Leu Ser Pro Glu Lys Leu Val Cys Ile Leu Leu Asn Ser
        450                 455                 460

Asn Lys Leu Glu Ser Glu Ile Asn Met Arg Thr Ile Lys Ser Lys Tyr
465                 470                 475                 480

Pro Tyr Pro Glu Tyr Val Cys Val Ser Cys Glu Ser Arg Leu Ser Asp
                485                 490                 495

Tyr Tyr Ser Glu Ile Ile Val Tyr Asp Arg Arg Glu Lys Gly Ile Ile
                500                 505                 510

Pro Lys Leu Leu Glu Met Phe Ile Gly Lys Arg Lys Glu Tyr Lys Asn
            515                 520                 525

Leu Leu Lys Thr Ala Ser Thr Thr Ile Glu Ser Thr Leu Tyr Asp Ser
        530                 535                 540

Leu Gln Tyr Ile Tyr Lys Ile Ile Ala Asn Ser Val Tyr Gly Leu Met
545                 550                 555                 560

Gly Phe Ser Asn Ser Thr Leu Tyr Ser Tyr Ser Ser Ala Lys Thr Cys
                565                 570                 575

Thr Thr Ile Gly Arg Asn Met Ile Thr Tyr Leu Asp Ser Ile Met Asn
                580                 585                 590

Gly Ala Val Trp Glu Asn Asp Lys Leu Ile Leu Ala Asp Phe Pro Arg
            595                 600                 605

Asn Ile Phe Ser Gly Glu Thr Met Phe Asn Lys Glu Leu Glu Val Pro
        610                 615                 620

Asn Met Asn Glu Ser Phe Lys Phe Arg Ser Val Tyr Gly Asp Thr Asp
625                 630                 635                 640

Ser Ile Phe Ser Glu Ile Ser Thr Lys Asp Ile Glu Lys Thr Ala Lys
                645                 650                 655

Ile Ala Lys His Leu Glu His Ile Ile Asn Thr Lys Ile Leu His Ala
                660                 665                 670

Asn Phe Lys Ile Glu Phe Glu Ala Ile Tyr Thr Gln Leu Ile Leu Gln
            675                 680                 685

Ser Lys Lys Lys Tyr Thr Thr Ile Lys Tyr Leu Ala Asn Tyr Lys Pro
        690                 695                 700

Gly Asp Lys Pro Ile Arg Val Asn Lys Gly Thr Ser Glu Thr Arg Arg
705                 710                 715                 720

Asp Val Ala Leu Phe His Lys His Met Ile Gln Arg Tyr Lys Asp Met
                725                 730                 735

Leu Met Lys Leu Leu Met Gln Ser Lys Gly Gln Gln Glu Ile Thr Arg
                740                 745                 750

Leu Ile Leu Gln Ser Leu Glu Thr Asp Met Ile Ser Glu Phe Thr His
            755                 760                 765

Asn Arg Glu Phe Glu Lys Tyr Leu Leu Ser Arg Lys His His Asn Asn
        770                 775                 780

Tyr Lys Ser Ala Thr His Ser Asn Phe Glu Leu Val Lys Arg Tyr Asn
785                 790                 795                 800

Leu Glu Asn Thr Glu Lys Ile Glu Ile Gly Glu Arg Tyr Tyr Tyr Ile
```

```
            805                 810                 815
Tyr Ile Cys Asp Ile Ser Leu Pro Trp Gln Lys Lys Leu Cys Asn Ile
                820                 825                 830

Leu Ser Tyr Glu Val Ile Ala Asp Ser Lys Phe Tyr Leu Pro Lys Asp
            835                 840                 845

Lys Arg Ile Phe Tyr Glu Ile Tyr Phe Lys Arg Ile Ala Ser Glu Val
        850                 855                 860

Val Asn Leu Leu Thr Asp Lys Thr Gln Cys
865                 870

<210> SEQ ID NO 6
<211> LENGTH: 738
<212> TYPE: PRT
<213> ORGANISM: Bos taurus (Bovine)

<400> SEQUENCE: 6

Pro Ser Phe Ala Pro Tyr Glu Ala Asn Val Asp Phe Glu Ile Arg Phe
1               5                   10                  15

Met Val Asp Thr Asp Ile Val Gly Cys Asn Trp Leu Glu Leu Pro Ala
            20                  25                  30

Gly Lys Tyr Ile Leu Arg Pro Glu Gly Lys Ala Thr Leu Cys Gln Leu
        35                  40                  45

Glu Ala Asp Val Leu Trp Ser Asp Val Ile Ser His Pro Pro Glu Gly
    50                  55                  60

Glu Trp Gln Arg Ile Ala Pro Leu Arg Val Leu Ser Phe Asp Ile Glu
65                  70                  75                  80

Cys Ala Gly Arg Lys Gly Ile Phe Pro Glu Pro Glu Arg Asp Pro Val
                85                  90                  95

Ile Gln Ile Cys Ser Leu Gly Leu Arg Trp Gly Glu Pro Glu Pro Phe
            100                 105                 110

Leu Arg Leu Ala Leu Thr Leu Arg Pro Cys Ala Pro Ile Leu Gly Ala
        115                 120                 125

Lys Val Gln Ser Tyr Glu Arg Glu Glu Asp Leu Leu Gln Ala Trp Ser
    130                 135                 140

Thr Phe Ile Arg Ile Met Asp Pro Asp Val Ile Thr Gly Tyr Asn Ile
145                 150                 155                 160

Gln Asn Phe Asp Leu Pro Tyr Leu Ile Ser Arg Ala Gln Thr Leu Lys
                165                 170                 175

Val Pro Gly Phe Pro Leu Leu Gly Arg Val Ile Gly Leu Arg Ser Asn
            180                 185                 190

Ile Arg Glu Ser Ser Phe Gln Ser Arg Gln Thr Gly Arg Arg Asp Ser
        195                 200                 205

Lys Val Val Ser Met Val Gly Arg Val Gln Met Asp Met Leu Gln Val
    210                 215                 220

Leu Leu Arg Glu Tyr Lys Leu Arg Ser Tyr Thr Leu Asn Ala Val Ser
225                 230                 235                 240

Phe His Phe Leu Gly Glu Gln Lys Glu Asp Val Gln His Ser Ile Ile
                245                 250                 255

Thr Asp Leu Gln Asn Gly Asn Asp Gln Thr Arg Arg Leu Ala Val
            260                 265                 270

Tyr Cys Leu Lys Asp Ala Phe Leu Pro Leu Arg Leu Leu Glu Arg Leu
        275                 280                 285

Met Val Leu Val Asn Ala Met Glu Met Ala Arg Val Thr Gly Val Pro
    290                 295                 300
```

```
Leu Gly Tyr Leu Leu Ser Arg Gly Gln Gln Val Lys Val Val Ser Gln
305                 310                 315                 320

Leu Leu Arg Gln Ala Met Arg Gln Gly Leu Leu Met Pro Val Val Lys
            325                 330                 335

Thr Glu Gly Gly Glu Asp Tyr Thr Gly Ala Thr Val Ile Glu Pro Leu
                340                 345                 350

Lys Gly Tyr Tyr Asp Val Pro Ile Ala Thr Leu Asp Phe Ser Ser Leu
            355                 360                 365

Tyr Pro Ser Ile Met Met Ala His Asn Leu Cys Tyr Thr Thr Leu Leu
370                 375                 380

Arg Pro Gly Ala Ala Gln Lys Leu Gly Leu Thr Glu Asp Gln Phe Ile
385                 390                 395                 400

Lys Thr Pro Thr Gly Asp Glu Phe Val Lys Ala Ser Val Arg Lys Gly
                405                 410                 415

Leu Leu Pro Gln Ile Leu Glu Asn Leu Leu Ser Ala Arg Lys Arg Ala
            420                 425                 430

Lys Ala Glu Leu Ala Lys Glu Thr Asp Pro Leu Arg Arg Gln Val Leu
            435                 440                 445

Asp Gly Arg Gln Leu Ala Leu Lys Val Ser Ala Asn Ser Val Tyr Gly
450                 455                 460

Phe Thr Gly Ala Gln Val Gly Arg Leu Pro Cys Leu Glu Ile Ser Gln
465                 470                 475                 480

Ser Val Thr Gly Phe Gly Arg Gln Met Ile Glu Lys Thr Lys Gln Leu
            485                 490                 495

Val Glu Thr Lys Tyr Thr Val Glu Asn Gly Tyr Ser Thr Ser Ala Lys
            500                 505                 510

Val Val Tyr Gly Asp Thr Asp Ser Val Met Cys Arg Phe Gly Val Ser
        515                 520                 525

Ser Val Ala Glu Ala Met Ala Leu Gly Arg Glu Ala Ala Asp Trp Val
530                 535                 540

Ser Gly His Phe Pro Ser Pro Ile Arg Leu Glu Phe Glu Lys Val Tyr
545                 550                 555                 560

Phe Pro Tyr Leu Leu Ile Ser Lys Lys Arg Tyr Ala Gly Leu Leu Phe
                565                 570                 575

Ser Ser Arg Pro Asp Ala His Asp Arg Met Asp Cys Lys Gly Leu Glu
            580                 585                 590

Ala Val Arg Arg Asp Asn Cys Pro Leu Val Ala Asn Leu Val Thr Ala
        595                 600                 605

Ser Leu Arg Arg Leu Leu Ile Asp Arg Asp Pro Ser Gly Ala Val Ala
            610                 615                 620

His Ala Gln Asp Val Ile Ser Asp Leu Leu Cys Asn Arg Ile Asp Ile
625                 630                 635                 640

Ser Gln Leu Val Ile Thr Lys Glu Leu Thr Arg Ala Ala Ala Asp Tyr
                645                 650                 655

Ala Gly Lys Gln Ala His Val Glu Leu Ala Glu Arg Met Arg Lys Arg
            660                 665                 670

Asp Pro Gly Ser Ala Pro Ser Leu Gly Asp Arg Val Pro Tyr Val Ile
                675                 680                 685

Ile Ser Ala Ala Lys Gly Val Ala Ala Tyr Met Lys Ser Glu Asp Pro
            690                 695                 700

Leu Phe Val Leu Glu His Ser Leu Pro Ile Asp Thr Gln Tyr Tyr Leu
705                 710                 715                 720

Glu Gln Gln Leu Ala Lys Pro Leu Leu Arg Ile Phe Glu Pro Ile Leu
```

Gly Glu

<210> SEQ ID NO 7
<211> LENGTH: 738
<212> TYPE: PRT
<213> ORGANISM: Homo sapiens

<400> SEQUENCE: 7

```
Pro Ser Phe Ala Pro Tyr Glu Ala Asn Val Asp Phe Glu Ile Arg Phe
  1               5                  10                  15

Met Val Asp Thr Asp Ile Val Gly Cys Asn Trp Leu Glu Leu Pro Ala
             20                  25                  30

Gly Lys Tyr Ala Leu Arg Leu Lys Glu Lys Ala Thr Gln Cys Gln Leu
         35                  40                  45

Glu Ala Asp Val Leu Trp Ser Asp Val Val Ser His Pro Pro Glu Gly
     50                  55                  60

Pro Trp Gln Arg Ile Ala Pro Leu Arg Val Leu Ser Phe Asp Ile Glu
 65                  70                  75                  80

Cys Ala Gly Arg Lys Gly Ile Phe Pro Glu Pro Glu Arg Asp Pro Val
                 85                  90                  95

Ile Gln Ile Cys Ser Leu Gly Leu Arg Trp Gly Glu Pro Glu Pro Phe
            100                 105                 110

Leu Arg Leu Ala Leu Thr Leu Arg Pro Cys Ala Pro Ile Leu Gly Ala
        115                 120                 125

Lys Val Gln Ser Tyr Glu Lys Glu Glu Asp Leu Leu Gln Ala Trp Ser
    130                 135                 140

Thr Phe Ile Arg Ile Met Asp Pro Asp Val Ile Thr Gly Tyr Asn Ile
145                 150                 155                 160

Gln Asn Phe Asp Leu Pro Tyr Leu Ile Ser Arg Ala Gln Thr Leu Lys
                165                 170                 175

Val Gln Thr Phe Pro Phe Leu Gly Arg Val Ala Gly Leu Cys Ser Asn
            180                 185                 190

Ile Arg Asp Ser Ser Phe Gln Ser Lys Gln Thr Gly Arg Arg Asp Thr
        195                 200                 205

Lys Val Val Ser Met Val Gly Arg Val Gln Met Asp Met Leu Gln Val
    210                 215                 220

Leu Leu Arg Glu Tyr Lys Leu Arg Ser His Thr Leu Asn Ala Val Ser
225                 230                 235                 240

Phe His Phe Leu Gly Glu Gln Lys Glu Asp Val Gln His Ser Ile Ile
                245                 250                 255

Thr Asp Leu Gln Asn Gly Asn Asp Gln Thr Arg Arg Arg Leu Ala Val
            260                 265                 270

Tyr Cys Leu Lys Asp Ala Tyr Leu Pro Leu Arg Leu Leu Glu Arg Leu
        275                 280                 285

Met Val Leu Val Asn Ala Val Glu Met Ala Arg Val Thr Gly Val Pro
    290                 295                 300

Leu Ser Tyr Leu Leu Ser Arg Gly Gln Gln Val Lys Val Val Ser Gln
305                 310                 315                 320

Leu Leu Arg Gln Ala Met His Glu Gly Leu Leu Met Pro Val Val Lys
                325                 330                 335

Ser Glu Gly Gly Glu Asp Tyr Thr Gly Ala Thr Val Ile Glu Pro Leu
            340                 345                 350

Lys Gly Tyr Tyr Asp Val Pro Ile Ala Thr Leu Asp Phe Ser Ser Leu
```

```
                355                 360                 365
Tyr Pro Ser Ile Met Met Ala His Asn Leu Cys Tyr Thr Thr Leu Leu
        370                 375                 380

Arg Pro Gly Thr Ala Gln Lys Leu Gly Leu Thr Glu Asp Gln Phe Ile
385                 390                 395                 400

Arg Thr Pro Thr Gly Asp Glu Phe Val Lys Thr Ser Val Arg Lys Gly
                405                 410                 415

Leu Leu Pro Gln Ile Leu Glu Asn Leu Leu Ser Ala Arg Lys Arg Ala
            420                 425                 430

Lys Ala Glu Leu Ala Lys Glu Thr Asp Pro Leu Arg Arg Gln Val Leu
        435                 440                 445

Asp Gly Arg Gln Leu Ala Leu Lys Val Ser Ala Asn Ser Val Tyr Gly
450                 455                 460

Phe Thr Gly Ala Gln Val Gly Lys Leu Pro Cys Leu Glu Ile Ser Gln
465                 470                 475                 480

Ser Val Thr Gly Phe Gly Arg Gln Met Ile Glu Lys Thr Lys Gln Leu
                485                 490                 495

Val Glu Ser Lys Tyr Thr Val Glu Asn Gly Tyr Ser Thr Ser Ala Lys
            500                 505                 510

Val Val Tyr Gly Asp Thr Asp Ser Val Met Cys Arg Phe Gly Val Ser
        515                 520                 525

Ser Val Ala Glu Ala Met Ala Leu Gly Arg Glu Ala Ala Asp Trp Val
530                 535                 540

Ser Gly His Phe Pro Ser Pro Ile Arg Leu Glu Phe Glu Lys Val Tyr
545                 550                 555                 560

Phe Pro Tyr Leu Leu Ile Ser Lys Lys Arg Tyr Ala Gly Leu Leu Phe
                565                 570                 575

Ser Ser Arg Pro Asp Ala His Asp Arg Met Asp Cys Lys Gly Leu Glu
            580                 585                 590

Ala Val Arg Arg Asp Asn Cys Pro Leu Val Ala Asn Leu Val Thr Ala
        595                 600                 605

Ser Leu Arg Arg Leu Leu Ile Asp Arg Asp Pro Glu Gly Ala Val Ala
610                 615                 620

His Ala Gln Asp Val Ile Ser Asp Leu Leu Cys Asn Arg Ile Asp Ile
625                 630                 635                 640

Ser Gln Leu Val Ile Thr Lys Glu Leu Thr Arg Ala Ala Ser Asp Tyr
                645                 650                 655

Ala Gly Lys Gln Ala His Val Glu Leu Ala Glu Arg Met Arg Lys Arg
            660                 665                 670

Asp Pro Gly Ser Ala Pro Ser Leu Gly Asp Arg Val Pro Tyr Val Ile
        675                 680                 685

Ile Ser Ala Ala Lys Gly Val Ala Ala Tyr Met Lys Ser Glu Asp Pro
690                 695                 700

Leu Phe Val Leu Glu His Ser Leu Pro Ile Asp Thr Gln Tyr Tyr Leu
705                 710                 715                 720

Glu Gln Gln Leu Ala Lys Pro Leu Leu Arg Ile Phe Glu Pro Ile Leu
                725                 730                 735

Gly Glu

<210> SEQ ID NO 8
<211> LENGTH: 734
<212> TYPE: PRT
<213> ORGANISM: Candida albicans (Yeast)
```

```
<400> SEQUENCE: 8

Ile Asp Pro Cys Ile Thr Tyr Asp Asn Ile Asn Tyr Leu Leu Arg Leu
  1               5                  10                  15

Met Ile Asp Cys Lys Ile Thr Gly Met Ser Trp Ile Thr Leu Pro Arg
             20                  25                  30

Asp Lys Tyr Lys Ile Val Asn Asn Lys Ile Ser Thr Cys Gln Ile Glu
         35                  40                  45

Cys Ser Ile Asp Tyr Arg Asp Leu Ile Ser His Pro Pro Glu Gly Glu
 50                  55                  60

Trp Leu Lys Met Ala Pro Leu Arg Ile Leu Ser Phe Asp Ile Glu Cys
 65                  70                  75                  80

Ala Gly Arg Lys Gly Val Phe Pro Glu Ala Glu His Asp Pro Val Ile
                 85                  90                  95

Gln Ile Ala Asn Val Val Gln Lys Ser Gly Glu Ser Lys Pro Phe Val
            100                 105                 110

Arg Asn Val Phe Thr Val Asn Thr Cys Ser Ser Ile Ile Gly Ser Gln
            115                 120                 125

Ile Phe Glu His Gln Arg Glu Glu Asp Met Leu Met His Trp Lys Glu
130                 135                 140

Phe Ile Thr Lys Val Asp Pro Asp Val Ile Ile Gly Tyr Asn Thr Ala
145                 150                 155                 160

Asn Phe Asp Ile Pro Tyr Val Leu Asn Arg Ala Lys Ala Leu Gly Leu
                165                 170                 175

Asn Asp Phe Pro Phe Phe Gly Arg Leu Lys Arg Val Lys Gln Glu Ile
            180                 185                 190

Lys Asp Ala Val Phe Ser Ser Arg Ala Tyr Gly Thr Arg Glu Asn Lys
            195                 200                 205

Val Val Asn Ile Asp Gly Arg Met Gln Leu Asp Leu Leu Gln Phe Ile
210                 215                 220

Gln Arg Glu Tyr Lys Leu Arg Ser Tyr Thr Leu Asn Ser Val Ser Ala
225                 230                 235                 240

His Phe Leu Gly Glu Gln Lys Glu Asp Val Gln His Ser Ile Ile Thr
                245                 250                 255

Asp Leu Gln Asn Gly Thr Lys Glu Thr Arg Arg Arg Leu Ala Val Tyr
            260                 265                 270

Cys Leu Lys Asp Ala Phe Leu Pro Leu Arg Leu Leu Asp Lys Leu Met
            275                 280                 285

Cys Leu Val Asn Tyr Thr Glu Met Ala Arg Val Thr Gly Val Pro Phe
290                 295                 300

Ser Tyr Leu Leu Ser Arg Gly Gln Gln Ile Lys Val Ile Ser Gln Leu
305                 310                 315                 320

Phe Arg Lys Cys Leu Gln Glu Asp Ile Val Ile Pro Asn Leu Lys Ser
                325                 330                 335

Glu Gly Ser Asn Glu Glu Tyr Glu Gly Ala Thr Val Ile Glu Pro Glu
            340                 345                 350

Arg Gly Tyr Tyr Asp Val Pro Ile Ala Thr Leu Asp Phe Ser Ser Leu
            355                 360                 365

Tyr Pro Ser Ile Met Met Ala His Asn Leu Cys Tyr Thr Thr Leu Leu
370                 375                 380

Asn Lys Asn Ser Ile Lys Ala Phe Gly Leu Thr Glu Asp Asp Tyr Thr
385                 390                 395                 400

Lys Thr Pro Asn Gly Asp Tyr Phe Val His Ser Asn Leu Arg Lys Gly
                405                 410                 415
```

-continued

```
Ile Leu Pro Thr Ile Leu Asp Glu Leu Leu Thr Ala Arg Lys Lys Ala
            420                 425                 430
Lys Ala Asp Leu Lys Lys Glu Thr Asp Pro Phe Lys Lys Asp Val Leu
        435                 440                 445
Asn Gly Arg Gln Leu Ala Leu Lys Ile Ser Ala Asn Ser Val Tyr Gly
    450                 455                 460
Phe Thr Gly Ala Thr Val Gly Lys Leu Pro Cys Leu Ala Ile Ser Ser
465                 470                 475                 480
Ser Val Thr Ala Phe Gly Arg Glu Met Ile Glu Lys Thr Lys Asn Glu
            485                 490                 495
Val Gln Glu Tyr Tyr Ser Lys Lys Asn Gly His Pro Tyr Asp Ala Lys
        500                 505                 510
Val Ile Tyr Gly Asp Thr Asp Ser Val Met Val Lys Phe Gly Tyr Gln
    515                 520                 525
Asp Leu Glu Thr Cys Met Lys Leu Gly Glu Glu Ala Ala Asn Tyr Val
    530                 535                 540
Ser Thr Lys Phe Lys Asn Pro Ile Lys Leu Glu Phe Glu Lys Val Tyr
545                 550                 555                 560
Phe Pro Tyr Leu Leu Ile Asn Lys Lys Arg Tyr Ala Gly Leu Tyr Trp
                565                 570                 575
Thr Arg Pro Glu Lys Phe Asp Lys Met Asp Thr Lys Gly Ile Glu Thr
            580                 585                 590
Val Arg Arg Asp Asn Cys Gln Leu Val Gln Asn Val Ile Thr Lys Val
        595                 600                 605
Leu Glu Phe Ile Leu Glu Glu Arg Asp Val Pro Lys Ala Gln Arg Phe
    610                 615                 620
Val Lys Gln Thr Ile Ala Asp Leu Leu Gln Asn Arg Ile Asp Leu Ser
625                 630                 635                 640
Gln Leu Val Ile Thr Lys Ala Tyr Ser Lys His Asp Tyr Ser Ala Lys
                645                 650                 655
Gln Ala His Val Glu Leu Ala Glu Arg Met Arg Lys Arg Asp Pro Gly
            660                 665                 670
Ser Ala Pro Thr Leu Gly Asp Arg Val Ala Tyr Val Ile Ile Lys Thr
        675                 680                 685
Gly Gly Asp Lys Asn Tyr Glu Lys Ser Glu Asp Pro Leu Tyr Val Leu
    690                 695                 700
Glu Asn Ser Leu Pro Ile Asp Val Lys Tyr Tyr Leu Asp Gln Gln Leu
705                 710                 715                 720
Thr Lys Pro Leu Glu Arg Ile Phe Ile Pro Ile Leu Gly Glu
                725                 730
```

<210> SEQ ID NO 9
<211> LENGTH: 734
<212> TYPE: PRT
<213> ORGANISM: Saccharomyces cerevisiae

<400> SEQUENCE: 9

```
Ser Asn Gly Thr Thr Thr Tyr Asp Asn Ile Ala Tyr Thr Leu Arg Leu
1               5                   10                  15
Met Val Asp Cys Gly Ile Val Gly Met Ser Trp Ile Thr Leu Pro Lys
            20                  25                  30
Gly Lys Tyr Ser Met Ile Glu Pro Asn Asn Arg Val Ser Ser Cys Gln
        35                  40                  45
Leu Glu Val Ser Ile Asn Tyr Arg Asn Leu Ile Ala His Pro Ala Glu
```

-continued

```
                    50                  55                  60
Gly Asp Trp Ser His Thr Ala Pro Leu Arg Ile Met Ser Phe Asp Ile
 65                  70                  75                  80
Glu Cys Ala Gly Arg Ile Gly Val Phe Pro Glu Pro Glu Tyr Asp Pro
                     85                  90                  95
Val Ile Gln Ile Ala Asn Val Val Ser Ile Ala Gly Ala Lys Lys Pro
                100                 105                 110
Phe Ile Arg Asn Val Phe Thr Leu Asn Thr Cys Ser Pro Ile Thr Gly
                115                 120                 125
Ser Met Ile Phe Ser His Ala Thr Glu Glu Met Leu Ser Asn Trp
130                 135                 140
Arg Asn Phe Ile Ile Lys Val Asp Pro Asp Val Ile Ile Gly Tyr Asn
145                 150                 155                 160
Thr Thr Asn Phe Asp Ile Pro Tyr Leu Leu Asn Arg Ala Lys Ala Leu
                165                 170                 175
Lys Val Asn Asp Phe Pro Tyr Phe Gly Arg Leu Lys Thr Val Lys Gln
                180                 185                 190
Glu Ile Lys Glu Ser Val Phe Ser Ser Lys Ala Tyr Gly Thr Arg Glu
                195                 200                 205
Thr Lys Asn Val Asn Ile Asp Gly Arg Leu Gln Leu Asp Leu Leu Gln
210                 215                 220
Phe Ile Gln Arg Glu Tyr Lys Leu Arg Ser Tyr Thr Leu Asn Ala Val
225                 230                 235                 240
Ser Ala His Phe Leu Gly Glu Gln Lys Glu Asp Val His Tyr Ser Ile
                245                 250                 255
Ile Ser Asp Leu Gln Asn Gly Asp Ser Glu Thr Arg Arg Arg Leu Ala
                260                 265                 270
Val Tyr Cys Leu Lys Asp Ala Tyr Leu Pro Leu Arg Leu Met Glu Lys
                275                 280                 285
Leu Met Ala Leu Val Asn Tyr Thr Glu Met Ala Arg Val Thr Gly Val
290                 295                 300
Pro Phe Ser Tyr Leu Leu Ala Arg Gly Gln Gln Ile Lys Val Val Ser
305                 310                 315                 320
Gln Leu Phe Arg Lys Cys Leu Glu Ile Asp Thr Val Ile Pro Asn Met
                325                 330                 335
Gln Ser Gln Ala Ser Asp Asp Gln Tyr Glu Gly Ala Thr Val Ile Glu
                340                 345                 350
Pro Ile Arg Gly Tyr Tyr Asp Val Pro Ile Ala Thr Leu Asp Phe Asn
                355                 360                 365
Ser Leu Tyr Pro Ser Ile Met Met Ala His Asn Leu Cys Tyr Thr Thr
                370                 375                 380
Leu Cys Asn Lys Ala Thr Val Glu Arg Leu Asn Leu Lys Ile Asp Glu
385                 390                 395                 400
Asp Tyr Val Ile Thr Pro Asn Gly Asp Tyr Phe Val Thr Thr Lys Arg
                405                 410                 415
Arg Arg Gly Ile Leu Pro Ile Ile Leu Asp Glu Leu Ile Ser Ala Arg
                420                 425                 430
Lys Arg Ala Lys Lys Asp Leu Arg Asp Glu Lys Asp Pro Phe Lys Arg
                435                 440                 445
Asp Val Leu Asn Gly Arg Gln Leu Ala Leu Lys Ile Ser Ala Asn Ser
                450                 455                 460
Val Tyr Gly Phe Thr Gly Ala Thr Val Gly Lys Leu Pro Cys Leu Ala
465                 470                 475                 480
```

-continued

```
Ile Ser Ser Ser Val Thr Ala Tyr Gly Arg Thr Met Ile Leu Lys Thr
                485                 490                 495
Lys Thr Ala Val Gln Glu Lys Tyr Cys Ile Lys Asn Gly Tyr Lys His
            500                 505                 510
Asp Ala Val Val Tyr Gly Asp Thr Asp Ser Val Met Val Lys Phe
        515                 520                 525
Gly Thr Thr Asp Leu Lys Glu Ala Met Asp Leu Gly Thr Glu Ala Ala
    530                 535                 540
Lys Tyr Val Ser Thr Leu Phe Lys His Pro Ile Asn Leu Glu Phe Glu
545                 550                 555                 560
Lys Ala Tyr Phe Pro Tyr Leu Leu Ile Asn Lys Lys Arg Tyr Ala Gly
                565                 570                 575
Leu Phe Trp Thr Asn Pro Asp Lys Phe Asp Lys Leu Asp Gln Lys Gly
                580                 585                 590
Leu Ala Ser Val Arg Arg Asp Ser Cys Ser Leu Val Ser Ile Val Met
            595                 600                 605
Asn Lys Val Leu Lys Lys Ile Leu Ile Glu Arg Asn Val Asp Gly Ala
        610                 615                 620
Leu Ala Phe Val Arg Glu Thr Ile Asn Asp Ile Leu His Asn Arg Val
625                 630                 635                 640
Asp Ile Ser Lys Leu Ile Ile Ser Lys Thr Leu Ala Pro Asn Tyr Thr
                645                 650                 655
Asn Pro Gln Pro His Ala Val Leu Ala Glu Arg Met Lys Arg Arg Glu
                660                 665                 670
Gly Val Gly Pro Asn Val Gly Asp Arg Val Asp Tyr Val Ile Ile Gly
            675                 680                 685
Gly Asn Asp Lys Leu Tyr Asn Arg Ala Glu Asp Pro Leu Phe Val Leu
        690                 695                 700
Glu Asn Asn Ile Gln Val Asp Ser Arg Tyr Tyr Leu Thr Asn Gln Leu
705                 710                 715                 720
Gln Asn Pro Ile Ile Ser Ile Val Ala Pro Ile Ile Gly Asp
                725                 730
```

<210> SEQ ID NO 10
<211> LENGTH: 735
<212> TYPE: PRT
<213> ORGANISM: Schizosaccharomyces pombe

<400> SEQUENCE: 10

```
Val Gly Val Thr Thr Phe Glu Ser Asn Thr Gln Tyr Leu Leu Arg Phe
1               5                   10                  15
Met Ile Asp Cys Asp Val Val Gly Met Asn Trp Ile His Leu Pro Ala
            20                  25                  30
Ser Lys Tyr Gln Phe Arg Tyr Gln Asn Arg Val Ser Asn Cys Gln Ile
        35                  40                  45
Glu Ala Trp Ile Asn Tyr Lys Asp Leu Ile Ser Leu Pro Ala Glu Gly
    50                  55                  60
Gln Trp Ser Lys Met Ala Pro Leu Arg Ile Met Ser Phe Asp Ile Glu
65                  70                  75                  80
Cys Ala Gly Arg Lys Gly Val Phe Pro Asp Pro Ser Ile Asp Pro Val
                85                  90                  95
Ile Gln Ile Ala Ser Ile Val Thr Gln Tyr Gly Asp Ser Thr Pro Phe
            100                 105                 110
Val Arg Asn Val Phe Cys Val Asp Thr Cys Ser Gln Ile Val Gly Thr
```

```
            115                 120                 125
Gln Val Tyr Glu Phe Gln Asn Gln Ala Glu Met Leu Ser Ser Trp Ser
    130                 135                 140

Lys Phe Val Arg Asp Val Asp Pro Asp Val Leu Ile Gly Tyr Asn Ile
145                 150                 155                 160

Cys Asn Phe Asp Ile Pro Tyr Leu Leu Asp Arg Ala Lys Ser Leu Arg
                165                 170                 175

Ile His Asn Phe Pro Leu Leu Gly Arg Ile His Asn Phe Phe Ser Val
            180                 185                 190

Ala Lys Glu Thr Ser Phe Ser Ser Lys Ala Tyr Gly Thr Arg Glu Ser
        195                 200                 205

Lys Thr Thr Ser Ile Pro Gly Arg Leu Gln Leu Asp Met Leu Gln Val
    210                 215                 220

Met Gln Arg Asp Phe Lys Leu Arg Ser Tyr Ser Leu Asn Ala Val Cys
225                 230                 235                 240

Ser Gln Phe Leu Gly Glu Gln Lys Glu Asp Val His Tyr Ser Ile Ile
                245                 250                 255

Thr Asp Leu Gln Asn Gly Thr Ala Asp Ser Arg Arg Arg Leu Ala Ile
            260                 265                 270

Tyr Cys Leu Lys Asp Ala Tyr Leu Pro Gln Arg Leu Met Asp Lys Leu
        275                 280                 285

Met Cys Phe Val Asn Tyr Thr Glu Met Ala Arg Val Thr Gly Val Pro
290                 295                 300

Phe Asn Phe Leu Leu Ala Arg Gly Gln Gln Ile Lys Val Ile Ser Gln
305                 310                 315                 320

Leu Phe Cys Lys Ala Leu Gln His Asp Leu Val Val Pro Asn Ile Arg
                325                 330                 335

Val Asn Gly Thr Asp Glu Gln Tyr Glu Gly Ala Thr Val Ile Glu Pro
            340                 345                 350

Ile Lys Gly Tyr Tyr Asp Thr Pro Ile Ala Thr Leu Asp Phe Ser Ser
        355                 360                 365

Leu Tyr Pro Ser Ile Met Gln Ala His Asn Leu Cys Tyr Thr Thr Leu
    370                 375                 380

Leu Asp Ser Asn Thr Ala Glu Leu Leu Lys Leu Lys Gln Asp Val Asp
385                 390                 395                 400

Tyr Ser Val Thr Pro Asn Gly Asp Tyr Phe Val Lys Pro His Val Arg
                405                 410                 415

Lys Gly Leu Leu Pro Ile Ile Leu Ala Asp Leu Leu Asn Ala Arg Lys
            420                 425                 430

Lys Ala Lys Ala Asp Leu Lys Lys Glu Thr Asp Pro Phe Lys Lys Ala
        435                 440                 445

Val Leu Asp Gly Arg Gln Leu Ala Leu Lys Val Ser Ala Asn Ser Val
450                 455                 460

Tyr Gly Phe Thr Gly Ala Thr Asn Gly Arg Leu Pro Cys Leu Ala Ile
465                 470                 475                 480

Ser Ser Ser Val Thr Ser Tyr Gly Arg Gln Met Ile Glu Lys Thr Lys
                485                 490                 495

Asp Val Val Glu Lys Arg Tyr Arg Ile Glu Asn Gly Tyr Ser His Asp
            500                 505                 510

Ala Val Val Ile Tyr Gly Asp Thr Asp Ser Val Met Val Lys Phe Gly
        515                 520                 525

Val Lys Thr Leu Pro Glu Ala Met Lys Leu Gly Glu Glu Ala Ala Asn
    530                 535                 540
```

```
Tyr Val Ser Asp Gln Phe Pro Asn Pro Ile Asn Trp Ser Phe Ser Thr
545                 550                 555                 560

Phe Pro Tyr Leu Leu Ile Ser Lys Lys Arg Tyr Ala Gly Leu Phe Trp
            565                 570                 575

Thr Arg Thr Asp Thr Tyr Asp Lys Met Asp Ser Lys Gly Ile Glu Thr
                580                 585                 590

Val Arg Arg Asp Asn Cys Pro Leu Val Ser Tyr Val Ile Asp Thr Ala
            595                 600                 605

Leu Arg Lys Met Leu Ile Asp Gln Asp Val Glu Gly Ala Gln Leu Phe
        610                 615                 620

Thr Lys Lys Val Ile Ser Asp Leu Leu Gln Asn Lys Ile Asp Met Ser
625                 630                 635                 640

Gln His Val Ile Thr Lys Ala Leu Ser Lys Thr Asp Tyr Ala Ala Lys
                645                 650                 655

Met Ala His Val Glu Leu Ala Glu Arg Met Arg Lys Arg Asp Ala Gly
            660                 665                 670

Ser Ala Pro Ala Ile Gly Asp Arg Val Ala Tyr Val Ile Ile Lys Gly
            675                 680                 685

Ala Gln Gly Asp Gln Phe Tyr Met Arg Ser Glu Asp Pro Ile Tyr Val
690                 695                 700

Leu Glu Asn Asn Ile Pro Ile Asp Ala Lys Tyr Tyr Leu Glu Asn Gln
705                 710                 715                 720

Leu Ser Lys Pro Leu Leu Arg Ile Phe Glu Pro Ile Leu Gly Glu
            725                 730                 735

<210> SEQ ID NO 11
<211> LENGTH: 741
<212> TYPE: PRT
<213> ORGANISM: Plasmodium falciparum

<400> SEQUENCE: 11

Ile Gly Gly Ile Val Tyr Glu Ala Asn Leu Pro Phe Ile Leu Arg Tyr
1               5                   10                  15

Ile Ile Asp His Lys Ile Thr Gly Ser Ser Trp Ile Asn Cys Lys Lys
            20                  25                  30

Gly His Tyr Tyr Ile Arg Asn Lys Asn Lys Lys Ile Ser Asn Cys Thr
        35                  40                  45

Phe Glu Ile Asp Ile Ser Tyr Glu His Val Glu Pro Ile Thr Leu Glu
    50                  55                  60

Asn Glu Tyr Gln Gln Ile Pro Lys Leu Arg Ile Leu Ser Phe Asp Ile
65                  70                  75                  80

Glu Cys Ile Lys Leu Asp Gly Lys Gly Phe Pro Glu Ala Lys Asn Asp
            85                  90                  95

Pro Ile Ile Gln Ile Ser Ser Ile Leu Tyr Phe Gln Gly Glu Pro Ile
            100                 105                 110

Asp Asn Cys Thr Lys Phe Ile Phe Thr Leu Leu Glu Cys Ala Ser Ile
        115                 120                 125

Pro Gly Ser Asn Val Ile Trp Phe Asn Asp Glu Lys Thr Leu Leu Glu
    130                 135                 140

Ala Trp Asn Glu Phe Ile Ile Arg Ile Asp Pro Asp Phe Leu Thr Gly
145                 150                 155                 160

Tyr Asn Ile Ile Asn Phe Asp Leu Pro Tyr Ile Leu Asn Arg Gly Thr
                165                 170                 175

Ala Leu Asn Leu Lys Lys Leu Lys Phe Leu Gly Arg Ile Lys Asn Val
```

-continued

```
              180                 185                 190
Ala Ser Thr Val Lys Asp Ser Ser Phe Ser Ser Lys Gln Phe Gly Thr
              195                 200                 205

His Glu Thr Lys Glu Ile Asn Ile Phe Gly Arg Ile Gln Phe Asp Val
    210                 215                 220

Tyr Asp Leu Ile Lys Arg Asp Tyr Lys Leu Lys Ser Tyr Thr Leu Asn
225                 230                 235                 240

Tyr Val Ser Phe Glu Phe Leu Lys Glu Gln Lys Glu Asp Val His Tyr
                245                 250                 255

Ser Ile Met Asn Asp Leu Gln Asn Glu Ser Pro Glu Ser Arg Lys Arg
            260                 265                 270

Ile Ala Thr Tyr Cys Ile Lys Asp Gly Val Leu Pro Leu Arg Leu Ile
        275                 280                 285

Asp Lys Leu Leu Phe Ile Tyr Asn Tyr Val Glu Met Ala Arg Val Thr
    290                 295                 300

Gly Thr Pro Phe Val Tyr Leu Leu Thr Arg Gly Gln Gln Ile Lys Val
305                 310                 315                 320

Thr Ser Gln Leu Tyr Arg Lys Cys Lys Glu Leu Asn Tyr Val Ile Pro
                325                 330                 335

Ser Thr Tyr Met Lys Val Asn Thr Asn Glu Lys Tyr Glu Gly Ala Thr
            340                 345                 350

Val Leu Glu Pro Ile Lys Gly Tyr Tyr Ile Glu Pro Ile Ser Thr Leu
        355                 360                 365

Asp Phe Ala Ser Leu Tyr Pro Ser Ile Met Ile Ala His Asn Leu Cys
    370                 375                 380

Tyr Ser Thr Leu Ile Lys Ser Asn His Glu Val Ser Asp Leu Gln Asn
385                 390                 395                 400

Asp Asp Ile Thr Thr Ile Gln Gly Lys Asn Asn Leu Lys Phe Val Lys
                405                 410                 415

Lys Asn Val Lys Lys Gly Ile Leu Pro Leu Ile Val Glu Glu Leu Ile
            420                 425                 430

Glu Ala Arg Lys Lys Val Lys Leu Leu Ile Lys Asn Glu Lys Asn Asn
        435                 440                 445

Ile Thr Lys Met Val Leu Asn Gly Arg Gln Leu Ala Leu Lys Ile Ser
    450                 455                 460

Ala Asn Ser Val Tyr Gly Tyr Thr Gly Ala Ser Ser Gly Gly Gln Leu
465                 470                 475                 480

Pro Cys Leu Glu Val Ala Val Ser Ile Thr Thr Leu Gly Arg Ser Met
                485                 490                 495

Ile Glu Lys Thr Lys Glu Arg Val Glu Ser Phe Tyr Cys Lys Ser Asn
            500                 505                 510

Gly Tyr Glu His Asn Ser Thr Val Ile Tyr Gly Asp Thr Asp Ser Val
        515                 520                 525

Met Val Lys Phe Gly Thr Asn Asn Ile Glu Glu Ala Met Thr Leu Gly
    530                 535                 540

Lys Asp Ala Ala Glu Arg Ile Ser Lys Glu Phe Leu Ser Pro Ile Lys
545                 550                 555                 560

Leu Glu Phe Glu Lys Val Tyr Cys Pro Tyr Leu Leu Leu Asn Lys Lys
                565                 570                 575

Arg Tyr Ala Gly Leu Leu Tyr Thr Asn Pro Asn Lys His Asp Lys Met
            580                 585                 590

Asp Cys Lys Gly Ile Glu Thr Val Arg Arg Asp Phe Cys Ile Leu Ile
        595                 600                 605
```

```
Gln Gln Met Met Glu Thr Val Leu Asn Lys Leu Leu Ile Glu Lys Asn
    610                 615                 620
Leu Asn Ser Ala Ile Glu Tyr Thr Lys Ser Lys Ile Lys Glu Leu Leu
625                 630                 635                 640
Thr Asn Asn Ile Asp Met Ser Leu Leu Val Val Thr Lys Ser Leu Gly
                645                 650                 655
Lys Thr Asp Tyr Glu Thr Arg Leu Pro His Val Glu Leu Ala Lys Lys
            660                 665                 670
Leu Lys Gln Arg Asp Ser Ala Thr Ala Pro Asn Val Gly Asp Arg Val
        675                 680                 685
Ser Tyr Ile Ile Val Lys Gly Val Lys Gly Gln Ala Gln Tyr Glu Arg
    690                 695                 700
Ala Glu Asp Pro Leu Tyr Val Leu Asp Asn Asn Leu Ala Ile Asp Tyr
705                 710                 715                 720
Asn His Tyr Leu Asp Ala Ile Lys Ser Pro Leu Ser Arg Ile Phe Glu
                725                 730                 735
Val Ile Met Gln Asn
            740

<210> SEQ ID NO 12
<211> LENGTH: 744
<212> TYPE: PRT
<213> ORGANISM: Chlorella virus NY-2A

<400> SEQUENCE: 12

Glu Tyr Gln Ile Tyr Glu Ser Ser Val Asp Pro Ile Ile Arg Ile Phe
1               5                   10                  15
His Leu Arg Asn Ile Asn Pro Ala Asp Trp Met His Val Ser Lys Ala
            20                  25                  30
Phe Pro Val Glu Thr Arg Ile Ser Asn Ser Asp Ile Glu Val Glu Thr
        35                  40                  45
Ser Phe Gln His Leu Gly Pro Ser Asp Leu Lys Glu Val Pro Pro Leu
    50                  55                  60
Ile Ile Ala Ser Trp Asp Ile Glu Thr Tyr Ser Lys Asp Arg Lys Phe
65                  70                  75                  80
Pro Leu Ala Glu Asn Pro Ala Asp Tyr Cys Ile Gln Ile Ala Thr Thr
                85                  90                  95
Phe Gln Lys Tyr Gly Glu Pro Glu Pro Tyr Arg Arg Val Val Val Cys
            100                 105                 110
Tyr Lys Gln Thr Ala Ser Val Glu Gly Val Glu Ile Ile Ser Cys Ala
        115                 120                 125
Glu Glu Ala Asp Val Met Asn Thr Trp Met Thr Ile Leu Gln Asp Glu
    130                 135                 140
Ile Thr Asp Val Ser Ile Gly Tyr Asn Leu Trp Gln Tyr Asp Leu Arg
145                 150                 155                 160
Tyr Ile His Gly Arg Ser Met Met Cys Val Asp Asp Ile Thr Gly Glu
                165                 170                 175
Asp Asn Val Arg Leu Lys Asn Leu Gly Arg Leu Leu Val Gly Gly Gly
            180                 185                 190
Glu Val Ile Glu Arg Asp Leu Ser Ser Asn Ala Phe Gly Gln Asn Lys
        195                 200                 205
Phe Phe Leu Leu Asp Met Pro Gly Val Met Gln Ile Asp Leu Leu Gln
    210                 215                 220
Trp Phe Arg Lys Asn Arg Asn Leu Glu Ser Tyr Ser Leu Asn Asn Val
```

-continued

```
225                 230                 235                 240

Ser Lys Leu Tyr Leu Gly Asp Gln Lys Asn Asp Leu Pro Ala Met Gln
                245                 250                 255

Ile Phe Glu Lys Phe Glu Gly Gly Ala Asp Asp Arg Ala Ile Ile Ala
                260                 265                 270

Ala Tyr Ala Arg Lys Asp Thr Asp Leu Pro Leu Lys Leu Leu Lys Lys
            275                 280                 285

Met Ala Ile Leu Glu Asp Ile Thr Glu Met Ala Asn Ala Val Lys Val
        290                 295                 300

Pro Val Asp Tyr Ile Asn Phe Arg Gly Gln Gln Val Arg Ala Phe Ser
305                 310                 315                 320

Cys Leu Val Gly Lys Ala Arg Gln Met Asn Tyr Ala Ile Pro Asp Asp
                325                 330                 335

Lys Met Trp Thr Val Asp Gly Lys Tyr Glu Gly Ala Thr Val Leu Asp
                340                 345                 350

Ala Lys Lys Gly Ala Tyr Phe Thr Ser Ile Ala Ala Leu Asp Phe Ala
            355                 360                 365

Ser Leu Tyr Pro Ser Ile Ile Arg Ala His Asn Met Ser Pro Glu Thr
        370                 375                 380

Leu Val Met Asp Lys Arg Phe Glu Asn Leu Pro Gly Ile Glu Tyr Tyr
385                 390                 395                 400

Glu Ile Glu Thr Gly Leu Gly Thr Phe Lys Tyr Pro Gln Lys Asn Asp
                405                 410                 415

Glu Thr Gly Glu Gly Gln Gly Val Val Pro Ala Leu Leu Asp Asp Leu
                420                 425                 430

Ala Lys Phe Arg Lys Gln Ala Lys Lys His Met Ala Glu Ala Lys Lys
            435                 440                 445

Asn Asp Asp Glu Phe Arg Glu Ala Leu Tyr Asp Ala Gln Gln Arg Ser
450                 455                 460

Tyr Lys Ile Val Met Asn Ser Val Tyr Gly Phe Leu Gly Ala Ser Arg
465                 470                 475                 480

Gly Phe Ile Pro Cys Val Pro Ile Ala Ala Ser Val Thr Ala Thr Gly
                485                 490                 495

Arg Lys Met Ile Glu His Thr Ala Lys Arg Val Thr Glu Leu Leu Pro
                500                 505                 510

Gly Ser Glu Val Ile Tyr Gly Asp Thr Asp Ser Val Met Ile Arg Met
            515                 520                 525

Lys Leu Pro Asp Asp Lys Ile His Asp Met Asp Glu Gln Phe Lys Met
        530                 535                 540

Ala Lys Trp Leu Ala Gly Glu Ile Thr Lys Asp Phe Lys Ala Pro Asn
545                 550                 555                 560

Asp Leu Glu Phe Glu Lys Ile Tyr Tyr Pro Tyr Ile Leu Tyr Ser Lys
                565                 570                 575

Lys Arg Tyr Ala Ala Ile Lys Phe Glu Asp Pro Asp Glu Lys Gly Lys
            580                 585                 590

Val Asp Val Lys Gly Leu Ala Leu Val Arg Arg Asp Phe Ser Pro Ile
        595                 600                 605

Thr Arg Glu Ile Leu Lys Glu Ser Leu Asp Thr Ile Leu Phe Lys Lys
        610                 615                 620

Asp Thr Pro Thr Ala Val Thr Glu Thr Val Glu Cys Ile Arg Lys Val
625                 630                 635                 640

Leu Asp Asn Glu Tyr Pro Met Glu Lys Phe Thr Met Ser Lys Thr Leu
                645                 650                 655
```

-continued

```
Lys Thr Gly Tyr Lys Asn Glu Cys Gln Pro His Leu His Val Ser Asn
            660                 665                 670
Lys Ile Phe Glu Arg Thr Gly Phe Pro Val Pro Ser Gly Ala Arg Val
        675                 680                 685
Pro Phe Val Tyr Ile Glu Asp Lys Lys Asn Leu Asp Thr Lys Gln Ser
        690                 695                 700
Phe Arg Ala Glu Asp Pro Thr Phe Ala Gln Glu Asn Asp Leu Ile Val
705                 710                 715                 720
Asp Arg Leu Phe Tyr Ile Glu His Gln Leu Met Lys Pro Ile Cys Ser
            725                 730                 735
Leu Phe Glu Pro Leu Leu Asp Asp
            740

<210> SEQ ID NO 13
<211> LENGTH: 743
<212> TYPE: PRT
<213> ORGANISM: Paramecium bursaria chlorella virus 1

<400> SEQUENCE: 13

Tyr Gln Ile Tyr Glu Ser Ser Val Asp Pro Ile Ile Arg Val Phe His
1               5                   10                  15
Leu Arg Asn Ile Asn Pro Ala Asp Trp Ile Arg Val Ser Lys Ala Tyr
            20                  25                  30
Pro Ala Gln Thr Arg Ile Ser Asn Ser Asp Ile Glu Val Glu Thr Ser
        35                  40                  45
Phe Gln His Leu Gly Pro Val Glu Asp Lys Thr Val Pro Pro Leu Val
    50                  55                  60
Ile Ala Ser Trp Asp Ile Glu Thr Tyr Ser Lys Asp Arg Lys Phe Pro
65                  70                  75                  80
Leu Ala Glu Asn Pro Thr Asp Tyr Cys Ile Gln Ile Ala Thr Thr Phe
                85                  90                  95
Gln Lys Tyr Gly Glu Pro Glu Pro Tyr Arg Arg Val Val Val Cys Tyr
            100                 105                 110
Lys Gln Thr Ala Pro Val Glu Gly Val Glu Ile Ile Ser Cys Leu Glu
        115                 120                 125
Glu Ser Asp Val Met Asn Thr Trp Met Lys Ile Leu Gln Asp Glu Lys
    130                 135                 140
Thr Asp Val Ser Ile Gly Tyr Asn Thr Trp Gln Tyr Asp Leu Arg Tyr
145                 150                 155                 160
Val His Gly Arg Thr Gln Met Cys Val Asp Asp Met Thr Gly Glu Asp
                165                 170                 175
Lys Val Lys Leu Ser Asn Leu Gly Arg Leu Leu Ser Gly Gly Gly Glu
            180                 185                 190
Val Val Glu Arg Asp Leu Ser Ser Asn Ala Phe Gly Gln Asn Lys Phe
        195                 200                 205
Phe Leu Leu Asp Met Pro Gly Val Met Gln Ile Asp Leu Leu Gln Trp
    210                 215                 220
Phe Arg Lys Asn Arg Asn Leu Glu Ser Tyr Ser Leu Asn Asn Val Ser
225                 230                 235                 240
Lys Leu Tyr Leu Gly Asp Gln Lys Asn Asp Leu Pro Ala Met Gln Ile
                245                 250                 255
Phe Glu Lys Phe Glu Gly Asn Ala Glu Asp Arg Ala Ile Ile Ala Ala
            260                 265                 270
Tyr Ala Ala Lys Asp Thr Asp Leu Pro Leu Lys Leu Leu Lys Lys Met
```

-continued

```
            275                 280                 285
Ala Ile Leu Glu Asp Leu Thr Glu Met Ala Asn Ala Val Lys Val Pro
            290                 295                 300

Val Asp Tyr Ile Asn Phe Arg Gly Gln Gln Ile Arg Ala Phe Ser Cys
305                 310                 315                 320

Leu Val Gly Lys Ala Arg Gln Met Asn Tyr Ala Ile Pro Asp Asp Lys
                325                 330                 335

Ala Trp Ala Thr Glu Gly Lys Tyr Glu Gly Ala Thr Val Leu Asp Ala
                340                 345                 350

Lys Lys Gly Ala Tyr Phe Thr Pro Ile Ala Ala Leu Asp Phe Ala Ser
                355                 360                 365

Leu Tyr Pro Ser Ile Ile Arg Ala His Asn Met Ser Pro Glu Thr Leu
    370                 375                 380

Val Met Glu Lys Arg Phe Glu Asn Val Pro Gly Val Glu Tyr Tyr Glu
385                 390                 395                 400

Ile Glu Thr Gly Leu Gly Lys Phe Lys Tyr Ala Gln Lys Asn Asp Glu
                405                 410                 415

Thr Gly Glu Gly Gln Gly Val Val Pro Ala Leu Leu Asp Asp Leu Ala
                420                 425                 430

Lys Phe Arg Lys Leu Ala Lys Lys His Met Ala Glu Ala Lys Arg Asn
                435                 440                 445

Gly Asp Asp Phe Lys Glu Ala Leu Tyr Asp Ala Gln Gln Arg Ser Phe
    450                 455                 460

Lys Val Val Met Asn Ser Val Tyr Gly Phe Leu Gly Ala Ser Lys Gly
465                 470                 475                 480

Phe Ile Pro Cys Val Pro Ile Ala Ala Ser Val Thr Ala Thr Gly Arg
                485                 490                 495

Lys Met Ile Glu His Thr Ala Lys Arg Ala Val Glu Leu Leu Pro Gly
                500                 505                 510

Ser Glu Val Ile Tyr Gly Asp Thr Asp Ser Val Met Val Lys Met Lys
                515                 520                 525

Leu Pro Asp Asp Lys Val His Asp Met Asp Glu Gln Phe Lys Met Ala
    530                 535                 540

Lys Trp Leu Ala Gly Glu Ile Thr Lys Asp Phe Arg Ala Pro Asn Asp
545                 550                 555                 560

Leu Glu Phe Glu Lys Ile Tyr Tyr Pro Tyr Ile Leu Tyr Ser Lys Lys
                565                 570                 575

Arg Tyr Ala Ala Val Lys Phe Glu Glu Pro Asp Glu Lys Gly Lys Val
                580                 585                 590

Asp Val Lys Gly Leu Ala Leu Val Arg Arg Asp Phe Ser Pro Ile Thr
                595                 600                 605

Arg Asp Ile Leu Lys Glu Ser Leu Asp Thr Ile Leu Tyr Lys Lys Asp
    610                 615                 620

Thr Pro Thr Ala Val Ser Glu Thr Leu Glu Arg Ile Arg Lys Val Leu
625                 630                 635                 640

Asp Asn Glu Tyr Pro Met Glu Lys Phe Met Met Ser Lys Leu Leu Lys
                645                 650                 655

Thr Gly Tyr Lys Asn Glu Cys Gln Pro His Leu His Val Ala Asn Lys
                660                 665                 670

Ile Tyr Glu Arg Thr Gly Phe Pro Val Pro Ser Gly Ala Arg Val Pro
                675                 680                 685

Phe Val Tyr Ile Glu Asp Lys Lys Asn Pro Asp Ile Lys Gln Ser Phe
    690                 695                 700
```

-continued

Lys Ala Glu Asp Pro Thr Phe Ala Gln Asp Asn Gly Leu Ile Val Asp
705                 710                 715                 720

Arg Leu Phe Tyr Ile Glu His Gln Leu Leu Lys Pro Ile Cys Ser Leu
            725                 730                 735

Phe Glu Pro Leu Leu Asp Asp
            740

<210> SEQ ID NO 14
<211> LENGTH: 773
<212> TYPE: PRT
<213> ORGANISM: Epstein-barr virus (strain B95-8)

<400> SEQUENCE: 14

Gly Cys Arg Ile Phe Glu Ala Asn Val Asp Ala Thr Arg Arg Phe Val
1               5                   10                  15

Leu Asp Asn Asp Phe Val Thr Phe Gly Trp Tyr Ser Cys Arg Arg Ala
            20                  25                  30

Ile Pro Arg Leu Gln His Arg Asp Ser Tyr Ala Glu Leu Glu Tyr Asp
            35                  40                  45

Cys Glu Val Gly Asp Leu Ser Val Arg Arg Glu Asp Ser Ser Trp Pro
    50                  55                  60

Ser Tyr Gln Ala Leu Ala Phe Asp Ile Glu Cys Leu Gly Glu Glu Gly
65                  70                  75                  80

Phe Pro Thr Ala Thr Asn Glu Ala Asp Leu Ile Leu Gln Ile Ser Cys
            85                  90                  95

Val Leu Trp Ser Thr Gly Glu Glu Ala Gly Arg Tyr Arg Arg Ile Leu
            100                 105                 110

Leu Thr Leu Gly Thr Cys Glu Asp Ile Glu Gly Val Glu Val Tyr Glu
            115                 120                 125

Phe Pro Ser Glu Leu Asp Met Leu Tyr Ala Phe Phe Gln Leu Ile Arg
            130                 135                 140

Asp Leu Ser Val Glu Ile Val Thr Gly Tyr Asn Val Ala Asn Phe Asp
145                 150                 155                 160

Trp Pro Tyr Ile Leu Asp Arg Ala Arg His Ile Tyr Ser Ile Asn Pro
            165                 170                 175

Ala Ser Leu Gly Lys Ile Arg Ala Gly Gly Val Cys Glu Val Arg Arg
            180                 185                 190

Pro His Asp Ala Gly Lys Gly Phe Leu Arg Ala Asn Thr Lys Val Arg
            195                 200                 205

Ile Thr Gly Leu Ile Pro Ile Asp Met Tyr Ala Val Cys Arg Asp Lys
210                 215                 220

Leu Ser Leu Ser Asp Tyr Lys Leu Asp Thr Val Ala Arg His Leu Leu
225                 230                 235                 240

Gly Ala Lys Lys Glu Asp Val His Tyr Lys Glu Ile Pro Arg Leu Phe
            245                 250                 255

Ala Ala Gly Pro Glu Gly Arg Arg Leu Gly Met Tyr Cys Val Gln
            260                 265                 270

Asp Ser Ala Leu Val Met Asp Leu Leu Asn His Phe Val Ile His Val
            275                 280                 285

Glu Val Ala Glu Ile Ala Lys Ile Ala His Ile Pro Cys Arg Arg Val
            290                 295                 300

Leu Asp Asp Gly Gln Gln Ile Arg Val Phe Ser Cys Leu Leu Ala Ala
305                 310                 315                 320

Ala Gln Lys Glu Asn Phe Ile Leu Pro Met Pro Ser Ala Ser Asp Arg

-continued

```
                  325                 330                 335
Asp Gly Tyr Gln Gly Ala Thr Val Ile Gln Pro Leu Ser Gly Phe Tyr
                340                 345                 350
Asn Ser Pro Val Leu Val Val Asp Phe Ala Ser Leu Tyr Pro Ser Ile
            355                 360                 365
Ile Gln Ala His Asn Leu Cys Tyr Ser Thr Met Ile Thr Pro Gly Glu
    370                 375                 380
Glu His Arg Leu Ala Gly Leu Arg Pro Gly Glu Asp Tyr Glu Ser Phe
385                 390                 395                 400
Arg Leu Thr Gly Gly Val Tyr His Phe Val Lys Lys His Val His Glu
                405                 410                 415
Ser Phe Leu Ala Ser Leu Leu Thr Ser Trp Leu Ala Lys Arg Lys Ala
                420                 425                 430
Ile Lys Lys Leu Leu Ala Ala Cys Glu Asp Pro Arg Gln Arg Thr Ile
            435                 440                 445
Leu Asp Lys Gln Gln Leu Ala Ile Lys Cys Thr Cys Asn Ala Val Tyr
    450                 455                 460
Gly Phe Thr Gly Val Ala Asn Gly Leu Phe Pro Cys Leu Ser Ile Ala
465                 470                 475                 480
Glu Thr Val Thr Leu Gln Gly Arg Thr Met Leu Glu Arg Ala Lys Ala
                485                 490                 495
Phe Val Glu Ala Leu Ser Pro Ala Asn Leu Gln Ala Leu Ala Pro Ser
                500                 505                 510
Pro Asp Ala Trp Ala Pro Leu Asn Pro Glu Gly Gln Leu Arg Val Ile
            515                 520                 525
Tyr Gly Asp Thr Asp Ser Leu Phe Ile Glu Cys Arg Gly Phe Ser Glu
    530                 535                 540
Ser Glu Thr Leu Arg Phe Ala Asp Ala Leu Ala Ala His Thr Thr Arg
545                 550                 555                 560
Ser Leu Phe Val Ala Pro Ile Ser Leu Glu Ala Glu Lys Thr Phe Ser
                565                 570                 575
Cys Leu Met Leu Ile Thr Lys Lys Arg Tyr Val Gly Val Leu Thr Asp
                580                 585                 590
Gly Lys Thr Leu Met Lys Gly Val Glu Leu Val Arg Lys Thr Ala Cys
            595                 600                 605
Lys Phe Val Gln Thr Arg Cys Arg Arg Val Leu Asp Leu Val Leu Ala
    610                 615                 620
Asp Ala Arg Val Lys Glu Ala Ala Ser Leu Leu Ser His Arg Pro Phe
625                 630                 635                 640
Gln Glu Ser Phe Thr Gln Gly Leu Pro Val Gly Phe Leu Pro Val Ile
                645                 650                 655
Asp Ile Leu Asn Gln Ala Tyr Thr Asp Leu Arg Glu Gly Arg Val Pro
            660                 665                 670
Met Gly Glu Leu Cys Phe Ser Thr Glu Leu Ser Arg Lys Leu Ser Ala
    675                 680                 685
Tyr Lys Ser Thr Gln Met Pro His Leu Ala Val Tyr Gln Lys Phe Val
    690                 695                 700
Glu Arg Asn Glu Glu Leu Pro Gln Ile His Asp Arg Ile Gln Tyr Val
705                 710                 715                 720
Phe Val Glu Pro Lys Gly Gly Val Lys Gly Ala Arg Lys Thr Glu Met
                725                 730                 735
Ala Glu Asp Pro Ala Tyr Ala Glu Arg His Gly Val Pro Val Ala Val
            740                 745                 750
```

```
Asp His Tyr Phe Asp Lys Leu Leu Gln Gly Ala Ala Asn Ile Leu Gln
            755                 760                 765

Cys Leu Phe Asp Asn
        770

<210> SEQ ID NO 15
<211> LENGTH: 764
<212> TYPE: PRT
<213> ORGANISM: Herpesvirus saimiri (strain 11)

<400> SEQUENCE: 15

Gly Cys Glu Val Phe Glu Thr Asn Val Asp Ala Ile Arg Arg Phe Val
  1               5                  10                  15

Ile Asp Asn Asp Phe Ser Thr Phe Gly Trp Tyr Thr Cys Lys Ser Ala
             20                  25                  30

Cys Pro Arg Ile Thr Asn Arg Asp Ser His Thr Asp Ile Glu Phe Asp
         35                  40                  45

Cys Gly Tyr Tyr Asp Leu Glu Phe His Ala Asp Arg Thr Glu Trp Pro
     50                  55                  60

Pro Tyr Asn Ile Met Ser Phe Asp Ile Glu Cys Ile Gly Glu Lys Gly
 65                  70                  75                  80

Phe Pro Cys Ala Lys Asn Glu Gly Asp Leu Ile Ile Gln Ile Ser Cys
                 85                  90                  95

Val Phe Trp His Ala Gly Ala Leu Asp Thr Thr Arg Asn Met Leu Leu
            100                 105                 110

Ser Leu Gly Thr Cys Ser Ala Val Glu Asn Thr Glu Val Tyr Glu Phe
        115                 120                 125

Pro Ser Glu Ile Asp Met Leu His Gly Phe Phe Ser Leu Ile Arg Asp
    130                 135                 140

Phe Asn Val Glu Ile Ile Thr Gly Tyr Asn Ile Ser Asn Phe Asp Leu
145                 150                 155                 160

Pro Tyr Leu Ile Asp Arg Ala Thr Gln Ile Tyr Asn Ile Lys Leu Ser
                165                 170                 175

Asp Tyr Ser Arg Val Lys Thr Gly Ser Ile Phe Gln Val His Thr Pro
            180                 185                 190

Lys Asp Thr Gly Asn Gly Phe Met Arg Ser Val Ser Lys Ile Lys Ile
        195                 200                 205

Ser Gly Ile Ile Ala Ile Asp Met Tyr Ile Val Cys Lys Asp Lys Leu
    210                 215                 220

Ser Leu Ser Asn Tyr Lys Leu Asp Thr Val Ala Asn His Cys Ile Gly
225                 230                 235                 240

Ala Lys Lys Glu Asp Val Ser Tyr Lys Asp Ile Met Pro Leu Phe Met
                245                 250                 255

Ser Gly Pro Glu Gly Arg Ala Lys Ile Gly Leu Tyr Cys Val Ile Asp
            260                 265                 270

Ser Val Leu Val Met Lys Leu Leu Lys Phe Phe Met Ile His Val Glu
        275                 280                 285

Ile Ser Glu Ile Ala Lys Leu Ala Lys Ile Pro Thr Arg Arg Val Leu
    290                 295                 300

Thr Asp Gly Gln Gln Ile Arg Val Phe Ser Cys Leu Leu Ala Ala Ala
305                 310                 315                 320

Arg Ala Glu Asn Tyr Ile Leu Pro Val Ser Asn Asp Val Asn Ala Asp
                325                 330                 335

Gly Phe Gln Gly Ala Thr Val Ile Asn Pro Ile Pro Gly Phe Tyr Asn
```

```
              340                 345                 350
Asn Ala Val Leu Val Val Asp Phe Ala Ser Leu Tyr Pro Ser Ile Ile
            355                 360                 365

Gln Ala His Asn Leu Cys Tyr Ser Thr Leu Ile Pro His His Ala Leu
370                 375                 380

His Asn Tyr Pro His Leu Lys Ser Ser Asp Tyr Glu Thr Phe Met Leu
385                 390                 395                 400

Ser Ser Gly Pro Ile His Phe Val Lys Lys His Ile Gln Ala Ser Leu
                405                 410                 415

Leu Ser Arg Leu Leu Thr Val Trp Leu Ser Lys Arg Lys Ala Ile Arg
            420                 425                 430

Gln Lys Leu Ala Glu Cys Glu Asp Leu Asp Thr Lys Thr Ile Leu Asp
        435                 440                 445

Lys Gln Gln Leu Ala Ile Lys Val Thr Cys Asn Ala Val Tyr Gly Phe
    450                 455                 460

Thr Gly Val Ala Ser Gly Leu Leu Pro Cys Ile Ser Ile Ala Glu Thr
465                 470                 475                 480

Val Thr Leu Gln Gly Arg Thr Met Leu Glu Lys Ser Lys Ile Phe Ile
                485                 490                 495

Glu Ala Met Thr Pro Asp Thr Leu Gln Glu Ile Val Pro His Ile Val
            500                 505                 510

Lys His Glu Pro Asp Ala Lys Phe Arg Val Ile Tyr Gly Asp Thr Asp
        515                 520                 525

Ser Leu Phe Val Glu Cys Val Gly Tyr Ser Val Asp Thr Val Val Lys
    530                 535                 540

Phe Gly Asp Phe Leu Ala Ala Phe Thr Ser Glu Lys Leu Phe Asn Ala
545                 550                 555                 560

Pro Ile Lys Leu Glu Ser Glu Lys Thr Phe Gln Cys Leu Leu Leu Leu
                565                 570                 575

Ala Lys Lys Arg Tyr Ile Gly Ile Leu Ser Asn Asp Lys Leu Leu Met
            580                 585                 590

Lys Gly Val Asp Leu Val Arg Lys Thr Ala Cys Lys Phe Val Gln Asn
        595                 600                 605

Thr Ser Ser Lys Ile Leu Asn Leu Ile Leu Lys Asp Pro Glu Val Lys
    610                 615                 620

Ala Ala Ala Gln Leu Leu Ser Thr Lys Asp Pro Asp Tyr Ala Phe Arg
625                 630                 635                 640

Glu Gly Leu Pro Asp Gly Phe Leu Lys Val Ile Asp Ile Leu Asn Glu
                645                 650                 655

Ser His Lys Asn Leu Arg Thr Gly Gln Val Pro Val Glu Glu Leu Thr
            660                 665                 670

Phe Ser Thr Glu Leu Ser Arg Pro Ile Ser Ser Tyr Lys Thr Glu Asn
        675                 680                 685

Leu Pro His Leu Thr Val Tyr Lys Lys Ile Ile Thr Arg His Glu Glu
    690                 695                 700

Pro Pro Gln Val His Asp Arg Ile Pro Tyr Val Phe Val Gly Lys Thr
705                 710                 715                 720

Thr Ser Cys Ile Ser Asn Met Ala Glu Asp Pro Thr Tyr Thr Val Gln
                725                 730                 735

Asn Asn Ile Pro Ile Ala Val Asp Leu Tyr Phe Asp Lys Leu Ile His
            740                 745                 750

Gly Val Ala Asn Ile Ile Gln Cys Leu Phe Lys Asp
        755                 760
```

<210> SEQ ID NO 16
<211> LENGTH: 892
<212> TYPE: PRT
<213> ORGANISM: Herpes simplex virus (type 1/strain 17)

<400> SEQUENCE: 16

```
Pro Ala Ile Lys Lys Tyr Glu Gly Gly Val Asp Ala Thr Thr Arg Phe
 1               5                  10                  15

Ile Leu Asp Asn Pro Gly Phe Val Thr Phe Gly Trp Tyr Arg Leu Lys
            20                  25                  30

Pro Gly Arg Asn Asn Thr Leu Ala Gln Pro Ala Ala Pro Met Ala Phe
        35                  40                  45

Gly Thr Ser Ser Asp Val Glu Phe Asn Cys Thr Ala Asp Asn Leu Ala
 50                  55                  60

Ile Glu Gly Gly Met Ser Asp Leu Pro Ala Tyr Lys Leu Met Cys Phe
 65                  70                  75                  80

Asp Ile Glu Cys Lys Ala Gly Gly Glu Asp Glu Leu Ala Phe Pro Val
                85                  90                  95

Ala Gly His Pro Glu Asp Leu Val Ile Gln Ile Ser Cys Leu Leu Tyr
            100                 105                 110

Asp Leu Ser Thr Thr Ala Leu Glu His Val Leu Leu Phe Ser Leu Gly
        115                 120                 125

Ser Cys Asp Leu Pro Glu Ser His Leu Asn Glu Leu Ala Ala Arg Gly
130                 135                 140

Leu Pro Thr Pro Val Val Leu Glu Phe Asp Ser Glu Phe Glu Met Leu
145                 150                 155                 160

Leu Ala Phe Met Thr Leu Val Lys Gln Tyr Gly Pro Glu Phe Val Thr
                165                 170                 175

Gly Tyr Asn Ile Ile Asn Phe Asp Trp Pro Phe Leu Leu Ala Lys Leu
            180                 185                 190

Thr Asp Ile Tyr Lys Val Pro Leu Asp Gly Tyr Gly Arg Met Asn Gly
        195                 200                 205

Arg Gly Val Phe Arg Val Trp Asp Ile Gly Gln Ser His Phe Gln Lys
210                 215                 220

Arg Ser Lys Ile Lys Val Asn Gly Met Val Asn Ile Asp Met Tyr Gly
225                 230                 235                 240

Ile Ile Thr Asp Lys Ile Lys Leu Ser Ser Tyr Lys Leu Asn Ala Val
                245                 250                 255

Ala Glu Ala Val Leu Lys Asp Lys Lys Asp Leu Ser Tyr Arg Asp
            260                 265                 270

Ile Pro Ala Tyr Tyr Ala Ala Gly Pro Ala Gln Arg Gly Val Ile Gly
        275                 280                 285

Glu Tyr Cys Ile Gln Asp Ser Leu Leu Val Gly Gln Leu Phe Phe Lys
290                 295                 300

Phe Leu Pro His Leu Glu Leu Ser Ala Val Ala Arg Leu Ala Gly Ile
305                 310                 315                 320

Asn Ile Thr Arg Thr Ile Tyr Asp Gly Gln Gln Ile Arg Val Phe Thr
                325                 330                 335

Cys Leu Leu Arg Leu Ala Asp Gln Lys Gly Phe Ile Leu Pro Asp Thr
            340                 345                 350

Gln Gly Arg Phe Arg Gly Ala Gly Glu Ala Pro Lys Arg Pro Ala
        355                 360                 365

Ala Ala Arg Glu Asp Glu Glu Arg Pro Glu Glu Glu Gly Glu Asp Glu
```

```
              370                 375                 380
Asp Glu Arg Glu Glu Gly Gly Glu Arg Glu Pro Glu Gly Ala Arg
385                 390                 395                 400

Glu Thr Ala Gly Arg His Val Gly Tyr Gln Gly Ala Arg Val Leu Asp
                405                 410                 415

Pro Thr Ser Gly Phe His Val Asn Pro Val Val Phe Asp Phe Ala
                420                 425                 430

Ser Leu Tyr Pro Ser Ile Ile Gln Ala His Asn Leu Cys Phe Ser Thr
                435                 440                 445

Leu Ser Leu Arg Ala Asp Ala Val Ala His Leu Glu Ala Gly Lys Asp
        450                 455                 460

Tyr Leu Glu Ile Glu Val Gly Gly Arg Leu Phe Phe Val Lys Ala
465                 470                 475                 480

His Val Arg Glu Ser Leu Leu Ser Ile Leu Leu Arg Asp Trp Leu Ala
                485                 490                 495

Met Arg Lys Gln Ile Arg Ser Arg Ile Pro Gln Ser Ser Pro Glu Glu
                500                 505                 510

Ala Val Leu Leu Asp Lys Gln Gln Ala Ala Ile Lys Val Val Cys Asn
        515                 520                 525

Ser Val Tyr Gly Phe Thr Gly Val Gln His Gly Leu Leu Pro Cys Leu
        530                 535                 540

His Val Ala Ala Thr Val Thr Thr Ile Gly Arg Glu Met Leu Leu Ala
545                 550                 555                 560

Thr Arg Glu Tyr Val His Ala Arg Trp Ala Ala Phe Glu Gln Leu Leu
                565                 570                 575

Ala Asp Phe Pro Glu Ala Ala Asp Met Arg Ala Pro Gly Pro Tyr Ser
                580                 585                 590

Met Arg Ile Ile Tyr Gly Asp Thr Asp Ser Ile Phe Val Leu Cys Arg
                595                 600                 605

Gly Leu Thr Ala Ala Gly Leu Thr Ala Val Gly Asp Lys Met Ala Ser
        610                 615                 620

His Ile Ser Arg Ala Leu Phe Leu Pro Pro Ile Lys Leu Glu Cys Glu
625                 630                 635                 640

Lys Thr Phe Thr Lys Leu Leu Leu Ile Ala Lys Lys Lys Tyr Ile Gly
                645                 650                 655

Val Ile Tyr Gly Gly Lys Met Leu Ile Lys Gly Val Asp Leu Val Arg
                660                 665                 670

Lys Asn Asn Cys Ala Phe Ile Asn Arg Thr Ser Arg Ala Leu Val Asp
                675                 680                 685

Leu Leu Phe Tyr Asp Asp Thr Val Ser Gly Ala Ala Ala Leu Ala
        690                 695                 700

Glu Arg Pro Ala Glu Glu Trp Leu Ala Arg Pro Leu Pro Glu Gly Leu
705                 710                 715                 720

Gln Ala Phe Gly Ala Val Leu Val Asp Ala His Arg Arg Ile Thr Asp
                725                 730                 735

Pro Glu Arg Asp Ile Gln Asp Phe Val Leu Thr Ala Glu Leu Ser Arg
                740                 745                 750

His Pro Arg Ala Tyr Thr Asn Lys Arg Leu Ala His Leu Thr Val Tyr
                755                 760                 765

Tyr Lys Leu Met Ala Arg Arg Ala Gln Val Pro Ser Ile Lys Asp Arg
                770                 775                 780

Ile Pro Tyr Val Ile Val Ala Gln Thr Arg Glu Val Glu Glu Thr Val
785                 790                 795                 800
```

```
Ala Arg Leu Ala Ala Leu Arg Glu Leu Asp Ala Ala Pro Gly Asp
            805                 810                 815

Glu Pro Ala Pro Pro Ala Ala Leu Pro Ser Pro Ala Lys Arg Pro Arg
            820                 825                 830

Glu Thr Pro Ser Pro Ala Asp Pro Pro Gly Gly Ala Ser Lys Pro Arg
            835                 840                 845

Lys Leu Leu Val Ser Glu Leu Ala Glu Asp Pro Ala Tyr Ala Ile Ala
            850                 855                 860

His Gly Val Ala Leu Asn Thr Asp Tyr Tyr Phe Ser His Leu Leu Gly
865                 870                 875                 880

Ala Ala Cys Val Thr Phe Lys Ala Leu Phe Gly Asn
                885                 890

<210> SEQ ID NO 17
<211> LENGTH: 896
<212> TYPE: PRT
<213> ORGANISM: Herpes simplex virus (type 2/strain 186)

<400> SEQUENCE: 17

Pro Ala Ile Arg Lys Tyr Glu Gly Gly Val Asp Ala Thr Thr Arg Phe
1               5                   10                  15

Ile Leu Asp Asn Pro Gly Phe Val Thr Phe Gly Trp Tyr Arg Leu Lys
            20                  25                  30

Pro Gly Arg Gly Asn Ala Pro Ala Gln Pro Arg Pro Pro Thr Ala Phe
        35                  40                  45

Gly Thr Ser Ser Asp Val Glu Phe Asn Cys Thr Ala Asp Asn Leu Ala
    50                  55                  60

Val Glu Gly Ala Met Cys Asp Leu Pro Ala Tyr Lys Leu Met Cys Phe
65                  70                  75                  80

Asp Ile Glu Cys Lys Ala Gly Gly Glu Asp Glu Leu Ala Phe Pro Val
                85                  90                  95

Ala Glu Arg Pro Glu Asp Leu Val Ile Gln Ile Ser Cys Leu Leu Tyr
            100                 105                 110

Asp Leu Ser Thr Thr Ala Leu Glu His Ile Leu Leu Phe Ser Leu Gly
        115                 120                 125

Ser Cys Asp Leu Pro Glu Ser His Leu Ser Asp Leu Ala Ser Arg Gly
    130                 135                 140

Leu Pro Ala Pro Val Val Leu Glu Phe Asp Ser Glu Phe Glu Met Leu
145                 150                 155                 160

Leu Ala Phe Met Thr Phe Val Lys Gln Tyr Gly Pro Glu Phe Val Thr
                165                 170                 175

Gly Tyr Asn Ile Ile Asn Phe Asp Trp Pro Phe Val Leu Thr Lys Leu
            180                 185                 190

Thr Glu Ile Tyr Lys Val Pro Leu Asp Gly Tyr Gly Arg Met Asn Gly
        195                 200                 205

Arg Gly Val Phe Arg Val Trp Asp Ile Gly Gln Ser His Phe Gln Lys
    210                 215                 220

Arg Ser Lys Ile Lys Val Asn Gly Met Val Asn Ile Asp Met Tyr Gly
225                 230                 235                 240

Ile Ile Thr Asp Lys Val Lys Leu Ser Ser Tyr Lys Leu Asn Ala Val
                245                 250                 255

Ala Glu Ala Val Leu Lys Asp Lys Lys Lys Asp Leu Ser Tyr Arg Asp
            260                 265                 270

Ile Pro Ala Tyr Tyr Ala Ser Gly Pro Ala Gln Arg Gly Val Ile Gly
```

-continued

```
              275                 280                 285
Glu Tyr Cys Val Gln Asp Ser Leu Leu Val Gly Gln Leu Phe Phe Lys
        290                 295                 300
Phe Leu Pro His Leu Glu Leu Ser Ala Val Ala Arg Leu Ala Gly Ile
305                 310                 315                 320
Asn Ile Thr Arg Thr Ile Tyr Asp Gly Gln Gln Ile Arg Val Phe Thr
                325                 330                 335
Cys Leu Arg Leu Ala Gly Gln Lys Gly Phe Ile Leu Pro Asp Thr
                340                 345                 350
Gln Gly Arg Phe Arg Gly Leu Asp Lys Glu Ala Pro Lys Arg Pro Ala
                355                 360                 365
Val Pro Arg Gly Glu Gly Glu Arg Pro Gly Asp Gly Asn Gly Asp Glu
        370                 375                 380
Asp Lys Asp Asp Asp Glu Asp Gly Asp Glu Asp Gly Asp Glu Arg Glu
385                 390                 395                 400
Glu Val Ala Arg Glu Thr Gly Gly Arg His Val Gly Tyr Gln Gly Ala
                405                 410                 415
Arg Val Leu Asp Pro Thr Ser Gly Phe His Val Asp Pro Val Val Val
                420                 425                 430
Phe Asp Phe Ala Ser Leu Tyr Pro Ser Ile Ile Gln Ala His Asn Leu
                435                 440                 445
Cys Phe Ser Thr Leu Ser Leu Arg Pro Glu Ala Val Ala His Leu Glu
        450                 455                 460
Ala Asp Arg Asp Tyr Leu Glu Ile Glu Val Gly Arg Arg Leu Phe
465                 470                 475                 480
Phe Val Lys Ala His Val Arg Glu Ser Leu Leu Ser Ile Leu Leu Arg
                485                 490                 495
Asp Trp Leu Ala Met Arg Lys Gln Ile Arg Ser Arg Ile Pro Gln Ser
                500                 505                 510
Pro Pro Glu Glu Ala Val Leu Leu Asp Lys Gln Gln Ala Ala Ile Lys
        515                 520                 525
Val Val Cys Asn Ser Val Tyr Gly Phe Thr Gly Val Gln His Gly Leu
        530                 535                 540
Leu Pro Cys Leu His Val Ala Ala Thr Val Thr Thr Ile Gly Arg Glu
545                 550                 555                 560
Met Leu Leu Ala Thr Arg Ala Tyr Val His Ala Arg Trp Ala Glu Phe
                565                 570                 575
Asp Gln Leu Leu Ala Asp Phe Pro Glu Ala Ala Gly Met Arg Ala Pro
                580                 585                 590
Gly Pro Tyr Ser Met Arg Ile Ile Tyr Gly Asp Thr Asp Ser Ile Phe
                595                 600                 605
Val Leu Cys Arg Gly Leu Thr Gly Glu Ala Leu Val Ala Met Gly Asp
        610                 615                 620
Lys Met Ala Ser His Ile Ser Arg Ala Leu Phe Leu Pro Pro Ile Lys
625                 630                 635                 640
Leu Glu Cys Glu Lys Thr Phe Thr Lys Leu Leu Leu Ile Ala Lys Lys
                645                 650                 655
Lys Tyr Ile Gly Val Ile Cys Gly Gly Lys Met Leu Ile Lys Gly Val
                660                 665                 670
Asp Leu Val Arg Lys Asn Asn Cys Ala Phe Ile Asn Arg Thr Ser Arg
                675                 680                 685
Ala Leu Val Asp Leu Leu Phe Tyr Asp Asp Thr Val Ser Gly Ala Ala
        690                 695                 700
```

-continued

```
Ala Ala Leu Ala Glu Arg Pro Ala Glu Glu Trp Leu Ala Arg Pro Leu
705                 710                 715                 720

Pro Glu Gly Leu Gln Ala Phe Gly Ala Val Leu Val Asp Ala His Arg
            725                 730                 735

Arg Ile Thr Asp Pro Glu Arg Asp Ile Gln Asp Phe Val Leu Thr Ala
        740                 745                 750

Glu Leu Ser Arg His Pro Arg Ala Tyr Thr Asn Lys Arg Leu Ala His
    755                 760                 765

Leu Thr Val Tyr Tyr Lys Leu Met Ala Arg Arg Ala Gln Val Pro Ser
770                 775                 780

Ile Lys Asp Arg Ile Pro Tyr Val Ile Ala Gln Thr Arg Glu Val
785                 790                 795                 800

Glu Glu Thr Val Ala Arg Leu Ala Ala Leu Arg Glu Leu Asp Ala Ala
                805                 810                 815

Ala Pro Gly Asp Glu Pro Ala Pro Pro Ala Ala Leu Pro Ser Pro Ala
            820                 825                 830

Lys Arg Pro Arg Glu Thr Pro Ser His Ala Asp Pro Pro Gly Gly Ala
        835                 840                 845

Ser Lys Pro Arg Lys Leu Leu Val Ser Glu Leu Ala Glu Asp Pro Gly
    850                 855                 860

Tyr Ala Ile Ala Arg Gly Val Pro Leu Asn Thr Asp Tyr Tyr Phe Ser
865                 870                 875                 880

His Leu Leu Gly Ala Ala Cys Val Thr Phe Lys Ala Leu Phe Gly Asn
                885                 890                 895

<210> SEQ ID NO 18
<211> LENGTH: 875
<212> TYPE: PRT
<213> ORGANISM: Equine herpesvirus type 1 (strain Ab4p)

<400> SEQUENCE: 18

Pro Glu Ile Thr Lys Phe Glu Gly Ser Val Asp Val Thr Thr Arg Leu
1               5                   10                  15

Leu Leu Asp Asn Glu Asn Phe Thr Ser Phe Gly Trp Tyr Arg Leu Arg
                20                  25                  30

Pro Gly Thr His Gly Glu Arg Val Gln Leu Arg Pro Val Glu Arg His
            35                  40                  45

Val Thr Ser Ser Asp Val Glu Ile Asn Cys Thr Pro Asp Asn Leu Glu
        50                  55                  60

Pro Ile Pro Asp Glu Ala Ala Trp Pro Asp Tyr Lys Leu Met Cys Phe
65                  70                  75                  80

Asp Ile Glu Cys Lys Ala Gly Thr Gly Asn Glu Met Ala Phe Pro Val
                85                  90                  95

Ala Thr Asn Gln Glu Asp Leu Val Ile Gln Ile Ser Cys Leu Leu Tyr
                100                 105                 110

Ser Leu Ala Thr Gln Asn His Glu His Thr Leu Leu Phe Ser Leu Gly
            115                 120                 125

Ser Cys Asp Ile Ser Glu Glu Tyr Ser Phe Ala Cys Val Gln Arg Gly
        130                 135                 140

Glu Pro Arg Pro Thr Val Leu Glu Phe Asp Ser Glu Tyr Glu Leu Leu
145                 150                 155                 160

Val Ala Phe Leu Thr Phe Leu Lys Gln Tyr Ser Pro Glu Phe Ala Thr
                165                 170                 175

Gly Tyr Asn Ile Val Asn Phe Asp Trp Ala Tyr Ile Val Asn Lys Val
```

-continued

```
                180                 185                 190
Thr Ser Val Tyr Asn Ile Lys Leu Asp Gly Tyr Gly Lys Phe Asn Lys
            195                 200                 205

Gly Gly Leu Phe Lys Val Trp Asp Ile Ala Thr Asn His Phe Gln Lys
210                 215                 220

Lys Ser Lys Val Lys Ile Asn Gly Leu Ile Ser Leu Asp Met Tyr Ser
225                 230                 235                 240

Val Ala Thr Glu Lys Leu Lys Leu Pro Ser Tyr Lys Leu Asp Ala Val
            245                 250                 255

Val Gly Asp Val Leu Gly Glu His Lys Ile Asp Leu Pro Tyr Lys Glu
            260                 265                 270

Ile Pro Ser Tyr Tyr Ala Gly Gly Pro Asp Arg Arg Gly Val Ile Gly
            275                 280                 285

Glu Tyr Cys Ile Gln Asp Ser Arg Leu Val Gly Lys Leu Phe Phe Lys
            290                 295                 300

Tyr Leu Pro His Leu Glu Leu Ser Ala Val Ala Lys Leu Ala Arg Ile
305                 310                 315                 320

Thr Leu Thr Arg Val Ile Phe Asp Gly Gln Gln Ile Arg Val Tyr Thr
            325                 330                 335

Cys Leu Leu Lys Leu Ala Arg Glu Arg Asn Phe Ile Leu Pro Asp Asn
            340                 345                 350

Arg Arg Arg Phe Asp Ser Gln Ala Asp Ala Ala Ser Glu Thr Ser Glu
            355                 360                 365

Leu Ala Met Asp Ser Gln Ser His Ala Phe Asp Ser Thr Asp Glu Pro
            370                 375                 380

Asp Gly Val Asp Gly Thr Pro Asp Ala Ala Gly Ser Gly Ala Thr Ser
385                 390                 395                 400

Glu Asn Gly Gly Gly Lys Pro Gly Val Gly Arg Ala Val Gly Tyr Gln
            405                 410                 415

Gly Ala Lys Val Leu Asp Pro Val Ser Gly Phe His Val Asp Pro Val
            420                 425                 430

Val Val Phe Asp Phe Ala Ser Leu Tyr Pro Ser Ile Ile Gln Ala His
            435                 440                 445

Asn Leu Cys Phe Thr Thr Leu Ala Leu Asp Glu Val Asp Leu Ala Gly
450                 455                 460

Leu Gln Pro Ser Val Asp Tyr Ser Thr Phe Glu Val Gly Asp Gln Lys
465                 470                 475                 480

Leu Phe Phe Val His Ala His Ile Arg Glu Ser Leu Leu Gly Ile Leu
            485                 490                 495

Leu Arg Asp Trp Leu Ala Met Arg Lys Ala Val Arg Ala Arg Ile Pro
            500                 505                 510

Thr Ser Thr Pro Glu Glu Ala Val Leu Leu Asp Lys Gln Gln Ser Ala
            515                 520                 525

Ile Lys Val Ile Cys Asn Ser Val Tyr Gly Phe Thr Gly Val Ala Asn
530                 535                 540

Gly Leu Leu Pro Cys Leu Arg Ile Ala Ala Thr Val Thr Thr Ile Gly
545                 550                 555                 560

Arg Asp Met Leu Leu Lys Thr Arg Asp Tyr Val His Ser Arg Trp Ala
            565                 570                 575

Thr Arg Glu Leu Leu Glu Asp Asn Phe Pro Gly Ala Ile Gly Phe Arg
            580                 585                 590

Asn His Lys Pro Tyr Ser Val Arg Val Ile Tyr Gly Asp Thr Asp Ser
            595                 600                 605
```

-continued

Val Phe Ile Lys Phe Val Gly Leu Thr Tyr Glu Gly Val Ser Glu Leu
            610                 615                 620

Gly Asp Ala Met Ser Arg Gln Ile Ser Ala Asp Leu Phe Arg Ala Pro
625                 630                 635                 640

Ile Lys Leu Glu Cys Glu Lys Thr Phe Gln Arg Leu Leu Ile Thr
                645                 650                 655

Lys Lys Lys Tyr Ile Gly Val Ile Asn Gly Gly Lys Met Leu Met Lys
                660                 665                 670

Gly Val Asp Leu Val Arg Lys Asn Asn Cys Ser Phe Ile Asn Leu Tyr
            675                 680                 685

Ala Arg His Leu Val Asp Leu Leu Tyr Asp Glu Asp Val Ala Thr
            690                 695                 700

Ala Ala Ala Glu Val Thr Asp Val Pro Pro Ala Glu Trp Val Gly Arg
705                 710                 715                 720

Pro Leu Pro Ser Gly Phe Asp Lys Phe Gly Arg Val Leu Val Glu Ala
                725                 730                 735

Tyr Asn Arg Ile Thr Ala Pro Asn Leu Asp Val Arg Glu Phe Val Met
            740                 745                 750

Thr Ala Glu Leu Ser Arg Ser Pro Glu Ser Tyr Thr Asn Lys Arg Leu
            755                 760                 765

Pro His Leu Thr Val Tyr Phe Lys Leu Ala Met Arg Asn Glu Glu Leu
            770                 775                 780

Pro Ser Val Lys Glu Arg Ile Pro Tyr Val Ile Val Ala Gln Thr Glu
785                 790                 795                 800

Ala Ala Glu Arg Glu Ala Gly Val Val Asn Ser Met Arg Gly Thr Ala
                805                 810                 815

Gln Asn Pro Val Val Thr Lys Thr Ala Arg Pro Gln Pro Lys Arg Lys
            820                 825                 830

Leu Leu Val Ser Asp Leu Ala Glu Asp Pro Thr Tyr Val Ser Glu Asn
            835                 840                 845

Asp Val Pro Leu Asn Thr Asp Tyr Tyr Phe Ser His Leu Leu Gly Thr
850                 855                 860

Ile Ser Val Thr Phe Lys Ala Leu Phe Gly Asn
865                 870                 875

<210> SEQ ID NO 19
<211> LENGTH: 852
<212> TYPE: PRT
<213> ORGANISM: Varicella-zoster virus (strain Dumas)

<400> SEQUENCE: 19

Pro Glu Leu Lys Lys Tyr Glu Gly Arg Val Asp Ala Thr Thr Arg Phe
1               5                   10                  15

Leu Met Asp Asn Pro Gly Phe Val Ser Phe Gly Trp Tyr Gln Leu Lys
                20                  25                  30

Pro Gly Val Asp Gly Glu Arg Val Arg Val Arg Pro Ala Ser Arg Gln
            35                  40                  45

Leu Thr Leu Ser Asp Val Glu Ile Asp Cys Met Ser Asp Asn Leu Gln
50                  55                  60

Ala Ile Pro Asn Asp Asp Ser Trp Pro Asp Tyr Lys Leu Leu Cys Phe
65                  70                  75                  80

Asp Ile Glu Cys Lys Ser Gly Gly Ser Asn Glu Leu Ala Phe Pro Asp
                85                  90                  95

Ala Thr His Leu Glu Asp Leu Val Ile Gln Ile Ser Cys Leu Leu Tyr

```
                  100                 105                 110
Ser Ile Pro Arg Gln Ser Leu Glu His Ile Leu Leu Phe Ser Leu Gly
            115                 120                 125

Ser Cys Asp Leu Pro Gln Arg Tyr Val Gln Glu Met Lys Asp Ala Gly
        130                 135                 140

Leu Pro Glu Pro Thr Val Leu Glu Phe Asp Ser Glu Phe Glu Leu Leu
145                 150                 155                 160

Ile Ala Phe Met Thr Leu Val Lys Gln Tyr Ala Pro Glu Phe Ala Thr
                165                 170                 175

Gly Tyr Asn Ile Val Asn Phe Asp Trp Ala Phe Ile Met Glu Lys Leu
            180                 185                 190

Asn Ser Ile Tyr Ser Leu Lys Leu Asp Gly Tyr Gly Ser Ile Asn Arg
        195                 200                 205

Gly Gly Leu Phe Lys Ile Trp Asp Val Gly Lys Ser Gly Phe Gln Arg
    210                 215                 220

Arg Ser Lys Val Lys Ile Asn Gly Leu Ile Ser Leu Asp Met Tyr Ala
225                 230                 235                 240

Ile Ala Thr Glu Lys Leu Lys Leu Ser Ser Tyr Lys Leu Asp Ser Val
                245                 250                 255

Ala Arg Glu Ala Leu Asn Glu Ser Lys Arg Asp Leu Pro Tyr Lys Asp
            260                 265                 270

Ile Pro Gly Tyr Tyr Ala Ser Gly Pro Asn Thr Arg Gly Ile Ile Gly
        275                 280                 285

Glu Tyr Cys Ile Gln Asp Ser Ala Leu Val Gly Lys Leu Phe Phe Lys
    290                 295                 300

Tyr Leu Pro His Leu Glu Leu Ser Ala Val Ala Arg Leu Ala Arg Ile
305                 310                 315                 320

Thr Leu Thr Lys Ala Ile Tyr Asp Gly Gln Gln Val Arg Ile Tyr Thr
                325                 330                 335

Cys Leu Leu Gly Leu Ala Ser Ser Arg Gly Phe Ile Leu Pro Asp Gly
            340                 345                 350

Gly Tyr Pro Ala Thr Phe Glu Tyr Lys Asp Val Ile Pro Asp Val Gly
        355                 360                 365

Asp Val Glu Glu Glu Met Asp Glu Asp Glu Ser Val Ser Pro Thr Gly
    370                 375                 380

Thr Ser Ser Gly Arg Asn Val Gly Tyr Lys Gly Ala Arg Val Phe Asp
385                 390                 395                 400

Pro Asp Thr Gly Phe Tyr Ile Asp Pro Val Val Leu Asp Phe Ala
                405                 410                 415

Ser Leu Tyr Pro Ser Ile Ile Gln Ala His Asn Leu Cys Phe Thr Thr
            420                 425                 430

Leu Thr Leu Asn Phe Glu Thr Val Lys Arg Leu Asn Pro Ser Asp Tyr
        435                 440                 445

Ala Thr Phe Thr Val Gly Gly Lys Arg Leu Phe Phe Val Arg Ser Asn
    450                 455                 460

Val Arg Glu Ser Leu Leu Gly Val Leu Leu Lys Asp Trp Leu Ala Met
465                 470                 475                 480

Arg Lys Ala Ile Arg Ala Arg Ile Pro Gly Ser Ser Asp Glu Ala
                485                 490                 495

Val Leu Leu Asp Lys Gln Gln Ala Ala Ile Lys Val Val Cys Asn Ser
            500                 505                 510

Val Tyr Gly Phe Thr Gly Val Ala Gln Gly Phe Leu Pro Cys Leu Tyr
        515                 520                 525
```

```
Val Ala Ala Thr Val Thr Thr Ile Gly Arg Gln Met Leu Leu Ser Thr
            530                 535                 540
Arg Asp Tyr Ile His Asn Asn Trp Ala Ala Phe Glu Arg Phe Ile Thr
545                 550                 555                 560
Ala Phe Pro Asp Ile Glu Ser Ser Val Leu Ser Gln Lys Ala Tyr Glu
                565                 570                 575
Val Lys Val Ile Tyr Gly Asp Thr Asp Ser Val Phe Ile Arg Phe Lys
                580                 585                 590
Gly Val Ser Val Glu Gly Ile Ala Lys Ile Gly Glu Lys Met Ala His
            595                 600                 605
Ile Ile Ser Thr Ala Leu Phe Cys Pro Pro Ile Lys Leu Glu Cys Glu
610                 615                 620
Lys Thr Phe Ile Lys Leu Leu Leu Ile Thr Lys Lys Tyr Ile Gly
625                 630                 635                 640
Val Ile Tyr Gly Gly Lys Val Leu Met Lys Gly Val Asp Leu Val Arg
                645                 650                 655
Lys Asn Asn Cys Gln Phe Ile Asn Asp Tyr Ala Arg Lys Leu Val Glu
                660                 665                 670
Leu Leu Leu Tyr Asp Asp Thr Val Ser Arg Ala Ala Ala Glu Ala Ser
            675                 680                 685
Cys Val Ser Ile Ala Glu Trp Asn Arg Arg Ala Met Pro Ser Gly Met
690                 695                 700
Ala Gly Phe Gly Arg Ile Ile Ala Asp Ala His Arg Gln Ile Thr Ser
705                 710                 715                 720
Pro Lys Leu Asp Ile Asn Lys Phe Val Met Thr Ala Glu Leu Ser Arg
                725                 730                 735
Pro Pro Ser Ala Tyr Ile Asn Arg Arg Leu Ala His Leu Thr Val Tyr
            740                 745                 750
Tyr Lys Leu Val Met Arg Gln Gly Gln Ile Pro Asn Val Arg Glu Arg
            755                 760                 765
Ile Pro Tyr Val Ile Val Ala Pro Thr Asp Glu Val Glu Ala Asp Ala
770                 775                 780
Lys Ser Val Ala Leu Leu Arg Gly Asp Pro Leu Gln Asn Thr Ala Gly
785                 790                 795                 800
Lys Arg Cys Gly Glu Ala Lys Arg Lys Leu Ile Ile Ser Asp Leu Ala
                805                 810                 815
Glu Asp Pro Ile His Val Thr Ser His Gly Leu Ser Leu Asn Ile Asp
            820                 825                 830
Tyr Tyr Phe Ser His Leu Ile Gly Thr Ala Ser Val Thr Phe Lys Ala
            835                 840                 845
Leu Phe Gly Asn
    850

<210> SEQ ID NO 20
<211> LENGTH: 978
<212> TYPE: PRT
<213> ORGANISM: Human cytomegalovirus (strain AD169)

<400> SEQUENCE: 20

Gly Phe Pro Val Tyr Glu Val Arg Val Asp Pro Leu Thr Arg Leu Val
 1               5                  10                  15

Ile Asp Arg Arg Ile Thr Thr Phe Gly Trp Cys Ser Val Asn Arg Tyr
                20                  25                  30

Asp Trp Arg Gln Gln Gly Arg Ala Ser Thr Cys Asp Ile Glu Val Asp
```

-continued

```
              35                  40                  45
Cys Asp Val Ser Asp Leu Val Ala Val Pro Asp Asp Ser Ser Trp Pro
 50                  55                  60
Arg Tyr Arg Cys Leu Ser Phe Asp Ile Glu Cys Met Ser Gly Glu Gly
 65                  70                  75                  80
Gly Phe Pro Cys Ala Glu Lys Ser Asp Asp Ile Val Ile Gln Ile Ser
                 85                  90                  95
Cys Val Cys Tyr Glu Thr Gly Gly Asn Thr Ala Val Asp Gln Gly Ile
                100                 105                 110
Pro Asn Gly Asn Asp Gly Arg Gly Cys Thr Ser Glu Gly Val Ile Phe
                115                 120                 125
Gly His Ser Gly Leu His Leu Phe Thr Ile Gly Thr Cys Gly Gln Val
                130                 135                 140
Gly Pro Asp Val Asp Val Tyr Glu Phe Pro Ser Glu Tyr Glu Leu Leu
145                 150                 155                 160
Leu Gly Phe Met Leu Phe Phe Gln Arg Tyr Ala Pro Ala Phe Val Thr
                165                 170                 175
Gly Tyr Asn Ile Asn Ser Phe Asp Leu Lys Tyr Ile Leu Thr Arg Leu
                180                 185                 190
Glu Tyr Leu Tyr Lys Val Asp Ser Gln Arg Phe Cys Lys Leu Pro Thr
                195                 200                 205
Ala Gln Gly Gly Arg Phe Phe Leu His Ser Pro Ala Val Gly Phe Lys
                210                 215                 220
Arg Gln Tyr Ala Ala Ala Phe Pro Ser Ala Ser His Asn Asn Pro Ala
225                 230                 235                 240
Ser Thr Ala Ala Thr Lys Val Tyr Ile Ala Gly Ser Val Val Ile Asp
                245                 250                 255
Met Tyr Pro Val Cys Met Ala Lys Thr Asn Ser Pro Asn Tyr Lys Leu
                260                 265                 270
Asn Thr Met Ala Glu Leu Tyr Leu Arg Gln Arg Lys Asp Asp Leu Ser
                275                 280                 285
Tyr Lys Asp Ile Pro Arg Cys Phe Val Ala Asn Ala Glu Gly Arg Ala
                290                 295                 300
Gln Val Gly Arg Tyr Cys Leu Gln Asp Ala Val Leu Val Arg Asp Leu
305                 310                 315                 320
Phe Asn Thr Ile Asn Phe His Tyr Glu Ala Gly Ala Ile Ala Arg Leu
                325                 330                 335
Ala Lys Ile Pro Leu Arg Arg Val Ile Phe Asp Gly Gln Gln Ile Arg
                340                 345                 350
Ile Tyr Thr Ser Leu Leu Asp Glu Cys Ala Cys Arg Asp Phe Ile Leu
                355                 360                 365
Pro Asn His Tyr Ser Lys Gly Thr Thr Val Pro Glu Thr Asn Ser Val
                370                 375                 380
Ala Val Ser Pro Asn Ala Ala Ile Ile Ser Thr Ala Ala Val Pro Gly
385                 390                 395                 400
Asp Ala Gly Ser Val Ala Ala Met Phe Gln Met Ser Pro Pro Leu Gln
                405                 410                 415
Ser Ala Pro Ser Ser Gln Asp Gly Val Ser Pro Gly Ser Gly Ser Asn
                420                 425                 430
Ser Ser Ser Ser Val Gly Val Phe Ser Val Gly Ser Ser Ser Gly
                435                 440                 445
Gly Val Gly Val Ser Asn Asp Asn His Gly Ala Gly Thr Ala Ala
450                 455                 460
```

```
Val Ser Tyr Gln Gly Ala Thr Val Phe Glu Pro Glu Val Gly Tyr Tyr
465                 470                 475                 480

Asn Asp Pro Val Ala Val Phe Asp Phe Ala Ser Leu Tyr Pro Ser Ile
            485                 490                 495

Ile Met Ala His Asn Leu Cys Tyr Ser Thr Leu Leu Val Pro Gly Gly
            500                 505                 510

Glu Tyr Pro Val Asp Pro Ala Asp Val Tyr Ser Val Thr Leu Glu Asn
            515                 520                 525

Gly Val Thr His Arg Phe Val Arg Ala Ser Val Arg Val Ser Val Leu
            530                 535                 540

Ser Glu Leu Leu Asn Lys Trp Val Ser Gln Arg Ala Val Arg Glu
545                 550                 555                 560

Cys Met Arg Glu Cys Gln Asp Pro Val Arg Arg Met Leu Leu Asp Lys
                565                 570                 575

Glu Gln Met Ala Leu Lys Val Thr Cys Asn Ala Phe Tyr Gly Phe Thr
                580                 585                 590

Gly Val Val Asn Gly Met Met Pro Cys Leu Pro Ile Ala Ala Ser Ile
            595                 600                 605

Thr Arg Ile Gly Arg Asp Met Leu Glu Arg Thr Ala Arg Phe Ile Lys
            610                 615                 620

Asp Asn Phe Ser Glu Pro Cys Phe Leu His Asn Phe Phe Asn Gln Glu
625                 630                 635                 640

Asp Tyr Val Val Gly Thr Arg Glu Gly Asp Ser Glu Ser Ser Ala
                645                 650                 655

Leu Pro Glu Gly Leu Glu Thr Ser Ser Gly Ser Asn Glu Arg Arg
                660                 665                 670

Val Glu Ala Arg Val Ile Tyr Gly Asp Thr Asp Ser Val Phe Val Arg
            675                 680                 685

Phe Arg Gly Leu Thr Pro Gln Ala Leu Val Ala Arg Gly Pro Ser Leu
690                 695                 700

Ala His Tyr Val Thr Ala Cys Leu Phe Val Glu Pro Val Lys Leu Glu
705                 710                 715                 720

Phe Glu Lys Val Phe Val Ser Leu Met Met Ile Cys Lys Lys Arg Tyr
                725                 730                 735

Ile Gly Lys Val Glu Gly Ala Ser Gly Leu Ser Met Lys Gly Val Asp
                740                 745                 750

Leu Val Arg Lys Thr Ala Cys Glu Phe Val Lys Gly Val Thr Arg Asp
                755                 760                 765

Val Leu Ser Leu Leu Phe Glu Asp Arg Glu Val Ser Glu Ala Ala Val
            770                 775                 780

Arg Leu Ser Arg Leu Ser Leu Asp Glu Val Lys Lys Tyr Gly Val Pro
785                 790                 795                 800

Arg Gly Phe Trp Arg Ile Leu Arg Arg Leu Val Gln Ala Arg Asp Asp
                805                 810                 815

Leu Tyr Leu His Arg Val Arg Val Glu Asp Leu Val Leu Ser Ser Val
            820                 825                 830

Leu Ser Lys Asp Ile Ser Leu Tyr Arg Gln Ser Asn Leu Pro His Ile
            835                 840                 845

Ala Val Ile Lys Arg Leu Ala Ala Arg Ser Glu Glu Leu Pro Ser Val
            850                 855                 860

Gly Asp Arg Val Phe Tyr Val Leu Thr Ala Pro Gly Val Arg Thr Ala
865                 870                 875                 880
```

```
Pro Gln Gly Ser Ser Asp Asn Gly Asp Ser Val Thr Ala Gly Val Val
                885                 890                 895

Ser Arg Ser Asp Ala Ile Asp Gly Thr Asp Asp Ala Asp Gly Gly
        900                 905                 910

Gly Val Glu Glu Ser Asn Arg Arg Gly Gly Glu Pro Ala Lys Lys Arg
            915                 920                 925

Ala Arg Lys Pro Pro Ser Ala Val Cys Asn Tyr Glu Val Ala Glu Asp
        930                 935                 940

Pro Ser Tyr Val Arg Glu His Gly Val Pro Ile His Ala Asp Lys Tyr
945                 950                 955                 960

Phe Glu Gln Val Leu Lys Ala Val Thr Asn Val Leu Ser Pro Val Phe
                965                 970                 975

Pro Gly

<210> SEQ ID NO 21
<211> LENGTH: 814
<212> TYPE: PRT
<213> ORGANISM: Murine cytomegalovirus (strain Smith)

<400> SEQUENCE: 21

Gly Arg Lys Val Tyr Glu Leu Gly Val Asp Pro Leu Ala Arg Phe Leu
1               5                   10                  15

Ile Asp Arg Lys Ile Pro Ser Phe Gly Trp Cys Leu Ala Arg Arg Tyr
            20                  25                  30

Ser Val Arg Ala Ala Gly Tyr Val Ser Arg Ala Gln Leu Glu Ile Asp
        35                  40                  45

Cys Asp Val Ala Asp Ile Leu Pro Ile Glu Glu Gln Ser Asn Trp Pro
    50                  55                  60

Phe Tyr Arg Cys Leu Ser Phe Asp Ile Glu Cys Met Ser Gly Thr Gly
65                  70                  75                  80

Ala Phe Pro Ala Ala Glu Asn Val Asp Asp Ile Ile Gln Ile Ser
                85                  90                  95

Cys Val Cys Phe Gly Val Gly Glu Met Val His His Ala Tyr Asp Val
            100                 105                 110

His Ala Asp Leu Ser Thr Pro Ala Val Pro Glu Asn His Leu Phe Thr
        115                 120                 125

Ile Gly Pro Cys Ala Pro Ile Pro Asp Val Lys Ile Tyr Thr Phe Pro
    130                 135                 140

Ser Glu Tyr Glu Met Leu Arg Gly Phe Phe Ile Phe Leu Ser Trp Tyr
145                 150                 155                 160

Ser Pro Glu Phe Ile Thr Gly Tyr Asn Ile Asn Gly Phe Asp Ile Lys
                165                 170                 175

Tyr Ile Leu Thr Arg Ala Glu Lys Leu Tyr Lys Met Asp Val Gly Gln
            180                 185                 190

Phe Thr Lys Leu Arg Arg Gly Arg Met Phe Val Phe Ser Pro Glu
        195                 200                 205

Lys Gly Lys Ala Gly Phe Gly Thr Ser Asn Thr Val Lys Val Phe Trp
    210                 215                 220

Ser Gly Thr Val Val Leu Asp Met Tyr Pro Val Cys Thr Ala Lys Ala
225                 230                 235                 240

Ser Ser Pro Asn Tyr Lys Leu Asp Thr Met Ala Glu Ile Tyr Leu Lys
                245                 250                 255

Lys Lys Lys Asp Asp Leu Ser Tyr Lys Glu Ile Pro Val Gln Phe Ser
            260                 265                 270
```

-continued

```
Ala Gly Asp Glu Gly Arg Ala Pro Gly Gly Lys Tyr Cys Leu Gln Asp
        275                 280                 285

Ala Val Leu Val Arg Glu Leu Phe Glu Met Leu Ala Phe His Phe Glu
        290                 295                 300

Ala Ala Ala Ile Ala Arg Leu Ala Arg Ile Pro Leu Arg Lys Val Ile
305                 310                 315                 320

Phe Asp Gly Gln Gln Ile Arg Ile Tyr Thr Cys Leu Leu Glu Glu Cys
                325                 330                 335

Ser Gly Arg Asp Met Ile Leu Pro Asn Met Pro Ser Leu Gly His Gly
            340                 345                 350

Ala Ala Ala Ile Glu Glu Ala Ala Gly Gly Glu Gly Asp Glu
                355                 360                 365

Thr Ser Glu Gly Glu Asn Ser Asn Asn Ser Arg Thr Val Gly Tyr Gln
        370                 375                 380

Gly Ala Thr Val Leu Glu Pro Glu Cys Gly Phe His His Val Pro Val
385                 390                 395                 400

Cys Val Phe Asp Phe Ala Ser Leu Tyr Pro Ser Ile Ile Met Ser Asn
                405                 410                 415

Asn Leu Cys Tyr Ser Thr Leu Leu Val Glu Gly Ser Pro Glu Val Pro
                420                 425                 430

Glu Lys Asp Val Leu Arg Val Glu Ile Gly Asp Gln Cys His Arg Phe
            435                 440                 445

Val Arg Glu Asn Val His Arg Ser Leu Leu Ala Glu Leu Leu Val Arg
        450                 455                 460

Trp Leu Thr Gln Arg Lys Leu Val Arg Glu Ala Met Lys Gln Cys Thr
465                 470                 475                 480

Asn Glu Met Gln Arg Met Ile Met Asp Lys Gln Leu Ala Leu Lys
                485                 490                 495

Val Thr Cys Asn Ala Phe Tyr Gly Phe Thr Gly Val Ala Ala Gly Met
                500                 505                 510

Leu Pro Cys Leu Pro Ile Ala Ala Ser Ile Thr Lys Ile Gly Arg Asp
        515                 520                 525

Met Leu Leu Ala Thr Ala Gly His Ile Glu Asp Arg Cys Asn Arg Pro
530                 535                 540

Asp Phe Leu Arg Thr Val Leu Gly Leu Pro Pro Glu Ala Ile Asp Pro
545                 550                 555                 560

Glu Ala Leu Arg Val Lys Ile Ile Tyr Gly Asp Thr Asp Ser Val Phe
                565                 570                 575

Ala Ala Phe Tyr Gly Ile Asp Lys Glu Ala Leu Leu Lys Ala Val Gly
            580                 585                 590

Ala Leu Ala Ala Asn Val Thr Asn Ala Leu Phe Lys Glu Pro Val Arg
        595                 600                 605

Leu Glu Phe Glu Lys Met Phe Val Ser Leu Met Met Ile Cys Lys Lys
        610                 615                 620

Arg Tyr Ile Gly Lys Val His Gly Ser Gln Asn Leu Ser Met Lys Gly
625                 630                 635                 640

Val Asp Leu Val Arg Arg Thr Ala Cys Gly Phe Val Lys Ala Val Val
                645                 650                 655

Ser Asp Val Leu His Met Val Phe Asn Asp Glu Thr Val Ser Glu Gly
            660                 665                 670

Thr Met Lys Leu Ser Arg Met Thr Phe Asp Asp Leu Lys Lys Asn Gly
        675                 680                 685

Ile Pro Cys Glu Phe Gly Pro Val Val Ser Arg Leu Cys Arg Ala Arg
```

```
                690               695               700
Asp Asp Leu His Leu Lys Lys Val Pro Val Pro Glu Leu Thr Leu Ser
705               710               715               720

Ser Val Leu Ser Gln Glu Leu Ser Cys Tyr Lys Gln Lys Asn Leu Pro
                725               730               735

His Leu Ala Val Ile Arg Arg Leu Ala Ala Arg Lys Glu Glu Leu Pro
                740               745               750

Ala Val Gly Asp Arg Val Glu Tyr Val Leu Thr Leu Pro Asp Gly Cys
                755               760               765

Lys Lys Asn Val Pro Asn Tyr Glu Ile Ala Glu Asp Pro Arg His Val
770               775               780

Val Glu Ala Lys Leu Ser Ile Asn Ala Glu Lys Tyr Tyr Glu Gln Val
785               790               795               800

Val Lys Ala Val Thr Asn Thr Leu Met Pro Val Phe Pro Arg
                805               810
```

<210> SEQ ID NO 22
<211> LENGTH: 771
<212> TYPE: PRT
<213> ORGANISM: Herpes simplex virus type 6/strain Uganda-1102

<400> SEQUENCE: 22

```
Gly Phe Val Val Tyr Glu Ile Asp Val Asp Val Leu Thr Arg Phe Phe
1               5                  10                  15

Val Asp Asn Gly Phe Leu Ser Phe Gly Trp Tyr Asn Val Lys Lys Tyr
                20                  25                  30

Ile Pro Gln Asp Met Gly Lys Gly Ser Asn Leu Glu Val Glu Ile Asn
                35                  40                  45

Cys His Val Ser Asp Leu Val Ser Leu Glu Asp Val Asn Trp Pro Leu
50                  55                  60

Tyr Gly Cys Trp Ser Phe Asp Ile Glu Cys Leu Gly Gln Asn Gly Asn
65                  70                  75                  80

Phe Pro Asp Ala Glu Asn Leu Gly Asp Ile Val Ile Gln Ile Ser Val
                85                  90                  95

Ile Ser Phe Asp Thr Glu Gly Asp Arg Asp Glu Arg His Leu Phe Thr
                100                 105                 110

Leu Gly Thr Cys Glu Lys Ile Asp Gly Val His Ile Tyr Glu Phe Ala
                115                 120                 125

Ser Glu Phe Glu Leu Leu Leu Gly Phe Phe Ile Phe Leu Arg Ile Glu
                130                 135                 140

Ser Pro Glu Phe Ile Thr Gly Tyr Asn Ile Asn Asn Phe Asp Leu Lys
145                 150                 155                 160

Tyr Leu Cys Ile Arg Met Asp Lys Ile Tyr His Tyr Asp Ile Gly Cys
                165                 170                 175

Phe Ser Lys Leu Lys Asn Gly Lys Ile Gly Ile Ser Val Pro His Glu
                180                 185                 190

Gln Tyr Arg Lys Gly Phe Leu Gln Ala Gln Thr Lys Val Phe Thr Ser
                195                 200                 205

Gly Val Leu Tyr Leu Asp Met Tyr Pro Val Tyr Ser Ser Lys Ile Thr
                210                 215                 220

Ala Gln Asn Tyr Lys Leu Asp Thr Ile Ala Lys Ile Cys Leu Gln Gln
225                 230                 235                 240

Glu Lys Glu Gln Leu Ser Tyr Lys Glu Ile Pro Lys Lys Phe Ile Ser
                245                 250                 255
```

-continued

```
Gly Pro Ser Gly Arg Ala Val Val Gly Lys Tyr Cys Leu Gln Asp Ser
            260                 265                 270

Val Leu Val Val Arg Leu Phe Lys Gln Ile Asn Tyr His Phe Glu Val
            275                 280                 285

Ala Glu Val Ala Arg Leu Ala His Val Thr Ala Arg Cys Val Val Phe
            290                 295                 300

Glu Gly Gln Gln Lys Lys Ile Phe Pro Cys Ile Leu Thr Glu Ala Lys
305                 310                 315                 320

Arg Arg Asn Met Ile Leu Pro Ser Met Val Ser Ser His Asn Arg Gln
                325                 330                 335

Gly Ile Gly Tyr Lys Gly Ala Thr Val Leu Glu Pro Lys Thr Gly Tyr
                340                 345                 350

Tyr Ala Val Pro Thr Val Val Phe Asp Phe Gln Ser Leu Tyr Pro Ser
            355                 360                 365

Ile Met Met Ala His Asn Leu Cys Tyr Ser Thr Leu Val Leu Asp Glu
        370                 375                 380

Arg Gln Ile Ala Gly Leu Ser Glu Ser Asp Ile Leu Thr Val Lys Leu
385                 390                 395                 400

Gly Asp Glu Thr His Arg Phe Val Lys Pro Cys Ile Arg Glu Ser Val
                405                 410                 415

Leu Gly Ser Leu Leu Lys Asp Trp Leu Ala Lys Arg Arg Glu Val Lys
            420                 425                 430

Ala Glu Met Gln Asn Cys Ser Asp Pro Met Met Lys Leu Leu Leu Asp
        435                 440                 445

Lys Lys Gln Leu Ala Leu Lys Thr Thr Cys Asn Ser Val Tyr Gly Val
450                 455                 460

Thr Gly Ala Ala His Gly Leu Leu Pro Cys Val Ala Ile Ala Ala Ser
465                 470                 475                 480

Val Thr Cys Leu Gly Arg Glu Met Leu Cys Ser Thr Val Asp Tyr Val
                485                 490                 495

Asn Ser Lys Met Gln Ser Glu Gln Phe Phe Cys Glu Glu Phe Gly Leu
            500                 505                 510

Thr Ser Ser Asp Phe Thr Gly Asp Leu Glu Val Glu Val Ile Tyr Gly
            515                 520                 525

Asp Thr Asp Ser Ile Phe Met Ser Val Arg Asn Met Val Asn Gln Ser
        530                 535                 540

Leu Arg Arg Ile Ala Pro Met Ile Ala Lys His Ile Thr Asp Arg Leu
545                 550                 555                 560

Phe Lys Ser Pro Ile Lys Leu Glu Phe Glu Lys Ile Leu Cys Pro Leu
                565                 570                 575

Ile Leu Ile Cys Lys Lys Arg Tyr Ile Gly Arg Gln Asp Asp Ser Leu
            580                 585                 590

Leu Ile Phe Lys Gly Val Asp Leu Val Arg Lys Thr Ser Cys Asp Phe
        595                 600                 605

Val Lys Gly Val Val Lys Asp Ile Val Asp Leu Leu Phe Phe Asp Glu
            610                 615                 620

Glu Val Gln Thr Ala Ala Val Glu Phe Ser His Met Thr Gln Thr Gln
625                 630                 635                 640

Leu Arg Glu Gln Gly Val Pro Val Gly Ile His Lys Ile Leu Arg Arg
                645                 650                 655

Leu Cys Glu Ala Arg Glu Glu Leu Phe Gln Asn Arg Ala Asp Val Arg
            660                 665                 670

His Leu Met Leu Ser Ser Val Leu Ser Lys Glu Met Ala Ala Tyr Lys
```

-continued

```
                675                 680                 685
Gln Pro Asn Leu Ala His Leu Ser Val Ile Arg Arg Leu Ala Gln Arg
    690                 695                 700
Lys Glu Glu Ile Pro Asn Val Gly Asp Arg Ile Met Tyr Val Leu Ile
705                 710                 715                 720
Ala Pro Ser Ile Gly Asn Lys Gln Thr His Asn Tyr Glu Leu Ala Glu
                725                 730                 735
Asp Pro Asn Tyr Val Ile Glu His Lys Ile Pro Ile His Ala Glu Lys
            740                 745                 750
Tyr Phe Asp Gln Ile Ile Lys Ala Val Thr Asn Ala Ile Ser Pro Ile
        755                 760                 765
Phe Pro Lys
    770

<210> SEQ ID NO 23
<211> LENGTH: 757
<212> TYPE: PRT
<213> ORGANISM: Homo sapiens

<400> SEQUENCE: 23

Ser His Val Phe Gly Thr Asn Thr Ser Ser Leu Glu Leu Phe Leu Met
1               5                   10                  15
Asn Arg Lys Ile Lys Gly Pro Cys Trp Leu Glu Val Lys Lys Ser Thr
            20                  25                  30
Ala Leu Asn Gln Pro Val Ser Trp Cys Lys Val Glu Ala Met Ala Leu
        35                  40                  45
Lys Pro Asp Leu Val Asn Val Ile Lys Asp Val Ser Pro Pro Leu
    50                  55                  60
Val Val Met Ala Phe Ser Met Lys Thr Met Gln Asn Ala Lys Asn His
65                  70                  75                  80
Gln Asn Glu Ile Ile Ala Met Ala Leu Val His His Ser Phe Ala
                85                  90                  95
Leu Asp Lys Ala Ala Pro Lys Pro Pro Phe Gln Ser His Phe Cys Val
            100                 105                 110
Val Ser Lys Pro Lys Asp Cys Ile Phe Pro Tyr Ala Phe Lys Glu Val
        115                 120                 125
Ile Glu Lys Lys Asn Val Lys Val Glu Val Ala Ala Thr Glu Arg Thr
    130                 135                 140
Leu Leu Gly Phe Phe Leu Ala Lys Val His Lys Ile Asp Pro Asp Ile
145                 150                 155                 160
Ile Val Gly His Asn Ile Tyr Gly Phe Glu Leu Glu Val Leu Leu Gln
                165                 170                 175
Arg Ile Asn Val Cys Lys Ala Pro His Trp Ser Lys Ile Gly Arg Leu
            180                 185                 190
Lys Arg Ser Asn Met Pro Lys Leu Gly Gly Arg Ser Gly Phe Gly Glu
        195                 200                 205
Arg Asn Ala Thr Cys Gly Arg Met Ile Cys Asp Val Glu Ile Ser Ala
    210                 215                 220
Lys Glu Leu Ile Arg Cys Lys Ser Tyr His Leu Ser Glu Leu Val Gln
225                 230                 235                 240
Gln Ile Leu Lys Thr Glu Arg Val Ile Pro Met Glu Asn Ile Gln
                245                 250                 255
Asn Met Tyr Ser Glu Ser Ser Gln Leu Leu Tyr Leu Leu Glu His Thr
            260                 265                 270
```

```
Trp Lys Asp Ala Lys Phe Ile Leu Gln Ile Met Cys Glu Leu Asn Val
        275                 280                 285

Leu Pro Leu Ala Leu Gln Ile Thr Asn Ile Ala Gly Asn Ile Met Ser
        290                 295                 300

Arg Thr Leu Met Gly Gly Arg Ser Glu Arg Asn Glu Phe Leu Leu Leu
305                 310                 315                 320

His Ala Phe Tyr Glu Asn Asn Tyr Ile Val Pro Asp Lys Gln Ile Phe
                325                 330                 335

Arg Lys Pro Gln Gln Lys Leu Gly Asp Glu Asp Glu Ile Asp Gly
            340                 345                 350

Asp Thr Asn Lys Tyr Lys Lys Gly Arg Lys Lys Gly Ala Tyr Ala Gly
            355                 360                 365

Gly Leu Val Leu Asp Pro Lys Val Gly Phe Tyr Asp Lys Phe Ile Leu
    370                 375                 380

Leu Leu Asp Phe Asn Ser Leu Tyr Pro Ser Ile Ile Gln Glu Phe Asn
385                 390                 395                 400

Ile Cys Phe Thr Thr Val Gln Arg Val Ala Ser Glu Ala Gln Lys Val
                405                 410                 415

Thr Glu Asp Gly Glu Gln Glu Gln Ile Pro Glu Leu Pro Asp Pro Ser
                420                 425                 430

Leu Glu Met Gly Ile Leu Pro Arg Glu Ile Arg Lys Leu Val Glu Arg
        435                 440                 445

Arg Lys Gln Val Lys Gln Leu Met Lys Gln Asp Leu Asn Pro Asp
450                 455                 460

Leu Ile Leu Gln Tyr Asp Ile Arg Gln Lys Ala Leu Lys Leu Thr Ala
465                 470                 475                 480

Asn Ser Met Tyr Gly Cys Leu Gly Phe Ser Tyr Ser Arg Phe Tyr Ala
                485                 490                 495

Lys Pro Leu Ala Ala Leu Val Thr Tyr Lys Gly Arg Glu Ile Leu Met
            500                 505                 510

His Thr Lys Glu Met Val Gln Lys Met Asn Leu Glu Val Ile Tyr Gly
        515                 520                 525

Asp Thr Asp Ser Ile Met Ile Asn Thr Asn Ser Thr Asn Leu Glu Glu
        530                 535                 540

Val Phe Lys Leu Gly Asn Lys Val Lys Ser Glu Val Asn Lys Leu Tyr
545                 550                 555                 560

Lys Leu Leu Glu Ile Asp Ile Asp Gly Val Phe Lys Ser Leu Leu Leu
                565                 570                 575

Leu Lys Lys Lys Tyr Ala Ala Leu Val Val Glu Pro Thr Ser Asp
            580                 585                 590

Gly Asn Tyr Val Thr Lys Gln Glu Leu Lys Gly Leu Asp Ile Val Arg
        595                 600                 605

Arg Asp Trp Cys Asp Leu Ala Lys Asp Thr Gly Asn Phe Val Ile Gly
610                 615                 620

Gln Ile Leu Ser Asp Gln Ser Arg Asp Thr Ile Val Glu Asn Ile Gln
625                 630                 635                 640

Lys Arg Leu Ile Glu Ile Gly Glu Asn Val Leu Asn Gly Ser Val Pro
                645                 650                 655

Val Ser Gln Phe Glu Ile Asn Lys Ala Leu Thr Lys Asp Pro Gln Asp
                660                 665                 670

Tyr Pro Asp Lys Lys Ser Leu Pro His Val His Val Ala Leu Trp Ile
            675                 680                 685

Asn Ser Gln Gly Gly Arg Lys Val Lys Ala Gly Asp Thr Val Ser Tyr
```

```
                    690                 695                 700
Val Ile Cys Gln Asp Gly Ser Asn Leu Thr Ala Ser Gln Arg Ala Tyr
705                 710                 715                 720

Ala Pro Glu Gln Leu Gln Lys Gln Asp Asn Leu Thr Ile Asp Thr Gln
                    725                 730                 735

Tyr Tyr Leu Ala Gln Gln Ile His Pro Val Val Ala Arg Ile Cys Glu
                740                 745                 750

Pro Ile Asp Gly Ile
            755

<210> SEQ ID NO 24
<211> LENGTH: 757
<212> TYPE: PRT
<213> ORGANISM: Mus musculus

<400> SEQUENCE: 24

Ser His Val Phe Gly Thr Asn Thr Ser Ser Leu Glu Leu Phe Leu Met
1               5                   10                  15

Asn Arg Lys Ile Lys Gly Pro Cys Trp Leu Glu Val Lys Asn Pro Gln
                20                  25                  30

Leu Leu Asn Gln Pro Ile Ser Trp Cys Lys Phe Glu Val Met Ala Leu
            35                  40                  45

Lys Pro Asp Leu Val Asn Val Ile Lys Asp Val Ser Pro Pro Leu
50                  55                  60

Val Val Met Ser Phe Ser Met Lys Thr Met Gln Asn Val Gln Asn His
65                  70                  75                  80

Gln His Glu Ile Ile Ala Met Ala Ala Leu Val His His Ser Phe Ala
                85                  90                  95

Leu Asp Lys Ala Pro Pro Glu Pro Pro Phe Gln Thr His Phe Cys Val
                100                 105                 110

Val Ser Lys Pro Lys Asp Cys Ile Phe Pro Cys Asp Phe Lys Glu Val
            115                 120                 125

Ile Ser Lys Lys Asn Met Lys Val Glu Ile Ala Ala Thr Glu Arg Thr
    130                 135                 140

Leu Ile Gly Phe Phe Leu Ala Lys Val His Lys Ile Asp Pro Asp Ile
145                 150                 155                 160

Leu Val Gly His Asn Ile Cys Ser Phe Glu Leu Glu Val Leu Leu Gln
                165                 170                 175

Arg Ile Asn Glu Cys Lys Val Pro Tyr Trp Ser Lys Ile Gly Arg Leu
                180                 185                 190

Arg Arg Ser Asn Met Pro Lys Leu Gly Ser Arg Ser Gly Phe Gly Glu
            195                 200                 205

Arg Asn Ala Thr Cys Gly Arg Met Ile Cys Asp Val Glu Ile Ser Ala
    210                 215                 220

Lys Glu Leu Ile His Cys Lys Ser Tyr His Leu Ser Glu Leu Val Gln
225                 230                 235                 240

Gln Ile Leu Lys Thr Glu Arg Ile Val Ile Pro Thr Glu Asn Ile Arg
                245                 250                 255

Asn Met Tyr Ser Glu Ser Ser Tyr Leu Leu Tyr Leu Leu Glu His Ile
                260                 265                 270

Trp Lys Asp Ala Arg Phe Ile Leu Gln Ile Met Cys Glu Leu Asn Val
            275                 280                 285

Leu Pro Leu Ala Leu Gln Ile Thr Asn Ile Ala Gly Asn Ile Met Ser
    290                 295                 300
```

-continued

```
Arg Thr Leu Met Gly Gly Arg Ser Glu Arg Asn Glu Phe Leu Leu Leu
305                 310                 315                 320

His Ala Phe Tyr Glu Asn Asn Tyr Ile Val Pro Asp Lys Gln Ile Phe
                325                 330                 335

Arg Lys Pro Gln Gln Lys Leu Gly Asp Glu Asp Glu Ile Asp Gly
                340                 345                 350

Asp Thr Asn Lys Tyr Lys Lys Gly Arg Lys Lys Ala Thr Tyr Ala Gly
                355                 360                 365

Gly Leu Val Leu Asp Pro Lys Val Gly Phe Tyr Asp Lys Phe Ile Leu
        370                 375                 380

Leu Leu Asp Phe Asn Ser Leu Tyr Pro Ser Ile Ile Gln Glu Phe Asn
385                 390                 395                 400

Ile Cys Phe Thr Thr Val Gln Arg Val Thr Ser Glu Val Gln Lys Ala
                405                 410                 415

Thr Glu Asp Glu Glu Gln Glu Gln Ile Pro Glu Leu Pro Asp Pro Asn
                420                 425                 430

Leu Glu Met Gly Ile Leu Pro Arg Glu Ile Arg Lys Leu Val Glu Arg
                435                 440                 445

Arg Lys Gln Val Lys Gln Leu Met Lys Gln Asp Leu Asn Pro Asp
450                 455                 460

Leu Val Leu Gln Tyr Asp Ile Arg Gln Lys Ala Leu Lys Leu Thr Ala
465                 470                 475                 480

Asn Ser Met Tyr Gly Cys Leu Gly Phe Ser Tyr Ser Arg Phe Tyr Ala
                485                 490                 495

Lys Pro Leu Ala Ala Leu Val Thr Tyr Lys Gly Arg Glu Ile Leu Met
                500                 505                 510

His Thr Lys Asp Met Val Gln Lys Met Asn Leu Glu Val Ile Tyr Gly
                515                 520                 525

Asp Thr Asp Ser Ile Met Ile Asn Thr Asn Ser Thr Asn Leu Glu Glu
                530                 535                 540

Val Phe Lys Leu Gly Asn Lys Val Lys Ser Glu Val Asn Lys Leu Tyr
545                 550                 555                 560

Lys Leu Leu Glu Ile Asp Ile Asp Ala Val Phe Lys Ser Leu Leu Leu
                565                 570                 575

Leu Lys Lys Lys Lys Tyr Ala Ala Leu Val Val Glu Pro Thr Ser Asp
                580                 585                 590

Gly Asn Tyr Ile Thr Lys Gln Glu Leu Lys Gly Leu Asp Ile Val Arg
                595                 600                 605

Arg Asp Trp Cys Asp Leu Ala Lys Asp Thr Gly Asn Phe Val Ile Gly
                610                 615                 620

Gln Ile Leu Ser Asp Gln Ser Arg Asp Thr Ile Val Glu Asn Ile Gln
625                 630                 635                 640

Lys Arg Leu Ile Glu Ile Gly Glu Asn Val Leu Asn Gly Ser Val Pro
                645                 650                 655

Val Ser Gln Phe Glu Ile Asn Lys Ala Leu Thr Lys Asp Pro Gln Asp
                660                 665                 670

Tyr Pro Asp Arg Lys Ser Leu Pro His Val His Val Ala Leu Trp Ile
                675                 680                 685

Asn Ser Gln Gly Gly Arg Lys Val Lys Ala Gly Asp Thr Val Ser Tyr
                690                 695                 700

Val Ile Cys Gln Asp Gly Ser Asn Leu Thr Ala Thr Gln Arg Ala Tyr
705                 710                 715                 720

Ala Pro Glu Gln Leu Gln Lys Leu Asp Asn Leu Ala Ile Asp Thr Gln
```

```
                        725                 730                 735
Tyr Tyr Leu Ala Gln Gln Ile His Pro Val Val Ala Arg Ile Cys Glu
                740                 745                 750

Pro Ile Asp Gly Ile
        755

<210> SEQ ID NO 25
<211> LENGTH: 748
<212> TYPE: PRT
<213> ORGANISM: Drosophila melanogaster

<400> SEQUENCE: 25

Ala His Ile Phe Gly Ala Thr Thr Asn Ala Leu Glu Arg Phe Leu Leu
  1               5                  10                  15

Asp Arg Lys Ile Lys Gly Pro Cys Trp Leu Gln Val Thr Gly Phe Lys
                 20                  25                  30

Val Ser Pro Thr Pro Met Ser Trp Cys Asn Thr Glu Val Thr Leu Thr
             35                  40                  45

Glu Pro Lys Asn Val Glu Leu Val Gln Asp Lys Gly Lys Pro Ala Pro
         50                  55                  60

Pro Pro Pro Leu Thr Leu Leu Ser Leu Asn Val Arg Thr Ser Met Asn
 65                  70                  75                  80

Pro Lys Thr Ser Arg Asn Glu Ile Cys Met Ile Ser Met Leu Thr His
                 85                  90                  95

Asn Arg Phe His Ile Asp Arg Pro Ala Pro Gln Pro Ala Phe Asn Arg
                100                 105                 110

His Met Cys Ala Leu Thr Arg Pro Ala Val Val Ser Trp Pro Leu Asp
            115                 120                 125

Leu Asn Phe Glu Met Ala Lys Tyr Lys Ser Thr Thr Val His Lys His
        130                 135                 140

Asp Ser Glu Arg Ala Leu Leu Ser Trp Phe Leu Ala Gln Tyr Gln Lys
145                 150                 155                 160

Ile Asp Ala Asp Leu Ile Val Thr Phe Asp Ser Met Asp Cys Gln Leu
                165                 170                 175

Asn Val Ile Thr Asp Gln Ile Val Ala Leu Lys Ile Pro Gln Trp Ser
            180                 185                 190

Arg Met Gly Arg Leu Arg Leu Ser Gln Ser Phe Gly Lys Arg Leu Leu
        195                 200                 205

Glu His Phe Val Gly Arg Met Val Cys Asp Val Lys Arg Ser Ala Glu
    210                 215                 220

Glu Cys Ile Arg Ala Arg Ser Tyr Asp Leu Gln Thr Leu Cys Lys Gln
225                 230                 235                 240

Val Leu Lys Leu Lys Glu Ser Glu Arg Met Glu Val Asn Ala Asp Asp
                245                 250                 255

Leu Leu Glu Met Tyr Glu Lys Gly Glu Ser Ile Thr Lys Leu Ile Ser
            260                 265                 270

Leu Thr Met Gln Asp Asn Ser Tyr Leu Leu Arg Leu Met Cys Glu Leu
        275                 280                 285

Asn Ile Met Pro Leu Ala Leu Gln Ile Thr Asn Ile Cys Gly Asn Thr
    290                 295                 300

Met Thr Arg Thr Leu Gln Gly Gly Arg Ser Glu Arg Asn Glu Phe Leu
305                 310                 315                 320

Leu Leu His Ala Ser Thr Glu Lys Asn Tyr Ile Val Pro Asp Lys Lys
                325                 330                 335
```

-continued

```
Pro Val Ser Lys Arg Ser Gly Ala Gly Asp Thr Asp Arg Thr Leu Ser
            340                 345                 350
Gly Ala Asp Ala Thr Met Gln Thr Lys Lys Ala Ala Tyr Ala Gly
            355                 360                 365
Gly Leu Val Leu Glu Pro Met Arg Gly Leu Tyr Glu Lys Tyr Val Leu
            370                 375                 380
Leu Met Asp Leu Asn Ser Leu Tyr Pro Ser Ile Ile Gln Glu Tyr Asn
385                 390                 395                 400
Ile Cys Phe Asn Pro Val Gln Gln Pro Val Asp Ala Asp Glu Leu Pro
                405                 410                 415
Thr Leu Pro Asp Ser Lys Thr Glu Pro Gly Ile Leu Pro Leu Gln Leu
            420                 425                 430
Lys Arg Leu Val Glu Ser Arg Lys Glu Val Lys Lys Leu Met Ala Ala
            435                 440                 445
Pro Asp Leu Ser Pro Glu Leu Gln Met Gln Tyr His Ile Arg Gln Met
            450                 455                 460
Ala Leu Lys Leu Thr Ala Asn Ser Met Tyr Gly Cys Leu Gly Phe Ala
465                 470                 475                 480
His Ser Arg Phe Phe Ala Gln His Leu Ala Ala Leu Val Thr His Lys
                485                 490                 495
Gly Arg Asp Leu Thr Asn Thr Gln Gln Leu Val Gln Lys Met Asn Tyr
            500                 505                 510
Asp Val Val Tyr Gly Asp Thr Asp Ser Leu Met Ile Asn Thr Asn Ile
            515                 520                 525
Thr Asp Tyr Asp Gln Val Tyr Lys Ile Gly His Asn Ile Lys Gln Ser
            530                 535                 540
Val Asn Lys Leu Tyr Lys Gln Leu Glu Leu Asp Ile Asp Gly Val Phe
545                 550                 555                 560
Gly Cys Leu Leu Leu Leu Lys Lys Lys Tyr Ala Ala Ile Lys Leu
            565                 570                 575
Ser Lys Asp Ser Lys Gly Asn Leu Arg Arg Glu Gln Glu His Lys Gly
            580                 585                 590
Leu Asp Ile Val Arg Arg Asp Trp Ser Gln Leu Ala Val Met Val Gly
            595                 600                 605
Lys Ala Val Leu Asp Glu Val Leu Ser Glu Lys Pro Leu Glu Glu Lys
            610                 615                 620
Leu Asp Ala Val His Ala Gln Leu Glu Lys Ile Lys Thr Gln Ile Ala
625                 630                 635                 640
Glu Gly Val Val Pro Leu Pro Leu Phe Val Ile Thr Lys Gln Leu Thr
                645                 650                 655
Arg Thr Pro Gln Asp Tyr Arg Asn Ser Ala Ser Leu Pro His Val Gln
            660                 665                 670
Val Ala Leu Arg Met Asn Arg Glu Arg Asn Arg Tyr Lys Lys Gly
            675                 680                 685
Asp Met Val Asp Leu Cys Asp Cys Leu Asp Gly Thr Thr Asn Ala Ala
            690                 695                 700
Met Gln Arg Ala Tyr His Leu Asp Glu Leu Lys Thr Ser Glu Asp Lys
705                 710                 715                 720
Lys Leu Gln Leu Asp Thr Asn Tyr Tyr Leu Gly His Gln Ile His Pro
                725                 730                 735
Val Val Thr Arg Met Val Glu Val Leu Glu Gly Thr
            740                 745
```

-continued

```
<210> SEQ ID NO 26
<211> LENGTH: 752
<212> TYPE: PRT
<213> ORGANISM: Schizosaccharomyces pombe

<400> SEQUENCE: 26
```

| | | | | | | | | | | | | | | | |
|---|---|---|---|---|---|---|---|---|---|---|---|---|---|---|---|
|Ser|His|Val|Phe|Gly|Thr|Asn|Thr|Ala|Leu|Phe|Glu|Gln|Phe|Val|Leu|
|1| | | |5| | | | |10| | | | |15| |
|Ser|Arg|Arg|Val|Met|Gly|Pro|Cys|Trp|Leu|Lys|Ile|Gln|Gln|Pro|Asn|
| | | |20| | | | |25| | | | |30| | |
|Phe|Asp|Ala|Val|Lys|Asn|Ala|Ser|Trp|Cys|Arg|Val|Glu|Ile|Gly|Cys|
| | |35| | | | |40| | | | |45| | | |
|Ser|Ser|Pro|Gln|Asn|Ile|Ser|Val|Ser|Phe|Glu|Lys|Asn|Glu|Ile|Thr|
| |50| | | | |55| | | | |60| | | | |
|Ser|Lys|Thr|Pro|Pro|Met|Thr|Val|Met|Ser|Leu|Ala|Phe|Arg|Thr|Leu|
|65| | | | |70| | | | |75| | | | |80|
|Ile|Asn|Lys|Glu|Gln|Asn|Lys|Gln|Glu|Val|Val|Met|Ile|Ser|Ala|Arg|
| | | | |85| | | | |90| | | | |95| |
|Ile|Phe|Glu|Asn|Val|Asp|Ile|Glu|Lys|Gly|Leu|Pro|Ala|Asn|Asp|Met|
| | | |100| | | | |105| | | | |110| | |
|Pro|Ser|Tyr|Ser|Phe|Ser|Leu|Ile|Arg|Pro|Leu|Lys|Gln|Ile|Phe|Pro|
| | |115| | | | |120| | | | |125| | | |
|Asn|Gly|Phe|Glu|Lys|Leu|Ala|Arg|Gln|His|Lys|Ser|Ser|Ile|Phe|Cys|
| |130| | | | |135| | | | |140| | | | |
|Glu|Arg|Ser|Glu|Val|Ser|Leu|Leu|Asn|Asn|Phe|Leu|Asn|Lys|Val|Arg|
|145| | | | |150| | | | |155| | | | |160|
|Thr|Tyr|Asp|Pro|Asp|Val|Tyr|Phe|Gly|His|Asp|Phe|Glu|Met|Cys|Tyr|
| | | | |165| | | | |170| | | | |175| |
|Ser|Val|Leu|Leu|Ser|Arg|Leu|Lys|Glu|Arg|Lys|Ile|His|Asn|Trp|Ser|
| | | |180| | | | |185| | | | |190| | |
|Ser|Ile|Gly|Arg|Leu|Arg|Arg|Ser|Glu|Trp|Pro|Arg|Ser|Phe|Asn|Arg|
| | |195| | | | |200| | | | |205| | | |
|Ser|Ser|Gln|Gln|Phe|Val|Glu|Lys|Gln|Ile|Ile|Ala|Gly|Arg|Leu|Met|
| |210| | | | |215| | | | |220| | | | |
|Cys|Asp|Leu|Ser|Asn|Asp|Phe|Gly|Arg|Ser|Met|Ile|Lys|Ala|Gln|Ser|
|225| | | | |230| | | | |235| | | | |240|
|Trp|Ser|Leu|Ser|Glu|Ile|Val|Leu|Lys|Glu|Leu|Asp|Ile|Lys|Arg|Gln|
| | | | |245| | | | |250| | | | |255| |
|Asp|Ile|Asn|Gln|Glu|Lys|Ala|Leu|Gln|Ser|Trp|Thr|Asp|Thr|Ala|His|
| | | |260| | | | |265| | | | |270| | |
|Gly|Leu|Leu|Asp|Tyr|Leu|Val|His|Cys|Glu|Ile|Asp|Thr|Phe|Phe|Ile|
| | |275| | | | |280| | | | |285| | | |
|Ala|Ala|Val|Ala|Phe|Lys|Ile|Gln|Met|Leu|Gln|Leu|Ser|Lys|Asn|Leu|
| |290| | | | |295| | | | |300| | | | |
|Thr|Asn|Ile|Ala|Gly|Asn|Ser|Trp|Ala|Arg|Thr|Leu|Thr|Gly|Thr|Arg|
|305| | | | |310| | | | |315| | | | |320|
|Ala|Glu|Arg|Asn|Glu|Tyr|Ile|Leu|Leu|His|Glu|Phe|Lys|Lys|Asn|Gly|
| | | | |325| | | | |330| | | | |335| |
|Tyr|Ile|Val|Pro|Asp|Lys|Gln|Gln|Ser|Ile|Arg|Arg|His|Ala|Glu|Ala|
| | | |340| | | | |345| | | | |350| | |
|Phe|Gly|Ala|Glu|Asp|Gly|Leu|Gln|Glu|Glu|Ser|Leu|Gly|Lys|Lys|Lys|
| | |355| | | | |360| | | | |365| | | |
|Asp|Lys|Tyr|Lys|Gly|Gly|Leu|Val|Phe|Glu|Pro|Gln|Lys|Gly|Leu|Tyr|
| |370| | | | |375| | | | |380| | | | |

-continued

```
Glu Thr Cys Ile Leu Val Met Asp Phe Asn Ser Leu Tyr Pro Ser Ile
385                 390                 395                 400

Ile Gln Glu Tyr Asn Ile Cys Phe Thr Thr Val Asp Arg Ser Pro Ser
            405                 410                 415

Asn Ser Asp Ser Asp Asp Gln Ile Pro Asp Thr Pro Ser Ala Ser Ala
            420                 425                 430

Asn Gln Gly Ile Phe Pro Arg Leu Ile Ala Asn Leu Val Glu Arg Arg
        435                 440                 445

Arg Gln Ile Lys Gly Leu Leu Lys Asp Asn Ser Ala Thr Pro Thr Gln
    450                 455                 460

Arg Leu Gln Trp Asp Ile Gln Gln Ala Leu Lys Leu Thr Ala Asn
465                 470                 475                 480

Ser Met Tyr Gly Cys Leu Gly Tyr Thr Lys Ser Arg Phe Tyr Ala Arg
            485                 490                 495

Pro Leu Ala Val Leu Ile Thr Tyr Lys Gly Arg Glu Ala Leu Met Asn
            500                 505                 510

Thr Lys Glu Leu Ala Asp Gln Met Gly Leu Gln Val Ile Tyr Gly Asp
        515                 520                 525

Thr Asp Ser Val Met Leu Asn Thr Asn Val Thr Asp Lys Asn His Ala
    530                 535                 540

Leu Arg Ile Gly Asn Glu Phe Lys Glu Lys Val Asn Glu Arg Tyr Ser
545                 550                 555                 560

Lys Leu Glu Ile Asp Ile Asp Asn Val Tyr Gln Arg Met Leu Leu His
            565                 570                 575

Ala Lys Lys Lys Tyr Ala Ala Leu Gln Leu Asp Ser Gln Gly Lys Pro
            580                 585                 590

Asn Leu Asp Val Lys Gly Leu Asp Met Lys Arg Arg Glu Phe Cys Thr
        595                 600                 605

Leu Ala Lys Glu Ala Ser Lys Phe Cys Leu Asp Gln Ile Leu Ser Gly
    610                 615                 620

Glu Leu Thr Glu Thr Val Ile Glu Asn Ile His Ser Tyr Leu Met Asp
625                 630                 635                 640

Phe Ser Glu Lys Met Arg Asn Gly Lys Phe Pro Ala Asn Lys Phe Ile
            645                 650                 655

Ile Phe Asn Arg Leu Gly Lys Asn Pro Glu Asp Tyr Pro Asn Gly Lys
            660                 665                 670

Thr Met Pro Phe Val Gln Val Ala Leu Lys Lys Lys Ala Arg Gly Glu
        675                 680                 685

Asn Val Arg Val Gly Asp Val Ile Pro Phe Ile Ile Ala Gly Ser Asp
    690                 695                 700

Ala Asp Gly His Pro Ala Asp Arg Ala Tyr Ser Pro Gln Glu Ile Met
705                 710                 715                 720

Asn Thr Asn Ser Thr Leu Val Ile Asp Tyr Asn Tyr Leu Ser His
            725                 730                 735

Gln Ile Leu Pro Pro Ile Glu Arg Val Ile Ala Pro Ile Glu Gly Thr
            740                 745                 750
```

<210> SEQ ID NO 27
<211> LENGTH: 761
<212> TYPE: PRT
<213> ORGANISM: Saccharomyces cerevisiae

<400> SEQUENCE: 27

```
Tyr His Val Phe Gly Gly Asn Ser Asn Ile Phe Glu Ser Phe Val Ile
1               5                   10                  15
```

-continued

```
Gln Asn Arg Ile Met Gly Pro Cys Trp Leu Asp Ile Lys Gly Ala Asp
             20                  25                  30
Phe Asn Ser Ile Arg Asn Ala Ser His Cys Ala Val Glu Val Ser Val
         35                  40                  45
Asp Lys Pro Gln Asn Ile Thr Pro Thr Thr Lys Thr Met Pro Asn
 50                  55                  60
Leu Arg Cys Leu Ser Leu Ser Ile Gln Thr Leu Met Asn Pro Lys Glu
 65                  70                  75                  80
Asn Lys Gln Glu Ile Val Ser Ile Thr Leu Ser Ala Tyr Arg Asn Ile
                 85                  90                  95
Ser Leu Asp Ser Pro Ile Pro Glu Asn Ile Lys Pro Asp Asp Leu Cys
             100                 105                 110
Thr Leu Val Arg Pro Pro Gln Ser Thr Ser Phe Pro Leu Gly Leu Ala
         115                 120                 125
Ala Leu Ala Lys Gln Lys Leu Pro Gly Arg Val Arg Leu Phe Asn Asn
     130                 135                 140
Glu Lys Ala Met Leu Ser Cys Phe Cys Ala Met Leu Lys Val Glu Asp
145                 150                 155                 160
Pro Asp Val Ile Ile Gly His Arg Leu Gln Asn Val Tyr Leu Asp Val
                 165                 170                 175
Leu Ala His Arg Met His Asp Leu Asn Ile Pro Thr Phe Ser Ser Ile
             180                 185                 190
Gly Arg Arg Leu Arg Arg Thr Trp Pro Glu Lys Phe Gly Arg Gly Asn
         195                 200                 205
Ser Asn Met Asn His Phe Phe Ile Ser Asp Ile Cys Ser Gly Arg Leu
     210                 215                 220
Ile Cys Asp Ile Ala Asn Glu Met Gly Gln Ser Leu Thr Pro Lys Cys
225                 230                 235                 240
Gln Ser Trp Asp Leu Ser Glu Met Tyr Gln Val Thr Cys Glu Lys Glu
                 245                 250                 255
His Lys Pro Leu Asp Ile Asp Tyr Gln Asn Pro Gln Tyr Gln Asn Asp
             260                 265                 270
Val Asn Ser Met Thr Met Ala Leu Gln Glu Asn Ile Thr Asn Cys Met
         275                 280                 285
Ile Ser Ala Glu Val Ser Tyr Arg Ile Gln Leu Leu Thr Leu Thr Lys
     290                 295                 300
Gln Leu Thr Asn Leu Ala Gly Asn Ala Trp Ala Gln Thr Leu Gly Gly
305                 310                 315                 320
Thr Arg Ala Gly Arg Asn Glu Tyr Ile Leu Leu His Glu Phe Ser Arg
                 325                 330                 335
Asn Gly Phe Ile Val Pro Asp Lys Glu Gly Asn Arg Ser Arg Ala Gln
             340                 345                 350
Lys Gln Arg Gln Asn Glu Glu Asn Ala Asp Ala Pro Val Asn Ser Lys
         355                 360                 365
Lys Ala Lys Tyr Gln Gly Gly Leu Val Phe Glu Pro Glu Lys Gly Leu
     370                 375                 380
His Lys Asn Tyr Val Leu Val Met Asp Phe Asn Ser Leu Tyr Pro Ser
385                 390                 395                 400
Ile Ile Gln Glu Phe Asn Ile Cys Phe Thr Thr Val Asp Arg Asn Lys
                 405                 410                 415
Glu Asp Ile Asp Glu Leu Pro Ser Val Pro Pro Ser Glu Val Asp Gln
             420                 425                 430
```

-continued

```
Gly Val Leu Pro Arg Leu Leu Ala Asn Leu Val Asp Arg Arg Glu
            435                 440                 445

Val Lys Lys Val Met Lys Thr Glu Thr Asp Pro His Lys Arg Val Gln
    450                 455                 460

Cys Asp Ile Arg Gln Gln Ala Leu Lys Leu Thr Ala Asn Ser Met Tyr
465                 470                 475                 480

Gly Cys Leu Gly Tyr Val Asn Ser Arg Phe Tyr Ala Lys Pro Leu Ala
                485                 490                 495

Met Leu Val Thr Asn Lys Gly Arg Glu Ile Leu Met Asn Thr Arg Gln
            500                 505                 510

Leu Ala Glu Ser Met Asn Leu Val Val Tyr Gly Asp Thr Asp Ser
        515                 520                 525

Val Met Ile Asp Thr Gly Cys Asp Asn Tyr Ala Asp Ala Ile Lys Ile
    530                 535                 540

Gly Leu Gly Phe Lys Arg Leu Val Asn Glu Arg Tyr Arg Leu Leu Glu
545                 550                 555                 560

Ile Asp Ile Asp Asn Val Phe Lys Lys Leu Leu His Ala Lys Lys
                565                 570                 575

Lys Tyr Ala Ala Leu Thr Val Asn Leu Asp Lys Asn Gly Asn Gly Thr
            580                 585                 590

Thr Val Leu Glu Val Lys Gly Leu Asp Met Lys Arg Arg Glu Phe Cys
        595                 600                 605

Pro Leu Ser Arg Asp Val Ser Ile His Val Leu Asn Thr Ile Leu Ser
        610                 615                 620

Asp Lys Asp Pro Glu Glu Ala Leu Gln Glu Val Tyr Asp Tyr Leu Glu
625                 630                 635                 640

Asp Ile Arg Ile Lys Val Glu Thr Asn Asn Ile Arg Ile Asp Lys Tyr
                645                 650                 655

Lys Ile Asn Met Lys Leu Ser Lys Asp Pro Lys Ala Tyr Pro Gly Gly
            660                 665                 670

Lys Asn Met Pro Ala Val Gln Val Ala Leu Arg Met Arg Lys Ala Gly
        675                 680                 685

Arg Val Val Lys Ala Gly Ser Val Ile Thr Phe Val Ile Thr Lys Gln
    690                 695                 700

Asp Glu Ile Asp Asn Ala Ala Asp Thr Pro Ala Leu Ser Val Ala Glu
705                 710                 715                 720

Arg Ala His Ala Leu Asn Glu Val Met Ile Lys Ser Asn Asn Leu Ile
                725                 730                 735

Pro Asp Pro Gln Tyr Tyr Leu Glu Lys Gln Ile Phe Ala Pro Val Glu
            740                 745                 750

Arg Leu Leu Glu Arg Ile Asp Ser Phe
        755                 760
```

<210> SEQ ID NO 28
<211> LENGTH: 761
<212> TYPE: PRT
<213> ORGANISM: Trypanosoma brucei

<400> SEQUENCE: 28

```
Gln Val Val Val Gly Ala Ser Arg Ser Leu Leu Glu Leu Phe Leu Ile
  1               5                  10                  15

Lys Lys Arg Leu Met Gly Pro Ser Tyr Leu Glu Ile Glu His Leu Val
            20                  25                  30

Thr Ala Met Asp Arg Val Ser His Cys Lys Thr Glu Phe Leu Val Pro
        35                  40                  45
```

```
Ser Pro Lys Asp Ile Lys Val Tyr Asn Ser Ser Lys Pro Pro Pro
 50                      55                      60

Phe Thr Val Ala Ser Ile Gln Leu His Ala Gln Leu Asp Ser Asp Gly
 65                  70                  75                  80

Val Lys Asn Glu Val Ile Ala Ala Ser Ile Ala Leu Tyr Gly Asp Val
                 85                  90                  95

Ser Ile Asp Gly Glu Arg Lys Pro Asn Ile Thr Glu Cys Phe Thr Gly
            100                 105                 110

Val Arg Gln Leu Ser Pro Asp Ala Pro Leu Pro Leu Asp Leu Glu Thr
        115                 120                 125

Tyr Cys Leu Ser Lys Arg Met Pro Gly Val His Arg Phe Ile Asn Glu
    130                 135                 140

Arg Ala Leu Leu Thr Trp Phe Ala Glu Thr Leu Ala Ala Leu Asp Pro
145                 150                 155                 160

Asp Ile Ile Val Gly His Asn Ile Ile Gly Tyr Thr Val Glu Thr Leu
                165                 170                 175

Leu Asn Arg Tyr Gln Glu Leu Asn Ile Val Arg Trp Ser Thr Ile Gly
            180                 185                 190

Arg Leu Asp Val Arg Arg Phe Pro Arg Ile Gln Gly Asn Asn Phe Asn
        195                 200                 205

Leu Ala Ile Glu Lys Glu Ala Cys Val Gly Arg Leu Val Val Asp Thr
210                 215                 220

Tyr Leu Leu Ala Arg Glu Tyr Tyr Lys Ser Thr Asn Tyr Lys Leu Leu
225                 230                 235                 240

Ser Leu Ser Thr Gln Met Glu Ile Lys Gly Ile Thr Asp Asn Arg Gly
                245                 250                 255

His Phe Glu Pro Gly Ser Thr Val Leu Val Lys Asp Ser Met Met Ser
            260                 265                 270

Ser Glu Ala Leu Cys Pro Ile Leu Leu Gln Leu Leu Asn Cys Ala Val
        275                 280                 285

Leu Ser Phe Asn Val Ala Ser Phe Leu Asp Val Ile Pro Leu Thr Lys
    290                 295                 300

Arg Leu Thr Leu Leu Ala Gly Asn Leu Trp Ser Arg Thr Leu Tyr Gly
305                 310                 315                 320

Ala Arg Ser Glu Arg Ile Glu Tyr Leu Leu Leu His Ala Phe His Asn
                325                 330                 335

Leu Lys Phe Val Thr Pro Asp Lys Lys Lys Arg Asp Leu Lys Arg Gly
            340                 345                 350

Arg Glu Asp Asp Asp Glu Gly Lys Arg Lys Thr Lys Tyr Gln Gly
        355                 360                 365

Gly Met Val Leu Glu Pro Lys Ser Gly Leu Tyr Ser Glu Tyr Ile Leu
    370                 375                 380

Leu Leu Asp Phe Asn Ser Leu Tyr Pro Ser Leu Ile Gln Glu Phe Asn
385                 390                 395                 400

Val Cys Tyr Thr Thr Ile Asp Arg Asp Glu Asn Thr Val Ser Ala Glu
                405                 410                 415

Val Pro Pro Pro Glu Ser Leu Ile Cys Leu Ser Cys Arg Ala Ala Gly
            420                 425                 430

Leu Pro Ser Pro Cys Leu His Lys Cys Ile Leu Pro Lys Val Ile Arg
        435                 440                 445

Gly Leu Val Asp Ser Arg Arg Glu Ile Lys Arg Met Met Lys Ser Glu
    450                 455                 460
```

-continued

```
Lys Asp Pro Gly Asn Leu Ala Met Leu Glu Ile Arg Gln Leu Ala Leu
465                 470                 475                 480

Lys Leu Thr Ala Asn Ser Met Tyr Gly Cys Leu Gly Phe Glu Tyr Ser
                485                 490                 495

Arg Phe Tyr Ala Gln Pro Leu Ala Glu Leu Val Thr Arg Gln Gly Arg
            500                 505                 510

Leu Ala Leu Gln Asn Thr Val Glu Leu Ile Pro Gln Ile Ser Pro Ser
        515                 520                 525

Ile Arg Val Ile Tyr Gly Asp Thr Asp Ser Val Met Ile Gln Thr Gly
    530                 535                 540

Ile Lys Asp Asp Ile Val Lys Val Arg Asn Leu Gly Phe Glu Ile Lys
545                 550                 555                 560

Gly Lys Val Asn Gln Arg Tyr Gln Ser Leu Glu Leu Asp Ile Asp Gly
                565                 570                 575

Val Phe Arg Ala Met Leu Leu Arg Lys Lys Tyr Ala Ala Leu
            580                 585                 590

Ser Val Val Asp Trp Gln Gly Glu Gly Lys Val Tyr Lys Arg Glu Val
            595                 600                 605

Lys Gly Leu Asp Met Val Arg Arg Asp Trp Cys Pro Leu Ser Gln His
    610                 615                 620

Val Ser Asp Ala Val Leu Lys Arg Ile Leu Asn Ala Glu Gly Gly Glu
625                 630                 635                 640

Asp Ile Leu Asp Phe Val Ile Lys Tyr Met Lys Gly Val Ala Gln Asp
                645                 650                 655

Val Arg Ser Gly Asn Val Tyr Pro Leu Glu Glu Phe Val Ile Ser Lys
            660                 665                 670

Ser Leu Thr Lys Glu Pro Glu Ser Tyr His Gly Thr Gly Tyr Pro His
        675                 680                 685

Ala Val Val Ala Leu Arg Met Lys Gln Arg Lys Glu Gly Val Arg Val
    690                 695                 700

Gly Asp Leu Ile Pro Tyr Val Ile Cys Glu Gly Asp Glu His Ile Asp
705                 710                 715                 720

Asp Lys Ala Tyr His Ile Asp Glu Val Arg Arg Ser Asp Gly Leu Ser
                725                 730                 735

Val Asp Val Glu Trp Tyr Leu Ser Gln Leu Tyr Pro Pro Val Met
            740                 745                 750

Arg Leu Cys Glu His Ile Gln Gly Phe
        755                 760

<210> SEQ ID NO 29
<211> LENGTH: 782
<212> TYPE: PRT
<213> ORGANISM: Autographa californica nucleopolynedrovirus

<400> SEQUENCE: 29

Asn Ala Ala Cys Leu Asp Lys Phe Leu His Asn Val Asn Arg Val His
1               5                   10                  15

Met Gln Thr Pro Phe Val Glu Gly Ala Tyr Met Arg Phe Lys Lys Thr
                20                  25                  30

Gln Arg Cys Gln Asn Asn Tyr Val Gly Gly Ser Thr Thr Arg Met Phe
            35                  40                  45

Asn Leu Gln His Phe Asn Glu Asp Phe Glu Leu Val Asp Glu Met Thr
        50                  55                  60

Leu Thr Ser Gly Ile Met Pro Val Leu Ser Cys Tyr Asp Ile Glu Thr
65                  70                  75                  80
```

-continued

```
His Ser Asp Gly His Asn Met Ser Lys Ala Ser Val Asp Cys Ile Met
                 85                  90                  95
Ser Ile Gly Phe Val Val Tyr Lys Asn Asp Glu Tyr Ala Lys Phe Cys
            100                 105                 110
Phe Met Tyr His Lys Leu Pro Thr Gln Ile Pro Glu Thr Tyr Asp Asp
        115                 120                 125
Asp Thr Tyr Val Val Met Phe Gln Asn Glu Ile Asp Met Ile Thr Ala
    130                 135                 140
Phe Phe Asp Met Ile Lys Ile Thr Asn Pro Asp Val Ile Leu Asp Phe
145                 150                 155                 160
Asn Gly Asp Val Phe Asp Leu Pro Tyr Ile Leu Gly Arg Leu Asn Lys
                165                 170                 175
Thr Lys Met Leu Leu Lys Arg Tyr Asp Leu Pro Ala Ala Ala Pro Thr
            180                 185                 190
Thr Lys Leu Phe Ile Asn Lys Leu Gly Asn Lys Val Asp Thr Tyr Tyr
        195                 200                 205
Phe Asn Tyr Tyr Ile His Ile Asp Leu Tyr Lys Phe Phe Ser Ser Asp
    210                 215                 220
Ser Asn Gln His Lys Val Glu Asn Phe Gln Leu Asn Thr Ile Ser Ser
225                 230                 235                 240
Tyr Tyr Leu Gly Glu Asn Lys Ile Asp Leu Pro Trp Thr Glu Met Val
                245                 250                 255
Lys Met Tyr Asn Thr Arg Arg Leu Asp Val Ile Ala Lys Tyr Asn Val
            260                 265                 270
Gln Asp Cys Met Leu Pro Ile Lys Leu Phe Val Lys Leu Lys Met Ala
        275                 280                 285
Asp Ser Val Tyr Ser Gln Cys Ile Leu His Arg Leu Cys Thr Asp Asp
    290                 295                 300
Val Ile Cys Asn Ile Ser His Leu Ile Ser Val Ala Cys Phe Tyr Ala
305                 310                 315                 320
Ala Ile Thr Asn Thr Arg Ile Asn Glu Ser Thr Gly Lys Glu Glu Pro
                325                 330                 335
Asp Pro Tyr Phe Phe Asn Lys Asn Asp Leu Ser Ile Ile Ser Gly Gln
            340                 345                 350
Phe Lys Ala Asp Lys Ala Ala Gly Ile Ser Asn Leu Lys Arg Lys
        355                 360                 365
Leu Ile Pro Leu Lys Asn Ile Pro Lys Asp Ala Ile Asn Leu Gly Pro
370                 375                 380
Ala Asn Gln Thr Val Lys Tyr Lys Gly Gly Lys Val Leu Lys Pro Arg
385                 390                 395                 400
Ala Gly Ile Tyr Lys Asn Ala Phe Ser Leu Asp Phe Asn Ser Leu Tyr
                405                 410                 415
Leu Thr Ile Met Ile Ala Ile Cys Ala Cys Leu Ser Asn Leu Ile Leu
            420                 425                 430
Cys Glu Asp Gly Asn Val Tyr Leu Asn His Asn Ser Arg Ala Ile Val
        435                 440                 445
Val Lys Leu Leu Leu Lys Leu Leu Ser Glu Arg Cys Lys Phe Lys Lys
    450                 455                 460
Asn Arg Asp Asn Gln Ser Glu Ser Ala Phe Leu Tyr Asp Leu Tyr Asp
465                 470                 475                 480
Gln Lys Gln Asn Ser Val Lys Arg Thr Ala Asn Ser Ile Tyr Gly Tyr
                485                 490                 495
```

-continued

```
Tyr Gly Ile Phe Tyr Lys Val Leu Ala Asn Tyr Ile Thr Arg Val Gly
            500                 505                 510

Arg Asn Gln Leu Arg Leu Ala Ile Ser Leu Ile Glu Gly Leu Ser Asn
        515                 520                 525

Asp Pro Glu Ile Leu Glu Lys Phe Asn Leu Gly Ser Ile Thr Phe Lys
    530                 535                 540

Val Val Tyr Gly Asp Thr Asp Ser Thr Phe Val Leu Pro Thr Phe Asn
545                 550                 555                 560

Tyr Asn Glu Ile Ser Asn Glu Thr Asp Thr Leu Lys Gln Ile Cys Thr
                565                 570                 575

His Val Glu Thr Arg Val Asn Asn Ser Phe Thr Asp Gly Tyr Lys Met
            580                 585                 590

Ala Phe Glu Asn Leu Met Lys Val Leu Ile Leu Lys Lys Lys
        595                 600                 605

Tyr Cys Tyr Leu Asn Ser Glu Asn Lys Ile Val Tyr Lys Gly Trp Leu
    610                 615                 620

Val Lys Lys Asp Met Pro Val Phe Met Arg Ile Ala Phe Arg Thr Ala
625                 630                 635                 640

Val Glu Gln Ile Leu Arg His Leu Asp Met Asp Lys Cys Leu Gln Ser
                645                 650                 655

Leu Gln Thr Ser Phe Tyr Glu Tyr Asp Glu Phe Ala Lys Ser Lys
            660                 665                 670

Ser Leu Thr Asp Tyr Ser Phe Ser Met Thr Tyr Asn Asp Asn Pro Gly
        675                 680                 685

Lys Lys Arg Lys Ser Thr Asp Asp Asn Glu Gly Pro Ser Pro Lys Arg
    690                 695                 700

Arg Val Ile Thr Val Ala Arg His Cys Arg Glu Ile Leu Val Asn Lys
705                 710                 715                 720

Gly Thr Asp Phe Val Pro Gly Asn Gly Asp Arg Ile Pro Tyr Leu Leu
                725                 730                 735

Ile Asp Ile Glu Gly Lys Val Thr Glu Lys Ala Tyr Pro Leu Arg Leu
            740                 745                 750

Phe Asp Pro Val Lys Met Arg Ile Ser Trp Ile Lys His Met Gly Ile
        755                 760                 765

Leu Cys Thr Phe Met Asn Glu Leu Leu Glu Ile Phe Gly Asp
    770                 775                 780

<210> SEQ ID NO 30
<211> LENGTH: 797
<212> TYPE: PRT
<213> ORGANISM: Lymantria dispar multicapsid nuclear polyhedrosis

<400> SEQUENCE: 30

Asp Lys Asn Cys Leu Asp Gly Tyr Leu Ala Asp Val Asn Arg Val His
1               5                   10                  15

Met Gln Thr Ser Leu Leu Glu Gly Gln Tyr Val Arg Phe Lys Asn Ala
            20                  25                  30

His Ala Cys Arg Asp Tyr Arg Leu Ser His Thr Ala Lys Asp Val His
        35                  40                  45

Glu Phe Glu Ser Met Leu Glu Arg Val Gln Val Ser Ala Leu Ser His
    50                  55                  60

Glu Ile Leu Pro Val Val Ala Cys Tyr Asp Ile Glu Thr His Ser Asp
65                  70                  75                  80

Gly Gln Arg Phe Ser Ala Pro Asp Ala Asp Phe Ile Ile Ser Ile Ala
                85                  90                  95
```

-continued

```
Val Val Val Arg Arg Asp Ala Ala Asp Thr Arg Ile Cys Leu Phe Tyr
            100                 105                 110
Ser Pro Asp Asp Pro Val Asp Leu Ser Ser Ser Ser Ser Pro Pro
        115                 120                 125
Ala Ala Pro Asp Thr Ala Ala Val His Phe Arg Ala Glu Arg Asp Met
    130                 135                 140
Ile Ala Ala Phe Phe Gln Leu Leu Pro Leu Leu Asn Ala Asp Val Val
145                 150                 155                 160
Leu Asp Phe Asn Gly Asp Lys Phe Asp Leu Pro Phe Leu Thr Gly Arg
                165                 170                 175
Ala Asn Lys Leu Cys Gly Pro Ala Glu Ala Arg Ala Thr Lys Ile
            180                 185                 190
Ala Arg Tyr Asp Leu Ser Pro Val Asn Val Val Thr Gln Gln Ser Tyr
        195                 200                 205
Asp Lys Phe Ser Asn Lys Leu His Ser His Tyr Leu Thr Tyr Tyr Ile
    210                 215                 220
His Ile Asp Leu Tyr Gln Phe Leu Ser Thr Asp Ser Glu His Asn Asp
225                 230                 235                 240
Leu Glu Asn Phe Gln Leu Asn Thr Val Ala Glu His Tyr Leu Lys Lys
                245                 250                 255
Ser Lys Val Asp Leu Pro Ile His Asp Met Leu Gln Met Tyr Gly Glu
            260                 265                 270
Lys Arg Leu Ser Arg Ile Val Glu Tyr Asn Val Gln Asp Cys Val Leu
        275                 280                 285
Pro Val Glu Leu Phe Leu Lys Leu Glu Ile Ala Asp Tyr Met Tyr Thr
    290                 295                 300
Gln Cys Met Leu Leu Tyr Leu Cys Thr Asp Asp Leu Leu Arg Asn Ile
305                 310                 315                 320
Ser His Lys Ile Thr Val Ala Tyr Phe His Leu Ala Leu Thr Asn Thr
                325                 330                 335
Val Ala Arg Arg Pro Asp Pro Thr Pro Asp Pro Tyr Phe Phe Asn Lys
            340                 345                 350
Tyr Asp Leu Ser Val Thr Ser Gly Ala Ser Ala Pro Ser Thr Ser Arg
        355                 360                 365
Pro Ala Asn Ala Ile Asp Leu Ser Gln Leu Lys Arg Thr Pro Val Asp
    370                 375                 380
Ala Ala Arg Ile Pro Pro Ser Ala Val Lys Leu Cys Ser Thr Arg Gln
385                 390                 395                 400
Ser Cys Thr Tyr Lys Gly Gly Lys Val Leu Ser Pro Lys Pro Gly Phe
                405                 410                 415
Asn Arg Trp Val Ala Thr Leu Asp Phe Asn Ala Leu Tyr Pro Thr Ile
            420                 425                 430
Met Met Trp Glu Gly Val Cys Met Ser Ser Asn Val Phe Ile Ala Ser
        435                 440                 445
Asp Gly Asn Val Tyr Leu Asp Lys Asn Val Asn Ala Val Asn Pro Lys
    450                 455                 460
Leu Leu Lys Thr Leu Ser Glu Met Arg Val Arg Tyr Lys Gly Leu Arg
465                 470                 475                 480
Asp Gln Cys Glu Tyr Asn Ser Phe Tyr Tyr Lys Leu Tyr Asp Lys Ile
                485                 490                 495
Gln Asn Ala Leu Lys Arg Ile Ala Asn Ser Ile Tyr Gly Tyr Tyr Gly
            500                 505                 510
```

-continued

```
Ile Phe Phe Lys Pro Leu Ala Asn Tyr Ile Thr Lys Met Gly Arg Gly
            515                 520                 525

Lys Leu Lys Glu Val Val Gly Lys Val Glu Ala Met Ser Asp Asp Pro
        530                 535                 540

Arg Ile Leu Arg Glu Phe Gly Leu Ser Lys Ile Asn Phe Ser Val Ile
545                 550                 555                 560

Tyr Gly Asp Thr Asp Ser Cys Phe Ile Arg Val Leu Phe Asp Glu Ala
                565                 570                 575

Glu Trp Arg Arg Thr Ala Ala Arg Pro Arg Ser Ala Pro Ser Cys Arg
            580                 585                 590

Thr Thr Cys Ala Lys Arg Ser Thr Thr Leu Trp Cys Gly Tyr Lys Met
        595                 600                 605

Ser Leu Glu Asn Ile Met Leu Ser Leu Ile Leu Lys Lys Lys Lys
    610                 615                 620

Tyr Cys Tyr Leu Asn Asn Glu Gln Arg Thr Lys Tyr Lys Gly Trp Leu
625                 630                 635                 640

Ile Lys Arg Asp Met Pro Leu Phe Met Arg Lys Ala Phe Arg Ala Thr
                645                 650                 655

Val Asp Ser Phe Ser Ala Ala Thr Arg Arg Val Arg Ala Arg Pro Ala
            660                 665                 670

Arg Arg Glu Met Leu Arg Tyr Tyr Arg Glu Phe Gly Ala Pro Arg Glu
        675                 680                 685

Asn Leu Val Asp Tyr Cys Phe Ser Met Ser Tyr Asn Glu Thr Ser Thr
    690                 695                 700

Thr Ala Lys Arg Arg Lys Glu Glu Asp Pro Ala Arg Lys Pro Val Ile
705                 710                 715                 720

Thr Ile Ala Lys His Cys Arg Glu Leu Leu Ala Asn Pro Gly Val Asp
                725                 730                 735

Phe Leu Pro Gly Asn Gly Asp Arg Ile Gln Tyr Val Leu Val Asp Val
            740                 745                 750

Lys Glu Lys Ile Thr Gln Lys Ala Phe Pro Leu Lys Leu Phe Asp Pro
        755                 760                 765

Asp Ser Pro Thr Leu Gln Ile Ser Trp Leu Lys His Met Asn Ile Leu
    770                 775                 780

Cys Thr Phe Met Asn Glu Leu Ile Gln Val Phe Gly Asn
785                 790                 795

<210> SEQ ID NO 31
<211> LENGTH: 745
<212> TYPE: PRT
<213> ORGANISM: Saccharomyces cerevisiae

<400> SEQUENCE: 31

Asn Lys Val Pro Ser Met Gly Asn Lys Lys Thr Glu Ser Gln Ile Ser
  1               5                  10                  15

Met His Thr Pro His Ser Lys Phe Leu Tyr Lys Phe Ala Ser Asp Val
             20                  25                  30

Ser Gly Lys Gln Lys Arg Lys Lys Ser Ser Val His Asp Ser Leu Thr
         35                  40                  45

His Leu Thr Leu Glu Ile His Ala Asn Thr Arg Ser Asp Lys Ile Pro
     50                  55                  60

Asp Pro Ala Ile Asp Glu Val Ser Met Ile Ile Trp Cys Leu Glu Glu
 65                  70                  75                  80

Glu Thr Phe Pro Leu Asp Leu Asp Ile Ala Tyr Glu Gly Ile Met Ile
                 85                  90                  95
```

-continued

```
Val His Lys Ala Ser Glu Asp Ser Thr Phe Pro Thr Lys Ile Gln His
                100                 105                 110
Cys Ile Asn Glu Ile Pro Val Met Phe Tyr Glu Ser Glu Phe Glu Met
            115                 120                 125
Phe Glu Ala Leu Thr Asp Leu Val Leu Leu Asp Pro Asp Ile Leu
        130                 135                 140
Ser Gly Phe Glu Ile His Asn Phe Ser Trp Gly Tyr Ile Ile Glu Arg
145                 150                 155                 160
Cys Gln Lys Ile His Gln Phe Asp Ile Val Arg Glu Leu Ala Arg Val
                165                 170                 175
Lys Cys Gln Ile Lys Thr Lys Leu Ser Asp Thr Trp Gly Tyr Ala His
                180                 185                 190
Ser Ser Gly Ile Met Ile Thr Gly Arg His Met Ile Asn Ile Trp Arg
        195                 200                 205
Ala Leu Arg Ser Asp Val Asn Leu Thr Gln Tyr Thr Ile Glu Ser Ala
        210                 215                 220
Ala Phe Asn Ile Leu His Lys Arg Leu Pro His Phe Ser Phe Glu Ser
225                 230                 235                 240
Leu Thr Asn Met Trp Asn Ala Lys Lys Ser Thr Thr Glu Leu Lys Thr
                245                 250                 255
Val Leu Asn Tyr Trp Leu Ser Arg Ala Gln Ile Asn Ile Gln Leu Leu
                260                 265                 270
Arg Lys Gln Asp Tyr Ile Ala Arg Asn Ile Glu Gln Ala Arg Leu Ile
            275                 280                 285
Gly Ile Asp Phe His Ser Val Tyr Tyr Arg Gly Ser Gln Phe Lys Val
        290                 295                 300
Glu Ser Phe Leu Ile Arg Ile Cys Lys Ser Glu Ser Phe Ile Leu Leu
305                 310                 315                 320
Ser Pro Gly Lys Lys Asp Val Arg Lys Gln Lys Ala Leu Glu Cys Val
                325                 330                 335
Pro Leu Val Met Glu Pro Glu Ser Ala Phe Tyr Lys Ser Pro Leu Ile
            340                 345                 350
Val Leu Asp Phe Gln Ser Leu Tyr Pro Ser Ile Met Ile Gly Tyr Asn
        355                 360                 365
Tyr Cys Tyr Ser Thr Met Ile Gly Arg Val Arg Glu Ile Asn Leu Thr
    370                 375                 380
Glu Asn Asn Leu Gly Val Ser Lys Phe Ser Leu Pro Arg Asn Ile Leu
385                 390                 395                 400
Ala Leu Leu Lys Asn Asp Val Thr Ile Ala Pro Asn Gly Val Val Tyr
                405                 410                 415
Ala Lys Thr Ser Val Arg Lys Ser Thr Leu Ser Lys Met Leu Thr Asp
                420                 425                 430
Ile Leu Asp Val Arg Val Met Ile Lys Lys Thr Met Asn Glu Ile Gly
            435                 440                 445
Asp Asp Asn Thr Thr Leu Lys Arg Leu Leu Asn Asn Lys Gln Leu Ala
        450                 455                 460
Leu Lys Leu Leu Ala Asn Val Thr Tyr Gly Tyr Thr Ser Ala Ser Phe
465                 470                 475                 480
Ser Gly Arg Met Pro Cys Ser Asp Leu Ala Asp Ser Ile Val Gln Thr
                485                 490                 495
Gly Arg Glu Thr Leu Glu Lys Ala Ile Asp Ile Ile Glu Lys Asp Glu
            500                 505                 510
```

```
Thr Trp Asn Ala Lys Val Val Tyr Gly Asp Thr Asp Ser Leu Phe Val
            515                 520                 525

Tyr Leu Pro Gly Lys Thr Ala Ile Glu Ala Phe Ser Ile Gly His Ala
        530                 535                 540

Met Ala Glu Arg Val Thr Gln Asn Asn Pro Lys Pro Ile Phe Leu Lys
545                 550                 555                 560

Phe Glu Lys Val Tyr His Pro Ser Ile Leu Ile Ser Lys Lys Arg Tyr
                565                 570                 575

Val Gly Phe Ser Tyr Glu Ser Pro Ser Gln Thr Leu Pro Ile Phe Asp
            580                 585                 590

Ala Lys Gly Ile Glu Thr Val Arg Arg Asp Gly Ile Pro Ala Gln Gln
        595                 600                 605

Lys Ile Ile Glu Lys Cys Ile Arg Leu Leu Phe Gln Thr Lys Asp Leu
    610                 615                 620

Ser Lys Ile Lys Lys Tyr Leu Gln Asn Glu Phe Phe Lys Ile Gln Ile
625                 630                 635                 640

Gly Lys Val Ser Ala Gln Asp Phe Cys Phe Ala Lys Glu Val Lys Leu
                645                 650                 655

Gly Ala Tyr Lys Ser Glu Lys Thr Ala Pro Ala Gly Ala Val Val Val
            660                 665                 670

Lys Arg Arg Ile Asn Glu Asp His Arg Ala Glu Pro Gln Tyr Lys Glu
        675                 680                 685

Arg Ile Pro Tyr Leu Val Val Lys Gly Lys Gln Gly Gln Leu Leu Arg
    690                 695                 700

Glu Arg Cys Val Ser Pro Glu Glu Phe Leu Glu Gly Glu Asn Leu Glu
705                 710                 715                 720

Leu Asp Ser Glu Tyr Tyr Ile Asn Lys Ile Leu Ile Pro Pro Leu Asp
                725                 730                 735

Arg Leu Phe Asn Leu Ile Gly Ile Asn
            740                 745

<210> SEQ ID NO 32
<211> LENGTH: 727
<212> TYPE: PRT
<213> ORGANISM: Pyrococcus woesei

<400> SEQUENCE: 32

Phe Lys Ile Glu His Asp Arg Thr Phe Arg Pro Tyr Ile Tyr Ala Leu
1               5                   10                  15

Leu Arg Asp Asp Ser Lys Ile Glu Glu Val Lys Lys Ile Thr Gly Glu
            20                  25                  30

Arg His Gly Lys Ile Val Arg Ile Val Asp Val Glu Lys Val Glu Lys
        35                  40                  45

Lys Phe Leu Gly Lys Pro Ile Thr Val Trp Lys Leu Tyr Leu Glu His
    50                  55                  60

Pro Gln Asp Val Pro Thr Ile Arg Glu Lys Val Arg Glu His Pro Ala
65                  70                  75                  80

Val Val Asp Ile Phe Glu Tyr Asp Ile Pro Phe Ala Lys Arg Tyr Leu
                85                  90                  95

Ile Asp Lys Gly Leu Ile Pro Met Glu Gly Glu Glu Leu Lys Ile
            100                 105                 110

Leu Ala Phe Asp Ile Glu Thr Leu Tyr His Glu Gly Glu Glu Phe Gly
        115                 120                 125

Lys Gly Pro Ile Ile Met Ile Ser Tyr Ala Asp Glu Asn Glu Ala Lys
    130                 135                 140
```

-continued

```
Val Ile Thr Trp Lys Asn Ile Asp Leu Pro Tyr Val Glu Val Val Ser
145                 150                 155                 160

Ser Glu Arg Glu Met Ile Lys Arg Phe Leu Arg Ile Ile Arg Glu Lys
                165                 170                 175

Asp Pro Asp Ile Ile Val Thr Tyr Asn Gly Asp Ser Phe Asp Phe Pro
            180                 185                 190

Tyr Leu Ala Lys Arg Ala Glu Lys Leu Gly Ile Lys Leu Thr Ile Gly
        195                 200                 205

Arg Asp Gly Ser Glu Pro Lys Met Gln Arg Ile Gly Asp Met Thr Ala
210                 215                 220

Val Glu Val Lys Gly Arg Ile His Phe Asp Leu Tyr His Val Ile Thr
225                 230                 235                 240

Arg Thr Ile Asn Leu Pro Thr Tyr Thr Leu Glu Ala Val Tyr Glu Ala
                245                 250                 255

Ile Phe Gly Lys Pro Lys Glu Lys Val Tyr Ala Asp Glu Ile Ala Lys
            260                 265                 270

Ala Trp Glu Ser Gly Glu Asn Leu Glu Arg Val Ala Lys Tyr Ser Met
        275                 280                 285

Glu Asp Ala Lys Ala Thr Tyr Glu Leu Gly Lys Glu Phe Leu Pro Met
290                 295                 300

Glu Ile Gln Leu Ser Arg Leu Val Gly Gln Pro Leu Trp Asp Val Ser
305                 310                 315                 320

Arg Ser Ser Thr Gly Asn Leu Val Glu Trp Phe Leu Leu Arg Lys Ala
                325                 330                 335

Tyr Glu Arg Asn Glu Val Ala Pro Asn Lys Pro Ser Glu Glu Glu Tyr
            340                 345                 350

Gln Arg Arg Leu Arg Glu Ser Tyr Thr Gly Gly Phe Val Lys Glu Pro
        355                 360                 365

Glu Lys Gly Leu Trp Glu Asn Ile Val Tyr Leu Asp Phe Arg Ala Leu
            370                 375                 380

Tyr Pro Ser Ile Ile Ile Thr His Asn Val Ser Pro Asp Thr Leu Asn
385                 390                 395                 400

Leu Glu Gly Cys Lys Asn Tyr Asp Ile Ala Pro Gln Val Gly His Lys
                405                 410                 415

Phe Cys Lys Asp Ile Pro Gly Phe Ile Pro Ser Leu Leu Gly His Leu
            420                 425                 430

Leu Glu Glu Arg Gln Lys Ile Lys Thr Lys Met Lys Glu Thr Gln Asp
        435                 440                 445

Pro Ile Glu Lys Ile Leu Leu Asp Tyr Arg Gln Lys Ala Ile Lys Leu
450                 455                 460

Leu Ala Asn Ser Phe Tyr Gly Tyr Tyr Gly Tyr Ala Lys Ala Arg Trp
465                 470                 475                 480

Tyr Cys Lys Glu Cys Ala Glu Ser Val Thr Ala Trp Gly Arg Lys Tyr
                485                 490                 495

Ile Glu Leu Val Trp Lys Glu Leu Glu Glu Lys Phe Gly Phe Lys Val
            500                 505                 510

Leu Tyr Ile Asp Thr Asp Gly Leu Tyr Ala Thr Ile Pro Gly Gly Glu
        515                 520                 525

Ser Glu Glu Ile Lys Lys Lys Ala Leu Glu Phe Val Lys Tyr Ile Asn
530                 535                 540

Ser Lys Leu Pro Gly Leu Leu Glu Leu Glu Tyr Glu Gly Phe Tyr Lys
545                 550                 555                 560
```

```
Arg Gly Phe Phe Val Thr Lys Lys Arg Tyr Ala Val Ile Asp Glu Glu
                565                 570                 575

Gly Lys Val Ile Thr Arg Gly Leu Glu Ile Val Arg Arg Asp Trp Ser
            580                 585                 590

Glu Ile Ala Lys Glu Thr Gln Ala Arg Val Leu Glu Thr Ile Leu Lys
        595                 600                 605

His Gly Asp Val Glu Glu Ala Val Arg Ile Val Lys Glu Val Ile Gln
    610                 615                 620

Lys Leu Ala Asn Tyr Glu Ile Pro Pro Glu Lys Leu Ala Ile Tyr Glu
625                 630                 635                 640

Gln Ile Thr Arg Pro Leu His Glu Tyr Lys Ala Ile Gly Pro His Val
                645                 650                 655

Ala Val Ala Lys Lys Leu Ala Ala Lys Gly Val Lys Ile Lys Pro Gly
            660                 665                 670

Met Val Ile Gly Tyr Ile Val Leu Arg Gly Asp Gly Pro Ile Ser Asn
        675                 680                 685

Arg Ala Ile Leu Ala Glu Glu Tyr Asp Pro Lys Lys His Lys Tyr Asp
    690                 695                 700

Ala Glu Tyr Tyr Ile Glu Asn Gln Val Leu Pro Ala Val Leu Arg Ile
705                 710                 715                 720

Leu Glu Gly Phe Gly Tyr Arg
                725

<210> SEQ ID NO 33
<211> LENGTH: 702
<212> TYPE: PRT
<213> ORGANISM: Sulfolobus solfataricus

<400> SEQUENCE: 33

Phe Asn Asn Tyr Met Tyr Asp Ile Gly Leu Ile Pro Gly Met Pro Tyr
1               5                   10                  15

Val Val Lys Asn Gly Lys Leu Glu Ser Val Tyr Leu Ser Leu Asp Glu
            20                  25                  30

Lys Asp Val Glu Glu Ile Lys Lys Ala Phe Ala Asp Ser Asp Glu Met
        35                  40                  45

Thr Arg Gln Met Ala Val Asp Trp Leu Pro Ile Phe Glu Thr Glu Ile
    50                  55                  60

Pro Lys Ile Lys Arg Val Ala Ile Asp Ile Glu Val Tyr Thr Pro Val
65                  70                  75                  80

Lys Gly Arg Ile Pro Asp Ser Gln Lys Ala Glu Phe Pro Ile Ile Ser
                85                  90                  95

Ile Ala Leu Ala Gly Ser Asp Gly Leu Lys Lys Val Leu Val Leu Asn
            100                 105                 110

Arg Asn Asp Val Asn Glu Gly Ser Val Lys Leu Asp Gly Ile Ser Val
        115                 120                 125

Glu Arg Phe Asn Thr Glu Tyr Glu Leu Leu Gly Arg Phe Phe Asp Ile
    130                 135                 140

Leu Leu Glu Tyr Pro Ile Val Leu Thr Phe Asn Gly Asp Asp Phe Asp
145                 150                 155                 160

Leu Pro Tyr Ile Tyr Phe Arg Ala Leu Lys Leu Gly Tyr Phe Pro Glu
                165                 170                 175

Glu Ile Pro Ile Asp Val Ala Gly Lys Asp Glu Ala Lys Tyr Leu Ala
            180                 185                 190

Gly Leu His Ile Asp Leu Tyr Lys Phe Phe Asn Lys Ala Val Arg
        195                 200                 205
```

-continued

```
Asn Tyr Ala Phe Glu Gly Lys Tyr Asn Glu Tyr Asn Leu Asp Ala Val
    210                 215                 220
Ala Lys Ala Leu Leu Gly Thr Ser Lys Val Lys Val Asp Thr Leu Ile
225                 230                 235                 240
Ser Phe Leu Asp Val Glu Lys Leu Ile Glu Tyr Asn Phe Arg Asp Ala
                245                 250                 255
Glu Ile Thr Leu Gln Leu Thr Thr Phe Asn Asn Asp Leu Thr Met Lys
            260                 265                 270
Leu Ile Val Leu Phe Ser Arg Ile Ser Arg Leu Gly Ile Glu Glu Leu
        275                 280                 285
Thr Arg Thr Glu Ile Ser Thr Trp Val Lys Asn Leu Tyr Tyr Trp Glu
    290                 295                 300
His Arg Lys Arg Asn Trp Leu Ile Pro Leu Lys Glu Ile Leu Ala
305                 310                 315                 320
Lys Ser Ser Asn Ile Arg Thr Ser Ala Leu Ile Lys Gly Lys Gly Tyr
                325                 330                 335
Lys Gly Ala Val Val Ile Asp Pro Pro Ala Gly Ile Phe Phe Asn Ile
            340                 345                 350
Thr Val Leu Asp Phe Ala Ser Leu Tyr Pro Ser Ile Ile Arg Thr Trp
        355                 360                 365
Asn Leu Ser Tyr Glu Thr Val Asp Ile Gln Gln Cys Lys Lys Pro Tyr
    370                 375                 380
Glu Val Lys Asp Glu Thr Gly Glu Val Leu His Ile Val Cys Met Asp
385                 390                 395                 400
Arg Pro Gly Ile Thr Ala Val Ile Thr Gly Leu Leu Arg Asp Phe Arg
                405                 410                 415
Val Lys Ile Tyr Lys Lys Ala Lys Asn Pro Asn Asn Ser Glu Glu
            420                 425                 430
Gln Lys Leu Leu Tyr Asp Val Gln Arg Ala Met Lys Val Phe Ile
        435                 440                 445
Asn Ala Thr Tyr Gly Val Phe Gly Ala Glu Thr Phe Pro Leu Tyr Ala
    450                 455                 460
Pro Arg Val Ala Glu Ser Val Thr Ala Leu Gly Arg Tyr Val Ile Thr
465                 470                 475                 480
Ser Thr Val Lys Lys Ala Arg Glu Glu Gly Leu Thr Val Leu Tyr Gly
                485                 490                 495
Asp Thr Asp Ser Leu Phe Leu Asn Pro Pro Lys Asn Ser Leu Glu
            500                 505                 510
Asn Ile Ile Lys Trp Val Lys Thr Thr Phe Asn Leu Asp Leu Glu Val
        515                 520                 525
Asp Lys Thr Tyr Lys Phe Val Ala Phe Ser Gly Leu Lys Lys Asn Tyr
    530                 535                 540
Phe Gly Val Tyr Gln Asp Gly Lys Val Asp Ile Lys Gly Met Leu Val
545                 550                 555                 560
Lys Lys Arg Asn Thr Pro Glu Phe Val Lys Lys Val Phe Asn Glu Val
                565                 570                 575
Lys Glu Leu Met Ile Ser Ile Asn Ser Pro Asn Asp Val Lys Glu Ile
            580                 585                 590
Lys Arg Lys Ile Val Asp Val Lys Gly Ser Tyr Glu Lys Leu Lys
        595                 600                 605
Asn Lys Gly Tyr Asn Leu Asp Glu Leu Ala Phe Lys Val Met Leu Ser
    610                 615                 620
```

```
Lys Pro Leu Asp Ala Tyr Lys Asn Thr Pro Gln His Val Lys Ala
625                 630                 635                 640

Ala Leu Gln Leu Arg Pro Phe Gly Val Asn Val Leu Pro Arg Asp Ile
            645                 650                 655

Ile Tyr Tyr Val Lys Val Arg Ser Lys Asp Gly Val Lys Pro Val Gln
                660                 665                 670

Leu Ala Lys Val Thr Glu Ile Asp Ala Glu Lys Tyr Leu Glu Ala Leu
        675                 680                 685

Arg Ser Thr Phe Glu Gln Ile Leu Arg Ala Phe Gly Val Ser
    690                 695                 700
```

<210> SEQ ID NO 34
<211> LENGTH: 719
<212> TYPE: PRT
<213> ORGANISM: Escherichia coli

<400> SEQUENCE: 34

```
Ala Gln His Ile Leu Gln Gly Glu Gln Gly Phe Arg Leu Thr Pro Leu
1               5                   10                  15

Ala Leu Lys Asp Phe His Arg Gln Pro Val Tyr Gly Leu Tyr Cys Arg
            20                  25                  30

Ala His Arg Gln Leu Met Asn Tyr Glu Lys Arg Leu Arg Glu Gly Gly
        35                  40                  45

Val Thr Val Tyr Glu Ala Asp Val Arg Pro Glu Arg Tyr Leu Met
50                  55                  60

Glu Arg Phe Ile Thr Ser Pro Val Trp Val Glu Gly Asp Met His Asn
65                  70                  75                  80

Gly Thr Ile Val Asn Ala Arg Leu Lys Pro His Pro Asp Tyr Arg Pro
                85                  90                  95

Pro Leu Lys Trp Val Ser Ile Asp Ile Glu Thr Thr Arg His Gly Glu
            100                 105                 110

Leu Tyr Cys Ile Gly Leu Glu Gly Cys Gly Gln Arg Ile Val Tyr Met
        115                 120                 125

Leu Gly Pro Glu Asn Gly Asp Ala Ser Ser Leu Asp Phe Glu Leu Glu
130                 135                 140

Tyr Val Ala Ser Arg Pro Gln Leu Leu Glu Lys Leu Asn Ala Trp Phe
145                 150                 155                 160

Ala Asn Tyr Asp Pro Asp Val Ile Ile Gly Trp Asn Val Val Gln Phe
                165                 170                 175

Asp Leu Arg Met Leu Gln Lys His Ala Glu Arg Tyr Arg Leu Pro Leu
            180                 185                 190

Arg Leu Gly Arg Asp Asn Ser Glu Leu Glu Trp Arg Glu His Gly Phe
        195                 200                 205

Lys Asn Gly Val Phe Phe Ala Gln Ala Lys Gly Arg Leu Ile Ile Asp
210                 215                 220

Gly Ile Glu Ala Leu Lys Ser Ala Phe Trp Asn Phe Ser Ser Phe Ser
225                 230                 235                 240

Leu Glu Thr Val Ala Gln Glu Leu Leu Gly Glu Gly Lys Ser Ile Asp
                245                 250                 255

Asn Pro Trp Asp Arg Met Asp Glu Ile Asp Arg Arg Phe Ala Glu Asp
            260                 265                 270

Lys Pro Ala Leu Ala Thr Tyr Asn Leu Lys Asp Cys Glu Leu Val Thr
        275                 280                 285

Gln Ile Phe His Lys Thr Glu Ile Met Pro Phe Leu Leu Glu Arg Ala
290                 295                 300
```

-continued

```
Thr Val Asn Gly Leu Pro Val Asp Arg His Gly Ser Val Ala Ala
305                 310                 315                 320

Phe Gly His Leu Tyr Phe Pro Arg Met His Arg Ala Gly Tyr Val Ala
                325                 330                 335

Pro Asn Leu Gly Glu Val Pro His Ala Ser Pro Gly Gly Tyr Val
            340                 345                 350

Met Asp Ser Arg Pro Gly Leu Tyr Asp Ser Val Leu Val Leu Asp Tyr
            355                 360                 365

Lys Ser Leu Tyr Pro Ser Ile Ile Arg Thr Phe Leu Ile Asp Pro Val
370                 375                 380

Gly Leu Val Glu Gly Met Ala Gln Pro Asp Pro Glu His Ser Thr Glu
385                 390                 395                 400

Gly Phe Leu Asp Ala Trp Phe Ser Arg Glu Lys His Cys Leu Pro Glu
                405                 410                 415

Ile Val Thr Asn Ile Trp His Gly Arg Asp Glu Ala Lys Arg Gln Gly
                420                 425                 430

Asn Lys Pro Leu Ser Gln Ala Leu Lys Ile Ile Met Asn Ala Phe Tyr
                435                 440                 445

Gly Val Leu Gly Thr Thr Ala Cys Arg Phe Phe Asp Pro Arg Leu Ala
450                 455                 460

Ser Ser Ile Thr Met Arg Gly His Gln Ile Met Arg Gln Thr Lys Ala
465                 470                 475                 480

Leu Ile Glu Ala Gln Gly Tyr Asp Val Ile Tyr Gly Asp Thr Asp Ser
                485                 490                 495

Thr Phe Val Trp Leu Lys Gly Ala His Ser Glu Glu Ala Ala Lys
                500                 505                 510

Ile Gly Arg Ala Leu Val Gln His Val Asn Ala Trp Trp Ala Glu Thr
                515                 520                 525

Leu Gln Lys Gln Arg Leu Thr Ser Ala Leu Glu Leu Glu Tyr Glu Thr
                530                 535                 540

His Phe Cys Arg Phe Leu Met Pro Thr Ile Arg Gly Ala Asp Thr Gly
545                 550                 555                 560

Ser Lys Lys Arg Tyr Ala Gly Leu Ile Gln Glu Gly Asp Lys Gln Arg
                565                 570                 575

Met Val Phe Lys Gly Leu Glu Thr Val Arg Thr Asp Trp Thr Pro Leu
                580                 585                 590

Ala Gln Gln Phe Gln Gln Glu Leu Tyr Leu Arg Ile Phe Arg Asn Glu
                595                 600                 605

Pro Tyr Gln Glu Tyr Val Arg Glu Thr Ile Asp Lys Leu Met Ala Gly
                610                 615                 620

Glu Leu Asp Ala Arg Leu Val Tyr Arg Lys Arg Leu Arg Arg Pro Leu
625                 630                 635                 640

Ser Glu Tyr Gln Arg Asn Val Pro Pro His Val Arg Ala Ala Arg Leu
                645                 650                 655

Ala Asp Glu Glu Asn Gln Lys Arg Gly Arg Pro Leu Gln Tyr Gln Asn
                660                 665                 670

Arg Gly Thr Ile Lys Tyr Val Trp Thr Thr Asn Gly Pro Glu Pro Leu
                675                 680                 685

Asp Tyr Gln Arg Ser Pro Leu Asp Tyr Glu His Tyr Leu Thr Arg Gln
                690                 695                 700

Leu Gln Pro Val Ala Glu Gly Ile Leu Pro Phe Ile Glu Asp Asn
705                 710                 715
```

```
<210> SEQ ID NO 35
<211> LENGTH: 773
<212> TYPE: PRT
<213> ORGANISM: Desilforococcus strain Tok

<400> SEQUENCE: 35

Met Ile Leu Asp Ala Asp Tyr Ile Thr Glu Asp Gly Lys Pro Val Ile
 1               5                  10                  15

Arg Val Phe Lys Lys Glu Lys Gly Glu Phe Lys Ile Asp Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Arg Gly Leu Ile Pro
        115                 120                 125

Met Glu Gly Asp Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Met Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Pro Val Phe Gly Gln Pro Lys Glu
        275                 280                 285

Lys Val Tyr Ala Glu Glu Ile Ala Arg Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Asp Val Ala
        355                 360                 365

Pro Asn Lys Pro Asp Glu Arg Glu Leu Ala Arg Arg Thr Glu Ser Tyr
    370                 375                 380
```

```
Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
            405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
            435                 440                 445

Ile Pro Ser Leu Leu Gly Asp Leu Leu Glu Glu Arg Gln Lys Val Lys
        450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Ala Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
530                 535                 540

Phe Ala Thr Ile Pro Gly Ala Asp Ala Glu Thr Val Lys Asn Lys Ala
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg His Glu Val Pro
                645                 650                 655

Pro Glu Lys Leu Val Ile Tyr Glu Gln Ile Thr Arg Asp Leu Arg Ser
            660                 665                 670

Tyr Arg Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
690                 695                 700

Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
        755                 760                 765

Leu Lys Pro Lys Thr
        770

<210> SEQ ID NO 36
<211> LENGTH: 871
```

```
<212> TYPE: PRT
<213> ORGANISM: Bacteriophage RM378

<400> SEQUENCE: 36

Met Lys Ile Thr Leu Ser Ala Ser Val Tyr Pro Arg Ser Met Lys Ile
1               5                   10                  15

Tyr Gly Val Glu Leu Ile Glu Gly Lys Lys His Leu Phe Gln Ser Pro
            20                  25                  30

Val Pro Pro His Leu Lys Arg Ile Ala Gln Gln Asn Arg Gly Lys Ile
            35                  40                  45

Glu Ala Glu Ala Ile Ser Tyr Tyr Ile Arg Glu Gln Lys Ser His Ile
50                  55                  60

Thr Pro Glu Ala Leu Ser Gln Cys Val Phe Ile Asp Ile Glu Thr Ile
65                  70                  75                  80

Ser Pro Lys Lys Ser Phe Pro Asp Pro Trp Arg Asp Pro Val Tyr Ser
                85                  90                  95

Ile Ser Ile Lys Pro Tyr Gly Lys Pro Val Val Val Leu Leu Leu
            100                 105                 110

Ile Thr Asn Pro Glu Ala His Ile Asp Asn Phe Asn Lys Phe Thr Thr
            115                 120                 125

Ser Val Gly Asp Asn Thr Phe Glu Ile His Tyr Arg Thr Phe Leu Ser
130                 135                 140

Glu Lys Arg Leu Leu Glu Tyr Phe Trp Asn Val Leu Lys Pro Lys Phe
145                 150                 155                 160

Thr Phe Met Leu Ala Trp Asn Gly Tyr Gln Phe Asp Tyr Pro Tyr Leu
                165                 170                 175

Leu Ile Arg Ser His Ile His Glu Val Asn Val Ile Ser Asp Lys Leu
            180                 185                 190

Leu Pro Asp Trp Lys Leu Val Arg Lys Ile Ser Asp Arg Asn Leu Pro
            195                 200                 205

Phe Tyr Phe Asn Pro Arg Thr Pro Val Glu Phe Val Phe Asp Tyr
            210                 215                 220

Met Arg Leu Tyr Arg Ser Phe Val Ala Tyr Lys Glu Leu Glu Ser Tyr
225                 230                 235                 240

Arg Leu Asp Tyr Ile Ala Arg Glu Glu Ile Gly Glu Gly Lys Val Asp
                245                 250                 255

Phe Asp Val Arg Phe Tyr His Glu Ile Pro Val Tyr Pro Asp Lys Lys
            260                 265                 270

Leu Val Glu Tyr Asn Ala Val Asp Ala Ile Leu Met Glu Glu Ile Glu
            275                 280                 285

Asn Lys Asn His Ile Leu Pro Thr Leu Phe Glu Ile Ala Arg Leu Ser
290                 295                 300

Asn Leu Thr Pro Ala Leu Ala Leu Asn Ala Ser Asn Ile Leu Ile Gly
305                 310                 315                 320

Asn Val Thr Gly Lys Leu Gly Val Lys Phe Val Asp Tyr Ile Lys Lys
                325                 330                 335

Ile Asp Thr Ile Asn Thr Met Phe Lys Lys Ile Pro Glu Met Asn Ile
            340                 345                 350

Asn Lys Tyr Arg Tyr Arg Gly Ala Tyr Ile Glu Leu Thr Asn Pro Asp
            355                 360                 365

Ile Tyr Phe Asn Val Phe Asp Leu Asp Phe Thr Ser Leu Tyr Pro Ser
            370                 375                 380

Val Ile Ser Lys Phe Asn Ile Asp Pro Ala Thr Phe Val Thr Glu Phe
385                 390                 395                 400
```

-continued

```
Tyr Gly Cys Met Arg Val Glu Asn Lys Val Ile Pro Val Asp Gln Glu
                405                 410                 415

Glu Pro Glu Phe Gly Phe Pro Leu Tyr Ile Phe Asp Ser Gly Met Asn
            420                 425                 430

Pro Ser Tyr Arg Ser Glu Pro Leu Phe Val Ile Asn Ser Phe Glu Glu
            435                 440                 445

Leu Arg Gln Phe Leu Lys Ser Arg Asn Ile Ile Met Val Pro Asn Pro
        450                 455                 460

Ser Gly Ile Cys Trp Phe Tyr Arg Lys Glu Pro Val Gly Val Leu Pro
465                 470                 475                 480

Ser Ile Ile Arg Glu Ile Phe Thr Arg Lys Glu Arg Lys Leu
                485                 490                 495

Phe Lys Glu Thr Gly Asn Met Glu His His Phe Arg Gln Trp Ala Leu
            500                 505                 510

Lys Ile Met Met Asn Ser Met Tyr Gly Ile Phe Gly Asn Arg Ser Val
            515                 520                 525

Tyr Met Gly Cys Leu Pro Ile Ala Glu Ser Val Thr Ala Ala Gly Arg
        530                 535                 540

Met Ser Ile Arg Ser Val Ile Ser Gln Ile Arg Asp Arg Phe Ile Tyr
545                 550                 555                 560

Ser His Thr Asp Ser Ile Phe Val Lys Ala Phe Thr Asp Pro Val
                565                 570                 575

Ala Glu Ala Gly Glu Leu Gln Glu His Leu Asn Ser Phe Ile Asn Asp
            580                 585                 590

Tyr Met Glu Asn Asn Phe Asn Ala Arg Glu Asp Phe Lys Leu Glu Leu
            595                 600                 605

Lys Gln Glu Phe Val Phe Lys Ser Ile Leu Ile Lys Glu Ile Asn Arg
        610                 615                 620

Tyr Phe Ala Val Thr Val Asp Gly Lys Glu Met Lys Gly Ile Glu
625                 630                 635                 640

Val Ile Asn Ser Ser Val Pro Glu Ile Val Lys Lys Tyr Phe Arg Gly
                645                 650                 655

Tyr Leu Lys Tyr Ile Ser Gln Pro Asp Ile Asp Val Ile Ser Ala Thr
        660                 665                 670

Ile Ala Phe Tyr Asn Asn Phe Val Ser Gln Lys Asn Phe Trp Ser Ile
        675                 680                 685

Glu Asp Leu Tyr His Lys Met Lys Ile Ser Ser Asp Ser Ala Glu
            690                 695                 700

Arg Tyr Val Glu Tyr Val Glu Glu Val Met Lys Met Lys Lys Glu Asn
705                 710                 715                 720

Val Pro Ile Ser Glu Ile Phe Ile Lys Met Tyr Asp His Thr Leu Pro
                725                 730                 735

Ile His Tyr Lys Gly Ala Leu Phe Ala Ser Ile Ile Gly Cys Lys Pro
            740                 745                 750

Pro Gln Met Gly Asp Lys Ile Tyr Trp Phe Tyr Cys Thr Met Leu Asp
            755                 760                 765

Pro Ser Arg Thr Asn Leu Pro Leu Ser Leu Glu Glu Val Asn Pro Glu
        770                 775                 780

His Gly Ser Gly Val Trp Asp Ile Leu Lys Ala Gly Lys Lys Thr His
785                 790                 795                 800

Ile Asn Arg Leu Arg Asn Ile His Ala Leu Ser Ile Arg Glu Asp Asp
                805                 810                 815
```

```
Glu Glu Gly Leu Glu Ile Val Lys Lys Tyr Ile Asp Arg Asp Lys Tyr
            820                 825                 830

Cys Gln Ile Ile Ser Glu Lys Thr Ile Asp Leu Leu Lys Ser Leu Gly
            835                 840                 845

Tyr Val Glu Asn Thr Thr Lys Ile Lys Thr Val Glu Asp Leu Ile Arg
            850                 855                 860

Phe Leu Val Glu Ser Asn
865                 870

<210> SEQ ID NO 37
<211> LENGTH: 898
<212> TYPE: PRT
<213> ORGANISM: Bacteriophage RB69

<400> SEQUENCE: 37

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
            35                  40                  45

Tyr Phe Asp Ile Tyr Gly Lys Pro Cys Thr Arg Lys Leu Phe Ala Asn
        50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320
```

```
Ile Ser Tyr Asn Ile Ile Asp Val Tyr Arg Val Leu Gln Ile Asp Ala
                325                 330                 335

Lys Arg Gln Phe Ile Asn Leu Ser Leu Asp Met Gly Tyr Tyr Ala Lys
                340                 345                 350

Ile Gln Ile Gln Ser Val Phe Ser Pro Ile Lys Thr Trp Asp Ala Ile
                355                 360                 365

Ile Phe Asn Ser Leu Lys Glu Gln Asn Lys Val Ile Pro Gln Gly Arg
                370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
                420                 425                 430

Thr Phe Lys Val Ala Pro Leu His Asp Tyr Ile Asn Ala Val Ala Glu
                435                 440                 445

Arg Pro Ser Asp Val Tyr Ser Cys Ser Pro Asn Gly Met Met Tyr Tyr
                450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
                500                 505                 510

Pro Leu Asp Val Asp Tyr Arg Phe Asp Phe Ser Asp Glu Ile Lys Glu
                515                 520                 525

Lys Ile Lys Lys Leu Ser Ala Lys Ser Leu Asn Glu Met Leu Phe Arg
                530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
                580                 585                 590

Ala Leu Gln Trp Ile Glu Arg Lys Val Asn Glu Tyr Leu Asn Glu Val
                595                 600                 605

Cys Gly Thr Glu Gly Glu Ala Phe Val Leu Tyr Gly Asp Thr Asp Ser
                610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
                660                 665                 670

Tyr Met Asn Asn Lys Gln His Leu Met Phe Met Asp Arg Glu Ala Ile
                675                 680                 685

Ala Gly Pro Pro Leu Gly Ser Lys Gly Ile Gly Gly Phe Trp Thr Gly
                690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735
```

```
Thr Pro Lys Ala Val Gln Lys Ala Leu Lys Glu Cys Ile Arg Arg Met
            740                 745                 750
Leu Gln Glu Gly Glu Glu Ser Leu Gln Glu Tyr Phe Lys Glu Phe Glu
            755                 760                 765
Lys Glu Phe Arg Gln Leu Asn Tyr Ile Ser Ile Ala Ser Val Ser Ser
            770                 775                 780
Ala Asn Asn Ile Ala Lys Tyr Asp Val Gly Phe Pro Gly Pro Lys
785                 790                 795                 800
Cys Pro Phe His Ile Arg Gly Ile Leu Thr Tyr Asn Arg Ala Ile Lys
            805                 810                 815
Gly Asn Ile Asp Ala Pro Gln Val Val Glu Gly Lys Val Tyr Val
            820                 825                 830
Leu Pro Leu Arg Glu Gly Asn Pro Phe Gly Asp Lys Cys Ile Ala Trp
            835                 840                 845
Pro Ser Gly Thr Glu Ile Thr Asp Leu Ile Lys Asp Asp Val Leu His
            850                 855                 860
Trp Met Asp Tyr Thr Val Leu Leu Glu Lys Thr Phe Ile Lys Pro Leu
865                 870                 875                 880
Glu Gly Phe Thr Ser Ala Ala Lys Leu Asp Tyr Glu Lys Lys Ala Ser
            885                 890                 895
Leu Phe

<210> SEQ ID NO 38
<211> LENGTH: 394
<212> TYPE: PRT
<213> ORGANISM: Autographa californica nucleopolynedrovirus

<400> SEQUENCE: 38

Met Leu His Val Ser Arg Leu Leu Ala Asn Gly Gly Val Lys Asn Leu
1               5                   10                  15
Cys Asp Lys Phe Lys Val Lys Ile Lys Asn Tyr Thr Glu His Asp Leu
            20                  25                  30
Met Val Leu Asn Tyr Glu Ser Phe Glu Arg Asp Arg Asp His Pro Val
            35                  40                  45
Val Val Glu Cys Arg Gly Leu Ile Leu Asn Ser Arg Thr Tyr Ala Val
        50                  55                  60
Val Ser Arg Ser Phe Asp Arg Phe Phe Asn Phe Gln Glu Leu Leu Gln
65                  70                  75                  80
Asn Ile Gly Gly Glu Asp Ala His His Lys Leu Phe Gln Ser Lys Glu
            85                  90                  95
Asn Phe Lys Phe Tyr Glu Lys Ile Asp Gly Ser Leu Ile Lys Ile Tyr
            100                 105                 110
Lys Tyr Asn Gly Glu Trp His Ala Ser Thr Arg Gly Ser Ala Phe Ala
            115                 120                 125
Glu Asn Leu Cys Val Ser Asp Val Thr Phe Lys Arg Leu Val Leu Gln
            130                 135                 140
Ala Leu Gln Leu Asp Glu Ala His Asn Gln Phe Gln Ala Leu Cys Asn
145                 150                 155                 160
Glu Tyr Leu Asp Cys Ala Ser Thr His Met Phe Glu Leu Thr Ser Lys
            165                 170                 175
His Asn Arg Ile Val Thr Val Tyr Asp Glu Gln Pro Thr Leu Trp Tyr
            180                 185                 190
Leu Ala Ser Arg Asn Asn Glu Thr Gly Asp Tyr Phe Tyr Cys Ser Asn
            195                 200                 205
```

-continued

```
Leu Pro Phe Cys Lys Tyr Pro Lys Cys Tyr Glu Phe Thr Ser Val Gln
    210                 215                 220

Glu Cys Val Glu His Ala Ala Gln Leu Lys Asn Leu Glu Glu Gly Phe
225                 230                 235                 240

Val Val Tyr Asp Lys Asn Asn Ala Pro Leu Cys Lys Ile Lys Ser Asp
                245                 250                 255

Val Tyr Leu Asn Met His Lys Asn Gln Ser Arg Ala Glu Asn Pro Thr
            260                 265                 270

Lys Leu Ala Gln Leu Val Ile Asn Gly Glu His Asp Asp Phe Leu Ala
        275                 280                 285

Leu Phe Pro His Leu Lys Ser Val Ile Lys Pro Tyr Val Asp Ala Arg
    290                 295                 300

Asn Thr Phe Thr Asn Glu Ser Thr Ile Asn Ile Met Val Ser Gly Leu
305                 310                 315                 320

Thr Leu Asn Gln Gln Arg Phe Asn Glu Leu Val Gln Thr Leu Pro Trp
                325                 330                 335

Lys Cys Leu Ala Tyr Arg Cys Arg Lys Ala Gln Thr Ile Asp Val Glu
            340                 345                 350

Ser Glu Phe Leu Lys Leu Thr Glu Pro Glu Lys Ile Lys Met Ile Lys
        355                 360                 365

Asn Ile Ile Lys Phe Val Ser Thr Lys Gln Ala Leu Asn Asn Lys Leu
    370                 375                 380

Ala Pro Thr Ile Lys Leu Pro Ser Ser Lys
385                 390

<210> SEQ ID NO 39
<211> LENGTH: 374
<212> TYPE: PRT
<213> ORGANISM: Bacteriophage T4

<400> SEQUENCE: 39

Met Gln Glu Leu Phe Asn Asn Leu Met Glu Leu Cys Lys Asp Ser Gln
  1               5                  10                  15

Arg Lys Phe Phe Tyr Ser Asp Asp Val Ser Ala Ser Gly Arg Thr Tyr
                20                  25                  30

Arg Ile Phe Ser Tyr Asn Tyr Ala Ser Tyr Ser Asp Trp Leu Leu Pro
            35                  40                  45

Asp Ala Leu Glu Cys Arg Gly Ile Met Phe Glu Met Asp Gly Glu Lys
     50                 55                  60

Pro Val Arg Ile Ala Ser Arg Pro Met Glu Lys Phe Phe Asn Leu Asn
 65                 70                  75                  80

Glu Asn Pro Phe Thr Met Asn Ile Asp Leu Asn Asp Val Asp Tyr Ile
                85                  90                  95

Leu Thr Lys Glu Asp Gly Ser Leu Val Ser Thr Tyr Leu Asp Gly Asp
            100                 105                 110

Glu Ile Leu Phe Lys Ser Lys Gly Ser Ile Lys Ser Glu Gln Ala Leu
        115                 120                 125

Met Ala Asn Gly Ile Leu Met Asn Ile Asn His His Arg Leu Arg Asp
    130                 135                 140

Arg Leu Lys Glu Leu Ala Glu Asp Gly Phe Thr Ala Asn Phe Glu Phe
145                 150                 155                 160

Val Ala Pro Thr Asn Arg Ile Val Leu Ala Tyr Gln Glu Met Lys Ile
                165                 170                 175

Ile Leu Leu Asn Val Arg Glu Asn Glu Thr Gly Glu Tyr Ile Ser Tyr
            180                 185                 190
```

-continued

```
Asp Asp Ile Tyr Lys Asp Ala Thr Leu Arg Pro Tyr Leu Val Glu Arg
            195                 200                 205

Tyr Glu Ile Asp Ser Pro Lys Trp Ile Glu Ala Lys Asn Ala Glu
    210                 215                 220

Asn Ile Glu Gly Tyr Val Ala Val Met Lys Asp Gly Ser His Phe Lys
225                 230                 235                 240

Ile Lys Ser Asp Trp Tyr Val Ser Leu His Ser Thr Lys Ser Ser Leu
                245                 250                 255

Asp Asn Pro Glu Lys Leu Phe Lys Thr Ile Ile Asp Gly Ala Ser Asp
            260                 265                 270

Asp Leu Lys Ala Met Tyr Ala Asp Asp Glu Tyr Ser Tyr Arg Lys Ile
        275                 280                 285

Glu Ala Phe Glu Thr Thr Tyr Leu Lys Tyr Leu Asp Arg Ala Leu Phe
    290                 295                 300

Leu Val Leu Asp Cys His Asn Lys His Cys Gly Lys Asp Arg Lys Thr
305                 310                 315                 320

Tyr Ala Met Glu Ala Gln Gly Val Ala Lys Gly Ala Gly Met Asp His
                325                 330                 335

Leu Phe Gly Ile Ile Met Ser Leu Tyr Gln Gly Tyr Asp Ser Gln Glu
            340                 345                 350

Lys Val Met Cys Glu Ile Glu Gln Asn Phe Leu Lys Asn Tyr Lys Lys
        355                 360                 365

Phe Ile Pro Glu Gly Tyr
    370

<210> SEQ ID NO 40
<211> LENGTH: 437
<212> TYPE: PRT
<213> ORGANISM: Bacteriophage RM378

<400> SEQUENCE: 40

Met Ser Met Asn Val Lys Tyr Pro Val Glu Tyr Leu Ile Glu His Leu
1               5                   10                  15

Asn Ser Phe Glu Ser Pro Glu Val Ala Val Glu Ser Leu Arg Lys Glu
            20                  25                  30

Gly Ile Met Cys Lys Asn Arg Gly Asp Leu Tyr Met Phe Lys Tyr His
        35                  40                  45

Leu Gly Cys Lys Phe Asp Lys Ile Tyr His Leu Ala Cys Arg Gly Ala
    50                  55                  60

Ile Leu Arg Lys Thr Asp Ser Gly Trp Lys Val Leu Ser Tyr Pro Phe
65                  70                  75                  80

Asp Lys Phe Phe Asn Trp Gly Glu Glu Leu Gln Pro Glu Ile Val Asn
                85                  90                  95

Tyr Tyr Gln Thr Leu Arg Tyr Ala Ser Pro Leu Asn Glu Lys Arg Lys
            100                 105                 110

Ala Gly Phe Met Phe Lys Leu Pro Met Lys Leu Val Glu Lys Leu Asp
        115                 120                 125

Gly Thr Cys Val Val Leu Tyr Tyr Asp Glu Gly Trp Lys Ile His Thr
    130                 135                 140

Leu Gly Ser Ile Asp Ala Asn Gly Ser Ile Val Lys Asn Gly Met Val
145                 150                 155                 160

Thr Thr His Met Asp Lys Thr Tyr Arg Glu Leu Phe Trp Glu Thr Phe
                165                 170                 175

Glu Lys Lys Tyr Pro Pro Tyr Leu Leu Tyr His Leu Asn Ser Ser Tyr
```

```
                180             185             190
Cys Tyr Ile Phe Glu Met Val His Pro Asp Ala Arg Val Val Pro
            195             200             205

Tyr Glu Glu Pro Asn Ile Ile Leu Ile Gly Val Arg Ser Val Asp Pro
210             215             220

Glu Lys Gly Tyr Phe Glu Val Gly Pro Ser Glu Glu Ala Val Arg Ile
225             230             235             240

Phe Asn Glu Ser Gly Gly Lys Ile Asn Leu Lys Leu Pro Ala Val Leu
            245             250             255

Ser Gln Glu Gln Asn Tyr Thr Leu Phe Arg Ala Asn Arg Leu Gln Glu
            260             265             270

Leu Phe Glu Glu Val Thr Pro Leu Phe Lys Ser Leu Arg Asp Gly Tyr
            275             280             285

Glu Val Val Tyr Glu Gly Phe Val Ala Val Gln Glu Ile Ala Pro Arg
            290             295             300

Val Tyr Tyr Arg Thr Lys Ile Lys His Pro Val Tyr Leu Glu Leu His
305             310             315             320

Arg Ile Lys Thr Thr Ile Thr Pro Glu Lys Leu Ala Asp Leu Phe Leu
            325             330             335

Glu Asn Lys Leu Asp Asp Phe Val Leu Thr Pro Asp Glu Gln Glu Thr
            340             345             350

Val Met Lys Leu Lys Glu Ile Tyr Thr Asp Met Arg Asn Gln Leu Glu
            355             360             365

Ser Ser Phe Asp Thr Ile Tyr Lys Glu Ile Ser Glu Gln Val Ser Pro
            370             375             380

Glu Glu Asn Pro Gly Glu Phe Arg Lys Arg Phe Ala Leu Arg Leu Met
385             390             395             400

Asp Tyr His Asp Lys Ser Trp Phe Phe Ala Arg Leu Asp Gly Asp Glu
            405             410             415

Glu Lys Met Gln Lys Ser Glu Lys Lys Leu Leu Thr Glu Arg Ile Glu
            420             425             430

Lys Gly Leu Phe Lys
            435

<210> SEQ ID NO 41
<211> LENGTH: 300
<212> TYPE: PRT
<213> ORGANISM: Escherichia coli

<400> SEQUENCE: 41

Met Val Gln Ile Pro Gln Asn Pro Leu Ile Leu Val Asp Gly Ser Ser
1               5               10              15

Tyr Leu Tyr Arg Ala Tyr His Ala Phe Pro Pro Leu Thr Asn Ser Ala
            20              25              30

Gly Glu Pro Thr Gly Ala Met Tyr Gly Val Leu Asn Met Leu Arg Ser
            35              40              45

Leu Ile Met Gln Tyr Lys Pro Thr His Ala Ala Val Val Phe Asp Ala
            50              55              60

Lys Gly Lys Thr Phe Arg Asp Glu Leu Phe Glu His Tyr Lys Ser His
65              70              75              80

Arg Pro Pro Met Pro Asp Asp Leu Arg Ala Gln Ile Glu Pro Leu His
            85              90              95

Ala Met Val Lys Ala Met Gly Leu Pro Leu Leu Ala Val Ser Gly Val
            100             105             110
```

```
Glu Ala Asp Asp Val Ile Gly Thr Leu Ala Arg Glu Ala Glu Lys Ala
        115                 120                 125
Gly Arg Pro Val Leu Ile Ser Thr Gly Asp Lys Asp Met Ala Gln Leu
    130                 135                 140
Val Thr Pro Asn Ile Thr Leu Ile Asn Thr Met Thr Asn Thr Ile Leu
145                 150                 155                 160
Gly Pro Glu Glu Val Val Asn Lys Tyr Gly Val Pro Pro Glu Leu Ile
                165                 170                 175
Ile Asp Phe Leu Ala Leu Met Gly Asp Ser Ser Asp Asn Ile Pro Gly
            180                 185                 190
Val Pro Gly Val Gly Glu Lys Thr Ala Gln Ala Leu Leu Gln Gly Leu
        195                 200                 205
Gly Gly Leu Asp Thr Leu Tyr Ala Glu Pro Glu Lys Ile Ala Gly Leu
    210                 215                 220
Ser Phe Arg Gly Ala Lys Thr Met Ala Ala Lys Leu Glu Gln Asn Lys
225                 230                 235                 240
Glu Val Ala Tyr Leu Ser Tyr Gln Leu Ala Thr Ile Lys Thr Asp Val
                245                 250                 255
Glu Leu Glu Leu Thr Cys Glu Gln Leu Glu Val Gln Gln Pro Ala Ala
            260                 265                 270
Glu Glu Leu Leu Gly Leu Phe Lys Lys Tyr Glu Phe Lys Arg Trp Thr
        275                 280                 285
Ala Asp Val Glu Ala Gly Lys Trp Leu Gln Ala Lys
    290                 295                 300

<210> SEQ ID NO 42
<211> LENGTH: 300
<212> TYPE: PRT
<213> ORGANISM: Thermus aquaticaus

<400> SEQUENCE: 42

Met Arg Gly Met Leu Pro Leu Phe Glu Pro Lys Gly Arg Val Leu Leu
  1               5                  10                  15
Val Asp Gly His His Leu Ala Tyr Arg Thr Phe His Ala Leu Lys Gly
                20                  25                  30
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Asp Ala Val Ile Val
 50                  55                  60
Val Phe Asp Ala Lys Ala Pro Ser Phe Arg His Glu Ala Tyr Gly Gly
 65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
        115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
            180                 185                 190
```

```
Leu Pro Gly Val Lys Gly Ile Gly Glu Lys Thr Ala Arg Lys Leu Leu
            195                 200                 205

Glu Glu Trp Gly Ser Leu Glu Ala Leu Leu Lys Asn Leu Asp Arg Leu
            210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
            275                 280                 285

Glu Ser Pro Lys Ala Leu Glu Glu Ala Pro Trp Pro
            290                 295                 300

<210> SEQ ID NO 43
<211> LENGTH: 318
<212> TYPE: PRT
<213> ORGANISM: Bacteriophage RM378

<400> SEQUENCE: 43

Met Lys Arg Leu Arg Asn Met Val Asn Leu Ile Asp Leu Lys Asn Gln
  1               5                  10                  15

Tyr Tyr Ala Tyr Ser Phe Lys Phe Phe Asp Ser Tyr Gln Ile Ser Trp
                 20                  25                  30

Asp Asn Tyr Pro His Leu Lys Glu Phe Val Ile Glu Asn Tyr Pro Gly
             35                  40                  45

Thr Tyr Phe Ser Cys Tyr Ala Pro Gly Ile Leu Tyr Lys Leu Phe Leu
 50                  55                  60

Lys Trp Lys Arg Gly Met Ile Ile Asp Asp Tyr Asp Arg His Pro Leu
 65                  70                  75                  80

Arg Lys Lys Leu Leu Pro Gln Tyr Lys Glu His Arg Tyr Glu Tyr Ile
                 85                  90                  95

Glu Gly Lys Tyr Gly Val Val Pro Phe Pro Gly Phe Leu Lys Tyr Leu
            100                 105                 110

Lys Phe His Phe Glu Asp Leu Arg Phe Lys Met Arg Asp Leu Gly Ile
            115                 120                 125

Thr Asp Phe Lys Tyr Ala Leu Ala Ile Ser Leu Phe Tyr Asn Arg Val
130                 135                 140

Met Leu Arg Asp Phe Leu Lys Asn Phe Thr Cys Tyr Tyr Ile Ala Glu
145                 150                 155                 160

Tyr Glu Ala Asp Asp Val Ile Ala His Leu Ala Arg Glu Ile Ala Arg
                165                 170                 175

Ser Asn Ile Asp Val Asn Ile Val Ser Thr Asp Lys Tyr Tyr Gln
            180                 185                 190

Leu Trp Asp Glu Glu Asp Ile Arg Glu Arg Val Tyr Ile Asn Ser Leu
            195                 200                 205

Ser Cys Ser Asp Val Lys Thr Pro Arg Tyr Gly Phe Leu Thr Ile Lys
210                 215                 220

Ala Leu Leu Gly Asp Lys Ser Asp Asn Ile Pro Lys Ser Leu Glu Lys
225                 230                 235                 240

Gly Lys Gly Glu Lys Tyr Leu Glu Lys Lys Gly Phe Ala Glu Glu Asp
                245                 250                 255

Tyr Asp Lys Glu Leu Phe Glu Asn Asn Leu Lys Val Ile Arg Phe Gly
```

```
                         260                 265                 270
Asp Glu Tyr Leu Gly Glu Arg Asp Lys Ser Phe Ile Glu Asn Phe Ser
            275                 280                 285

Thr Gly Asp Thr Leu Trp Asn Phe Tyr Glu Phe Tyr Tyr Asp Pro
        290                 295                 300

Leu His Glu Leu Phe Leu Arg Asn Ile Arg Lys Arg Leu
305                 310                 315

<210> SEQ ID NO 44
<211> LENGTH: 305
<212> TYPE: PRT
<213> ORGANISM: Bacteriophage T4

<400> SEQUENCE: 44

Met Asp Leu Glu Met Met Leu Asp Glu Asp Tyr Lys Glu Gly Ile Cys
 1               5                  10                  15

Leu Ile Asp Phe Ser Gln Ile Ala Leu Ser Thr Ala Leu Val Asn Phe
                20                  25                  30

Pro Asp Lys Glu Lys Ile Asn Leu Ser Met Val Arg His Leu Ile Leu
            35                  40                  45

Asn Ser Ile Lys Phe Asn Val Lys Lys Ala Lys Thr Leu Gly Tyr Thr
50                  55                  60

Lys Ile Val Leu Cys Ile Asp Asn Ala Lys Ser Gly Tyr Trp Arg Arg
65                  70                  75                  80

Asp Phe Ala Tyr Tyr Lys Leu Asn Arg Gly Lys Ala Arg Glu Glu
                85                  90                  95

Ser Thr Trp Asp Trp Glu Gly Tyr Phe Glu Ser Ser His Lys Val Ile
                100                 105                 110

Asp Glu Leu Lys Ala Tyr Met Pro Tyr Ile Val Met Asp Ile Asp Lys
            115                 120                 125

Tyr Glu Ala Asp Asp His Ile Ala Val Leu Val Lys Lys Phe Ser Leu
        130                 135                 140

Glu Gly His Lys Ile Leu Ile Ser Ser Asp Gly Asp Phe Thr Gln
145                 150                 155                 160

Leu His Lys Tyr Pro Asn Val Lys Gln Trp Ser Pro Met His Lys Lys
                165                 170                 175

Trp Val Lys Ile Lys Ser Gly Ser Ala Glu Ile Asp Cys Met Thr Lys
            180                 185                 190

Ile Leu Lys Gly Asp Lys Asp Asn Val Ala Ser Val Lys Val Arg
        195                 200                 205

Ser Asp Phe Trp Phe Thr Arg Val Glu Gly Glu Arg Thr Pro Ser Met
210                 215                 220

Lys Thr Ser Ile Val Glu Ala Ile Ala Asn Asp Arg Glu Gln Ala Lys
225                 230                 235                 240

Val Leu Leu Thr Glu Ser Glu Tyr Asn Arg Tyr Lys Glu Asn Leu Val
                245                 250                 255

Leu Ile Asp Phe Asp Tyr Ile Pro Asp Asn Ile Ala Ser Asn Ile Val
            260                 265                 270

Asn Tyr Tyr Asn Ser Tyr Lys Leu Pro Pro Arg Gly Lys Ile Tyr Ser
        275                 280                 285

Tyr Phe Val Lys Ala Gly Leu Ser Lys Leu Thr Asn Ser Ile Asn Glu
        290                 295                 300

Phe
305
```

```
<210> SEQ ID NO 45
<211> LENGTH: 300
<212> TYPE: PRT
<213> ORGANISM: Bacteriophage T7

<400> SEQUENCE: 45

Met Ala Leu Leu Asp Leu Lys Gln Phe Tyr Glu Leu Arg Glu Gly Cys
1               5                   10                  15

Asp Asp Lys Gly Ile Leu Val Met Asp Gly Asp Trp Leu Val Phe Gln
            20                  25                  30

Ala Met Ser Ala Ala Glu Phe Asp Ala Ser Trp Glu Glu Ile Trp
        35                  40                  45

His Arg Cys Cys Asp His Ala Lys Ala Arg Gln Ile Leu Glu Asp Ser
    50                  55                  60

Ile Lys Ser Tyr Glu Thr Arg Lys Lys Ala Trp Ala Gly Ala Pro Ile
65                  70                  75                  80

Val Leu Ala Phe Thr Asp Ser Val Asn Trp Arg Lys Glu Leu Val Asp
                85                  90                  95

Pro Asn Tyr Lys Ala Asn Arg Lys Ala Val Lys Lys Pro Val Gly Tyr
            100                 105                 110

Phe Glu Phe Leu Asp Ala Leu Phe Glu Arg Glu Glu Phe Tyr Cys Ile
            115                 120                 125

Arg Glu Pro Met Leu Glu Gly Asp Asp Val Met Gly Val Ile Ala Ser
130                 135                 140

Asn Pro Ser Ala Phe Gly Ala Arg Lys Ala Val Ile Ile Ser Cys Asp
145                 150                 155                 160

Lys Asp Phe Lys Thr Ile Pro Asn Cys Asp Phe Leu Trp Cys Thr Thr
                165                 170                 175

Gly Asn Ile Leu Thr Gln Thr Glu Glu Ser Ala Asp Trp Trp His Leu
            180                 185                 190

Phe Gln Thr Ile Lys Gly Asp Ile Thr Asp Gly Tyr Ser Gly Ile Ala
        195                 200                 205

Gly Trp Gly Asp Thr Ala Glu Asp Phe Leu Asn Asn Pro Phe Ile Thr
210                 215                 220

Glu Pro Lys Thr Ser Val Leu Lys Ser Gly Lys Asn Lys Gly Gln Glu
225                 230                 235                 240

Val Thr Lys Trp Val Lys Arg Asp Pro Glu Pro His Glu Thr Leu Trp
                245                 250                 255

Asp Cys Ile Lys Ser Ile Gly Ala Lys Ala Gly Met Thr Glu Glu Asp
            260                 265                 270

Ile Ile Lys Gln Gly Gln Met Ala Arg Ile Leu Arg Phe Asn Glu Tyr
        275                 280                 285

Asn Phe Ile Asp Lys Glu Ile Tyr Leu Trp Arg Pro
    290                 295                 300

<210> SEQ ID NO 46
<211> LENGTH: 287
<212> TYPE: PRT
<213> ORGANISM: Escherichia coli

<400> SEQUENCE: 46

Val Leu Asp Ala Thr Val Ala Arg Ile Glu Gln Leu Phe Gln Gln Pro
1               5                   10                  15

His Asp Gly Val Thr Gly Val Asn Thr Gly Tyr Asp Asp Leu Asn Lys
            20                  25                  30
```

```
Lys Thr Ala Gly Leu Gln Pro Ser Asp Leu Ile Ile Val Ala Ala Arg
            35                  40                  45

Pro Ser Met Gly Lys Thr Thr Phe Ala Met Asn Leu Val Glu Asn Ala
        50                  55                  60

Ala Met Leu Gln Asp Lys Pro Val Leu Ile Phe Ser Leu Glu Met Pro
 65                  70                  75                  80

Ser Glu Gln Ile Met Met Arg Ser Leu Ala Ser Leu Ser Arg Val Asp
                85                  90                  95

Gln Thr Lys Ile Arg Thr Gly Gln Leu Asp Asp Glu Asp Trp Ala Arg
            100                 105                 110

Ile Ser Gly Thr Met Gly Ile Leu Leu Glu Lys Arg Asn Ile Tyr Ile
        115                 120                 125

Asp Asp Ser Ser Gly Leu Thr Pro Thr Glu Val Arg Ser Arg Ala Arg
    130                 135                 140

Arg Ile Ala Arg Glu His Gly Gly Ile Gly Leu Ile Met Ile Asp Tyr
145                 150                 155                 160

Leu Gln Leu Met Arg Val Pro Ala Leu Ser Asp Asn Arg Thr Leu Glu
                165                 170                 175

Ile Ala Glu Ile Ser Arg Ser Leu Lys Ala Leu Ala Lys Glu Leu Asn
            180                 185                 190

Val Pro Val Val Ala Leu Ser Gln Leu Asn Arg Ser Leu Glu Gln Arg
        195                 200                 205

Ala Asp Lys Arg Pro Val Asn Ser Asp Leu Arg Glu Ser Gly Ser Ile
    210                 215                 220

Glu Gln Asp Ala Asp Leu Ile Met Phe Ile Tyr Arg Asp Glu Val Tyr
225                 230                 235                 240

His Glu Asn Ser Asp Leu Lys Gly Ile Ala Glu Ile Ile Gly Lys
                245                 250                 255

Gln Arg Asn Gly Pro Ile Gly Thr Val Arg Leu Thr Phe Asn Gly Gln
            260                 265                 270

Trp Ser Arg Phe Asp Asn Tyr Ala Gly Pro Gln Tyr Asp Asp Glu
        275                 280                 285

<210> SEQ ID NO 47
<211> LENGTH: 291
<212> TYPE: PRT
<213> ORGANISM: Haemophilus influenza

<400> SEQUENCE: 47

Val Leu Glu Ser Thr Ile Glu Lys Ile Asp Ile Leu Ser Lys Leu Glu
 1               5                  10                  15

Asn His Ser Gly Val Thr Gly Val Thr Thr Gly Phe Thr Asp Leu Asp
            20                  25                  30

Lys Lys Thr Ala Gly Leu Gln Pro Ser Asp Leu Ile Ile Val Ala Ala
        35                  40                  45

Arg Pro Ser Met Gly Lys Thr Thr Phe Ala Met Asn Leu Cys Glu Asn
    50                  55                  60

Ala Ala Met Ala Ser Glu Lys Pro Val Leu Val Phe Ser Leu Glu Met
 65                  70                  75                  80

Pro Ala Glu Gln Ile Met Met Arg Met Ile Ala Ser Leu Ala Arg Val
                85                  90                  95

Asp Gln Thr Lys Ile Arg Thr Gly Gln Asn Leu Asp Glu Ile Glu Trp
            100                 105                 110

Asn Lys Ile Ala Ser Val Val Gly Met Phe Lys Gln Lys Asn Asn Leu
        115                 120                 125
```

```
Phe Ile Asp Asp Ser Ser Gly Leu Thr Pro Thr Asp Val Arg Ser Arg
        130                 135                 140

Ala Arg Arg Val Tyr Arg Glu Asn Gly Gly Leu Ser Met Ile Met Val
145                 150                 155                 160

Asp Tyr Leu Gln Leu Met Arg Ala Pro Ala Phe Ser Asp Asn Arg Thr
                165                 170                 175

Leu Glu Ile Ala Glu Ile Ser Arg Ser Leu Lys Ala Leu Ala Lys Glu
                180                 185                 190

Leu Gln Val Pro Val Val Ala Leu Ser Gln Leu Asn Arg Thr Leu Glu
            195                 200                 205

Gln Arg Gly Asp Lys Arg Pro Val Asn Ser Asp Leu Arg Glu Ser Gly
        210                 215                 220

Ser Ile Glu Gln Asp Ala Asp Leu Ile Met Phe Ile Tyr Arg Asp Glu
225                 230                 235                 240

Val Tyr Asn Asp Asn Ser Glu Asp Lys Gly Val Ala Glu Ile Ile Ile
                245                 250                 255

Gly Lys Gln Arg Asn Gly Pro Ile Gly Arg Val Arg Leu Lys Phe Asn
                260                 265                 270

Gly Gln Phe Ser Arg Phe Asp Asn Leu Ala Glu Gln Arg Glu Tyr Arg
            275                 280                 285

Asp Asp Tyr
    290

<210> SEQ ID NO 48
<211> LENGTH: 287
<212> TYPE: PRT
<213> ORGANISM: Chlamydomonas trachomatis

<400> SEQUENCE: 48

Ala Leu Gln Glu Arg Gln Glu Ala Phe Gln Ala Ser Ala His Asp Ser
  1               5                  10                  15

Ser Ser Pro Met Leu Ser Gly Phe Pro Thr His Phe Leu Asp Leu Asp
             20                  25                  30

Lys Met Ile Ser Gly Phe Ser Pro Ser Asn Leu Ile Ile Leu Ala Ala
         35                  40                  45

Arg Pro Ala Met Gly Lys Thr Ala Leu Ala Leu Asn Ile Val Glu Asn
     50                  55                  60

Phe Cys Phe Asp Ser Arg Leu Pro Val Gly Ile Phe Ser Leu Glu Met
65                  70                  75                  80

Thr Val Asp Gln Leu Ile His Arg Ile Ile Cys Ser Arg Ser Glu Val
                 85                  90                  95

Glu Ala Lys Lys Ile Ser Val Gly Asp Ile Ser Gly Arg Asp Phe Gln
            100                 105                 110

Arg Val Val Ser Val Val Arg Glu Met Glu Glu His Thr Leu Leu Ile
            115                 120                 125

Asp Asp Tyr Pro Gly Leu Lys Ile Thr Asp Leu Arg Ala Arg Ala Arg
        130                 135                 140

Arg Met Lys Glu Ser Tyr Asp Ile Gln Phe Leu Val Ile Asp Tyr Leu
145                 150                 155                 160

Gln Leu Ile Ser Ser Ser Gly Asn Leu Arg Asn Ser Asp Ser Arg Asn
                165                 170                 175

Gln Glu Ile Ser Glu Ile Ser Arg Met Leu Lys Asn Leu Ala Arg Glu
                180                 185                 190

Leu Asn Ile Pro Ile Leu Cys Leu Ser Gln Leu Ser Arg Lys Val Glu
```

```
                195                 200                 205
Asp Arg Ala Asn His Arg Pro Leu Met Ser Asp Leu Arg Glu Ser Gly
            210                 215                 220

Ser Ile Glu Gln Asp Ala Asp Gln Ile Met Phe Leu Leu Arg Arg Glu
225                 230                 235                 240

Tyr Tyr Asp Pro Asn Asp Lys Pro Gly Thr Ala Glu Leu Ile Val Ala
                245                 250                 255

Lys Asn Arg His Gly Ser Ile Gly Ser Val Gln Leu Val Phe Glu Lys
            260                 265                 270

Asp Phe Ala Arg Phe Arg Asn Tyr Ala Gly Cys Glu Phe Pro Gly
            275                 280                 285

<210> SEQ ID NO 49
<211> LENGTH: 290
<212> TYPE: PRT
<213> ORGANISM: Bacillus stearothermophilus

<400> SEQUENCE: 49

Ile Leu Val Gln Thr Tyr Asp Asn Ile Glu Met Leu His Asn Arg Asp
1               5                   10                  15

Gly Glu Ile Thr Gly Ile Pro Thr Gly Phe Thr Glu Leu Asp Arg Met
            20                  25                  30

Thr Ser Gly Phe Gln Arg Ser Asp Leu Ile Ile Val Ala Ala Arg Pro
        35                  40                  45

Ser Val Gly Lys Thr Ala Phe Ala Leu Asn Ile Ala Gln Asn Val Ala
    50                  55                  60

Thr Lys Thr Asn Glu Asn Val Ala Ile Phe Ser Leu Glu Met Ser Ala
65                  70                  75                  80

Gln Gln Leu Val Met Arg Met Leu Cys Ala Glu Gly Asn Ile Asn Ala
                85                  90                  95

Gln Asn Leu Arg Thr Gly Lys Leu Thr Pro Glu Asp Trp Gly Lys Leu
            100                 105                 110

Thr Met Ala Met Gly Ser Leu Ser Asn Ala Gly Ile Tyr Ile Asp Asp
        115                 120                 125

Thr Pro Ser Ile Arg Val Ser Asp Ile Arg Ala Lys Cys Arg Arg Leu
130                 135                 140

Lys Gln Glu Ser Gly Leu Gly Met Ile Val Ile Asp Tyr Leu Gln Leu
145                 150                 155                 160

Ile Gln Gly Ser Gly Arg Ser Lys Glu Asn Arg Gln Gln Glu Val Ser
                165                 170                 175

Glu Ile Ser Arg Ser Leu Lys Ala Leu Ala Arg Glu Leu Glu Val Pro
            180                 185                 190

Val Ile Ala Leu Ser Gln Leu Ser Arg Ser Val Glu Gln Arg Gln Asp
        195                 200                 205

Lys Arg Pro Met Met Ser Asp Ile Arg Glu Ser Gly Ser Ile Glu Gln
            210                 215                 220

Asp Ala Asp Ile Val Ala Phe Leu Tyr Arg Asp Asp Tyr Tyr Asn Lys
225                 230                 235                 240

Asp Ser Glu Asn Lys Asn Ile Ile Glu Ile Ile Ala Lys Gln Arg
                245                 250                 255

Asn Gly Pro Val Gly Thr Val Gln Leu Ala Phe Ile Lys Glu Tyr Asn
            260                 265                 270

Lys Phe Val Asn Leu Glu Arg Arg Phe Asp Glu Ala Gln Ile Pro Pro
        275                 280                 285
```

Gly Ala
    290

<210> SEQ ID NO 50
<211> LENGTH: 332
<212> TYPE: PRT
<213> ORGANISM: Halobacter pylori

<400> SEQUENCE: 50

Val Leu Glu Ser Ala Met Asp Leu Ile Thr Glu Asn Gln Arg Lys Gly
 1               5                  10                  15

Ser Leu Glu Val Thr Gly Ile Pro Thr Gly Phe Val Gln Leu Asp Asn
            20                  25                  30

Tyr Thr Ser Gly Phe Asn Lys Gly Ser Leu Val Ile Ile Gly Ala Arg
        35                  40                  45

Pro Ser Met Gly Lys Thr Ser Leu Met Met Asn Met Val Leu Ser Ala
    50                  55                  60

Leu Asn Asp Asp Arg Gly Val Ala Val Phe Ser Leu Glu Met Ser Ala
65                  70                  75                  80

Glu Gln Leu Ala Leu Arg Ala Leu Ser Asp Leu Thr Ser Ile Asn Met
                85                  90                  95

His Asp Leu Glu Ser Gly Arg Leu Asp Asp Gln Trp Glu Asn Leu
            100                 105                 110

Ala Lys Cys Phe Asp His Leu Ser Gln Lys Leu Phe Phe Tyr Asp
        115                 120                 125

Lys Ser Tyr Val Arg Ile Glu Gln Ile Arg Leu Gln Leu Arg Lys Leu
130                 135                 140

Lys Ser Gln His Lys Glu Leu Gly Ile Ala Phe Ile Asp Tyr Leu Gln
145                 150                 155                 160

Leu Met Ser Gly Ser Lys Ala Thr Lys Glu Arg His Glu Gln Ile Ala
                165                 170                 175

Glu Ile Ser Arg Glu Leu Lys Thr Leu Ala Arg Glu Leu Glu Ile Pro
            180                 185                 190

Ile Ile Ala Leu Val Gln Leu Asn Arg Ser Leu Glu Asn Arg Asp Asp
        195                 200                 205

Lys Arg Pro Ile Leu Ser Asp Ile Lys Asp Ser Gly Gly Ile Glu Gln
    210                 215                 220

Asp Ala Asp Ile Val Leu Phe Leu Tyr Arg Gly Tyr Ile Tyr Gln Met
225                 230                 235                 240

Arg Ala Glu Asp Asn Lys Ile Asp Lys Leu Lys Lys Glu Gly Lys Ile
                245                 250                 255

Glu Glu Ala Gln Glu Leu Tyr Leu Lys Val Asn Glu Glu Arg Arg Ile
            260                 265                 270

His Lys Gln Asn Gly Ser Ile Glu Glu Ala Glu Ile Ile Val Ala Lys
        275                 280                 285

Asn Arg Asn Gly Ala Thr Gly Thr Val Tyr Thr Arg Phe Asn Ala Pro
    290                 295                 300

Phe Thr Arg Tyr Glu Asp Met Pro Ile Asp Ser His Leu Glu Glu Gly
305                 310                 315                 320

Gln Glu Thr Lys Val Asp Tyr Asp Ile Val Thr Thr
                325                 330

<210> SEQ ID NO 51
<211> LENGTH: 295
<212> TYPE: PRT
<213> ORGANISM: Mycolplasma genitalium

<400> SEQUENCE: 51

```
Glu Ile Asn Gln Glu Ala Leu Ile Lys Lys Val His Arg Gly
 1               5                  10                  15

Glu Leu Ile Ile Ser Gly Leu Ser Ser Gly Phe Leu Lys Leu Asp Gln
                20                  25                  30

Leu Thr Ser Gly Trp Lys Pro Gly Glu Leu Ile Val Ile Ala Ala Arg
            35                  40                  45

Pro Gly Arg Gly Lys Thr Ala Leu Leu Ile Asn Phe Met Ala Ser Ala
    50                  55                  60

Ala Lys Gln Ile Asp Pro Lys Thr Asp Val Val Leu Phe Phe Ser Leu
65                  70                  75                  80

Glu Met Arg Asn Arg Glu Ile Tyr Gln Arg His Leu Met His Glu Ser
                85                  90                  95

Gln Thr Ser Tyr Thr Leu Thr Asn Arg Gln Arg Ile Asn Asn Val Phe
            100                 105                 110

Glu Glu Leu Met Glu Ala Ser Ser Arg Ile Lys Asn Leu Pro Ile Lys
        115                 120                 125

Leu Phe Asp Tyr Ser Ser Leu Thr Leu Gln Glu Ile Arg Asn Gln Ile
    130                 135                 140

Thr Glu Val Ser Lys Thr Ser Asn Val Arg Leu Val Ile Ile Asp Tyr
145                 150                 155                 160

Leu Gln Leu Val Asn Ala Leu Lys Asn Asn Tyr Gly Leu Thr Arg Gln
                165                 170                 175

Gln Glu Val Thr Met Ile Ser Gln Ser Leu Lys Ala Phe Ala Lys Glu
            180                 185                 190

Phe Asn Thr Pro Ile Ile Ala Ala Ala Gln Leu Ser Arg Arg Ile Glu
        195                 200                 205

Glu Arg Lys Asp Ser Arg Pro Ile Leu Ser Asp Leu Arg Glu Ser Gly
    210                 215                 220

Ser Ile Glu Gln Asp Ala Asp Met Val Leu Phe Ile His Arg Thr Asn
225                 230                 235                 240

Asp Asp Lys Lys Glu Gln Glu Glu Asn Thr Asn Leu Phe Glu Val
                245                 250                 255

Glu Leu Ile Leu Glu Lys Asn Arg Asn Gly Pro Asn Gly Lys Val Lys
            260                 265                 270

Leu Asn Phe Arg Ser Asp Thr Ser Ser Phe Ile Ser Gln Tyr Ser Pro
        275                 280                 285

Ser Phe Asp Asp Gln Tyr Ser
    290                 295
```

<210> SEQ ID NO 52
<211> LENGTH: 283
<212> TYPE: PRT
<213> ORGANISM: Borrelia burgdorferi

<400> SEQUENCE: 52

```
Ile Ala Glu Arg Val His Asn Glu Ile Tyr Glu Arg Ser Met Lys Lys
 1               5                  10                  15

Lys Glu Ala Asn Phe Gly Ile Pro Ser Gly Phe Arg Lys Val Asp Ser
                20                  25                  30

Leu Ile Gly Gly Phe Arg Asn Ser Asp Phe Ile Ile Val Gly Ala Arg
            35                  40                  45

Pro Ser Ile Gly Lys Thr Ala Phe Ala Leu Asn Ile Ala Ser Tyr Ile
    50                  55                  60
```

Ala Leu Arg Lys Glu Glu Lys Lys Val Gly Phe Phe Ser Leu Glu
65                  70                  75                  80

Met Thr Ala Asp Ala Leu Ile Lys Arg Ile Ile Ser Gln Ser Cys
                85                  90                  95

Ile Asp Ser Phe Lys Val Gln Asn Ser Ile Leu Ser Gly Gln Glu Ile
            100                 105                 110

Lys Ser Leu Asn Asp Ile Ile Asn Glu Ile Ser Asp Ser Glu Leu Tyr
        115                 120                 125

Ile Glu Asp Thr Pro Asn Ile Ser Leu Leu Thr Leu Ala Thr Gln Ala
    130                 135                 140

Arg Lys Leu Lys Arg Phe Tyr Gly Ile Asp Ile Phe Val Asp Tyr
145                 150                 155                 160

Ile Ser Leu Ile Ser Phe Glu Thr Lys Asn Leu Pro Arg His Glu Gln
                165                 170                 175

Val Ala Ser Ile Ser Lys Ser Leu Lys Glu Leu Ala Arg Glu Leu Glu
            180                 185                 190

Ile Pro Ile Val Ala Leu Ser Gln Leu Thr Arg Asp Thr Glu Gly Arg
    195                 200                 205

Glu Pro Asn Leu Ala Ser Leu Arg Glu Ser Gly Ala Leu Glu Gln Asp
210                 215                 220

Ala Asp Ile Val Ile Leu Leu His Arg Asp Lys Asp Phe Lys Phe Glu
225                 230                 235                 240

Ser Ser Ala Glu Ile Glu Pro Ile Glu Thr Lys Val Ile Val Ala Lys
                245                 250                 255

His Arg Asn Gly Pro Thr Gly Arg Ala Asp Ile Leu Phe Leu Pro His
            260                 265                 270

Ile Thr Lys Phe Val Asn Lys Asp His Gln Tyr
    275                 280

<210> SEQ ID NO 53
<211> LENGTH: 327
<212> TYPE: PRT
<213> ORGANISM: Bacteriophage T4

<400> SEQUENCE: 53

Tyr Val Gly His Asp Trp Met Asp Asp Tyr Glu Ala Arg Trp Leu Ser
1               5                   10                  15

Tyr Met Asn Lys Ala Arg Lys Val Pro Phe Lys Leu Arg Ile Leu Asn
            20                  25                  30

Lys Ile Thr Lys Gly Gly Ala Glu Thr Gly Thr Leu Asn Val Leu Met
        35                  40                  45

Ala Gly Val Asn Val Gly Lys Ser Leu Gly Leu Cys Ser Leu Ala Ala
    50                  55                  60

Asp Tyr Leu Gln Leu Gly His Asn Val Leu Tyr Ile Ser Met Glu Met
65                  70                  75                  80

Ala Glu Glu Val Cys Ala Lys Arg Ile Asp Ala Asn Met Leu Asp Val
                85                  90                  95

Ser Leu Asp Asp Ile Asp Asp Gly His Ile Ser Tyr Ala Glu Tyr Lys
            100                 105                 110

Gly Lys Met Glu Lys Trp Arg Glu Lys Ser Thr Leu Gly Arg Leu Ile
        115                 120                 125

Val Lys Gln Tyr Pro Thr Gly Gly Ala Asp Ala Asn Thr Phe Arg Ser
    130                 135                 140

Leu Leu Asn Glu Leu Lys Leu Lys Lys Asn Phe Val Pro Thr Ile Ile

-continued

```
                145                 150                 155                 160
Ile Val Asp Tyr Leu Gly Ile Cys Lys Ser Cys Arg Ile Arg Val Tyr
                    165                 170                 175
Ser Glu Asn Ser Tyr Thr Thr Val Lys Ala Ile Ala Glu Glu Leu Arg
                180                 185                 190
Ala Leu Ala Val Glu Thr Glu Thr Val Leu Trp Thr Ala Ala Gln Val
                195                 200                 205
Gly Lys Gln Ala Trp Asp Ser Asp Val Asn Met Ser Asp Ile Ala
                210                 215                 220
Glu Ser Ala Gly Leu Pro Ala Thr Ala Asp Phe Met Leu Ala Val Ile
225                 230                 235                 240
Glu Thr Glu Glu Leu Ala Ala Ala Glu Gln Gln Leu Ile Lys Gln Ile
                245                 250                 255
Lys Ser Arg Tyr Gly Asp Lys Asn Lys Trp Asn Lys Phe Leu Met Gly
                260                 265                 270
Val Gln Lys Gly Asn Gln Lys Trp Val Glu Ile Glu Gln Asp Ser Thr
                275                 280                 285
Pro Thr Glu Val Asn Glu Val Ala Gly Ser Gln Gln Ile Gln Ala Glu
                290                 295                 300
Gln Asn Arg Tyr Gln Arg Asn Glu Ser Thr Arg Ala Gln Leu Asp Ala
305                 310                 315                 320
Leu Ala Asn Glu Leu Lys Phe
                325

<210> SEQ ID NO 54
<211> LENGTH: 302
<212> TYPE: PRT
<213> ORGANISM: Bacteriophage T7

<400> SEQUENCE: 54

Val Val Ser Ala Leu Ser Leu Arg Glu Arg Ile Arg Glu His Leu Ser
1               5                   10                  15
Ser Glu Glu Ser Val Gly Leu Leu Phe Ser Gly Cys Thr Gly Ile Asn
                20                  25                  30
Asp Lys Thr Leu Gly Ala Arg Gly Gly Glu Val Ile Met Val Thr Ser
                35                  40                  45
Gly Ser Gly Met Gly Lys Ser Thr Phe Val Arg Gln Gln Ala Leu Gln
50                  55                  60
Trp Gly Thr Ala Met Gly Lys Lys Val Gly Leu Ala Met Leu Glu Glu
65                  70                  75                  80
Ser Val Glu Glu Thr Ala Glu Asp Leu Ile Gly Leu His Asn Arg Val
                85                  90                  95
Arg Leu Arg Gln Ser Asp Ser Leu Lys Arg Glu Ile Ile Glu Asn Gly
                100                 105                 110
Lys Phe Asp Gln Trp Phe Asp Glu Leu Phe Gly Asn Asp Thr Phe His
                115                 120                 125
Leu Tyr Asp Ser Phe Ala Glu Ala Glu Thr Asp Arg Leu Leu Ala Lys
                130                 135                 140
Leu Ala Tyr Met Arg Ser Gly Leu Gly Cys Asp Val Ile Ile Leu Asp
145                 150                 155                 160
His Ile Ser Ile Val Val Ser Ala Ser Gly Glu Ser Asp Glu Arg Lys
                165                 170                 175
Met Ile Asp Asn Leu Met Thr Lys Leu Lys Gly Phe Ala Lys Ser Thr
                180                 185                 190
```

```
Gly Val Val Leu Val Val Ile Cys His Leu Lys Asn Pro Asp Lys Gly
            195                 200                 205

Lys Ala His Glu Glu Gly Arg Pro Val Ser Ile Thr Asp Leu Arg Gly
    210                 215                 220

Ser Gly Ala Leu Arg Gln Leu Ser Asp Thr Ile Ile Ala Leu Glu Arg
225                 230                 235                 240

Asn Gln Gln Gly Asp Met Pro Asn Leu Val Leu Val Arg Ile Leu Lys
                245                 250                 255

Cys Arg Phe Thr Gly Asp Thr Gly Ile Ala Gly Tyr Met Glu Tyr Asn
            260                 265                 270

Lys Glu Thr Gly Trp Leu Glu Pro Ser Ser Tyr Ser Gly Glu Glu Glu
            275                 280                 285

Ser His Ser Glu Ser Thr Asp Trp Ser Asn Asp Thr Asp Phe
            290                 295                 300

<210> SEQ ID NO 55
<211> LENGTH: 270
<212> TYPE: PRT
<213> ORGANISM: Bacteriophage RM378

<400> SEQUENCE: 55

Val Ser Leu Val Glu Glu Phe Asp Leu Ala Thr Ser Glu Phe Asn Glu
1               5                   10                  15

Leu Phe Val Lys Glu Glu Arg Ile Pro Thr Pro Trp Glu Ser Val Asn
            20                  25                  30

Lys Asn Met Ala Gly Gly Leu Gly Arg Gly Glu Leu Gly Ile Val Met
            35                  40                  45

Leu Pro Ser Gly Trp Gly Lys Ser Trp Phe Leu Val Ser Leu Gly Leu
    50                  55                  60

His Ala Phe Arg Thr Gly Lys Arg Val Ile Tyr Phe Thr Leu Glu Leu
65                  70                  75                  80

Asp Gln Lys Tyr Val Met Lys Arg Phe Leu Lys Met Phe Ala Pro Tyr
                85                  90                  95

Cys Lys Gly Arg Ala Ser Ser Tyr Arg Asp Val Tyr Gln Ile Met Lys
            100                 105                 110

Glu Leu Met Phe Ser Gln Asp Asn Leu Leu Lys Ile Val Phe Cys Asn
            115                 120                 125

Ala Met Glu Asp Ile Glu His Tyr Ile Ala Leu Tyr Asn Pro Asp Val
130                 135                 140

Val Leu Ile Asp Tyr Ala Asp Leu Ile Tyr Asp Val Glu Thr Asp Lys
145                 150                 155                 160

Glu Lys Asn Tyr Leu Leu Leu Gln Lys Ile Tyr Arg Lys Leu Arg Leu
                165                 170                 175

Ile Ala Lys Val Tyr Asn Thr Ala Val Trp Ser Ala Ser Gln Leu Asn
            180                 185                 190

Arg Gly Ser Leu Ser Lys Gln Ala Asp Val Asp Phe Ile Glu Lys Tyr
            195                 200                 205

Ile Ala Asp Ser Phe Ala Lys Val Val Glu Ile Asp Phe Gly Met Ala
            210                 215                 220

Phe Ile Pro Asp Ser Glu Asn Ser Thr Pro Asp Ile His Val Gly Phe
225                 230                 235                 240

Gly Lys Ile Phe Lys Asn Arg Met Gly Ala Val Arg Lys Leu Glu Tyr
                245                 250                 255

Thr Ile Asn Phe Glu Asn Tyr Thr Val Asp Val Ala Val Lys
            260                 265                 270
```

```
<210> SEQ ID NO 56
<211> LENGTH: 1197
<212> TYPE: DNA
<213> ORGANISM: Bacteriophage RM378
<220> FEATURE:
<221> NAME/KEY: CDS
<222> LOCATION: (112)...(1158)

<400> SEQUENCE: 56
```

| | |
|---|---:|
| attttctgtt ttttcacagg caagtattcg acatgctcga aacccgcgaa gcttattatc | 60 |
| agttgcttca atcgttaaac gatttcctcg aagaagacct gaaggagaat t atg aag<br>                                                                                                       Met Lys<br>                                                                                                        1 | 117 |
| atc acg cta agc gca agc gta tac ccc cga tcg atg aaa att tac gga<br>Ile Thr Leu Ser Ala Ser Val Tyr Pro Arg Ser Met Lys Ile Tyr Gly<br>         5                    10                   15 | 165 |
| gtg gag cta atc gag ggg aaa aaa cac tta ttt caa tca ccc gta ccc<br>Val Glu Leu Ile Glu Gly Lys Lys His Leu Phe Gln Ser Pro Val Pro<br> 20                      25                   30 | 213 |
| cca cat ttg aag cgc atc gct cag cag aat cga ggg aag att gag gct<br>Pro His Leu Lys Arg Ile Ala Gln Gln Asn Arg Gly Lys Ile Glu Ala<br>35                  40                   45                 50 | 261 |
| gag gct ata tcc tat tac atc aga gaa caa aaa agc cac atc acg ccg<br>Glu Ala Ile Ser Tyr Tyr Ile Arg Glu Gln Lys Ser His Ile Thr Pro<br>               55                   60                   65 | 309 |
| gaa gct ttg tct cag tgc gtc ttt atc gat att gag acg att tcc ccg<br>Glu Ala Leu Ser Gln Cys Val Phe Ile Asp Ile Glu Thr Ile Ser Pro<br>              70                   75                   80 | 357 |
| aaa aaa agc ttt ccc gac ccg tgg aga gac cca gtt tat tcc att tcc<br>Lys Lys Ser Phe Pro Asp Pro Trp Arg Asp Pro Val Tyr Ser Ile Ser<br>85                  90                   95 | 405 |
| atc aaa ccg tat gga aaa ccg gtg gtg gta gtg ctt ctc ctt atc acc<br>Ile Lys Pro Tyr Gly Lys Pro Val Val Val Val Leu Leu Leu Ile Thr<br>          100                  105                 110 | 453 |
| aac ccg gag gct cat atc gat aac ttt aac aaa ttt acc acc agc gta<br>Asn Pro Glu Ala His Ile Asp Asn Phe Asn Lys Phe Thr Thr Ser Val<br>115                120                125              130 | 501 |
| ggg gat aac aca ttt gaa att cat tac aga aca ttc ctt tcg gaa aaa<br>Gly Asp Asn Thr Phe Glu Ile His Tyr Arg Thr Phe Leu Ser Glu Lys<br>              135                 140                145 | 549 |
| aga ttg ctc gag tat ttc tgg aat gtg ctg aaa cca aaa ttt act ttc<br>Arg Leu Leu Glu Tyr Phe Trp Asn Val Leu Lys Pro Lys Phe Thr Phe<br>          150                  155                 160 | 597 |
| atg ctc gca tgg aac ggt tat cag ttc gat tat ccc tac ctg ctc att<br>Met Leu Ala Trp Asn Gly Tyr Gln Phe Asp Tyr Pro Tyr Leu Leu Ile<br>165                170                175 | 645 |
| cgt agt cat atc cat gag gtg aat gtc att agt gat aag ttg ctt ccg<br>Arg Ser His Ile His Glu Val Asn Val Ile Ser Asp Lys Leu Leu Pro<br>          180                  185                 190 | 693 |
| gac tgg aag ctg gtg cgg aaa att tcc gat cga aac cta cca ttc tat<br>Asp Trp Lys Leu Val Arg Lys Ile Ser Asp Arg Asn Leu Pro Phe Tyr<br>195                200                205              210 | 741 |
| ttc aat ccc cgt acc cct gta gaa ttt gtg ttt ttt gat tac atg cgg<br>Phe Asn Pro Arg Thr Pro Val Glu Phe Val Phe Phe Asp Tyr Met Arg<br>              215                 220                225 | 789 |
| ctt tat cgc tcc ttt gtg gca tac aaa gag ttg gag tcc tac cgg ctc<br>Leu Tyr Arg Ser Phe Val Ala Tyr Lys Glu Leu Glu Ser Tyr Arg Leu<br>          230                  235                 240 | 837 |
| gac tat att gcg cga gag gaa ata gga gaa ggt aag gtg gat ttc gac | 885 |

```
Asp Tyr Ile Ala Arg Glu Glu Ile Gly Glu Gly Lys Val Asp Phe Asp
         245                 250                 255 gta aga ttc tat cat gag att cct gtc tac ccg gat aaa aag ttg gtg        933
Val Arg Phe Tyr His Glu Ile Pro Val Tyr Pro Asp Lys Lys Leu Val
     260                 265                 270 gaa tac aac gcc gta gac gcc att ttg atg gaa gaa atc gaa aat aaa        981
Glu Tyr Asn Ala Val Asp Ala Ile Leu Met Glu Glu Ile Glu Asn Lys
275                 280                 285                 290 aac cat att ctc ccg acg ctg ttt gaa att gca aga ctt tca aat ctg       1029
Asn His Ile Leu Pro Thr Leu Phe Glu Ile Ala Arg Leu Ser Asn Leu
             295                 300                 305 act ccc gca ctg gca ttg aac gct tcc aat att ctt atc gga aat gtt       1077
Thr Pro Ala Leu Ala Leu Asn Ala Ser Asn Ile Leu Ile Gly Asn Val
         310                 315                 320 aca gga aaa ctt ggt gtc aaa ttc gtt gat tac atc aag aaa atc gac       1125
Thr Gly Lys Leu Gly Val Lys Phe Val Asp Tyr Ile Lys Lys Ile Asp
     325                 330                 335 acc att aat aca atg ttc aaa aaa ata cct gag taaactatga atatgcagac     1178
Thr Ile Asn Thr Met Phe Lys Lys Ile Pro Glu
 340                 345 cattgacgaa acgctttat                                                  1197

<210> SEQ ID NO 57
<211> LENGTH: 349
<212> TYPE: PRT
<213> ORGANISM: Bacteriophage RM378

<400> SEQUENCE: 57

Met Lys Ile Thr Leu Ser Ala Ser Val Tyr Pro Arg Ser Met Lys Ile
 1                5                  10                  15

Tyr Gly Val Glu Leu Ile Glu Gly Lys Lys His Leu Phe Gln Ser Pro
             20                  25                  30

Val Pro Pro His Leu Lys Arg Ile Ala Gln Gln Asn Arg Gly Lys Ile
         35                  40                  45

Glu Ala Glu Ala Ile Ser Tyr Tyr Ile Arg Glu Gln Lys Ser His Ile
     50                  55                  60

Thr Pro Glu Ala Leu Ser Gln Cys Val Phe Ile Asp Ile Glu Thr Ile
 65                  70                  75                  80

Ser Pro Lys Lys Ser Phe Pro Asp Pro Trp Arg Asp Pro Val Tyr Ser
                 85                  90                  95

Ile Ser Ile Lys Pro Tyr Gly Lys Pro Val Val Val Leu Leu Leu
            100                 105                 110

Ile Thr Asn Pro Glu Ala His Ile Asp Asn Phe Asn Lys Phe Thr Thr
        115                 120                 125

Ser Val Gly Asp Asn Thr Phe Glu Ile His Tyr Arg Thr Phe Leu Ser
    130                 135                 140

Glu Lys Arg Leu Leu Glu Tyr Phe Trp Asn Val Leu Lys Pro Lys Phe
145                 150                 155                 160

Thr Phe Met Leu Ala Trp Asn Gly Tyr Gln Phe Asp Tyr Pro Tyr Leu
                165                 170                 175

Leu Ile Arg Ser His Ile His Glu Val Asn Val Ile Ser Asp Lys Leu
            180                 185                 190

Leu Pro Asp Trp Lys Leu Val Arg Lys Ile Ser Asp Arg Asn Leu Pro
        195                 200                 205

Phe Tyr Phe Asn Pro Arg Thr Pro Val Glu Phe Val Phe Phe Asp Tyr
    210                 215                 220
```

```
Met Arg Leu Tyr Arg Ser Phe Val Ala Tyr Lys Glu Leu Glu Ser Tyr
225                 230                 235                 240

Arg Leu Asp Tyr Ile Ala Arg Glu Glu Ile Gly Glu Gly Lys Val Asp
                245                 250                 255

Phe Asp Val Arg Phe Tyr His Glu Ile Pro Val Tyr Pro Asp Lys Lys
                260                 265                 270

Leu Val Glu Tyr Asn Ala Val Asp Ala Ile Leu Met Glu Glu Ile Glu
                275                 280                 285

Asn Lys Asn His Ile Leu Pro Thr Leu Phe Glu Ile Ala Arg Leu Ser
            290                 295                 300

Asn Leu Thr Pro Ala Leu Ala Leu Asn Ala Ser Asn Ile Leu Ile Gly
305                 310                 315                 320

Asn Val Thr Gly Lys Leu Gly Val Lys Phe Val Asp Tyr Ile Lys Lys
                325                 330                 335

Ile Asp Thr Ile Asn Thr Met Phe Lys Lys Ile Pro Glu
                340                 345
```

<210> SEQ ID NO 58
<211> LENGTH: 1764
<212> TYPE: DNA
<213> ORGANISM: Bacteriophage RM378
<220> FEATURE:
<221> NAME/KEY: CDS
<222> LOCATION: (142)...(1707)

<400> SEQUENCE: 58

```
ctatacggat gaagttttga gaattattga tctttctcca ctcgatggcg tattatacaa    60
atgtgattta aaagacacct accttatcga ggtgaaagat acccattttg atcccgcaat   120
gtaaaacaaa cgtattctgc t atg aac atc aac aag tat cgt tat cgc ggt   171
                        Met Asn Ile Asn Lys Tyr Arg Tyr Arg Gly
                         1               5                  10 gct tac att gaa ctt acc aac ccc gat att tac ttc aac gta ttc gat   219
Ala Tyr Ile Glu Leu Thr Asn Pro Asp Ile Tyr Phe Asn Val Phe Asp
                15                  20                  25 ctt gat ttt aca tcg ctg tac ccc tct gta atc agc aaa ttc aat atc   267
Leu Asp Phe Thr Ser Leu Tyr Pro Ser Val Ile Ser Lys Phe Asn Ile
            30                  35                  40 gat ccc gct acg ttc gta acg gag ttt tac ggg tgt atg cgg gtg gag   315
Asp Pro Ala Thr Phe Val Thr Glu Phe Tyr Gly Cys Met Arg Val Glu
        45                  50                  55 aac aaa gtg att ccg gta gat cag gaa gaa ccg gaa ttc ggg ttt ccc   363
Asn Lys Val Ile Pro Val Asp Gln Glu Glu Pro Glu Phe Gly Phe Pro
    60                  65                  70 ctc tac atc ttc gat tca ggg atg aac cct tct tac cgg agt gaa ccc   411
Leu Tyr Ile Phe Asp Ser Gly Met Asn Pro Ser Tyr Arg Ser Glu Pro
75                  80                  85                  90 ctc ttt gtc atc aac agc ttt gag gaa ctc cgg caa ttt tta aaa agt   459
Leu Phe Val Ile Asn Ser Phe Glu Glu Leu Arg Gln Phe Leu Lys Ser
                95                 100                 105 cga aat atc att atg gtg ccc aac ccg tcg ggt atc tgc tgg ttt tac   507
Arg Asn Ile Ile Met Val Pro Asn Pro Ser Gly Ile Cys Trp Phe Tyr
            110                 115                 120 agg aaa gag ccg gtt ggc gtg ctt cct tct atc att cgg gag att ttc   555
Arg Lys Glu Pro Val Gly Val Leu Pro Ser Ile Ile Arg Glu Ile Phe
        125                 130                 135 acc cga cgt aag gaa gaa cgt aag ctt ttc aaa gaa act ggc aac atg   603
Thr Arg Arg Lys Glu Glu Arg Lys Leu Phe Lys Glu Thr Gly Asn Met
    140                 145                 150
```

```
gaa cac cat ttc cgt caa tgg gca ctt aaa att atg atg aac tcc atg        651
Glu His His Phe Arg Gln Trp Ala Leu Lys Ile Met Met Asn Ser Met
155                 160                 165                 170 tac ggt atc ttc gga aac cgt tcg gtg tac atg ggg tgc ctt ccc att        699
Tyr Gly Ile Phe Gly Asn Arg Ser Val Tyr Met Gly Cys Leu Pro Ile
                175                 180                 185 gcg gaa agt gta acc gcc gcc ggg cgc atg tct att cgc tcc gtg att        747
Ala Glu Ser Val Thr Ala Ala Gly Arg Met Ser Ile Arg Ser Val Ile
                190                 195                 200 tct cag att cgc gat cgc ttc att tat tcg cat acc gac tcc att ttc        795
Ser Gln Ile Arg Asp Arg Phe Ile Tyr Ser His Thr Asp Ser Ile Phe
            205                 210                 215 gtc aaa gct ttt acg gat gat ccg gtg gcg gaa gcc ggt gag ctt caa        843
Val Lys Ala Phe Thr Asp Asp Pro Val Ala Glu Ala Gly Glu Leu Gln
            220                 225                 230 gaa cat ctc aac tct ttt atc aat gac tat atg gaa aat aac ttt aat        891
Glu His Leu Asn Ser Phe Ile Asn Asp Tyr Met Glu Asn Asn Phe Asn
235                 240                 245                 250 gca aga gaa gat ttc aag ctg gag tta aag cag gag ttc gtg ttc aaa        939
Ala Arg Glu Asp Phe Lys Leu Glu Leu Lys Gln Glu Phe Val Phe Lys
                255                 260                 265 tcc att ctt atc aaa gaa atc aac cgc tac ttt gcg gtt act gta gac        987
Ser Ile Leu Ile Lys Glu Ile Asn Arg Tyr Phe Ala Val Thr Val Asp
                270                 275                 280 ggt aaa gaa gag atg aag gga atc gaa gtg atc aac tct tcg gtg cct       1035
Gly Lys Glu Glu Met Lys Gly Ile Glu Val Ile Asn Ser Ser Val Pro
                285                 290                 295 gaa att gtc aag aag tat ttc agg ggt tac ctg aag tat atc agc caa       1083
Glu Ile Val Lys Lys Tyr Phe Arg Gly Tyr Leu Lys Tyr Ile Ser Gln
300                 305                 310 ccc gac atc gat gtc att tcc gcc acc ata gcg ttc tac aat aac ttt       1131
Pro Asp Ile Asp Val Ile Ser Ala Thr Ile Ala Phe Tyr Asn Asn Phe
315                 320                 325                 330 gtg tct caa aag aat ttc tgg tct att gaa gat ctc tat cac aaa atg       1179
Val Ser Gln Lys Asn Phe Trp Ser Ile Glu Asp Leu Tyr His Lys Met
                335                 340                 345 aaa ata tct tcg tct gac agc gcc gaa aga tat gtg gag tat gta gag       1227
Lys Ile Ser Ser Ser Asp Ser Ala Glu Arg Tyr Val Glu Tyr Val Glu
                350                 355                 360 gaa gtt atg aag atg aaa aag gag aat gtc cca atc tct gag ata ttc       1275
Glu Val Met Lys Met Lys Lys Glu Asn Val Pro Ile Ser Glu Ile Phe
                365                 370                 375 ata aaa atg tat gac cat aca ctt ccc att cat tat aag gga gcg ctt       1323
Ile Lys Met Tyr Asp His Thr Leu Pro Ile His Tyr Lys Gly Ala Leu
380                 385                 390 ttc gct tcc att ata gga tgc aaa ccc ccg caa atg gga gac aag atc       1371
Phe Ala Ser Ile Ile Gly Cys Lys Pro Pro Gln Met Gly Asp Lys Ile
395                 400                 405                 410 tac tgg ttc tac tgc acc atg ctg gat cct tcc aga acc aat ctc ccg       1419
Tyr Trp Phe Tyr Cys Thr Met Leu Asp Pro Ser Arg Thr Asn Leu Pro
                415                 420                 425 ctt tct ctg gaa gaa gtt aac ccc gaa cat ggg agc ggc gtg tgg gat       1467
Leu Ser Leu Glu Glu Val Asn Pro Glu His Gly Ser Gly Val Trp Asp
                430                 435                 440 att ctg aaa gcg gga aag aaa acg cat atc aac agg ctc cgc aat atc       1515
Ile Leu Lys Ala Gly Lys Lys Thr His Ile Asn Arg Leu Arg Asn Ile
            445                 450                 455 cac gca ctt agc ata cgt gag gat gat gag gag ggt ctt gaa atc gtt       1563
His Ala Leu Ser Ile Arg Glu Asp Asp Glu Glu Gly Leu Glu Ile Val
            460                 465                 470
```

```
aaa aaa tac ata gat aga gac aaa tac tgt cag atc att tca gag aaa    1611
Lys Lys Tyr Ile Asp Arg Asp Lys Tyr Cys Gln Ile Ile Ser Glu Lys
475             480             485             490 aca att gat ctg ctg aaa agt ctc ggg tat gtt gaa aat act aca aag    1659
Thr Ile Asp Leu Leu Lys Ser Leu Gly Tyr Val Glu Asn Thr Thr Lys
        495             500             505 ata aaa acc gtt gag gat ctt att cgt ttt ctt gta gag agt gaa aac    1707
Ile Lys Thr Val Glu Asp Leu Ile Arg Phe Leu Val Glu Ser Glu Asn
510             515             520 taaacccatt agcgccatga ttctcaaatt cgacactgaa ggcattgttc gtatcct     1764

<210> SEQ ID NO 59
<211> LENGTH: 522
<212> TYPE: PRT
<213> ORGANISM: Bacteriophage RM378

<400> SEQUENCE: 59

Met Asn Ile Asn Lys Tyr Arg Tyr Arg Gly Ala Tyr Ile Glu Leu Thr
1               5                   10                  15

Asn Pro Asp Ile Tyr Phe Asn Val Phe Asp Leu Asp Phe Thr Ser Leu
            20                  25                  30

Tyr Pro Ser Val Ile Ser Lys Phe Asn Ile Asp Pro Ala Thr Phe Val
        35                  40                  45

Thr Glu Phe Tyr Gly Cys Met Arg Val Glu Asn Lys Val Ile Pro Val
    50                  55                  60

Asp Gln Glu Glu Pro Glu Phe Gly Phe Pro Leu Tyr Ile Phe Asp Ser
65                  70                  75                  80

Gly Met Asn Pro Ser Tyr Arg Ser Glu Pro Leu Phe Val Ile Asn Ser
                85                  90                  95

Phe Glu Glu Leu Arg Gln Phe Leu Lys Ser Arg Asn Ile Ile Met Val
            100                 105                 110

Pro Asn Pro Ser Gly Ile Cys Trp Phe Tyr Arg Lys Glu Pro Val Gly
        115                 120                 125

Val Leu Pro Ser Ile Ile Arg Glu Ile Phe Thr Arg Arg Lys Glu Glu
    130                 135                 140

Arg Lys Leu Phe Lys Glu Thr Gly Asn Met Glu His His Phe Arg Gln
145                 150                 155                 160

Trp Ala Leu Lys Ile Met Met Asn Ser Met Tyr Gly Ile Phe Gly Asn
                165                 170                 175

Arg Ser Val Tyr Met Gly Cys Leu Pro Ile Ala Glu Ser Val Thr Ala
            180                 185                 190

Ala Gly Arg Met Ser Ile Arg Ser Val Ile Ser Gln Ile Arg Asp Arg
        195                 200                 205

Phe Ile Tyr Ser His Thr Asp Ser Ile Phe Val Lys Ala Phe Thr Asp
    210                 215                 220

Asp Pro Val Ala Glu Ala Gly Glu Leu Gln Glu His Leu Asn Ser Phe
225                 230                 235                 240

Ile Asn Asp Tyr Met Glu Asn Asn Phe Asn Ala Arg Glu Asp Phe Lys
                245                 250                 255

Leu Glu Leu Lys Gln Glu Phe Val Phe Lys Ser Ile Leu Ile Lys Glu
            260                 265                 270

Ile Asn Arg Tyr Phe Ala Val Thr Val Asp Gly Lys Glu Glu Met Lys
        275                 280                 285

Gly Ile Glu Val Ile Asn Ser Ser Val Pro Glu Ile Val Lys Lys Tyr
    290                 295                 300
```

```
Phe Arg Gly Tyr Leu Lys Tyr Ile Ser Gln Pro Asp Ile Asp Val Ile
305                 310                 315                 320

Ser Ala Thr Ile Ala Phe Tyr Asn Asn Phe Val Ser Gln Lys Asn Phe
                325                 330                 335

Trp Ser Ile Glu Asp Leu Tyr His Lys Met Lys Ile Ser Ser Ser Asp
                340                 345                 350

Ser Ala Glu Arg Tyr Val Glu Tyr Val Glu Val Met Lys Met Lys
                355                 360                 365

Lys Glu Asn Val Pro Ile Ser Glu Ile Phe Ile Lys Met Tyr Asp His
                370                 375                 380

Thr Leu Pro Ile His Tyr Lys Gly Ala Leu Phe Ala Ser Ile Ile Gly
385                 390                 395                 400

Cys Lys Pro Pro Gln Met Gly Asp Lys Ile Tyr Trp Phe Tyr Cys Thr
                405                 410                 415

Met Leu Asp Pro Ser Arg Thr Asn Leu Pro Leu Ser Leu Glu Glu Val
                420                 425                 430

Asn Pro Glu His Gly Ser Gly Val Trp Asp Ile Leu Lys Ala Gly Lys
                435                 440                 445

Lys Thr His Ile Asn Arg Leu Arg Asn Ile His Ala Leu Ser Ile Arg
                450                 455                 460

Glu Asp Asp Glu Glu Gly Leu Glu Ile Val Lys Lys Tyr Ile Asp Arg
465                 470                 475                 480

Asp Lys Tyr Cys Gln Ile Ile Ser Glu Lys Thr Ile Asp Leu Leu Lys
                485                 490                 495

Ser Leu Gly Tyr Val Glu Asn Thr Thr Lys Ile Lys Thr Val Glu Asp
                500                 505                 510

Leu Ile Arg Phe Leu Val Glu Ser Glu Asn
                515                 520

<210> SEQ ID NO 60
<211> LENGTH: 1619
<212> TYPE: DNA
<213> ORGANISM: Bacteriophage RM378

<400> SEQUENCE: 60
ccggtttgat acccgtattg gtcatttcct tgtggaaacc ccggttgaaa agtggagtaa      60
caaaatgttg cgcgtagctg aaaaacttgt aaccaattcc cgtaaacaga tttacgaagg     120
aggtgtgtga ttgctacggt ttcctatccg gaaactatga agttgtagac gaactccctg     180
atcaaccgac gcttccgaaa actcaaaaca agacttatag tacgctatgg aatcgatgaa     240
cgtaaaatac ccgttgagt accttatcga acacctgaac tcttttgagt ctccggaagt     300
agccgtcgaa tcccttcgca aggagggat tatgtgcaaa aaccggggtg atctatacat      360
gttcaaatat caccttggtt gtaagtttga taagatatat caccttgcct gtcgcggggc     420
gattctccgc aaaacggata gtggttggaa agttctgtct tatccctttg acaaattttt     480 caactgggg gaagaactcc agccggaaat cgtaaactat tatcagacgc ttcgttacgc      540
gtctcccctg aatgaaaagc gcaaagccgg tttcatgttc aaacttccca tgaaactggt     600
tgaaaagctg gatggtactt gtgtggtttt atattatgat gaagggtgga aaattcacac     660
tcttgggagt attgacgcaa atggatccat tgtcaaaaac ggaatggtta ccactcatat     720
ggataaaaca tatcgagaat tgttctggga aacctttgaa aagaaatatc cgccttacct     780
tctctatcat ttgaactcct catactgtta catatttgaa atggttcatc cggacgcgcg     840
```

-continued

```
agtggtggtt ccttatgagg agccaaatat cattctgatc ggtgtgcgtt cggtggatcc      900
ggagaaggga tatttcgagg tgggtccctc cgaagaagcc gtacgcattt caacgaaag      960 tggcggaaaa ataaatctta agctaccggc tgttctgtct caagagcaaa actatactct     1020
ttttcgtgcc aatcgccttc aggaactatt tgaggaagtt acaccgcttt tcaaaagcct     1080
gagagacggt tatgaggtgg tatatgaagg atttgtagcc gtacaggaaa ttgccccgcg     1140
tgtttattac cgcacaaaga tcaagcaccc ggtatatctg gagctccacc ggattaaaac     1200
tacaatcact cctgagaagc tcgccgatct ttttcttgaa acaaacttg atgattttgt     1260 acttaccccg gatgaacagg aaaccgtgat gaaactcaaa gaaatttata ccgatatgcg     1320
aaatcagctt gagtcatctt ttgatacgat ttataaagag atttccgaac aggtttctcc     1380
ggaagaaaac cccggagagt ttcgcaaaag gttcgctctt cgacttatgg attatcatga     1440
taaaagttgg ttttttgccc gccttgacgg cgacgaagag aaaatgcaaa agtcggaaaa     1500
gaagcttcta acgagagaa ttgaaaaggg gttatttaaa taaaaatgat aaaaaagcgt     1560
aatcctcttt tctggggaag acgggaactc aatcttcttc agcattttgc ccttgaagc     1619
```

<210> SEQ ID NO 61
<211> LENGTH: 1440
<212> TYPE: DNA
<213> ORGANISM: Bacteriophage RM378

<400> SEQUENCE: 61

```
gcttcgtcaa aactcacgtc tatagtatct atgtcgtagg gttcgaggtt ggaggcaatc      60
aggttgaaca gttcatcata atcataattc tcgaaaagaa tgttgcgaat accgatccct     120 cttttctggat cgtagggata ttcccccggc tcgatgaaaa gcaggagttt tatcttatcg     180
atcaggagtt ttaccgggtc atcaggaaat ctgaaattcg gtgcagtgtc gttcagatag     240
aacatttcat ttttgtttaa ataaatcctc gaggaatctt caaataaaga ggggcgttaa     300
tggatgaaaa gactgaggaa tatggtcaat cttatcgatc tcaaaaatca gtattatgct     360 tactcttta gttttttcga ctcctatcag atcagctggg ataattaccc gcatcttaaa     420
gagttcgtca ttgaaaacta tcccggcact tatttttcat gctacgctcc ggggattctg     480
tacaagcttt tcctcaaatg gaagcggggt atgatcattg acgactatga ccgacacccg     540
ctccgaaaga agttacttcc tcagtacaaa gagcaccgct atgaatacat tgagggaaaa     600
tacggtgtgg ttccttttccc cgggtttctg aaatatctga agttccactt tgaggacttg     660
cggtttaaaa tgcgcgatct tggaatcacc gatttcaaat atgcacttgc catttctctt     720
ttttacaacc gggtaatgct cagagatttt ctgaaaact ttacctgtta ttacattgcc     780
gaatatgaag ctgacgatgt aatcgcacat ctggcgcgtg agattgcacg aagcaatatc     840
gacgtaaaca tcgtctcaac ggataaagat tattaccagc tatgggatga agaggatata     900
agagaaaggg tttatatcaa ttctctttca tgtagtgatg tgaagacacc ccgctacgga     960
tttcttacca ttaaagcact tcttggagac aaaagcgata acattcccaa atctctggaa    1020
aaaggaaaag gcgaaaagta tcttgaaaag aaaggatttg cggaggaaga ttacgataag    1080
gaactattcg agaataatct gaaggtgatc aggtttggag acgaatatct ggagaaagg    1140 gataaaagct ttatagaaaa ttttttctacg ggggatactc tgtggaactt ttatgaattt    1200
ttttactatg acccttttgca tgaacttttc ctcagaaata taagaaagag gagactatga    1260
aagtactcgc atttaccgat gcacctacgt ttcccacggg ggtgggtcat cagcttcaca    1320
acattatcaa ttacgggttt gacgcaaccg atcgctgggt tgtggtgcac ccgcccggt    1380
```

```
cgccaagggc tgagagagact aaaaacgtcg ttattggaaa cactccagtc aagcttatca    1440
```

<210> SEQ ID NO 62
<211> LENGTH: 1508
<212> TYPE: DNA
<213> ORGANISM: Bacteriophage RM378

<400> SEQUENCE: 62

```
acttcccaaa tgctatgtgg aggtggatga tagaaagcgt attgttaatg aagaggcggt      60
caagtctttt ctccataagc atgttaccga actgctgaag aattatcagt aacccaaacc     120
taaacccgaa aaatatatgg aaacgattgt aatttcccaa acaatacga cggagatgac      180
ggaaccccccc cagaacattt ccgattcggt taaaagcggg tttatctatc ttatcgaaaa    240
gtctcatttc cttgaaaaga aaacttcct taaaatcata tcgaacatgg accccgccg      300
catttccaat ccggaggtgc gcgtggtggc ggagtacata tatgattatt tcaaaagtca    360
tagtaatttc ccttctaaaa gaaatctttg ccatcacttt gagtggagcg aagatctgga    420
aggagacccc gccgattatc agcgtatcat tcagtatctc aaatcttctt acattcgatc    480
ctctataaca aaaacgcttt catatcttga aaggatgac cttttcgcgt tgaaagaaat     540
tgtcagagcc attcgggtgg tggaggatag tggggtgtcg ctggtggagg aattcgatct    600
tgcaaccagc gagtttaatg aacttttttgt taaagaagaa cgcattccca cccctggga    660
gagtgtaaac aaaaatatgg cggcggtct tggtcgggga gagcttggaa tcgttatgct     720
tccttcgggg tgggtaagt catggttcct tgtttcactt ggtcttcatg cctttcgaac    780
gggtaagcgc gtgatttatt tcactctgga gcttgaccaa aaatatgtga tgaagcggtt    840
tttaaagatg tttgcacctt attgcaaagg acgcgcttct tcctatcgcg acgtttatca    900
aataatgaaa gagcttatgt tttctcagga taatcttttg ragattgttt tctgtaatgc    960
gatggaagat attgagcact atattgcgct gtataacccc gacgttgtgc tgattgacta   1020
tgccgatctt atttatgatg tggaaaccga caaagagaaa aattatctgc ttttgcaaaa   1080
aattttatagg aaacttcgtc tcattgcaaa ggtatataat acagcagtat ggagcgcctc   1140
tcagcttaat cgcggttccc tttcaaagca agccgacgtc gatttcattg agaaatacat   1200
tgccgattca tttgcaaaag ttkttgaaat cgacttcggg atggcgttta ttccggatag   1260
cgagaactca accccccgata ttcacgtcgg attcggtaaa atcttcaaaa accgtatggg   1320
tgcggtaaga aagctggaat atacaattaa ctttgaaaac tatacggtag acgttgctgt   1380
taaatgacac aagttaagac aaaagggctt aaagacatca gaataggtag aaaggagggt    1440
aagttcacac atgtaaatac aacaaagaaa ggaaagaata agaaatattt cagggcggaa   1500
catgaacg                                                            1508
```

<210> SEQ ID NO 63
<211> LENGTH: 8
<212> TYPE: PRT
<213> ORGANISM: Artificial Sequence
<220> FEATURE:
<223> OTHER INFORMATION: Peptide
<221> NAME/KEY: VARIANT
<222> LOCATION: (0)...(0)
<223> OTHER INFORMATION: Xaa = Any amino acid

<400> SEQUENCE: 63

```
Asp Xaa Xaa Ser Leu Tyr Pro Ser
 1               5
```

```
<210> SEQ ID NO 64
<211> LENGTH: 33
<212> TYPE: DNA
<213> ORGANISM: Artificial Sequence
<220> FEATURE:
<223> OTHER INFORMATION: Nucleic acid

<400> SEQUENCE: 64
cacgagctca tgaagatcac gctaagcgca agc                                33

<210> SEQ ID NO 65
<211> LENGTH: 33
<212> TYPE: DNA
<213> ORGANISM: Artificial Sequence
<220> FEATURE:
<223> OTHER INFORMATION: Nucleic acid

<400> SEQUENCE: 65
acaggtacct tactcaggta tttttttgaa cat                                33

<210> SEQ ID NO 66
<211> LENGTH: 33
<212> TYPE: DNA
<213> ORGANISM: Artificial Sequence
<220> FEATURE:
<223> OTHER INFORMATION: Nucleic acid

<400> SEQUENCE: 66
cacgagctca tgaacatcaa caagtatcgt tat                                33

<210> SEQ ID NO 67
<211> LENGTH: 30
<212> TYPE: DNA
<213> ORGANISM: Artificial Sequence
<220> FEATURE:
<223> OTHER INFORMATION: Nucleic acid

<400> SEQUENCE: 67
acaggtacct tagttttcac tctctacaag                                    30

<210> SEQ ID NO 68
<211> LENGTH: 28
<212> TYPE: DNA
<213> ORGANISM: Artificial Sequence
<220> FEATURE:
<223> OTHER INFORMATION: Nucleic acid

<400> SEQUENCE: 68
gggaattctt atgaacgtaa aatacccg                                      28

<210> SEQ ID NO 69
<211> LENGTH: 28
<212> TYPE: DNA
<213> ORGANISM: Artificial Sequence
<220> FEATURE:
<223> OTHER INFORMATION: Nucleic acid

<400> SEQUENCE: 69
ggagatctta tttaaataac ccctttc                                       28

<210> SEQ ID NO 70
<211> LENGTH: 30
<212> TYPE: DNA
<213> ORGANISM: Artificial Sequence
<220> FEATURE:
<223> OTHER INFORMATION: Nucleic acid
```

```
<400> SEQUENCE: 70
gggaattctt atgaaaagac tgaggaatat                                          30

<210> SEQ ID NO 71
<211> LENGTH: 26
<212> TYPE: DNA
<213> ORGANISM: Artificial Sequence
<220> FEATURE:
<223> OTHER INFORMATION: Nucleic acid

<400> SEQUENCE: 71
ggagatctca tagtctcctc tttctt                                              26

<210> SEQ ID NO 72
<211> LENGTH: 31
<212> TYPE: DNA
<213> ORGANISM: Artificial Sequence
<220> FEATURE:
<223> OTHER INFORMATION: Nucleic acid

<400> SEQUENCE: 72
gggcaattgt tatggaaacg attgtaattt c                                        31

<210> SEQ ID NO 73
<211> LENGTH: 26
<212> TYPE: DNA
<213> ORGANISM: Artificial Sequence
<220> FEATURE:
<223> OTHER INFORMATION: Nucleic acid

<400> SEQUENCE: 73
cgggatcctc atttaacagc aacgtc                                              26
```